(12) United States Patent
Brogdon et al.

(10) Patent No.: US 11,578,130 B2
(45) Date of Patent: *Feb. 14, 2023

(54) REGULATABLE CHIMERIC ANTIGEN RECEPTOR

(71) Applicants: Novartis AG, Basel (CH); The Trustees of the University of Pennsylvania, Philadelphia, PA (US)

(72) Inventors: Jennifer Brogdon, Sudbury, MA (US); Boris Engels, Arlington, MA (US); David Jonathan Glass, Cambridge, MA (US); Brian Granda, Salisbury, MA (US); John Hastewell, Cambridge, MA (US); Andreas Loew, Boston, MA (US); Joan Mannick, Cambridge, MA (US); Michael C. Milone, Moorestown, NJ (US); Leon Murphy, Cambridge, MA (US); William Raj Sellers, Cambridge, MA (US); Huijuan Song, Shanghai (CN); Brian Edward Vash, Cambridge, MA (US); Jan Weiler, Cambridge, MA (US); Qilong Wu, Shanghai (CN); Li Zhou, Cambridge, MA (US)

(73) Assignees: Novartis AG, Basel (CH); The Trustees of the University of Pennsylvania, Philadelphia, PA (US)

( * ) Notice: Subject to any disclaimer, the term of this patent is extended or adjusted under 35 U.S.C. 154(b) by 162 days.

This patent is subject to a terminal disclaimer.

(21) Appl. No.: 16/210,480

(22) Filed: Dec. 5, 2018

(65) Prior Publication Data

US 2019/0263914 A1 Aug. 29, 2019

Related U.S. Application Data

(63) Continuation of application No. 15/105,074, filed as application No. PCT/CN2014/094383 on Dec. 19, 2014, now Pat. No. 10,287,354.

(60) Provisional application No. 61/919,588, filed on Dec. 20, 2013, provisional application No. 61/953,818, filed on Mar. 15, 2014.

(30) Foreign Application Priority Data

Jul. 21, 2014 (CN) ................ PCT/CN2014/082615
Nov. 6, 2014 (CN) ................ PCT/CN2014/090494

(51) Int. Cl.
| | |
|---|---|
| *C07K 16/28* | (2006.01) |
| *A61K 31/436* | (2006.01) |
| *A61K 35/17* | (2015.01) |
| *C07K 14/705* | (2006.01) |
| *C07K 14/71* | (2006.01) |
| *C07K 14/725* | (2006.01) |
| *C07K 14/74* | (2006.01) |
| *C12N 9/12* | (2006.01) |
| *C12N 9/90* | (2006.01) |

(52) U.S. Cl.
CPC ........ *C07K 16/2863* (2013.01); *A61K 31/436* (2013.01); *A61K 35/17* (2013.01); *C07K 14/7051* (2013.01); *C07K 14/70521* (2013.01); *C07K 14/70539* (2013.01); *C07K 14/70578* (2013.01); *C07K 14/71* (2013.01); *C12N 9/1205* (2013.01); *C12N 9/90* (2013.01); *C12Y 502/00* (2013.01); *C07K 2317/622* (2013.01); *C07K 2319/00* (2013.01); *C07K 2319/03* (2013.01); *C07K 2319/41* (2013.01); *C07K 2319/43* (2013.01); *C07K 2319/70* (2013.01)

(58) Field of Classification Search
None
See application file for complete search history.

(56) References Cited

U.S. PATENT DOCUMENTS

| | | |
|---|---|---|
| 5,359,046 A | 10/1994 | Capon et al. |
| 5,686,281 A | 11/1997 | Roberts |
| 5,712,149 A | 1/1998 | Roberts |
| 5,874,240 A | 2/1999 | Ni et al. |

(Continued)

FOREIGN PATENT DOCUMENTS

| | | |
|---|---|---|
| EP | 0574512 A1 | 12/1993 |
| EP | 0871495 A1 | 10/1998 |

(Continued)

OTHER PUBLICATIONS

Ginalski, et al. (2005) "Survey and Summary: Practical lessons from protein structure prediction", Nucleic Acids Research: 33(6): 1874-91. (Year: 2005).*

(Continued)

*Primary Examiner* — Robert M Kelly
(74) *Attorney, Agent, or Firm* — K&L Gates LLP

(57) ABSTRACT

Compositions and methods relating to regulatable chimeric antigen receptors (RCARs), where the intracellular signaling or proliferation of the RCAR can be controlled to optimize the use of an RCAR-expressing cell to provide an immune response, are provided. For example, a RCAR can comprise a dimerization switch that, upon the presence of a dimerization molecule, can couple an intracellular signaling domain to an extracellular recognition element, e.g., an antigen binding domain, an inhibitory counter ligand binding domain, or costimulatory ECD domain. An RCAR can be engineered to include an appropriate antigen binding domain that is specific to a desired antigen target and used in the treatment of a disease.

30 Claims, 59 Drawing Sheets

Specification includes a Sequence Listing.

(56) References Cited

U.S. PATENT DOCUMENTS

| | | |
|---|---|---|
| 5,906,936 A | 5/1999 | Eshhar et al. |
| 6,103,521 A | 8/2000 | Capon et al. |
| 6,319,494 B1 | 11/2001 | Capon et al. |
| 6,355,779 B1 | 3/2002 | Goodwin et al. |
| 6,410,319 B1 | 6/2002 | Raubitschek et al. |
| 6,569,997 B1 | 5/2003 | Kwon |
| 7,049,136 B2 | 5/2006 | Seed et al. |
| 7,052,906 B1 | 5/2006 | Lawson et al. |
| 7,070,995 B2 | 7/2006 | Jensen |
| 7,265,209 B2 | 9/2007 | Jensen |
| 7,319,143 B2 | 1/2008 | Gross et al. |
| 7,320,787 B2 | 1/2008 | Seed et al. |
| 7,446,190 B2 | 11/2008 | Sadelain et al. |
| 7,446,191 B2 | 11/2008 | Jensen |
| 7,514,537 B2 | 4/2009 | Jensen |
| 7,638,326 B2 | 12/2009 | June et al. |
| 7,741,465 B1 | 6/2010 | Eshhar et al. |
| 7,745,140 B2 | 6/2010 | June et al. |
| 7,754,482 B2 | 7/2010 | Riley et al. |
| 7,994,298 B2 | 8/2011 | Zhang et al. |
| 8,211,422 B2 | 7/2012 | Eshhar et al. |
| 8,252,914 B2 | 8/2012 | Zhang et al. |
| 8,389,282 B2 | 3/2013 | Sadelain et al. |
| 8,399,645 B2 | 3/2013 | Campana et al. |
| 8,465,743 B2 | 6/2013 | Rosenberg et al. |
| 8,637,307 B2 | 1/2014 | June et al. |
| 8,722,400 B2 | 5/2014 | Riley et al. |
| 8,906,682 B2 | 12/2014 | June et al. |
| 8,911,993 B2 | 12/2014 | June et al. |
| 8,916,381 B1 | 12/2014 | June et al. |
| 8,975,071 B1 | 3/2015 | June et al. |
| 9,101,584 B2 | 8/2015 | June et al. |
| 9,102,760 B2 | 8/2015 | June et al. |
| 9,102,761 B2 | 8/2015 | June et al. |
| 9,394,368 B2 | 7/2016 | Brogdon et al. |
| 9,573,988 B2 | 2/2017 | Brogdon et al. |
| 9,587,020 B2 | 3/2017 | Wu et al. |
| 9,745,368 B2 | 8/2017 | Milone et al. |
| 9,777,061 B2 | 10/2017 | Ebersbach et al. |
| 9,815,901 B2 | 11/2017 | Brogdon et al. |
| 10,174,095 B2 | 1/2019 | Brogdon et al. |
| 2003/0060444 A1 | 3/2003 | Finney et al. |
| 2003/0077249 A1 | 4/2003 | Bebbington et al. |
| 2003/0148982 A1 | 8/2003 | Brenner et al. |
| 2003/0224520 A1 | 12/2003 | June et al. |
| 2004/0038886 A1 | 2/2004 | Finney et al. |
| 2004/0043401 A1 | 3/2004 | Sadelain et al. |
| 2005/0113564 A1 | 5/2005 | Campana et al. |
| 2005/0129671 A1 | 6/2005 | Cooper et al. |
| 2007/0036773 A1 | 2/2007 | Cooper et al. |
| 2008/0131415 A1 | 6/2008 | Riddell et al. |
| 2008/0274475 A1 | 11/2008 | Braud et al. |
| 2009/0257994 A1 | 10/2009 | Jensen |
| 2011/0003385 A1 | 1/2011 | Crabtree et al. |
| 2011/0052554 A1 | 3/2011 | Zakrzewski et al. |
| 2012/0029063 A1 | 2/2012 | Zhang et al. |
| 2012/0148552 A1 | 6/2012 | Jensen |
| 2012/0213783 A1 | 8/2012 | Rosenberg et al. |
| 2012/0321667 A1 | 12/2012 | Sentman |
| 2013/0071409 A1 | 3/2013 | Riley et al. |
| 2013/0071414 A1 | 3/2013 | Dotti et al. |
| 2013/0149337 A1 | 6/2013 | Cooper et al. |
| 2013/0155909 A1 | 6/2013 | Jackson et al. |
| 2013/0158098 A1 | 6/2013 | Liang et al. |
| 2013/0280285 A1 | 10/2013 | Schonfeld et al. |
| 2013/0287748 A1 | 10/2013 | June et al. |
| 2013/0309258 A1 | 11/2013 | June et al. |
| 2014/0050708 A1 | 2/2014 | Powell et al. |
| 2014/0099309 A1 | 4/2014 | Powell, Jr. et al. |
| 2014/0099340 A1 | 4/2014 | June et al. |
| 2014/0106449 A1 | 4/2014 | June et al. |
| 2014/0186947 A1 | 7/2014 | June et al. |
| 2014/0212446 A1 | 7/2014 | Riley et al. |
| 2014/0219975 A1 | 8/2014 | June et al. |
| 2014/0227237 A1 | 8/2014 | June et al. |
| 2014/0271635 A1 | 9/2014 | Brogdon et al. |
| 2014/0322169 A1 | 10/2014 | Harper et al. |
| 2014/0322183 A1 | 10/2014 | Milone et al. |
| 2014/0322212 A1 | 10/2014 | Brogdon et al. |
| 2014/0322275 A1 | 10/2014 | Brogdon et al. |
| 2014/0370045 A1 | 12/2014 | June et al. |
| 2015/0017141 A1 | 1/2015 | June et al. |
| 2015/0140019 A1 | 5/2015 | June et al. |
| 2015/0190428 A1 | 7/2015 | June et al. |
| 2015/0202286 A1 | 7/2015 | June et al. |
| 2015/0283178 A1 | 10/2015 | June et al. |
| 2015/0290244 A1 | 10/2015 | June et al. |
| 2015/0342994 A1 | 12/2015 | Riley et al. |
| 2015/0368342 A1 | 12/2015 | Wu et al. |
| 2016/0046724 A1 | 2/2016 | Brogdon et al. |
| 2016/0051651 A1 | 2/2016 | Brogdon et al. |
| 2016/0068601 A1 | 3/2016 | Brogdon et al. |
| 2016/0096892 A1 | 4/2016 | Brogdon et al. |
| 2016/0185861 A1 | 6/2016 | Bedoya et al. |
| 2016/0185862 A1 | 6/2016 | Wu et al. |
| 2016/0311907 A1 | 10/2016 | Brogdon et al. |
| 2016/0311917 A1 | 10/2016 | Beatty et al. |
| 2016/0340406 A1 | 11/2016 | Zhao et al. |
| 2016/0362472 A1 | 12/2016 | Bitter et al. |
| 2017/0008963 A1 | 1/2017 | Brogdon et al. |
| 2017/0081411 A1 | 3/2017 | Engels et al. |
| 2017/0137783 A1 | 5/2017 | Bedoya et al. |
| 2017/0143765 A1 | 5/2017 | Wu et al. |
| 2017/0183415 A1 | 6/2017 | Brogdon et al. |
| 2017/0209492 A1 | 7/2017 | June et al. |
| 2017/0211055 A1 | 7/2017 | Brogdon et al. |
| 2017/0226495 A1 | 8/2017 | Guimaraes |
| 2017/0239294 A1 | 8/2017 | Thomas-Tikhonenko et al. |
| 2017/0260268 A1 | 9/2017 | Beatty et al. |
| 2017/0274014 A1 | 9/2017 | Brogdon et al. |
| 2017/0306416 A1 | 10/2017 | Bedoya et al. |
| 2017/0334967 A1 | 11/2017 | Siegel et al. |
| 2017/0335281 A1 | 11/2017 | Loew et al. |
| 2018/0022795 A1 | 1/2018 | Milone et al. |
| 2018/0044423 A1 | 2/2018 | Ebersbach et al. |
| 2018/0044424 A1 | 2/2018 | June et al. |
| 2018/0118834 A1 | 5/2018 | Brogdon et al. |
| 2018/0125892 A1 | 5/2018 | Brannetti et al. |
| 2018/0133296 A1 | 5/2018 | Barrett |
| 2018/0140602 A1 | 5/2018 | Angst et al. |
| 2018/0230193 A1 | 8/2018 | Loew et al. |
| 2018/0252727 A1 | 9/2018 | Garfall et al. |
| 2018/0258149 A1 | 9/2018 | Motz et al. |
| 2018/0298068 A1 | 10/2018 | Albelda |
| 2018/0312595 A1 | 11/2018 | Brogdon et al. |
| 2019/0000880 A1 | 1/2019 | Motz et al. |
| 2019/0000944 A1 | 1/2019 | Brogdon et al. |
| 2019/0135940 A1 | 5/2019 | Brogdon et al. |
| 2019/0151365 A1 | 5/2019 | Anak et al. |
| 2019/0153061 A1 | 5/2019 | Brogdon et al. |
| 2019/0161542 A1 | 5/2019 | Gill et al. |
| 2019/0292238 A1 | 9/2019 | Bitter et al. |
| 2019/0292257 A1 | 9/2019 | Bedoya et al. |
| 2019/0298715 A1 | 10/2019 | Motz et al. |
| 2019/0330356 A1 | 10/2019 | Brogdon et al. |
| 2019/0336504 A1 | 11/2019 | Gill et al. |
| 2019/0375815 A1 | 12/2019 | Engels et al. |
| 2019/0382500 A1 | 12/2019 | Abujoub et al. |
| 2019/0388471 A1 | 12/2019 | June et al. |
| 2019/0389928 A1 | 12/2019 | Posey et al. |
| 2020/0048359 A1 | 2/2020 | Albelda et al. |
| 2020/0055948 A1 | 2/2020 | Daley et al. |
| 2020/0061113 A1 | 2/2020 | Kassim et al. |
| 2020/0085869 A1 | 3/2020 | Schuster et al. |
| 2020/0087376 A1 | 3/2020 | Fraietta et al. |
| 2020/0113941 A1 | 4/2020 | Brannetti et al. |
| 2020/0179511 A1 | 6/2020 | Daley et al. |
| 2020/0215171 A1 | 7/2020 | Brogdon et al. |
| 2020/0281973 A1 | 9/2020 | Dranoff |
| 2020/0283729 A1 | 9/2020 | Loew et al. |
| 2020/0291354 A1 | 9/2020 | Johnson et al. |
| 2020/0339704 A1 | 10/2020 | Bradner et al. |
| 2020/0360431 A1 | 11/2020 | Garfall et al. |
| 2020/0368268 A1 | 11/2020 | Johnson et al. |

(56) References Cited

U.S. PATENT DOCUMENTS

| | | |
|---|---|---|
| 2020/0370012 A1 | 11/2020 | Fraietta et al. |
| 2020/0371091 A1 | 11/2020 | Pruteanu-Malinici et al. |
| 2020/0399383 A1 | 12/2020 | Scholler et al. |
| 2021/0002377 A1 | 1/2021 | Brogdon et al. |
| 2021/0047405 A1 | 2/2021 | Nobles et al. |
| 2021/0079073 A1 | 3/2021 | Milone et al. |
| 2021/0087279 A1 | 3/2021 | Engels et al. |
| 2021/0139595 A1 | 5/2021 | Ebersbach et al. |
| 2021/0171909 A1 | 6/2021 | Golovina |
| 2021/0172020 A1 | 6/2021 | Bedoya et al. |
| 2021/0177896 A1 | 6/2021 | Porter et al. |
| 2021/0177900 A1 | 6/2021 | Engels et al. |
| 2021/0213063 A1 | 7/2021 | Isaacs et al. |
| 2021/0220404 A1 | 7/2021 | Abujoub et al. |
| 2021/0246423 A1 | 8/2021 | Bedoya et al. |
| 2021/0284752 A1 | 9/2021 | Brogdon et al. |
| 2021/0317183 A1 | 10/2021 | Zhao et al. |
| 2021/0347851 A1 | 11/2021 | Isaacs et al. |

FOREIGN PATENT DOCUMENTS

| | | |
|---|---|---|
| EP | 1226244 A2 | 7/2002 |
| WO | 1992015322 A1 | 9/1992 |
| WO | 09418317 A1 | 8/1994 |
| WO | 199530014 A1 | 11/1995 |
| WO | 9623814 A1 | 8/1996 |
| WO | 9624671 A1 | 8/1996 |
| WO | 09640140 A1 | 12/1996 |
| WO | 1997015669 A1 | 5/1997 |
| WO | 9723613 A2 | 7/1997 |
| WO | 9818809 A1 | 5/1998 |
| WO | 9900494 A2 | 1/1999 |
| WO | 9941258 A1 | 8/1999 |
| WO | 9957268 A1 | 11/1999 |
| WO | 0014257 A1 | 3/2000 |
| WO | 2001042444 A2 | 6/2001 |
| WO | 2002033101 A1 | 4/2002 |
| WO | 02077029 A2 | 10/2002 |
| WO | 02088334 A1 | 11/2002 |
| WO | 2003057171 A2 | 7/2003 |
| WO | 2005019429 A2 | 3/2005 |
| WO | 2005044996 A2 | 5/2005 |
| WO | 2005/118788 A2 | 12/2005 |
| WO | 2006036445 A2 | 4/2006 |
| WO | 2006060878 A1 | 6/2006 |
| WO | 2007/002905 A1 | 1/2007 |
| WO | 2008045437 A2 | 4/2008 |
| WO | 2010085660 A2 | 7/2010 |
| WO | 2011059836 A2 | 5/2011 |
| WO | 2011097477 A1 | 8/2011 |
| WO | 2011119773 A1 | 9/2011 |
| WO | 2012058460 A2 | 5/2012 |
| WO | 2012079000 A1 | 6/2012 |
| WO | 2012082841 A2 | 6/2012 |
| WO | 2012/099973 A2 | 7/2012 |
| WO | 2012127464 A2 | 9/2012 |
| WO | 2012129514 A1 | 9/2012 |
| WO | 2012135854 A2 | 10/2012 |
| WO | 2012138858 A1 | 10/2012 |
| WO | 2013019615 A2 | 2/2013 |
| WO | 2013033626 A2 | 3/2013 |
| WO | 2013040371 A2 | 3/2013 |
| WO | 2013040557 A2 | 3/2013 |
| WO | 2013059593 A1 | 4/2013 |
| WO | 2013/126712 A1 | 8/2013 |
| WO | 2013126726 A1 | 8/2013 |
| WO | 2013126729 A1 | 8/2013 |
| WO | 2013126733 A1 | 8/2013 |
| WO | 2013153270 A1 | 10/2013 |
| WO | 2013166051 A1 | 11/2013 |
| WO | 2014/011984 A1 | 1/2014 |
| WO | 2014/011987 A1 | 1/2014 |
| WO | 2014/011993 A2 | 1/2014 |
| WO | 2014/012001 A2 | 1/2014 |
| WO | 2014011988 A2 | 1/2014 |
| WO | 2014011996 A1 | 1/2014 |
| WO | 2014031687 A1 | 2/2014 |
| WO | 2014039513 A2 | 3/2014 |
| WO | 2014/055442 A2 | 4/2014 |
| WO | 2014055657 A1 | 4/2014 |
| WO | 2014127261 A1 | 8/2014 |
| WO | 2014130635 A1 | 8/2014 |
| WO | 2014/145252 A2 | 9/2014 |
| WO | 2014153270 A1 | 9/2014 |
| WO | 2015017214 A1 | 2/2015 |
| WO | 2015090229 A1 | 6/2015 |
| WO | 2015090230 A1 | 6/2015 |
| WO | 2015112626 A1 | 7/2015 |
| WO | 2015/142661 A1 | 9/2015 |
| WO | 2015142675 A2 | 9/2015 |
| WO | 2015157252 A1 | 10/2015 |
| WO | 2016014501 A1 | 1/2016 |
| WO | 2016014530 A1 | 1/2016 |
| WO | 2016014535 A1 | 1/2016 |
| WO | 2016014553 A1 | 1/2016 |
| WO | 2016014565 A2 | 1/2016 |
| WO | 2016014576 A1 | 1/2016 |
| WO | 2016019300 A1 | 2/2016 |
| WO | 2016025880 A1 | 2/2016 |
| WO | 2016028896 A1 | 2/2016 |
| WO | 2016044605 A1 | 3/2016 |

OTHER PUBLICATIONS

Teng et al., "T cells gene-engineered with DAP12 mediate effector function in an NKG2D-dependent and major histocompatibility complex-independent manner" J Biol Chem (2005) vol. 280 No. 46 pp. 38235-38241.

Thielens et al. "NK cell MHC class I specific receptors (KIR): from biology to clinical intervention" Current Opinion in Immunology (2012) vol. 24, pp. 239-245.

Thielens et al., "NK cell MHC class I specific receptors (KIR): from biology to clinical intervention" Curent Opinion in Immunology (2012) vol. 24 pp. 239-245.

Thomas, "Of ITAMs and ITIMs: turning on and off the B cell antigen receptor." J Exp Med (1995) vol. 181 No. 6 pp. 1953-1956.

Till et al., "Adoptive immunotherapy for indolent non-Hodgkin lymphoma and mantle cell lymphoma using genetically modified autologous CD20-specific T cells" Blood (2008) vol. 112 No. 6 pp. 2261-2271.

Uckun et al., "Detailed studies on expression and function of CD19 surface determinant by using B43 monoclonal antibody and the clinical potential of anti-CD19 immunotoxins" Blood (1988) vol. 71 pp. 13-29.

Varela-Rohena et al., "Control of HIV-1 immune escape by CD8 T cells expressing enhanced T-cell receptor." Nat Med (2008) vol. 14 No. 12 pp. 1390-1395.

Vinay & Kwon, "Role of 4-1BB in immune responses" Immunology (1998) vol. 10 pp. 481-489.

Vivier et al., "Signaling Function of Reconstituted CD16:Zeta:Gamma Receptor Complex Isoforms" International Immunology (1992) vol. 4 No. 11 pp. 1313-1323.

Vivier et al. "Signaling Function of Reconstituted CD16-Zeta-Gamma Receptor Complex Isoforms" International Immunology (1992) vol. 4 No. 11.

Wang et al. "A Chimeric Antigen Receptor (CARs) Based Upon a Killer Immunoglobulin-Like Receptor (KIR) Triggers Robust Cytotoxic Activity in Solid Tumors" Molecular Therapy (2014) vol. 22, No. 1, Suppl. 1, pp. S57.

Wang et al. "Generation of Potent T-cell Immunotherapy for Cancer Using DAP12-Based, Multichain, Chimeric Immunoreceptors" Cancer Immunology Research (2015) vol. 3, pp. 815-826.

Willemsen et al., "Genetic Engineering of T Cell Specificity for Immunotherapy of Cancer" Human Immunology (2003) vol. 64 pp. 56-68.

Wu et al. "Remote control of therapeutic T cells through a small molecule-gated chimeric receptor" Science (2015) vol. 350, Issue 6258 pp. aab4077-1-aab4077-10.

(56) References Cited

OTHER PUBLICATIONS

Zhang et al. "An NKp30-Based Chimeric Antigen Receptor Promotes T Cell Effector Functions and Antitumor Efficacy in vivo" Journal of Immunology (2012) vol. 189 No. 5.
Zhang et al. "Generation of Antitumor Responses by Genetic Modification of Primary Human T Cells with a Chimeric NKG2D Receptor" Cancer Research (2006) vol. 66, No. 11, pp. 5927-5933.
Zhang et al., "An NKp30-Based Chimeric Antigen Receptor Promotes T Cell Effector Functions and Antitumor Efficacy in Vivo" The Journal of Immunology (2012) vol. 189 No. 5 pp. 2290-2299.
Zhao et al., "A Herceptin-Based Chimeric Antigen Receptor with Modified Signaling Domains Leads to Enhanced Survival of Transduced T Lymphocytes and Antitumor Activity" The Journal of Immunology (2009) vol. 183 pp. 5563-5574.
Zufferey et al., "Multiply attenuated lentiviral vector achieves efficient gene delivery in vivo" Nature Biotechnology (1997) vol. 15 pp. 871-876.
Arnon et al., "Inhibition of the NKp30 activating receptor by pp65 of human cytomegalovirus" Nature Immunology (2005) vol. 6 No. 5 pp. 515-523.
Baba et al. "N-Linked Carboydrate on Human Leukocyte Antigen-C and Recognition by Natural Killer Cell Inhibitory Receptors" Humman Immunology (2000) vol. 61, pp. 1202-1218.
Baeksgaard & Sorensen, "Acute tumor lysis syndrome in solid tumors—a case report and review of the literature" Cancer Chemotherapy Pharmacology (2003) vol. 51 pp. 187-192.
Barrett et al., "Chimeric Antigen Receptor Therapy for Cancer" Annu Rev Med (2014) vol. 65 pp. 333-347.
Barrow et al., "You say ITAM and I say ITIM, let's call the whole thing off: the ambiguity of immunoreceptor signalling" European Journal of Immunology (2006) vol. 36 No. 7 pp. 1646-1653.
Biassoni et al., "Chapter 4 Natural Killer Cell Receptors" Multichain Immune Recognition Receptor Signaling (2008) vol. 640 pp. 35-52.
Bondanza et al. "Suicide gene therapy of graft-versus-host disease induced by central memory human T lymphocytes" Blood (2006) vol. 107 No. 5 pp. 1828-1836.
Borszcz et al. "KIR enrichment at the effector-target cell interface is more sensitive than signaling to the strength of ligand binding" European Journal of Immunology (2003) vol. 33, pp. 1084-1093.
Bottino et al., "NK Cell Activating Receptors and Tumor Recognition in Humans" CTMI (2006) No. 298 pp. 175-182.
Brentjens et al. "Genetically Targeted T Cells Eradicate Systemic Acute Lymphoblastic Leukemia Xenografts", Clinical Cancer Research(2007) vol. 13, No. 18, pp. 5426-5435.
Brentjens et al. "Treatment of Chronic Lymphocytic Leukemia With Genetically Targeted Autologous T Cells: Case Report of an Unforeseen Adverse Event in a Phase I Clinical Trial" The American Society of Gene Therapy (2010) vol. 18 No. 4 pp. 666-668.
Brentjens et al., "A Phase 1 Trial for the Treatment of chemo-Refractory Chronic Lymphocytic Leukemia with CD19-Targeted Autologous T Cells" Molecular Therapy (2008) vol. 16 Suppl 1 p. S15.
Brentjens et al., "CD19-Targeted T Cells Rapidly Induce Molecular Remissions in Adults with Chemotherapy-Refractory Acute Lymphoblastic Leukemia," Sci. Transl. Med 5:177ra138 (2013).
Brentjens et al., "Eradication of systemic B-cell tumors by genetically targeted human T lymphocytes co-stimulated by CD80 and interleukin-15" Nature Medicine (2003) vol. 9 No. 3 pp. 279-286.
Brentjens et al., "Safety and persistence of adoptively transferred autologous CD19-targeted T cells in patients with relapsed or chemotherapy refractory B-cell leukemias" Blood (2011) vol. 118 No. 18 pp. 4817-4828.
Brocker and Karjalainen, "Signals through T Cell Receptor-Chain alone Are Insufficient to Prime Resting T Lymphocytes" J. Exp Med. (1995) vol. 181 pp. 1653-1659.
Brocker, "Chimeric Fv-zeta or Fv-epsilon receptors are not sufficient to induce activation or cytokine production in peripheral T cells" Blood (2000) vol. 96 No. 5.

Brooks et al. "Growth Hormone receptor; mechanism of action" The International Journal of Biochemistry & Cell Biology (2008) vol. 40, pp. 1984-1989.
Bryceson & Long, "Line of attack: NK cell specificity and integration of signals" Current Opinion Immunology (2008) vol. 20 No. 3 pp. 344-352.
Call & Wucherpfennig, "The T Cell Receptor: Critical Role of the Membrane Environment in Receptor Assembly and Function" Annu. Rev. Immunol. (2005) vol. 23 pp. 101-125.
Campbell et al., "Natural killer cell biology: an update and future directions" Journal of Allergy and Clinical Immunology (2013) vol. 132 No. 3 pp. 536-544.
Carpenito et al. "Control of large, established tumor xenografts with genetically retargeted human T cells containing CD28 and CD137 domains", Proc Natl Acad Sci USA (2009) vol. 106 pp. 3360-3365.
Choudhuri et al., "T-cell receptor triggering is critically dependent on the dimensions of its peptide-MHC ligand" Nature (2005) vol. 436 pp. 578-582.
Christensen et al. "Recruitment of SHP-1 Protein Tyrosine Phosphatase and Signalling by a Chimeric T-Cell Receptor-Killer Inhibitory Receptor" Scand. J. Immunol (2000) vol. 51, pp. 557-564.
Clackson "Controlling Protein—Protein Interactions Using Chemical Inducers and Disrupters of Dimerization" Chemical Biology (2007) Eds Schreiber et al., Chapter 4.2, pp. 227-249.
Daeron et al., "The Same Tyrosine-Based Inhibition Motif, in the Intra-cytoplasmic Domain of FcyRIIB, Regulates Negatively BCR-, TcR-, and FcR-Dependent Cell Activation" Immunity (1995) vol. 3 pp. 635-646.
Davila et al. "B Cell Aplasia In a Patient with Relapsed B Cell Acute Lymphoblastic Leukemia Following Re-Induction and Consolidation with Autologous T Cells Genetically Targeted to the CD 19 Antigen" 53rd ASH Annual Meeting and Exposition (2010) Oral and Poster Abstract.
Dohner et al., "p53 Gene Deletion Predicts for Poor Survival and Non-Response to Therapy With Purine Analogs in Chronic B-Cell Leukemias" Blood (1995) vol. 85 No. 6 pp. 1580-1589.
Dropulic and June, "Gene-Based Immunotherapy for Human Immunodeficiency Virus Infection and Acquired mmunodeficiency Syndrome" Human Gene Therapy (2006) vol. 17 pp. 577-588.
Dull et al., "A Third-Generation Lentivirus Vector with a Conditional Packaging System" Journal of Virology (1998) vol. 72 No. 11 pp. 8463-8471.
Enxiu et al., "A Chimeric Antigen Receptor (CARs) Based Upon a Killer Immunoglobulin-Like Receptor (KIR) Triggers Robust Cytotoxic Activity in Solid Tumors" Molecular Therapy (2014) vol. 22 No. Supplm. 1.
Eshhar et al., "Specific activation and targeting of cytotoxic lymphocytes through chimeric single chains consisting of antibody-binding domains and the gamma or zeta subunits of the immuno-globulin and T-cell receptors," PNAS USA 90: 720-724 (1993).
Extended European Search Report for EP Application No. 15764851.0 dated Oct. 23, 2017.
Extended European Search Report for European Application No. 14872734 dated Oct. 25, 2017.
Falk et al., "Non-MHC-Restricted CD4+ T Lymphocytes are Regulated by HLA-Cw 7-mediated Inhibition" Human Immunology (2000) vol. 61 pp. 1219-1232.
Fegan et al. "Chemically Controlled Protein Assembly: Techniques and Applications", Chem Rev (2010) vol. 110, pp. 3315-3336.
Feng et al., "The assembly of diverse immune receptors is focused on polar membrane-embedded interaction site." PLoS Biol. (2006) vol. 4 No. 5 e142.
Finney et al., "Activation of resting human primary T cells with chimeric receptors: costimulation from CD28, inducible costimulator, CD 134, and CD 137 (4-1BB) in series with signals from the TCR zeta chain," J. Immunol. 172: 104-113 (2004).
Finney et al., "Chimeric receptors providing both primary and costimulatory signaling in T cells from a single gene product," J. Immunol 161: 2791-2797 (1998).
Frey, N. "Genetically Engineered Lymphocyte Therapy in Treating Patients With B-Cell Leukemia or Lymphoma That s Resistant or Refractory to Chemotherapy" (2015) Clinical Trial NCT01029366.

(56) References Cited

OTHER PUBLICATIONS

Friedmann-Morvinski et al., "Redirected primary T cells harboring a chimeric receptor require costimulation for their antigen-specific activation," Blood 105:3087-3093 (2005).
Garfall, et al. "Imunotherapy with chimeric antigen receptors for multiple myeloma." Discovery Medicine. 17 (91) (pp. 37-46), Jan. 2014.
Geiger & Jyothi, "Development and Application of Receptor-Modified T Lymphocytes for Adoptive Immunotherapy" Transfusion Medicine Reviews (2001) vol. 15 No. 1 pp. 21-34.
Geiger et al., "Integrated src kinase and costimulatory activity enhances signal transduction through single-chain chimeric receptors in T lymphocytes," Blood 98(8): 2364-2371 (2001).
GenBank Accession No. NP_000725.1 accessed on Jan. 7, 2016 from http://www.ncbi.nlm.nih.gov/protein/NP_000725.
GenBank Accession No. NP_932170.1 accessed Jan. 7, 2016 from http://www.ncbi.nlm.nih.gov/protein/NP_932170.
Gilham et al., "Primary Polyclonal Human T Lymphocytes Targeted to Carcino-Embryonic Antigens and Neural Cell Adhesion Molecule Tumor Antigens by CD3-Based Chimeric Immune Receptors" Journal of Immunotherapy (2002) vol. 25 No. 2 pp. 139-151.
Gong et al. "Cancer Patient T Cells Genetically Targeted to Prostate-Specific Membrane Antigen Specifically Lyse Prostate Cancer Cells and Release Cytokines in Response to Prostate-Specific Membrane Antigen" Neoplasia (1999) vol. 1 No. 2 pp. 123-127.
Gribben et al., "Stem cell transplantation for indolent lymphoma and chronic lymphocytic leukemia" Biol Blood Marrow Transplant (2011) vol. 17 (1 Suppl): S63-S70.
Griffin, "Development and applications of surface-linked single chain antibodies against T-cell antigens" Journal of Immunological Methods (2001) vol. 248 pp. 77-90.
Extended European Search Report for European Application No. 19187938.6 dated Feb. 18, 2020.
Varla-Leftherioti et al. "14th International HLA and Immunogenetics Workshop: Report from the reproductive immunology component" Tissue Antigens, The Authors Journal Compilation (2007) vol. 69, Supp 1, pp. 297-303.
Gross et al., "Endowing T cells with antibody specificity using chimeric T cell receptors," The FASEB Journal 6: 3370-3378 (1992).
Grupp et al. "Chimeric Antigen Receptor-Modified T Cells for Acute Lymphoid Leukemia", New England Journal of Medicine (2013) vol. 368 No. 16 pp. 1509-1518.
Hallek et al., "Guidelines for the diagnosis and treatment of chronic lymphocytic leukemia: a report from the International Workshop on Chronic Lymphocytic Leukemia updating the National Cancer Institute Working Group 1996 guidelines" Blood (2008) vol. 111 No. 12 pp. 5446-5456.
Haso et al. "Anti-CD22-chimeric antigen receptors targeting B-cell precursor acute lymphoblastic leukemia" Blood (2013) vol. 121, No. 7, pp. 1165-1174.
Hassan et al., "Antitumor activity of SS(dsFv)PE38 and SS1(dsFv)PE38, recombinant antimesothelin immunotoxins against human gynecologic cancers grown in organotypic culture in vitro" Clinical Cancer Research (2002) vol. 8 No. 11 pp. 3520-3526.
Hekele et al., "Growth Retardation of Tumors By Adoptive Transfer of Cytotoxic T Lymphocytes Reprogrammed By CD44V6-SPECIFIC SCFV:~-Chimera" Int J. Cancer (1996) vol. 68 pp. 232-238.
Ho et al., "Adoptive immunotherapy: Engineering T cell responses as biological weapons for tumor mass destruction" Cancer Cell (2003) vol. 3 pp. 431-437.
Hollyman et al. "Manufacturing validation of biologically functional T cells targeted to CD 19 antigen for autologous adoptive cell therapy" J Immunother (2009) vol. 32 No. 2 pp. 169-180.
Hornback et al., "The Recombinant T Cell Receptor Strategy: Insights into Structure and Function of Recombinant Immunoreceptors on the Way Towards an Optimal Receptor Design for Cellular Immunotherapy," Current Gene Therapy 2:211-226 (2002).
Imai et al., "Chimeric receptors with 4-1BB signaling capacity provoke potent cytotoxicity against acute lymphoblastic eukemia," Leukemia 18: 676-684 (2004).
Imai et al., "Genetic modification of primary natural killer cells overcomes inhibitory signals and induces specific killing of leukemic cells" Blood (2005) vol. 106 No. 1 pp. 376-383.
International Preliminary Report on Patentability and Written Opinion of the International Searching Authority for PCT/US2014/029983 dated Sep. 15, 2015.
International Preliminary Report on Patentability for International Application No. PCT/CN2014/094383 dated Jun. 21, 2016.
International Preliminary Report on Patentability for International Application No. PCT/US2015/020533 dated Sep. 20, 2016.
International Preliminary Report on Patentability for International Application No. PCT/US2015/050715 dated Mar. 21, 2017.
International Search Report and Written Opinion for International Application No. PCT/CN2014/082615 dated Oct. 27, 2014.
International Search Report and Written Opinion for International Application No. PCT/CN2014/086694 dated Feb. 3, 2015.
International Search Report and Written Opinion for International Application No. PCT/CN2014/094383, dated Mar. 20, 2015.
International Search Report and Written Opinion for International Application No. PCT/US2015/050715 dated Feb. 1, 2016.
International Search Report and Written Opinion for International Application No. PCT/US2015/20533 dated Jun. 26, 2015.
International Search Report and Written Opinion of the International Searching Authority for PCT/CN2014/090578 dated Jun. 17, 2015.
International Search Report for PCT/US2014/029983 dated Oct. 28, 2014.
International Search Report from PCT/US2011/064191 dated Jan. 5, 2012.
Irving et al., "The cytoplasmic domain of the T cell receptor zeta chain is sufficient to couple to receptor-associated signal transduction pathways," Cell 64: 891-901 (1991).
James et al. "Biophysical mechanism of T-cell receptor triggering in a reconstituted system", Nature (2012) vol. 487 pp. 64-69.
Jena, Bipulendu et al. "Redirecting T-cell specificity by introducing a tumor-specific chimeric antigen receptor, Blood, May , 2010", vol. 116, No. 7, pp. 1035-1044.
Jensen et al., "Anti-Transgene Rejection Responses Contribute to Attenuated Persistence of Adoptively Transferred CD20/CD19-Specific Chimeric Antigen Receptor Re-directed T Cells in Humans" Biol Blood Marrow Transplant (2010) vol. 16 No. 9 pp. 1245-1256.
Johnson et al., "Gene therapy with human and mouse T-cell receptors mediates cancer regression and targets normal tissues expressing cognate antigen" Blood (2009) vol. 114 No. 3 pp. 535-545.
June et al., "Engineering lymphocyte subsets: tools, trials and tribulations" Nat Rev Immunol (2009) vol. 9 No. 10 pp. 704-716.
Kalos et al. "T Cells with Chimeric Antigen Receptors Have Potent Antitumor Effects and Can Establish Memory in Patients with Advanced Leukemia", Science Translation Medicine (2011) vol. 3 No. 95 95ra73.
Karre et al., "Selective rejection of H-2-deficient lymphoma variants suggests alternative immune defence strategy." Nature (1986) vol. 319 No. 6055 pp. 675-678.
Katz et al. "Recognition of HLA-Cw4 but Not HLA-Cw6 by the NK Cell Receptor Killer Cell Ig-Like Receptor Two-Domain ShortTail No. 4" The Journal of Immunology (2001) vol. 166, pp. 7260-7267.
Kershaw et al., "A Phase I Study on Adoptive Immunotherapy Using Gene-Modified T Cells for Ovarian Cancer," Clin. Cancer Res. 12(20 Pt 1): 6106-6115 (2006).
Kim et al., "Human 4-1BB regulates CD28 co-stimulation to promote Th1 cell responses" Eur. J. Immunol. (1998) vol. 28 pp. 881-890.
Klingemann, "Are natural killer cells superior CAR drivers?" Oncoimmunology (2014) vol. 3 No. 1.
Kloss et al., "Combinatorial antigen recognition with balanced signaling promotes selective tumor eradication by angineered T cells" Nature Biotechnology (2013) vol. 31 No. 1 pp. 71-75.
Kochenderfer et al., "A Phase I Clinical Trial of Treatment of B-Cell Malignancies with Autologous Anti-Cd19-CAR-Transduced T Cells" Blood (2010) vol. 116 No. 21 pp. 1179-1180 & 52nd Annual

(56) References Cited

OTHER PUBLICATIONS

Meeting of the American-Society-Of-Hematology (Ash); Orlando, FL, USA; Dec. 4-7, 2010 abstract.
Kochenderfer et al. "Construction and Pre-clinical Evaluation of an Anti-CD19 Chimeric Antigen Receptor", J Immunother (2009) vol. 32, No. 7, pp. 689-702.
Kochenderfer et al., "Eradication of B-lineage cells and regression of lymphoma in a patient treated with autologous T cells genetically-engineered to recognize CD19," Blood 116:4099-4102 (2010).
Kohn et al. "CARs on Track in the Clinic", Molecular Therapy (2011) vol. 19, No. 3, pp. 432-438.
Kraus et al., "Antigen-dependent CD28 Signaling Selectively Enhances Survival and Proliferation in Genetically Modified Activated Human Primary T Lymphocytes" J. Exp. Med. (1998) vol. 188 Np 4 pp. 619-626.
Kruse et al., "Natural cytotoxicity receptors and their ligands" Immunology and Cell Biology (2013) vol. 92 No. 3 pp. 221-229.
Kwon et al., "cDNA sequences of two inducible T-cell genes". Proc. Natl. Acad. Sci. U.S.A. 86(6): 1963-1967 (1989).
Lamanna et al., "Pentostatin, Cyclophosphamide, and Rutuximab Is an Active, Well-Tolerated Regimen for Patients With Previously Treated Chronic Lymphocytic Leukemia" Journal of Clinical Oncology (2008) vol. 24 No. 10 pp. 1575-1581.
Lamers et al., "Treatment of Metastatic Renal Cell Carcinoma With Autologous T-Lymphocytes Genetically Retargeted Against Carbonic Anhydrase IX: First Clinical Experience," J. Clin. Oncol. 24(13): e20-e22 (2006).
Lanier et al., "Immunoreceptor DAP12 bearing a tyrosine-based activation motif is involved in activating NK cells" Nature (1998) vol. 391 pp. 703-707.
Lanier, "Up on the tightrope: natural killer cell activation and inhibition." Nat Immunol (2008) vol. 9 No. 5 pp. 495-502.
Laport et al., "Adoptive transfer of costimulated T cells induces lymphocytosis in patients with relapsed/refractory non-Hodgkin lymphoma following CD34 +-selected hematopoietic cell transplantation" Blood (2003) vol. 102 No. 6 pp. 2004-2013.
Lee et al., "In vivo Inhibition of Human CD19-Targeted Effector T Cells by Natural T Regulatory Cells in a Xenotransplant Murine Model of B Cell Malignancy" Cancer Research (2011) vol. 71 No. 8 pp. 2871-2881.
Lee et al., "The Future is Now: Chimeric Antigen Receptors as New Targeted Therapies for Childhood Cancer," Clin. Cancer Res. 18:2780-2790 (2012).
Letourneur et al., "T-cell and basophil activation through the cytoplasmic tail of T-cell-receptor zeta family proteins," Proc. Natl. Acad. Sci. U.S.A 88: 8905-8909 (1991).
Levine et al., "Gene transfer in humans using a conditionally replicating lentiviral vector" PNAS (2006) vol. 103 No. 46 pp. 17372-17377.
Lo et al., "Anti-GD3 chimeric sFv-CD28/T-cell receptor zeta designer T cells for treatment of metastatic melanoma and other neuroectodermal tumors." Clin Cancer Res (2010) vol. 16 No. 10 pp. 2769-2780.
Loskog et al. "Addition of the CD28 signaling domain to chimeric T-cell receptors enhances chimeric T-cell resistance to T regulatory cells" Leukemia (2006) vol. 20 No. 10 pp. 1819-1828.
Ma et al., "Recognition of mesothelin by the therapeutic antibody MORAb-009: structural and mechanistic insights." J Biol Chem (2012) vol. 287 No. 40 pp. 33123-33131.
Macallan et al., "Measurement and modeling of human T cell kinetics" European Journal of Immunology (2003) vol. 33 pp. 2316-2326.
Maher et al., "Human T lymphocyte cytotoxicity and proliferation directed by a single chimeric TCRzeta/CD28 receptor," Nat. Biotechnol. 20: 70-75 (2002).
McGuinness et al., "Anti-tumor activity of human T cells expressing the CC49-zeta chimeric immune receptor," Hum. Gene Ther. 10: 165-173 (1999).

Milone et al., "Chimeric Receptors Containing CD137 Signal Transduction Domains Mediate Enhanced Survival of T Cells and Increased Antileukemic Efficacy In Vivo" Molecular Therapy (2009) vol. 17 No. 8 pp. 1453-1464.
Molina, "A Decade of Rituximab: Improving Survival Outcomes in Non-Hodgkin's Lymphoma" Annu. Rev. Med. (2008) vol. 59 pp. 237-250.
Morello et al. "Mesothelin-Targeted CARs: Driving T Cells to Solid Tumors" Cancer Discovery (2016) doi:10.1158/2159-8290.CD-15-0583; pp. OF1-OF15.
Moretta et al., "Major histocompatibility complex class I-specific receptors on human natural killer and T lymphocytes" Immunological Reviews (1997) vol. 155 pp. 105-117.
Morgan et al., "Case Report of a Serious Adverse Event Following the Administration of T Cells Transduced With a Chimeric Anitgen Receptor Recognizing ErbB2," Mol. Ther. 18(4): 843-851 (2010).
Moritz and Groner, "A spacer region between the single chain antibody- and the CD3 zeta-chain domain of chimeric T cell receptor components is required for efficient ligand binding and signaling activity," Gene Therapy 2(8): 539-546 (1995).
Moritz et al., "Cytotoxic T lymphocytes with a grafted recognition specificity for ERBB2-expressing tumor cells" Proc. Natl. Acad. Sci (1994) vol. 91 pp. 4318-4322.
Nakagawa et al. "Development of next-generation adoptive immunotherapy using cytotoxic T-lymphocyte (CTL) axpressing chimeric antigen-receptor (CAR)" Drug Delivery System (2013) 28-1, pp. 35-44.
Naldini et al., "In Vivo Gene Delivery and Stable Transduction of Nondividing Cells by a Lentiviral Vector" Science (1996) vol. 272 pp. 263-267.
NCBI accession HM_852952 accessed Sep. 29, 2015 from http://www.ncbi.nlm.nih.gov/nuccore/hm852952.
Nicholson et al., "Construction and Characterisation of a Function CD19 Specific Single Chain Fv Fragment for Immunotherapy of B Lineage Leukaemia and Lymphoma," Molecular Immunology 34(I6-I7): 1157-1165 (1997).
Ohlen et al., "Prevention of Allogeneic Bone Marrow Graft Rejection by H-2 Transgene in Donor Mice" Science (1989) vol. 246 pp. 666-668.
Okazaki et al. "PD-1 immunoreceptor inhibits B cell receptor-mediated signaling by recruiting src homology 2-domain-containing tyrosine phosphatase 2 to phosphotyrosine" PNAS (2001) vol. 98, No. 24, pp. 13866-13871.
Olcese et al., "Human killer cell activatory receptors for MHC class I molecules are included in a multimeric complex axpressed by natural kill cells" J Immunol (1997) vol. 158 pp. 5083-5086.
Park and Brentjens "Adoptive Immunotherapy for B-cell Malignancies with Autologous Chimeric Antigen Receptor Modified Tumor Targeted T Cells" Discovery Medicine (2010) vol. 9 No. 47 pp. 277-288.
Park et al. "Adoptive Transfer of Chimeric Antigen Receptor Re-directed Cytolytic T Lymphocyte Clones in Patients with Neuroblastoma", Molecular Therapy (2007) vol. 15 No. 4 pp. 825-833.
Pasquale, "Eph receptors and ephrins in cancer: bidirectional signalling and beyond." Nat Rev Cancer (2010) vol. 10 No. 3 pp. 165-180.
Patel et al., "Impact of chimeric immune receptor extracellular protein domains on T cell function" Gene Therapy (1999) vol. 6 pp. 412-419.
Porter et al. "Chimeric Antigen Receptor-Modified T Cells in Chronic Lymphoid Leukemia", The New England Journal of Medicine (2011) vol. 365 No. 8 pp. 725-733.
Porter et al., "A phase 1 trial of donor lumphocyte infusions expanded and activated ex vivo via CD3/CD28 costimulation" Blood (2006) vol. 107 No. 4 pp. 1325-1331.
Porter et al., "Chimeric Antigen Receptor Therapy for B-cell Malignancies" Journal of Cancer (2011) vol. 2 pp. 331-332.
Pule et al., "Virus-specific T cells engineered to coexpress tumor-specific receptors: persistence and antitumor activity in individuals with neuroblastoma" Nat. Med. (2008) vol. 14 No. 11 pp. 1264-1270.

(56) References Cited

OTHER PUBLICATIONS

Rapoport et al., "Restoration of immunity in lymphopenic individuals with cancer by vaccination and adoptive T-cell transfer" Nature Medicine (2005) vol. 11 No. 11 pp. 1230-1237.
Ravetch & Bolland, "IcG Fc Receptors" Annu. Rev. Immunol. (2001) vol. 19 pp. 275-290.
Remtoula et al., "Selective expression of inhibitory or activating killer cell Ig-like receptors in circulating CD4 T lymphocytes" Journal of Immunology (2008) vol. 180 No. 5 pp. 2767-2771.
Roederer, "T-cell dynamics of immunodeficiency" Nature Medicine (1995) vol. 1 No. 7 pp. 621-622.
Romeo et al., "Cellular immunity to HIV activated by CD4 fused to T cell or Fc receptor polypeptides," Cell 64:1037-1046 (1991).
Rosen et al., "A Structural basis for the association of DAP12 with mouse, but not human, NKG2D." J Immunol (2004) vol. 173 No. 4 pp. 2470-2478.
Sabbagh et al., "TNF family ligands define niches for T cell memory" Trends in Immunology (2007) vol. 28 No. 8 pp. 333-339.
Sadelain et al. "The promise and potential pitfalls of chimeric antigen receptors." Current Opinion Immunology (2009) vol. 21 No. 2 pp. 215-223.
Sadelain et al., "Targeting Tumours with Genetically Enhanced T Lymphocytes," Nature Reviews: Cancer 3: 35-45 (2003).
Sadelain et al., "The Basic Principles of Chimeric Antigen Receptor Design" Cacner Discovery (2013) vol. 3 No. 4 pp. 388-398.
Savoldo et al., "CD28 costimulation improves expansion and persistence of chimeric antigen receptor-modified T cells in lymphoma patients" The Journal of Clinical Investigation (2011) vol. 121 No. 5 pp. 1822-1826.
Sebestyen et al., "Human TCR That Incorporate CD3 Induce Highly Preferred Pairing between TCR and Chains following Gene Transfer" Journal of Immunology (2008) vol. 180 pp. 7736-7746.
Shirasu et al., "Functional Design of Chimeric T-Cell Antigen Receptors for Adoptive Immunotherapy of Cancer Architecture and Outcomes," AntiCancer Res. 32: 2377-2384 (2012).
Shook et al., "Natural killer cell engineering for cellular therapy of cancer" Tissue Antigens (2011) vol. 78 No. 6 pp. 109-115.
Singh et al., "Claudin Family of Proteins and Cancer: An Overview" Journal of Oncology (2010) Article ID 541957.
Snyder et al., "Stimulatory killer Ig-like receptors modulate T cell activation through DAP12-dependent and DAP12-independent mechanisms." J Immunol (2004) vol. 173 No. 6 pp. 3725-3731.
Sorror et al., "Outcomes after allogeneic hematopoietic cell transplantation with nonmyeloablative or myeloablative conditioning regimens for treatment of lymphoma and chronic lymphocytic leukemia" Blood (2008) vol. 111 No. 1 pp. 446-452.
Stewart et al., "Strategies of Natural Killer Cell Recognition and Signaling" CTMI (2006) vol. 298 pp. 1-21.
Takase et al., "A new 12-kilodalton dimer associated with pre-TCR complex and clonotype-independent CD3 complex on immature thymocytes." J Immunol (1997) vol. 159 pp. 741-747.
Tal et al., "An NCR1-based chimeric receptor endows T-cells with multiple anti-tumor specificities" Oncotarget (2014) pp. 1-10.
Extended European Search Report for European Application No. 20191324.1 dated Mar. 30, 2021.

\* cited by examiner

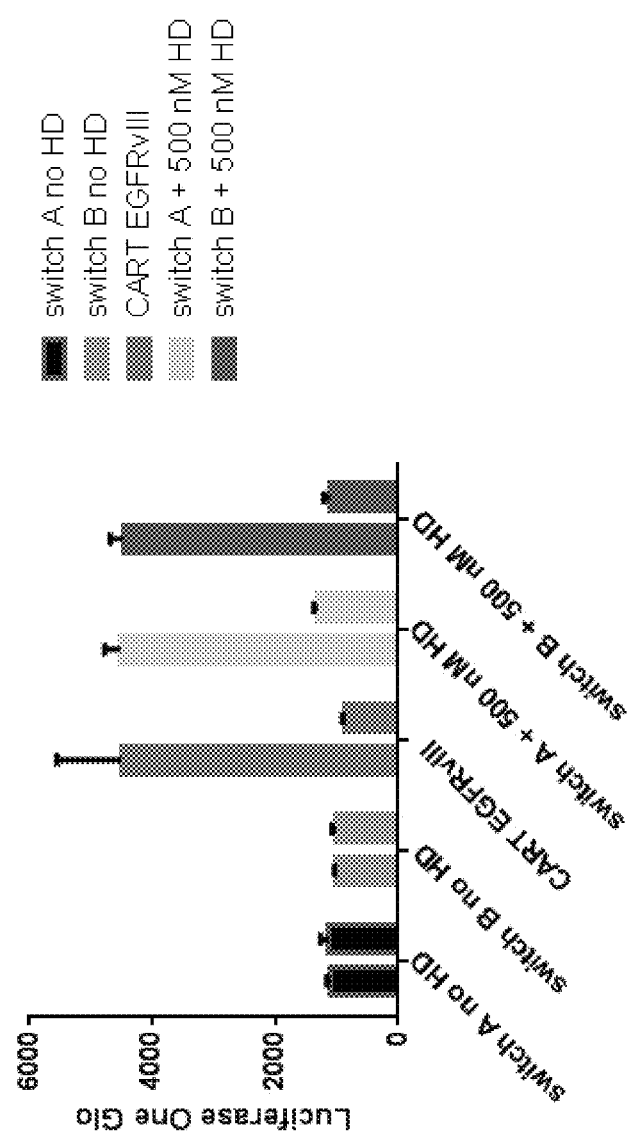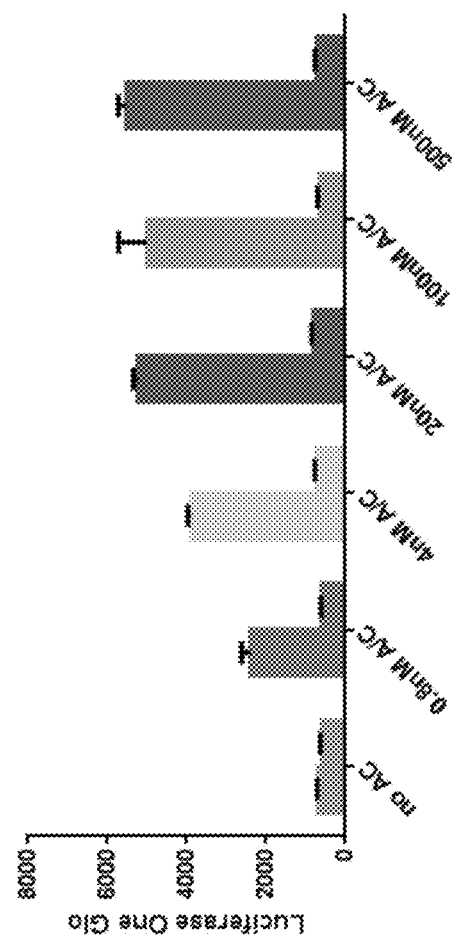
FIG. 12 A
FIG. 12 B

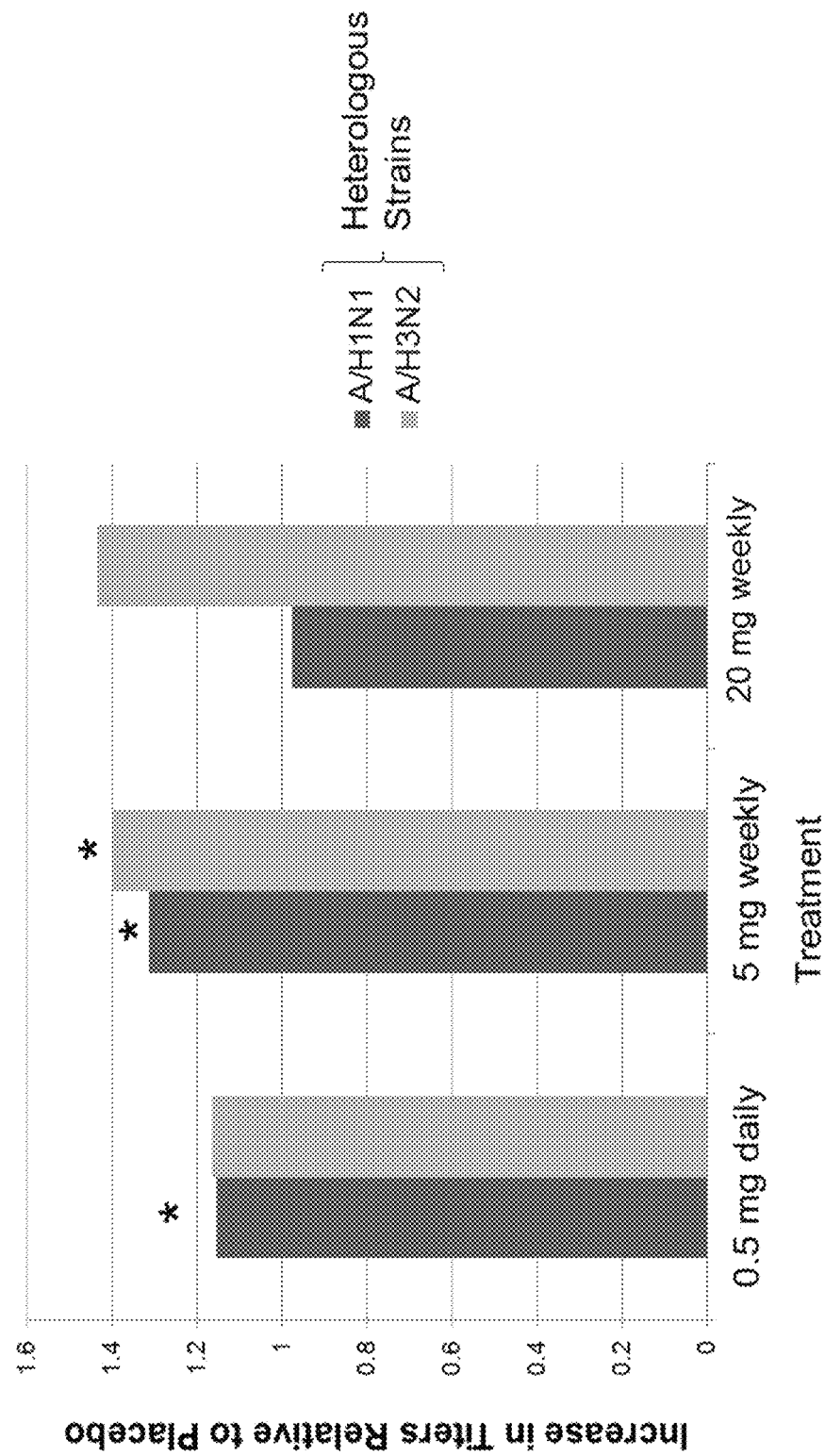

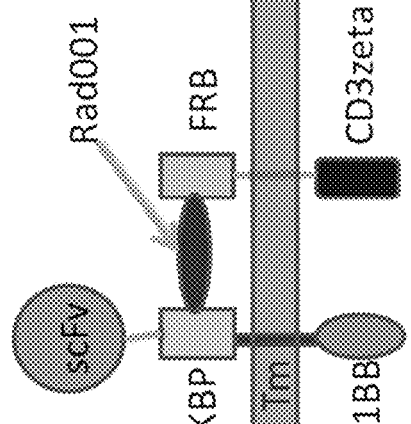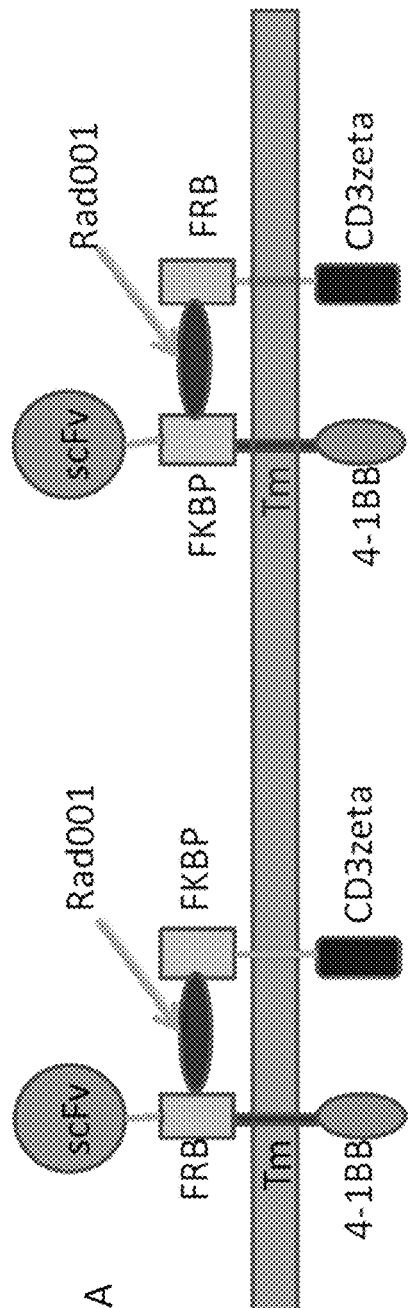
FIG. 42A
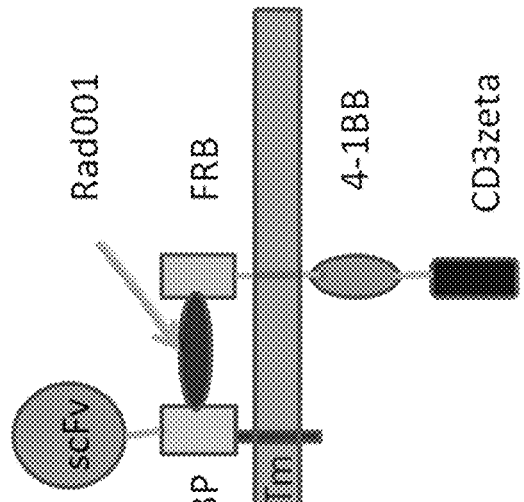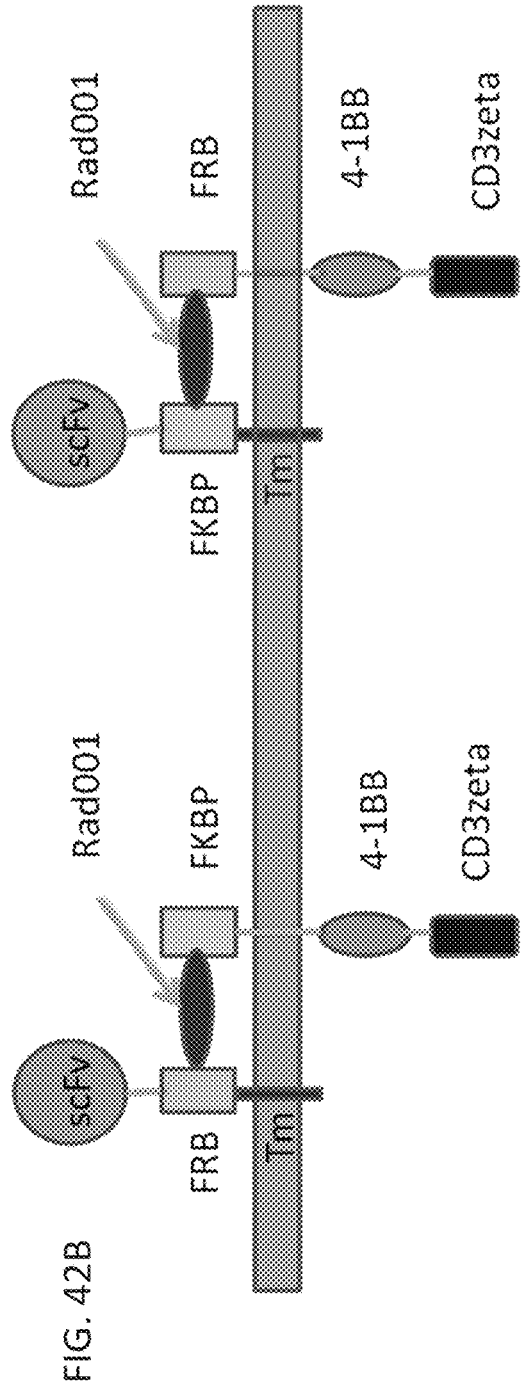
FIG. 42B

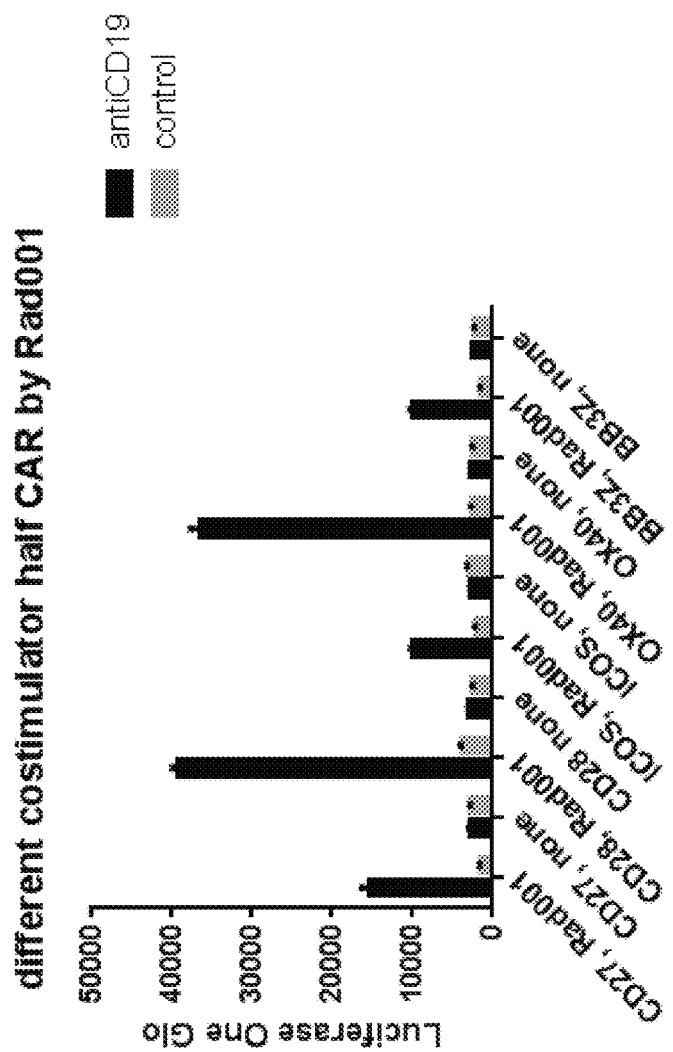
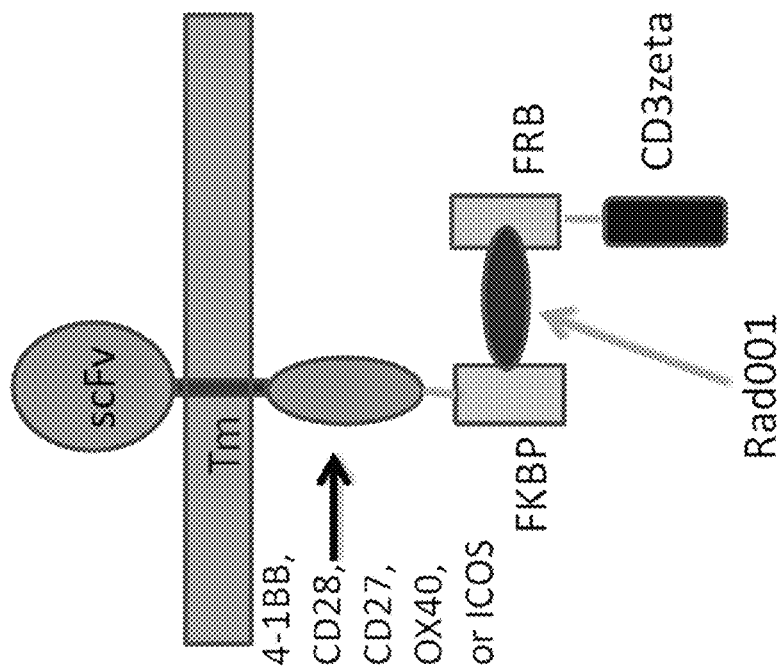
FIG. 44A
FIG. 44B

REGULATABLE CHIMERIC ANTIGEN RECEPTOR

This application is a continuation of U.S. application Ser. No. 15/105,074, filed Jun. 16, 2016, now U.S. Pat. No. 10,287,354, which is a U.S. national phase application and claims the benefit of priority under 35 U.S.C. § 371 of International Application No. PCT/CN2014/094383, filed Dec. 19, 2014, which claims priority to U.S. Ser. No. 61/919,588, filed Dec. 20, 2013, U.S. Ser. No. 61/953,818, filed Mar. 15, 2014, International Application No. PCT/CN2014/082615, filed Jul. 21, 2014, and International Application No. PCT/CN2014/090494, filed Nov. 6, 2014, and the entire contents of each of these applications are incorporated herein by reference.

SEQUENCE LISTING

The instant application contains a Sequence Listing which has been submitted electronically in ASCII format and is hereby incorporated by reference in its entirety. Said ASCII copy, created on Aug. 23, 2016, is named N2067-7003US-_SL.txt and is 516,908 bytes in size.

FIELD OF THE INVENTION

The invention relates generally to a Regulatable Chimeric Antigen Receptor (RCAR) and cells expressing RCARs, as well as methods of making and using the same, e.g., to target and inactivate or kill target cells, e.g., cancer cells.

BACKGROUND

Adoptive cell transfer (ACT) therapy with autologous T-cells, especially with T-cells transduced with Chimeric Antigen Receptors (CARs), has shown promise in pilot hematologic cancer trials.

SUMMARY

Embodiments of the invention address the optimization of safety and efficacy in the use of RCARX cells to provide an immune response. Embodiments of the invention are based, in part, on the discovery that a CAR molecule can be partitioned such that a "binding domain" and a "signaling domain" are each linked to two separate "switch domains." In such embodiments, activation of signaling through the CAR only occurs when the switch domains, and hence the binding domain and the signaling domain, are brought together by a dimerization molecule, i.e. to switch "on" signaling through the CAR. Embodiments of the invention include, inter alia, the use of a dimerization switch that turns "on" the activation of a signal to allow external, e.g., temporal, control over the immune effector response mediated by a cell containing a RCAR. As discussed in more detail below, in embodiments, the RCAR includes a dimerization switch that, upon the presence of a dimerization molecule, can couple an intracellular signaling domain to an extracellular recognition element, e.g., an antigen binding domain, an inhibitory counter ligand binding domain, or costimulatory ECD domain.

In a first aspect, the invention features, a regulatable chimeric antigen receptor (RCAR), e.g., an isolated RCAR, wherein the RCAR comprises:
a) an intracellular signaling member comprising:
an intracellular signaling domain, e.g., a primary intracellular signaling domain, and
a first switch domain;

b) an antigen binding member comprising:
an antigen binding domain,
a second switch domain; and
optionally, one or a plurality, of co-stimulatory signaling domains, and
c) optionally, a transmembrane domain. See, e.g., FIGS. 2 and 5.
(Unless otherwise indicated, when members or elements of an RCAR are described herein, the order can be as provided, but other orders are included as well. In otherwords, in an embodiment, the order is as set out in the text, but in other embodiments, the order can be different.)

In an embodiment, the transmembrane domain can be disposed on the intracellular signaling member or the antigen binding member. In an embodiment, a transmembrane domain can be disposed on the intracellular signaling member and a transmembrane domain or membrane anchor (membrane anchor and membrane anchoring domain are used interchangeably herein) can be disposed on the antigen binding member.

In an embodiment, the first and second switch domains can form an intracellular or an extracellular dimerization switch.

In an embodiment, the dimerization switch can be a homodimerization switch or a heterodimerization switch.

As is discussed herein, embodiments of an RCAR can include a member, e.g., an intracellular signaling member, that comprises one or more intracellular signaling domains, as, e.g., is described above. In embodiments, an antigen binding member, can comprise an intracellular signaling domain, e.g., a costimulatory signaling domain. Embodiments of such members, and intracellular signaling domains, are described in the section following immediately hereafter, sometimes referred to herein as the Intracellular Signaling domain Module.

In an embodiment, the intracellular signaling domain is a primary intracellular signaling domain, selected, e.g., from the list in Table 1.

In an embodiment, the primary intracellular signaling domain comprises a CD3zeta domain.

In an embodiment, the intracellular signaling domain is a costimulatory signaling domain, e.g., selected from the list in Table 2.

In an embodiment, the costimulatory signaling domain comprises a 4-1BB domain.

In an embodiment, the RCAR comprises a second intracellular signaling domain.

In an embodiment, the second intracellular signaling domain is a primary intracellular signaling domain, e.g., selected from the list in Table 1.

In an embodiment, the second intracellular signaling domain is a costimulatory signaling domain, e.g., selected from the list in Table 2.

In an embodiment, the first and second intracellular signaling domains comprise:
a 4-1BB domain and a CD3zeta domain; or
a CD28 domain and a 4-1BB domain.

In an embodiment, the RCAR comprises a third intracellular signaling domain.

In an embodiment, the third intracellular signaling domain is a primary intracellular signaling domain, e.g., selected from the list in Table 1.

In an embodiment, the third intracellular signaling domain is a costimulatory signaling domain, e.g., selected from the list in Table 2.

In an embodiment, one of the first, second and third intracellular signaling domain is a primary intracellular signaling domain, e.g., selected from the list in Table 1, and the other two are costimulatory signaling domains, e.g., selected from, Table 2.

In an embodiment, two of the first, second and third intracellular signaling domains are primary intracellular signaling domains, e.g., selected from the list in Table 1, and the other is a costimulatory signaling domain, e.g., selected from, Table 2.

In an embodiment each of the first, second and third intracellular signaling domains is a primary intracellular signaling domain, e.g., selected from the list in Table 1, In an embodiment, each of the first, second and third intracellular signaling domains is a costimulatory signaling domain, e.g., selected from the list in Table 2.

In an embodiment, the first, second, and third intracellular signaling domains comprise: a CD28 domain; a 4-1BB domain, and a CD3zeta domain.

In an embodiment, the RCAR comprises a fourth intracellular signaling domain.

In an embodiment, the fourth intracellular signaling domain is a primary intracellular signaling domain, e.g., selected from the list in Table 1.

In an embodiment, the fourth intracellular signaling domain is a costimulatory signaling domain, e.g., selected from the list in Table 2.

In an embodiment, one of the first, second, third and fourth intracellular signaling domain is a primary intracellular signaling domain, e.g., selected from the list in Table 1 and the other three are costimulatory signaling domains, e.g., selected from the list in Table 2.

In an embodiment, two of the first, second, third, and fourth intracellular signaling domains are primary intracellular signaling domains, e.g., selected from the list in Table 1, and the other two are costimulatory signaling domain, e.g., selected from the list in Table 2.

In an embodiment, three of the first, second, third, and fourth intracellular signaling domains a In an embodiment re primary intracellular signaling domains, e.g., selected from the list in Table 1, and the other is a costimulatory signaling domain, e.g., selected from the list in Table 2.

In an embodiment, each of the first, second, third, and fourth intracellular signaling domains is a primary intracellular signaling domain, e.g., selected from the list in Table 1.

In an embodiment, each of the first, second, third, and fourth intracellular signaling domains is a costimulatory signaling domain, e.g., selected from the list in Table 2.

In an embodiment, the order of switch domain and the intracellular signaling domain (isd) or domains is as follows, beginning with the amino terminus:
switch/isd;
switch/isd1/isd2;
isd1/switch/isd2;
isd1/isd2/switch;
switch/isd1/isd2/isd3;
isd1/isd2/isd3/switch;
isd1/switch/isd2/isd3; and
isd1/isd2/switch/isd3.

In an embodiment, the order of switch domain and the intracellular signaling domain (isd) or domains is as follows, beginning with the carboxy terminus:
switch/isd;
switch/isd1/isd2;
isd1/switch/isd2;
isd1/isd2/switch;
switch/isd1/isd2/isd3;
isd1/isd2/isd3/switch;
isd1/switch/isd2/isd3; and
isd1/isd2/switch/isd3.

In an embodiment, the invention features, a RCAR, e.g., an isolated RCAR, wherein the RCAR comprises:
 a) an antigen binding member comprising:
 an antigen binding domain,
 a first transmembrane domain, and
 a first switch domain; and
 b) an intracellular signaling member comprising:
 a second transmembrane domain or membrane anchor,
 a second switch domain,
 and an intracellular signaling domain, e.g., a primary intracellular signaling domain.
See, e.g., FIG. 54.

In an embodiment, the antigen binding member optionally comprises one or more co-stimulatory signaling domains described herein. In an embodiment, the intracellular signaling domain further comprises one or more co-stimulatory signaling domains described herein.

In an embodiment, the first and second switch domains can form an intracellular or an extracellular dimerization switch.

In an embodiment, the dimerization switch can be a homodimerization switch or a heterodimerization switch.

In an embodiment, the first and/or second transmembrane domain comprises the transmembrane region(s) of e.g., the alpha, beta or zeta chain of the T-cell receptor, CD28, CD3 epsilon, CD45, CD4, CD5, CD8 (e.g., CD8 alpha, CD8 beta), CD9, CD16, CD22, CD33, CD37, CD64, CD80, CD86, CD134, CD137, CD154, KIRDS2, OX40, CD2, CD27, LFA-1 (CD11a, CD18), ICOS (CD278), 4-1BB (CD137), GITR, CD40, BAFFR, HVEM (LIGHTR), SLAMF7, NKp80 (KLRF1), CD160, CD19, IL2R beta, IL2R gamma, IL7R α, ITGA1, VLA1, CD49a, ITGA4, IA4, CD49D, ITGA6, VLA-6, CD49f, ITGAD, CD11d, ITGAE, CD103, ITGAL, CD11a, LFA-1, ITGAM, CD11b, ITGAX, CD11c, ITGB1, CD29, ITGB2, CD18, LFA-1, ITGB7, TNFR2, DNAM1 (CD226), SLAMF4 (CD244, 2B4), CD84, CD96 (Tactile), CEACAM1, CRTAM, Ly9 (CD229), CD160 (BY55), PSGL1, CD100 (SEMA4D), SLAMF6 (NTB-A, Ly108), SLAM (SLAMF1, CD150, IPO-3), BLAME (SLAMF8), SELPLG (CD162), LTBR, PAG/Cbp. The first transmembrane domain disposed on the antigen binding member and the second transmembrane domain disposed on the intracellular signaling member can be the same transmembrane domain, e.g., have the same sequence, or can be different transmembrane domains, e.g., have different sequences.

As is discussed herein, the RCAR can include any of a variety of dimerization switches, e.g., a dimerization switch described in the section following immediately hereafter, sometimes referred to herein as the Dimerization Switch Module.

In an embodiment, the switch domains are components of a heterodimerization switch.

In an embodiment, the switch domains are components of a homodimerization switch.

In an embodiment, the dimerization switch is intracellular.

In an embodiment, the dimerization switch is extracellular.

In an embodiment, the transmembrane domain disposed on the antigen binding member and the dimerization switch, e.g., a heterodimerization switch or homodimerization switch, is intracellular.

In an embodiment, where the transmembrane domain disposed on the intracellular signaling member and the dimerization switch, e.g., heterodimerization or homodimerization switch, is extracellular.

In an embodiment, the dimerization switch comprises a FKBP-FRB based switch.

In an embodiment, the dimerization switch comprises: a switch domain comprising a rapamycin analog binding sequence having at least 80, 85, 90, 95, 98, or 99% identity with FKBP, and a switch domain comprising a rapamycin analog binding sequence binding sequence having at least 80, 85, 90, 95, 98, or 99% identity with FRB.

In an embodiment the dimerization switch comprises an FKBP-based switch domain and an FRB-based switch domain described herein.

In an embodiment, the dimerization switch comprises: a switch domain comprising a rapamycin analog binding sequence that differs by no more than 10, 9, 8, 7, 6, 5, 4, 3, 2, or 1 amino acid residues from the corresponding sequence of FKBP, and a switch domain comprising a rapamycin analog binding sequence that differs by no more than 10, 9, 8, 7, 6, 5, 4, 3, 2, or 1 amino acid residues from the corresponding sequence of FRB.

In an embodiment, the dimerization switch comprises an FRB binding fragment or analog of FKBP and an FKBP binding fragment or analog of FRB, and the FKBP binding fragment or analog of FRB comprises one or more mutations which enhances the formation of a complex between an FKBP switch domain, an FRB switch domain, and the dimerization molecule, or a mutation described in the section herein entitled MODIFIED FKBP/FRB-BASED DIMERIZATION SWITCHES. E.g., the FKBP binding fragment or analog of FRB comprises: an E2032 mutation, e.g., an E2032I mutation or E2032L mutation; a T2098 mutation, e.g., a T2098L mutation; or an E2032 and a T2098 mutation, e.g., an E2032I and a T2098L or an E2032L and a T2098L mutation.

In an embodiment, wherein the switch is an FKBP-FRB based switch, the dimerization molecule is an mTOR inhibitor, e.g., an allosteric mTOR inhibitor, e.g., rapamycin or a rapalog, e.g., RAD001.

In an embodiment, any of the dosing regimes or formulations of an allosteric mTOR inhibitor, e.g., RAD001, described in the section here for a low, immune enhancing, dose of an allosteric mTOR inhibitor, e.g., RAD001, can be administered to dimerize an FKBP-FRB based switch.

In an embodiment, the switch is an FKBP-FRB based switch and the dimerization molecule is RAD001.

In an embodiment, 0.1 to 20, 0.5 to 10, 2.5 to 7.5, 3 to 6, or about 5, mgs of RAD001 per week, e.g., delivered once per week, is administered.

In an embodiment, 0.3 to 60, 1.5 to 30, 7.5 to 22.5, 9 to 18, or about 15 mgs of RAD001 in a sustained release formuation, per week, e.g., delivered once per week, is administered.

In an embodiment, 0.005 to 1.5, 0.01 to 1.5, 0.1 to 1.5, 0.2 to 1.5, 0.3 to 1.5, 0.4 to 1.5, 0.5 to 1.5, 0.6 to 1.5, 0.7 to 1.5, 0.8 to 1.5, 1.0 to 1.5, 0.3 to 0.6, or about 0.5 mgs of RAD001 per day, e.g., delivered once once per day, is administered.

In an embodiment, 0.015 to 4.5, 0.03 to 4.5, 0.3 to 4.5, 0.6 to 4.5, 0.9 to 4.5, 1.2 to 4.5, 1.5 to 4.5, 1.8 to 4.5, 2.1 to 4.5, 2.4 to 4.5, 3.0 to 4.5, 0.9 to 1.8, or about 1.5 mgs of RAD001 in a sustained release formulation, per day, e.g., delivered once once per day, is administered.

In an embodiment, 0.1 to 30, 0.2 to 30, 2 to 30, 4 to 30, 6 to 30, 8 to 30, 10 to 30, 1.2 to 30, 14 to 30, 16 to 30, 20 to 30, 6 to 12, or about 10 mgs of RAD001 in a sustained release formulation, per week, e.g., delivered once once per week, is administered.

In an embodiment, the dimerization switch comprises: a switch domain comprising a rapamycin, or rapamycin analog, binding sequence from FKBP, and a switch domain comprising a rapamycin, or rapamycin analog, binding sequence from FRB, e.g., a sequence comprising a lysine at residue 2098.

In an embodiment, the dimerization switch comprises: a switch domain comprising a rapamycin analog binding sequence from FKBP, and a switch domain comprising a rapamycin analog binding sequence from FRB, e.g., a sequence comprising a lysine at residue 2098.

In an embodiment, the dimerization switch comprises: a switch domain comprising an AP21967 binding sequence from FKBP, and a switch domain comprising an AP21967 binding sequence from FRB, e.g., a sequence comprising a lysine at residue 2098.

In an embodiment:
the first switch domain comprises,
a rapamycin, or rapamycin analog, binding sequence from FKBP;
a rapamycin analog binding sequence from FKBP; or
an AP21967 binding sequence from FKBP; and,
the second switch domain comprises,
a rapamycin, or rapamycin analog, binding sequence from FRB;
a rapamycin analog binding sequence from FRB; or
an AP21967 binding sequence from FRB, e.g., a sequence comprising a lysine at residue 2098.

In an embodiment:
the first switch domain comprises,
a rapamycin, or rapamycin analog, binding sequence from FRB;
a rapamycin analog binding sequence from FRB; or
an AP21967 binding sequence from FRB, e.g., a sequence comprising a lysine at residue 2098; and,
the second switch domain comprises,
a rapamycin, or rapamycin analog, binding sequence from FKBP;
a rapamycin analog binding sequence from FKBP; or
an AP21967 binding sequence from FKBP.

In an embodiment:
the first switch domain comprises an AP21967 binding sequence from FKBP; and,
the second switch domain comprises an AP21967 binding sequence from FRB, e.g., a sequence comprising a lysine at residue 2098.

In an embodiment, the first switch domain comprises an AP21967 binding sequence from FRB, e.g., a sequence comprising a lysine at residue 2098; and,
the second switch domain comprises an AP21967 binding sequence from FKBP.

In an embodiment, the dimerization molecule is a rapamycin analogue, e.g., AP21967.

In an embodiment, the dimerization switch comprises a GyrB-GyrB based switch.

In an embodiment, the dimerization switch comprises: a switch domain comprising a coumermycin binding sequence having at least 80, 85, 90, 95, 98, or 99% identity with the 24 K Da amino terminal sub-domain of GyrB.

In an embodiment the dimerization switch comprises: a switch domain comprising a coumermycin binding sequence that differs by no more than 10, 9, 8, 7, 6, 5, 4, 3, 2, or 1 amino acid residues from the corresponding sequence of 24 K Da amino terminal sub-domain of GyrB.

In an embodiment, the dimerization switch comprises: a switch domain comprising a coumermycin binding sequence from the 24 K Da amino terminal sub-domain of GyrB.

In an embodiment, the dimerization switch comprises: the 24 K Da amino terminal sub-domain of GyrB.

In an embodiment, the dimerization molecule is a coumermycin.

In an embodiment, the dimerization switch comprises a GAI-GID1 based switch.

In an embodiment, the dimerization switch comprises: a GID1 switch domain comprising a gibberellin, or gibberellin analog, e.g., $GA_3$, binding sequence having at least 80, 85, 90, 95, 98, or 99% identity with GID1, and a switch domain comprising a GAI switch domain having at least 80, 85, 90, 95, 98, or 99% identity with GAI.

In an embodiment, the dimerization switch comprises: a GID1 switch domain comprising a gibberellin, or gibberellin analog, e.g., $GA_3$, binding sequence that differs by no more than 10, 9, 8, 7, 6, 5, 4, 3, 2, or 1 amino acid residues from the corresponding sequence of a GID1 described herein, and a GAI switch domain that differs by no more than 10, 9, 8, 7, 6, 5, 4, 3, 2, or 1 amino acid residues from the corresponding sequence of a GAI described herein.

In an embodiment:
the first switch domain comprises a GID1 switch domain; and,
the second switch domain comprises a GAI switch domain.

In an embodiment:
the first switch domain comprises a GAI switch domain; and,
the second switch domain comprises a GID1 switch domain.

In an embodiment, the dimerization molecule is $GA_3$-AM.

In an embodiment, the dimerization molecule is $GA_3$.

In an embodiment, the dimerization molecule is a small molecule, e.g., is other than a polypeptide.

In an embodiment, the dimerization molecule is a polypeptide, e.g., a polypeptide, e.g., an antibody molecule, or a non-antibody scaffold, e.g., a fribronectin or adnectin, having specific affinity for one or both of the first and second switch domains.

In an embodiment, the dimerization molecule, e.g. a polypeptide, is an antibody molecule.

In an embodiment, the dimerization switch comprises a Halo-tag/SNAP-tag based switch.

In an embodiment, the dimerization switch comprises: a Halo-tag switch domain comprising having at least 80, 85, 90, 95, 98, or 99% identity with SEQ ID NO: 14, and a SNAP-tag switch domain having at least 80, 85, 90, 95, 98, or 99% identity with SEQ ID NO: 15.

In an embodiment, the dimerization switch comprises: a Halo-tag switch domain comprising that differs by no more than 10, 9, 8, 7, 6, 5, 4, 3, 2, or 1 amino acid residues from SEQ ID NO: 14, and a SNAP-tag switch domain that differs by no more than 10, 9, 8, 7, 6, 5, 4, 3, 2, or 1 amino acid residues from SEQ ID: 15.

In an embodiment:
the first switch domain comprises a Halo-tag switch domain; and,
the second switch domain comprises a SNAP-tag switch domain.

In an embodiment:
the first switch domain comprises a SNAP-tag switch domain; and,
the second switch domain comprises a Halo-tag switch domain.

In an embodiment, the dimerization molecule comprises structure 5.

In an embodiment, the dimerization molecule comprises three or more domains, e.g., protein tags that bind a switch domain, e.g., a polypeptide, e.g., an antibody molecule or non-antibody scaffold, having affinity for the domain.

In an embodiment, the dimerization molecule is a non-covalent dimerization molecule.

In an embodiment, the dimerization molecule is covalent dimerization molecule.

In an embodiment, the dimerization switch, e.g., a homodimerization switch, e.g., an extracellular homodimerization switch, comprises switch domains that comprise tag molecules, e.g., a c-myc peptide tag, flag peptide tag, HA peptide tag or V5 peptide tag, and the dimerization switch comprises polypeptides with affinity for the switch domains, e.g., antibody molecules and non-antibody scaffold.

In an embodiment, the RCAR further comprises a second order dimerization switch.

In an embodiment, the dimerization molecule has a valency of greater than two, e.g., it is multi-valent, and binds, and thus clusters or dimerizes, more than two switch domains.

Embodiments of the dimerization switches described herein may feature multiple switch domains, sometimes referred to herein as a multi switch. A multi switch comprises plurality of, e.g., 2, 3, 4, 5, 6, 7, 8, 9, or 10, switch domains, independently, on a first member, e.g., an antigen binding member, and a second member, e.g., an intracellular signaling member, as described in the section herein entitled MULTIPLE SWITCH DOMAINS.

In an embodiment, the first member, e.g., an antigen binding member, comprises a plurality of first switch domains, e.g., FKBP-based switch domains, and the second member, e.g., an intracellular signaling member, comprises a plurality of second switch domains, e.g., FRB-based switch domains. See, e.g., FIG. 55A. In an embodiment, the first member comprises a first and a second switch domain, e.g., a FKBP-based switch domain and a FRB-based switch domain, and the second member comprises a first and a second switch domain, e.g., a FKBP-based switch domain and a FRB-based switch domain. See, e.g., FIG. 55B.

In an embodiment, the first member and the second member comprises a plurality of homodimerization switch domains, e.g., GyrB-based switch domains.

As is discussed herein, embodiments of an RCAR can include a member, e.g., an antigen binding member, comprising an intracellular signaling domain, e.g., a costimulatory signaling domain. While not wishing to be bound by theory, it is believed that the presence of such a domain promotes persistence of the member in a cell without significant activation in the absence of dimerization switch mediated association of members of the RCAR. Embodiments of such members are described in the section following immediately hereafter, sometimes referred to herein as the Persistence Module.

In an embodiment, the RCAR comprises:
a) an intracellular signaling member comprising:
  an intracellular signaling domain, e.g., a primary intracellular signaling domain, e.g., selected from Table 1, e.g., a CD3zeta domain, and
  a first switch domain, e.g., and FKBP switch domain; and
b) an antigen binding member comprising:
  an antigen binding domain,
  a transmembrane domain, an intracellular signaling domain, e.g., a costimulatory signaling domain, e.g., selected from Table 2, e.g., a 4-1BB domain, and a second switch domain, e.g., a FRB switch domain.
See, e.g., FIGS. 26, 42A, and 44A.

In an embodiment, the antigen binding member comprises: a plurality, e.g., 2 or 3 costimulatory signaling domains, chosen e.g., from Table 2, and in embodiments, no primary intracellular signaling domain.

In an embodiment, the antigen binding member comprises: a plurality, e.g., 2 or 3, costimulatory signaling domains selected from 41BB, CD28, CD27, ICOS, and OX40.

In an embodiment, the two or more costimulatory domains can be the same costimulatory signaling domain or different costimulatory signaling domains.

In an embodiment, the antigen binding member comprises the following costimulatory signaling domains, from the extracellular to intracellular direction:
41BB-CD27;
CD27-41BB;
41BB-CD28;
CD28-41BB;
OX40-CD28;
CD28-OX40;
CD28-41BB; or
41BB-CD28.

In an embodiment, the antigen binding member comprises the following costimulatory signaling domains: CD28-41BB.

In an embodiment, the antigen binding member comprises the following costimulatory signaling domains: CD28-OX40.

In an embodiment, the antigen binding member comprises: a plurality, e.g., 2 or 3 costimulatory signaling domains, chosen e.g., from Table 2, e.g., a combination of costimulatory signaling domains described herein, and the intracellular binding domain comprises a CD3zeta domain.

In an embodiment, an antigen binding member having two or more costimulatory signaling domains does not comprise a primary intracellular signaling domain.

In an embodiment, the first and second switch domains comprise a FKBP-FRB based switch, which comprises a switch domain comprising a FRB binding fragment or analog of FKBP and a switch domain comprising an FKBP binding fragment or analog of FRB, and the FKBP binding fragment or analog of FRB comprises one or more mutations which enhances the formation of a complex between an FKBP switch domain, an FRB switch domain, and the dimerization molecule, or a mutation described in the section herein entitled MODIFIED FKBP/FRB-BASED DIMERIZATION SWITCHES. E.g., the FKBP binding fragment or analog of FRB comprises: an E2032 mutation, e.g., an E2032I mutation or E2032L mutation; a T2098 mutation, e.g., a T2098L mutation; or an E2032 and a T2098 mutation, e.g., an E2032I and a T2098L or an E2032L and a T2098L mutation.

In such embodiments, the RCAR comprises a multi switch comprising a plurality of, e.g., 2, 3, 4, 5, 6, 7, 8, 9, or 10, switch domains, independently, on a first member, e.g., an antigen binding member, and a the second member, e.g., an intracellular signaling member, as described in the section herein entitled MULTIPLE SWITCH DOMAINS. In an embodiment, the first member comprises a plurality of first switch domains, e.g., FKBP-based switch domains, and the second member comprises a plurality of second switch domains, e.g., FRB-based switch domains. In an embodiment, the first member comprises a first and a second switch domain, e.g., a FKBP-based switch domain and a FRB-based switch domain, and the second member comprises a first and a second switch domain, e.g., a FKBP-based switch domain and a FRB-based switch domain.

Also provided herein are RCARs wherein the antigen binding member comprises a plurality of antigen binding domains. In an embodiment, the antigen binding member comprises a plurality of, e.g., 2, 3, 4, or 5, antigen binding domains, e.g., scFvs, wherein each antigen binding domain binds to a target antigen. In an embodiment, two or more of the antigen binding domains can bind to different antigens. In an embodiment, two or more of the antigen binding domains can bind to the same antigen, e.g., the same or different epitopes on the same antigen. In embodiments, a linker or hinge region is optionally disposed between two or each of the antigen binding domains.

In an embodiment, the RCAR comprises
a) an intracellular signaling member comprising:
an intracellular signaling domain, e.g., a primary intracellular signaling domain, e.g., selected from Table 1, e.g., a CD3zeta domain, and a FKBP switch domain; and
b) an antigen binding member comprising:
(i) an antigen binding domain, e.g., an antigen binding domain that targets CD19, e.g., an anti-CD19 antigen binding domain described herein,
(ii) a transmembrane domain,
(iii) one of:
(A) a CD28 costimulatory signaling domain and a 4-1BB costimulatory signaling domain; or
(B) a CD28 costimulatory signaling domain and an OX-40 costimulatory signaling domain; and
(iv) a FRB switch domain comprising one or more mutations described in the section herein entitled, MODIFIED FKBP/FRB-BASED DIMERIZATION SWITCHES, e.g., an E2032I and a T2098L or an E2032L and a T2098L mutation.

In an embodiment, the order of elements on the antigen binding member is as follows, beginning with the amino terminus:
antigen binding domain/transmembrane domain/intracellular signaling domain, e.g., a costimulatory signaling domain, e.g., selected from Table 2, e.g., a 4-1BB domain/switch domain; or
antigen binding domain/transmembrane domain/switch domain/intracellular signaling domain, e.g., a costimulatory signaling domain, e.g., selected from Table 2, e.g., a 4-1BB domain.

In an embodiment, the order of elements on the intracellular signaling member is as follows, with beginning with the amino terminus:
switch domain/intracellular signaling domain, e.g., a primary intracellular signaling domain, e.g., selected from Table 1, e.g., a CD3zeta domain; or
intracellular signaling domain, e.g., a primary intracellular signaling domain, e.g., selected from Table 1, e.g., a CD3zeta domain/switch domain.

In an embodiment, the order of elements on the antigen binding member is as follows, with beginning with the carboxy terminus:
antigen binding domain/transmembrane domain/intracellular signaling domain, e.g., a costimulatory signaling domain, e.g., selected from Table 2, e.g., a 4-1BB domain/switch domain; or antigen binding domain/transmembrane domain/switch domain/intracellular signaling domain, e.g., a costimulatory signaling domain, e.g., selected from Table 2, e.g., a 4-1BB domain.

In an embodiment, the order of elements on the intracellular signaling member is as follows, beginning with the carboxy terminus:

switch domain/intracellular signaling domain, e.g., a primary intracellular signaling domain, e.g., selected from Table 1, e.g., a CD3zeta domain; or intracellular signaling domain, e.g., a primary intracellular signaling domain, e.g., selected from Table 1, e.g., a CD3zeta domain/switch domain.

In an embodiment, the first and second switch domains form a FKBP-FRB based switch.

In an embodiment, the one of the first and second dimerization switches comprises: a switch domain comprising a rapamycin or rapamycin analog binding sequence having at least 80, 85, 90, 95, 98, or 99% identity with FKBP, and the other comprises a switch domain comprising a rapamycin or rapamycin analog binding sequence binding sequence having at least 80, 85, 90, 95, 98, or 99% identity with FRB.

In an embodiment, wherein the switch is an FKBP-FRB based switch, the dimerization molecule is an mTOR inhibitor, e.g., an allosteric mTOR inhibitor, e.g., rapamycin or a rapalog, e.g., RAD001.

In an embodiment, any of the dosing regimes or formulations of an allosteric mTOR inhibitor, e.g., RAD001, described in the section here for a low, immune enhancing, dose of an allosteric mTOR inhibitor, e.g., RAD001, can be administered to dimerize an FKBP-FRB based switch.

In an embodiment, the switch is an FKBP-FRB based switch and the dimerization molecule is RAD001.

In an embodiment, 0.1 to 20, 0.5 to 10, 2.5 to 7.5, 3 to 6, or about 5, mgs of RAD001 per week, e.g., delivered once per week, is administered.

In an embodiment, 0.3 to 60, 1.5 to 30, 7.5 to 22.5, 9 to 18, or about 15 mgs of RAD001 in a sustained release formulation, per week, e.g., delivered once per week, is administered.

In an embodiment 0.005 to 1.5, 0.01 to 1.5, 0.1 to 1.5, 0.2 to 1.5, 0.3 to 1.5, 0.4 to 1.5, 0.5 to 1.5, 0.6 to 1.5, 0.7 to 1.5, 0.8 to 1.5, 1.0 to 1.5, 0.3 to 0.6, or about 0.5 mgs of RAD001 per day, e.g., delivered once once per day, is administered.

In an embodiment, 0.015 to 4.5, 0.03 to 4.5, 0.3 to 4.5, 0.6 to 4.5, 0.9 to 4.5, 1.2 to 4.5, 1.5 to 4.5, 1.8 to 4.5, 2.1 to 4.5, 2.4 to 4.5, 3.0 to 4.5, 0.9 to 1.8, or about 1.5 mgs of RAD001 in a sustained release formulation, per day, e.g., delivered once once per day, is administered.

In an embodiment, 0.1 to 30, 0.2 to 30, 2 to 30, 4 to 30, 6 to 30, 8 to 30, 10 to 30, 1.2 to 30, 14 to 30, 16 to 30, 20 to 30, 6 to 12, or about 10 mgs of RAD001 in a sustained release formulation, per week, e.g., delivered once once per week, is administered.

In an embodiment, the dimerization switch comprises a GyrB-GyrB based switch, e.g., an GyrB-GyrB based switch described herein, e.g., an GyrB-GyrB based switch as described herein, e.g., in the Dimerization Switch Module.

In an embodiment, the dimerization switch comprises a GAI-GID1 based switch, e.g., an GAI-GID1 based switch described herein, e.g., an GAI-GID1 based switch as described herein, e.g., in the Dimerization Switch Module.

In an embodiment, the dimerization switch comprises a Halotag/SNAP-tag based switch, e.g., a Halotag/SNAP-tag based switch described herein, e.g., a Halotag/SNAP-tag based switch as described herein, e.g., in the Dimerization Switch Module.

In an embodiment, the RCAR comprises:
a) an intracellular signaling member comprising, beginning with the amino terminus:
a CD3zeta domain, and
a first switch domain; and
b) an antigen binding member comprising, beginning with the amino terminus:
an antigen binding domain,
a transmembrane domain,
a 4-1BB domain, and
a second switch domain,
wherein the first and second switch domains form a FKBP-FRB based switch.

In an embodiment, an RCAR comprises an auxiliary antigen binding member. Embodiments of such are described in the section below, sometimes referred to herein as the Auxilliary Binding Domain Module.

In an embodiment, the RCAR further comprises
c) an auxiliary antigen binding member comprising:
an antigen binding domain that binds a second antigen; and
a transmembrane domain or membrane anchoring domain.

In an embodiment, the auxiliary antigen binding domain does not comprise a switch domain that can form a dimerization switch with a switch domain on the antigen binding member or the intracellular signaling member.

In an embodiment, the auxiliary antigen binding member does not comprise an intracellular signaling domain.

In an embodiment, said second antigen is a cancer cell surface antigen.

In an embodiment the RCAR further comprises
d) a second auxiliary antigen binding member comprising
an antigen binding domain that binds a third antigen; and
a transmembrane domain or membrane anchoring domain.

In an embodiment, said third antigen is different from the antigen recognized by the antigen binding domain of the antigen binding member and different from the antigen recognized by the antigen binding domain of the auxiliary antigen binding member.

In an embodiment, the RCAR further comprises:
an antigen binding domain that binds to first target, a transmembrane domain linked to first switch domain of a heterodimerization switch,
an intracellular signaling domain, e.g., a primary intracellular signaling domain, wherein the intracellular signaling domain is linked to a second switch domain of a heterodimerization switch, and
an antigen binding domain that binds to a second target that is different from the first target and a transmembrane domain, wherein the heterodimermerization switch is present on the inside of a cell, wherein first switch domain and second switch domain interact together to form a complex in the presence of a heterodimerization molecule on the inside of the cell.

In an embodiment, the RCAR further comprises comprises
an unswitched auxiliary antigen binding member comprising:
an antigen binding domain, e.g., which binds a second antigen,
a transmembrane domain, and an intracellular signaling domain, e.g., a primary intracellular signaling domain.

See, e.g., FIG. 9.

In an embodiment, the unswitched auxiliary antigen binding member further comprises a costimulatory signaling domain.

In an embodiment, the intracellular signaling member unswitched auxiliary antigen binding member comprises a primary intracellular signaling domain and a costimulatory signaling domain.

In an embodiment, the unswitched auxiliary antigen binding member comprises a 4-1BB domain.

In an embodiment, the unswitched auxiliary antigen binding member comprises a CD3zeta domain.

In an embodiment, unswitched auxiliary antigen binding member comprises a CD3zeta domain and a 4-1BB domain.

In an embodiment, the RCAR is associated with, e.g., is provided in the same cell with:
an inhibitor of an inhibitory molecule, e.g., an inhibitor of an inhibitory molecule of Table 3.

In an embodiment, the RCAR is associated with, e.g., is provided in the same cell with, an shRNA that targets a inhibitory molecule, e.g. a coinhibitory molecule from Table 3.

In an embodiment, the shRNA targets PD1.

In an embodiment, the antigen binding domain binds to a target antigen on a cancer cell but does not activate the RCARX cell, e.g., a RCART cell, until a dimerization molecule is administered.

In an embodiment, the antigen binding domain binds to a target antigen on a target cell, e.g., a cancer cell, but does not promote an immune effector response, e.g., a T cell activation, until the dimerization molecule, e.g., a heterodimerization molecule or homodimerization molecule, is administered.

In an embodiment, the intracellular signaling member comprises a primary intracellular signaling domain and a costimulatory signaling domain.

In an embodiment, the intracellular signaling member comprises a 4-1BB domain.

In an embodiment, the intracellular signaling member comprises a CD3zeta domain.

In an embodiment, the intracellular signaling member comprises a CD3zeta domain and a 4-1BB domain.

In an embodiment, the RCAR further comprises
an inhibitory counter ligand binding member comprising,
an inhibitory counter ligand binding domain, and
a transmembrane domain or membrane anchor.

In an embodiment, the inhibitory counter ligand binding member comprises a switch domain that can form a dimerization switch with a switch domain on the intracellular signaling member.

In an embodiment, the inhibitory counter ligand binding member does not comprise a switch domain that can form a dimerization switch with a switch domain on the intracellular signaling member.

In an embodiment, the inhibitory counter ligand binding domain is selected from Table 4.

In an embodiment the RCAR comprises:
a) an intracellular signaling member comprising,
an intracellular signaling domain, e.g., a primary intracellular signaling domain, and
a first switch domain;
b) an antigen binding member comprising,
an antigen binding domain,
a second switch domain; and
a transmembrane domain,
wherein the first and second switch domains are intracellular.

In an embodiment, the RCAR comprises
an antigen binding domain, a transmembrane domain, and a primary intracellular signaling domain,
wherein the antigen binding domain is separated from the primary intracellular signaling domain by a dimerization switch comprising the first switch domain and the second switch domain,
wherein the second switch domain is linked to the antigen binding domain and the first switch domain is linked to the intracellular signaling domain, wherein the first and second switch domain interact together to form a complex in the presence of a dimerization molecule.

In an embodiment, the RCAR comprises:
an antigen binding domain, a transmembrane domain and an intracellular signaling domain, e.g., a primary intracellular signaling domain,
wherein the antigen binding domain is separated from the intracellular signaling domain by a heterodimermerization switch present on the inside of a cell,
wherein the heterodimerization switch comprises first switch domain and second switch domain, wherein the first switch domain is linked to the transmembrane domain and the second switch domain is linked to the intracellular signaling domain,
wherein the first switch domain and second switch domain interact together to form a complex in the presence of a heterodimerization molecule on the inside of the cell.

In an embodiment, the transmembrane domain is disposed between the second switch domain and the antigen binding domain.

In an embodiment, the intracellular signaling member does not comprise a transmembrane domain.

In an embodiment, the RCAR comprises:
a) an intracellular signaling member comprising
an intracellular signaling domain, e.g., a primary intracellular signaling domain,
a first switch domain,
a transmembrane domain; and
b) an antigen binding member comprising
an antigen binding domain, and
a second switch domain,
wherein the first and second switch domains are extracellular.

In an embodiment, the RCAR comprises:
an antigen binding domain, a transmembrane domain, and an intracellular signaling domain, e.g., a primary intracellular signaling,
wherein the antigen binding domain is separated from the intracellular signaling domain by a dimerization switch present on the outside of a cell,
wherein the dimerization switch comprises the first switch domain and the second switch domain,
wherein the second switch domain is linked to the antigen binding domain tethered to a membrane anchor and the first switch domain is linked to the transmembrane domain,
wherein the first switch domain and second switch domain interact together to form a complex in the presence of a dimerization molecule on the outside of the cell.

In an embodiment, the RCAR comprises
an antigen binding domain, a transmembrane domain, and an intracellular signaling domain, e.g., a primary intracellular signaling,
wherein the antigen binding domain is separated from the intracellular signaling domain by a homodimerization switch present on the outside of a cell, wherein the homodimerization switch comprises the first switch domain and the second switch domain, wherein the second switch domain is linked to the antigen binding domain tethered to a membrane anchor and first switch domain is linked to the transmembrane domain, wherein the first switch domain and second switch domain interact together to form a complex in the presence of a homodimerization molecule on the outside of the cell.

In an embodiment, the second switch domain is disposed between the antigen binding domain and a membrane anchor or transmembrane domain.

In an embodiment, the antigen binding member does not comprise a transmembrane domain.

In an embodiment the second switch domain is linked to the antigen binding domain tethered to a membrane anchor and the first switch domain is linked to the transmembrane domain.

In an embodiment, the dimerization molecule is selected from an antibody molecule, a dual-specific antibody, a monospecific antibody, a non-antibody scaffold, e.g., a fibronectin or adnectin, and a peptide.

In an embodiment, first switch domain and second switch domain are different and the heterodimerization molecule is a dual specific antibody molecule that binds to the first switch domain and the second switch domain.

In an embodiment, the RCAR comprises:

a) an intracellular signaling member comprising:

an intracellular signaling domain, e.g., a primary intracellular signaling domain, and a first switch domain;

b) an antigen binding member comprising:

an antigen binding domain, a second switch domain; and c) and optionally, a transmembrane domain, wherein said first and second switch domain form an FKBP-FRB based switch.

In an embodiment, the dimerization switch comprises a first and second FKBP-FRB based switch domain described herein, e.g., in the Switch Domain Module herein above.

In an embodiment, the FKBP-FRB based switch comprises a switch domain comprising a FRB binding fragment or analog of FKBP and a switch domain comprising an FKBP binding fragment or analog of FRB, and the FKBP binding fragment or analog of FRB comprises one or more mutations which enhances the formation of a complex between an FKBP switch domain, an FRB switch domain, and the dimerization molecule, or a mutation described in the section herein entitled MODIFIED FKBP/FRB-BASED DIMERIZATION SWITCHES. E.g., the FKBP binding fragment or analog of FRB comprises: an E2032 mutation, e.g., an E2032I mutation or E2032L mutation; a T2098 mutation, e.g., a T2098L mutation; or an E2032 and a T2098 mutation, e.g., an E2032I and a T2098L or an E2032L and a T2098L mutation.

In an embodiment, the RCAR comprises an extracelluar FKBP-FRB based switch, e.g., the RCAR comprises:

a) an intracellular signaling member comprising (in the direction of extracellular to cytoplasmic, when positioned in the membrane of a cell):

a first switch domain, a transmembrane domain, and an intracellular signaling domain, e.g., a primary intracellular signaling domain;

b) an antigen binding member comprising (in the direction of extracellular to cytoplasmic, when positioned in the membrane of a cell):

an antigen binding domain, a second switch domain, and a transmembrane domain or membrane anchoring domain, wherein said first and second switch domains form an extracellular FKPB-FRB based switch.

In an embodiment, the dimerization switch comprises a first and second FKBP-FRB based switch domain described herein, e.g., in the Switch Domain Module herein above.

In an embodiment, wherein the switch is an FKBP-FRB based switch, the dimerization molecule is an mTOR inhibitor, e.g., an allosteric mTOR inhibitor, e.g., rapamycin or a rapalog, e.g., RAD001.

In an embodiment, any of the dosing regimes or formulations of an allosteric mTOR inhibitor, e.g., RAD001, described in the section here for a low, immune enhancing, dose of an allosteric mTOR inhibitor, e.g., RAD001, can be administered to dimerize an FKBP-FRB based switch.

In an embodiment, the switch is an FKBP-FRB based switch and the dimerization molecule is RAD001.

In an embodiment, 0.1 to 20, 0.5 to 10, 2.5 to 7.5, 3 to 6, or about 5, mgs of RAD001 per week, e.g., delivered once per week, is administered.

In an embodiment, 0.3 to 60, 1.5 to 30, 7.5 to 22.5, 9 to 18, or about 15 mgs of RAD001 in a sustained release formuation, per week, e.g., delivered once per week, is administered.

In an embodiment, 0.005 to 1.5, 0.01 to 1.5, 0.1 to 1.5, 0.2 to 1.5, 0.3 to 1.5, 0.4 to 1.5, 0.5 to 1.5, 0.6 to 1.5, 0.7 to 1.5, 0.8 to 1.5, 1.0 to 1.5, 0.3 to 0.6, or about 0.5 mgs of RAD001 per day, e.g., delivered once once per day, is administered.

In an embodiment, 0.015 to 4.5, 0.03 to 4.5, 0.3 to 4.5, 0.6 to 4.5, 0.9 to 4.5, 1.2 to 4.5, 1.5 to 4.5, 1.8 to 4.5, 2.1 to 4.5, 2.4 to 4.5, 3.0 to 4.5, 0.9 to 1.8, or about 1.5 mgs of RAD001 in a sustained release formulation, per day, e.g., delivered once once per day, is administered.

In an embodiment, 0.1 to 30, 0.2 to 30, 2 to 30, 4 to 30, 6 to 30, 8 to 30, 10 to 30, 1.2 to 30, 14 to 30, 16 to 30, 20 to 30, 6 to 12, or about 10 mgs of RAD001 in a sustained release formulation, per week, e.g., delivered once once per week, is administered.

In an embodiment, the RCAR comprises an intracelluar FKBP-FRB based switch, e.g., the RCAR comprises:

a) an intracellular signaling member comprising (e.g, in the direction of amino terminal to carboxy terminal):

a first switch domain, and an intracellular signaling domain, e.g., a primary intracellular signaling domain;

b) an antigen binding member comprising (in the direction of extracellular to cytoplasmic, when positioned in the membrane of a cell):

an antigen binding domain, a transmembrane domain, and a second switch domain wherein said first and second switch domains form an intracellular FKPB-FRB based switch.

In an embodiment, the dimerization switch comprises a first and second FKBP-FRB based switch domain described herein, e.g., in the Switch Domain Module herein above.

In an embodiment, wherein the switch is an FKBP-FRB based switch, the dimerization molecule is an mTOR inhibitor, e.g., an allosteric mTOR inhibitor, e.g., rapamycin or a rapalog, e.g., RAD001.

In an embodiment, any of the dosing regimes or formulations of an allosteric mTOR inhibitor, e.g., RAD001, described in the section here for a low, immune enhancing, dose of an allosteric mTOR inhibitor, e.g., RAD001, can be administered to dimerize an FKBP-FRB based switch.

In an embodiment, the switch is an FKBP-FRB based switch and the dimerization molecule is RAD001.

In an embodiment, 0.1 to 20, 0.5 to 10, 2.5 to 7.5, 3 to 6, or about 5, mgs of RAD001 per week, e.g., delivered once per week, is administered.

In an embodiment, 0.3 to 60, 1.5 to 30, 7.5 to 22.5, 9 to 18, or about 15 mgs of RAD001 in a sustained release formulation, per week, e.g., delivered once per week, is administered.

In an embodiment, 0.005 to 1.5, 0.01 to 1.5, 0.1 to 1.5, 0.2 to 1.5, 0.3 to 1.5, 0.4 to 1.5, 0.5 to 1.5, 0.6 to 1.5, 0.7 to 1.5, 0.8 to 1.5, 1.0 to 1.5, 0.3 to 0.6, or about 0.5 mgs of RAD001 per day, e.g., delivered once once per day, is administered.

In an embodiment, 0.015 to 4.5, 0.03 to 4.5, 0.3 to 4.5, 0.6 to 4.5, 0.9 to 4.5, 1.2 to 4.5, 1.5 to 4.5, 1.8 to 4.5, 2.1 to 4.5, 2.4 to 4.5, 3.0 to 4.5, 0.9 to 1.8, or about 1.5 mgs of RAD001 in a sustained release formulation, per day, e.g., delivered once once per day, is administered.

In an embodiment, 0.1 to 30, 0.2 to 30, 2 to 30, 4 to 30, 6 to 30, 8 to 30, 10 to 30, 1.2 to 30, 14 to 30, 16 to 30, 20 to 30, 6 to 12, or about 10 mgs of RAD001 in a sustained release formulation, per week, e.g., delivered once once per week, is administered.

In an embodiment the RCAR comprises:
a) an intracellular signaling member comprising (e.g., in the amino terminal to carboxy terminal direction):
a first switch domain, and
an intracellular signaling domain, e.g., a primary intracellular signaling domain;
b) an antigen binding member comprising (in the direction of extracellular to cytoplasmic, when positioned in the membrane of a cell):
an antigen binding domain,
a transmembrane domain, and
a second switch domain.
wherein said first and second switch domains form an intracellular switch.

In an embodiment, the switch domains are components of a heterodimerization switch.

In an embodiment, the switch domains are components of a homodimerization switch.

In an embodiment, the dimerization switch comprises a FKBP-FRB based switch, e.g., an FKBP-FRB based switch described herein, e.g., an FKBP-FRB based switch as described herein, e.g., in the Dimerization Switch Module.

In an embodiment, the dimerization switch comprises a GyrB-GyrB based switch, e.g., an GyrB-GyrB based switch described herein, e.g., an GyrB-GyrB based switch as described herein, e.g., in the Dimerization Switch Module.

In an embodiment, the dimerization switch comprises a GAI-GID1 based switch, e.g., an GAI-GID1 based switch described herein, e.g., an GAI-GID1 based switch as described herein, e.g., in the Dimerization Switch Module.

In an embodiment, the dimerization switch comprises a Halotag/SNAP-tag based switch, e.g., a Halotag/SNAP-tag based switch described herein, e.g., a Halotag/SNAP-tag based switch as described herein, e.g., in the Dimerization Switch Module.

In an embodiment, the RCAR comprises:
a) an extracellular signaling member comprising (in the direction of extracellular to cytoplasmic, when positioned in the membrane of a cell):
a first switch domain, e.g., an FKBP switch domain,
a transmembrane domain, and
an intracellular signaling domain, e.g., a primary intracellular signaling domain;
b) an antigen binding member comprising (in the direction of extracellular to cytoplasmic, when inserted into the membrane of a cell):
an antigen binding domain,
a second switch domain, e.g., a FRB switch domain, and
a transmembrane domain or membrane anchoring domain,
wherein said first and second switch domains form an extracellular switch.

In an embodiment, the switch domains are components of a heterodimerization switch.

In an embodiment, the switch domains are components of a homodimerization switch.

In an embodiment, the dimerization switch comprises a FKBP-FRB based switch, e.g., an FKBP-FRB based switch described herein, e.g., an FKBP-FRB based switch as described herein, e.g., in the Dimerization Switch Module.

In an embodiment, the dimerization switch comprises a GyrB-GyrB based switch, e.g., an GyrB-GyrB based switch described herein, e.g., an GyrB-GyrB based switch as described herein, e.g., in the Dimerization Switch Module.

In an embodiment, the dimerization switch comprises a GAI-GID1 based switch, e.g., an GAI-GID1 based switch described herein, e.g., an GAI-GID1 based switch as described herein, e.g., in the Dimerization Switch Module.

In an embodiment, the dimerization switch comprises a Halotag/SNAP-tag based switch, e.g., a Halotag/SNAP-tag based switch described herein, e.g., a Halotag/SNAP-tag based switch as described herein, e.g., in the Dimerization Switch Module.

An embodiment provides RCARs wherein the antigen binding member is not tethered to the surface of the CAR cell. This allows a cell having an intracellular signaling member to be conveniently be paired with one or more antigen binding domains, without transforming the cell with sequence that encodes the antigen binding member, as is discussed in the section herein entitled, UNIVERSAL RCARs. These are sometimes referred to herein as universal RCARs.

In an embodiment, the RCAR comprises:
a) an intracellular signaling member comprising:
a transmembrane domain,
an intracellular signaling domain, e.g., a primary intracellular signaling domain, and
a first switch domain, e.g., an FKPB switch domain; and
b) an antigen binding member comprising:
an antigen binding domain, and
a second switch domain, e.g., a FRB switch domain,
wherein the antigen binding member does not comprise a transmembrane domain or membrane anchoring domain, and, optionally, does not comprise an intracellular signaling domain.

In an embodiment, the first and second switch domains comprises FKBP/FRB based switch.

In an embodiment, the first switch domain comprises an FRB binding fragment of FKBP.

In an embodiment, the second switch domain comprises an FKBP binding fragment of FRB.

In an embodiment, the FKBP-FRB based switch comprises a switch domain comprising a FRB binding fragment or analog of FKBP and a switch domain comprising an FKBP binding fragment or analog of FRB, and the FKBP binding fragment or analog of FRB comprises one or more mutations which enhances the formation of a complex between an FKBP switch domain, an FRB switch domain, and the dimerization molecule, or a mutation described in the section herein entitled MODIFIED FKBP/FRB-BASED DIMERIZATION SWITCHES. E.g., the FKBP binding fragment or analog of FRB comprises: an E2032 mutation, e.g., an E2032I mutation or E2032L mutation; a T2098 mutation, e.g., a T2098L mutation; or an E2032 and a T2098 mutation, e.g., an E2032I and a T2098L or an E2032L and a T2098L mutation.

In such embodiments, the RCAR comprises a multi switch comprising a plurality of, e.g., 2, 3, 4, 5, 6, 7, 8, 9, or 10, switch domains, independently, on a first member, e.g., an antigen binding member, and a the second member, e.g., an intracellular signaling member, as described in the section herein entitled MULTIPLE SWITCH DOMAINS. In an embodiment, the first member comprises a plurality of first switch domains, e.g., FKBP-based switch domains, and the second member comprises a plurality of second switch domains, e.g., FRB-based switch domains. In an embodiment, the first member comprises a first and a second switch domain, e.g., a FKBP-based switch domain and a FRB-based switch domain, and the second member comprises a first and a second switch domain, e.g., a FKBP-based switch domain and a FRB-based switch domain.

In an embodiment the intracellular signaling member comprises a primary signaling domain, e.g., form Table 1, and a costimulatory signaling domain, e.g., from Table 2.

In an embodiment the intracellular signaling member comprises a primary signaling domain, e.g., form Table 1, and plurality, e.g., 2 or 3, costimulatory signaling domain, e.g., from Table 2.

In an embodiment, the two or more costimulatory domains can be the same costimulatory signaling domain or different costimulatory signaling domains.

In an embodiment, the intracellular signaling member comprises CD3zeta.

In an embodiment, the RCAR further comprises:
c) a second antigen binding member comprising:
a second antigen binding domain, e.g., a second antigen binding domain that binds a different antigen than is bound by the antigen binding domain; and
a second switch domain.

In an embodiment, the antigen binding member comprises a plurality of, e.g., 2, 3, 4, or 5, antigen binding domains, e.g., scFvs, wherein each antigen binding domain binds to a target antigen. In an embodiment, two or more of the antigen binding domains can bind to different antigens. In an embodiment, two or more of the antigen binding domains can bind to the same antigen, e.g., the same or different epitopes on the same antigen. In embodiments, a linker or hinge region is optionally disposed between two or each of the antigen binding domains.

In a second aspect, the invention features, a RCAR, e.g., an isolated RCAR comprising:
a) an intracellular signaling member comprising,
an intracellular signaling domain, e.g., a primary intracellular signaling domain,
a first switch domain, and
a transmembrane domain; and
b) an antigen binding member comprises
an antigen binding domain, and
a membrane anchor or a second transmembrane domain.
See, e.g., FIG. 6 right panel.

In an embodiment, the antigen binding member does not comprise a switch domain that forms a dimerization switch with an intracellular signaling member switch.

In an embodiment the antigen binding member does not comprise an intracellular signaling domain.

In an embodiment, two copies of the first switch domain are components of a homodimerization switch.

In an embodiment, the RCAR further comprises:
a second intracellular signaling member comprising
an intracellular signaling domain, e.g., a primary intracellular signaling domain, and
a second switch domain,
wherein the first switch domain and the second switch domain are components of a heterodimerization switch.

In an embodiment, dimerization of the switch domains results in clustering of intracellular signaling members.

In an embodiment, dimerization of the switch domains results in an increase in signaling by the intracellular signaling domains.

In an embodiment, the dimerization switch is extracellular.

In an embodiment, the dimerization switch is intracellular.

In an embodiment:
the dimerization switch is a an extracellular homodimerization switch, and
the antigen binding member does not comprise a switch domain that can dimerize with a switch domain on the intracellular signaling member.

In an embodiment:
the dimerization switch is an intracellular homodimerization switch, and
the antigen binding member does not comprise a switch domain that can dimerize with a switch domain on the intracellular signaling member.

In an embodiment, the RCAR comprises:
a second intracellular signaling member comprising an intracellular signaling domain and a second switch domain, which together with the first switch domain, forms an extracellular heterodimerization switch, and
the antigen binding member does not comprise a switch domain that can dimerize with a switch domain on an intracellular signaling member.

In an embodiment, the RCAR comprises:
a second intracellular signaling member comprising an intracellular signaling domain and a second switch domain, which together with the first switch domain, forms an intracellular heterodimerization switch, and
the antigen binding member does not comprise a switch domain that can dimerize with a switch domain on an intracellular signaling member.

In an embodiment, the RCAR comprises:
a second intracellular signaling member comprising an intracellular signaling domain and a second switch domain, which together with the first switch domain, forms an extracellular homodimerization switch, and
the antigen binding member does not comprise a switch domain that can dimerize with a switch domain on an intracellular signaling member.

In an embodiment, the RCAR comprises:
a second intracellular signaling member comprising an intracellular signaling domain and a second switch domain, which together with the first switch domain, forms an intracellular homodimerization switch, and
the antigen binding member does not comprise a switch domain that can dimerize with a switch domain on an intracellular signaling member.

In an embodiment, the intracellular signaling domain is a primary intracellular signaling domain, selected, e.g., from Table 1.

In an embodiment, the primary intracellular signaling domain comprises a CD3zeta domain.

In an embodiment, the intracellular signaling domain is a costimulatory signaling domain, e.g., selected from the list in Table 2.

In an embodiment, the costimulatory signaling domain comprises a 4-1BB domain.

In an embodiment, the RCAR comprises a second intracellular signaling domain.

In an embodiment, the second intracellular signaling domain is a primary intracellular signaling domain, e.g., selected from the list in Table 1.

In an embodiment, the second intracellular signaling domain is a costimulatory signaling domain, e.g., selected from the list in Table 2.

In an embodiment, the first and second intracellular signaling domains comprise:
 a 4-1BB domain and a CD3zeta domain; or
 a CD28 domain and a 4-1BB domain.

In an embodiment, the RCAR comprises a third intracellular signaling domain.

In an embodiment, the third intracellular signaling domain is a primary intracellular signaling domain, e.g., selected from the list in Table 1.

In an embodiment, the third intracellular signaling domain is a costimulatory signaling domain, e.g., selected from the list in Table 2.

In an embodiment, one of the first, second and third intracellular signaling domain is a primary intracellular signaling domain, e.g., selected from the list in Table 1, and the other two are costimulatory signaling domains, e.g., selected from the list in Table 2.

In an embodiment, two of the first, second and third intracellular signaling domains are primary intracellular signaling domains, e.g., selected from the list in Table 1, and the other is a costimulatory signaling domain, e.g., selected from the list in Table 2.

In an embodiment, each of the first, second and third intracellular signaling domains is a primary intracellular signaling domain, e.g., selected from the list in Table 1.

In an embodiment, each of the first, second and third intracellular signaling domains is a costimulatory signaling domain, e.g., selected from the list in Table 2.

In an embodiment, the first, second, and third intracellular signaling domains comprise: A CD28 domain; a 4-1BB domain, and a CD3zeta domain.

In an embodiment, the RCAR comprises a fourth intracellular signaling domain.

In an embodiment, the fourth intracellular signaling domain is a primary intracellular signaling domain, e.g., selected from the list in Table 1.

In an embodiment, the fourth intracellular signaling domain is a costimulatory signaling domain, e.g., selected from the list in Table 2.

In an embodiment, one of the first, second, third and fourth intracellular signaling domain is a primary intracellular signaling domain, e.g., selected from the list in Table 1 and the other three are costimulatory signaling domains, e.g., selected from the list in Table 2.

In an embodiment, two of the first, second, third, and fourth intracellular signaling domains are primary intracellular signaling domains, e.g., selected from the list in Table 1, and the other two are costimulatory signaling domain, e.g., selected from the list in Table 2.

In an embodiment, three of the first, second, third, and fourth intracellular signaling domains are primary intracellular signaling domains, e.g., selected from the list in Table 1, and the other is a costimulatory signaling domain, e.g., selected from the list in Table 2.

In an embodiment, each of the first, second, third, and fourth intracellular signaling domains is a primary intracellular signaling domain, e.g., selected from the list in Table 1.

In an embodiment, each of the first, second, third, and fourth intracellular signaling domains is a costimulatory signaling domain, e.g., selected from the list in Table 2.

In an embodiment, the order of switch domain and the intracellular signaling domain (isd) or domains is as follows, beginning with the amino terminus:
 switch/isd;
 switch/isd1/isd2;
 isd1/switch/isd2;
 isd1/isd2/switch;
 switch/isd1/isd2/isd3;
 isd1/isd2/isd3/switch;
 isd1/switch/isd2/isd3; and
 isd1/isd2/switch/isd3.

In an embodiment, the order of switch domain and the intracellular signaling domain (isd) or domains is as follows, beginning with the carboxy terminus:
 switch/isd;
 switch/isd1/isd2;
 isd1/switch/isd2;
 isd1/isd2/switch;
 switch/isd1/isd2/isd3;
 isd1/isd2/isd3/switch;
 isd1/switch/isd2/isd3; and
 isd1/isd2/switch/isd3.

In an embodiment, the dimerization molecule, e.g., a polypeptide, e.g., an antibody molecule, comprises a first moiety, e.g., a first variable region, that specifically binds the first switch domain, and a second moiety, e.g., a second variable region, that specifically binds the second switch domain, wherein the first and second switch domains are components of a heterodimerization switch.

In an embodiment, the dimerization molecule is a polypeptide, e.g., an antibody molecule that binds the switch domains.

In an embodiment, the dimerization molecule, e.g., a polypeptide, e.g., an antibody molecule, specifically binds the first and second switch domain, wherein the first and second switch domains are components of a homodimerization switch.

In an embodiment, the heterodimermerization molecule is selected from the group consisting of an antibody molecule, a non-antibody scaffold, e.g., a fibronectin or adnectin, molecule switch, and a peptide.

In an embodiment, the homodimerization molecule is a monospecific antibody molecule.

In an embodiment, the dimerization molecule is a dual-specific antibody molecule.

In an embodiment, the antigen binding domain binds to a target antigen on a cancer cell but does not promote an immune effector response of a T cell, until the dimerization molecule is administered.

In an embodiment, the dimerization switch comprises a FKBP-FRB based switch.

In an embodiment, the dimerization switch comprises: a switch domain comprising a rapamycin analog binding sequence having at least 80, 85, 90, 95, 98, or 99% identity with FKBP, and a switch domain comprising a rapamycin analog binding sequence binding sequence having at least 80, 85, 90, 95, 98, or 99% identity with FRB.

In an embodiment, the FKBP-FRB based switch comprises a switch domain comprising a FRB binding fragment or analog of FKBP and a switch domain comprising an FKBP binding fragment or analog of FRB, and the FKBP binding fragment or analog of FRB comprises one or more mutations which enhances the formation of a complex between an FKBP switch domain, an FRB switch domain, and the dimerization molecule, or a mutation described in the section herein entitled MODIFIED FKBP/FRB-BASED DIMERIZATION SWITCHES. E.g., the FKBP binding fragment or analog of FRB comprises: an E2032 mutation, e.g., an E2032I mutation or E2032L mutation; a T2098 mutation, e.g., a T2098L mutation; or an E2032 and a T2098 mutation, e.g., an E2032I and a T2098L or an E2032L and a T2098L mutation.

In an embodiment, the dimerization switch comprises: a switch domain comprising a rapamycin analog binding sequence that differs by no more than 10, 9, 8, 7, 6, 5, 4, 3, 2, or 1 amino acid residues from the corresponding sequence of FKBP, and a switch domain comprising a rapamycin analog binding sequence that differs by no more than 10, 9, 8, 7, 6, 5, 4, 3, 2, or 1 amino acid residues from the corresponding sequence of FRB.

In an embodiment, wherein the switch is an FKBP-FRB based switch, the dimerization molecule is an mTOR inhibitor, e.g., an allosteric mTOR inhibitor, e.g., rapamycin or a rapalog, e.g., RAD001.

In an embodiment, any of the dosing regimes or formulations of an allosteric mTOR inhibitor, e.g., RAD001, described in the section here for a low, immune enhancing, dose of an allosteric mTOR inhibitor, e.g., RAD001, can be administered to dimerize an FKBP-FRB based switch.

In an embodiment, the switch is an FKBP-FRB based switch and the dimerization molecule is RAD001.

In an embodiment, 0.1 to 20, 0.5 to 10, 2.5 to 7.5, 3 to 6, or about 5, mgs of RAD001 per week, e.g., delivered once per week, is administered.

In an embodiment, 0.3 to 60, 1.5 to 30, 7.5 to 22.5, 9 to 18, or about 15 mgs of RAD001 in a sustained release formulation, per week, e.g., delivered once per week, is administered.

In an embodiment 0.005 to 1.5, 0.01 to 1.5, 0.1 to 1.5, 0.2 to 1.5, 0.3 to 1.5, 0.4 to 1.5, 0.5 to 1.5, 0.6 to 1.5, 0.7 to 1.5, 0.8 to 1.5, 1.0 to 1.5, 0.3 to 0.6, or about 0.5 mgs of RAD001 per day, e.g., delivered once once per day, is administered.

In an embodiment, 0.015 to 4.5, 0.03 to 4.5, 0.3 to 4.5, 0.6 to 4.5, 0.9 to 4.5, 1.2 to 4.5, 1.5 to 4.5, 1.8 to 4.5, 2.1 to 4.5, 2.4 to 4.5, 3.0 to 4.5, 0.9 to 1.8, or about 1.5 mgs of RAD001 in a sustained release formulation, per day, e.g., delivered once once per day, is administered.

In an embodiment, 0.1 to 30, 0.2 to 30, 2 to 30, 4 to 30, 6 to 30, 8 to 30, 10 to 30, 1.2 to 30, 14 to 30, 16 to 30, 20 to 30, 6 to 12, or about 10 mgs of RAD001 in a sustained release formulation, per week, e.g., delivered once once per week, is administered.

In an embodiment the dimerization switch comprises: a switch domain comprising a rapamycin, or rapamycin analog, binding sequence from FKBP, and a switch domain comprising a rapamycin, or rapamycin analog, binding sequence from FRB, e.g., a sequence comprising a lysine at residue 2098.

In an embodiment, the dimerization switch comprises: a switch domain comprising a rapamycin analog binding sequence from FKBP, and a switch domain comprising a rapamycin analog binding sequence from FRB, e.g., a sequence comprising a lysine at residue 2098.

In an embodiment, the dimerization switch comprises: a switch domain comprising a AP21967 binding sequence from FKBP, and a switch domain comprising a AP21967 binding sequence from FRB, e.g., a sequence comprising a lysine at residue 2098.

In an embodiment:
the first switch domain comprises,
a rapamycin, or rapamycin analog, binding sequence from FKBP;
a rapamycin analog binding sequence from FKBP; or
an AP21967 binding sequence from FKBP; and, the second switch domain comprises,
a rapamycin, or rapamycin analog, binding sequence from FRB;
a rapamycin analog binding sequence from FRB; or
an AP21967 binding sequence from FRB, e.g., a sequence comprising a lysine at residue 2098.

In an embodiment:
the first switch domain comprises,
a rapamycin, or rapamycin analog, binding sequence from FRB;
a rapamycin analog binding sequence from FRB; or
an AP21967 binding sequence from FRB, e.g., a sequence comprising a lysine at residue 2098; and,
the second switch domain comprises,
a rapamycin, or rapamycin analog, binding sequence from FKBP;
a rapamycin analog binding sequence from FKBP; or
an AP21967 binding sequence from FKBP.

In an embodiment:
the first switch domain comprises an AP21967 binding sequence from FKBP; and,
the second switch domain comprises an AP21967 binding sequence from FRB, e.g., a sequence comprising a lysine at residue 2098.

In an embodiment, the first switch domain comprises an AP21967 binding sequence from FRB, e.g., a sequence comprising a lysine at residue 2098; and,
the second switch domain comprises an AP21967 binding sequence from FKBP.

In an embodiment, the dimerization molecule is a rapamycin analogue, e.g., AP21967.

In an embodiment, the dimerization switch comprises a GyrB-GyrB based switch.

In an embodiment, the dimerization switch comprises: a switch domain comprising a coumermycin binding sequence having at least 80, 85, 90, 95, 98, or 99% identity with the 24 K Da amino terminal sub-domain of GyrB.

In an embodiment, the dimerization switch comprises: a switch domain comprising a coumermycin binding sequence that differs by no more than 10, 9, 8, 7, 6, 5, 4, 3, 2, or 1 amino acid residues from the corresponding sequence of 24 K Da amino terminal sub-domain of GyrB.

In an embodiment, the dimerization switch comprises: a switch domain comprising a coumermycin binding sequence from the 24 K Da amino terminal sub-domain of GyrB.

In an embodiment, the dimerization switch comprises: the 24 K Da amino terminal sub-domain of GyrB.

In an embodiment, the dimerization molecule is a coumermycin.

In an embodiment, the dimerization switch comprises a GAI-GID1 based switch.

In an embodiment, the dimerization switch comprises: a GID1 switch domain comprising a gibberellin, or gibberellin analog, e.g., $GA_3$, binding sequence having at least 80, 85, 90, 95, 98, or 99% identity with GID1, and a switch domain comprising a GAI switch domain having at least 80, 85, 90, 95, 98, or 99% identity with GAI.

In an embodiment, the dimerization switch comprises: a GID1 switch domain comprising a gibberellin, or gibberellin analog, e.g., GA$_3$, binding sequence that differs by no more than 10, 9, 8, 7, 6, 5, 4, 3, 2, or 1 amino acid residues from the corresponding sequence of FKBP, and a GAI switch domain that differs by no more than 10, 9, 8, 7, 6, 5, 4, 3, 2, or 1 amino acid residues from the corresponding sequence of FRB.

In an embodiment:
the first switch domain comprises a GID1 switch domain; and,
the second switch domain comprises a GAI switch domain.

In an embodiment:
the first switch domain comprises a GAI switch domain; and,
the second switch domain comprises a GID1 switch domain.

In an embodiment, the dimerization molecule is GA$_3$-AM.

In an embodiment, the dimerization molecule is GA$_3$.

In an embodiment, the dimerization molecule is a small molecule, e.g., is other than a polypeptide.

In an embodiment, the dimerization molecule is a polypeptide, e.g., a polypeptide, e.g., an antibody molecule, or a non-antibody scaffold, e.g., a fribronectin or adnectin, having specific affinity for one or both of the first and second switch domains.

In an embodiment, the dimerization molecule, e.g. a polypeptide, is an antibody molecule.

In an embodiment, the dimerization switch comprises a Halotag/SNAP-tag based switch.

In an embodiment, the dimerization switch comprises: a Halotag switch domain comprising having at least 80, 85, 90, 95, 98, or 99% identity with SEQ ID NO: 14, and a SNAP-tag switch domain having at least 80, 85, 90, 95, 98, or 99% identity with SEQ ID NO: 15.

In an embodiment, the dimerization switch comprises: a Halotag switch domain comprising that differs by no more than 10, 9, 8, 7, 6, 5, 4, 3, 2, or 1 amino acid residues from SEQ ID NO: 14, and a SNAP-tag switch domain that differs by no more than 10, 9, 8, 7, 6, 5, 4, 3, 2, or 1 amino acid residues from SEQ ID NO: 15.

In an embodiment:
the first switch domain comprises a Halotag switch domain; and,
the second switch domain comprises a SNAP-tag switch domain.

In an embodiment:
the first switch domain comprises a SNAP-tag switch domain; and,
the second switch domain comprises a Halotag switch domain.

In an embodiment, the dimerization molecule comprises structure 5.

In an embodiment, the dimerization molecule comprises three or more domains, e.g., protein tags, that bind a switch domain, e.g., a polypeptide, e.g., an antibody molecule or non-antibody scaffold, having affinity for the domain.

In an embodiment, the dimerization molecule is a non-covalent dimerization molecule.

In an embodiment, the dimerization molecule is covalent dimerization molecule.

In an embodiment, the dimerization switch, e.g., a homodimerization switch, e.g., an extracellular homodimerization switch, comprises switch domains that comprise tag molecules, e.g., a c-myc peptide tag, flag peptide tag, HA peptide tag or V5 peptide tag, and the dimerization switch comprises polypeptides with affinity for the switch domains, e.g., antibody molecules and non-antibody scaffold.

In an embodiment, the RCAR further comprises a second order dimerization switch.

In an embodiment, the dimerization molecule has a valency of greater than two, e.g., it is multi-valent, and binds, and thus clusters or dimerizes, more than two switch domains.

In an embodiment, the RCAR comprises:
a first transmembrane domain and a first intracellular signaling domain, e.g., a primary intracellular signaling domain, and
a second transmembrane domain and a second intracellular signaling domain, e.g., a primary intracellular signaling domain, and
an antigen binding domain tethered to a membrane anchor,
wherein the first and second transmembrane domains are separated from each other by a heterodimerization switch present on the outside of a cell,
wherein the heterodimerization switch comprises first switch domain and second switch domain, wherein the first and second switch domains of the heterodimerization switch interact together to form a complex in the presence of a heterodimerization molecule on the either the inside or outside of the cell.

In an embodiment, the antigen binding member comprises
an antigen binding domain,
a second transmembrane domain, and
a costimulatory signaling domain, e.g., a costimulatory signaling domain from Table 2, e.g., a 4-1BB domain.

In an embodiment, the RCAR further comprises:
an unswitched auxiliary antigen binding member comprising:
an antigen binding domain, e.g., which binds a second antigen,
a transmembrane domain, and
an intracellular signaling domain, e.g., a primary intracellular signaling domain.

In an embodiment, the unswitched auxiliary antigen binding member further comprises a costimulatory signaling domain.

In an embodiment, the intracellular signaling member unswitched auxiliary antigen binding member comprises a primary intracellular signaling domain and a costimulatory signaling domain.

In an embodiment, the unswitched auxiliary antigen binding member comprises a 4-1BB domain.

In an embodiment, the unswitched auxiliary antigen binding member comprises a CD3zeta domain.

In an embodiment, the unswitched auxiliary antigen binding member comprises a CD3zeta domain and a 4-1BB domain.

In an embodiment, the RCAR is associated with, e.g., is provided in the same cell with an inhibitor of an inhibitory molecule, e.g., an inhibitor of a inhibitory molecule of Table 3.

In an embodiment, the RCAR is associated with, e.g., is provided in the same cell with, an shRNA that targets an inhibitory molecule, e.g. a coinhibitory molecule from Table 3.

In an embodiment, the shRNA targets PD1.

In an embodiment, the antigen binding domain binds to a target antigen on a cancer cell but does not activate the RCARX cell, e.g., a RCART cell, until a dimerization molecule is administered.

In an embodiment, the antigen binding domain binds to a target antigen on a target cell, e.g., a cancer cell, but does not promote an immune effector response, e.g., a T cell activation, until the dimerization molecule, e.g., a heterodimerization molecule or homodimerization molecule, is administered.

RCARs disclosed herein can include, e.g., in place of an scFv-based antigen binding domain, an extracellular domain of an inhibitory receptor, e.g., PD1. While not wising to be bound by theory, it is believed that engagement of the inhibitory extracellular domain with its counter ligand (which normally down regulates the immune response), activates the immune response. This is discussed immediately below.

In a third aspect, the invention features, an RCAR, e.g., an isolated RCAR, comprising:
a) an inhibitory extracellular domain member comprising,
an inhibitory extracellular domain,
a transmembrane region, and
a switch domain;
b) an intracellular signaling member comprising,
an intracellular signaling domain, e.g., a primary intracellular signaling domain, and
a switch domain; and optionally,
c) an antigen binding member comprising,
an antigen binding domain, and
a membrane anchoring domain or a transmembrane domain.

See, e.g., FIG. 10.

In an embodiment:
the antigen binding member does not comprise an intracellular signaling domain and does not comprise a switch domain that forms a dimerization switch with a switch domain on the inhibitory extracellular domain member or the switch domain on the intracellular signaling member. See, e.g., FIG. 10, far right panel.

In an embodiment, the antigen binding member comprises an antigen binding domain,
a second transmembrane domain, and
a costimulatory signaling domain, e.g., a costimulatory signaling domain from Table 2, e.g., a 4-1BB domain.

In an embodiment: the inhibitory extracellular domain is selected from Table 4.

In an embodiment: the first switch domain is linked to the intracellular signaling domain and second switch domain is linked to the transmembrane domain.

In an embodiment: the inhibitory extracellular domain binds to its ligand on the target cell and redirects signal activation in the presence of a heterodimerization molecule.

In an embodiment, the intracellular signaling domain is a primary intracellular signaling domain, selected, e.g., from Table 1.

In an embodiment, the primary intracellular signaling domain comprises a CD3zeta domain.

In an embodiment, the intracellular signaling domain is a costimulatory signaling domain, e.g., selected from the list in Table 2.

In an embodiment, the costimulatory signaling domain comprises a 4-1BB domain.

In an embodiment, the RCAR comprises a second intracellular signaling domain.

In an embodiment, the second intracellular signaling domain is a primary intracellular signaling domain, e.g., selected from the list in Table 1.

In an embodiment the second intracellular signaling domain is a costimulatory signaling domain, e.g., selected from the list in Table 2.

In an embodiment, the first and second intracellular signaling domains comprise:
a 4-1BB domain and a CD3zeta domain; or
a CD28 domain and a 4-1BB domain.

In an embodiment, the RCAR comprises a third intracellular signaling domain.

In an embodiment, the third intracellular signaling domain is a primary intracellular signaling domain, e.g., selected from the list in Table 1.

In an embodiment, the third intracellular signaling domain is a costimulatory signaling domain, e.g., selected from the list in Table 2.

In an embodiment, one of the first, second and third intracellular signaling domain is a primary intracellular signaling domain, e.g., selected from the list in Table 1, and the other two are costimulatory signaling domains, e.g., selected from, Table 2.

In an embodiment, two of the first, second and third intracellular signaling domains are primary intracellular signaling domains, e.g., selected from the list in Table 1, and the other is a costimulatory signaling domain, e.g., selected from, Table 2.

In an embodiment, each of the first, second and third intracellular signaling domains is a primary intracellular signaling domain, e.g., selected from the list in Table 1.

In an embodiment, each of the first, second, and third intracellular signaling domains is a costimulatory signaling domain, e.g., selected from the list in Table 2.

In an embodiment, the first, second, and third intracellular signaling domains comprise: A CD28 domain; a 4-1BB domain, and a CD3zeta domain.

In an embodiment, the RCAR comprises a fourth intracellular signaling domain.

In an embodiment, the fourth intracellular signaling domain is a primary intracellular signaling domain, e.g., selected from the list in Table 1.

In an embodiment, the fourth intracellular signaling domain is a costimulatory signaling domain, e.g., selected from the list in Table 2.

In an embodiment, one of the first, second, third and fourth intracellular signaling domain is a primary intracellular signaling domain, e.g., selected from the list in Table 1 and the other three are costimulatory signaling domains, e.g., selected from the list in Table 2.

In an embodiment, two of the first, second, third, and fourth intracellular signaling domains are primary intracellular signaling domains, e.g., selected from the list in Table 1, and the other two are costimulatory signaling domains, e.g., selected from the list in Table 2.

In an embodiment, three of the first, second, third, and fourth intracellular signaling domains are primary intracellular signaling domains, e.g., selected from the list in Table 1, and the other is a costimulatory signaling domain, e.g., selected from the list in Table 2.

In an embodiment, each of the first, second, third, and fourth intracellular signaling domains is a primary intracellular signaling domain, e.g., selected from the list in Table 1.

In an embodiment, each of the first, second, third, and fourth intracellular signaling domains is a costimulatory signaling domain, e.g., selected from the list in Table 2.

In an embodiment, the order of switch domain and the intracellular signaling domain (isd) or domains is as follows, beginning with amino terminus:
switch/isd;
switch/isd1/isd2;
isd1/switch/isd2;
isd1/isd2/switch;
switch/isd1/isd2/isd3;
isd1/isd2/isd3/switch;
isd1/switch/isd2/isd3; and
isd1/isd2/switch/isd3.

In an embodiment, the order of switch domain and the intracellular signaling domain (isd) or domains is as follows, beginning with carboxy terminus:
switch/isd;
switch/isd1/isd2;
isd1/switch/isd2;
isd1/isd2/switch;
switch/isd1/isd2/isd3;
isd1/isd2/isd3/switch;
isd1/switch/isd2/isd3; and
isd1/isd2/switch/isd3.

In an embodiment, the switch domains are components of a heterodimerization switch.

In an embodiment, the switch domains are components of a homodimerization switch.

In an embodiment, the dimerization switch is intracellular.

In an embodiment, the dimerization switch is extracellular.

In an embodiment, the transmembrane domain disposed on the antigen binding member and the dimerization switch, e.g., a heterodimerization switch or homodimerization switch, is intracellular.

In an embodiment, where the transmembrane domain disposed on the intracellular signaling member and the dimerization switch, e.g., heterodimerization or homodimerization switch, is extracellular.

In an embodiment, the dimerization switch comprises a FKBP-FRB based switch.

In an embodiment, the dimerization switch comprises:
a switch domain comprising a rapamycin analog binding sequence having at least 80, 85, 90, 95, 98, or 99% identity with FKBP, and a switch domain comprising a rapamycin analog binding sequence binding sequence having at least 80, 85, 90, 95, 98, or 99% identity with FRB.

In an embodiment, the FKBP-FRB based switch comprises a switch domain comprising a FRB binding fragment or analog of FKBP and a switch domain comprising an FKBP binding fragment or analog of FRB, and the FKBP binding fragment or analog of FRB comprises one or more mutations which enhances the formation of a complex between an FKBP switch domain, an FRB switch domain, and the dimerization molecule, or a mutation described in the section herein entitled MODIFIED FKBP/FRB-BASED DIMERIZATION SWITCHES. E.g., the FKBP binding fragment or analog of FRB comprises: an E2032 mutation, e.g., an E2032I mutation or E2032L mutation; a T2098 mutation, e.g., a T2098L mutation; or an E2032 and a T2098 mutation, e.g., an E2032I and a T2098L or an E2032L and a T2098L mutation.

In an embodiment, the dimerization switch comprises:
a switch domain comprising a rapamycin analog binding sequence that differs by no more than 10, 9, 8, 7, 6, 5, 4, 3, 2, or 1 amino acid residues from the corresponding sequence of FKBP, and a switch domain comprising a rapamycin analog binding sequence that differs by no more than 10, 9, 8, 7, 6, 5, 4, 3, 2, or 1 amino acid residues from the corresponding sequence of FRB.

In an embodiment, wherein the switch is an FKBP-FRB based switch, the dimerization molecule is an mTOR inhibitor, e.g., an allosteric mTOR inhibitor, e.g., rapamycin or a rapalog, e.g., RAD001.

In an embodiment, any of the dosing regimes or formulations of an allosteric mTOR inhibitor, e.g., RAD001, described in the section here for a low, immune enhancing, dose of an allosteric mTOR inhibitor, e.g., RAD001, can be administered to dimerize an FKBP-FRB based switch.

In an embodiment, the switch is an FKBP-FRB based switch and the dimerization molecule is RAD001.

In an embodiment, 0.1 to 20, 0.5 to 10, 2.5 to 7.5, 3 to 6, or about 5, mgs of RAD001 per week, e.g., delivered once per week, is administered.

In an embodiment, 0.3 to 60, 1.5 to 30, 7.5 to 22.5, 9 to 18, or about 15 mgs of RAD001 in a sustained release formuation, per week, e.g., delivered once per week, is administered.

In an embodiment, 0.005 to 1.5, 0.01 to 1.5, 0.1 to 1.5, 0.2 to 1.5, 0.3 to 1.5, 0.4 to 1.5, 0.5 to 1.5, 0.6 to 1.5, 0.7 to 1.5, 0.8 to 1.5, 1.0 to 1.5, 0.3 to 0.6, or about 0.5 mgs of RAD001 per day, e.g., delivered once per day, is administered.

In an embodiment, 0.015 to 4.5, 0.03 to 4.5, 0.3 to 4.5, 0.6 to 4.5, 0.9 to 4.5, 1.2 to 4.5, 1.5 to 4.5, 1.8 to 4.5, 2.1 to 4.5, 2.4 to 4.5, 3.0 to 4.5, 0.9 to 1.8, or about 1.5 mgs of RAD001 in a sustained release formulation, per day, e.g., delivered once once per day, is administered.

In an embodiment, 0.1 to 30, 0.2 to 30, 2 to 30, 4 to 30, 6 to 30, 8 to 30, 10 to 30, 1.2 to 30, 14 to 30, 16 to 30, 20 to 30, 6 to 12, or about 10 mgs of RAD001 in a sustained release formulation, per week, e.g., delivered once once per week, is administered.

In an embodiment, the dimerization switch comprises:
a switch domain comprising a rapamycin, or rapamycin analog, binding sequence from FKBP, and a switch domain comprising a rapamycin, or rapamycin analog, binding sequence from FRB, e.g., a sequence comprising a lysine at residue 2098.

In an embodiment, the dimerization switch comprises:
a switch domain comprising a rapamycin analog binding sequence from FKBP, and a switch domain comprising a rapamycin analog binding sequence from FRB, e.g., a sequence comprising a lysine at residue 2098.

In an embodiment, the dimerization switch comprises:
a switch domain comprising a AP21967 binding sequence from FKBP, and a switch domain comprising a AP21967 binding sequence from FRB, e.g., a sequence comprising a lysine at residue 2098.

In an embodiment:
the first switch domain comprises,
a rapamycin, or rapamycin analog, binding sequence from FKBP;
a rapamycin analog binding sequence from FKBP; or
an AP21967 binding sequence from FKBP; and,
the second switch domain comprises,
a rapamycin, or rapamycin analog, binding sequence from FRB;
a rapamycin analog binding sequence from FRB; or
an AP21967 binding sequence from FRB, e.g., a sequence comprising a lysine at residue 2098.

In an embodiment:
the first switch domain comprises,
a rapamycin, or rapamycin analog, binding sequence from FRB;
a rapamycin analog binding sequence from FRB; or an AP21967 binding sequence from FRB, e.g., a sequence comprising a lysine at residue 2098; and, the second switch domain comprises, a rapamycin, or rapamycin analog, binding sequence from FKBP;

a rapamycin analog binding sequence from FKBP; or an AP21967 binding sequence from FKBP.

In an embodiment:

the first switch domain comprises an AP21967 binding sequence from FKBP; and, the second switch domain comprises an AP21967 binding sequence from FRB, e.g., a sequence comprising a lysine at residue 2098.

In an embodiment the first switch domain comprises an AP21967 binding sequence from FRB, e.g., a sequence comprising a lysine at residue 2098; and, the second switch domain comprises an AP21967 binding sequence from FKBP.

In an embodiment, the dimerization molecule is a rapamycin analogue, e.g., AP21967.

In an embodiment, the dimerization switch comprises a GyrB-GyrB based switch.

In an embodiment, the dimerization switch comprises:
a switch domain comprising a coumermycin binding sequence having at least 80, 85, 90, 95, 98, or 99% identity with the 24 K Da amino terminal sub-domain of GyrB.

In an embodiment, the dimerization switch comprises:
a switch domain comprising a coumermycin binding sequence that differs by no more than 10, 9, 8, 7, 6, 5, 4, 3, 2, or 1 amino acid residues from the corresponding sequence of 24 K Da amino terminal sub-domain of GyrB.

In an embodiment, the dimerization switch comprises:
a switch domain comprising a coumermycin binding sequence from the 24 K Da amino terminal sub-domain of GyrB.

In an embodiment, the dimerization switch comprises: the 24 K Da amino terminal sub-domain of GyrB.

In an embodiment, the dimerization molecule is a coumermycin.

In an embodiment, the dimerization switch comprises a GAI-GID1 based switch.

In an embodiment, the dimerization switch comprises:
a GID1 switch domain comprising a gibberellin, or gibberellin analog, e.g., GA$_3$, binding sequence having at least 80, 85, 90, 95, 98, or 99% identity with GID1, and a switch domain comprising a GAI switch domain having at least 80, 85, 90, 95, 98, or 99% identity with GAI.

In an embodiment, the dimerization switch comprises:
a GID1 switch domain comprising a gibberellin, or gibberellin analog, e.g., GA$_3$, binding sequence that differs by no more than 10, 9, 8, 7, 6, 5, 4, 3, 2, or 1 amino acid residues from the corresponding sequence of GID1, and a GAI switch domain that differs by no more than 10, 9, 8, 7, 6, 5, 4, 3, 2, or 1 amino acid residues from the corresponding sequence of GAI.

In an embodiment:
the first switch domain comprises a GID1 switch domain; and, the second switch domain comprises a GAI switch domain.

In an embodiment:
the first switch domain comprises a GAI switch domain; and, the second switch domain comprises a GID1 switch domain.

In an embodiment, the dimerization molecule is GA$_3$-AM.

In an embodiment, the dimerization molecule is GA$_3$.

In an embodiment, the dimerization molecule is a small molecule, e.g., is other than a polypeptide.

In an embodiment, the dimerization molecule is a polypeptide, e.g., a polypeptide, e.g., an antibody molecule, or a non-antibody scaffold, e.g., a fribronectin or adnectin, having specific affinity for one or both of the first and second switch domains.

In an embodiment, the dimerization molecule, e.g. a polypeptide, is an antibody molecule.

In an embodiment, the dimerization switch comprises a Halotag/SNAP-tag based switch.

In an embodiment, the dimerization switch comprises:
a Halotag switch domain comprising having at least 80, 85, 90, 95, 98, or 99% identity with SEQ ID NO 14, and a SNAP-tag switch domain having at least 80, 85, 90, 95, 98, or 99% identity with SEQ ID NO 15.

In an embodiment, the dimerization switch comprises:
a Halotag switch domain comprising that differs by no more than 10, 9, 8, 7, 6, 5, 4, 3, 2, or 1 amino acid residues from SEQ ID NO 14, and a SNAP-tag switch domain that differs by no more than 10, 9, 8, 7, 6, 5, 4, 3, 2, or 1 amino acid residues from SEQ ID NO: 15.

In an embodiment:
the first switch domain comprises a Halotag switch domain; and, the second switch domain comprises a SNAP-tag switch domain.

In an embodiment:
the first switch domain comprises a SNAP-tag switch domain; and, the second switch domain comprises a Halotag switch domain.

In an embodiment, the dimerization molecule comprises structure 5.

In an embodiment the dimerization molecule comprises three or more domains, e.g., protein tags, that bind a switch domain, e.g., a polypeptide, e.g., an antibody molecule or non-antibody scaffold, having affinity for the domain.

In an embodiment, the dimerization molecule is a non-covalent dimerization molecule.

In an embodiment, the dimerization molecule is covalent dimerization molecule.

In an embodiment, the dimerization switch, e.g., a homodimerization switch, e.g., an extracellular homodimerization switch, comprises switch domains that comprise tag molecules, e.g., a c-myc peptide tag, flag peptide tag, HA peptide tag or V5 peptide tag, and the dimerization switch comprises polypeptides with affinity for the switch domains, e.g., antibody molecules and non-antibody scaffold.

In an embodiment, the RCAR further comprises a second order dimerization switch.

In an embodiment the dimerization molecule has a valency of greater than two, e.g., it is multi-valent, and binds, and thus clusters or dimerizes, more than two switch domains.

As is discussed herein, embodiments of an RCAR can include a member, e.g., an inhibitory extracellular domain member, comprising an intracellular signaling domain, e.g., a costimulatory signaling domain. While not wishing to be bound by theory, it is believed that the presence of such a domain promotes persistence of the member in a cell without significant activation in the absence of dimerization switch mediated association of members of the RCAR. Embodiments of such members are described in the section following immediately hereafter.

In an embodiment, the RCAR comprises:
a) an inhibitory extracellular domain member comprising,
an inhibitory extracellular domain,
a transmembrane region,
an intracellular signaling domain, e.g., a costimulatory signaling domain, e.g., selected from Table 2, e.g., a 4-1BB domain, and
a switch domain;
b) an intracellular signaling member comprising,
an intracellular signaling domain, e.g., a primary intracellular signaling domain, e.g., selected from Table 1, e.g., a CD3zeta domain, and
a switch domain; and optionally,
c) an antigen binding member comprising,
an antigen binding domain,
a membrane anchoring domain or a transmembrane domain, and
optionally, a costimulatory signaling domain, e.g., selected from Table 2, e.g., a 4-1BB domain
See, e.g., FIG. 11.

In an embodiment, the order of elements on the inhibitory extracellular domain member is as follows, with beginning with the amino terminus:
inhibitory extracellular domain/transmembrane domain/intracellular signaling domain, e.g., a costimulatory signaling domain, e.g., selected from Table 2, e.g., a 4-1BB domain/switch domain; or
inhibitory extracellular domain/transmembrane domain/switch domain/intracellular signaling domain, e.g., a costimulatory signaling domain, e.g., selected from Table 2, e.g., a 4-1BB domain.

In an embodiment, the order of elements on the intracellular signaling member is as follows, beginning with the amino terminus:
switch domain/intracellular signaling domain, e.g., a primary intracellular signaling domain, e.g., selected from Table 1, e.g., a CD3zeta domain; or
intracellular signaling domain, e.g., a primary intracellular signaling domain, e.g., selected from Table 1, e.g., a CD3zeta domain/switch domain.

In an embodiment, the order of elements on the inhibitory extracellular domain member is as follows, beginning with the carboxy terminus:
inhibitory extracellular domain/transmembrane domain/intracellular signaling domain, e.g., a costimulatory signaling domain, e.g., selected from Table 2, e.g., a 4-1BB domain/switch domain; or
inhibitory extracellular domain/transmembrane domain/switch domain/intracellular signaling domain, e.g., a costimulatory signaling domain, e.g., selected from Table 2, e.g., a 4-1BB domain.

In an embodiment, the order of elements on the intracellular signaling member is as follows, beginning with the carboxy terminus:
switch domain/intracellular signaling domain, e.g., a primary intracellular signaling domain, e.g., selected from Table 1, e.g., a CD3zeta domain; or
intracellular signaling domain, e.g., a primary intracellular signaling domain, e.g., selected from Table 1, e.g., a CD3zeta domain/switch domain.

In an embodiment, the first and second switch domains form a FKBP-FRB based switch.

In an embodiment, the one of the first and second dimerization switches comprises:
a switch domain comprising rapamycin or a rapamycin analog binding sequence having at least 80, 85, 90, 95, 98, or 99% identity with FKBP, and the other comprises a switch domain comprising a rapamycin or rapamycin analog binding sequence binding sequence having at least 80, 85, 90, 95, 98, or 99% identity with FRB.

In an embodiment, the FKBP-FRB based switch comprises a switch domain comprising a FRB binding fragment or analog of FKBP and a switch domain comprising an FKBP binding fragment or analog of FRB, and the FKBP binding fragment or analog of FRB comprises one or more mutations which enhances the formation of a complex between an FKBP switch domain, an FRB switch domain, and the dimerization molecule, or a mutation described in the section herein entitled MODIFIED FKBP/FRB-BASED DIMERIZATION SWITCHES. E.g., the FKBP binding fragment or analog of FRB comprises: an E2032 mutation, e.g., an E2032I mutation or E2032L mutation; a T2098 mutation, e.g., a T2098L mutation; or an E2032 and a T2098 mutation, e.g., an E2032I and a T2098L or an E2032L and a T2098L mutation.

In an embodiment, wherein the switch is an FKBP-FRB based switch, the dimerization molecule is an mTOR inhibitor, e.g., an allosteric mTOR inhibitor, e.g., rapamycin or a rapalog, e.g., RAD001.

In an embodiment, any of the dosing regimes or formulations of an allosteric mTOR inhibitor, e.g., RAD001, described in the section here for a low, immune enhancing, dose of an allosteric mTOR inhibitor, e.g., RAD001, can be administered to dimerize an FKBP-FRB based switch.

In an embodiment, the switch is an FKBP-FRB based switch and the dimerization molecule is RAD001.

In an embodiment, 0.1 to 20, 0.5 to 10, 2.5 to 7.5, 3 to 6, or about 5, mgs of RAD001 per week, e.g., delivered once per week, is administered.

In an embodiment, 0.3 to 60, 1.5 to 30, 7.5 to 22.5, 9 to 18, or about 15 mgs of RAD001 in a sustained release formuation, per week, e.g., delivered once per week, is administered.

In an embodiment, 0.005 to 1.5, 0.01 to 1.5, 0.1 to 1.5, 0.2 to 1.5, 0.3 to 1.5, 0.4 to 1.5, 0.5 to 1.5, 0.6 to 1.5, 0.7 to 1.5, 0.8 to 1.5, 1.0 to 1.5, 0.3 to 0.6, or about 0.5 mgs of RAD001 per day, e.g., delivered once once per day, is administered.

In an embodiment, 0.015 to 4.5, 0.03 to 4.5, 0.3 to 4.5, 0.6 to 4.5, 0.9 to 4.5, 1.2 to 4.5, 1.5 to 4.5, 1.8 to 4.5, 2.1 to 4.5, 2.4 to 4.5, 3.0 to 4.5, 0.9 to 1.8, or about 1.5 mgs of RAD001 in a sustained release formulation, per day, e.g., delivered once once per day, is administered.

In an embodiment, 0.1 to 30, 0.2 to 30, 2 to 30, 4 to 30, 6 to 30, 8 to 30, 10 to 30, 1.2 to 30, 14 to 30, 16 to 30, 20 to 30, 6 to 12, or about 10 mgs of RAD001 in a sustained release formulation, per week, e.g., delivered once once per week, is administered.

In an embodiment, the dimerization switch comprises a GyrB-GyrB based switch, e.g., an GyrB-GyrB based switch described herein, e.g., an GyrB-GyrB based switch as described herein, e.g., in the Dimerization Switch Module.

In an embodiment, the dimerization switch comprises a GAI-GID1 based switch, e.g., an GAI-GID1 based switch described herein, e.g., an GAI-GID1 based switch as described herein, e.g., in the Dimerization Switch Module.

In an embodiment, the dimerization switch comprises a Halotag/SNAP-tag based switch, e.g., a Halotag/SNAP-tag based switch described herein, e.g., a Halotag/SNAP-tag based switch as described herein, e.g., in the Dimerization Switch Module.

In an embodiment, the RCAR comprises:
a) an intracellular signaling member comprising, beginning with the amino terminus:
a CD3zeta domain, and
a first switch domain; and b) an inhibitory extracellular domain member comprising, beginning with the amino terminus:
  an inhibitory extracellular domain,
  a transmembrane domain,
  a 4-1BB domain, and
  a second switch domain,
wherein the first and second switch domains form a FKBP-FRB based switch.

In an embodiment, the RCAR is associated with, e.g., is provided in the same cell with:
  an inhibitor of an inhibitory molecule, e.g., an inhibitor of a inhibitory molecule of Table 3.

In an embodiment, the RCAR is associated with, e.g., is provided in the same cell with, an shRNA that targets a inhibitory molecule, e.g. a coinhibitory molecule from Table 3.

In an embodiment the RCAR comprises a shRNA that targets PD1.

In an embodiment, the antigen binding domain binds to a target antigen on a cancer cell but does not activate the RCARX cell, e.g., a RCART cell, until a dimerization molecule is administered.

In an embodiment, the antigen binding domain binds to a target antigen on a target cell, e.g., a cancer cell, but does not promote an immune effector response, e.g., a T cell activation, until the dimerization molecule, e.g., a heterodimerization molecule or homodimerization molecule, is administered.

In an embodiment:
  the antigen binding member comprises
    an antigen binding domain;
    a transmembrane domain; and
    an intracellular signaling domain, e.g., a costimulatory signaling domain,
e.g., a costimulatory signaling domain from Table 2, e.g., a 4-1BB domain.
  See, e.g., FIG. 11.

In an embodiment:
  the antigen binding member does not comprise a switch domain that forms a dimerization switch with the switch on the inhibitory counter ligand binding member or the switch on the intracellular signaling member.

In an embodiment the inhibitory counter ligand binding domain is selected from Table 4.

As discussed in the above embodiment, the antigen binding member comprises an intracellular signaling domain, further embodiments of which are discussed immediately below.

In an embodiment, the intracellular signaling domain of antigen binding member is a primary intracellular signaling domain, selected, e.g., from Table 1.

In an embodiment, the primary intracellular signaling domain of antigen binding member comprises a CD3zeta domain.

In an embodiment, the intracellular signaling domain of antigen binding member is a costimulatory signaling domain, e.g., selected from the list in Table 2.

In an embodiment, the costimulatory signaling domain comprises a 4-1BB domain.

In an embodiment, the antigen binding member comprises a second intracellular signaling domain.

In an embodiment, the second intracellular signaling domain of antigen binding member is a primary intracellular signaling domain, e.g., selected from the list in Table 1.

In an embodiment, the second intracellular signaling domain of antigen binding member is a costimulatory signaling domain, e.g., selected from the list in Table 2.

In an embodiment, the first and second intracellular signaling domains of antigen binding member comprise:
  a 4-1BB domain and a CD3zeta domain; or
  a CD28 domain and a 4-1BB domain.

In an embodiment, the antigen binding member comprises a third intracellular signaling domain.

In an embodiment, the third intracellular signaling domain of antigen binding member is a primary intracellular signaling domain, e.g., selected from the list in Table 1.

In an embodiment, the third intracellular signaling domain of antigen binding member is a costimulatory signaling domain, e.g., selected from the list in Table 2.

In an embodiment, one of the first, second and third intracellular signaling domain of antigen binding member is a primary intracellular signaling domain, e.g., selected from the list in Table 1, and the other two are costimulatory signaling domains, e.g., selected from the list in Table 2.

In an embodiment, two of the first, second and third intracellular signaling domains of antigen binding member are primary intracellular signaling domains, e.g., selected from the list in Table 1, and the other is a costimulatory signaling domain, e.g., selected from the list in Table 2.

In an embodiment, each of the first, second and third intracellular signaling domains of antigen binding member is a primary intracellular signaling domain, e.g., selected from the list in Table 1.

In an embodiment, each of the first, second and third intracellular signaling domains of antigen binding member is a costimulatory signaling domain, e.g., selected from the list in Table 2.

In an embodiment, the first, second, and third intracellular signaling domains of antigen binding member comprise: a CD28 domain; a 4-1BB domain, and a CD3zeta domain.

In an embodiment, antigen binding member comprises a fourth intracellular signaling domain.

In an embodiment, the fourth intracellular signaling domain of antigen binding member is a primary intracellular signaling domain, e.g., selected from the list in Table 1.

In an embodiment, the fourth intracellular signaling domain of antigen binding member is a costimulatory signaling domain, e.g., selected from the list in Table 2.

In an embodiment, one of the first, second, third and fourth intracellular signaling domain of antigen binding member is a primary intracellular signaling domain, e.g., selected from the list in Table 1 and the other three are costimulatory signaling domains, e.g., selected from the list in Table 2.

In an embodiment, two of the first, second, third, and fourth intracellular signaling domains of antigen binding member are primary intracellular signaling domains, e.g., selected from the list in Table 1, and the other two are costimulatory signaling domain, e.g., selected from the list in Table 2.

In an embodiment, three of the first, second, third, and fourth intracellular signaling domains of antigen binding members are selected from the list in Table 1, and the other is a costimulatory signaling domain, e.g., selected from the list in Table 2.

In an embodiment, each of the first, second, third, and fourth intracellular signaling domains of antigen binding member is a primary intracellular signaling domain, e.g., selected from the list in Table 1.

In an embodiment, each of the first, second, third, and fourth intracellular signaling domains of antigen binding member is a costimulatory signaling domain, e.g., selected from the list in Table 2.

In an embodiment, the two or more costimulatory domains can be the same costimulatory signaling domain, e.g., selected from the list in Table 2, or different costimulatory signaling domains, e.g., selected from the list in Table 2.

In an embodiment, the order of switch domain and the intracellular signaling domain (isd) or domains of antigen binding member is as follows, beginning with amino:
switch/isd;
switch/isd1/isd2;
isd1/switch/isd2;
isd1/isd2/switch;
switch/isd1/isd2/isd3;
isd1/isd2/isd3/switch;
isd1/switch/isd2/isd3; and
isd1/isd2/switch/isd3.

In an embodiment, the order of switch domain and the intracellular signaling domain (isd) or domains of antigen binding member is as follows, beginning with carboxy terminus:
switch/isd;
switch/isd1/isd2;
isd1/switch/isd2;
isd1/isd2/switch;
switch/isd1/isd2/isd3;
isd1/isd2/isd3/switch;
isd1/switch/isd2/isd3; and
isd1/isd2/switch/isd3.

In an embodiment:
the antigen binding member comprises
an antigen binding domain;
a switch domain; and
a transmembrane domain.

In an embodiment:
the intracellular binding member switch domain forms a heterodimerization switch with one or both of:
the inhibitory extracellular domain member switch, and
the antigen binding domain switch.

As discussed above, the switched antigen binding member comprises an intracellular signaling domain, further embodiments of which are discussed immediately below.

In an embodiment, the intracellular signaling domain of switched antigen binding member is a primary intracellular signaling domain, selected, e.g., from the list in Table 1.

In an embodiment, the primary intracellular signaling domain of switched antigen binding member comprises a CD3zeta domain.

In an embodiment, the intracellular signaling domain of switched antigen binding member is a costimulatory signaling domain, e.g., selected from the list in Table 2.

In an embodiment, the costimulatory signaling domain comprises a 4-1BB domain.

In an embodiment, the switched antigen binding member comprises a second intracellular signaling domain.

In an embodiment, the second intracellular signaling domain of switched antigen binding member is a primary intracellular signaling domain, e.g., selected from the list in Table 1.

In an embodiment, the second intracellular signaling domain of switched antigen binding member is a costimulatory signaling domain, e.g., selected from the list in Table 2.

In an embodiment, the first and second intracellular signaling domains of switched antigen binding member comprise:
a 4-1BB domain and a CD3zeta domain; or
a CD28 domain and a 4-1BB domain.

In an embodiment, the antigen binding member comprises a third intracellular signaling domain.

In an embodiment, the third intracellular signaling domain of switched antigen binding member is a primary intracellular signaling domain, e.g., selected from the list in Table 1.

In an embodiment, the third intracellular signaling domain of switched antigen binding member is a costimulatory signaling domain, e.g., selected from the list in Table 2.

In an embodiment, one of the first, second and third intracellular signaling domain of switched antigen binding member is a primary intracellular signaling domain, e.g., selected from the list in Table 1, and the other two are costimulatory signaling domains, e.g., selected from the list in Table 2.

In an embodiment, two of the first, second and third intracellular signaling domains of switched antigen binding member are primary intracellular signaling domains, e.g., selected from the list in Table 1, and the other is a costimulatory signaling domain, e.g., selected from the list in Table 2.

In an embodiment, each of the first, second and third intracellular signaling domains of switched antigen binding member is a primary intracellular signaling domain, e.g., selected from the list in Table 1.

In an embodiment, each of the first, second and third intracellular signaling domains of switched antigen binding member is a costimulatory signaling domain, e.g., selected from the list in Table 2.

In an embodiment, the first, second, and third intracellular signaling domains of switched antigen binding member comprise: a CD28 domain; a 4-1BB domain, and a CD3zeta domain.

In an embodiment, switched antigen binding member comprises a fourth intracellular signaling domain.

In an embodiment, the fourth intracellular signaling domain of switched antigen binding member is a primary intracellular signaling domain, e.g., selected from the list in Table 1.

In an embodiment, the fourth intracellular signaling domain of switched antigen binding member is a costimulatory signaling domain, e.g., selected from the list in Table 2.

In an embodiment, one of the first, second, third and fourth intracellular signaling domain of switched antigen binding member is a primary intracellular signaling domain, e.g., selected from the list in Table 1 and the other three are costimulatory signaling domains, e.g., selected from the list in Table 2.

In an embodiment, two of the first, second, third, and fourth intracellular signaling domains of switched antigen binding member are primary intracellular signaling domains, e.g., selected from the list in Table 1, and the other two are costimulatory signaling domain, e.g., selected from the list in Table 2.

In an embodiment, three of the first, second, third, and fourth intracellular signaling domains of switched antigen binding members are selected from the list in Table 1, and the other is a costimulatory signaling domain, e.g., selected from the list in Table 2.

In an embodiment, each of the first, second, third, and fourth intracellular signaling domains of switched antigen binding member is a primary intracellular signaling domain, e.g., selected from the list in Table 1.

In an embodiment, each of the first, second, third, and fourth intracellular signaling domains of switched antigen binding member is a costimulatory signaling domain, e.g., selected from the list in Table 2.

In an embodiment, the two or more costimulatory domains can be the same costimulatory signaling domain, e.g., selected from the list in Table 2, or different costimulatory signaling domains, e.g., selected from the list in Table 2.

In an embodiment, the order of switch domain and the intracellular signaling domain (isd) or domains of switched antigen binding member is as follows, beginning with amino terminus:
switch/isd;
switch/isd1/isd2;
isd1/switch/isd2;
isd1/isd2/switch;
switch/isd1/isd2/isd3;
isd1/isd2/isd3/switch;
isd1/switch/isd2/isd3; and
isd1/isd2/switch/isd3.

In an embodiment, the order of switch domain and the intracellular signaling domain (isd) or domains of switched antigen binding member is as follows, the beginning with carboxy terminus:
switch/isd;
switch/isd1/isd2;
isd1/switch/isd2;
isd1/isd2/switch;
switch/isd1/isd2/isd3;
isd1/isd2/isd3/switch;
isd1/switch/isd2/isd3; and
isd1/isd2/switch/isd3.

In a switched antigen binding domain embodiment the RCAR is associated with, e.g., is provided in the same cell with:
an inhibitor of an inhibitory molecule, e.g., an inhibitor of a inhibitory molecule of Table 3.

In a switched antigen binding domain embodiment the RCAR is associated with, e.g., is provided in the same cell with an shRNA that targets a inhibitory molecule, e.g. a coinhibitory molecule from Table 3.

In a switched antigen binding domain embodiment the RCAR further comprises a shRNA that targets PD1.

In a switched antigen binding domain embodiment the antigen binding domain binds to a target antigen on a cancer cell but does not activate the RCARX cell, e.g., a RCART cell, until a dimerization molecule is administered.

In a switched antigen binding domain embodiment the antigen binding domain binds to a target antigen on a target cell, e.g., a cancer cell, but does not promote an immune effector response, e.g., a T cell activation, until the dimerization molecule, e.g., a heterodimerization molecule or homodimerization molecule, is administered.

RCARs disclosed herein can include, e.g., in place of an scFv-based antigen binding domain, an extracellular domain of an a costimulatory ECD domain. While not wising to be bound by theory, it is believed that engagement of the ECD with its counter ligand activates the immune response via the RCAR. This is discussed immediately below.

In a fourth aspect, the invention features, a RCAR, e.g., an isolated, RCAR comprising:
a) a costimulatory ECD member comprising
a costimulatory ECD domain;
a transmembrane region, and
a switch domain;
b) an intracellular signaling member comprising
an intracellular signaling domain, e.g., a primary intracellular signaling domain, and
a switch domain; and optionally,
c) an antigen binding member comprising
an antigen binding domain;
a transmembrane domain; and
a switch domain.
See, e.g., FIG. 11.

In an embodiment:
the intracellular binding member switch domain forms a heterodimerization switch with one or both of:
the costimulatory ECD member switch, and
the antigen binding member switch.

In an embodiment, the costimulatory ECD domain is selected from Table 5.

In an embodiment the intracellular signaling domain is a primary intracellular signaling domain, selected, e.g., from Table 1.

In an embodiment, the primary intracellular signaling domain comprises a CD3zeta domain.

In an embodiment, the intracellular signaling domain is a costimulatory signaling domain, e.g., selected from the list in Table 2.

In an embodiment, the costimulatory signaling domain comprises a 4-1BB domain.

In an embodiment, the RCAR comprises a second intracellular signaling domain.

In an embodiment, the second intracellular signaling domain is a primary intracellular signaling domain, e.g., selected from the list in Table 1.

In an embodiment, the second intracellular signaling domain is a costimulatory signaling domain, e.g., selected from the list in Table 2.

In an embodiment, the first and second intracellular signaling domains comprise:
a 4-1BB domain and a CD3zeta domain; or
a CD28 domain and a 4-1BB domain.

In an embodiment, the RCAR comprises a third intracellular signaling domain.

In an embodiment, the third intracellular signaling domain is a primary intracellular signaling domain, e.g., selected from the list in Table 1.

In an embodiment, the third intracellular signaling domain is a costimulatory signaling domain, e.g., selected from the list in Table 2.

In an embodiment, one of the first, second and third intracellular signaling domain is a primary intracellular signaling domain, e.g., selected from the list in Table 1, and the other two are costimulatory signaling domains, e.g., selected from the list in Table 2.

In an embodiment, two of the first, second and third intracellular signaling domains are primary intracellular signaling domains, e.g., selected from the list in Table 1, and the other is a costimulatory signaling domain, e.g., selected from the list in Table 2.

In an embodiment, each of the first, second and third intracellular signaling domains is a primary intracellular signaling domain, e.g., selected from the list in Table 1.

In an embodiment, each of the first, second, and third intracellular signaling domains is a costimulatory signaling domain, e.g., selected from the list in Table 2.

In an embodiment, the first, second, and third intracellular signaling domains comprise: a CD28 domain; a 4-1BB domain, and a CD3zeta domain.

In an embodiment, the RCAR comprises a fourth intracellular signaling domain.

In an embodiment, the fourth intracellular signaling domain is a primary intracellular signaling domain, e.g., selected from the list in Table 1.

In an embodiment the fourth intracellular signaling domain is a costimulatory signaling domain, e.g., selected from the list in Table 2.

In an embodiment, one of the first, second, third and fourth intracellular signaling domain is a primary intracellular signaling domain, e.g., selected from the list in Table 1 and the other three are costimulatory signaling domains, e.g., selected from the list in Table 2.

In an embodiment, two of the first, second, third, and fourth intracellular signaling domains are primary intracellular signaling domains, e.g., selected from the list in Table 1, and the other two are costimulatory signaling domain, e.g., selected from the list in Table 2.

In an embodiment, three of the first, second, third, and fourth intracellular signaling domains are primary intracellular signaling domains, e.g., selected from the list in Table 1, and the other is a costimulatory signaling domain, e.g., selected from the list in Table 2.

In an embodiment, each of the first, second, third, and fourth intracellular signaling domains is a primary intracellular signaling domain, e.g., selected from the list in Table 1.

In an embodiment, each of the first, second, third, and fourth intracellular signaling domains is a costimulatory signaling domain, e.g., selected from the list in Table 2.

In an embodiment, the two or more costimulatory domains can be the same costimulatory signaling domain, e.g., selected from the list in Table 2, or different costimulatory signaling domains, e.g., selected from the list in Table 2.

In an embodiment, the order of switch domain and the intracellular signaling domain (isd) or domains is as follows, beginning with the amino terminus:
switch/isd;
switch/isd1/isd2;
isd1/switch/isd2;
isd1/isd2/switch;
switch/isd1/isd2/isd3;
isd1/isd2/isd3/switch;
isd1/switch/isd2/isd3; and
isd1/isd2/switch/isd3.

In an embodiment, the order of switch domain and the intracellular signaling domain (isd) or domains is as follows, beginning with the carboxy terminus:
switch/isd;
switch/isd1/isd2;
isd1/switch/isd2;
isd1/isd2/switch;
switch/isd1/isd2/isd3;
isd1/isd2/isd3/switch;
isd1/switch/isd2/isd3; and
isd1/isd2/switch/isd3.

In an embodiment, the switch domains are components of a heterodimerization switch.

In an embodiment, the switch domains are components of a homodimerization switch.

In an embodiment, the dimerization switch is intracellular.

In an embodiment, the dimerization switch is extracellular.

In an embodiment, the transmembrane domain disposed on the antigen binding member and the dimerization switch, e.g., a heterodimerization switch or homodimerization switch, is intracellular.

In an embodiment, where the transmembrane domain disposed on the intracellular signaling member and the dimerization switch, e.g., heterodimerization or homodimerization switch, is extracellular.

In an embodiment, the dimerization switch comprises a FKBP-FRB based switch.

In an embodiment, the dimerization switch comprises: a switch domain comprising a rapamycin analog binding sequence having at least 80, 85, 90, 95, 98, or 99% identity with FKBP, and a switch domain comprising a rapamycin analog binding sequence binding sequence having at least 80, 85, 90, 95, 98, or 99% identity with FRB.

In an embodiment, the FKBP-FRB based switch comprises a switch domain comprising a FRB binding fragment or analog of FKBP and a switch domain comprising an FKBP binding fragment or analog of FRB, and the FKBP binding fragment or analog of FRB comprises one or more mutations which enhances the formation of a complex between an FKBP switch domain, an FRB switch domain, and the dimerization molecule, or a mutation described in the section herein entitled MODIFIED FKBP/FRB-BASED DIMERIZATION SWITCHES. E.g., the FKBP binding fragment or analog of FRB comprises: an E2032 mutation, e.g., an E2032I mutation or E2032L mutation; a T2098 mutation, e.g., a T2098L mutation; or an E2032 and a T2098 mutation, e.g., an E2032I and a T2098L or an E2032L and a T2098L mutation.

In an embodiment, the dimerization switch comprises: a switch domain comprising a rapamycin analog binding sequence that differs by no more than 10, 9, 8, 7, 6, 5, 4, 3, 2, or 1 amino acid residues from the corresponding sequence of FKBP, and a switch domain comprising a rapamycin analog binding sequence that differs by no more than 10, 9, 8, 7, 6, 5, 4, 3, 2, or 1 amino acid residues from the corresponding sequence of FRB.

In an embodiment, wherein the switch is an FKBP-FRB based switch, the dimerization molecule is an mTOR inhibitor, e.g., an allosteric mTOR inhibitor, e.g., rapamycin or a rapalog, e.g., RAD001.

In an embodiment, any of the dosing regimes or formulations of an allosteric mTOR inhibitor, e.g., RAD001, described in the section here for a low, immune enhancing, dose of an allosteric mTOR inhibitor, e.g., RAD001, can be administered to dimerize an FKBP-FRB based switch.

In an embodiment, the switch is an FKBP-FRB based switch and the dimerization molecule is RAD001.

In an embodiment, 0.1 to 20, 0.5 to 10, 2.5 to 7.5, 3 to 6, or about 5, mgs of RAD001 per week, e.g., delivered once per week, is administered.

In an embodiment, 0.3 to 60, 1.5 to 30, 7.5 to 22.5, 9 to 18, or about 15 mgs of RAD001 in a sustained release formuation, per week, e.g., delivered once per week, is administered.

In an embodiment, 0.005 to 1.5, 0.01 to 1.5, 0.1 to 1.5, 0.2 to 1.5, 0.3 to 1.5, 0.4 to 1.5, 0.5 to 1.5, 0.6 to 1.5, 0.7 to 1.5, 0.8 to 1.5, 1.0 to 1.5, 0.3 to 0.6, or about 0.5 mgs of RAD001 per day, e.g., delivered once once per day, is administered.

In an embodiment, 0.015 to 4.5, 0.03 to 4.5, 0.3 to 4.5, 0.6 to 4.5, 0.9 to 4.5, 1.2 to 4.5, 1.5 to 4.5, 1.8 to 4.5, 2.1 to 4.5, 2.4 to 4.5, 3.0 to 4.5, 0.9 to 1.8, or about 1.5 mgs of RAD001 in a sustained release formulation, per day, e.g., delivered once once per day, is administered.

In an embodiment, 0.1 to 30, 0.2 to 30, 2 to 30, 4 to 30, 6 to 30, 8 to 30, 10 to 30, 1.2 to 30, 14 to 30, 16 to 30, 20 to 30, 6 to 12, or about 10 mgs of RAD001 in a sustained release formulation, per week, e.g., delivered once once per week, is administered.

In an embodiment, the dimerization switch comprises: a switch domain comprising a rapamycin, or rapamycin analog, binding sequence from FKBP, and a switch domain comprising a rapamycin, or rapamycin analog, binding sequence from FRB, e.g., a sequence comprising a lysine at residue 2098.

In an embodiment, the dimerization switch comprises: a switch domain comprising a rapamycin analog binding sequence from FKBP, and a switch domain comprising a rapamycin analog binding sequence from FRB, e.g., a sequence comprising a lysine at residue 2098.

In an embodiment, the dimerization switch comprises: a switch domain comprising a AP21967 binding sequence from FKBP, and a switch domain comprising a AP21967 binding sequence from FRB, e.g., a sequence comprising a lysine at residue 2098.

In an embodiment:
the first switch domain comprises,
a rapamycin, or rapamycin analog, binding sequence from FKBP;
a rapamycin analog binding sequence from FKBP; or
an AP21967 binding sequence from FKBP; and,
the second switch domain comprises,
a rapamycin, or rapamycin analog, binding sequence from FRB;
a rapamycin analog binding sequence from FRB; or
an AP21967 binding sequence from FRB, e.g., a sequence comprising a lysine at residue 2098.

In an embodiment:
the first switch domain comprises,
a rapamycin, or rapamycin analog, binding sequence from FRB;
a rapamycin analog binding sequence from FRB; or
an AP21967 binding sequence from FRB, e.g., a sequence comprising a lysine at residue 2098; and,
the second switch domain comprises,
a rapamycin, or rapamycin analog, binding sequence from FKBP;
a rapamycin analog binding sequence from FKBP; or
an AP21967 binding sequence from FKBP.

In an embodiment:
the first switch domain comprises an AP21967 binding sequence from FKBP; and,
the second switch domain comprises an AP21967 binding sequence from FRB, e.g., a sequence comprising a lysine at residue 2098.

In an embodiment, the first switch domain comprises an AP21967 binding sequence from FRB, e.g., a sequence comprising a lysine at residue 2098; and,
the second switch domain comprises an AP21967 binding sequence from FKBP.

In an embodiment, the dimerization molecule is a rapamycin analogue, e.g., AP21967.

In an embodiment, the dimerization switch comprises a GyrB-GyrB based switch.

In an embodiment, the dimerization switch comprises: a switch domain comprising a coumermycin binding sequence having at least 80, 85, 90, 95, 98, or 99% identity with the 24 K Da amino terminal sub-domain of GyrB.

In an embodiment, the dimerization switch comprises: a switch domain comprising a coumermycin binding sequence that differs by no more than 10, 9, 8, 7, 6, 5, 4, 3, 2, or 1 amino acid residues from the corresponding sequence of 24 K Da amino terminal sub-domain of GyrB.

In an embodiment, the dimerization switch comprises: a switch domain comprising a coumermycin binding sequence from the 24 K Da amino terminal sub-domain of GyrB.

In an embodiment, the dimerization switch comprises: the 24 K Da amino terminal sub-domain of GyrB.

In an embodiment, the dimerization molecule is a coumermycin.

In an embodiment, the dimerization switch comprises a GAI-GID1 based switch.

In an embodiment, the dimerization switch comprises: a GID1 switch domain comprising a gibberellin, or gibberellin analog, e.g., $GA_3$, binding sequence having at least 80, 85, 90, 95, 98, or 99% identity with GID1, and a switch domain comprising a GAI switch domain having at least 80, 85, 90, 95, 98, or 99% identity with GAI.

In an embodiment, the dimerization switch comprises: a GID1 switch domain comprising a gibberellin, or gibberellin analog, e.g., $GA_3$, binding sequence that differs by no more than 10, 9, 8, 7, 6, 5, 4, 3, 2, or 1 amino acid residues from the corresponding sequence of FKBP, and a GAI switch domain that differs by no more than 10, 9, 8, 7, 6, 5, 4, 3, 2, or 1 amino acid residues from the corresponding sequence of FRB.

In an embodiment:
the first switch domain comprises a GID1 switch domain; and,
the second switch domain comprises a GAI switch domain.

In an embodiment:
the first switch domain comprises a GAI switch domain; and,
the second switch domain comprises a GID1 switch domain.

In an embodiment, the dimerization molecule is $GA_3$-AM.

In an embodiment, the dimerization molecule is $GA_3$.

In an embodiment, the dimerization molecule is a small molecule, e.g., is other than a polypeptide.

In an embodiment, the dimerization molecule is a polypeptide, e.g., a polypeptide, e.g., an antibody molecule, or a non-antibody scaffold, e.g., a fribronectin or adnectin, having specific affinity for one or both of the first and second switch domains.

In an embodiment, the dimerization molecule, e.g. a polypeptide, is an antibody molecule.

In an embodiment, the dimerization switch comprises a Halotag/SNAP-tag based switch.

In an embodiment, the dimerization switch comprises: a Halotag switch domain comprising having at least 80, 85, 90, 95, 98, or 99% identity with SEQ ID NO: 14, and a SNAP-tag switch domain having at least 80, 85, 90, 95, 98, or 99% identity with SEQ ID NO: 15.

In an embodiment the dimerization switch comprises: a Halotag switch domain comprising that differs by no more than 10, 9, 8, 7, 6, 5, 4, 3, 2, or 1 amino acid residues from SEQ ID NO: 14, and a SNAP-tag switch domain that differs by no more than 10, 9, 8, 7, 6, 5, 4, 3, 2, or 1 amino acid residues from SEQ ID NO: 15.

In an embodiment:
the first switch domain comprises a Halotag switch domain; and,
the second switch domain comprises a SNAP-tag switch domain.

In an embodiment:
the first switch domain comprises a SNAP-tag switch domain; and,
the second switch domain comprises a Halotag switch domain.

In an embodiment the dimerization molecule comprises structure 5.

In an embodiment the dimerization molecule comprises three or more domains, e.g., protein tags that bind a switch domain, e.g., a polypeptide, e.g., an antibody molecule or non-antibody scaffold, having affinity for the domain.

In an embodiment, the dimerization molecule is a non-covalent dimerization molecule.

In an embodiment, the dimerization molecule is covalent dimerization molecule.

In an embodiment, the dimerization switch, e.g., a homodimerization switch, e.g., an extracellular homodimerization switch, comprises switch domains that comprise tag molecules, e.g., a c-myc peptide tag, flag peptide tag, HA peptide tag or V5 peptide tag, and the dimerization switch comprises polypeptides with affinity for the switch domains, e.g., antibody molecules and non-antibody scaffold.

In an embodiment, the RCAR further comprises a second order dimerization switch.

In an embodiment, the dimerization molecule has a valency of greater than two, e.g., it is multi-valent, and binds, and thus clusters or dimerizes, more than two switch domains.

In an embodiment, the antigen binding member comprises
an antigen binding domain,
a transmembrane domain,
a switch domain, and
a costimulatory signaling domain, e.g., a costimulatory signaling domain from Table 2, e.g., a 4-1BB domain.

In an embodiment, the RCAR comprises:
a) a costimulatory ECD member comprising
a costimulatory ECD domain;
a transmembrane region,
an intracellular signaling domain, e.g., a costimulatory signaling domain, e.g., selected from Table 2, e.g., a 4-1BB domain, and
a switch domain;
b) an intracellular signaling member comprising
an intracellular signaling domain, e.g., a primary intracellular signaling domain, e.g., selected from Table 1, e.g., a CD3zeta domain, and
a switch domain; and optionally,
c) an antigen binding member comprising
an antigen binding domain;
a transmembrane domain;
a switch domain and,
optionally, an intracellular signaling domain, e.g., a costimulatory signaling domain, e.g., selected from Table 2, e.g., a 4-1BB domain.

In an embodiment, the order of elements on the costimulatory ECD member is as follows, beginning with the amino terminus:
a costimulatory ECD domain/transmembrane domain/intracellular signaling domain, e.g., a costimulatory signaling domain, e.g., selected from Table 2, e.g., a 4-1BB domain/switch domain; or
a costimulatory ECD domain/transmembrane domain/switch domain/intracellular signaling domain, e.g., a costimulatory signaling domain, e.g., selected from Table 2, e.g., a 4-1BB domain.

In an embodiment, the order of elements on the intracellular signaling member is as follows, beginning with the amino terminus:
switch domain/intracellular signaling domain, e.g., a primary intracellular signaling domain, e.g., selected from Table 1, e.g., a CD3zeta domain; or
intracellular signaling domain, e.g., a primary intracellular signaling domain, e.g., selected from Table 1, e.g., a CD3zeta domain/switch domain.

In an embodiment, the order of elements on the a costimulatory ECD member is as follows, beginning with the carboxy terminus:
a costimulatory ECD domain/transmembrane domain/intracellular signaling domain, e.g., a costimulatory signaling domain, e.g., selected from Table 2, e.g., a 4-1BB domain/switch domain; or
a costimulatory ECD domain/transmembrane domain/switch domain/intracellular signaling domain, e.g., a costimulatory signaling domain, e.g., selected from Table 2, e.g., a 4-1BB domain.

In an embodiment, the order of elements on the intracellular signaling member is as follows, beginning with the carboxy terminus:
switch domain/intracellular signaling domain, e.g., a primary intracellular signaling domain, e.g., selected from Table 1, e.g., a CD3zeta domain; or
intracellular signaling domain, e.g., a primary intracellular signaling domain, e.g., selected from Table 1, e.g., a CD3zeta domain/switch domain.

In an embodiment, the first and second switch domains form a FKBP-FRB based switch.

In an embodiment, the one of the first and second dimerization switches comprises: a switch domain comprising rapamycin or a rapamycin analog binding sequence having at least 80, 85, 90, 95, 98, or 99% identity with FKBP, and the other comprises a switch domain comprising a rapamycin or rapamycin analog binding sequence binding sequence having at least 80, 85, 90, 95, 98, or 99% identity with FRB.

In an embodiment, wherein the switch is an FKBP-FRB based switch, the dimerization molecule is an mTOR inhibitor, e.g., an allosteric mTOR inhibitor, e.g., rapamycin or a rapalog, e.g., RAD001.

In an embodiment, any of the dosing regimes or formulations of an allosteric mTOR inhibitor, e.g., RAD001, described in the section here for a low, immune enhancing, dose of an allosteric mTOR inhibitor, e.g., RAD001, can be administered to dimerize an FKBP-FRB based switch.

In an embodiment, the switch is an FKBP-FRB based switch and the dimerization molecule is RAD001.

In an embodiment, 0.1 to 20, 0.5 to 10, 2.5 to 7.5, 3 to 6, or about 5, mgs of RAD001 per week, e.g., delivered once per week, is administered.

In an embodiment, 0.3 to 60, 1.5 to 30, 7.5 to 22.5, 9 to 18, or about 15 mgs of RAD001 in a sustained release formuation, per week, e.g., delivered once per week, is administered.

In an embodiment, 0.005 to 1.5, 0.01 to 1.5, 0.1 to 1.5, 0.2 to 1.5, 0.3 to 1.5, 0.4 to 1.5, 0.5 to 1.5, 0.6 to 1.5, 0.7 to 1.5, 0.8 to 1.5, 1.0 to 1.5, 0.3 to 0.6, or about 0.5 mgs of RAD001 per day, e.g., delivered once once per day, is administered.

In an embodiment, 0.015 to 4.5, 0.03 to 4.5, 0.3 to 4.5, 0.6 to 4.5, 0.9 to 4.5, 1.2 to 4.5, 1.5 to 4.5, 1.8 to 4.5, 2.1 to 4.5, 2.4 to 4.5, 3.0 to 4.5, 0.9 to 1.8, or about 1.5 mgs of RAD001 in a sustained release formulation, per day, e.g., delivered once once per day, is administered.

In an embodiment, 0.1 to 30, 0.2 to 30, 2 to 30, 4 to 30, 6 to 30, 8 to 30, 10 to 30, 1.2 to 30, 14 to 30, 16 to 30, 20 to 30, 6 to 12, or about 10 mgs of RAD001 in a sustained release formulation, per week, e.g., delivered once once per week, is administered.

In an embodiment, the dimerization switch comprises a GyrB-GyrB based switch, e.g., an GyrB-GyrB based switch described herein, e.g., an GyrB-GyrB based switch as described herein, e.g., in the Dimerization Switch Module.

In an embodiment, the dimerization switch comprises a GAI-GID1 based switch, e.g., an GAI-GID1 based switch described herein, e.g., an GAI-GID1 based switch as described herein, e.g., in the Dimerization Switch Module.

In an embodiment, the dimerization switch comprises a Halotag/SNAP-tag based switch, e.g., a Halotag/SNAP-tag based switch described herein, e.g., a Halotag/SNAP-tag based switch as described herein, e.g., in the Dimerization Switch Module.

In an embodiment, the RCAR comprises:
a) an intracellular signaling member comprising, beginning with the amino terminus:
a CD3zeta domain, and
a first switch domain; and
b) a costimulatory ECD domain member comprising, beginning with the amino terminus:
a costimulatory ECD domain,
a transmembrane domain,
a 4-1BB domain, and
a second switch domain,
wherein the first and second switch domains form a FKBP-FRB based switch.

In an embodiment, the RCAR is associated with, e.g., is provided in the same cell with:
an inhibitor of an inhibitory molecule, e.g., an inhibitor of a inhibitory molecule of Table 3.

In an embodiment, the RCAR is associated with, e.g., is provided in the same cell with an shRNA that targets a inhibitory molecule, e.g. a coinhibitory molecule from Table 3.

In an embodiment, the RCAR further comprises: a shRNA that targets PD1.

In an embodiment, the antigen binding domain binds to a target antigen on a cancer cell but does not activate the RCARX cell, e.g., a RCART cell, until a dimerization molecule is administered.

In an embodiment, the antigen binding domain binds to a target antigen on a target cell, e.g., a cancer cell, but does not promote an immune effector response, e.g., a T cell activation, until the dimerization molecule, e.g., a heterodimerization molecule or homodimerization molecule, is administered.

The invention also provides RCARs having a configuration that allows switching of proliferation. For example, upon antigen encounter, the RCAR exhibits constitute primary signal, e.g., target cell killing, and allows regulation of a second signal, e.g., proliferation, survival, and cytokine secretion.

Accordingly, in another aspect, the invention features, a regulatable chimeric antigen receptor (RCAR), e.g., an isolated RCAR, wherein the RCAR comprises:
a) an intracellular signaling member comprising:
optionally, a transmembrane domain or membrane tethering domain;
a co-stimulatory signaling domain, selected e.g., from Table 2, and
a switch domain; and
b) an antigen binding member comprising:
an antigen binding domain,
a transmembrane domain, and
a primary intracellular signaling domain, e.g., selected from Table 1, e.g., a CD3zeta domain,
wherein the antigen binding member does not comprise a switch domain, or does not comprise a switch domain that dimerizes with a switch domain on the intracellular signaling member.

In an embodiment, the antigen binding member does not comprise a costimulatory signaling domain.

In an embodiment, the intracellular signaling member comprises a second costimulatory signaling domain, selected, e.g., from Table 2. In an embodiment, the two or more costimulatory domains can be the same costimulatory signaling domain, e.g., selected from the list in Table 2, or different costimulatory signaling domains, e.g., selected from the list in Table 2. In an embodiment the intracellular signaling member comprises: a plurality, e.g., 2 or 3, co-stimulatory signaling domains selected from 41BB, CD28, CD27, ICOS, and OX40.

In an embodiment, the intracellular signaling member comprises the following co-stimulatory signaling domains, from the extracellular to intracellular direction:
41BB-CD27;
CD27-41BB;
41BB-CD28;
CD28-41BB;
OX40-CD28;
CD28-OX40;
CD28-41BB; or
41BB-CD28.

In an embodiment, the intracellular signaling member comprises the following co-stimulatory signaling domains: CD28-41BB.

In an embodiment, intracellular signaling member comprises the following co-stimulatory signaling domains: CD28-OX40.

In an embodiment, in addition to one or a plurality of co-stimulatory signaling domains, the intracellular signaling member comprises a primary intracellular signaling domain, e.g., selected from Table 1, e.g., a CD3zeta domain.

In an embodiment, the intracellular signaling domain comprises a CD28 co-stimulatory signaling domain, a 4-1BB co-stimulatory signaling domain, and a CD3zeta domain.

In an embodiment, the intracellular signaling domain comprises a CD28 co-stimulatory signaling domain, a OX40 co-stimulatory signaling domain, and a CD3zeta domain.

In an embodiment, the intracellular signaling member does not comprise a transmembrane domain or membrane tethering domain. In such embodiments, the switch domain is intracellular. In such embodiments, the intracellular signaling member comprises two costimulatory signaling domains, where the two costimulatory domains are selected from 4-1BB, OX40, CD27, CD28, and ICOS. In an embodiment, the order of elements on the intracellular signaling member is as follows, from the extracellular to intracellular direction:
a first co-stimulatory signaling domain/a second costimulatory signaling domain and a switch domain disposed between any of the signaling elements, or, from the extracellular to intracellular direction, after all other signaling elements. See, e.g., FIG. 56D.

In an embodiment, the intracellular signaling member comprises a transmembrane domain. In such embodiments the switch domain can be intracellular or extracellular. In such embodiments, the intracellular signaling member comprises two costimulatory signaling domains, where the two costimulatory domains are selected from 4-1BB, OX40, CD27, CD28, and ICOS.

In an embodiment where the switch domain is extracellular, the order of elements on the intracellular signaling member is as follows, from the extracellular to intracellular direction:

a switch domain/a transmembrane domain/a first co-stimulatory signaling domain/a second costimulatory signaling domain. See, e.g., FIG. 56C.

In an embodiment where the switch domain is intracellular, the order of elements on the intracellular signaling member is as follows, rom the extracellular to intracellular direction:

transmembrane domain/a first co-stimulatory signaling domain/a second costimulatory signaling domain and a switch domain disposed intracellularly between any of the signaling elements, or, from extracellular to intracellular, after all other signaling elements. See, e.g., FIG. 56A.

In an embodiment, the intracellular signaling member comprises a membrane tethering domain. In one such embodiment, the switch domain is intracellular. In such embodiments, the intracellular signaling member comprises two costimulatory signaling domains, where the two costimulatory domains are selected from 4-1BB, OX40, CD27, CD28, and ICOS. In an embodiment, the order of elements on the intracellular signaling member is as follows, from the extracellular to intracellular direction:

a membrane tethering domain/a first co-stimulatory signaling domain/a second costimulatory signaling domain and a switch domain disposed extracellularly, between any of the signaling elements, or, from extracellular to intracellular, after all other signaling elements. See, e.g., FIG. 56B.

In an embodiment, the switch domain is: extracellular; disposed between the transmembrane domain or membrane tethering domain and a co-stimulatory signaling domain, e.g., the costimulatory signaling domain closest to the membrane; between a first and second costimulatory signaling domain; between a costimulatory signaling domain and a primary intracellular signaling domain; or, from extracellular to intracellular, after all intracellular signaling domains.

In an embodiment, the order of elements on the intracellular signaling member, from extracellular to intracellular, is as follows:

transmembrane domain or membrane tethering domain/a first co-stimulatory signaling domain/optionally a second costimulatory signaling domain/and optionally a primary intracellular signaling domain, and a switch domain disposed extracellularly, between any of the elements, or, from extracellular to intracellular, after all other elements.

In an embodiment, the order of elements on the antigen binding member, from extracellular to intracellular, is as follows:

antigen binding domain/transmembrane domain/primary intracellular signaling domain, e.g., selected from Table 1, e.g., a CD3zeta domain.

In an embodiment, the intracellular signaling member comprises a switch domain from a homodimerization switch.

In an embodiment, the intracellular signaling member comprises a first switch domain of a heterodimerization switch and the RCAR comprises a second intracellular signaling member which comprises a second switch domain of the heterodimerization switch. In embodiments, the second intracellular signaling member comprises the same intracellular signaling domains as the intracellular signaling member.

In an embodiment, the antigen binding member comprises a plurality of, e.g., 2, 3, 4, or 5, antigen binding domains, e.g., scFvs, wherein each antigen binding domain binds to a target antigen. In an embodiment, two or more of the antigen binding domains can bind to different antigens. In an embodiment, two or more of the antigen binding domains can bind to the same antigen, e.g., the same or different epitopes on the same antigen. In embodiments, a linker or hinge region is optionally disposed between two or each of the antigen binding domains.

In an embodiment the dimerization switch is intracellular.

In an embodiment the dimerization switch is extracellular.

In an embodiment, the dimerization switch comprises a FKBP-FRB based switch.

In an embodiment, the dimerization switch comprises: a switch domain comprising a rapamycin analog binding sequence having at least 80, 85, 90, 95, 98, or 99% identity with FKBP, and a switch domain comprising a rapamycin analog binding sequence binding sequence having at least 80, 85, 90, 95, 98, or 99% identity with FRB.

In an embodiment, the dimerization switch comprises: a switch domain comprising a rapamycin analog binding sequence that differs by no more than 10, 9, 8, 7, 6, 5, 4, 3, 2, or 1 amino acid residues from the corresponding sequence of FKBP, and a switch domain comprising a rapamycin analog binding sequence that differs by no more than 10, 9, 8, 7, 6, 5, 4, 3, 2, or 1 amino acid residues from the corresponding sequence of FRB.

In an embodiment, the dimerization switch comprises a FRB binding fragment or analog of FKBP and an FKBP binding fragment or analog of FRB, and the FKBP binding fragment or analog of FRB comprises one or more mutations which increase the affinity of binding with rapamycin or a rapalog, e.g., RAD001, or a mutation described in the section herein entitled MODIFIED FKBP/FRB-BASED DIMERIZATION SWITCHES. E.g., the FKBP binding fragment or analog of FRB comprises: an E2032 mutation, e.g., an E2032I mutation or E2032L mutation; a T2098 mutation, e.g., a T2098L mutation; or an E2032 and a T2098 mutation, e.g., an E2032I and a T2098L or an E2032L and a T2098L mutation.

In an embodiment, the dimerization switch is a multi switch comprising a plurality of, e.g., 2, 3, 4, 5, 6, 7, 8, 9, or 10, switch domains, independently, on the intracellular signaling member. In embodiments where the intracellular signaling member comprises a plurality of first switch domains of a heterodimerization switch, e.g., FKBP-based switch domains, the RCAR further comprises a second intracellular signaling member comprising a plurality of second switch domains of a heterodimerization switch, e.g., FRB-based switch domains. In embodiments where the intracellular signaling member comprises a first and a second switch domain, e.g., a FKBP-based switch domain and a FRB-based switch domain, the RCAR further comprises a second intracellular signaling member comprising a first and a second switch domain, e.g., a FKBP-based switch domain and a FRB-based switch domain.

In an embodiment, wherein the switch is an FKBP-FRB based switch, the dimerization molecule is an mTOR inhibitor, e.g., an allosteric mTOR inhibitor, e.g., rapamycin or a rapalog, e.g., RAD001.

In an embodiment, any of the dosing regimes or formulations of an allosteric mTOR inhibitor, e.g., RAD001, described in the section here for a low, immune enhancing, dose of an allosteric mTOR inhibitor, e.g., RAD001, can be administered to dimerize an FKBP-FRB based switch.

In an embodiment, the switch is an FKBP-FRB based switch and the dimerization molecule is RAD001.

In an embodiment, 0.1 to 20, 0.5 to 10, 2.5 to 7.5, 3 to 6, or about 5, mgs of RAD001 per week, e.g., delivered once per week, is administered.

In an embodiment, 0.3 to 60, 1.5 to 30, 7.5 to 22.5, 9 to 18, or about 15 mgs of RAD001 in a sustained release formulation, per week, e.g., delivered once per week, is administered.

In an embodiment, 0.005 to 1.5, 0.01 to 1.5, 0.1 to 1.5, 0.2 to 1.5, 0.3 to 1.5, 0.4 to 1.5, 0.5 to 1.5, 0.6 to 1.5, 0.7 to 1.5, 0.8 to 1.5, 1.0 to 1.5, 0.3 to 0.6, or about 0.5 mgs of RAD001 per day, e.g., delivered once once per day, is administered.

In an embodiment, 0.015 to 4.5, 0.03 to 4.5, 0.3 to 4.5, 0.6 to 4.5, 0.9 to 4.5, 1.2 to 4.5, 1.5 to 4.5, 1.8 to 4.5, 2.1 to 4.5, 2.4 to 4.5, 3.0 to 4.5, 0.9 to 1.8, or about 1.5 mgs of RAD001 in a sustained release formulation, per day, e.g., delivered once once per day, is administered.

In an embodiment, 0.1 to 30, 0.2 to 30, 2 to 30, 4 to 30, 6 to 30, 8 to 30, 10 to 30, 1.2 to 30, 14 to 30, 16 to 30, 20 to 30, 6 to 12, or about 10 mgs of RAD001 in a sustained release formulation, per week, e.g., delivered once once per week, is administered.

In an embodiment, the dimerization switch comprises: a switch domain comprising a rapamycin, or rapamycin analog, binding sequence from FKBP, and a switch domain comprising a rapamycin, or rapamycin analog, binding sequence from FRB, e.g., a sequence comprising a lysine at residue 2098.

In an embodiment, the dimerization switch comprises: a switch domain comprising a rapamycin analog binding sequence from FKBP, and a switch domain comprising a rapamycin analog binding sequence from FRB, e.g., a sequence comprising a lysine at residue 2098.

In an embodiment, the dimerization switch comprises: a switch domain comprising an AP21967 binding sequence from FKBP, and a switch domain comprising an AP21967 binding sequence from FRB, e.g., a sequence comprising a lysine at residue 2098.

In an embodiment:
the first switch domain comprises,
a rapamycin, or rapamycin analog, binding sequence from FKBP;
a rapamycin analog binding sequence from FKBP; or
an AP21967 binding sequence from FKBP; and,
the second switch domain comprises,
a rapamycin, or rapamycin analog, binding sequence from FRB;
a rapamycin analog binding sequence from FRB; or
an AP21967 binding sequence from FRB, e.g., a sequence comprising a lysine at residue 2098.

In an embodiment:
the first switch domain comprises,
a rapamycin, or rapamycin analog, binding sequence from FRB;
a rapamycin analog binding sequence from FRB; or
an AP21967 binding sequence from FRB, e.g., a sequence comprising a lysine at residue 2098; and,
the second switch domain comprises,
a rapamycin, or rapamycin analog, binding sequence from FKBP;
a rapamycin analog binding sequence from FKBP; or
an AP21967 binding sequence from FKBP.

In an embodiment:
the first switch domain comprises an AP21967 binding sequence from FKBP; and,
the second switch domain comprises an AP21967 binding sequence from FRB, e.g., a sequence comprising a lysine at residue 2098.

In an embodiment, the first switch domain comprises an AP21967 binding sequence from FRB, e.g., a sequence comprising a lysine at residue 2098; and,
the second switch domain comprises an AP21967 binding sequence from FKBP.

In an embodiment, the dimerization molecule is a rapamycin analogue, e.g., AP21967.

In an embodiment, the dimerization switch comprises a GyrB-GyrB based switch.

In an embodiment, the dimerization switch comprises: a switch domain comprising a coumermycin binding sequence having at least 80, 85, 90, 95, 98, or 99% identity with the 24 K Da amino terminal sub-domain of GyrB.

In an embodiment the dimerization switch comprises: a switch domain comprising a coumermycin binding sequence that differs by no more than 10, 9, 8, 7, 6, 5, 4, 3, 2, or 1 amino acid residues from the corresponding sequence of 24 K Da amino terminal sub-domain of GyrB.

In an embodiment, the dimerization switch comprises: a switch domain comprising a coumermycin binding sequence from the 24 K Da amino terminal sub-domain of GyrB.

In an embodiment, the dimerization switch comprises: the 24 K Da amino terminal sub-domain of GyrB.

In an embodiment, the dimerization molecule is a coumermycin.

In an embodiment, the dimerization switch comprises a GAI-GID1 based switch.

In an embodiment, the dimerization switch comprises: a GID1 switch domain comprising a gibberellin, or gibberellin analog, e.g., $GA_3$, binding sequence having at least 80, 85, 90, 95, 98, or 99% identity with GID1, and a switch domain comprising a GAI switch domain having at least 80, 85, 90, 95, 98, or 99% identity with GAI.

In an embodiment, the dimerization switch comprises: a GID1 switch domain comprising a gibberellin, or gibberellin analog, e.g., $GA_3$, binding sequence that differs by no more than 10, 9, 8, 7, 6, 5, 4, 3, 2, or 1 amino acid residues from the corresponding sequence of G1D1, and a GAI switch domain that differs by no more than 10, 9, 8, 7, 6, 5, 4, 3, 2, or 1 amino acid residues from the corresponding sequence of GAI.

In an embodiment:
the first switch domain comprises a GID1 switch domain; and,
the second switch domain comprises a GAI switch domain.

In an embodiment:
the first switch domain comprises a GAI switch domain; and,
the second switch domain comprises a GID1 switch domain.

In an embodiment, the dimerization molecule is $GA_3$-AM.

In an embodiment, the dimerization molecule is $GA_3$.

In an embodiment, the dimerization molecule is a small molecule, e.g., is other than a polypeptide.

In an embodiment, the dimerization molecule is a polypeptide, e.g., a polypeptide, e.g., an antibody molecule, or a non-antibody scaffold, e.g., a fribronectin or adnectin, having specific affinity for one or both of the first and second switch domains.

In an embodiment, the dimerization molecule, e.g. a polypeptide, is an antibody molecule.

In an embodiment, the dimerization switch comprises a Halotag/SNAP-tag based switch.

In an embodiment, the dimerization switch comprises: a Halotag switch domain comprising having at least 80, 85, 90, 95, 98, or 99% identity with SEQ ID NO: 14, and a SNAP-tag switch domain having at least 80, 85, 90, 95, 98, or 99% identity with SEQ ID NO: 15.

In an embodiment, the dimerization switch comprises: a Halotag switch domain comprising that differs by no more than 10, 9, 8, 7, 6, 5, 4, 3, 2, or 1 amino acid residues from SEQ ID NO: 14, and a SNAP-tag switch domain that differs by no more than 10, 9, 8, 7, 6, 5, 4, 3, 2, or 1 amino acid residues from SEQ ID NO: 15.

In an embodiment:

the first switch domain comprises a Halotag switch domain; and, the second switch domain comprises a SNAP-tag switch domain.

In an embodiment:

the first switch domain comprises a SNAP-tag switch domain; and, the second switch domain comprises a Halotag switch domain.

In an embodiment, the dimerization molecule comprises structure 5.

In an embodiment, the dimerization molecule comprises three or more domains, e.g., protein tags that bind a switch domain, e.g., a polypeptide, e.g., an antibody molecule or non-antibody scaffold, having affinity for the domain.

In an embodiment, the dimerization molecule is a non-covalent dimerization molecule.

In an embodiment, the dimerization molecule is covalent dimerization molecule.

In an embodiment, the dimerization switch, e.g., a homodimerization switch, e.g., an extracellular homodimerization switch, comprises switch domains that comprise tag molecules, e.g., a c-myc peptide tag, flag peptide tag, HA peptide tag or V5 peptide tag, and the dimerization switch comprises polypeptides with affinity for the switch domains, e.g., antibody molecules and non-antibody scaffold.

In an embodiment, the RCAR further comprises a second order dimerization switch.

In an embodiment, the dimerization molecule has a valency of greater than two, e.g., it is multi-valent, and binds, and thus clusters or dimerizes, more than two switch domains.

In an embodiment, the RCAR is associated with, e.g., is provided in the same cell with:

an inhibitor of an inhibitory molecule, e.g., an inhibitor of an inhibitory molecule of Table 3.

In an embodiment, the RCAR is associated with, e.g., is provided in the same cell with, a nucleic acid inhibitor, e.g., an siRNA, an shRNA, or an antisense molecule, that targets a inhibitory molecule, e.g. a coinhibitory molecule from Table 3.

In an embodiment, the shRNA targets PD1.

In an embodiment, dimerization increases the level of proliferation or persistence of the RCARX, e.g., RCART, cell.

In an embodiment, the RCAR further comprises:

an inhibitory counter ligand binding member comprising, an inhibitory counter ligand binding domain, selected e.g., from Table 4, and a transmembrane domain or membrane anchor.

In a fifth aspect, the invention features, a nucleic acid, e.g., an isolated nucleic acid, encoding a RCAR described herein.

In an embodiment, sequence encoding the antigen binding member and the intracellular signaling member are present in a single nucleic acid molecule.

In an embodiment, sequence encoding the antigen binding member is operatively linked to a first control region and sequence encoding the intracellular signaling member is operatively linked to a second control region.

In an embodiment, sequence encoding the antigen binding member is transcribed as a first RNA and sequence encoding intracellular signaling member is translated as a second RNA.

In an embodiment, sequence encoding the antigen binding member is present on a first nucleic acid molecule and sequence encoding intracellular signaling member is present on a second nucleic acid molecule.

In an embodiment, sequence encoding the antigen binding member and the intracellular signaling member are present in a single nucleic acid molecule.

In an embodiment, the nucleic acid further comprises a sequence encoding a shRNA targeting a coinhibitory domain.

In an embodiment, sequence encoding the antigen binding member, the intracellular signaling member, and a sequence encoding a shRNA targeting a coinhibitory domain, are present in a single nucleic acid molecule.

In an embodiment, sequence encoding the antigen binding member is present on a first nucleic acid molecule and sequence encoding intracellular signaling member is present on a second nucleic acid molecule and a sequence encoding a shRNA targeting a coinhibitory domain is present on one or both of the first and second nucleic acid molecules.

In an embodiment, sequence encoding the antigen binding member is present on a first nucleic acid molecule, sequence encoding intracellular signaling member is present on a second nucleic acid molecule, and a sequence encoding a shRNA targeting a coinhibitory domain is present on a third nucleic acid molecule.

In an embodiment, the nucleic acid encodes a RCAR as described in any of Tables 6, 7, 8, 9, 10, or 11.

In an embodiment the nucleic acid encodes a RCAR which comprises:

a) an intracellular signaling member comprising:
   an intracellular signaling domain, e.g., a primary intracellular signaling domain, and
   a first switch domain;
b) an antigen binding member comprising:
   an antigen binding domain,
   a second switch domain; and
   optionally, an intracellular signaling domain, e.g., a costimulatory signaling domain, e.g., selected from Table 2, e.g., a 4-1BB domain; and
c) a transmembrane domain wherein:
   i) sequence encoding a and b is disposed on a single nucleic acid molecule, e.g., a viral vector, e.g., a lentivirus vector; or
   ii) sequence encoding a is disposed on a first nucleic acid molecule, e.g., a viral vector, e.g., a lentivirus vector, and sequence encoding b is disposed on a second nucleic acid molecule, e.g., a viral vector, e.g., a lentivirus vector.

In an embodiment the nucleic acid encodes a RCAR which comprises:

a) an intracellular signaling member comprising:
   an intracellular signaling domain, e.g., a primary intracellular signaling domain, and
   a first switch domain;
b) an antigen binding member comprising:
   an antigen binding domain,
   a second switch domain; and
   a transmembrane domain in a or b; and
c) an auxiliary antigen binding member comprising:
   an antigen binding domain that binds a second antigen; and a transmembrane domain or membrane anchoring domain, wherein:
  i) sequence encoding a, b, and c, is disposed on a single nucleic acid molecule, e.g., a viral vector, e.g., a lentivirus vector;
  ii) sequence encoding a and b is disposed on a first nucleic acid molecule, e.g., a viral vector, e.g., a lentivirus vector, and sequence encoding c is disposed on a second nucleic acid molecule, e.g., a viral vector, e.g., a lentivirus vector.
  iii) sequence encoding a and c is disposed on a first nucleic acid molecule, e.g., a viral vector, e.g., a lentivirus vector, and sequence encoding b is disposed on a second nucleic acid molecule, e.g., a viral vector, e.g., a lentivirus vector.
  iv) sequence encoding b and c is disposed on a first nucleic acid molecule, e.g., a viral vector, e.g., a lentivirus vector, and sequence encoding c is disposed on a second nucleic acid molecule, e.g., a viral vector, e.g., a lentivirus vector; or
  v) sequence encoding each of a, b, and c is provided on each of three a separate nucleic acid molecules, e.g., viral vectors, e.g., lentivirus vectors.

In an embodiment, the nucleic acid comprises:
a first nucleic acid molecule encoding a first transmembrane domain and a first intracellular signaling domain, e.g., a primary intracellular signaling domain, and
a second nucleic acid molecule encoding a second transmembrane domain and a second intracellular signaling domain, e.g., a primary intracellular signaling domain, and
a third nucleic acid molecule encoding an antigen binding domain tethered to a membrane anchor,
wherein the first and second transmembrane domains are separated from each other by a heterodimerization switch present on the outside of a cell,
wherein the heterodimerization switch comprises first switch domain and second switch domain, wherein the first and second switch domains of the heterodimerization switch interact together to form a complex in the presence of a heterodimerization molecule on the either the inside or outside of the cell.

In an embodiment, the nucleic acid comprises:
a first nucleic acid molecule encoding an antigen binding domain linked to a membrane anchor,
a second nucleic acid molecule encoding an inhibitory extracellular domain, and a transmembrane domain linked to first switch domain of a heterodimerization switch; and
a third nucleic acid molecule encoding second switch domain of a heterodimerization switch linked to an intracellular signaling domain, e.g., a primary intracellular signaling domain,
wherein the inhibitory extracellular domain is separated from the intracellular signaling domain by a heterodimermerization switch, and
wherein the first and second switch domain interact together to form a complex in the presence of a heterodimerization molecule on the inside or outside, of the cell.

In an embodiment, the nucleic acid comprises:
a first nucleic acid molecule encoding an antigen binding domain that binds to first target, a transmembrane domain linked to first switch domain of a heterodimerization switch,
a second nucleic acid molecule encoding and an intracellular signaling domain, e.g., a primary intracellular signaling domain, wherein the intracellular signaling domain is linked to a second switch domain of a heterodimerization switch, and
a third nucleic acid molecule encoding an antigen binding domain that binds to a second target that is different from the first target and a transmembrane domain, wherein the heterodimermerization switch is present on the inside of a cell, wherein first switch domain and second switch domain interact together to form a complex in the presence of a heterodimerization molecule on the inside of the cell.

In an embodiment, the nucleic acid encodes a RCAR comprising:
  a) an intracellular signaling member;
  b) an antigen binding member;
  c) a second intracellular signaling member,
wherein
  i) sequence encoding a, b and c, is provided on a single nucleic acid molecule;
  ii) sequence encoding two of a, b, and c, is provided on a first nucleic acid molecule and sequence encoding the other is provided on a second nucleic acid molecule; or
  iii) sequence encoding a is provided on a first nucleic acid molecule, sequence encoding b is provided on a second nucleic acid molecule, and sequence encoding c is provided on a third nucleic acid molecule.

In an embodiment the nucleic acid encode a RCAR comprising
  a) an intracellular signaling member;
  b) an antigen binding member;
  c) a second intracellular signaling member,
wherein,
  sequence encoding a and b is provided on a first nucleic acid molecule and sequence encoding c is provided on a second nucleic acid molecule;
  sequence encoding a and c is provided on a first nucleic acid molecule and sequence encoding b is provided on a second nucleic acid molecule; or
  sequence encoding b and c is provided on a first nucleic acid molecule and sequence encoding a is provided on a second nucleic acid molecule.

In an embodiment, the nucleic acid encodes a RCAR comprising:
  a) an intracellular signaling member;
  b) an antigen binding member;
  c) an auxiliary antigen binding member,
wherein
  i) sequence encoding a, b and c, is provided on a single nucleic acid molecule;
  ii) sequence encoding two of a, b, and c, is provided on a first nucleic acid molecule and sequence encoding the other is provided on a second nucleic acid molecule; or
  iii) sequence encoding a is provided on a first nucleic acid molecule, sequence encoding b is provided on a second nucleic acid molecule, and sequence encoding c is provided on a third nucleic acid molecule.

In an embodiment, the nucleic acid encode a RCAR comprising
  a) an intracellular signaling member;
  b) an antigen binding member;
  c) a second intracellular signaling member,
wherein
  sequence encoding a and b is provided on a first nucleic acid molecule and sequence encoding c is provided on a second nucleic acid molecule;
  sequence encoding a and c is provided on a first nucleic acid molecule and sequence encoding b is provided on a second nucleic acid molecule; or sequence encoding b and c is provided on a first nucleic acid molecule and sequence encoding a is provided on a second nucleic acid molecule.

In an embodiment, the nucleic acid encode a RCAR in which the antigen binding domain is separated from the intracellular signaling domain by a dimerization switch comprising a first and a second switch domain, wherein the first switch domain is linked to the antigen binding domain and the second switch domain is linked to the intracellular signaling domain, wherein the first and second switch domains interact together to form a complex in the presence of a dimerization molecule.

In a sixth aspect, the invention features, a vector system, e.g., a vector system comprising one or more vectors, comprising nucleic acid encoding a RCAR described herein.

In an embodiment, all of the elements of a RCAR are encoded on a single vector.

In an embodiment, an element of a RCAR is encoded on a first vector and another element of the RCAR is encoded on a second vector, of the vector system.

In an embodiment, the vector system comprises a DNA, a RNA, a plasmid, a lentivirus vector, adenoviral vector, or a retrovirus vector.

In an embodiment, the vector system comprises a bi-cistronic or tri-cistronic lentivirus vector.

In an embodiment, the vector system comprises a bi-cistronic or tri-cistronic promoter.

In a seventh aspect, the invention features, a cell comprising a vector system described herein.

In an embodiment, the cell is a human cell.

In an embodiment, the cell is a T cell.

In an embodiment, the cell is a NK cell.

In an eighth aspect, the invention features, a method of making a RCARX cell described herein comprising introducing a vector system described herein into said cell.

In a ninth aspect, the invention features, a method of treating a mammal, e.g., a method of providing an anti-tumor immunity in a mammal, comprising administering to the mammal an effective amount of a RCARX cell described herein.

In an embodiment, the RCARX cell is an autologous T cell.

In an embodiment, the RCARX cell is an allogeneic T cell.

In an embodiment, the RCARX cell is an autologous NK cell.

In an embodiment, the RCARX cell is an allogeneic NK cell.

In an embodiment, the mammal is a human.

In an embodiment, the method comprises treating a mammal, e.g., a human, having a disease associated with expression of EGFRvIII.

In an embodiment, the disease associated with EGFRvIII expression is a proliferative disease, cancer, a precancerous condition, or a non-cancer related indication associated with expression of EGFRvIII.

In an embodiment, the proliferative disease is a glioblastoma.

In an embodiment, the proliferative disease is chronic lymphocytic leukemia (CLL).

In an embodiment, the proliferative disease is CLL and the antigen binding domain of the RCAR targets CD19.

In an embodiment, the cancer is selected from glioblastoma multiforme (GBM), anaplastic astrocytoma, giant cell glioblastoma, gliosarcoma, anaplastic oligodendroglioma, anaplastic ependymoma, choroid plexus carcinoma, anaplastic ganglioglioma, pineoblastoma, medulloepithelioma, ependymoblastoma, medulloblastoma, supratentorial primitive neuroectodermal tumor, and atypical teratoid/rhabdoid tumor, non-small cell lung carcinomas, lung, breast, prostate, ovarian, colorectal and bladder carcinoma.

In an embodiment, further comprising evaluating said human for a side effect of said treatment.

In an embodiment, the side effect comprises acute respiratory distress syndrome, febrile neutropenia, hypotension, encephalopathy, hepatic transaminitis, seizure, or macrophage activation syndrome.

In an embodiment, the method further comprises treating said human, e.g., a human having a side effect, with anti-cytokine agent, e.g., a tumor necrosis factor antagonist, e.g., a TNF-Ig fusion, e.g., etanercept, an IL-6 antagonist, e.g., an IL-6 receptor antagonist, e.g., an anti-IL6 receptor antibody, e.g., tocilizumab, or a corticosteroid.

In an embodiment the method comprises administering an anti-IL6 receptor antibody to said human.

In an embodiment, wherein the switch is an FKBP-FRB based switch, the dimerization molecule is an mTOR inhibitor, e.g., an allosteric mTOR inhibitor, e.g., rapamycin or a rapalog, e.g., RAD001.

In an embodiment, the FKBP-FRB based switch comprises a switch domain comprising a FRB binding fragment or analog of FKBP and a switch domain comprising an FKBP binding fragment or analog of FRB, and the FKBP binding fragment or analog of FRB comprises one or more mutations which enhances the formation of a complex between an FKBP switch domain, an FRB switch domain, and the dimerization molecule, or a mutation described in the section herein entitled MODIFIED FKBP/FRB-BASED DIMERIZATION SWITCHES. E.g., the FKBP binding fragment or analog of FRB comprises: an E2032 mutation, e.g., an E2032I mutation or E2032L mutation; a T2098 mutation, e.g., a T2098L mutation; or an E2032 and a T2098 mutation, e.g., an E2032I and a T2098L or an E2032L and a T2098L mutation.

In an embodiment, any of the dosing regimes or formulations of an allosteric mTOR inhibitor, e.g., RAD001, described in the section here for a low, immune enhancing, dose of an allosteric mTOR inhibitor, e.g., RAD001, can be administered to dimerize an FKBP-FRB based switch.

In an embodiment, the switch is an FKBP-FRB based switch and the dimerization molecule is RAD001.

In an embodiment, the switch is an FKBP-FRB based switch and 0.1 to 20, 0.5 to 10, 2.5 to 7.5, 3 to 6, or about 5, mgs of RAD001 per week, e.g., delivered once per week, is administered.

In an embodiment, the switch is an FKBP-FRB based switch and 0.3 to 60, 1.5 to 30, 7.5 to 22.5, 9 to 18, or about 15 mgs of RAD001 in a sustained release formuation, per week, e.g., delivered once per week, is administered.

In an embodiment, the switch is an FKBP-FRB based switch and 0.005 to 1.5, 0.01 to 1.5, 0.1 to 1.5, 0.2 to 1.5, 0.3 to 1.5, 0.4 to 1.5, 0.5 to 1.5, 0.6 to 1.5, 0.7 to 1.5, 0.8 to 1.5, 1.0 to 1.5, 0.3 to 0.6, or about 0.5 mgs of RAD001 per day, e.g., delivered once once per day, is administered.

In an embodiment, the switch is an FKBP-FRB based switch and 0.015 to 4.5, 0.03 to 4.5, 0.3 to 4.5, 0.6 to 4.5, 0.9 to 4.5, 1.2 to 4.5, 1.5 to 4.5, 1.8 to 4.5, 2.1 to 4.5, 2.4 to 4.5, 3.0 to 4.5, 0.9 to 1.8, or about 1.5 mgs of RAD001 in a sustained release formulation, per day, e.g., delivered once once per day, is administered.

In an embodiment, the switch is an FKBP-FRB based switch and 0.1 to 30, 0.2 to 30, 2 to 30, 4 to 30, 6 to 30, 8 to 30, 10 to 30, 1.2 to 30, 14 to 30, 16 to 30, 20 to 30, 6 to 12, or about 10 mgs of RAD001 in a sustained release formulation, per week, e.g., delivered once once per week, is administered.

The use of low, immune enhancing, doses of mTOR inhibitors, e.g., for optimizing the ratio of PD-1 negative immune effector cells/PD-1 positive immune effector cells, is described herein (see the section entitled "Adjunctive Treatment With A Low, Immune Enhancing, Dose of An mTOR Inhibitor"). In an embodiment, an allosteric mTOR inhibitor, e.g., RAD001, dosing regime, or formulation, from that section can be used as a dimerization molecule with FKBP/FRB dimerization switches.

In an embodiment, the method comprises administering to the subject a low, immune enhancing, dose of an mTOR inhibitor, e.g., RAD001 or rapamycin, e.g., to optimize the ratio of PD1 negative T cells/PD1 positive T cells.

In an embodiment, the dose comprises an allosteric mTOR inhibitor, a catalytic mTOR inhibitor, or both.

In an embodiment, the mTOR inhibitor is administered for an amount of time sufficient to decrease the proportion of PD-1 positive T cells, increase the proportion of PD-1 negative T cells, or increase the ratio of PD-1 negative T cells/PD-1 positive T cells, in the peripheral blood of the subject, or in a preparation of T cells isolated from the subject.

In an embodiment, the low, immune enhancing, dose of an mTOR inhibitor is administered prior to administration of immune effector cells, e.g., T cells to be engineered to express an RCAR, (e.g., prior to or after harvest of the immune effector cells) for an amount of time sufficient for one or more of the following to occur:

i) a decrease in the number of PD-1 positive immune effector cells;

ii) an increase in the number of PD-1 negative immune effector cells;

iii) an increase in the ratio of PD-1 negative immune effector cells/PD-1 positive immune effector cells;

iv) an increase in the number of naive T cells;

v) an increase in the expression of one or more of the following markers: $CD62L^{high}$, $CD127^{high}$, $CD27^+$, and BCL2, e.g., on memory T cells, e.g., memory T cell precursors;

vi) a decrease in the expression of KLRG1, e.g., on memory T cells, e.g., memory T cell precursors; or vii) an increase in the number of memory T cell precursors, e.g., cells with any one or combination of the following characteristics: increased $CD62L^{high}$, increased $CD127^{high}$, increased $CD27^+$, decreased KLRG1, and increased BCL2;

and wherein i), ii), iii), iv), v), vi), or vii) occurs e.g., at least transiently, e.g., as compared to a non-treated subject.

In an embodiment, the low, immune enhancing, dose of an mTOR inhibitor is administered prior to harvest of immune effector cells, e.g., T cells to be engineered to express an RCAR, for an amount of time sufficient for one or more of the following to occur, e.g., to occur in the harvested cells or in the engineered cells (or in non-harvested cells, or in both):

i) a decrease in the number of PD-1 positive immune effector cells;

ii) an increase in the number of PD-1 negative immune effector cells;

iii) an increase in the ratio of PD-1 negative immune effector cells/PD-1 positive immune effector cells;

iv) an increase in the number of naive T cells;

v) an increase in the expression of one or more of the following markers: $CD62L^{high}$, $CD127^{high}$, $CD27^+$, and BCL2, e.g., on memory T cells, e.g., memory T cell precursors;

vi) a decrease in the expression of KLRG1, e.g., on memory T cells, e.g., memory T cell precursors; or vii) an increase in the number of memory T cell precursors, e.g., cells with any one or combination of the following characteristics: increased $CD62L^{high}$, increased $CD127^{high}$, increased $CD27^+$, decreased KLRG1, and increased BCL2;

and wherein i), ii), iii), iv), v), vi), or vii) occurs e.g., at least transiently, e.g., as compared to a non-treated subject.

In an embodiment, the immune effector cell, e.g., T cell, to be engineered to express a RCAR, is harvested at least 5, 10, 15, 20, 25, 30, 35, 40, 45, 50, 55, or 60 days after initiation, or completion, of dosing with the low, immune enhancing, dose of an mTOR inhibitor.

In an embodiment, the low, immune enhancing, dose of an mTOR inhibitor is administered after harvest of immune effector cells, e.g., T cells to be engineered to express an RCAR, for an amount of time sufficient for one or more of the following to occur:

i) a decrease in the number of PD-1 positive immune effector cells;

ii) an increase in the number of PD-1 negative immune effector cells;

iii) an increase in the ratio of PD-1 negative immune effector cells/PD-1 positive immune effector cells;

iv) an increase in the number of naive T cells;

v) an increase in the expression of one or more of the following markers: $CD62L^{high}$, $CD127^{high}$, $CD27^+$, and BCL2, e.g., on memory T cells, e.g., memory T cell precursors;

vi) a decrease in the expression of KLRG1, e.g., on memory T cells, e.g., memory T cell precursors; or vii) an increase in the number of memory T cell precursors, e.g., cells with any one or combination of the following characteristics: increased $CD62L^{high}$, increased $CD127^{high}$, increased $CD27^+$, decreased KLRG1, and increased BCL2;

and wherein i), ii), iii), iv), v), vi), or vii) occurs e.g., at least transiently, e.g., as compared to a non-treated subject.

In an embodiment, the low, immune enhancing, dose of an mTOR inhibitor is administered after administration of immune effector cells, e.g., T cells to be engineered to express an RCAR, for an amount of time sufficient for one or more of the following to occur:

i) a decrease in the number of PD-1 positive immune effector cells;

ii) an increase in the number of PD-1 negative immune effector cells;

iii) an increase in the ratio of PD-1 negative immune effector cells/PD-1 positive immune effector cells;

iv) an increase in the number of naive T cells;

v) an increase in the expression of one or more of the following markers: $CD62L^{high}$, $CD127^{high}$, $CD27^+$, and BCL2, e.g., on memory T cells, e.g., memory T cell precursors;

vi) a decrease in the expression of KLRG1, e.g., on memory T cells, e.g., memory T cell precursors; or vii) an increase in the number of memory T cell precursors, e.g., cells with any one or combination of the following characteristics: increased $CD62L^{high}$, increased $CD127^{high}$, increased $CD27^+$, decreased KLRG1, and increased BCL2;

and wherein i), ii), iii), iv), v), vi), or vii) occurs e.g., at least transiently, e.g., as compared to a non-treated subject.

In other embodiments, immune effector cells, e.g., T cells, which have, or will be engineered to express a RCAR, are treated ex vivo by contact with an amount of an mTOR inhibitor that optimizes performance. While not wishing to be bound by theory, it is believed that in an embodiment, one or more of the following occurs:

a decrease in the number of PD-1 positive immune effector cells;

an increase in the number of PD-1 negative immune effector cells;

an increase in the ratio of PD-1 negative immune effector cells/PD-1 positive immune effector cells;

an increase in the number of naive T cells;

an increase in the expression of one or more of the following markers: $CD62L^{high}$, $CD127^{high}$, $CD27^+$, and BCL2, e.g., on memory T cells, e.g., memory T cell precursors;

a decrease in the expression of KLRG1, e.g., on memory T cells, e.g., memory T cell precursors; or an increase in the number of memory T cell precursors, e.g., cells with any one or combination of the following characteristics: increased $CD62L^{high}$, increased $CD127^{high}$, increased $CD27^+$, decreased KLRG1, and increased BCL2;

and wherein any of the changes described above occurs, e.g., at least transiently, e.g., as compared to a non-treated cell.

In an embodiment, the dose of an mTOR inhibitor is associated with mTOR inhibition of at least 5 but no more than 90%, e.g., as measured by p70 S6K inhibition.

In an embodiment, the dose of an mTOR inhibitor is associated with mTOR inhibition of at least 10% but no more than 40%, e.g., as measured by p70 S6K inhibition.

In an embodiment, administering comprises administering, e.g., once per week, e.g., in an immediate release dosage form, 0.1 to 20, 0.5 to 10, 2.5 to 7.5, 3 to 6, or about 5, mgs of RAD001, or an mTOR inhibitor other than RAD001 that is bioequivalent to a once per week, immediate release dosage form of 0.1 to 20, 0.5 to 10, 2.5 to 7.5, 3 to 6, or about 5, mgs of RAD001.

In an embodiment, administering comprises administering, e.g., once per week, e.g., in a sustained release dosage form, 0.3 to 60, 1.5 to 30, 7.5 to 22.5, 9 to 18, or about 15 mgs of RAD001, or an mTOR inhibitor other than RAD001 that is bioequivalent to a once per week, sustained release dosage form of 0.3 to 60, 1.5 to 30, 7.5 to 22.5, 9 to 18, or about 15 mgs of RAD001.

In an embodiment, administering comprises administering, e.g., once per day, e.g., in an immediate release dosage form, 0.005 to 1.5, 0.01 to 1.5, 0.1 to 1.5, 0.2 to 1.5, 0.3 to 1.5, 0.4 to 1.5, 0.5 to 1.5, 0.6 to 1.5, 0.7 to 1.5, 0.8 to 1.5, 1.0 to 1.5, 0.3 to 0.6, or about 0.5 mgs of RAD001, or an mTOR inhibitor other than RAD001 that is bioequivalent to a once per day, immediate release dosage form of 0.005 to 1.5, 0.01 to 1.5, 0.1 to 1.5, 0.2 to 1.5, 0.3 to 1.5, 0.4 to 1.5, 0.5 to 1.5, 0.6 to 1.5, 0.7 to 1.5, 0.8 to 1.5, 1.0 to 1.5, 0.3 to 0.6, or about 0.5 mgs of RAD001.

In an embodiment, administering comprises administering, e.g., once per day, e.g., in a sustained release dosage form, 0.015 to 4.5, 0.03 to 4.5, 0.3 to 4.5, 0.6 to 4.5, 0.9 to 4.5, 1.2 to 4.5, 1.5 to 4.5, 1.8 to 4.5, 2.1 to 4.5, 2.4 to 4.5, 3.0 to 4.5, 0.9 to 1.8, or about 1.5 mgs of RAD001, or an mTOR inhibitor other than RAD001 that is bioequivalent to a once per day, sustained release dosage form of 0.015 to 4.5, 0.03 to 4.5, 0.3 to 4.5, 0.6 to 4.5, 0.9 to 4.5, 1.2 to 4.5, 1.5 to 4.5, 1.8 to 4.5, 2.1 to 4.5, 2.4 to 4.5, 3.0 to 4.5, 0.9 to 1.8, or about 1.5 mgs of RAD001.

Other low, immune enhancing, doses of mTOR inhibitors, as well as dosing regimes and formulations, are provided in the section herein entitled "Adjunctive Treatment With A Low, Immune Enhancing, Dose of An mTOR Inhibitor".

In a tenth aspect, the invention features, a method of evaluating a human who has been treated with a RCARX cell for a side effect of said treatment.

In an embodiment, said side effect comprises acute respiratory distress syndrome, febrile neutropenia, hypotension, encephalopathy, hepatic transaminitis, seizure, or macrophage activation syndrome.

In an embodiment, the method further compriseins treating said human, e.g., a human having a side effect, with anti-cytokine agent, e.g., a tumor necrosis factor antagonist, e.g., a TNF-Ig fusion, e.g., etanercept, an IL-6 antagonist, e.g., an IL-6 receptor antagonist, e.g., an anti-IL6 receptor antibody, e.g., tocilizumab, or a corticosteroid.

In an embodiment, the method comprises administering an anti-IL6 receptor antibody to said human.

In an eleventh aspect, the invention features, a method of providing an RCARX cell comprising:

providing an immune effector cell, e.g., a T cell from a human, to a recipient entity, e.g., a laboratory or hospital; and receiving from said entity, an RCARX cell derived from said immune effector cell, or a daughter cell thereof.

In an embodiment, said entity inserted a nucleic acid encoding a RCAR into said immune effector cell or a daughter cell thereof.

In an embodiment, the method further comprises administering said RCARX to said human.

In a twelfth aspect, the invention features, a method of providing an RCARX cell comprising:

receiving from an entity, e.g., a health care provider, an immune effector cell, e.g., a T cell, from a human; inserting a nucleic acid encoding an RCAR into said immune effector cell, or a daughter cell thereof, to form an RCARX cell; and, optionally, providing said RCARX cell to said entity.

In a thirteenth aspect, the invention features, a nucleic acid described herein, a RCAR described herein, a vector system described herein, or an RCARX cell described herein for use as a medicament.

In another aspect, the invention features, a nucleic acid described herein for use as a medicament.

In another aspect, the invention features, a RCAR described herein for use as a medicament.

In another aspect, the invention features, a vector system described herein for use as a medicament.

In another aspect, the invention features, a RCARX cell described herein for use as a medicament.

In a fourteenth aspect, the invention features, a nucleic acid described herein, a RCAR described herein, a vector system described herein, or an RCARX cell described herein for use in the treatment of a disease characterized by the need of an enhanced immune response.

In another aspect, the invention features, a nucleic acid described herein for use in the treatment of a disease characterized by the need of an enhanced immune response.

In another aspect, the invention features, a nucleic acid described herein for use in the treatment of a disease characterized by unwanted expression of EGFRvIII.

In another aspect, the invention features, a nucleic acid described herein for use in the treatment of a disease characterized by unwanted expression of EGFRvIII and the disease is a proliferative disease, cancer, a precancerous condition, or a non-cancer related indication associated with expression of EGFRvIII.

In another aspect, the invention features, a nucleic acid described herein for use in the treatment of a disease characterized by sub-optimal anti-tumor immunity.

In another aspect, the invention features, a nucleic acid described herein for use in the treatment of a disease wherein said disease is cancer.

In another aspect, the invention features, a nucleic acid described herein for use in the treatment of a disease wherein said disease glioblastoma.

In another aspect, the invention features, a nucleic acid described herein for use in the treatment of a disease wherein said disease is glioblastoma multiforme (GBM), anaplastic astrocytoma, giant cell glioblastoma, gliosarcoma, anaplastic oligodendroglioma, anaplastic ependymoma, choroid plexus carcinoma, anaplastic ganglioglioma, pineoblastoma, medulloepithelioma, ependymoblastoma, medulloblastoma, supratentorial primitive neuroectodermal tumor, and atypical teratoid/rhabdoid tumor, non-small cell lung carcinomas, lung, breast, prostate, ovarian, colorectal or bladder carcinoma.

In another aspect, the invention features, a RCAR described herein for use in the treatment of a disease, characterized by the need of an enhanced immune response.

In another aspect, the invention features, a RCAR described herein for use in the treatment of a disease characterized by unwanted expression of EGFRvIII.

In another aspect, the invention features, a RCAR described herein for use in the treatment of a disease characterized by unwanted expression of EGFRvIII wherein the disease is a proliferative disease, cancer, a precancerous condition, or a non-cancer related indication associated with expression of EGFRvIII.

In another aspect, the invention features, a RCAR described herein for use in the treatment of a disease characterized by sub-optimal anti-tumor immunity.

In another aspect, the invention features, a RCAR described herein for use in the treatment of cancer.

In another aspect, the invention features, a RCAR described herein for use in the treatment of glioblastoma.

In another aspect, the invention features, a RCAR described herein for use in the treatment of glioblastoma multiforme (GBM), anaplastic astrocytoma, giant cell glioblastoma, gliosarcoma, anaplastic oligodendroglioma, anaplastic ependymoma, choroid plexus carcinoma, anaplastic ganglioglioma, pineoblastoma, medulloepithelioma, ependymoblastoma, medulloblastoma, supratentorial primitive neuroectodermal tumor, and atypical teratoid/rhabdoid tumor, non-small cell lung carcinomas, lung, breast, prostate, ovarian, colorectal or bladder carcinoma.

In another aspect, the invention features, a vector system described herein for use in the treatment of a disease, characterized by the need of an enhanced immune response.

In another aspect, the invention features, a vector system described herein for use in the treatment of a disease, characterized by unwanted expression of EGFRvIII.

In another aspect, the invention features, a vector system described herein for use in the treatment of a disease characterized by unwanted expression of EGFRvIII wherein the disease is a proliferative disease, cancer, a precancerous condition, or a non-cancer related indication associated with expression of EGFRvIII.

In another aspect, the invention features, a vector system described herein for use in the treatment of a disease, characterized by sub-optimal anti-tumor immunity.

In another aspect, the invention features, a vector system described herein for use in the treatment of cancer.

In another aspect, the invention features, a vector system described herein, wherein said disease is glioblastoma.

In another aspect, the invention features, a vector system described herein, wherein said disease is glioblastoma multiforme (GBM), anaplastic astrocytoma, giant cell glioblastoma, gliosarcoma, anaplastic oligodendroglioma, anaplastic ependymoma, choroid plexus carcinoma, anaplastic ganglioglioma, pineoblastoma, medulloepithelioma, ependymoblastoma, medulloblastoma, supratentorial primitive neuroectodermal tumor, and atypical teratoid/rhabdoid tumor, non-small cell lung carcinomas, lung, breast, prostate, ovarian, colorectal or bladder carcinoma.

In another aspect, the invention features, a RCARX cell described herein, for use in the treatment of a disease, characterized by the need of an enhanced immune response.

In another aspect, the invention features, a RCARX cell described herein, for use in the treatment of a disease characterized by unwanted expression of EGFRvIII.

In another aspect, the invention features, a RCARX cell described herein, for use in the treatment of a disease characterized by unwanted expression of EGFRvIII wherein the disease is a proliferative disease, cancer, a precancerous condition, or a non-cancer related indication associated with expression of EGFRvIII.

In another aspect, the invention features, a RCARX cell described herein, for use in the treatment of a disease, characterized by sub-optimal anti-tumor immunity.

In another aspect, the invention features, a RCARX cell described herein, for use in the treatment of cancer.

In another aspect, the invention features, a RCARX cell described herein, for use in the treatment of glioblastoma.

In another aspect, the invention features, a RCARX cell described herein, for use in the treatment of glioblastoma multiforme (GBM), anaplastic astrocytoma, giant cell glioblastoma, gliosarcoma, anaplastic oligodendroglioma, anaplastic ependymoma, choroid plexus carcinoma, anaplastic ganglioglioma, pineoblastoma, medulloepithelioma, ependymoblastoma, medulloblastoma, supratentorial primitive neuroectodermal tumor, and atypical teratoid/ rhabdoid tumor, non-small cell lung carcinomas, lung, breast, prostate, ovarian, colorectal or bladder carcinoma.

In an aspect, the invention features a regulatable chimeric antigen receptor (RCAR), e.g., an isolated RCAR, wherein the RCAR comprises:
  a) an intracellular signaling member comprising:
    an intracellular signaling domain, e.g., a primary intracellular signaling domain, and
    a first switch domain;
  b) an antigen binding member comprising:
    an antigen binding domain, and
    a second switch domain; and
  c) a transmembrane domain,
wherein,
  (i) the antigen binding member comprises more than one intracellular signaling domains, e.g., two costimulatory domains;
  (ii) the first and second switch domains comprise a FKBP-FRB based switch, which comprises a switch domain comprising a FRB binding fragment or analog of FKBP and a switch domain comprising an FKBP binding fragment or analog of FRB, and the FKBP binding fragment or analog of FRB comprises one or more mutations which increase the affinity of binding with rapamycin or a rapalog, e.g., RAD001;
  (iii) the RCAR comprises four intracellular signaling domain, e.g., wherein,
    (A) one of the first, second, third and fourth intracellular signaling domain is a primary intracellular signaling domain, e.g., selected from the list in Table 1 and the other three are costimulatory domains, e.g., selected from the list in Table 2, or
    (B) two of the first, second, third, and fourth intracellular signaling domains are primary intracellular signaling domains, e.g., selected from the list in Table 1, and the other two are costimulatory domain, e.g., selected from the list in Table 2.

(iv) the antigen binding domain does not comprise a transmembrane domain or membrane tethering domain;

(v) the RCAR further comprises d) an auxiliary antigen binding member comprising:

an antigen binding domain that binds a second antigen; and a transmembrane domain or membrane anchoring domain;

(vi) the RCAR further comprises an inhibitory counter ligand binding member comprising, an inhibitory counter ligand binding domain, e.g., from Table 4, and a transmembrane domain or membrane anchor;

(vii) the RCAR further comprises an inhibitory CAR (iCAR) member, wherein the iCAR member comprises:

an antigen binding domain (or other extracelluar domain) that recognizes an antigen on a non-target, e.g., a noncancer, cell;

a transmembrane domain; and, a domain from an inhibitory molecule, e.g., an intracellular domain from an inhibitory molecule, e.g., from PD-1, CTLA4, or from a protein listed in Table 12;

(viii) the RCAR further comprising a second RCAR, or second antigen binding member, wherein the antigen binding domain of one of the RCARs or antigen binding members does not comprise a variable light domain and a variable heavy domain, e.g., the antigen binding domain of one of is an scFv and the other is not an scFv, e.g., the antigen binding domain of one comprises a single VH domain;

(ix) the antigen binding member comprises: an antigen binding domain; a transmembrane domain; a first intracellular switch domain; and an intracellular signaling domain, e.g., a primary signaling domain, e.g., a CD3zeta domain, or a costimulatory signaling domain, e.g., a 4-1BB domain;

(x) the first and second switch domains can form an extracellular dimerization switch; or (xi) the RCAR comprises an inhibitor of an inhibitory molecule, e.g., an inhibitor of an inhibitory molecule of Table 3.

In an embodiment, the antigen binding member comprises: a plurality of costimulatory domains chosen, e.g., from Table 2, and no primary intracellular signaling domain. In an embodiment, the plurality of costimulatory domains are the same costimulatory domains, e.g., chosen from Table 2.

In an embodiment, the plurality comprises the following costimulatory signaling domains: CD28-41BB.

In an embodiment, the plurality comprises the following costimulatory signaling domains: CD28-OX40.

In an embodiment, the antigen binding domain does not comprise a transmembrane domain and the intracellular signaling domain comprises a primary signaling domain and a co-stimulatory signaling domain.

In an embodiment, the dimerization switch can be a homodimerization switch or a heterodimerization switch.

In an embodiment, the intracellular signaling domain on the intracellular signaling member is a primary intracellular signaling domain, e.g., from Table 1.

In an embodiment, the primary intracellular signaling domain comprises a CD3zeta domain.

In an embodiment, the intracellular signaling domain on the intracellular signaling member is a costimulatory signaling domain.

In an embodiment, the intracellular signaling domain is a costimulatory signaling domain selected from Table 2.

In an embodiment, the costimulatory signaling domain comprises a 4-1BB domain.

In an embodiment, the RCAR comprises a second intracellular signaling domain.

In an embodiment, the second intracellular signaling domain is a costimulatory signaling domain, e.g., selected from Table 2.

In an embodiment, one of the first and second switch domains comprises an FKBP-based switch domain and the other comprises an FRB-based switch domain.

In an embodiment, the switch domain is dimerized by RAD001.

In an embodiment, the switch domain comprises an FKBP binding fragment or analog of FRB comprising: an E2032 mutation, e.g., an E2032I mutation or E2032L mutation; a T2098 mutation, e.g., a T2098L mutation; or an E2032 and a T2098 mutation, e.g., an E2032I and a T2098L or an E2032L and a T2098L mutation.

In an embodiment, the RCAR comprises an inhibitor of an inhibitory molecule wherein the inhibitor comprises an inhibitory nucleic acid, e.g., a dsRNA, e.g., an siRNA or shRNA.

In an embodiment, the antigen binding domain binds to a target antigen on a cancer cell, e.g., a tumor antigen described herein, but does not activate the RCARX cell, e.g., a RCART cell, until a dimerization molecule is administered.

In an aspect, the invention features an RCAR, e.g., an isolated RCAR, comprising:

a) an inhibitory extracellular domain member comprising, an inhibitory extracellular domain, e.g., selected from Table 4, a transmembrane region, and a switch domain;

b) an intracellular signaling member comprising, an intracellular signaling domain, e.g., a primary intracellular signaling domain, and a switch domain.

In an embodiment, the inhibitory extracellular domain binds to its ligand on the target cell and redirects signal activation in the presence of a heterodimerization molecule.

In another aspect, the invention features an RCAR, e.g., an isolated, RCAR comprising:

a) a costimulatory ECD member comprising a costimulatory ECD domain, other than that of CD27;

a transmembrane region, and a switch domain;

b) an intracellular signaling member comprising an intracellular signaling domain, e.g., a primary intracellular signaling domain, and a switch domain.

In an embodiment, the costimulatory ECD domains is selected from Table 5.

In another aspect, the invention features an RCAR, e.g., an isolated RCAR, wherein the RCAR comprises:

a) an intracellular signaling member comprising:

a transmembrane domain or membrane anchoring domain;

a co-stimulatory signaling domain, selected e.g., from Table 2, and a switch domain; and b) an antigen binding member comprising:

an antigen binding domain, a transmembrane domain, and a primary intracellular signaling domain, e.g., selected from Table 1, e.g., a CD3zeta domain, wherein the antigen binding member does not comprise a switch domain, or does not comprise a switch domain that dimerizes with the switch domain on the intracellular signaling member.

In an aspect, the invention features a nucleic acid, e.g., an isolated nucleic acid, encoding a RCAR, or an element of an RCAR described herein.

In an embodiment, the nucleic acid encodes an RCAR described herein, wherein:
  i) the sequence encoding an antigen binding member and the sequence encoding an intracellular signaling member is disposed on a single nucleic acid molecule, e.g., a viral vector, e.g., a lentivirus vector; or
  ii) the sequence encoding an antigen binding member is disposed on a first nucleic acid molecule, e.g., a viral vector, e.g., a lentivirus vector, and sequence encoding an intracellular signaling member is disposed on a second nucleic acid molecule, e.g., a viral vector, e.g., a lentivirus vector.

In an embodiment, the nucleic acid further comprises a sequence encoding an inhibitor of an inhibitory molecule from Table 3, e.g., PD1, e.g., wherein the inhibitor comprises an inhibitory nucleic acid, e.g., a dsRNA, e.g., an siRNA or shRNA.

In an aspect, the invention features an isolated nucleic acid, encoding an RCAR comprising:
  a) an intracellular signaling member comprising:
    an intracellular signaling domain, e.g., a primary intracellular signaling domain,
    a first switch domain, and
    optionally, a transmembrane domain or a membrane anchoring domain;
  b) an antigen binding member comprising:
    an antigen binding domain,
    a second switch domain, and
    optionally, a transmembrane domain; and
  wherein:
    i) a sequence encoding the antigen binding member (a) and a sequence encoding the intracellular signaling member (b), are present on a single nucleic acid molecule, are transcribed as a single transcription product, and are configured as follows:
  a promoter, e.g., a promoter described herein, e.g., an EF1alpha promoter, is operably linked to (a), (b), and (c), wherein (c) encodes a peptide, e.g., a cleavable peptide, e.g., a P2A or F2A sequence, and element (c) is disposed between (a) and (b); or
    ii) a sequence encoding the antigen binding member (a) and a sequence encoding the intracellular signaling member (b), are present on a single nucleic acid molecule, are transcribed as a single transcription product, and are configured as follows:
  a promoter, e.g., a promoter described herein is operably linked to (a), (b), and (c), wherein element (c) encodes an IRES, e.g., an EMCV IRES, and element (c) is disposed between (a) and (b).

In an aspect, the invention features a vector system, e.g., one or more vectors, comprising a nucleic acid described herein.

In an embodiment, the vector system comprises a DNA, a RNA, a plasmid, a lentivirus vector, adenoviral vector, or a retrovirus vector.

In an aspect, the invention features a cell comprising an RCAR described herein, a nucleic acid described herein, or a vector system described herein.

In another aspect, the disclosure features a method of making a cell described herein, comprising introducing a nucleic acid described herein or a vector system described herein into said cell.

In an embodiment of any of the aspects described herein, the cell is a human cell.

In an embodiment of any of the aspects described herein, the cell is a T cell.

In an embodiment of any of the aspects described herein, the cell is a NK cell.

In an aspect, the invention features a method of treating a subject, e.g., a mammal, e.g., a method of providing an anti-tumor immunity in a subject, comprising administering to the subject an effective amount of a RCARX cell described herein, e.g., a cell of claims 30 to 33, or providing a subject comprising the cell.

In an embodiment, the RCARX cell is an autologous T cell.

In an embodiment, the RCARX cell is an allogeneic T cell.

In an embodiment, the RCARX cell is selected from: an autologous NK cell; and an allogeneic NK cell.

In an embodiment, the subject is a human.

In an embodiment, the method comprises treating the subject for cancer.

In an embodiment, the method further comprises administering a dimerization molecule to the subject.

In an embodiment, the RCAR comprises an FKBP-FRB based switch, and the method further comprises administering a dimerization molecule comprising an mTOR inhibitor, e.g., an allosteric mTOR inhibitor, e.g., rapamycin or a rapalog, e.g., RAD001.

In an embodiment, the method further comprises administering a low, immune enhancing, dose of an allosteric mTOR inhibitor, e.g., RAD001.

In an aspect, the invention features a method of treating a subject, e.g., a mammal, e.g., a method of providing an anti-tumor immunity in a subject, comprising:
  (a) administering to the subject an effective amount of a RCARX cell, e.g., a RCART cell, or providing a subject comprising the RCARX cell, e.g., a RCART cell, wherein the cell comprises, an RCAR, a nucleic acid encoding the RCAR, or a nucleic acid encoding the RCAR; and
  (b) administering
    (i) a dimerization molecule which comprises RAD001; or
    (ii) a low, immune enhancing, dose of an allosteric mTOR inhibitor, e.g., RAD001,
  wherein the RCAR comprises:
  A) an intracellular signaling member comprising:
    an intracellular signaling domain, e.g., a primary intracellular signaling domain, and
    a first switch domain;
  B) an antigen binding member comprising:
    an antigen binding domain, and
    a second switch domain; and
  C) a transmembrane domain,
wherein the first and second switch domains comprise a FKBP-FRB based switch.

In an embodiment, the cell is an autologous T cell.

In an embodiment, the cell is an allogeneic T cell.

In an embodiment, the cell is selected from: an autologous NK cell; and an allogeneic NK cell.

In an embodiment, the subject is a human.

In an embodiment, the method comprises treating the subject for cancer.

In an embodiment, the method further comprises administering a RAD001 dimerization molecule to the subject.

In an embodiment, the method further comprises administering a low, immune enhancing, dose of an allosteric mTOR inhibitor, e.g., RAD001.

In an aspect, the invention features a method of providing an RCARX cell comprising: providing an immune effector cell, e.g., a T cell from a human, to a recipient entity, e.g., a laboratory or hospital; and receiving from said entity, an RCARX cell derived from said immune effector cell, or a daughter cell thereof, wherein the RCARX comprises an RCAR described herein, or a nucleic acid or vector encoding the RCAR described herein.

In an embodiment, the entity inserted a nucleic acid encoding the RCAR into said immune effector cell or a daughter cell thereof.

In an embodiment, the method further comprises administering said RCARX to said human.

In another aspect, the invention features providing an RCARX cell comprising:

receiving from an entity, e.g., a health care provider, an immune effector cell, e.g., a T cell, from a human; inserting a nucleic acid encoding an RCAR of any of claims 1-23 into said immune effector cell, or a daughter cell thereof, to form an RCARX cell; and, optionally, providing said RCARX cell to said entity.

In an aspect, the invention features a nucleic acid described herein for use as a medicament.

In an aspect, the invention features a RCAR described herein for use as a medicament.

In an aspect, the invention features a vector system described herein for use as a medicament.

In an aspect, the invention features an RCARX cell described herein, e.g., the cell described herein, e.g., the cell comprising an RCAR described herein, a nucleic acid described herein, or a vector system described herein, for use as a medicament.

In an aspect, the invention features a nucleic acid described herein for use in the treatment of a disease, wherein the disease is characterized by the need of an enhanced immune response.

In an aspect, the invention features an RCAR described herein for use in the treatment of a disease, wherein the disease is characterized by the need of an enhanced immune response.

In an aspect, the invention features a vector system described herein for use in the treatment of a disease, wherein the disease is characterized by the need of an enhanced immune response.

In an embodiment of any of the aforementioned aspects, the disease is characterized by sub-optimal anti-tumor immunity.

In an embodiment of any of the aforementioned aspects, the disease is cancer.

All references, publications, patent applications, patents, and the like are hereby incorporated by reference.

BRIEF DESCRIPTION OF DRAWINGS

The drawings are first briefly described.

FIGS. 12A and 12B depict activation as seen with RCAR cells expressing RCAR constructs as shown in FIG. 2. A standard EGFRvIII CART was used for positive control. RCARs were incubated with no heterodimerization molecule (no HD) or with 500 nM heterodimerization molecule (HD), where the heterodimerization molecule was AP21967 (FIG. 12A). A dose-response assay was performed using varying concentrations of the heterodimerization molecule A/C heterodimerizer (FIG. 12B). The RCARs tested contained scFv domain that targeted EGFRvIII (left bar in each set) or IgG1 for control (right bar in each set).

FIG. 17A shows the results from a NFAT inducible promoter driven luciferase activity of a PD1 CAR as compared to the control treatment by IgG1-Fc. FIG. 17B shows the results from NFAT inducible promoter driven luciferase activity of a PD1 RCAR which include PD1-ECD-TM-FRB and FKBP-4 1BB-CD3 zeta as compared to the control treatment by IgG1-Fc.

In FIG. 27A, the increase above baseline in influenza geometric mean titers to each of the 3 influenza vaccine strains (H1N1 A/California/07/2009, H3N2 A/Victoria/210/2009, B/Brisbane/60/2008) relative to the increase in the placebo cohort 4 weeks after vaccination is shown for each of the RAD001 dosing cohorts in the intention to treat population. The bold black line indicates the 1.2 fold increase in titers relative to placebo that is required to be met for 2 out of 3 influenza vaccine strains to meet the primary endpoint of the study. The star "*" indicates that the increase in GMT titer relative to placebo exceeds 1 with posterior probability of at least 80%. FIG. 27B is a graph of the same data as in FIG. 27A for the subset of subjects with baseline influenza titers <=1:40.

FIG. 29 is a graphic representation showing increase in titers to heterologous influenza strains as compared to placebo. The increase above baseline in influenza geometric mean titers to 2 heterologous influenza strains (A/H1N1 strain A/New Jersey/8/76 and A/H3N2 strain A/Victoria/361/11) not contained in the influenza vaccine relative to the increase in the placebo cohort 4 weeks after vaccination is shown for each of the RAD001 dosing cohorts in the intention to treat population. * indicates increase in titer relative to placebo exceeds 1 with a posterior probability of at least 80%.

FIG. 31A shows there was a significant decrease (−37.1-−28.5%) in PD-1-positive CD4 T cells at week 12 in cohorts receiving RAD001 at dose levels 0.5 mg/Day (n=25), 5 mg/Week (n=29) and 20 mg/Week (n=30) as compared to the placebo cohort (n=25) with p=0.002 (0.02), p=0.003 (q=0.03), and p=0.01 (q=0.05) respectively. FIG. 31B shows there was a significant decrease (−43.3-−38.5%) in PD-1-positive CD8 T cells at week 12 in cohorts receiving RAD001 (n=109) at dose levels 0.5 mg/Day (n=25), 5 mg/Week (n=29) and 20 mg/Week (n=30) as compared to the placebo cohort (n=25) with p=0.01 (0.05), p=0.007 (q=0.04), and p=0.01 (q=0.05) respectively. FIG. 31C shows was a significant increase (3.0-4.9%) in PD-1-negative CD4 T cells at week 12 in cohorts receiving RAD001 (n=109) at dose levels 0.5 mg/Day (n=25), 5 mg/Week (n=29) and 20 mg/Week (n=30) as compared to the placebo cohort (n=25) with p=0.0007 (0.02), p=0.03 (q=0.07), and p=0.03 (q=0.08) respectively.

FIG. 32A shows a significant decrease of 30.2% in PD-1+CD4 T cells at week 6 in the pooled RAD cohort (n=84) compared to placebo cohort (n=25) with p=0.03 (q=0.13). The decrease in PD-1-positive CD4 T cells at week 12 in the pooled RAD as compared to the placebo cohort is 32.7% with p=0.05 (q=0.19). FIG. 32B shows a significant decrease of 37.4% in PD-1-positive CD8 T cells at week 6 in the pooled RAD001 cohort (n=84) compared to placebo cohort (n=25) with p=0.008 (q=0.07). The decrease in PD-1-positive CD8 T cells at week 12 in the pooled RAD001 as compared to the placebo cohort is 41.4% with p=0.066 (q=0.21). FIGS. 32A and 32B represent the data in FIGS. 31A, 31B, and 31C but with the different RAD001 dosage groups of FIGS. 31A, 31B, and 31C pooled into the single RAD001-treated group in FIGS. 32A and 32B.

FIG. 34A depicts P70 S6 kinase inhibition with higher doses of weekly and daily RAD001; FIG. 34B depicts P70 S6 kinase inhibition with lower doses of weekly RAD001.

In FIG. 37A, the y-axis shows the percent of wells expressing the mutant FRB. In FIG. 37B, the y-axis shows the average protein concentration determined for each library.

FIGS. 42A and 42B are schematic representations of various RCAR constructs with extracellular switches evaluated in FIG. 43. Half RCARs with the extracellular switch are shown in FIG. 42A, with the FKBP and FRB switch domains in two different orientations. Full RCAR full switches with the extracellular switch are shown in FIG. 42B, with the FKBP and FRB switch domains in two different orientations.

FIGS. 43A and 43B show results of activation of the RCAR half switch with the switch domains in both orientations. FIGS. 43C and 43D show results of activation of the RCAR full switch with the switch domains in both orientations. NFAT activation is represented by luminescence detected by Luciferase One Glo (y-axis) and the different RAD001 concentrations are listed on the x-axis.

FIGS. 44A and 44B show the half RCAR constructs with an intracellular switch. FIG. 44A shows a schematic representation of the half RCAR constructs. FIG. 44B shows the activation of the half RCARs with different costimulatory signaling domains in the presence or absence of RAD001.

In FIG. 55A, the antigen binding member comprises a plurality of first switch domains, e.g., a FKBP switch domain, while the intracellular signaling member comprises a plurality of second switch domains, e.g., a FRB switch domain. The bracketed switch domains represent 1 or more additional switch domains that comprise the multi switch. In FIG. 55B, the antigen binding member comprises a first switch domain, e.g., a FKBP switch domain, and a second switch domain, e.g., a FRB switch domain, and the intracellular binding member comprises a second switch domain, e.g., a FRB switch domain, and a first switch domain, e.g., a FKBP switch domain.

In FIG. 56A, the two intracellular signaling members comprise a transmembrane domain and one or more intracellular switch domains. In FIG. 56B, the two intracellular signaling members comprise a membrane anchor, e.g., myristoylation, and one or more intracellular switch domains. In FIG. 56C, the two intracellular signaling members comprise one or more extracellular switch domains and a transmembrane domain. In FIG. 56D, the two intracellular signaling members comprise one or more intracellular switch domains, and does not comprise a transmembrane domain or a membrane anchor.

DETAILED DESCRIPTION

Definitions

Figure 1:
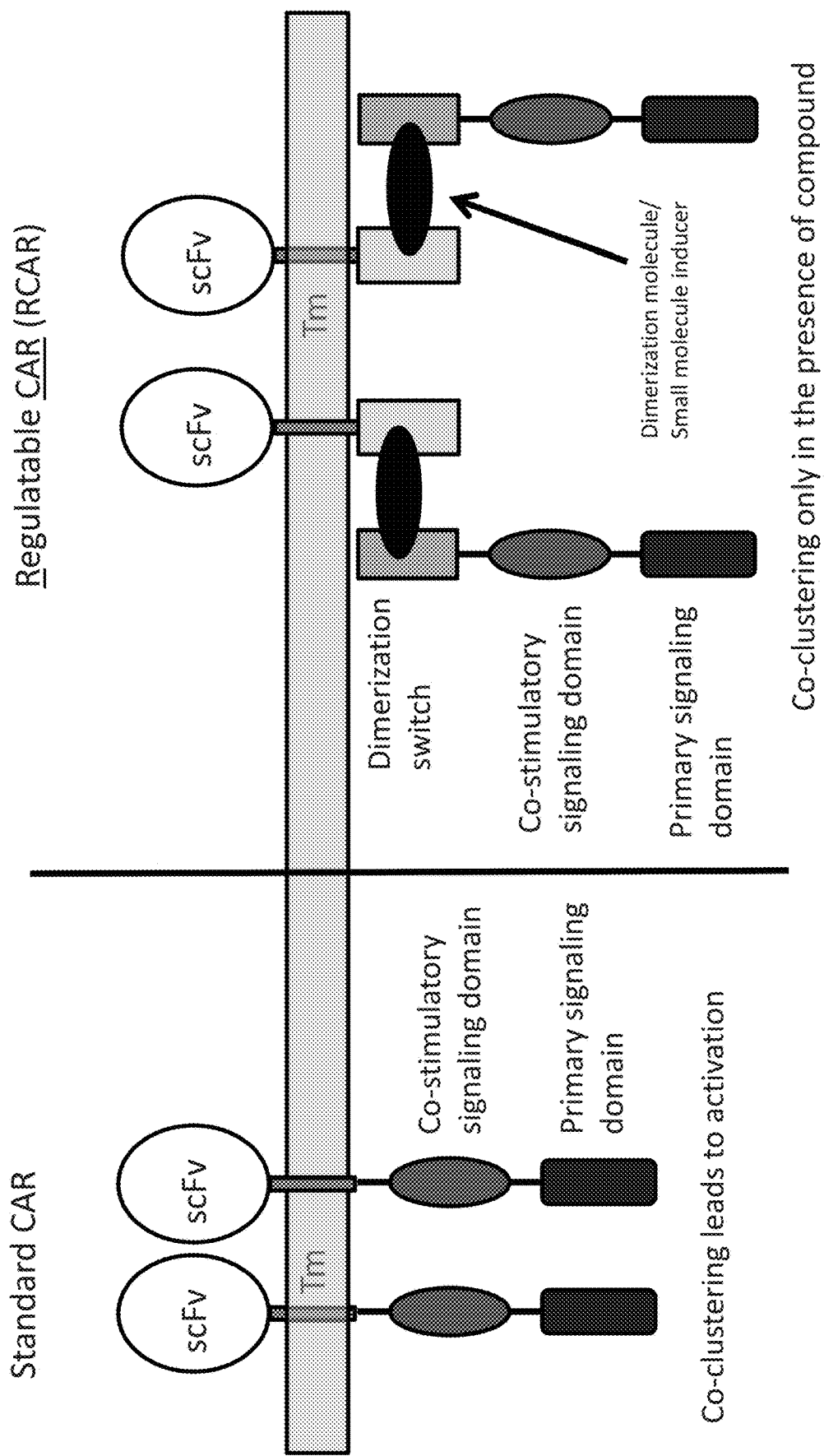
FIG. 1 depicts the structures of a standard CAR compared to a regulatable CAR (RCAR).

Unless defined otherwise, all technical and scientific terms used herein have the same meaning as commonly understood by one of ordinary skill in the art to which the invention pertains.

"A" and "an" as the term is used herein, refers to one or to more than one (i.e., to at least one) of the grammatical object of the article. By way of example, "an element" means one element or more than one element.

"About" as the term is used herein, when referring to a measurable value such as an amount, a temporal duration, and the like, is meant to encompass variations of ±20% or in some embodiments ±10%, or in some embodiments ±5%, or in some embodiments ±1%, or in some embodiments ±0.1% from the specified value, as such variations are appropriate to perform the disclosed methods.

"Autologous" as the term is used herein refers to any material derived from the same individual to whom it is later to be re-introduced.

"Allogeneic" as the term is used herein refers to any material derived from a different animal of the same species as the individual to whom the material is introduced. Two or more individuals are said to be allogeneic to one another when the genes at one or more loci are not identical. In some aspects, allogeneic material from individuals of the same species may be sufficiently unlike genetically to interact antigenically.

An "antigen binding domain" as the term is used herein, refers to a molecule that has affinity for a target antigen, typically an antigen on a target cell, e.g., a cancer cell. An exemplary antigen binding domain comprises a polypeptide, e.g., an antibody molecule (which includes an antibody, and antigen binding fragments thereof, e.g., a immunoglobulin, single domain antibody (sdAb, e.g., a nanobody, and an scFv), or a non-antibody scaffold, e.g., a fibronectin, and the like. In embodiments, the antigen binding domain is a single polypeptide. In embodiments, the antigen binding domain comprises, one, two, or more, polypeptides. In embodiments the antigen binding domain comprises a fragment of an antibody, that is sufficient to confer recognition and specific binding to the target antigen. The term "antibody fragment" refers to at least one portion of an antibody, that retains the ability to specifically interact with (e.g., by binding, steric hinderance, stabilizing/destabilizing, spatial distribution) an epitope of an antigen. Examples of an antibody fragment include, but are not limited to, an Fab, Fab', F(ab')$_2$, or Fv fragment, an scFv antibody fragment, an disulfide-linked Fv (sdFv), a Fd fragment consisting of the VH and CH1 domains, a linear antibody, single domain antibody such as an sdAb, e.g., a nanobody, (either VL or VH), a camelid VHH domain, multi-specific antibodies formed from antibody fragments such as a bivalent fragment comprising two Fab fragments linked by a disulfide brudge at the hinge region, and an isolated CDR or other epitope binding fragments of an antibody. An antigen binding fragment can also be incorporated into single domain antibodies, maxibodies, minibodies, nanobodies, intrabodies, diabodies, triabodies, tetrabodies, v-NAR and bis-scFv (see, e.g., Hollinger and Hudson, Nature Biotechnology 23:1126-1136, 2005). Antigen binding fragments can also be grafted into scaffolds based on polypeptides such as a fibronectin type III (Fn3)(see U.S. Pat. No. 6,703,199, which describes fibronectin polypeptide minibodies).

In an embodiment, the antigen binding domain is a "scFv," which can comprise a fusion protein comprising a VL chain and a VH chain of an antibody, where the VH and VL are linked via a short flexible polypeptide linker. The scFv is capable of being expressed as a single chain polypeptide and retains the specificity of the intact antibody from which it is derived. Moreover, the VL and VH variable chains can be linked in either order, e.g., with respect to the N-terminal and C-terminal ends of the polypeptide, the scFv may comprise VL-linker-VH or may comprise VH-linker-VL. In embodiments, the antigen binding domain comprises a non antibody scaffold, e.g., a fibronectin, ankyrin, domain antibody, e.g., a nanobody, lipocalin, small modular immuno-pharmaceutical, maxybody, Protein A, or affilin. The non antibody scaffold has the ability to bind to target antigen on a cell. In embodiments, the antigen binding domain is a polypeptide or fragment thereof of a naturally occurring protein expressed on a cell. In an embodiment, the antigen binding domain binds a growth factor or hormone receptor. While not wishing to be bound by theory, the antigen binding domain serves to provide specificity for target cells, and in embodiments, optimize and immune effector function by coupling antigen binding to generation of a signal by an intracellular signaling domain on an intracellular signaling member.

"Antigen binding member," as that term is used herein, comprises an antigen binding domain, and, optionally, a transmembrane domain or a membrane anchor. An antigen binding member can also comprise a switch domain. In embodiments, the switch domain on the antigen binding member can form a dimerization switch with a switch domain on an intracellular signaling member. The dimerization switch formed by these two switch domains can couple antigen binding to intracellular signal generation, and thereby optimize an immune effector function of the cell. In embodiments, the antigen binding member comprises an antigen binding domain which is other than the native extracellular domain of a molecule from which an intracellular signaling domain on the intracellular signaling member is derived. In embodiments, the antigen binding member comprises an antigen binding domain which binds an antigen which is not the ligand of the native extracellular domain of a molecule from which an intracellular signaling domain on the intracellular signaling member is derived.

"Anti-cancer effect", as that term is used herein, refers to a biological effect which can be manifested by various means, including but not limited to, e.g., a decrease in tumor volume, a decrease in the number of cancer cells, a decrease in the number of metastases, an increase in life expectancy, decrease in cancer cell proliferation, decrease in cancer cell survival, or amelioration of various physiological symptoms associated with the cancerous condition. An "anti-cancer effect" can also be manifested by the ability of the peptides, polynucleotides, cells and antibodies in prevention of the occurrence of cancer in the first place. The term "anti-tumor effect" refers to a biological effect which can be manifested by various means, including but not limited to, e.g., a decrease in tumor volume, a decrease in the number of cancer cells, a decrease in tumor cell proliferation, or a decrease in tumor cell survival.

"Auxiliary antigen binding member," as that term is used herein, refers to a molecule comprising an antigen binding domain that binds an antigen other than the antigen bound by another antigen binding domain of the RCAR, e.g., other than the antigen binding domain of the antigen binding member. In embodiments it comprises a transmembrane domain or membrane anchoring domain.

"Cancer" as the term is used herein, refers to a disease characterized by the uncontrolled growth of aberrant cells. Cancer cells can spread locally or through the bloodstream and lymphatic system to other parts of the body. Examples of various cancers include but are not limited to, breast cancer, prostate cancer, ovarian cancer, cervical cancer, skin cancer, pancreatic cancer, colorectal cancer, renal cancer, liver cancer, brain cancer, lymphoma, leukemia, lung cancer and the like.

"Costimulatory signaling domain," as that term is used herein, refers to a molecule, e.g., an endogenous molecule, of the RCARX cell that, upon binding to its cognate counter ligand on a target cell, enhance, e.g., increases, an immune effector response.

"Derived from" as that term is used herein, indicates a relationship between a first and a second molecule. It generally refers to structural similarity between the first molecule and a second molecule and does not connotate or include a process or source limitation on a first molecule that is derived from a second molecule. For example, in the case of an intracellular signaling domain that is derived from a CD3zeta molecule, the intracellular signaling domain retains sufficient CD3zeta structure such that is has the required function, namely, the ability to generate a signal under the appropriate conditions. It does not connotate or include a limitation to a particular process of producing the intracellular signaling domain, e.g., it does not mean that, to provide the intracellular signaling domain, one must start with a CD3zeta sequence and delete unwanted sequence, or impose mutations, to arrive at the intracellular signaling domain.

"Dimerization molecule," as that term is used herein, refers to a molecule that promotes the association of a first switch domain with a second switch domain. In embodiments, e.g., where the dimerization switch is disposed intracellularly, the dimerization molecule can cross the plasma membrane. In embodiments, e.g., where the dimerization switch is disposed extracellularly, the dimerization molecule need not cross the plasma membrane. In embodiments, the dimerization molecule does not naturally occur in the subject, or does not occur in concentrations that would result in significant dimerization. In embodiments, the dimerization molecule is a small molecule, e.g., rapamycin or a rapalogue. In embodiments, the dimerization molecule is a polypeptide. In embodiments, the dimerization molecule is an antibody molecule, e.g., antibody or antigen-binding fragment thereof. In embodiments, the first and second switch domains of a homodimerization switch or heterodimerization switch associate together in the presence of small molecule dimerization molecule e.g., rapamycin or a rapalogue. In embodiments, the first and second switch domains of a homodimerization switch or heterodimerization switch associate together in the presence of polypeptide dimerization molecule. In embodiments, the first and second switch domains of a homodimerization switch or heterodimerization switch associate together in the presence of a multimeric peptide dimerization molecule. In embodiments, the first and second switch domains of a homodimerization switch or heterodimerization switch associate together in the presence of an antibody molecule dimerization molecule. In embodiments, the antibody molecule comprises a monospecific antibody molecule. In embodiments, the antibody molecule is a dual specific antibody molecule.

Generally, a dimerization molecule will promote the association of at least two switch molecules (and thereby the association of intracellular domains linked to the switch domains). In embodiments the dimerization molecule has a valency of greater than two, e.g., it is multi-valent, and binds, and thus clusters or dimerizes, more than two switch domains. E.g., a dimerization molecule can comprise a plurality, e.g., at least 2, 3, 4, 5, 6, 7, 8, 9 or 10, binding domains, each of which can bind a switch domain.

"dsRNA," as that term is used herein, refers to a nucleic acid molecule, having at least a region of duplexed structure, that is capable of mediating sequence specific inhibition of the expression of a target gene. dsRNAs comprise short interfering RNA (siRNA) and short hairpin RNA (shRNA). In embodiments, shRNA is similar in structure to an siRNA but includes a moiety, typically one or more RNA monomers, that connect a duplex region of sense and an antisense sequence. In an embodiment the shRNA, after intracellular processing (e.g., by Dicer), results in a 19-23 nucleotide duplex siRNA with 2 nucleotide 3' overhangs.

"Endogenous" as that term is used herein, refers to any material, e.g., a polypeptide, from or produced inside an organism, cell, tissue or system.

"Exogenous" as that term is used herein, refers to any material, e.g., a polypeptide, or dimerization molecule, introduced from or produced outside an organism, cell, tissue or system.

"Immune effector cell," as that term is used herein, refers to a cell that is involved in an immune response, e.g., in the promotion of an immune effector response. Examples of immune effector cells include T cells, e.g., alpha/beta T cells and gamma/delta T cells, B cells, natural killer (NK) cells, natural killer T (NKT) cells, mast cells, and myeloic-derived phagocytes.

"Immune effector function or immune effector response," as that term is used herein, refers to function or response, e.g., of an immune effector cell, that enhances or promotes an immune attack of a target cell. E.g., an immune effector function or response refers a property of a T or NK cell that promotes killing or the inhibition of growth or proliferation, of a target cell. In the case of a T cell, primary stimulation and costimulation are examples of immune effector function or response. An immune effector function or response can be promoted by the action of a RCAR, and can, e.g., result in a RCARX cell that is more effective at proliferation, cytokine production, cytotoxicity or upregulation of cell surface markers such asCD25, CD69, CD107a.

An "inhibitory extracellular domain," as that term is used herein, refers to polypeptide comprising an extracellular domain of an inhibitory molecule. Normally, binding to its conterligand has an inhibitory effect on the generation of an immune effector response. When linked, e.g., fused, or coupled by a dimerization switch, to an intracellular signaling domain, it redirects an interaction that normally inhibits the generation of an immune effector response into one that promotes an immune effector response.

"Inhibitory binding member," as that term is used herein, refers to a polypeptide that comprises an inhibitory extracellular domain, a transmembrane domain, and a switch domain.

"Inhibitory molecule," as that term is used herein, refers to a molecule, e.g., an endogenous molecule, of RCARX cell, e.g., a RCART cell that, upon binding to its cognate counter ligand on a target cell, minimizes, e.g., suppresses or inhibits, an immune effector response. Examples of inhibitory molecules include PD1, PD-L1, CTLA4, TIM3, LAGS, VISTA, BTLA, TIGIT, LAIR1, and TGFR beta.

"Intracellular signaling domain," as the term is used herein, refers to an intracellular portion of a molecule. The intracellular signaling domain generates a signal that promotes an immune effector function of the RCARX cell, e.g., a RCART cell. Examples of immune effector function, e.g., in a RCART cell, include cytolytic activity and helper activity, including the secretion of cytokines.

In an embodiment, the intracellular signaling domain can comprise a primary intracellular signaling domain. Exemplary primary intracellular signaling domains include those derived from the molecules responsible for primary stimulation, or antigen dependent simulation. In an embodiment, the intracellular signaling domain can comprise a costimulatory intracellular domain. Exemplary costimulatory intracellular signaling domains include those derived from molecules responsible for costimulatory signals, or antigen independent stimulation. For example, in the case of a RCART, a primary intracellular signaling domain can comprise cytoplasmic sequences of the T cell receptor, and a costimulatory intracellular signaling domain can comprise cytoplasmic sequence from co-receptor or costimulatory molecule.

A primary cytoplasmic signaling sequence (also referred to as a "primary signaling domain") that acts in a stimulatory manner may contain a signaling motif which is known as immunoreceptor tyrosine-based activation motif or ITAM. Examples of an ITAM containing cytoplasmic signaling sequence that is of particular use in the invention includes, but is not limited to, those derived from CD3 zeta, common FcR gamma (FCER1G), Fc gamma RIIa, FcR beta (Fc Epsilon Rib), CD3 gamma, CD3 delta, CD3 epsilon, CD79a, CD79b, DAP10, and DAP12. In a specific RCAR of the invention, the intracellular signaling domain in any one or more RCARS of the invention comprises an intracellular signaling sequence, e.g., a primary signaling sequence of CD3-zeta.

A costimulatory intracellular signaling domain can be derived from the intracellular portion of a costimulatory molecule. A costimulatory molecule can be represented by the following protein families: TNF receptor proteins, Immunoglobulin-like proteins, cytokine receptors, integrins, signaling lymphocytic activation molecules (SLAM proteins), and activating NK cell receptors. Examples of such molecules include CD27, CD28, 4-1BB (CD137), OX40, GITR, CD30, CD40, ICOS, BAFFR, HVEM, ICAM-1, lymphocyte function-associated antigen-1 (LFA-1), CD2, CD5, CD7, CD287, LIGHT, NKG2C, SLAMF7, NKp80, CD160, B7-H3, and a ligand that specifically binds with CD83, and the like. Further examples of such costimulatory molecules include CD5, ICAM-1, GITR, BAFFR, HVEM (LIGHTR), SLAMF7, NKp80 (KLRF1), CD160, CD19, CD4, CD8alpha, CD8beta, IL2R beta, IL2R gamma, IL7R alpha, ITGA4, VLA1, CD49a, ITGA4, IA4, CD49D, ITGA6, VLA-6, CD49f, ITGAD, CD11d, ITGAE, CD103, ITGAL, CD11a, LFA-1, ITGAM, CD11b, ITGAX, CD11c, ITGB1, CD29, ITGB2, CD18, LFA-1, ITGB7, TNFR2, TRANCE/RANKL, DNAM1 (CD226), SLAMF4 (CD244, 2B4), CD84, CD96 (Tactile), CEACAM1, CRTAM, Ly9 (CD229), CD160 (BY55), PSGL1, CD100 (SEMA4D), CD69, SLAMF6 (NTB-A, Ly108), SLAM (SLAMF1, CD150, IPO-3), BLAME (SLAMF8), SELPLG (CD162), LTBR, LAT, GADS, SLP-76, and PAG/Cbp.

The intracellular signaling domain can comprise the entire intracellular portion, or the entire native intracellular signaling domain, of the molecule from which it is derived, or a functional fragment or derivative thereof.

"Intracellular signaling member," as that term is used herein, refers to a polypeptide comprising an intracellular signaling domain and a switch domain. In embodiments it comprises a primary intracellular signal domain, and, optionally, a costimulatory signaling domain. In embodiments with more than one intracellular signaling domain, such domains may be linked to each other in a random or specified order. Optionally, a short oligo- or polypeptide linker, for example, between 2 and 10 amino acids in length, may be disposed between intracellular signaling domains. A glycine-serine doublet provides a particularly suitable linker. In an embodiment, the intracellular signaling member comprises the signaling domain of CD3-zeta and the signaling domain of CD28. In an embodiment, the intracellular signaling member comprises the signaling domain of CD3-zeta and the signaling domain of 4-1BB. In an embodiment, the intracellular signaling domain of 4-1BB is a signaling domain from SEQ ID NO: 138. In an embodiment, the signaling domain of CD3-zeta is a signaling domain from SEQ ID NO: 139.

"Isolated" as that term is used herein refers to a nucleic acid or polypeptide means separated from at least one contaminating compound. With regard to a nucleic acid or polypeptide that exists in nature, it means free of a compound with which it occurs in nature, wherein in embodiments, the contaminating compound is a polynucleotide or polypeptide. With regard to a nucleic acid or polypeptide that is made synthetically, it means free of a sude reactant or compound used in its preparation, e.g., a solvent or starting reactant. For example, a nucleic acid or a polypeptide naturally present in a living animal is not "isolated," but the same nucleic acid or polypeptide partially or completely separated from the coexisting materials of its natural state is "isolated." An isolated nucleic acid or protein can exist in substantially purified form, or can exist in a non-native environment such as, for example, a host cell.

"Membrane anchor," "membrane anchoring domain", or "membrane tethering domain" as that term is used herein, refers to a moiety or polypeptide sufficient to anchor an extracellular domain to the plasma membrane. Examples of non-polypeptide moieties include glycophosphatidylinositol (GPI anchor) or a myristoyl group (myristoylation).

"Nucleic acid-based inhibitor," as that term is used herein, refers to a nucleic acid molecule that can inhibit expression of a target gene, e.g., an inhibitory molecule. It comprises double stranded RNA (dsRNA), including short hairpin RNA (shRNA) and short interfering RNA (siRNA), antisense RNA, and microRNA (miRNA). In an embodiment, the nucleic-acid based inhibitor binds to the target mRNA and inhibits the production of protein therefrom, e.g., by cleavage of the target mRNA.

"Regulatable chimeric antigen receptor (RCAR)," as that term is used herein, refers to a set of polypeptides, typically two in the simplest embodiments, which when in a RCARX cell, provides the RCARX cell with specificity for a target cell, typically a cancer cell, and with regulatable intracellular signal generation which can optimize an immune effector property of the RCARX cell, e.g., cytolytic activity, cytokine secretion, cell survival, or proliferation. An RCARX cell relies at least in part, on an antigen binding domain to provide specificity to a target cell that comprises the antigen bound by the antigen binding domain. In an embodiment, an RCAR includes a dimerization switch that, upon the presence of a dimerization molecule, can couple an intracellular signaling domain to a extracellular recognition element. An extracellular recognition element can be an antigen binding domain, an inhibitory counter ligand binding domain, or costimulatory ECD domain. In an embodiment, an RCAR includes a dimerization switch that, upon the presence of a dimerization molecule, can couple an intracellular signaling domain to a extracellular recognition element, which is not expressed by the RCARX cell but provided exogenously.

"RCARX cell," as that term is used herein, refers to a cell comprising RCAR. Any cell that is engineered to express a RCAR can be used as a RCARX cell. In an embodiment the RCARX cell is a T cell, and is referred to as a RCART cell. In an embodiment the RCARX cell is an NK cell, and is referred to as a RCARN cell.

In an embodiment the RCARX cell is autologous to the patient. In an embodiment the RCARX is allogeneic to the patient. In an embodiment, a patient receives more than one kind of RCARX cell, e.g., the patient receives a RCART cell and a RCARN cell.

"Specifically binds," as that term is used herein, refers to an antibody, or a ligand, which recognizes and binds with a binding partner (e.g., tumor antigen) protein present in a sample, but which antibody or ligand does not substantially recognize or bind other molecules in the sample.

"Switch domain," as that term is used herein, refers to an entity, typically a polypeptide-based entity, that, in the presence of a dimerization molecule, associates with another switch domain. The association results in a functional coupling of a first entity linked to, e.g., fused to, a first switch domain, and a second entity linked to, e.g., fused to, a second switch domain. A first and second switch domain are collectively referred to as a dimerization switch. In embodiments, the first and second switch domains are the same as one another, e.g., they are polypeptides having the same primary amino acid sequence, and are referred to collectively as a homodimerization switch. In embodiments, the first and second switch domains are different from one another, e.g., they are polypeptides having different primary amino acid sequence, and are referred to collectively as a heterodimerization switch. In an embodiment, the switch is intracellular. In embodiments, the switch is extracellular. In embodiments, the switch domain is a polypeptide-based entity, e.g., FKBP-FRB, and the dimerization molecule is small molecule, e.g., a rapalogue. In embodiments, the switch domain is a polypeptide-based entity, e.g., an scFv that binds a myc peptide, and the dimerization molecule is a polypeptide, a fragment thereof, or a multimer of a polypeptide, e.g., a myc ligand or multimers of a myc ligand that bind to one or more myc scFvs. In embodiments, the switch domain is a polypeptide-based entity, e.g., myc receptor, and the dimerization molecule is an antibody or fragments thereof, e.g., myc antibody.

"Transmembrane domain," as that term is used herein, refers to a polypeptide that spans the plasma membrane. In an embodiment, it links an extracellular sequence, e.g., a switch domain, an extracellular recognition element, e.g., an antigen binding domain, an inhibitory counter ligand binding domain, or costimulatory ECD domain, to an intracellular sequence, e.g., to a switch domain or an intracellular signaling domain. A transmembrane domain of particular use in this invention may include at least the transmembrane region(s) of e.g., the alpha, beta or zeta chain of the T-cell receptor, CD28, CD3 epsilon, CD45, CD4, CD5, CD8 (e.g., CD8 alpha, CD8 beta), CD9, CD16, CD22, CD33, CD37, CD64, CD80, CD86, CD134, CD137, CD154. In some embodiments, a transmembrane domain may include at least the transmembrane region(s) of, e.g., KIRDS2, OX40, CD2, CD27, LFA-1 (CD11a, CD18), ICOS (CD278), 4-1BB (CD137), GITR, CD40, BAFFR, HVEM (LIGHTR), SLAMF7, NKp80 (KLRF1), CD160, CD19, IL2R beta, IL2R gamma, IL7R α, ITGA1, VLA1, CD49a, ITGA4, IA4, CD49D, ITGA6, VLA-6, CD49f, ITGAD, CD11d, ITGAE, CD103, ITGAL, CD11a, LFA-1, ITGAM, CD11b, ITGAX, CD11c, ITGB1, CD29, ITGB2, CD18, LFA-1, ITGB7, TNFR2, DNAM1 (CD226), SLAMF4 (CD244, 2B4), CD84, CD96 (Tactile), CEACAM1, CRTAM, Ly9 (CD229), CD160 (BY55), PSGL1, CD100 (SEMA4D), SLAMF6 (NTB-A, Ly108), SLAM (SLAMF1, CD150, IPO-3), BLAME (SLAMF8), SELPLG (CD162), LTBR, PAG/Cbp.

"Treat", "treatment" and "treating", as those terms are interchangeably used herein, refer to the reduction or amelioration of the progression, severity and/or duration of a proliferative disorder, or the amelioration of one or more symptoms (preferably, one or more discernible symptoms) of a proliferative disorder resulting from the administration of one or more therapies (e.g., one or more therapeutic agents such as a CAR of the invention). In specific embodiments, the terms "treat", "treatment" and "treating" refer to the amelioration of at least one measurable physical parameter of a proliferative disorder, such as growth of a tumor, not necessarily discernible by the patient. In other embodiments the terms "treat", "treatment" and "treating"-refer to the inhibition of the progression of a proliferative disorder, either physically by, e.g., stabilization of a discernible symptom, physiologically by, e.g., stabilization of a physical parameter, or both. In other embodiments the terms "treat", "treatment" and "treating" refer to the reduction or stabilization of tumor size or cancerous cell count.

"Tumor antigen" or "cancer-associated antigen", as those terms are interchangeably used herein, refers to a molecule (typically a protein, carbohydrate or lipid) that is expressed on the surface of a cancer cell, either entirely or as a fragment (e.g., MHC/peptide), and which is useful for the preferential targeting of a pharmacological agent to the cancer cell. In some embodiments, a tumor antigen is a marker expressed by both normal cells and cancer cells, e.g., a lineage marker, e.g., CD19 on B cells. In some embodiments, a tumor antigen is a cell surface molecule that is overexpressed in a cancer cell in comparison to a normal cell, for instance, 1-fold over expression, 2-fold overexpression, 3-fold overexpression or more in comparison to a normal cell. In some embodiments, a tumor antigen is a cell surface molecule that is inappropriately synthesized in the cancer cell, for instance, a molecule that contains deletions, additions or mutations in comparison to the molecule expressed on a normal cell. In some embodiments, a tumor antigen will be expressed exclusively on the cell surface of a cancer cell, entirely or as a fragment (e.g., MHC/peptide), and not synthesized or expressed on the surface of a normal cell. In some embodiments, the RCARs of the present invention includes RCARs comprising an antigen binding domain (e.g., antibody or antibody fragment) that binds to a MHC presented peptide. Normally, peptides derived from endogenous proteins fill the pockets of Major histocompatibility complex (MHC) class I molecules, and are recognized by T cell receptors (TCRs) on CD8+ T lymphocytes. The MHC class I complexes are constitutively expressed by all nucleated cells. In cancer, virus-specific and/or tumor-specific peptide/MHC complexes represent a unique class of cell surface targets for immunotherapy. TCR-like antibodies targeting peptides derived from viral or tumor antigens in the context of human leukocyte antigen (HLA)-A1 or HLA-A2 have been described (see, e.g., Sastry et al., J Virol. 2011 85(5):1935-1942; Sergeeva et al., Blood, 2011 117(16): 4262-4272; Verma et al., J Immunol 2010 184(4):2156-2165; Willemsen et al., Gene Ther 2001 8(21):1601-1608; Dao et al., Sci Transl Med 2013 5(176):176ra33; Tassev et al., Cancer Gene Ther 2012 19(2):84-100). For example, TCR-like antibody can be identified from screening a library, such as a human scFv phage displayed library.

"Unswitched auxiliary antigen binding member," as the term is used herein, refers to a polypeptide that comprises: an antigen binding domain which binds an antigen other than the antigen bound by another antigen binding domain of the RCAR; a transmembrane domain; and an intracellular signaling domain, e.g., a primary intracellular signaling domain. Typically, it does not comprise a switch domain that can form a dimerization switch with a switch domain on another component of the RCAR.

"Unit dosage form" as the term is used herein refers to a dosage for suitable one administration. By way of example a unit dosage form can be a tablet, a capsule, or an amount of therapeutic disposed in a delivery device, e.g., a syringe or intravenous drip bag. In an embodiment a unit dosage form is administered in a single administration. In an embodiment more than one unit dosage form, e.g., two tablets, can be administered simultaneously.

"Xenogeneic" as the term is used herein refers to a graft derived from an animal of a different species.

"Bioequivalent", as the term is used herein, refers to an amount of an agent other than the reference compound (e.g., RAD001), required to produce an effect equivalent to the effect produced by the reference dose or reference amount of the reference compound (e.g., RAD001). In an embodiment the effect is the level of mTOR inhibition, e.g., as measured by P70 S6 kinase inhibition, e.g., as evaluated in an in vivo or in vitro assay, e.g., as measured by an assay described herein, e.g., the Boulay assay, or measurement of phosphorylated S6 levels by western blot. In an embodiment, the effect is alteration of the ratio of PD-1 positive/PD-1 negative T cells, as measured by cell sorting. In an embodiment a bioequivalent amount or dose of an mTOR inhibitor is the amount or dose that achieves the same level of P70 S6 kinase inhibition as does the reference dose or reference amount of a reference compound. In an embodiment, a bioequivalent amount or dose of an mTOR inhibitor is the amount or dose that achieves the same level of alteration in the ratio of PD-1 positive/PD-1 negative T cells as does the reference dose or reference amount of a reference compound.

"Low, immune enhancing, dose" when used herein in conjunction with an mTOR inhibitor, e.g., an allosteric mTOR inhibitor, e.g., RAD001 or rapamycin, or a catalytic mTOR inhibitor, refers to a dose of mTOR inhibitor that partially, but not fully, inhibits mTOR activity, e.g., as measured by the inhibition of P70 S6 kinase activity. Methods for evaluating mTOR activity, e.g., by inhibition of P70 S6 kinase, are discussed herein. The dose is insufficient to result in complete immune suppression but is sufficient to enhance the immune response. In an embodiment, the low, immune enhancing, dose of mTOR inhibitor results in a decrease in the number of PD-1 positive T cells and/or an increase in the number of PD-1 negative T cells, or an increase in the ratio of PD-1 negative T cells/PD-1 positive T cells. In an embodiment, the low, immune enhancing, dose of mTOR inhibitor results in an increase in the number of naive T cells. In an embodiment, the low, immune enhancing, dose of mTOR inhibitor results in one or more of the following:

an increase in the expression of one or more of the following markers: $CD62L^{high}$, $CD127^{high}$, $CD27^+$, and BCL2, e.g., on memory T cells, e.g., memory T cell precursors;

a decrease in the expression of KLRG1, e.g., on memory T cells, e.g., memory T cell precursors; and an increase in the number of memory T cell precursors, e.g., cells with any one or combination of the following characteristics: increased $CD62L^{high}$, increased $CD127^{high}$, increased $CD27^+$, decreased KLRG1, and increased BCL2; wherein any of the changes described above occurs, e.g., at least transiently, e.g., as compared to a non-treated subject.

Antigen Binding Domain

The CARs described herein, e.g., the RCARs described herein, include an antigen binding domain in the extracellular region of the antigen binding member. An "antigen binding domain" as the term is used herein, refers to a molecule that has affinity for a target antigen, typically an antigen on a target cell, e.g., a cancer cell. An exemplary antigen binding domain comprises a polypeptide, e.g., an antibody molecule (which includes an antibody, and antigen binding fragments thereof, e.g., a immunoglobulin, single domain antibody (sdAb), and an scFv), or a non-antibody scaffold, e.g., a fibronectin, and the like. In embodiments, the antigen binding domain is a single polypeptide. In embodiments, the antigen binding domain comprises, one, two, or more, polypeptides.

The choice of an antigen binding domain can depend upon the type and number of ligands or receptors that define the surface of a target cell. For example, the antigen binding domain may be chosen to recognize a ligand or receptor that acts as a cell surface marker on target cells associated with a particular disease state. Examples of cell surface markers that may act as ligands or receptors include a cell surface marker associated with a particular disease state, e.g., cell surface makers for viral diseases, bacterial diseases parasitic infections, autoimmune diseases and disorders associated with unwanted cell proliferation, e.g., a cancer, e.g., a cancer described herein.

In the context of the present disclosure, "tumor antigen" or "proliferative disorder antigen" or "antigen associated with a proliferative disorder" refers to antigens that are common to specific proliferative disorders. In certain aspects, the proliferative disorder antigens of the present invention are derived from, cancers including but not limited to primary or metastatic melanoma, thymoma, lymphoma, sarcoma, lung cancer (e.g., NSCLC or SCLC), liver cancer, non-Hodgkin's lymphoma, Hodgkin's lymphoma, leukemias, multiple myeloma, glioblastoma, neuroblastoma, uterine cancer, cervical cancer, renal cancer, thyroid cancer, bladder cancer, kidney cancer, mesothelioma, and adenocarcinomas such as breast cancer, prostate cancer, ovarian cancer, pancreatic cancer, colon cancer and the like. In some embodiments, the cancer is B-cell acute lymphoid leukemia ("BALL"), T-cell acute lymphoid leukemia ("TALL"), acute lymphoid leukemia (ALL), acute myelogenous leukemia (AML); one or more chronic leukemias including but not limited to chronic myelogenous leukemia (CML), chronic lymphocytic leukemia (CLL); additional hematologic cancers or hematologic conditions including, but not limited to B cell prolymphocytic leukemia, blastic plasmacytoid dendritic cell neoplasm, Burkitt's lymphoma, diffuse large B cell lymphoma, follicular lymphoma, hairy cell leukemia, small cell- or a large cell-follicular lymphoma, malignant lymphoproliferative conditions, MALT lymphoma, mantle cell lymphoma, Marginal zone lymphoma, multiple myeloma, myelodysplasia and myelodysplastic syndrome, non-Hodgkin's lymphoma, plasmablastic lymphoma, plasmacytoid dendritic cell neoplasm, Waldenstrom macroglobulinemia.

In one embodiment, the tumor antigen comprises one or more antigenic cancer epitopes immunologically recognized by tumor infiltrating lymphocytes (TIL) derived from a cancer tumor of a mammal.

Tumor antigens are proteins that are produced by tumor cells that elicit an immune response, particularly T-cell mediated immune responses. The selection of the antigen binding domain of the invention will depend on the particular type of cancer to be treated. Tumor antigens are well known in the art and include, for example, a glioma-associated antigen, carcinoembryonic antigen (CEA), EGFRvIII, IL-11Ra, IL-13Ra, EGFR, FAP, B7H3, Kit, CA-IX, CS-1, MUC1, BCMA, bcr-abl, HER2, β-human chorionic gonadotropin, alphafetoprotein (AFP), ALK, CD19, CD123, cyclin B1, lectin-reactive AFP, Fos-related antigen 1, ADRB3, thyroglobulin, EphA2, RAGE-1, RU1, RU2, SSX2, AKAP-4, LCK, OY-TES1, PAX5, SART3, CLL-1, fucosyl GM1, GloboH, MN-CA IX, EPCAM, EVT6-AML, TGS5, human telomerase reverse transcriptase, plysialic acid, PLAC1, RU1, RU2 (AS), intestinal carboxyl esterase, lewisY, sLe, LY6K, mut hsp70-2, M-CSF, MYCN, RhoC, TRP-2, CYP1B1, BORIS, prostase, prostate-specific antigen (PSA), PAX3, PAP, NY-ESO-1, LAGE-1a, LMP2, NCAM, p53, p53 mutant, Ras mutant, gp100, prostein, OR51E2, PANX3, PSMA, PSCA, Her2/neu, hTERT, HMWMAA, HAVCR1, VEGFR2, PDGFR-beta, survivin and telomerase, legumain, HPV E6,E7, sperm protein 17, SSEA-4, tyrosinase, TARP, WT1, prostate-carcinoma tumor antigen-1 (PCTA-1), ML-IAP, MAGE, MAGE-A1,MAD-CT-1, MAD-CT-2, MelanA/MART1, XAGE1, ELF2M, ERG (TMPRSS2 ETS fusion gene), NA17, neutrophil elastase, sarcoma translocation breakpoints, NY-BR-1, ephrinB2, CD20, CD22, CD24, CD30, CD33, CD38, CD44v6, CD97, CD171, CD179a, androgen receptor, FAP, insulin growth factor (IGF)-I, IGF-II, IGF-I receptor, GD2, o-acetyl-GD2, GD3, GM3, GPRC5D, GPR20, CXORF61, folate receptor (FRa), folate receptor beta, ROR1, Flt3, TAG72, TN Ag, Tie 2, TEM1, TEM7R, CLDN6, TSHR, UPK2, and mesothelin. In a preferred embodiment, the tumor antigen is selected from the group consisting of folate receptor (FRa), mesothelin, EGFRvIII, IL-13Ra, CD123, CD19, CD33, BCMA, GD2, CLL-1, CA-IX, MUC1, HER2, and any combination thereof.

In one embodiment, the tumor antigen comprises one or more antigenic cancer epitopes associated with a malignant tumor. Malignant tumors express a number of proteins that can serve as target antigens for an immune attack. These molecules include but are not limited to tissue-specific antigens such as MART-1, tyrosinase and GP 100 in melanoma and prostatic acid phosphatase (PAP) and prostate-specific antigen (PSA) in prostate cancer. Other target antigens include transformation-related molecules such as the oncogene HER-2/Neu/ErbB-2. Yet another group of target antigens are onco-fetal antigens such as carcinoembryonic antigen (CEA). In B-cell lymphoma the tumor-specific idiotype immunoglobulin constitutes a truly tumor-specific immunoglobulin antigen that is unique to the individual tumor. B-cell differentiation antigens such as CD19, CD20 and CD37 are other candidates for target antigens in B-cell lymphoma.

Non-limiting examples of tumor antigens include the following: Differentiation antigens such as MART-1/MelanA (MART-I), gp100 (Pmel 17), tyrosinase, TRP-1, TRP-2 and tumor-specific multilineage antigens such as MAGE-1, MAGE-3, BAGE, GAGE-1, GAGE-2, p15; overexpressed embryonic antigens such as CEA; overexpressed oncogenes and mutated tumor-suppressor genes such as p53, Ras, HER-2/neu; unique tumor antigens resulting from chromosomal translocations; such as BCR-ABL, E2A-PRL, H4-RET, IGH-IGK, MYL-RAR; and viral antigens, such as the Epstein Barr virus antigens EBVA and the human papillomavirus (HPV) antigens E6 and E7. Other large, protein-based antigens include TSP-180, MAGE-4, MAGE-5, MAGE-6, RAGE, NY-ESO, p185erbB2, p180erbB-3, c-met, nm-23H1, PSA, TAG-72, CA 19-9, CA 72-4, CAM 17.1, NuMa, K-ras, beta-Catenin, CDK4, Mum-1, p 15, p 16, 43-9F, 5T4, 791Tgp72, alpha-fetoprotein, beta-HCG, BCA225, BTAA, CA 125, CA 15-3\CA 27.29\BCAA, CA 195, CA 242, CA-50, CAM43, CD68\P1, CO-029, FGF-5, G250, Ga733\EpCAM, HTgp-175, M344, MA-50, MG7-Ag, MOV18, NB/70K, NY-CO-1, RCAS1, SDCCAG16, TA-90\Mac-2 binding protein\cyclophilin C-associated protein, TAAL6, TAG72, TLP, and TPS.

Depending on the desired antigen to be targeted, the RCAR of the invention can be engineered to include the appropriate antigen bind domain that is specific to the desired antigen target.

A RCAR as described herein, includes a CAR comprising an antigen binding domain (e.g., antibody or antibody fragment) that binds to a MHC presented-peptide. Normally, peptides derived from endogenous proteins fill the pocket of Major histocompatibility complex (MHC) class I molecules, and are recognized by T cell receptors (TCRs) on CD8+T lymphocytes. The MHC class I complexes are constitutively expressed by all nucleated cells. In cancer, virus-specific and/or tumor-specific peptide/MHC complexes represent a unique class of cell surface targets for immunotherapy. TCR-like antibodies targeting peptides derived from viral or tumor antigens in the context of human leukocyte antigen (HLA)-A1 or HLA-A2 have been described (see, e.g., Sastry et al., J Virol. 2011 85(5):1935-1942; Sergeeva et al., Bood, 2011 117(16):4262-4272; Verma et al., J Immunol 2010 184(4):2156-2165; Willemsen et al., Gene Ther 2001 8(21): 1601-1608; Dao et al., Sci Transl Med 2013 5(176):176ra33; Tassev et al., Cancer Gene Ther 2012 19(2):84-100). For example, TCR-like antibody can be identified from screening a library, such as a human scFv phage displayed library. Accordingly, the present invention provides a CAR, e.g., a RCAR described herein, that comprises an antigen binding domain that binds to a MHC presented peptide of a molecule selected from any tumor antigen described above that is expressed intracellularly, e.g., p53, BCR-Abl, Ras, K-ras, NY-ESO-1, and c-met.

Also provided herein are RCARs wherein the antigen binding member comprises a plurality of antigen binding domains. Without wishing to be bound by theory, it is believed that an antigen binding member comprising two or more antigen binding domains can result in additive or synergistic enhancement of activation and effector functions when the two or more corresponding antigens are encountered. Without wishing to be bound by theory, it is also believed that an antigen binding member comprising two or more antigen binding domains can increase the specificity of the effector cells for cancer cells versus normal cell, to offset antigen escape or to allow for targeting the cancer cell and the cancer microenvironment.

In this embodiment, the antigen binding member can comprise a plurality of, e.g., 2, 3, 4, or 5, antigen binding domains, e.g., scFvs, wherein each antigen binding domain binds to a target antigen. In an embodiment, two or more of the antigen binding domains can bind to different antigens. In an embodiment, two or more of the antigen binding domains can bind to the same antigen, e.g., the same or different epitopes on the same antigen. In an embodiment, the plurality of antigen binding domains are linked to each other, e.g., the C-terminus of a first antigen binding domain is linked to the N-terminus of a second antigen binding domain. In an embodiment, the C-terminus of a first antigen binding domain is linked to the N-terminus of a second antigen binding domain by a covalent bond, e.g., a peptide bond. The order of the antigen binding domains can be optimized for increased binding of the target antigens simultaneously, e.g., by the relative size of the corresponding target antigens. For example, for the larger of the target antigens, the corresponding antigen binding domain is disposed closer to the transmembrane domain of the antigen binding member; and for the smaller of the target antigens, the corresponding antigen binding domain is disposed farther from the transmembrane domain of the antigen binding member, e.g., more extracellularly. (See, e.g., Grada et al., 2013, *Mol Ther*, 2:e105).

In some embodiments, a linker or hinge region is disposed between each of the antigen binding domains, e.g., a linker or hinge region is disposed between the C-terminus of a first antigen binding domain and the N-terminus of a second antigen binding domain. By way of example, an antigen binding member comprising two antigen binding domains (e.g., $ABD_1$ and $ABD_2$) can be arranged in the following configuration: $[ABD_1]$-[linker/hinge]-$[ABD_2]$. Additional antigen binding domains can be added in a similar manner, optionally with linker or hinge regions disposed between the C-terminus of an antigen binding domain and the N-terminus of the next antigen binding domain. Linkers or hinge regions suitable for use in linking a plurality of antigen binding members are flexible, non-cleavable, and allow near-free motion of each antigen binding domain independent from the other antigen binding domains to encourage binding with multiple target antigens simultaneously. Any flexible linker or hinge region known in the art can be used. Examples of linkers include peptide linkers comprising glycine and serine residues, e.g., (GGGS)n, where n is a positive integer equal to or greater than 1, e.g., n=1, 2, 3, 4, 5, 6, 7, 8, 9, or 10 (SEQ ID NO:327). Examples of hinge regions include SEQ ID NO: 136.

Antigen Binding Domains Derived from an Antibody Molecule

The antigen binding domain can be derived from an antibody molecule, e.g., one or more of monoclonal antibodies, polyclonal antibodies, recombinant antibodies, human antibodies, humanized antibodies, single-domain antibodies e.g., a heavy chain variable domain (VH), a light chain variable domain (VL) and a variable domain (VHH) from, e.g., human or camelid origin. In some instances, it is beneficial for the antigen binding domain to be derived from the same species in which the RCAR will ultimately be used in, e.g., for use in humans, it may be beneficial for the antigen binding domain of the CAR, e.g., the RCAR, e.g., described herein, to comprise a human or a humanized antigen binding domain. Antibodies can be obtained using known techniques known in the art.

The term "antibody," as used herein, refers to an immunoglobulin molecule which specifically binds with a target antigen. An antibody can be intact immunoglobulin derived from natural sources or from recombinant sources and can be an immunoreactive portion of intact immunoglobulin. Antibodies are typically tetramers of immunoglobulin molecules. The antibody molecule described herein may exist in a variety of forms where the antigen binding portion of the antibody is expressed as part of a contiguous polypeptide chain including, for example, a single domain antibody fragment (sdAb), a single chain antibody (scFv) and a humanized or human antibody, e.g., as described herein.

The term "antibody fragment" refers to a portion of an intact antibody and refers to the antigenic determining variable regions of an intact antibody. Examples of antibody fragments include, but are not limited to, a single chain domain antibody (sdAb), Fab, Fab', F(ab')$_2$, and Fv fragments, linear antibodies, scFv antibodies, a linear antibody, single domain antibody such as an sdAb (either VL or VH), a camelid VHH domain, and multispecific antibodies formed from antibody fragments.

An "antibody heavy chain," as used herein, refers to the larger of the two types of polypeptide chains present in all antibody molecules in their naturally occurring conformations.

An "antibody light chain," as used herein, refers to the smaller of the two types of polypeptide chains present in all antibody molecules in their naturally occurring conformations. κ and λ light chains refer to the two major antibody light chain isotypes.

By the term "synthetic antibody" as used herein, is meant an antibody molecule which is generated using recombinant DNA technology, such as, for example, an antibody molecule expressed by a bacteriophage as described herein. The term should also be construed to mean an antibody molecule which has been generated by the synthesis of a DNA molecule encoding the antibody molecule and which DNA molecule expresses an antibody protein, or an amino acid sequence specifying the antibody, wherein the DNA or amino acid sequence has been obtained using synthetic DNA or amino acid sequence technology which is available and well known in the art.

In embodiments, the antigen binding domain comprises a fragment of an antibody that is sufficient to confer recognition and specific binding to the target antigen. Examples of an antibody fragment include, but are not limited to, an Fab, Fab', F(ab')$_2$, or Fv fragment, an scFv antibody fragment, a linear antibody, single domain antibody such as an sdAb (either VL or VH), a camelid VHH domain, and multispecific antibodies formed from antibody fragments.

In an embodiment, the antigen binding domain is a "scFv," which can comprise a fusion protein comprising a VL chain and a VH chain of an antibody, where the VH and VL are, e.g., linked via a short flexible polypeptide linker, e.g., a linker described herein. The scFv is capable of being expressed as a single chain polypeptide and retains the specificity of the intact antibody from which it is derived. Moreover, the VL and VH variable chains can be linked in either order, e.g., with respect to the N-terminal and C-terminal ends of the polypeptide, the scFv may comprise VL-linker-VH or may comprise VH-linker-VL. An scFv that can be prepared according to method known in the art (see, for example, Bird et al., (1988) Science 242:423-426 and Huston et al., (1988) Proc. Natl. Acad. Sci. USA 85:5879-5883).

As described above and elsewhere, scFv molecules can be produced by linking VH and VL chians together using flexible polypeptide linkers. In some embodiments, the scFv molecules comprise flexible polypeptide linker with an optimized length and/or amino acid composition. The flexible polypeptide linker length can greatly affect how the variable regions of a scFv fold and interact. In fact, if a short polypeptide linker is employed (e.g., between 5-10 amino acids, intrachain folding is prevented. For examples of linker orientation and size see, e.g., Hollinger et al. 1993 Proc Natl Acad. Sci. U.S.A. 90:6444-6448, U.S. Patent Application Publication Nos. 2005/0100543, 2005/0175606, 2007/0014794, and PCT publication Nos. WO2006/020258 and WO2007/024715, is incorporated herein by reference. In one embodiment, the peptide linker of the scFv consists of amino acids such as glycine and/or serine residues used alone or in combination, to link variable heavy and variable light chain regions together. In one embodiment, the flexible polypeptide linker is a Gly/Ser linker and, e.g., comprises the amino acid sequence (Gly-Gly-Gly-Ser)n (SEQ ID NO: 327), where n is a positive integer equal to or greater than 1. For example, n=1, n=2, n=3. n=4, n=5 and n=6, n=7, n=8, n=9 and n=10. In one embodiment, the flexible polypeptide linkers include, but are not limited to, (Gly4 Ser)4 (SEQ ID NO: 328) or (Gly4 Ser)3 (SEQ ID NO: 329). In another embodiment, the linkers include multiple repeats of (Gly2Ser), (GlySer) or (Gly3Ser) (SEQ ID NO: 330).

In some embodiments, the antigen binding domain is a single domain antigen binding (SDAB) molecules. A SDAB molecule includes molecules whose complementary determining regions are part of a single domain polypeptide. Examples include, but are not limited to, heavy chain variable domains, binding molecules naturally devoid of light chains, single domains derived from conventional 4-chain antibodies, engineered domains and single domain scaffolds other than those derived from antibodies (e.g., described in more detail below). SDAB molecules may be any of the art, or any future single domain molecules. SDAB molecules may be derived from any species including, but not limited to mouse, human, camel, llama, fish, shark, goat, rabbit, and bovine. This term also includes naturally occurring single domain antibody molecules from species other than *Camelidae* and sharks.

In one aspect, an SDAB molecule can be derived from a variable region of the immunoglobulin found in fish, such as, for example, that which is derived from the immunoglobulin isotype known as Novel Antigen Receptor (NAR) found in the serum of shark. Methods of producing single domain molecules derived from a variable region of NAR ("IgNARs") are described in WO 03/014161 and Streltsov (2005) *Protein Sci.* 14:2901-2909.

According to another aspect, an SDAB molecule is a naturally occurring single domain antigen binding molecule known as a heavy chain devoid of light chains. Such single domain molecules are disclosed in WO 9404678 and Hamers-Casterman, C. et al. (1993) Nature 363:446-448, for example. For clarity reasons, this variable domain derived from a heavy chain molecule naturally devoid of light chain is known herein as a VHH or nanobody to distinguish it from the conventional VH of four chain immunoglobulins. Such a VHH molecule can be derived from *Camelidae* species, for example in camel, llama, dromedary, alpaca and guanaco. Other species besides *Camelidae* may produce heavy chain molecules naturally devoid of light chain; such VHHs are within the scope of the invention.

Antibody proteins obtained from members of the camel and dromedary (*Camelus bactrianus* and *Calelus dromaderius*) family including new world members such as llama species (*Lama paccos, Lama glama* and *Lama vicugna*) have been characterized with respect to size, structural complexity and antigenicity for human subjects. Certain IgG antibodies from this family of mammals as found in nature lack light chains, and are thus structurally distinct from the typical four chain quaternary structure having two heavy and two light chains, for antibodies from other animals. See PCT/EP93/02214 (WO 94/04678 published 3 Mar. 1994).

A region of the camelid antibody which is the small single variable domain identified as VHH can be obtained by genetic engineering to yield a small protein having high affinity for a target, resulting in a low molecular weight antibody-derived protein known as a "camelid nanobody". See U.S. Pat. No. 5,759,808 issued Jun. 2, 1998; see also Stijlemans et al., (2004) J Biol Chem 279:1256-1261; Dumoulin et al., (2003) Nature 424:783-788; Pleschberger et al., (2003) Bioconjugate Chem 14:440-448; Cortez-Retamozo et al., (2002) Int J Cancer 89:456-62; and Lauwereys et al., (1998) EMBO J 17:3512-3520. Engineered libraries of camelid antibodies and antibody fragments are commercially available, for example, from Ablynx, Ghent, Belgium. (e.g., US20060115470; Domantis (US20070065440, US20090148434). As with other antibodies of non-human origin, an amino acid sequence of a camelid antibody can be altered recombinantly to obtain a sequence that more closely resembles a human sequence, i.e., the nanobody can be "humanized". Thus the natural low antigenicity of camelid antibodies to humans can be further reduced.

The camelid nanobody has a molecular weight approximately one-tenth that of a human IgG molecule, and the protein has a physical diameter of only a few nanometers. One consequence of the small size is the ability of camelid nanobodies to bind to antigenic sites that are functionally invisible to larger antibody proteins, i.e., camelid nanobodies are useful as reagents detect antigens that are otherwise cryptic using classical immunological techniques, and as possible therapeutic agents. Thus yet another consequence of small size is that a camelid nanobody can inhibit as a result of binding to a specific site in a groove or narrow cleft of a target protein, and hence can serve in a capacity that more closely resembles the function of a classical low molecular weight drug than that of a classical antibody.

The low molecular weight and compact size further result in camelid nanobodies being extremely thermostable, stable to extreme pH and to proteolytic digestion, and poorly antigenic. Another consequence is that camelid nanobodies readily move from the circulatory system into tissues, and even cross the blood-brain barrier and can treat disorders that affect nervous tissue. Nanobodies can further facilitated drug transport across the blood brain barrier. See U.S. patent application 20040161738 published Aug. 19, 2004. These features combined with the low antigenicity to humans indicate great therapeutic potential. Further, these molecules can be fully expressed in prokaryotic cells such as E. coli and are expressed as fusion proteins with bacteriophage and are functional.

An antigen binding domain can comprise a a camelid antibody or nanobody, or an antigen binding fragment thereof. Such antibodies can have high affinity for its cognate antigen. In certain embodiments herein, the camelid antibody or nanobody is naturally produced in the camelid animal, i.e., is produced by the camelid following immunization with antigen or a peptide fragment thereof. Alternatively, the camelid nanobody is engineered, i.e., produced by selection for example from a library of phage displaying appropriately mutagenized camelid nanobody proteins using panning procedures with the target antigen. Engineered nanobodies can further be customized by genetic engineering to have a half life in a recipient subject of from 45 minutes to two weeks. In a specific embodiment, the camelid antibody or nanobody is obtained by grafting the CDRs sequences of the heavy or light chain of the human antibodies of the invention into nanobody or single domain antibody framework sequences, as described for example in PCT/EP93/02214.

An antigen binding domain can comprise a single domain antibody, e.g., which relies only on a heavy chain variable region for binding, e.g., a nanobody. Nanobodies suitable for use herein can be made by the methods described in US2010/0028341, WO2009/030285, and WO2010/007376.

In certain embodiments, the SDAB molecule is a single chain fusion polypeptide comprising one or more single domain molecules (e.g., nanobodies), devoid of a complementary variable domain or an immunoglobulin constant, e.g., Fc, region, that binds to one or more target antigens.

The SDAB molecules can be recombinant, CDR-grafted, humanized, camelized, de-immunized and/or in vitro generated (e.g., selected by phage display).

In one embodiment, the antigen biding domain portion comprises a human antibody or a fragment thereof.

In some embodiments, a non-human antibody is humanized, where specific sequences or regions of the antibody are modified to increase similarity to an antibody naturally produced in a human. In an embodiment, the antigen binding domain is humanized.

Non human antibodies can be humanized using a variety of techniques known in the art, e.g., CDR-grafting (see, e.g., European Patent No. EP 239,400; International Publication No. WO 91/09967; and U.S. Pat. Nos. 5,225,539, 5,530,101, and 5,585,089, each of which is incorporated herein in its entirety by reference), veneering or resurfacing (see, e.g., European Patent Nos. EP 592,106 and EP 519,596; Padlan, 1991, Molecular Immunology, 28(4/5):489-498; Studnicka et al., 1994, Protein Engineering, 7(6):805-814; and Roguska et al., 1994, PNAS, 91:969-973, each of which is incorporated herein by its entirety by reference), chain shuffling (see, e.g., U.S. Pat. No. 5,565,332, which is incorporated herein in its entirety by reference), and techniques disclosed in, e.g., U.S. Patent Application Publication No. US2005/0042664, U.S. Patent Application Publication No. US2005/0048617, U.S. Pat. Nos. 6,407,213, 5,766,886, International Publication No. WO 9317105, Tan et al., 2002, J. Immunol., 169:1119-25; Caldas et al., 2000, Protein Eng., 13(5):353-60; Morea et al., 2000, Methods, 20:267-79; Baca et al., 1997, J. Biol. Chem., 272:10678-84; Roguska et al., 1996, Protein Eng., 9(10):895-904; Couto et al., 1995, Cancer Res., 55:5973s-5977; Couto et al., 1995, Cancer Res., 55(8):1717-22; Sandhu 1994 Gene, 150(2):409-10; and Pedersen et al., 1994, J. Mol. Biol., 235(3):959-73, each of which is incorporated herein in its entirety by reference. Often, framework residues in the framework regions will be substituted with the corresponding residue from the CDR donor antibody to alter, for example improve, antigen binding. These framework substitutions are identified by methods well-known in the art, e.g., by modeling of the interactions of the CDR and framework residues to identify framework residues important for antigen binding and sequence comparison to identify unusual framework residues at particular positions. (See, e.g., Queen et al., U.S. Pat. No. 5,585,089; and Riechmann et al., 1988, Nature, 332: 323, which are incorporated herein by reference in their entireties). In preferred embodiments, the humanized antibody molecule comprises a sequence described herein, e.g., a variable light chain and/or a variable heavy chain described herein, e.g., a humanized variable light chain and/or variable heavy chain described in Table X.

A humanized antibody has one or more amino acid residues introduced into it from a source which is nonhuman. These nonhuman amino acid residues are often referred to as "import" residues, which are typically taken from an "import" variable domain. Thus, humanized antibodies comprise one or more CDRs from nonhuman immunoglobulin molecules and framework regions from human. Humanization of antibodies is well-known in the art and can essentially be performed following the method of Winter and co-workers (Jones et al., Nature, 321:522-525 (1986); Riechmann et al., Nature, 332:323-327 (1988); Verhoeyen et al., Science, 239:1534-1536 (1988)), by substituting rodent CDRs or CDR sequences for the corresponding sequences of a human antibody, i.e., CDR-grafting (EP 239,400; PCT Publication No. WO 91/09967; and U.S. Pat. Nos. 4,816, 567; 6,331,415; 5,225,539; 5,530,101; 5,585,089; 6,548, 640, the contents of which are incorporated herein by reference herein in their entirety). In such humanized chimeric antibodies, substantially less than an intact human variable domain has been substituted by the corresponding sequence from a nonhuman species. In practice, humanized antibodies are typically human antibodies in which some CDR residues and possibly some framework (FR) residues are substituted by residues from analogous sites in rodent antibodies. Humanization of antibodies can also be achieved by veneering or resurfacing (EP 592,106; EP 519,596; Padlan, 1991, Molecular Immunology, 28(4/5):489-498; Studnicka et al., Protein Engineering, 7(6):805-814 (1994); and Roguska et al., PNAS, 91:969-973 (1994)) or chain shuffling (U.S. Pat. No. 5,565,332), the contents of which are incorporated herein by reference herein in their entirety.

In some embodiments, the antibody of the invention is further prepared using an antibody having one or more of the VH and/or VL sequences disclosed herein can be used as starting material to engineer a modified antibody, which modified antibody may have altered properties as compared to the starting antibody. In various embodiments, the antibody is engineered by modifying one or more amino acids within one or both variable regions (i.e., VH and/or VL), for example within one or more CDR regions and/or within one or more framework regions.

In another aspect, the antigen binding domain is a T cell receptor ("TCR"), or a fragment thereof, for example, a single chain TCR (scTCR). Methods to make such TCRs are known in the art. See, e.g., Willemsen R A et al, Gene Therapy 7: 1369-1377 (2000); Zhang T et al, Cancer Gene Ther 11: 487-496 (2004); Aggen et al, Gene Ther. 19(4): 365-74 (2012) (references are incorporated herein by its entirety). For example, scTCR can be engineered that contains the Vα and Vβ genes from a T cell clone linked by a linker (e.g., a flexible peptide). This approach is very useful to cancer associated target that itself is intracellular, however, a fragment of such antigen (peptide) is presented on the surface of the cancer cells by MHC. The TCR sequences may be naturally occurring, or a non-naturally occurring synthetic sequences.

An antigen binding domain can comprise a sequence from Table 11.

TABLE 11

Exemplary Sequences for Antigen Binding Domains

| Target Antigen | Name | Amino Acid Sequence | SEQ ID NO: |
|---|---|---|---|
| CD19 | huscFv1 | EIVMTQSPATLSLSPGERATLSCRASQDISKYLNWYQQKPGQAPRL LIYHTSRLHSGIPARFSGSGSGTDYTLTISSLQPEDFAVYFCQQGN TLPYTFGQGTKLEIKGGGGSGGGGSGGGGSQVQLQESGPGLVKPSE TLSLTCTVSGVSLPDYGVSWIRQPPGKGLEWIGVIWGSETTYYSSS LKSRVTISKDNSKNQVSLKLSSVTAADTAVYYCAKHYYYGGSYAMD YWGQGTLVTVSS | 143 |
| CD19 | huscFv2 | Eivmtqspatlslspgeratlscrasqdiskylnwyqqkpgqaprlliyhtsrlh sgiparfsgsgsgtdytltisslqpedfavyfcqqgntlpytfgqgtkleikggg gsggggsggggsqvqlqesgpglvkpsetlsltctvsgvslpdygvswirqppgk glewigviwgsettyyqsslksrvtiskdnsknqvslklssvtaadtavyycakh yyyggsyamdywgqgtlvtvss | 144 |
| CD19 | huscFv3 | Qvqlqesgpglvkpsetlsltctvsgvslpdygvswirqppgkglewigviwgse ttyyssslksrvtiskdnsknqvslklssvtaadtavyycakhyyyggsyamdyw gqgtlvtvssggggsggggsggggseivmtqspatlslspgeratlscrasqdis kylnwyqqkpgqaprlliyhtsrlhsgiparfsgsgsgtdytltisslqpedfav yfcqqgntlpytfgqgtkleik | 145 |
| CD19 | huscFv4 | Qvqlqesgpglvkpsetlsltctvsgvslpdygvswirqppgkglewigviwgse ttyyqsslksrvtiskdnsknqvslklssvtaadtavyycakhyyyggsyamdyw gqgtivtvssggggsggggsggggseivmtqspatlslspgeratlscrasqdis kylnwyqqkpgqaprlliyhtsrlhsgiparfsgsgsgtdytltisslqpedfav yfcqqgntlpytfgqgtkleik | 146 |
| CD19 | huscFv5 | Eivmtqspatlslspgeratlscrasqdiskylnwyqqkpgqaprlliyhtsrlh sgiparfsgsgsgtdytltisslqpedfavyfcqqgntlpytfgqgtkleikggg gsggggsggggsggggsqvqlqesgpglvkpsetlsltctvsgvslpdygvswir qppgkglewigviwgsettyyssslksrvtiskdnsknqvslklssvtaadtavy ycakhyyyggsyamdywgqgtlvtvss | 147 |
| CD19 | huscFv6 | Eivmtqspatlslspgeratlscrasqdiskylnwyqqkpgqaprlliyhtsrlh sgiparfsgsgsgtdytltisslqpedfavyfcqqgntlpytfgqgtkleikggg gsggggsggggsggggsqvqlqesgpglvkpsetlsltctvsgvslpdygvswir qppgkglewigviwgsettyyqsslksrvtiskdnsknqvslklssvtaadtavy ycakhyyyggsyamdywgqgtlvtvss | 148 |
| CD19 | huscFv7 | Qvqlqesgpglvkpsetlsltctvsgvslpdygvswirqppgkglewigviwgse ttyyssslksrvtiskdnsknqvslklssvtaadtavyycakhyyyggsyamdyw gqgtlvtvssggggsggggsggggsggggseivmtqspatlslspgeratlscra sqdiskylnwyqqkpgqaprlliyhtsrlhsgiparfsgsgsgtdytltisslqp edfavyfcqqgntlpytfgqgtkleik | 149 |
| CD19 | huscFv8 | Qvqlqesgpglvkpsetlsltctvsgvslpdygvswirqppgkglewigviwgse ttyyqsslksrvtiskdnsknqvslklssvtaadtavyycakhyyyggsyamdyw gqgtlvtvssggggsggggsggggsggggseivmtqspatlslspgeratlscra sqdiskylnwyqqkpgqaprlliyhtsrlhsgiparfsgsgsgtdytltisslqp edfavyfcqqgntlpytfgqgtkleik | 150 |
| CD19 | huscFv9 | Eivmtqspatlslspgeratlscrasqdiskylnwyqqkpgqaprlliyhtsrlh sgiparfsgsgsgtdytltisslqpedfavyfcqqgntlpytfgqgtkleikggg gsggggsggggsggggsqvqlqesgpglvkpsetlsltctvsgvslpdygvswir qppgkglewigviwgsettyynsslksrvtiskdnsknqvslklssvtaadtavy ycakhyyyggsyamdywgqgtivtvss | 151 |
| CD19 | HuscFv10 | Qvqlqesgpglvkpsetlsltctvsgvslpdygvswirqppgkglewigviwgse ttyynsslksrvtiskdnsknqvslklssvtaadtavyycakhyyyggsyamdyw gqgtlvtvssggggsggggsggggsggggseivmtqspatlslspgeratlscra sqdiskylnwyqqkpgqaprlliyhtsrlhsgiparfsgsgsgtdytltisslqp edfavyfcqqgntlpytfgqgtkleik | 152 |
| CD19 | HuscFv11 | Eivmtqspatlslspgeratlscrasqdiskylnwyqqkpgqaprlliyhtsrlh sgiparfsgsgsgtdytltisslqpedfavyfcqqgntlpytfgqgtkleikggg gsggggsggggsqvqlqesgpglvkpsetlsltctvsgvslpdygvswirqppgk glewigviwgsettyynsslksrvtiskdnsknqvslklssvtaadtavyycakh yyyggsyamdywgqgtvtvss | 153 |

TABLE 11-continued

Exemplary Sequences for Antigen Binding Domains

| Target Antigen | Name | Amino Acid Sequence | SEQ ID NO: |
|---|---|---|---|
| CD19 | HuscFv12 | Qvqlqesgpglvkpsetlsltctvsgvslpdygvswirqppkglewigviwgse ttyynsslksrvtiskdnsknqvslklssvtaadtavyycakhyyyggsyamdyw gqgtlvtvssggggsggggsggggseivmtqspatlslspgeratlscrasqdis kylnwyqqkpgqaprlliyhtsrlhsgiparfsgsgsgtdytltisslqpedfav yfcqqgntlpytfgqgtkleik | 154 |
| CD19 | muCTL019 | Diqmtqttsslsaslgdrvtiscrasqdiskylnwyqqkpdgtvklliyhtsrlh sgvpsrfsgsgsgtdysltisnleqediatyfcqqgntlpytfgggtkleitggg gsggggsggggsevklqesgpglvapsqslsvtctvsgvslpdygvswirqpprk glewlgviwgsettyynsalksrltiikdnsksqvflkmnslqtddtaiyycakh yyyggsyamdywgqgtsvtvss | 155 |
| CD123 | Mu1172 | DIVLTQSPASLAVSLGQRATISC<u>RASESVDNYGNTFMH</u>WYQQKPGQPPKLL IY<u>RASNLES</u>GIPARFSGSGSRTDFTLTINPVEADDVATYYC<u>QQSNEDPPT</u>FG AGTKLELKGGGGSGGGGSGGGGSQIQLVQSGPELKKPGETVKISCKASGYI F<u>TNYGMN</u>WVKQAPGKSFKWMG<u>WINTYTGESTYSADFKG</u>RFAFSLETSAS TAYLHINDLKNEDTATYFCARS<u>GGYDPMDY</u>WGQGTSVTVSS | 156 |
| CD123 | Mu1176 | DVQITQSPSYLAASPGETITINC<u>RASKSISKDLA</u>WYQEKPGKTNKLLIY<u>SGST LQS</u>GIPSRFSGSGSGTDFTLTISSLEPEDFAMYYC<u>QQHNKYPYT</u>FGGGTKLEI KGGGGSGGGGSGGGGSQVQLQQPGAELVRPGASVKLSCKASGYTFT<u>SYW MN</u>WVKQRPDQGLEWIG<u>RIDPYDSETHYNQKFKD</u>KAILTVDKSSSTAYMQL SSLTSEDSAVYYCAR<u>GNWDDY</u>WGQGTTLTVSS | 157 |
| CD123 | huscFv1 | Divltqspdslavslgeratincrasesvdnygntfmhwyqqkpgqp pklliyrasnlesgvpdrfsgsgsrtdftltisslqaedvavyycqq snedpptfgqgtkleikggggsggggsggggsggggsqiqlvqsgse lkkpgasvkvsckasgyiftnygmnwvrqapgqglewmgwintytge stysadfkgrfvfsldtsvstaylqinalkaedtavyycarsggydp mdywgqgttvtvss | 158 |
| CD123 | huscFv2 | Divltqspdslavslgeratincrasesvdnygntfmhwyqqkpgqp pklliyrasnlesgvpdrfsgsgsrtdftltisslqaedvavyycqq snedpptfgqgtkleikggggsggggsggggsggggsqiqlvqsgae vkkpgasvkvsckasgyiftnygmnwvrqapgqrlewmgwintytge stysadfkgrvtitldtsastaymelsslrsedtavyycarsggydp mdywgqgttvtvss | 159 |
| CD123 | huscFv3 | Eivltqspatlslspgeratlscrasesvdnygntfmhwyqqkpgqa prlliyrasnlesgiparfsgsgsrtdftltisslepedvavyycqq snedpptfgqgtkleikggggsggggsggggsggggsqiqlvqsgse lkkpgasvkvsckasgyiftnygmnwvrqapgqglewmgwintytge stysadfkgrfvfsldtsvstaylqinalkaedtavyycarsggydp mdywgqgttvtvss | 160 |
| CD123 | huscFv4 | Eivltqspatlslspgeratlscrasesvdnygntfmhwyqqkpgqa prlliyrasnlesgiparfsgsgsrtdftltisslepedvavyycqq snedpptfgqgtkleikggggsggggsggggsggggsqiqlvqsgae vkkpgasvkvsckasgyiftnygmnwvrqapgqrlewmgwintytge stysadfkgrvtitldtsastaymelsslrsedtavyycarsggydp mdywgqgttvtvss | 161 |
| CD123 | huscFv5 | Qiqlvqsgselkkpgasvkvsckasgyiftnygmnwvrqapgqglew mgwintytgestysadfkgrfvfsldtsvstaylqinalkaedtavy ycarsggydpmdywgqgttvtvssggggsggggsggggsggggsdiv ltqspdslavslgeratincrasesvdnygntfmhwyqqkpgqppkl liyrasnlesgvpdrfsgsgsrtdftltisslqaedvavyycqqsne dpptfgqgtkleik | 162 |
| CD123 | huscFv6 | Qiqlvqsgselkkpgasvkvsckasgyiftnygmnwvrqapgqglew mgwintytgestysadfkgrfvfsldtsvstaylqinalkaedtavy ycarsggydpmdywgqgttvtvssggggsggggsggggsggggseiv ltqspatlslspgeratlscrasesvdnygntfmhwyqqkpgqaprl liyrasnlesgiparfsgsgsrtdftltisslepedvavyycqqsne dpptfgqgtkleik | 163 |
| CD123 | huscFv7 | Qiqlvqsgaevkkpgasvkvsckasgyiftnygmnwvrqapgqrlew mgwintytgestysadfkgrvtitldtsastaymelsslrsedtavy ycarsggydpmdywgqgttvtvssggggsggggsggggsggggsdiv ltqspdslavslgeratincrasesvdnygntfmhwyqqkpgqppkl liyrasnlesgvpdrfsgsgsrtdftltisslqaedvavyycqqsne dpptfgqgtkleik | 164 |

TABLE 11-continued

Exemplary Sequences for Antigen Binding Domains

| Target Antigen | Name | Amino Acid Sequence | SEQ ID NO: |
|---|---|---|---|
| CD123 | huscFv8 | Qiqlvqsgaevkkpgasvkvsckasgyiftnygmnwvrqapgqrlew mgwintytgestysadfkgrvtitldtsastaymelsslrsedtavy ycarsggydpmdywgqgttvtvssggggsggggsggggsggggseiv ltqspatlslspgeratlscrasesvdnygntfmhwyqqkpgqaprl liyrasnlesgiparfsgsgsrtdftltisslepedvavyycqqsne dpptfgqgtkleik | 165 |
| EGFRvIII | huscFv1 | Eiqlvqsgaevkkpgatvkisckgsgfniedyyihwvqqapgkglew mgridpendetkygpifqgrvtitadtstntvymelsslrsedtavy ycafrggvywgqgttvtvssggggsggggsggggsggggsdvvmtqs pdslavslgeratinckssqslldsdgktylnwlqqkpgqppkrlis lvskldsgvpdrfsgsgsgtdftltisslqaedvavyycwqgthfpg tfgggtkveik | 166 |
| EGFRvIII | huscFv2 | Dvvmtqspdslavslgeratinckssqslldsdgktylnwlqqkpgq ppkrlislvskldsgvpdrfsgsgsgtdftltisslqaedvavyycw qgthfpgtfgggtkveikggggsggggsggggsggggseiqlvqsga evkkpgatvkisckgsgfniedyyihwvqqapgkglewmgridpend etkygpifqgrvtitadtstntvymelsslrsedtavyycafrggvy wgqgttvtvss | 167 |
| EGFRvIII | huscFv3 | Eiqlvqsgaevkkpgeslrisckgsgfniedyyihwvrqmpgkglew mgridpendetkygpifqghvtisadtsintvylqwsslkasdtamy ycafrggvywgqgttvtvssggggsggggsggggsggggsdvvmtqs plslpvtlgqpasisckssqslldsdgktylnwlqqrpgqsprrlis lvskldsgvpdrfsgsgsgtdftlkisrveaedvgvyycwqgthfpg tfgggtkveik | 168 |
| EGFRvIII | huscFv4 | Dvvmtqsplslpvtlgqpasisckssqslldsdgktylnwlqqrpgq sprrlislvskldsgvpdrfsgsgsgtdftlkisrveaedvgvyycw qgthfpgtfgggtkveikggggsggggsggggsggggseiqlvqsga evkkpgeslrisckgsgfniedyyihwvrqmpgkglewmgridpend etkygpifqghvtisadtsintvylqwsslkasdtamyycafrggvy wgqgttvtvss | 169 |
| EGFRvIII | huscFv5 | Eiqlvqsgaevkkpgatvkisckgsgfniedyyihwvqqapgkglew mgridpendetkygpifqgrvtitadtstntvymelsslrsedtavy ycafrggvywgqgttvtvssggggsggggsggggsggggsdvvmtqs plslpvtlgqpasisckssqslldsdgktylnwlqqrpgqsprrlis lvskldsgvpdrfsgsgsgtdftlkisrveaedvgvyycwqgthfpg tfgggtkveik | 170 |
| EGFRvIII | huscFv6 | Eiqlvqsgaevkkpgeslrisckgsgfniedyyihwvrqmpgkglew mgridpendetkygpifqghvtisadtsintvylqwsslkasdtamy ycafrggvywgqgttvtvssggggsggggsggggsggggsdvvmtqs pdslavslgeratinckssqslldsdgktylnwlqqkpgqppkrlis lvskldsgvpdrfsgsgsgtdftltisslqaedvavyycwqgthfpg tfgggtkveik | 171 |
| EGFRvIII | huscFv7 | Dvvmtqspdslavslgeratinckssqslldsdgktylnwlqqkpgq ppkrlislvskldsgvpdrfsgsgsgtdftltisslqaedvavyycw qgthfpgtfgggtkveikggggsggggsggggsggggseiqlvqsga evkkpgeslrisckgsgfniedyyihwvrqmpgkglewmgridpend etkygpifqghvtisadtsintvylqwsslkasdtamyycafrggvy wgqgttvtvss | 172 |
| EGFRvIII | huscFv8 | Dvvmtqsplslpvtlgqpasisckssqslldsdgktylnwlqqrpgq sprrlislvskldsgvpdrfsgsgsgtdftlkisrveaedvgvyycw qgthfpgtfgggtkveikggggsggggsggggsggggseiqlvqsga evkkpgatvkisckgsgfniedyyihwvqqapgkglewmgridpend etkygpifqgrvtitadtstntvymelsslrsedtavyycafrggvy wgqgttvtvss | 173 |
| EGFRvIII | Mu310C | eiqlqqsgaelvkpgasvklsctgsgfniedyyihwvkqrteqglew igridpendetkygpifqgratitadtssntvylqlssltsedtavy ycafrggvywgpgttltvssggggsggggsggggshmdvvmtqsplt lsvaigqsasisckssqslldsdgktylnwllqrpgqspkrlislvs kldsgvpdrftgsgsgtdftlrisrveaedlgiyycwqgthfpgtfg ggtkleik | 174 |
| mesothelin | ss1 (mu) | Q V Q L Q Q S G P E L E K P G A S V K I S C K A S G Y S F T G Y T M N W V K Q S H G K S L E W I G L I T P Y N G A S S Y N Q K F R G K A T L T V D K S S S T A Y M D L L | 175 |

TABLE 11-continued

Exemplary Sequences for Antigen Binding Domains

| Target Antigen | Name | Amino Acid Sequence | SEQ ID NO: |
|---|---|---|---|
| | | SLTSEDSAVYFCARGGYDGRGFDYWGQG TTVTVSSGGGGSGGGGSGGGGSDIELTQ SPAIMSASPGEKVTMTCSASSSVSYMHW YQQKSTSPPKRWIYDTSKLASGVPGRFS GSGSGNSYSLTISSVEAEDDATYYCQQW SGYPLTFGAGTKLEI | |
| mesothelin | M1 (human) | QVQLQQSGAEVKKPGASVKVSCKAS<u>GYTFTGYYMH</u>WVRQAPGQGLEWM G<u>RINPNSGGTNYAQKFQ</u>GRVTMTRDTSISTAYMELSRLRSEDTAVYYCAR G<u>RYYGMDV</u>WGQGTMVTVSSGGGGSGGGGSGGGGSGGGGSEIVLTQSPAT LSLSPGERATISC<u>RASQSVSSNFA</u>WYQQRPGQAPRLLIY<u>DASNRAT</u>GIPPRFS GSGSGTDFTLTISSLEPEDFAAYYC<u>HQRSNWLYT</u>FGQGTKVDIK | 176 |
| mesothelin | M2 (human) | QVQLVQSGAEVKKPGASVKVSCKAS<u>GYTFTGYYMH</u>WVRQAPGQGLEWMG<u>WINPNS GGTNYAQKFQ</u>GRVTMTRDTSISTAYMELSRLSDDTAVYYCARD<u>LRRTVVTPRAY YGMDV</u>WGQGTTVTVSSGGGGSGGGGSGGGGSGGGGSDIQLTQSPSTLSASVGDRV TITC<u>QASQDISNSLN</u>WYQQKAGKAPKLLIY<u>DASTLET</u>GVPSRFSGSGSGTDFSFT ISSLQPEDIATYYC<u>QQHDNLPLT</u>FGQGTKVEIK | 177 |
| mesothelin | M3 (human) | QVQLVQSGAEVKKPGAPVKVSCKAS<u>GYTFTGYYMH</u>WVRQAPGQGLEWMG<u>WINPNS GGTNYAQKFQ</u>GRVTMTRDTSISTAYMELSRLSDDTAVYYCARG<u>EWDGSYYYDY</u>W GQGTLVTVSSGGGGSGGGGSGGGGSGGGGSDIVLTQTPSSLSASVGDRVTITC<u>RA SQSINTYLN</u>WYQHKPGKAPKLLIY<u>AASSLQS</u>GVPSRFSGSGSGTDFTLTISSLQP EDFATYYC<u>QQSFSPLT</u>FGGGTKLEIK | 178 |
| mesothelin | M4 (human) | QVQLVESGGGLVQPGGSLRLSCAAS<u>GFTFSSYWMH</u>WVRQVPGKGLVWVS<u>RINTDG STTTYADSVE</u>GRFTISRDNAKNTLYLQMNSLRDDDTAVYYCVGG<u>HWAVV</u>GQGTTV TVSSGGGGSGGGGSGGGGSGGGGSDIQMTQSPSTLSASVGDRVTITC<u>RASQSISD RLA</u>WYQQKPGKAPKLLIY<u>KASSLES</u>GVPSRFSGSGSGTEFTLTISSLQPDDFAVY YC<u>QQYGHLPMYT</u>FGQGTKVEIK | 179 |
| mesothelin | M5 (human) | QVQLVQSGAEVEKPGASVKVSCKAS<u>GYTFTDYYMH</u>WVRQAPGQGLEWMG<u>WINPNS GGTNYAQKFQ</u>GRVTMTRDTSISTAYMELSRLSDDTAVYYCAS<u>GWDFDY</u>WGQGTL VTVSSGGGGSGGGGSGGGGSGGGGSDIVMTQSPSSLSASVGDRVTITC<u>R ASQSIRYYLS</u>WYQQKPGKAPKLLIY<u>TASILQN</u>GVPSRFSGSGSGTDFTLTISSLQ PEDFATYYC<u>LQTYTTPD</u>FGPGTKVEIK | 180 |
| mesothelin | M6 (human) | QVQLVQSGAEVKKPGASVKVSCKAS<u>GYTFTSYYMH</u>WVRQAPGQGLEWMG<u>IINPSG GSTSYAQKFQ</u>GRVTMTRDTSTSTVYMELSSLRSEDTAVYYCAR<u>YRLIAVAGDYYY YGMDV</u>WGQGTMVTVSSGGGGSGGGGSGGGGSGGGGSDIQMTQSPSSVSASVGDRV TITC<u>RASQVGRWLA</u>WYQQKPGTAPKLLIY<u>AASTLQS</u>GVPSRFSGSGSGTDFTLT INNLQPEDFATYYC<u>QQANSFPLT</u>FGGGTRLEIK | 181 |
| mesothelin | M7 (human) | QVQLVQSGGGVVQPGRSLRLSCAAS<u>GFTFSSYAMH</u>WVRQAPGKGLEWVA<u>VISYDG SNKYYADSVK</u>GRFTISRDNSKNTLYLQMNSLRAEDTAVYYCARW<u>KVSSSSPAFDY</u> WGQGTLVTVSSGGGGSGGGGSGGGGSGGGGSEIVLTQSPATLSLSPGERAILSC<u>R ASQSVYTKYLG</u>WYQQKPGQAPRLLIYDASTRATGIPDRFSGSGSGTDFTLTINRL EPEDFAVYYC<u>QHYGGSPLIT</u>FGQGTRLEIK | 182 |
| mesothelin | M8 (human) | QVQLQQSGAEVKKPGASVKVSCKTS<u>GYPFTGYSLH</u>WVRQAPGQGLEWMG<u>WINPNS GGTNYAQKFQ</u>GRVTMTRDTSISTAYMELSRLSDDTAVYYCARD<u>HYGGNSLFY</u>WG QGTLVTVSSGGGGSGGGGSGGGGSGGGGSDIQLTQSPSSISASVGDTVSITC<u>RAS QDSGTWLA</u>WYQQKPGKAPNLLMY<u>DASTLED</u>GVPSRFSGSASGTEFTLTVNRLQPE DSATYYC<u>QQYNSYPLT</u>FGGGTKVDIK | 183 |
| mesothelin | M9 (human) | QVQLVQSGAEVKKPGASVEVSCKAS<u>GYTFTSYYMH</u>WVRQAPGQGLEWMG<u>IINPSG GSTGYAQKFQ</u>GRVTMTRDTSTSTVHMELSSLRSEDTAVYYCARG<u>GYSSSSDAFDI</u> WGQGTMVTVSSGGGGSGGGGSGGGGSGGGGSDIQMTQSPPSLSASVGDRVTITC<u>R ASQDISSALA</u>WYQQKPGTPPKLLIY<u>DASSLES</u>GVPSRFSGSGSGTDFTLTISSLQ PEDFATYYC<u>QQFSSYPLT</u>FGGGTRLEIK | 184 |
| mesothelin | M10 (human) | QVQLVQSGAEVKKPGASVKVSCKAS<u>GYTFTSYGIS</u>WVRQAPGQGLEWMG<u>WISAYN GNTNYAQKLQ</u>GRVTMTTDTSTSTAYMELRSLDDTAVYYCARV<u>AGGIYYYYGMD VW</u>GQGTTITVSSGGGGSGGGGSGGGGSGGGGSDIVMTQTPDSLAVSLGERATISC <u>KSSHSVLYNRNNKNYLA</u>WYQQKPGQPPKLLFY<u>WASTRKS</u>GVPDRFSGSGSGTDFT LTISSLQPEDFATYFC<u>QQTQTFPLT</u>FGQGTRLEIN | 185 |
| mesothelin | M11 (human) | QVQLQQSGAEVKKPGASVKVSCKAS<u>GYTFTGYYMH</u>WVRQAPGQGLEWMG<u>WINPNS GGTNYAQNFQ</u>GRVTMTRDTSISTAYMELRRLDDTAVYYCAS<u>GWDFDY</u>WGQGTL VTVSSGGGGSGGGGSGGGGSGGGGSDIRMTQSPSLSASVGDRVTITC<u>RASQSIR YYLS</u>WYQQKPGKAPKLLIY<u>TASILQN</u>GVPSRFSGSGSGTDFTLTISSLQPEDFAT YYC<u>LQTYTTPD</u>FGPGTKVEIK | 186 |

TABLE 11-continued

Exemplary Sequences for Antigen Binding Domains

| Target Antigen | Name | Amino Acid Sequence | SEQ ID NO: |
|---|---|---|---|
| mesothelin (human) | | QVQLVQSGAEVKKPGASVKVSCKAS<u>GYTFTGYYMH</u>WVRQAPGQGLEWMG<u>RINPNS GGTNYAQKFQG</u>RVTMTTDTSTSTAYMELRSLRSDDTAVYYCAR<u>TTTSYAF</u>DIWGQ GTMVTVSSGGGGSGGGGSGGGGSGGGGSDIQLTQSPSTLSASVGDRVTITC<u>RASQ SISTWLA</u>WYQQKPGKAPNLLIY<u>KASTLES</u>GVPSRFSGSGSGTEFTLTISSLQPDD FATYYC<u>QQYNTYSPYT</u>FGQGTKLEIK | 187 |
| mesothelin (human) | M13 | QVQLVQSGGGLVKPGGSLRLSCEAS<u>GFIFSDYYMG</u>WIRQAPGKGLEWVS<u>YIGRSG SSMYYADSVKG</u>RFTFSRDNAKNSLYLQMNSLRAEDTAVYYCAAS<u>PVVAATEDFQH</u> WGQGTLVTVSSGGGGSGGGGSGGGGSGGGGSDIVMTQTPATLSLSPGERATLSCR <u>ASQSVTSNYLA</u>WYQQKPGQAPRLLLF<u>GASTRAT</u>GIPDRFSGSGSGTDFTLTINRL EPEDFAMYYC<u>QQYGSAPVT</u>FGQGTKLEIK | 188 |
| mesothelin (human) | M14 | QVQLVQSGAEVRAPGASVKISCKAS<u>GFTFRGYYIH</u>WVRQAPGQGLEWMG<u>IINPSG GSRAYAQKFQG</u>RVTMTRDTSTSTVYMELSSLRSDDTAMYYCAR<u>TASCGGDCYYLD YW</u>GQGTLVTVSSGGGGSGGGGSGGGGSGGGGSDIQMTQSPPTLSASVGDRVTITC <u>RASENVNIWLA</u>WYQQKPGKAPKLLIY<u>KSSSLAS</u>GVPSRFSGSGSGAEFTLTISSL QPDDFATYYC<u>QQYQSYPLT</u>FGGGTKVDIK | 189 |
| mesothelin (human) | M15 | QVQLVQSGGGLVQPGRSLRLSCAAS<u>GFTFDDYAMH</u>WVRQAPGKGLEWVS<u>GISWN GSIGYADSVKG</u>RFTISRDNAKNSLYLQMNSLRAEDTAVYYCAKD<u>GSSSWSWGYFD YW</u>GQGTLVTVSSGGGGSGGGGSGGGGSSSELTQDPAVSVALGQTVRTTC<u>QGDALR SYYAS</u>WYQQKPGQAPMLVIY<u>GKNNRPS</u>GIPDRFSGSDSGDTASLTITGAQAEDEA DYYC<u>NSRDSSGYPV</u>FGTGTKVTVL | 190 |
| mesothelin (human) | M16 | EVQLVESGGGLVQPGRSLRLSCAAS<u>GFTFDDYAMH</u>WVRQAPGKGLEWVS<u>GISWNS GSTGYADSVKG</u>RFTISRDNAKNSLYLQMNSLRAEDTALYYCAKD<u>SSSWYGGGSAF DIW</u>GQGTMVTVSSGGGGSGGGGSGGGGSSSELTQEPAVSVALGQTVRITC<u>QGDSL RSYYAS</u>WYQQKPGQAPVLVIF<u>GRSRRPS</u>GIPDRFSGSSSGNTASLIITGAQAEDE ADYYC<u>NSRDNTANHYV</u>FGTGTKLTVL | 191 |
| mesothelin (human) | M17 | EVQLVESGGGLVQPGRSLRLSCAAS<u>GFTFDDYAMH</u>WVRQAPGKGLEWVS<u>GISWNS GSTGYADSVKG</u>RFTISRDNAKNSLYLQMNSLRAEDTALYYCAKD<u>SSSWYGGGSAF DIW</u>GQGTMVTVSSGGGGSGGGGSGGGGSSSELTQDPAVSVALGQTVRITC<u>QGDSL RSYYAS</u>WYQQKPGQAPVLVIY<u>GKNNRPS</u>GIPDRFSGSSSGNTASLTITGAQAEDE ADYYC<u>NSRGSSGNHYV</u>FGTGTKVTVL | 192 |
| mesothelin (human) | M18 | QVQLVQSGGGLVQPGGSLRLSCAAS<u>GFTFSSYWMH</u>WVRQAPGKGLVWVS<u>RINSDG SSTSYADSVKG</u>RFTISRDNAKNTLYLQMNSLRAEDTAVYYCVRT<u>GWVGSYYYYMD VW</u>GKGTTVTVSSGGGGSGGGGSGGGGSGGGGSEIVLTQSPGTLSLSPGERATLSC <u>RASQSVSSNYLA</u>WYQQKPGQPPRLLIY<u>DVSTRAT</u>GIPARFSGGGSGTDFTLTISS LEPEDFAVYYC<u>QQRSNWPPWT</u>FGQGTKVEIK | 193 |
| mesothelin (human) | M19 | QVQLVQSGGGVVQPGRSLRLSCAAS<u>GFTFSSYGMH</u>WVRQAPGKGLEWVA<u>VISYDG SNKYYADSVKG</u>RFTISRDNSKNTLYLQMNSLRAEDTAVYYCAK<u>GYSRYYYYGMDV</u> WGQGTTVTVSSGGGGSGGGGSGGGGSGGGGSEIVMTQSPATLSLSPGERAILSC<u>R ASQSVYTKYLG</u>WYQQKPGQAPRLLIY<u>DASTRAT</u>GIPDRFSGSGSGTDFTLTINRL EPEDFAVYYC<u>QHYGGSPLIT</u>FGQGTKVDIK | 194 |
| mesothelin (human) | M20 | QVQLVQSGGGLVQPGGSLRLSCAAS<u>GFTFSSYAMS</u>WVRQAPGKGLEWVS<u>AISGSG GSTYYADSVKG</u>RFTISRDNSKNTLYLQMNSLRAEDTAVYYCAK<u>REAAAGHDWYFD LW</u>GRGTLVTVSSGGGGSGGGGSGGGGSGGGGSDIRVTQSPSSLSASVGDRVTITC <u>RASQSISSYLN</u>WYQQKPGKAPKLLIY<u>AASSLQS</u>GVPSRFSGSGSGTDFTLTISSL QPEDFATYYC<u>QQSYSIPLT</u>FGQGTKVEIK | 195 |
| mesothelin (human) | M21 | QVQLVQSWAEVKKPGASVKVSCKAS<u>GYTFTSYYMH</u>WVRQAPGQGLEWMG<u>IINPSG GSTSYAQKFQG</u>RVTMTRDTSTSTVYMELSNLRSEDTAVYYCARS<u>PRVTTGYFDYW</u> GQGTLVTVSSGGGGSGGGGSGGGGSGGGGSDIQLTQSPSTLSASVGDRVTITC<u>RA SQSISSWLA</u>WYQQKPGKAPKLLIY<u>KASSLES</u>GVPSRFSGSGSGTEFTLTISSLQP DDFATYYC<u>QQYSSYPLT</u>FGGGTRLEIK | 196 |
| mesothelin (human) | M22 | QVQLVQSGAEVRRPGASVKISCRAS<u>GDTSTRHYIH</u>WLRQAPGQGPEWMG<u>VINPTT GPATGSPAYAQMLQG</u>RVTMTRDTSTRTVYMELRSLRFEDTAVYYCARS<u>VVGRSAP YYFDYW</u>GQGTLVTVSSGGGGSGGGGSGGGGSGGGGSDIQMTQSPSSLSASVGDRV TITC<u>RASQGISDYSA</u>WYQQKPGKAPKLLIY<u>AASTLQS</u>GVPSRFSGSGSGTDFTLT ISYLQSEDFATYYC<u>QQYYSYPLT</u>FGGGTKVDIK | 197 |
| mesothelin (human) | M23 | QVQLQQSGAEVKKPGASVKVSCKAS<u>GYTFTNYYMH</u>WVRQAPGQGLEWMG<u>IINPSG GYTTYAQKFQG</u>RLTMTRDTSTSTVYMELSSLRSEDTAVYYCAR<u>IRSCGGDCYYFD NW</u>GQGTLVTVSSGGGGSGGGGSGGGGSGGGGSDIQLTQSPSTLSASVGDRVTITC <u>RASENVNIWLA</u>WYQQKPGKAPKLLIY<u>KSSSLAS</u>GVPSRFSGSGSGAEFTLTISSL QPDDFATYYC<u>QQYQSYPLT</u>FGGGTKVDIK | 198 |

TABLE 11-continued

Exemplary Sequences for Antigen Binding Domains

| Target Antigen | Name | Amino Acid Sequence | SEQ ID NO: |
|---|---|---|---|
| mesothelin | M24 (human) | QITLKESGPALVKPTQTLTLTCTFSGFSLSTAGVHVGWIRQPPGKALEWLALISW ADDKRYRPSLRSRLDITRVTSKDQVVLSMTNMQPEDTATYYCALQGFDGYEANWG PGTLVTVSSGGGGSGGGGSGGGGSGGGGSDIVMTQSPSSLSASAGDRVTITCRAS RGISSALAWYQQKPGKPPKLLIYDASSLESGVPSRFSGSGSGTDFTLTIDSLEPE DFATYYCQQSYSTPWTFGQGTKVDIK | 199 |
| CLL-1 | 139115 (human) | EVQLQQSGAEVKKPGSSVKVSCKASGGTFSSYAISWVRQAPGQGLEWMGGIIPIFGTANYAQ KFQGRVTITADESTSTAYMELSSLRSEDTAVYYCARDLEMATIMGGYWGQGTLVTVSSGGGG SGGGGSGGGGSQSALTQPASVSGSPGQSITISCTGTSSDVGGYNYVSWYQQHPGKAPKLMIY DVSNRPSGVSNRFSGSKSGNTASLTISGLQAEDEADYYCSSYTSSSTLDVVFGGGTKLTVL | 200 |
| CLL-1 | 139116 (human) | EVQLVESGGGVVQPGGSLRLSCAASGFTFDDYAMHWVRQAPGKGLEWVSLISGDGGSTYYAD SVKGRFTISRDNSKNTLYLQMNSLRVEDTAVYYCARVFDSYYMDVWGKGTTVTVSSGGGGSG GGGSGGGSEIVLTQSPLSLPVTPGQPASISCRSSQSLVYTDGNTYLNWFQQRPGQSPRRLI YKVSNRDSGVPDRFSGSGSDTFTLKISRVEAEDVGIYYCMQGTHWSFTFGQGTRLEIK | 201 |
| CLL-1 | 139118 (human) | QVQLQESGPGLVKPSETLSLTCTVSGGSISSSSYYWGWIRQPPGKGLEWIGSIYYSGSTYYN PSLKSRVSISVDTSKNQFSLKLKYVTAADTAVYYCATPGTYYDFLSGYYPFYWGQGTLVTVS SGGGGSGGGGSGGGGSDIVMTQSPSSLSASVGDRVTITCRASQGISSYLAWYQQKPGKAPKL LIYAASTLQSGVPSRFSGSGSGTDFTLTISSLQPEDFATYYCQQLNSYPYTFGQGTKLEIK | 202 |
| CLL-1 | 139122 (human) | QVQLVESGGGLVQPGGSLRLSCAASGFTFSSYWMSWVRQAPGKGLEWVANINEDGSAKFYVD SVKGRFTISRDNAKNSLYLQMNSLRAEDTAVYFCARDLRSGRYWGQGTLVTVSSGGGGSGGG GSGGGGSEIVLTQSPGTLSLSPGGRATLSCRASQSISGSFLAWYQQKPGQAPRLLIYGASSR ATGIPDRFSGSGSGTDFTLTISRLEPEDFAVYYCQQYGSSPPTFGLGTKLEIK | 203 |
| CLL-1 | 139117 (human) | EVQLQQSGPGLVRPSETLSLTCTVSGGPVRSGSHYWNWIRQPPGRGLEWIGYIYYSGSTNYN PSLENRVTISIDTSNNHFSLKLSSVTAADTALYFCARGTATFDWNFPFDSWGQGTLVTVSSG GGGSGGGGSGSGGSDIQMTQSPSSLSASIGDRVTITCRASQSISSYLNWYQQKPGKAPKLLI YAASSLQSGVPSRFSGSGSGTDFTLTISSLQPEDFATYYCQQSYSTPWTFGQGTKLEIK | 204 |
| CLL-1 | 139119 (human) | QVQLQESGAGLLKPSETLSLTCAVYGGSFSGYYWSWIRQPPGKGLEWVGEINHSGSTNYNPS LKSRVTISVDTSKNQFSLKLSSVTAADTAVYYCARGSGLVVYAIRVGSGWFDYWGQGTLVTV SSGGGGSGGGDSGGGGSDIQMTQSPSSLSASVGDRVTITCRASQSISSYLNWYQQKPGKAPK LLMYAASSLQSGVPSRFSGSGSGTDFTLTISSLQPEDFATYYCQQSYSTPPWTFGQGTKVDI K | 205 |
| CLL-1 | 139120 (human) | EVQLVESGGGLVKPGGSLRLSCAASGFTFSSYSMNWVRQAPGKGLEWVSSISSSSSYIYYAD SVKGRFTISRDNAKNSLYLQMNSLRAEDTAVYYCARDPSSSGSYYMEDSVGMDVWGQGTT VTVSSGGGGSGGGGSGGGGSNFMLTQPHSVSESPGKTVTISCTGSSGSIASNYVQWYQQRPG SAPTTVIYEDNQRPSGVPDRFSGSIDSSSNSASLTISGLKTEDEADYYCQSYDSSNQVVFGG GTKLTVL | 206 |
| CLL-1 | 139121 (human) | QVNLRESGGGLVQPGGSLRLSCAASGFTFSSYEMNWVRQAPGKGLEWVSYISSSGSTIYYAD SVKGRFTISRDNAKNSLYLQMNSLRAEDTAVYYCAREALGSSWEWGQGTTVTVSSGGGGSGG GGSGGGGSDIQMTQSPSSLSASVGDRVTITCQASQDISNYLNWYQQKPGKAPKLLIYDASNL ETGVPSRFSGSGSGTDFTFTISSLQPEDIATYYCQQYDNLPLTFGGGTKLEIK | 207 |
| CLL-1 | 146259 (human) | QVQLVQSGAEVKEPGASVKVSCKAPANTFSDHVMHWVRQAPGQRFEWMGYIHAANGGTHYSQ KFQDRVTITRDTSANTVYMDLSSLRSEDTAVYYCARGGYNSDAFDIWGQGTMVTVSSGGGGS GGGGSGGGGSGGGGSDIVMTQSPSSVSASVGDRVTITCRASQDISSWLAWYQQKPGKAPKLL IYAASSLQSGVPSRFNGSGSGTDFTLTISSLQPEDFATYYCQQSYSTPLTFGGGTKVEIK | 208 |
| CLL-1 | 146261 (human) | QVQLVQSGGGLVQPGGSLRLSCAASGFTFSSYSMNWVRQAPGKGLEWVSYISSSSSTIYYAD SVKGRFTISRDNAKNSLYLQMNSLRAEDTAVYYCARDLSVRAIDAFDIWGQGTMVTVSSGGG GSGGGGSGGGGSGGGGSDIVLTQSPSSLSASVGDRVTITCQASQDISNYLNWYQQKPGKAPK LLIYDASNLETGVPSRFSGSGSGTDFTFTISSLQPEDFATYYCQQAYSTPFTFGPGTKVEIK | 209 |
| CLL-1 | 146262 (human) | EVQLVQSGGGVVRSGRSLRLSCAASGFTFNSYGLHWVRQAPGKGLEWVALIEYDGSNKYYGD SVKGRFTISRDKSKSTLYLQMDNLRAEDTAVYYCAREGNEDLAFDIWGQGTLVTVSSGGGGS GGGGSGGGGSGGGGSEIVLTQSPSSLSASVGDRVTITCQASQFIKKNLNWYQHKPGKAPKLL IYDASSLQTGVPSRFSGNRSGTTFSFTISSLQPEDVATYYCQQHDNLPLTFGGGTKVEIK | 210 |
| CLL-1 | 146263 (human) | QVQLVESGGGLVQPGGSLRLSCAASGFNVSSNYMTWVRQAPGKGLEWVSVIYSGGATYYGDS VKGRFTVSRDNSKNTVYLQMNRLTAEDTAVYYCARDRLYCGNNCYLYYYYGMDVWGQGTLVT VSSGGGGSGGGGSGGGGSGGGGSDIQVTQSPSSLSASVGDRVTITCRASQSISSYLNWYQQK PGKAPKLLIYAASSLQSGVPSRFSGSGSGTDFTLTISSLQPEDFATYYCQQSYSTPPLTFGQ GTKVEIK | 211 |
| CLL-1 | 146264 (human) | QVQLVQSGAEVKKSGASVKVSCKASGYPFTGYYIQWVRQAPGQGLEWMGWIDPNSGNTGYAQ KFQGRVTMTRNTSISTAYMELSSLRSEDTAVYYCASDSYGYYYGMDVWGQGTLVTVSSGGGG SGGGGSGGGGSGGGGSDIQMTQSPSSLSASVGDRVTFTCRASQGISSALAWYQQKPGKPPKL LIYDASSLESGVPSRFSGSGSGTDFTLTISSLQPEDFATYYCQQFNNYPLTFGGGTKVEIK | 212 |

TABLE 11-continued

Exemplary Sequences for Antigen Binding Domains

| Target Antigen | Name | Amino Acid Sequence | SEQ ID NO: |
|---|---|---|---|
| CLL-1 | 181268 (human) | EVQLVESGGGLVQPGGSLRLSCAASGFTFSSYEMNWVRQAPGKGLEWVSYISSSGSTIYYAD SVKGRFTISRDNAKNSLYLQMNSLRAEDTAVYYCARDPYSSSWHDAFDIWGQGTMVTVSSGG GGSGGGGSGGGGSEIVLTQSPGTLSLSPGERATLSCRASQSVSSSYLAWYQQKPGQAPRLLI YGASSRATGIPDRFSGSGSGTDFTLTISRLEPEDFAVYYCQQYGSSPLTFGGGTKVDIK | 213 |
| BCMA | 139103 (human) | QVQLVESGGGLVQPGRSLRLSCAASGFTFSNYAMSWVRQAPGKGLGWVSGISRSGENTYYAD SVKGRFTISRDNSKNTLYLQMNSLRDEDTAVYYCARSPAHYYGGMDVWGQGTTVTVSSASGG GGSGGRASGGGGSDIVLTQSPGTLSLSPGERATLSCRASQSISSSFLAWYQQKPGQAPRLLI YGASRRATGIPDRFSGSGSGTDFTLTISRLEPEDSAVYYCQQYHSSPSWTFGQGTKLEIK | 214 |
| BCMA | 139105 (human) | QVQLVESGGGLVQPGRSLRLSCAASGFTFDDYAMHWVRQAPGKGLEWVSGISWNSGSIGYAD SVKGRFTISRDNAKNSLYLQMNSLRAEDTALYYCSVHSFLAYWGQGTLVTVSSASGGGGSGG RASGGGGSDIVMTQTPLSLPVTPGEPASISCRSSQSLLHSNGYNYLDWYLQKPGQSPQLLIY LGSNRASGVPDRFSGSGSGTDFTLKISRVEAEDVGVYYCMQALQTPYTFGQGTKVEIK | 215 |
| BCMA | 139111 (human) | EVQLLESGGGLVQPGGSLRLSCAVSGFALSNHGMSWVRRAPGKGLEWVSGIVYSGSTYYAAS VKGRFTISRDNSRNTLYLQMNSLRPEDTAIYYCSAHGGESDVWGQGTTVTVSSASGGGGSGG RASGGGGSDIVMTQTPLSLSVTPGQPASISCKSSQSLLRNDGKTPLYWYLQKAGQPPQLLIY EVSNRFSGVPDRFSGSGSGTDFTLKISRVEAEDVGAYYCMQNIQFPSFGGGTKLEIK | 216 |
| BCMA | 139100 (human) | QVQLVQSGAEVRKTGASVKVSCKASGYIFDNFGINWVRQAPGQGLEWMGWINPKNNNTNYAQ KFQGRVTITADESTNTAYMEVSSLRSEDTAVYYCARGPYYYQSYMDVWGQGTMVTVSSASGG GGSGGRASGGGGSDIVMTQTPLSLPVTPGEPASISCRSSQSLLHSNGYNYLNWYLQKPGQSP QLLIYLGSKRASGVPDRFSGSGSGTDFTLHITRVGAEDVGVYYCMQALQTPYTFGQGTKLEI K | 217 |
| BCMA | 139101 (human) | QVQLQESGGGLVQPGGSLRLSCAASGFTFSSDAMTWVRQAPGKGLEWVSVISGSGGTTYYAD SVKGRFTISRDNSKNTLYLQMNSLRAEDTAVYYCAKLDSSGYYYARGPRYWGQGTLVTVSSA SGGGGSGGRASGGGGSDIQLTQSPSSLSASVGDRVTITCRASQSISSYLNWYQQKPGKAPKL LIYGASTLASGVPARFSGSGSGTHFTLTINSLQSEDSATYYCQQSYKRASFGQGTKVEIK | 218 |
| BCMA | 139102 (human) | QVQLVQSGAEVKKPGASVKVSCKASGYTFSNYGITWVRQAPGQGLEWMGWISAYNGNTNYAQ KFQGRVTMTRNTSISTAYMELSSLRSEDTAVYYCARGPYYYMDVWGKGTMVTVSSASGGGG SGGRASGGGGSEIVMTQSPLSLPVTPGEPASISCRSSQSLLYSNGYNYVDWYLQKPGQSPQL LIYLGSNRASGVPDRFSGSGSGTDFKLQISRVEAEDVGIYYCMQGRQFPYSFGQGTKVEIK | 219 |
| BCMA | 139104 (human) | EVQLLETGGGLVQPGGSLRLSCAVSGFALSNHGMSWVRRAPGKGLEWVSGIVYSGSTYYAAS VKGRFTISRDNSRNTLYLQMNSLRPEDTAIYYCSAHGGESDVWGQGTTVTVSSASGGGGSGG RASGGGGSEIVLTQSPATLSVSPGESATLSCRASQSVSSNLAWYQQKPGQAPRLLIYGASTR ASGIPDRFSGSGSGTDFTLTISSLQAEDVAVYYCQQYGSSLTFGGGTKVEIK | 220 |
| BCMA | 139106 (human) | EVQLVETGGGLVQPGGSLRLSCAVSGFALSNHGMSWVRRAPGKGLEWVSGIVYSGSTYYAAS VKGRFTISRDNSRNTLYLQMNSLRPEDTAIYYCSAHGGESDVWGQGTTVTVSSASGGGGSGG RASGGGGSEIVMTQSPATLSVSPGERATLSCRASQSVSSKLAWYQQKPGQAPRLLMYGASIR ATGIPDRFSGSGSGTEFTLTISSLEPEDFAVYYCQQYGSSSWTFGQGTKVEIK | 221 |
| BCMA | 139107 (human) | EVQLVETGGGVVQPGGSLRLSCAVSGFALSNHGMSWVRRAPGKGLEWVSGIVYSGSTYYAAS VKGRFTISRDNSRNTLYLQMNSLRPEDTAIYYCSAHGGESDVWGQGTTVTVSSASGGGGSGG RASGGGGSEIVLTQSPGTLSLSPGERATLSCRASQSVGSTNLAWYQQKPGQAPRLLIYDASN RATGIPDRFSGGGSGTDFTLTISRLEPEDFAVYYCQQYGSSPPWTFGQGTKVEIK | 222 |
| BCMA | 139108 (human) | QVQLVESGGGLVKPGGSLRLSCAASGFTFSDYYMSWIRQAPGKGLEWVSYISSSGSTIYYAD SVKGRFTISRDNAKNSLYLQMNSLRAEDTAVYYCARESGDGMDVWGQGTTVTVSSASGGGGS GGRASGGGGSDIQMTQSPSSLSASVGDRVTITCRASQSISSYLNWYQQKPGKAPKLLIYAAS SLQSGVPSRFSGSGSGTDFTLTISSLQPEDFATYYCQQSYTLAFGQGTKVDIK | 223 |
| BCMA | 139109 (human) | EVQLVESGGGLVQPGGSLRLSCAVSGFALSNHGMSWVRRAPGKGLEWVSGIVYSGSTYYAAS VKGRFTISRDNSRNTLYLQMNSLRPEDTAIYYCSAHGGESDVWGQGTTVTVSSASGGGGSGG RASGGGGSDIQLTQSPSSLSASVGDRVTITCRASQSISSYLNWYQQKPGKAPKLLIYAASSL QSGVPSRFSGSGSGTDFTLTISSLQPEDFATYYCQQSYSTPYTFGQGTKVEIK | 224 |
| BCMA | 139110 (human) | QVQLVQSGGGLVKPGGSLRLSCAASGFTFSDYYMSWIRQAPGKGLEWVSYISSSGNTIYYAD SVKGRFTISRDNAKNSLYLQMNSLRAEDTAVYYCARSTMVREDYWGQGTLVTVSSASGGGGS GGRASGGGGSDIVLTQSPLSLPVTLGQPASISCKSSESLVHNSGKTYLNWFHQRPGQSPRRL IYEVSNRDSGVPDRFTGSGSGTDFTLKISRVEAEDVGVYYCMQGTHWPGTFGQGTKLEIK | 225 |
| BCMA | 139112 (human) | QVQLVESGGGLVQPGGSLRLSCAVSGFALSNHGMSWVRRAPGKGLEWVSGIVYSGSTYYAAS VKGRFTISRDNSRNTLYLQMNSLRPEDTAIYYCSAHGGESDVWGQGTTVTVSSASGGGGSGG RASGGGGSDIRLTQSPSPLSASVGDRVTITCQASEDINKFLNWYHQTPGKAPKLLIYDASTL QTGVPSRFSGSGSGTDFTLTINSLQPEDIGTYYCQQYESLPLTFGGGTKVEIK | 226 |
| BCMA | 139113 (human) | EVQLVETGGGLVQPGGSLRLSCAVSGFALSNHGMSWVRRAPGKGLEWVSGIVYSGSTYYAAS VKGRFTISRDNSRNTLYLQMNSLRPEDTAIYYCSAHGGESDVWGQGTTVTVSSASGGGGSGG | 227 |

TABLE 11-continued

Exemplary Sequences for Antigen Binding Domains

| Target Antigen | Name | Amino Acid Sequence | SEQ ID NO: |
|---|---|---|---|
| | | RASGGGGSETTLTQSPATLSVSPGERATLSC<u>RASQSVGSNLA</u>WYQQKPGQGPRLLIY<u>GASTR</u><br><u>AT</u>GIPARFSGSGSTEFTLTISSLQPEDFAVYYC<u>QQYNDWLPVT</u>FGQGTKVEIK | |
| BCMA | 139114<br>(human) | EVQLVESGGGLVQPGGSLRLSCAVS<u>GFALSNHGMS</u>WVRRAPGKGLEWVS<u>GIVYSGSTYYAAS</u><br><u>VKG</u>RFTISRDNSRNTLYLQMNSLRPEDTAIYYC<u>SAHGGESDV</u>WGQGTTVTVSSASGGGGSGG<br>RASGGGGSEIVLTQSPGTLSLSPGERATLSC<u>RASQSIGSSSLA</u>WYQQKPGQAPRLLMY<u>GASS</u><br><u>RAS</u>GIPDRFSGSGSGTDFTLTISRLEPEDFAVYYC<u>QQYAGSPPFT</u>FGQGTKVEIK | 228 |
| BCMA | 149362<br>(human) | QVQLQESGPGLVKPSETLSLTCTVS<u>GGSISSSYYYWG</u>WIRQPPGKGLEWIG<u>SIYYSGSAYYN</u><br><u>PSLKS</u>RVTISVDTSKNQFSLRLSSVTAADTAVYYCAR<u>HWQEWPDAFDI</u>WGQGTMVTVSSGGG<br>GSGGGGSGGGGSETTLTQSPAFMSATPGDKVIISC<u>KASQDIDDAMN</u>WYQQKPGEAPLFIIQS<br><u>ATSPVPG</u>IPPRFSGSGFGTDFSLTINNIESEDAAYYFC<u>LQHDNFPLT</u>FGQGTKLEIK | 229 |
| BCMA | 149363<br>(human) | VNLRESGPALVKPTQTLTLTCTFS<u>GFSLRTSGMCVS</u>WIRQPPGKALEWLA<u>RIDWDEDKFYST</u><br><u>SLKTR</u>LTISKDTSDNQVVLRMTNMDPADTATYYC<u>ARSGAGGTSATAFDI</u>WGPGTMVTVSSGG<br>GGSGGGGSGGGGSDIQMTQSPSSLSASVGDRVTITC<u>RASQDIYNNLA</u>WFQLKPGSAPRSLMY<br><u>AANKSQS</u>GVPSRFSGSASGTDFTLTISSLQPEDFATYYC<u>QHYYRFPYS</u>FGQGTKLEIK | 230 |
| BCMA | 149364<br>(human) | EVQLVESGGGLVKPGGSLRLSCAAS<u>GFTFSSYSMN</u>WVRQAPGKGLEWVS<u>SISSSSSYIYYAD</u><br><u>SVKG</u>RFTISRDNAKNSLYLQMNSLRAEDTAVYYC<u>AKTIAAVYAFDI</u>WGQGTTVTVSSGGGGS<br>GGGGSGGGGSEIVLTQSPLSLPVTPEEPASISC<u>RSSQSLLHSNGYNYLD</u>WYLQKPGQSPQLL<br>IY<u>LGSNRAS</u>GVPDRFSGSGSGTDFTLKISRVEAEDVGVYYC<u>MQALQTPYT</u>FGQGTKLEIK | 231 |
| BCMA | 149365<br>(human) | EVQLVESGGGLVKPGGSLRLSCAAS<u>GFTFSDYYMS</u>WIRQAPGKGLEWVS<u>YISSSGSTIYYAD</u><br><u>SVKG</u>RFTISRDNAKNSLYLQMNSLRAEDTAVYYCAR<u>DLRGAFDI</u>WGQGTMVTVSSGGGGSGG<br>GGSGGGGSSYVLTQSPSVSAAPGYTATISC<u>GGNNIGTKSVH</u>WYQQKPGQAPLLVIR<u>DDSVRP</u><br><u>SKI</u>PGRFSGSNSGNMATLTISGVQAGDEADFYC<u>QVWDSDSEHVV</u>FGGGTKLTVL | 232 |
| BCMA | 149366<br>(human) | QVQLVQSGAEVKKPGASVKVSCKPS<u>GYTVTSHYIH</u>WVRRAPGQGLEWMG<u>MINPSGGVTAYSQ</u><br><u>TLQG</u>RVTMTSDTSSSTVYMELSSLRSEDTAMYYCARE<u>GSGSGWYFDF</u>WGRGTLVTVSSGGGG<br>SGGGGSGGGGSSYVLTQPPSVSVSPGQTASITC<u>SGDGLSKKYVS</u>WYQQKAGQSPVVLIS<u>RDK</u><br><u>ERPS</u>GIPDRFSGSNSADTATLTISGTQAMDEADYYC<u>QAWDDTTVV</u>FGGGTKLTVL | 233 |
| BCMA | 149367<br>(human) | QVQLQESGPGLVKPSQTLSLTCTVS<u>GGSISSGGYYWS</u>WIRQHPGKGLEWIG<u>YIYYSGSTYYN</u><br><u>PSLKS</u>RVTISVDTSKNQFSLKLSSVTAADTAVYYCAR<u>AGIAARLRGAFDI</u>WGQGTMVTVSSGG<br>GGSGGGGSGGGGSDIVMTQSPSSVSASVGDRVIITC<u>RASQGIRNWLA</u>WYQQKPGKAPNLLI<br>Y<u>AASNLQS</u>GVPSRFSGSGSGADFTLTISSLQPEDVATYYC<u>QKYNSAPFT</u>FGPGTKVDIK | 234 |
| BCMA | 149368<br>(human) | QVQLVQSGAEVKKPGSSVKVSCKAS<u>GGTFSSYAIS</u>WVRQAPGQGLEWMG<u>GIIPIFGTANYAQ</u><br><u>KFQG</u>RVTITADESTSTAYMELSSLRSEDTAVYYCAR<u>RGGYQLLRWDVGLLRSAFDI</u>WGQGTM<br>VTVSSGGGGSGGGGSGGGGSSYVLTQPPSVSVAPGQTARITC<u>GGNNIGSKSVH</u>WYQQKPGQA<br>PVLVLY<u>GKNNRPS</u>GVPDRFSGSRSGTTASLTITGAQAEDEADYYC<u>SRDSSGDHLRV</u>FGTGT<br>KVTVL | 235 |
| BCMA | 149369<br>(human) | EVQLQQSGPGLVKPSQTLSLTCAIS<u>GDSVSSNSAAWN</u>WIRQSPSRGLEWLG<u>RTYYRSKWYSF</u><br><u>YAISLKS</u>RIIINPDTSKNQFSLQLKSVTPEDTAVYCARS<u>SPEGLFLYWFDPW</u>GQGTLVTVS<br>SGGDGSGGGGSGGGGSSSELTQDPAVSVALGQTIRITC<u>QGDSLGNYYAT</u>WYQQKPGQAPVLV<br>IY<u>GTNNRPS</u>GIPDRFSASSSGNTASLTITGAQAEDEADYYC<u>NSRDSSGHHLL</u>FGTGTKVTVL | 236 |
| BCMA | EBB-<br>C1978-<br>A4<br>(human) | EVQLVESGGGLVQPGGSLRLSCAAS<u>GFTFSSYAMS</u>WVRQAPGKGLEWVS<u>AISGSGGSTYYAD</u><br><u>SVKG</u>RFTISRDNSKNTLYLQMNSLRAEDTAVYYC<u>AKVEGSSLDY</u>WGQGTLVTVSSGGGGSG<br>GGGSGGGGSEIVMTQSPGTLSLSPGERATLSC<u>RASQSVSSAYLA</u>WYQQKPGQPPRLLIS<u>GAS</u><br><u>TRAT</u>GIPDRFGGSGSGTDFTLTISRLEPEDFAVYYC<u>QHYGSSFNGSSLFT</u>FGQGTRLEIK | 237 |
| BCMA | EBB-<br>C1978-<br>G1<br>(human) | EVQLVETGGGLVQPGGSLRLSCAAS<u>GITFSRYPMS</u>WVRQAPGKGLEWVS<u>GISDSGV</u><br><u>STYYADSAKG</u>RFTISRDNSKNTLFLQMSSLRDEDTAVYYCVT<u>RAGSEASDI</u>WGQGT<br>MVTVSSGGGGSGGGGSGGGGSEIVLTQSPATLSLSPGERATLSC<u>RASQSVSNSLA</u>WY<br>QQKPGQAPRLLIY<u>DASSRAT</u>GIPDRFSGSGSGTDFTLTISRLEPEDFAIYYC<u>QQFGTSS</u><br><u>GLT</u>FGGGTKLEIK | 238 |
| BCMA | EBB-<br>C1979-<br>C1<br>(human) | QVQLVESGGGLVQPGGSLRLSCAAS<u>GFTFSSYAMS</u>WVRQAPGKGLEWVS<u>AISGSGGSTYYAD</u><br><u>SVKG</u>RFTISRDNAKNSLYLQMNSLRAEDTAIYYCAR<u>ATYKRELRYYYGMDV</u>WGQGTMVTVSS<br>GGGGSGGGGSGGGGSEIVMTQSPGTVSLSPGERATLSC<u>RASQSVSSSFLA</u>WYQQKPGQAPRL<br>LIY<u>GASSRAT</u>GIPDRFSGSGSGTDFTLTISRLEPEDSAVYYC<u>QQYHSSPSWT</u>FGQGTRLEIK | 239 |
| BCMA | EBB-<br>1978-<br>C7<br>(human) | EVQLVETGGGLVQPGGSLRLSCAAS<u>GFTFSSYAMS</u>WVRQAPGKGLEWVS<u>AISGSGGSTYYAD</u><br><u>SVKG</u>RFTISRDNSKNTLYLQMNTLKAEDTAIYYCAR<u>ATYKRELRYYYGMDV</u>WGQGTTVTVSS<br>GGGGSGGGGSGGGGSEIVLTQSPSTLSLSPGESATLSC<u>RASQSVSTTFLA</u>WYQQKPGQAPRL<br>LIY<u>GSSNRAT</u>GIPDRFSGSGSGTDFTLTIRRLEPEDFAVYYC<u>QQYHSSPSWT</u>FGQGTKVEIK | 240 |
| BCMA | EBB-<br>1978-<br>D10 | EVQLVETGGGLVQPGRSLRLSCAAS<u>GFTFDDYAMH</u>WVRQAPGKGLEWVS<u>GISWNSGSIGYAD</u><br><u>SVKG</u>RFTISRDNAKNSLYLQMNSLRDEDTAVYYCAR<u>VGKAVPDV</u>WGQGTTVTVSSGGGGSGG<br>GGSGGGGSDIVMTQTPSSLSASVGDRVTITC<u>RASQSISSYLN</u>WYQQKPGKAPKLLIY<u>AASSL</u><br><u>QS</u>GVPSRFSGSGSGTDFTLTISSLQPEDFATYYC<u>QQSYSTPYS</u>FGQGTRLEIK | 241 |

TABLE 11-continued

Exemplary Sequences for Antigen Binding Domains

| Target Antigen | Name | Amino Acid Sequence | SEQ ID NO: |
|---|---|---|---|
| BCMA | EBB-1979-C12 (human) | EVQLVESGGGLVQPGRSLRLSCTASGFTFDDYAMHWVRQRPGKGLEWVASINWKGNSLAYGD SVKGRFAISRDNAKNTVFLQMNSLRTEDTAVYYCASHQGVAYYNYAMDVWGRGTLVTVSSGG GGSGGGGSGGGGSEIVLTQSPGTLSLSPGERATLSCRATQSIGSSFLAWYQQRPGQAPRLLI YGASQRATGIPDRFSGRGSGTDFTLTISRVEPEDSAVYYCQHYESSPSWTFGQGTKVEIK | 242 |
| BCMA | EBB-1980-G4 (human) | EVQLVESGGGLVQPGGSLRLSCAASGFTFSSYAMSWVRQAPGKGLEWVSAISGSGG STYYADSVKGRFTISRDNSKNTLYLQMNSLRAEDTAVYYCAKVVRDGMDVWGQG TTVTVSSGGGGSGGGGSGGGGSEIVLTQSPATLSLSPGERATLSCRASQSVSSSYLA WYQQKPGQAPRLLIYGASSRATGIPDRFSGNGSGTDFTLTISRLEPEDFAVYYCQQY GSPPRFTFGPGTKVDIK | 243 |
| BCMA | EBB-1980-D2 (human) | EVQLLESGGGLVQPGGSLRLSCAASGFTFSSYAMSWVRQAPGKGLEWVSAISGSGGSTYYAD SVKGRFTISRDNSKNTLYLQMNSLRAEDTAVYYCAKIPQTGTFDYWGQGTLVTVSSGGGGSG GGGSGGGGSEIVLTQSPGTLSLSPGERATLSCRASQSVSSSYLAWYQQRPGQAPRLLIYGAS SRATGIPDRFSGSGSGTDFTLTISRLEPEDFAVYYCQHYGSSPSWTFGQGTRLEIK | 244 |
| BCMA | EBB-1978-A10 (human) | EVQLVETGGGLVQPGGSLRLSCAASGFTFSSYAMSWVRQAPGKGLEWVSAISGSGG STYYADSVKGRFTMSRENDKNSVFLQMNSLRVEDTGVYYCARANYKRELRYYYG MDVWGQGTMVTVSSGGGGSGGGGSGGGGSEIVMTQSPGTLSLPGESATLSCRAS QRVASNYLAWYQHKPGQAPSLLISGASSRATGVPDRFSGSGSGTDFTLAISRLEPED SAVYYCQHYDSSPSWTFGQGTKVEIK | 245 |
| BCMA | EBB-1978-D4 (human) | EVQLLETGGGLVQPGGSLRLSCAASGFSFSSYAMSWVRQAPGKGLEWVSAISGSGGSTYYAD SVKGRFTISRDNSKNTLYLQMNSLRAEDTAVYYCAKALVGATGAFDIWGQGTLVTVSSGGGG SGGGGSGGGGSEIVLTQSPGTLSLSPGERATLSCRASQSLSSNFLAWYQQKPGQAPGLLIYG ASNWATGTPDRFSGSGSGTDFTLTITRLEPEDFAVYYCQYYGTSPMYTFGQGTKVEIK | 246 |
| BCMA | EBB-1980-A2 (human) | EVQLLESGGGLVQPGGSLRLSCAASGFTFSSYAMSWVRQAPGKGLEWVSAISGSGGSTYYAD SVKGRFTISRDNSKNTLYLQMNSLRAEDTAVYYCVLWFGEGFDPWGQGTLVTVSSGGGGSGG GGSGGGGSDIVLTQSPLSLPVTPGEPASISCRSSQSLLHSNGYNYLDWYLQKPGQSPQLLIY LGSNRASGVPDRFSGSGSGTDFTLKISRVEAEDVGVYYCMQALQTPLTFGGGTKVDIK | 247 |
| BCMA | EBB-1981-C3 (human) | QVQLVESGGGLVQPGGSLRLSCAASGFTFSSYAMSWVRQAPGKGLEWVSAISGSGGSTYYAD SVKGRFTISRDNSKNTLYLQMNSLRAEDTAVYYCAKVGYDSSGYYRDYYGMDVWGQGTTVTV SSGGGGSGGGGSGGGGSEIVLTQSPGTLSLSPGERATLSCRASQSVSSSYLAWYQQKPGQAP RLLIYGTSSRATGISDRFSGSGSGTDFTLTISRLEPEDFAVYYCQHYGNSPPKFTFGPGTKL EIK | 248 |
| BCMA | EBB-1978-G4 (human) | EVQLVESGGGLVQPGGSLRLSCAASGFTFSSYAMSWVRQAPGKGLEWVSAISGSGGSTYYAD SVKGRFTISRDNSKNTLYLQMNSLRAEDTAVYYCAKMGWSSGYLGAFDIWGQGTTVTVSSGG GGSGGGGSGGGGSEIVLTQSPGTLSLSPGERATLSCRASQSVASSFLAWYQQKPGQAPRLLI YGASGRATGIPDRFSGSGSGTDFTLTISRLEPEDFAVYYCQHYGGSPRLTFGGGTKVDIK | 249 |
| BCMA | humanized | Q V Q L V Q S G A E V K K P G S S V K V S C K A S G G T F S N Y W M H W V R Q A P G Q G L E W M G A T Y R G H S D T Y Y N Q K F K G R V T I T A D K S T S T A Y M E L S S L R S E D T A V Y Y C A R G A I Y N G Y V L D N W G Q G T L V T V S S G G G G S G G G G S G G G G S G G G G S D I Q M T Q S P S S L S A S V G D R V T I T C S A S Q D I S N Y L N W Y Q Q K P G K A P K L L I Y Y T S N L H S G V P S R F S G S G S G T D F T L T I S S L Q P E D F A T Y Y C Q Q Y R K L P W T F G Q G T K L E I K R | 250 |
| BCMA | humanized | DIQMTQSPSS LSASVGDRVT ITCSASQDIS NYLNWYQQKP GKAPKLLIYY TSNLHSGVPSRFSGSGSGTD FTLTISSLQP EDFATYYCQQ YRKLPWTFGQ GTKLEIKRGG GGSGGGGSGGGGSGGGGSQV QLVQSGAEVK KPGSSVKVSC KASGGTFSNY WMHWVRQAPG QGLEWMGATYRGHSDTYYNQ KFKGRVTITA DKSTSTAYME LSSLRSEDTA VYYCARGAIYNGYDVLDNWGQGTLVTVSS | 251 |
| CD33 | 141643 (human) | QVQLVQSGAEVKKPGESLKISCKGSGYSFTSYWIGWVRQMPGKGLEWMGIIYPGDSDTRYSP SFQGQVTISADKSISTAYLQWSSLKASDTAMYYCARLGGSLPDYGMDVWGQGTMVTVSSASG GGSGGGGSGGGGSEIVLTQSPLSLPVTPGEPASISCRSSQSLLHSNGYNYLDWYLQKPGQS PQLLIYLGSNRASGVPDRFSGSGSGTDFTLKISRVEAEDVGVYYCMQALQTLITFGQGTKVD IK | 252 |
| CD33 | 141644 (human) | QVQLVQSGAEVKKPGASVRVSCKASGYIFTNYYVHWVRQAPGQGLEWMGIISPSGGSPTYAQ RLQGRVTMTRDLSTSTVYMELSSLTSEDTAVYFCARESRLRGNRLGLQSSIFDHWGQGTLVT VSSASGGGGSGGGGSGGGGSDIRMTQSPPSLSASVGDRVTIPCQASQDINNHLNWYQQKPGK APQLLIYDTSNLEIGVPSRFSGSGSGTDFTLTISSLQPEDIATYYCQQYENLPLTFGGGTKV EIK | 253 |

TABLE 11-continued

Exemplary Sequences for Antigen Binding Domains

| Target Antigen | Name | Amino Acid Sequence | SEQ ID NO: |
|---|---|---|---|
| CD33 | 141645 (human) | QVQLVQSGGGLVQPGGSLRLSCAAS<u>GFTFSSYAMS</u>WVRQAPGKGLEWVS<u>AISGSGGSTYYAD SVKG</u>RFTISRDNSKNTLYLQMNSLRAEDTAVYYCAK<u>EDTIRGPNYYYYGMD</u>VWGQGTTVTVS SASGGGGSGGGGSGGGGSETTLTQSPSSVSASVGDRVSITC<u>RASQDIDTWLA</u>WYQLKPGKAP KLLMY<u>AASNLQG</u>GVPSRFSGSGSGTDFILTISSLQPEDFATYYC<u>QQASIFPPT</u>FGGGTKVDI K | 254 |
| CD33 | 141646 (human) | QVQLVQSGAEVKKPGESLKISCKGS<u>GYSFTSYWIG</u>WVRQMPGKGLEWMG<u>IIYPGDSDTRYSP SFQG</u>QVTISADKSITTAYLQWSSLRASDSAMYYCAR<u>GYSDYDYYFDF</u>WGQGTLVTVSSASG GGGSGGGGSGGGGSEIVMTQSPLSLPVTPGEPASISC<u>RSSQSLLHSNGYNYLD</u>WYLQKPGQS PQLLIY<u>LGSNRAS</u>GVPDRFSGSGSGTDFTLKISRVEAEDVGVYYC<u>MQALQTPFT</u>FGGGTKVE IK | 255 |
| CD33 | 141647 (human) | QVQLVQSGGDLAQPGRSLRLSCAAS<u>GFTFDDYAMH</u>WVRQAPGKGLEWVA<u>VIWPDGGQKYYGD SVKG</u>RFTVSRDNPKNTLYLQMNSLRAEDTAIYYCVR<u>HFNAWDY</u>WGQGTLVTVSSASGGGGSG GGGSGGGGSDIQLTQSPSSLSAYVGGRVTITC<u>QASQGISQFLN</u>WFQQKPGKAPKLLIS<u>DASN LEP</u>GVPSRFSGSGSGTDFTFTITNLQPEDIATYYC<u>QQYDDLPLT</u>FGGGTKVEIK | 256 |
| CD33 | 141648 (human) | QVQLVQSGGGVVQPGKSLRLSCAAS<u>GFTFSIFAMH</u>WVRQAPGKGLEWVA<u>TISYDGSNAFYAD SVEG</u>RFTISRDNSKDSLYLQMDSLRPEDTAVYYCVK<u>AGDGGYDVFDS</u>WGQGTLVTVSSASGG GGSGGGGSGGGGSEIVMTQSPLSLPVTPGEPASISC<u>RSSQSLLHSNGYNYLD</u>WYLQKPGQSP QLLIY<u>LGSNRAS</u>GVPDRFSGSGSGTDFTLKISRVEAEDVGVYYC<u>MQALQTPFT</u>FGPGTKVDIK | 257 |
| CD33 | 141649 (human) | EVQLVESGGGLVQPGGSLRLSCAAS<u>GFTFSSYAMS</u>WVRQAPGKGLEWVS<u>AISGSGGSTYYAD SVKG</u>RFTISRDNSKNTLYLQMNSLRAEDTAVYYCAK<u>ETDYYGSGTFDY</u>WGQGTLVTVSSASG GGGSGGGGSGGGGSDIQMTQSPSSLSASVGDRVTISC<u>RASQGIGIYLA</u>WYQQRSGKPPQLLI HG<u>ASTLQS</u>GVPSRFSGSGSGTDFTLTISSLQPEEFASYWC<u>QQSNNFPPT</u>FGQGTKVEIK | 258 |
| CD33 | 141650 (human) | QVQLVQSGAEVKKPGASVRVSCKAS<u>GYMFTDFFIH</u>WVRQGQGLEWMG<u>WINPNSGVTKYAQ KFQG</u>RVTMTRNTSISTAYMELSSLRSEDTAVYYCAT<u>WYSSGWYGIANI</u>WGQGTMVTVSSASG GGGSGGGGSGGGGSDIQLTQSPSSLSASVGDRVTITC<u>QASHDISNYLW</u>YQQKPGKAPKLLI YD<u>ASNLET</u>GVPSRFTGSGSGTDFTLTIRSLQPEDVAAYYC<u>QQSDDLPHT</u>FGQGTKVDIK | 259 |
| CD33 | 141651 (human) | QVQLVQSGAEVKKPGESLKISCKGS<u>GYSFTNYWIG</u>WVRQMPGKGLEWMG<u>IIYPGDSDTRYSP SFQG</u>QVTISADKSISTAYLQWSSLKASDTAMYYCAR<u>HGPSSWGEFDY</u>WGQGTLVTVSSASGG GGSGGGGSGGGGSDIRLTQSPSSLSASVGDRVTITC<u>RASQSISSYLN</u>WYQQKPGKAPKLLIY <u>AASSLQS</u>GVPSRFSGSGSGTDFTLTISSLQPEDFATYYC<u>QQSYSTPLT</u>FGGGTKVDIK | 260 |
| CD33 | 2213 (humanized) | NIMLTQSPSSLAVSAGEKVTMSCKSSQSVFFSSSQKNYLAWY QQIPGQSPKLLIYWASTRESGVPDRFTGSGSGTDFTLTISSVQS EDLAIYYCHQYLSSRTFGGGTKLEIKRGGGGSGGGGSSGGGS QVQLQQPGAEVKKPGASVKMSCKASGYTFTSYYIHWIKQTP GQGLEWVGVIYPGNDDISYNQKFKGKATLTADKSSTTAYMQ LSSLTSEDSAVYYCAREVRLRYFDVWGAGTTVTVSS | 261 |
| CD33 | My96 (humanized) | EIVLTQSPGSLAVSPGERVTMSCKSSQSVFFSSSQKNYLAWYQQIP GQSPRLLIYWASTRESGVPDRFTGSGSGTDFTLTISSVQPEDLAIY YCHQYLSSRTFGQGTKLEIKRGGGGSGGGGSSGGGSQVQLQQPGAE VVKPGASVKMSCKASGYTFTSYYIHWIKQTPGQGLEWVGVIYPGND DISYNQKFQGKATLTADKSSTTAYMQLSSLTSEDSAVYYCAREVRL RYFDVWGQGTTVTVSS | 262 |
| Claudin 6 | muMAB64A | EVQLQQSGPELVKPGASMKISCKAS<u>GYSFTGYTMN</u>WVKQSHGKNLEWIG<u>LINPYN GGTIYNQKFKG</u>KATLTVDKSSSTAYMELLSLTSEDSAVYYCARD<u>YGFVLDY</u>WGQG TTLTVSSGGGGSGGGGSGGGGSGGGGSQIVLTQSPSIMSVSPGEKVTITC<u>SASSS VSYMH</u>WFQQKPGTSPKLCIY<u>STSNLAS</u>GVPARFSGRGSGTSYSLTISRVAAEDAA TYYC<u>QQRSNYPPWT</u>FGGGTKLEIK | 263 |
| Claudin 6 | mAb206-LCC | EVQLQQSGPELVKPGASMKISCKAS<u>GYSFTGYTMN</u>WVKQSHGKNLEWIG<u>LINPYN GGTIYNQKFKG</u>KATLTVDKSSSTAYMELLSLTSEDSAVYYCARD<u>YGFVLDY</u>WGQG TTLTVSSGGGGSGGGGSGGGGSGGGGSQIVLTQSPAIMSASPGEKVTITC<u>SASSS VSYLH</u>WFQQKPGTSPKLWVY<u>STSNLPS</u>GVPARFGGSGSGTSYSLTISRMEAEDAA TYYC<u>QQRSIYPPWT</u>FGGGTKLEIK | 264 |
| Claudin6 | mAb206-SUBG | EVQLQQSGPELVKPGASMKISCKAS<u>GYSFTGYTMN</u>WVKQSHGKNLEWIG<u>LINPYN GGTIYNQKFKG</u>KATLTVDKSSSTAYMELLSLTSEDSAVYYCARD<u>YGFVLDY</u>WGQG TTLTVSSGGGGSGGGGSGGGGSGGGGSQIVLTQSPSIMSVSPGEKVTITC<u>SASSS VSYMH</u>WFQQKPGTSPKLGIY<u>STSNLAS</u>GVPARFSGRGSGTSYSLTISRVAAEDAA TYYC<u>QQRSNYPPWT</u>FGGGTKLEIK | 265 |
| WT1 | ESK-1 | QAVVTQPPSA SGTPGQRVTI SCSGSSSNIG SNTVNWYQQV PGTAPKLLIY SNNQRPSGVP DRFSGSKSGT SASLAISGLQ SEDEADYYCA AWDDSLNGWV FGGGTKLTVL GSRGGGGSGG GGSGGGGSLE MAQMQLVQSG AEVKEPGESL RISCKGSGYS FTNFWISWVR QMPGKGLEWM GRVDPGYSYS TYSPSFQGHV TISADKSTST AYLQWNSLKA SDTAMYYCAR VQYSGYYDWF DPWGQGTLVT VSS | 266 |

TABLE 11-continued

Exemplary Sequences for Antigen Binding Domains

| Target Antigen | Name | Amino Acid Sequence | SEQ ID NO: |
|---|---|---|---|
| WT1 | WT1-2 | QTVVTQPPSA SGTPGQRVTI SCSGSSSNIG SNYVYWYQQL PGTAPKLLIY RSNQRPSGVP DRFSGSKSGT SASLAISGPR SVDEADYYCA AWDDSLNGVV FGGGTKLTVL GSRGGGGSGG GGSGGGSLEM AQVQLVQSGA EVKKPGSSVK VSCKASGGTF SSYAISWVRQ APGQGLEWMG GIIPIFGTAN YAQKFQGRVT ITADESTSTA YMELSSLRSE DTAVYYCARR IPPYYGMDVW GQGTTVTVSS | 267 |
| WT1 | WT1-3 | DIQMTQSPSS LSASVGDRVT ITCRASQSIS SYLNWYQQKP GKAPKLLIYA ASSLQSGVPS RFSGSGSGTD FTLTISSLQP EDFATYYCQQ SYSTPLTFGG GTKVDIKRSR GGGGSGGGGS GGGGSLEMAQ VQLQQSGPGL VKPSQTLSLT CAISGDSVSS NSAAWNWIRQ SPSRGLEWLG RTYYGSKWYN DYAVSVKSRI TINPDTSKNQ FSLQLNSVTP EDTAVYYCAR GRLGDAFDIW GQGTMVTVSS | 268 |
| WT1 | WT1-4 | DIQMTQSPST LSASVGDRVT ITCRASQNIN KWLAWYQQRP GKAPQLLIYK ASSLESGVPS RFSGSGSGTE YTLTISSLQP DDFATYYCQQ YNSYATFGQG TKVEIKRSRG GGGSGGGGSG GGGSLEMAQV QLVQSGAEVK KPGESLKISC KGSGYNFSNK WIGWVRQLPG RGLEWIAIIY PGYSDITYSP SFQGRVTISA DTSINTAYLH WHSLKASDTA MYYCVRHTAL AGFDYWGLGT LVTVSS | 269 |
| WT1 | WT1-5 | QSVVTQPPSV SVAPGKTARI TCGRNNIGSK SVHWYQQKPG QAPVLVVYDD SDRPSGIPER FSGSNSGNTA TLTISRVEAG DEADYYCQVW DSSSDHVVFG GGTKLTVLGS RGGGGSGGGG SGGSLEMAEV QLVQSGGGVV RPGGSLRLSC AASGFTFDDY GMSWVRQAPG KGLEWVSGIN WNGGSTGYAD SVRGRFTISR DNAKNSLYLQ MNSLRAEDTA LYYCARERGY GYHDPHDYWG QGTLVTVSS | 270 |
| WT1 | WT1-6 | QSVLTQPPSV SGAPGQRVTI SCTGSSSNIG AGYDVHWYQQ LPGTAPKLLI YGNSNRPSGV PDRFSGSKSG TSASLAISGL QSEDEADYYC AAWDDSLNGY VFGTGTKLTV LGSRGGGGSG GGGSGGGGSL EMAEVQLVET GGGLLQPGGS LRLSCAASGF SVSGTYMGWV RQAPGKGLEW VALLYSGGGT YHPASLQGRF IVSRDSSKNM VYLQMNSLKA EDTAVYYCAK GGAGGGHFDS WGQGTLVTVS S | 271 |
| WT1 | WT1-7 | EVQLLESGGG LVQPGGSLRL SCAASGFTFS SYAMSWVRQA PGKGLEWVSQ IDPWGQETLY ADSVKGRFTI SRDNSKNTLY LQMNSLRAED TAVYYCAKLT GRFDYWGQGT LVTVSSGGGG SGGGGSGGGG STDIQMTQSP SSLSASVGDR VTITCRASQS ISSYLNWYQQ KPGKAPKLLI YSASQLQSGV PSRFSGSGSG TDFTLTISSL QPEDFATYYC QQGPGTPNTF GQGTKVEIKR A | 272 |

In an embodiment, the antigen binding domain comprises an anti-CD19 antibody, or fragment thereof, e.g., an scFv. For example, the antigen binding domain comprises a variable heavy chain and a variable light chain listed in Table 12. The linker sequence joining the variable heavy and variable light chains can be any of the linker sequences described herein, or alternatively, can be GSTSGSGKPGSGEGSTKG (SEQ ID NO: 273). Table 12: Anti-CD 19 antibody binding domains Non-Antibody Scaffolds In embodiments, the antigen binding domain comprises a non antibody scaffold, e.g., a fibronectin, ankyrin, domain antibody, lipocalin, small modular immuno-pharmaceutical, maxybody, Protein A, or affilin. The non antibody scaffold has the ability to bind to target antigen on a cell. In embodiments, the antigen binding domain is a polypeptide or fragment thereof of a naturally occurring protein expressed on a cell. In some embodiments, the antigen

| Antibody | VH Sequence | VL Sequence |
|---|---|---|
| SJ25-C1 | QVQLLESGAELVRPGSSVKISCKASGYAFSSY WMNWVKQRPGQGLEWIGQIYPGDGDTNYNGKF KGQATLTADKSSTAYMQLSGLTSEDSAVYSC ARKTISSVVDFYFDYWGQGTTVT (SEQ ID NO: 274) | ELVLTQSPKFMSTSVGDRVSVTCKASQNVGTNVA WYQQKPGQSPKPLIYSATYRNSGVPDRFTGSGSG TDFTLTITNVQSKDLADYFYFCQYNRYPYTSGGG TKLEIKRRS (SEQ ID NO: 275) |

A CD19 antigen binding domain from any known CD19 CAR in the art can be used in accordance with the instant invention. For example, LG-740; CD19 CAR described in the U.S. Pat. Nos. 8,399,645; 7,446,190; Xu et al., Leuk Lymphoma. 2013 54(2):255-260(2012); Cruz et al., Blood 122(17):2965-2973 (2013); Brentjens et al., Blood, 118(18): 4817-4828 (2011); Kochenderfer et al., Blood 116(20): 4099-102 (2010); Kochenderfer et al., Blood 122 (25):4129-39(2013); and 16th Annu Meet Am Soc Gen Cell Ther (ASGCT) (May 15-18, Salt Lake City) 2013, Abst 10.

binding domain comprises a non-antibody scaffold. A wide variety of non-antibody scaffolds can be employed so long as the resulting polypeptide includes at least one binding region which specifically binds to the target antigen on a target cell.

Non-antibody scaffolds include: fibronectin (Novartis, MA), ankyrin (Molecular Partners AG, Zurich, Switzerland), domain antibodies (Domantis, Ltd., Cambridge, Mass., and Ablynx nv, Zwijnaarde, Belgium), lipocalin (Pieris Proteolab AG, Freising, Germany), small modular immuno-pharmaceuticals (Trubion Pharmaceuticals Inc., Seattle, Wash.), maxybodies (Avidia, Inc., Mountain View, Calif.), Protein A (Affibody AG, Sweden), and affilin (gamma-crystallin or ubiquitin) (Scil Proteins GmbH, Halle, Germany).

Fibronectin scaffolds can be based on fibronectin type III domain (e.g., the tenth module of the fibronectin type III ($^{10}$Fn3 domain)). The fibronectin type III domain has 7 or 8 beta strands which are distributed between two beta sheets, which themselves pack against each other to form the core of the protein, and further containing loops (analogous to CDRs) which connect the beta strands to each other and are solvent exposed. There are at least three such loops at each edge of the beta sheet sandwich, where the edge is the boundary of the protein perpendicular to the direction of the beta strands (see U.S. Pat. No. 6,818,418). Because of this structure, this non-antibody scaffold mimics antigen binding properties that are similar in nature and affinity to those of antibodies. These scaffolds can be used in a loop randomization and shuffling strategy in vitro that is similar to the process of affinity maturation of antibodies in vivo.

The ankyrin technology is based on using proteins with ankyrin derived repeat modules as scaffolds for bearing variable regions which can be used for binding to different targets. The ankyrin repeat module is a 33 amino acid polypeptide consisting of two anti-parallel α-helices and a β-turn. Binding of the variable regions is mostly optimized by using ribosome display.

Avimers are derived from natural A-domain containing protein such as HERS. These domains are used by nature for protein-protein interactions and in human over 250 proteins are structurally based on A-domains. Avimers consist of a number of different "A-domain" monomers (2-10) linked via amino acid linkers. Avimers can be created that can bind to the target antigen using the methodology described in, for example, U.S. Patent Application Publication Nos. 20040175756; 20050053973; 20050048512; and 20060008844.

Affibody affinity ligands are small, simple proteins composed of a three-helix bundle based on the scaffold of one of the IgG-binding domains of Protein A. Protein A is a surface protein from the bacterium *Staphylococcus aureus*. This scaffold domain consists of 58 amino acids, 13 of which are randomized to generate affibody libraries with a large number of ligand variants (See e.g., U.S. Pat. No. 5,831,012). Affibody molecules mimic antibodies, they have a molecular weight of 6 kDa, compared to the molecular weight of antibodies, which is 150 kDa. In spite of its small size, the binding site of affibody molecules is similar to that of an antibody.

Protein epitope mimetics (PEM) are medium-sized, cyclic, peptide-like molecules (MW 1-2 kDa) mimicking beta-hairpin secondary structures of proteins, the major secondary structure involved in protein-protein interactions. Antigen binding domains, e.g., those comprising scFv, single domain antibodies, or camelid antibodies, can be directed to any target receptor/ligand described herein, e.g., the the PD1 receptors, PD1-L1 or PD1-L2.

Mismatched Antigen Binding Domains

It has been discovered, that cells having a plurality of chimeric membrane embedded receptors each comprising an antigen binding domain (CMERs) that interactions between the antigen binding domain of the CMER can be undesirable, e.g., because it inhibits the ability of one or more of the antigen binding domains to bind its cognate antigen. Accordingly, disclosed herein are a first and a second non-naturally occurring CMER, comprising antigen binding domains that minimize such interactions when expressed in the same cell wherein said first CMER is an RCAR. In an embodiment a plurality of CMERs comprises two RCARs. In an embodiment a plurality of CMERs comprises a CAR and another RCAR.

In some embodiments, the claimed invention comprises a first and second CMER, wherein the antigen binding domain of one of said first CMER said second CMER does not comprise a variable light domain and a variable heavy domain, wherein one of said first and second CMER is a RCAR. In some embodiments, the antigen binding domain of one of said first CMER said second CMER is an scFv, and the other is not an scFv, wherein one of said first and second CMER is a RCAR. In some embodiments, the antigen binding domain of one of said first CMER said second CMER comprises a single VH domain, e.g., a camelid, shark, or lamprey single VH domain, or a single VH domain derived from a human or mouse sequence or a non-antibody scaffold, wherein one of said first and second CMER is a RCAR. In some embodiments, the antigen binding domain of one of said first CMER said second CMER comprises a nanobody, wherein one of said first and second CMER is a RCAR. In some embodiments, the antigen binding domain of one of said first CMER said second CMER comprises a camelid VHH domain, wherein one of said first and second CMER is a RCAR.

In some embodiments, the antigen binding domain of one of said first CMER said second CMER comprises an scFv, and the other comprises a single VH domain, e.g., a camelid, shark, or lamprey single VH domain, or a single VH domain derived from a human or mouse sequence, wherein one of said first and second CMER is a RCAR. In some embodiments, the antigen binding domain of one of said first CMER said second CMER comprises an scFv, and the other comprises a nanobody, wherein one of said first and second CMER is a RCAR. In some embodiments, the antigen binding domain of one of said first CMER said second CMER comprises an scFv, and the other comprises a camelid VHH domain, wherein one of said first and second CMER is a RCAR.

In some embodiments, when present on the surface of a cell, binding of the antigen binding domain of said first CMER to its cognate antigen is not substantially reduced by the presence of said second CMER, wherein one of said first and second CMER is a RCAR. In some embodiments, binding of the antigen binding domain of said first CMER to its cognate antigen in the presence of said second CMER is 85%, 90%, 95%, 96%, 97%, 98% or 99% of binding of the antigen binding domain of said first CMER to its cognate antigen in the absence of said second CMER, wherein one of said first and second CMER is a RCAR.

In some embodiments, when present on the surface of a cell, the antigen binding domains of said first CMER said second CMER, associate with one another less than if both were scFv antigen binding domains, wherein one of said first and second CMER is a RCAR. In some embodiments, the antigen binding domains of said first CMER said second CMER, associate with one another 85%, 90%, 95%, 96%, 97%, 98% or 99% less than if both were scFv antigen binding domains, wherein one of said first and second CMER is a RCAR.

Dimerization Switches

Dimerization switches can be non-covalent or covalent, depending on the form of interaction between the switch domains.

Non-Covalent Dimerization Switches

In a non-covalent dimerization switch, the dimerization molecule promotes a non-covalent interaction between the switch domains. Examples of non-covalent dimerization switches include the FKBP/FRAP-Based Dimerization Switches, GyrB-GyrB Based Dimerization Switches and Gibberelin-Based Dimerization Switches, described herein.

FKBP/FRB-Based Dimerization Switches.

FKBP12 (FKBP, or FK506 binding protein) is an abundant cytoplasmic protein that serves as the initial intracellular target for the natural product immunosuppressive drug, rapamycin. Rapamycin binds to FKBP and to the large PI3K homolog FRAP (RAFT, mTOR), thereby acting to dimerize these molecules.

In embodiments, an FKBP/FRAP based switch, also referred to herein as an FKBP/FRB, based switch can use a heterodimerization molecule, e.g., rapamycin or a rapamycin analog. FRB is a 93 amino acid portion of FRAP, that is sufficient for binding the FKBP-rapamycin complex (Chen, J., Zheng, X. F., Brown, E. J. & Schreiber, S. L. (1995) *Identification of an 11-kDa FKBP12-rapamycin-binding domain within the 289-kDa FKBP12-rapamycin-associated protein and characterization of a critical serine residue.* Proc Natl Acad Sci USA 92: 4947-51).

The sequences of FKBP is as follows:

```
FKBP
                                        (SEQ ID NO: 1)
D V P D Y A S L G G P S S P K K K R K V S R G V Q

V E T I S P G D G R T F P K R G Q T C V V H Y T G

M L E D G K K F D S S R D R N K P F K F M L G K Q

E V I R G W E E G V A Q M S V G Q R A K L T I S P

D Y A Y G A T G H P G I I P P H A T L V F D V E L

L K L E T S Y
```

In embodiments, an FKBP switch domain can comprise a FRB binding fragment of FKBP, e.g., the underlined portion of SEQ ID NO 1, which is:

```
                                        (SEQ ID NO: 141)
V Q V E T I S P G D G R T F P K R G Q T C V V H Y

T G M L E D G K K F D S S R D R N K P F K F M L G

K Q E V I R G W E E G V A Q M S V G Q R A K L T I

S P D Y A Y G A T G H P G I I P P H A T L V F D V

E L L K L E T S.
```

The sequence of FRB is as follows:

```
                                        (SEQ ID NO: 2)
ILWHEMWHEG LEEASRLYFG ERNVKGMFEV LEPLHAMMER

GPQTLKETSF NQAYGRDLME AQEWCRKYMK SGNVKDLTQA

WDLYYHVFRR ISK
```

In an embodiment, one switch domain comprises amino acid residues disclosed in SEQ ID NO: 1, or an FRB binding fragment or analog thereof, e.g., SEQ ID NO:141, and one switch domain comprises amino acid residues disclosed in SEQ ID NO: 2 or an FKPB binding fragment or analog thereof. In an embodiment, the FRB binding fragment of FKBP comprises 30, 35, 40, 45, 50, 55, 60, 70, 75, 80, 85 or 90 amino acids of the sequence of FKBP, SEQ ID NO:1, or SEQ ID NO: 141. In an embodiment, the FRB binding fragment of FKBP is at least 5, 10, 15, 20, 25, 30, 35, 40 amino acids shorter than the sequence of FKBP, SEQ ID NO:1, or SEQ ID NO: 141. In an embodiment, the FKBP binding fragment of FRB comprises 30, 35, 40, 45, 50, 55, 60, 70, 75, 80, 85 or 90 amino acids of the sequence of FRB, SEQ ID NO:2. In an embodiment, the FKBP binding fragment of FRB is at least 5, 10, 15, 20, 25, 30, 35, 40 amino acids shorter than the sequence of FRB, SEQ ID NO:2. In an embodiment, the FKBP binding fragment or analog of FRB comprises one or more mutations which enhances the formation of a complex between an FKBP switch domain, an FRB switch domain, and the dimerization molecule, e.g., rapamycin, or a rapalog, e.g., RAD001, or a mutation described in the section herein entitled MODIFIED FKBP/FRB-BASED DIMERIZATION SWITCHES. E.g., the FKBP binding fragment or analog of FRB comprises: an E2032 mutation, e.g., an E2032I mutation or E2032L mutation; a T2098 mutation, e.g., a T2098L mutation; or an E2032 and a T2098 mutation, e.g., an E2032I and a T2098L or an E2032L and a T2098L mutation.

In an embodiment, one switch domain comprises amino acid residues disclosed in SEQ ID NO: 1 (or SEQ ID NO:141) and one switch domain comprises amino acid residues disclosed in SEQ ID NO: 2.

In embodiments, a switch domain, or a rapamycin, or rapalog, e.g., RAD001, binding sequence of thereof, will have at least 60, 70, 75, 80, 85, 90, 95, 96, 97, 98, or 99% identity with the FKBP sequence of SEQ ID NO: 1 (or SEQ ID NO: 141). In embodiments, a switch domain, or a rapamycin, or rapalog, e.g., RAD001, binding sequence thereof, will differ by no more than 35, 30, 25, 20, 15, 10, 5, 4, 3, 2, or 1 amino acid residues from the corresponding the sequence of SEQ ID NO: 1 (or SEQ ID NO: 141).

In an embodiment, one switch domain binds FRB (or FRB and rapamycin, or a rapamycin analog) and has at least 60, 70, 75, 80, 85, 90, 95, 96, 97, 98, or 99% identity with, or differs by no more than 35, 30, 25, 20, 15, 10, 5, 4, 3, 2, or 1 amino acid residues from, the FKBP sequence of SEQ ID NO: 1.

In embodiments, a switch domain, or a rapamycin, or rapalog, e.g., RAD001, binding sequence of thereof, will have at least 60, 70, 75, 80, 85, 90, 95, 96, 97, 98, or 99% identity with the FRB sequence of SEQ ID NO: 2. In embodiments, a switch domain, or a rapamycin, or rapalog, e.g., RAD001, binding sequence thereof, will differ by no more than 35, 30, 25, 20, 15, 10, 5, 4, 3, 2, or 1 amino acid residues from the corresponding the sequence of SEQ ID NO: 2.

Figure 2:
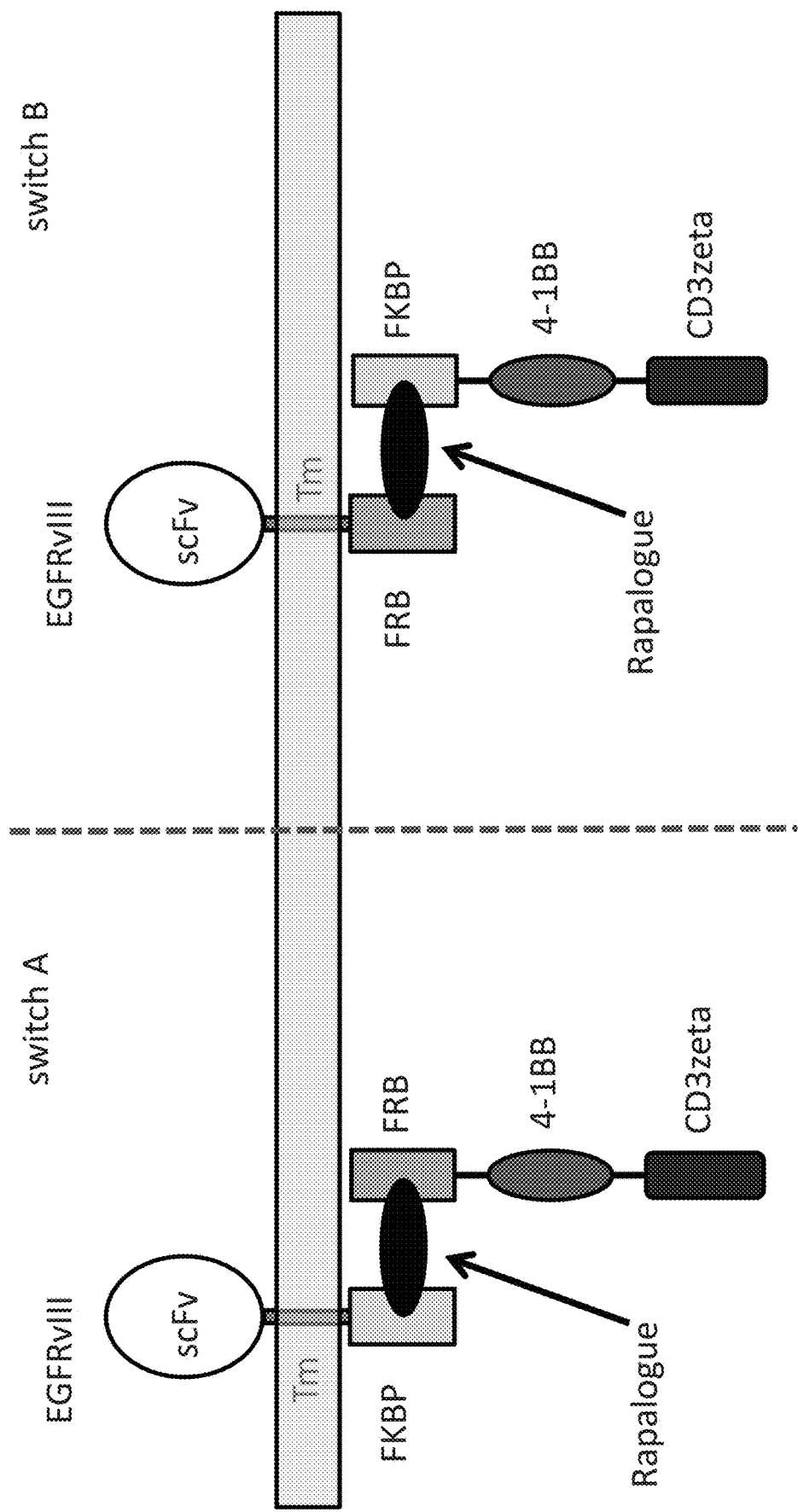
FIG. 2 depicts RCARs having a FKBP/FRB heterodimerization induced by a rapamycin analogue. The antigen binding domain may be an scFv, e.g., that targets EGFRvIII. Switch A and switch B show the FKBP and FRB switch domains in different orientations with respect to the antigen binding member and the intracellular signaling member.

In an embodiment the other switch domain binds FKBP (or FKBP and rapamycin, or a rapamycin analog) and has at least 60, 70, 75, 80, 85, 90, 95, 96, 97, 98, or 99% identity with, or differs by no more than 35, 30, 25, 20, 15, 10, 5, 4, 3, 2, or 1 amino acid residues from, the FRB sequence of SEQ ID NO: 2. See, e.g., FIG. 2.

In embodiments a switch domain, or a rapamycin, or rapalog, e.g., RAD001, binding sequence of thereof, will have at least 60, 70, 75, 80, 85, 90, 95, 96, 97, 98, or 99% identity with a non-human, e.g., mammalian, e.g., rodent, e.g., mouse, rat or hamster, FKBP sequence. In embodiments, a switch domain, or a rapamycin, or rapalog, e.g., RAD001, binding sequence thereof, will differ by no more than 35, 30, 25, 20, 15, 10, 5, 4, 3, 2, or 1 amino acid residues from a non-human, e.g., mammalian, e.g., rodent, e.g., mouse, rat or hamster FKBP.

In an embodiment, the one switch domain binds FRB (or FRB and rapamycin, or a rapamycin analog) and has at least 60, 70, 75, 80, 85, 90, 95, 96, 97, 98, or 99% identity with, or differs by no more than 35, 30, 25, 20, 15, 10, 5, 4, 3, 2, or 1 amino acid residues from, a non-human, e.g., mammalian, e.g., rodent, e.g., mouse, rat or hamster, FKBP.

In embodiments, a switch domain, or a rapamycin, or rapalog, e.g., RAD001, binding sequence of thereof, will have at least 60, 70, 75, 80, 85, 90, 95, 96, 97, 98, or 99% identity with a non-human, e.g., mammalian, e.g., rodent, e.g., mouse, rat or hamster, FRB sequence. In embodiments, a switch domain, or a rapamycin, or rapalog, e.g., RAD001, binding sequence thereof, will differ by no more than 35, 30, 25, 20, 15, 10, 5, 4, 3, 2, or 1 amino acid residues from a non-human, e.g., mammalian, e.g., rodent, e.g., mouse, rat or hamster, FRB sequence.

In an embodiment the other switch domain binds FKBP (or FKBP and rapamycin, or a rapamycin analog) and has at least 60, 70, 75, 80, 85, 90, 95, 96, 97, 98, or 99% identity with, or differs by no more than 35, 30, 25, 20, 15, 10, 5, 4, 3, 2, or 1 amino acid residues from a non-human, e.g., mammalian, e.g., rodent, e.g., mouse, rat or hamster, FRB.

"FKBP/FRAP, e.g., an FKBP/FRB, based switch" as that term is used herein, refers to a dimerization switch comprising: a first switch domain, which binds rapamycin, or a rapamycin analog, and has at least 70, 75, 80, 85, 90, 95, 96, 97, 98, or 99% identity with, or differs by no more than 30, 25, 20, 15, 10, 5, 4, 3, 2, or 1 amino acid residues from, the FKBP sequence of SEQ ID NO:1 or SEQ ID NO: 141; and a second switch domain, which binds rapamycin, or a rapamycin analog, and has at least 70, 75, 80, 85, 90, 95, 96, 97, 98, or 99% identity with, or differs by no more than 30, 25, 20, 15, 10, 5, 4, 3, 2, or 1 amino acid residues from, the FRB sequence of SEQ ID NO: 2. See, e.g., FIG. 2.

In embodiments, an FKBP/FRB, based switch can use a heterodimerization molecule, e.g., a rapamycin analog, that lacks rapamycin's undesirable properties, e.g., it lacks or has less immunosuppressive activity.

Modified FKBP/FRB-Based Dimerization Switches

Also provided herein are improved FKBP/FRB dimerization switches, in which the FRB-based switch domain comprises one or more mutations that optimize performance, e.g., that alter, e.g., enhance the formation of a complex between an FKBP switch domain, an FRB switch domain, and the dimerization molecule, e.g., rapamycin, or a rapalog, e.g., RAD001. In an embodiment, the FRB-based switch domain comprising one or more mutations, also referred to herein as a "mutant FRB", comprises increased affinity for a dimerization molecule, e.g., rapamycin or a rapalog, e.g., in comparison to the affinity of a wild-type FRB-based switch domain for the dimerization molecule.

Without wishing to be bound by theory, it is believed that mutations described herein can allow the use of lower concentrations of the dimerization molecule to assemble the RCAR. Some dimerization molecules that dimerize FKBP/FRB dimerization switches exhibit immunosuppressive effects, and therefore prevent or mitigate the beneficial effects of RCAR therapy. Thus, the ability to use lower concentrations of the dimerization molecule to assemble RCAR can increase the therapeutic window for RCAR-expressing cell activity, e.g., increase the range of dosages of dimerization molecule that can be used without inducing immunosuppression, and therefore results in the increase of therapeutic benefit of the RCAR-expressing cell. Alternatively or in addition, without wishing to be bound by theory, it is believed that mutations described herein can result in preferential binding of the dimerization molecule to the mutant FRB instead of binding and inhibiting endogenous FRAP/mTOR. Preventing the inhibition of endogenous FRAP/mTOR decreases or inhibits adverse effects associated with endogenous FRAP/mTOR inhibition, e.g., toxicity or immunosuppression.

A mutant FRB can be identified using the screening method described herein. First, regions or amino acid residues in a wild-type FRB that are present in the dimerization molecule-binding pocket of the natively folded wild-type FRB, or contribute to the interaction, e.g., directly or indirectly, with the dimerization molecule, can be determined from structural data, e.g., x-ray crystallographic structures, or computer modeling, e.g., homology or comparative modeling of homologous proteins bound to the dimerization molecule or derivatives thereof. A candidate mutant FRB can be generated by mutating a target region or target residue e.g., by PCR site-directed mutagenesis. In an embodiment, a library of candidate FRB mutants comprising one or more point mutations can be generated using a saturation mutagenesis approach, where a target residue is mutated to all other possible amino acids by randomizing the codon that encodes the target residue. Randomization of each codon corresponding to a target residue can be achieved by using a codon library that represents all 20 amino acids, e.g., a NNK library, where N can be adenine (A), cytosine (C), guanine (G), or thymine (T), and K can be guanine (G) or thymine (T). Table 13 shows the codon distribution of an exemplary NNK library and the corresponding amino acids. Each codon in the NNK library is incorporated at the target residue position, thereby producing a library of candidate FRB mutants for each target residue position where the target residue position has been mutated to every other possible amino acid. The library of candidate FRB mutants can then be screened to identify FRB mutants described herein.

TABLE 13

NNK Library
DNA base N defined to be A/C/G/T and K defined to be G/T.

| NNK | Amino Acid |
|---|---|
| AAG | Lysine, Lys, K |
| AAT | Asparagine, Asn, N |
| ACG | Theronine, Thr, T |
| ACT | Theronine, Thr, T |
| AGG | Arginine, Arg, R |
| AGT | Serine, Ser, S |
| ATG | Methionine, Met, M |
| ATT | Isoleucine, Ile, I |
| CAG | Glutamine, Gln, Q |
| CAT | Histidine, His, H |
| CCG | Proline, Pro, P |
| CCT | Proline, Pro, P |
| CGG | Arginine, Arg, R |
| CGT | Arginine, Arg, R |
| CTG | Leucine, Leu, L |
| CTT | Leucine, Leu, L |
| GAG | Glutamic acid, Glu, E |
| GAT | Aspartic acid, Asp, D |
| GCG | Alanine, Ala, A |
| GCT | Alanine, Ala, A |
| GGG | Glycine, Gly, G |
| GGT | Glycine, Gly, G |
| GTG | Valine, Val, V |
| GTT | Valine, Val, V |
| TAG | Stop |
| TAT | Tyrosine, Tyr, Y |
| TCG | Serine, Ser, S |
| TCT | Serine, Ser, S |
| TGG | Tryptophan, Trp, W |
| TGT | Cysteine, Cys, C |

TABLE 13-continued

NNK Library
DNA base N defined to be A/C/G/T and K defined to be G/T.

| NNK | Amino Acid |
|---|---|
| TTG | Leucine, Leu, L |
| TTT | Phenylalanine, Phe, F |

Various screening assays can be used to evaluate each candidate mutant FRB to identify mutant FRB which enhances the formation of a complex between an FKBP switch domain, an FRB switch domain, and the dimerization molecule, e.g., rapamycin, or a rapalog, e.g., RAD001. In a direct binding assay, unlabeled candidate mutant FRB is incubated in solution with tagged wild-type FKBP in the presence of the dimerization molecule, e.g., under conditions suitable for binding of FRB to the dimerization molecule and dimerization of FRB and FKBP. Tagged FKBP can be removed from the reaction by affinity purification; candidate mutant FRB that is able to bind the dimerization molecule and dimerize with the tagged FKBP will also be removed. The amount of free candidate mutant FRB that does not dimerize with the tagged wild-type FKBP can be calculated by determining protein concentration of the reaction. EC50 values for direct binding affinity can then be calculated using methods known in the art.

Alternatively or in addition to the direct binding assay described above, a competition binding assay can also be performed to identify a mutant FRB. In this assay, an untagged candidate mutant FRB is incubated in solution with: 1) wild-type FKBP linked to a first tag, e.g., biotinylated wild-type FKBP; 2) wild-type FRB linked to a second tag, e.g., FLAG-tagged wild-type FRB; and 3) the dimerization molecule; under conditions suitable for binding of FRB to the dimerization molecule and dimerization of FRB and FKBP. The tagged wild-type FKBP and tagged wild-type FRB can be removed from the reaction by affinity purification. The amount of free candidate mutant FRB that does not dimerize with the tagged wild-type FKBP in the presence of wild-type FRB can be calculated by determining protein concentration of the reaction. EC50 values for competition binding affinity can then be calculated using methods known in the art.

In an embodiment, a mutant FRB comprises one or more, e.g., 2, 3, 4, 5, 6, 7, 8, 9, 10 or more, mutations in the amino acid sequence of a wild-type FRB, e.g., a FRB comprising SEQ ID NO: 2. The mutant FRB comprises increased affinity for a dimerization molecule, e.g., as compared to the affinity of wild-type FRB for the dimerization molecule. The amino acid position numbering of a wild-type or mutant FRB referred to herein can be determined from SEQ ID NO: 2, where the first amino acid of SEQ ID NO: 2 is position 2021 and the last amino acid of SEQ ID NO: 2 is position 2113.

In an embodiment, a mutant FRB comprises one or more mutations at the amino acid(s) selected from a leucine at position 2031 (L2031), a glutamic acid at position 2032 (E2032), a serine at position 2035 (S2035), an arginine at position 2036 (R2036), a phenylalanine at position 2039 (F2039), a glycine at position 2040 (G2040), a threonine at position 2098 (T2098), a tryptophan at position 2101 (W2101), an aspartic acid at position 2102(D2102), a tyrosine at position 2105(Y2105), and a phenylalanine at position 2108 (F2108), where L2031, E2032, S2035, R2036, F2039, G2040, T2098, W2101, D2102, Y2105, and/or F2108 is mutated to any other naturally-occurring amino acid. In an embodiment, a mutant FRB comprises an amino acid sequence selected from SEQ ID NOs: 276-286, where X can be any naturally occurring amino acid. Amino acid sequences of exemplary mutant FRB switch domains having increased affinity for RAD001 are provided in Table 14 below. A screen as described herein can be performed to identify a mutant FRB.

TABLE 14

Exemplary mutant FRBs.

| FRB mutant | Amino Acid Sequence | SEQ ID NO: |
|---|---|---|
| L2031 mutant | ILWHEMWHEGXEEASRLYFGERNVKGMFEVLEPLHAMMERGPQTLKETSFNQAYGRDLMEAQEWCRKYMKSGNVKDLTQAWDLYYHVFRRISKTS | 276 |
| E2032 mutant | ILWHEMWHEGLXEASRLYFGERNVKGMFEVLEPLHAMMERGPQTLKETSFNQAYGRDLMEAQEWCRKYMKSGNVKDLTQAWDLYYHVFRRISKTS | 277 |
| S2035 mutant | ILWHEMWHEGLEEAXRLYFGERNVKGMFEVLEPLHAMMERGPQTLKETSFNQAYGRDLMEAQEWCRKYMKSGNVKDLTQAWDLYYHVFRRISKTS | 278 |
| R2036 mutant | ILWHEMWHEGLEEASXLYFGERNVKGMFEVLEPLHAMMERGPQTLKETSFNQAYGRDLMEAQEWCRKYMKSGNVKDLTQAWDLYYHVFRRISKTS | 279 |
| F2039 mutant | ILWHEMWHEGLEEASRLYXGERNVKGMFEVLEPLHAMMERGPQTLKETSFNQAYGRDLMEAQEWCRKYMKSGNVKDLTQAWDLYYHVFRRISKTS | 280 |
| G2040 mutant | ILWHEMWHEGLEEASRLYFXERNVKGMFEVLEPLHAMMERGPQTLKETSFNQAYGRDLMEAQEWCRKYMKSGNVKDLTQAWDLYYHVFRRISKTS | 281 |
| T2098 mutant | ILWHEMWHEGLEEASRLYFGERNVKGMFEVLEPLHAMMERGPQTLKETSFNQAYGRDLMEAQEWCRKYMKSGNVKDLXQAWDLYYHVFRRISKTS | 282 |
| W2101 mutant | ILWHEMWHEGLEEASRLYFGERNVKGMFEVLEPLHAMMERGPQTLKETSFNQAYGRDLMEAQEWCRKYMKSGNVKDLTQAXDLYYHVFRRISKTS | 283 |
| D2102 mutant | ILWHEMWHEGLEEASRLYFGERNVKGMFEVLEPLHAMMERGPQTLKETSFNQAYGRDLMEAQEWCRKYMKSGNVKDLTQAWXLYYHVFRRISKTS | 284 |

TABLE 14-continued

Exemplary mutant FRBs.

| FRB mutant | Amino Acid Sequence | SEQ ID NO: |
|---|---|---|
| Y2105 mutant | ILWHEMWHEGLEEASRLYFGERNVKGMFEVLEPLHAMMERGPQTLKETSFNQAYGR DLMEAQEWCRKYMKSGNVKDLTQAWDLYXHVFRRISKTS | 285 |
| F2108 mutant | ILWHEMWHEGLEEASRLYFGERNVKGMFEVLEPLHAMMERGPQTLKETSFNQAYGR DLMEAQEWCRKYMKSGNVKDLTQAWDLYYHVXRRISKTS | 286 |

A screen was performed to evaluate candidate mutant FRBs, as further described in Example 21.

In an embodiment, a mutant FRB e.g., comprises one or more mutations at the amino acid(s) selected from L2031, E2032, 52035, R2036, F2039, G2040, T2098, W2101, D2102, Y2105, and F2108, where the wild-type amino acid is mutated to any other naturally-occurring amino acid. In an embodiment, a mutant FRB comprises a mutation at E2032, where E2032 is mutated to phenylalanine (E2032F), methionine (E2032M), arginine (E2032R), valine (E2032V), tyrosine (E2032Y), isoleucine (E2032I), e.g., SEQ ID NO: 287, or leucine (E2032L), e.g., SEQ ID NO: 288. In an embodiment, a mutant FRB comprises a mutation at T2098, where T2098 is mutated to phenylalanine (T2098F) or leucine (T2098L), e.g., SEQ ID NO: 289. In an embodiment, a mutant FRB comprises a mutation at E2032 and at T2098, where E2032 is mutated to any amino acid, and where T2098 is mutated to any amino acid, e.g., SEQ ID NO: 290. In an embodiment, a mutant FRB comprises an E2032I and a T2098L mutation, e.g., SEQ ID NO: 291. In an embodiment, a mutant FRB comprises an E2032L and a T2098L mutation, e.g., SEQ ID NO: 292. Amino acid sequences of exemplary mutant FRB switch domains are provided in Table 15 below.

dimerization of a modified FKBP-FRB based switch, e.g., comprising a mutant FRB described herein, is lower than the dosage currently used to treat cancer, e.g., a dose of RAD001 comprises less than 10 mg per day, e.g., less than 10 mg, 9 mg, 8 mg, 7 mg, 6 mg, 5 mg, 4 mg, 3 mg, 2 mg, 1 mg per day. In an embodiment, a dose of RAD001 that stimulates dimerization of a modified FKBP-FRB based switch, e.g., comprising a mutant FRB described herein, comprises less than 1 mg per day, e.g., 0.5 mg per day. In an embodiment, a dose of RAD001 that stimulates dimerization of a modified FKBP-FRB based switch, e.g., comprising a mutant FRB described herein, comprises less than 10 mg per week, e.g., 5 mg per week. Additional dosages of dimerization molecules suitable for use with the modified FKBP-FRB based switches are described herein in the section entitled "Pharmaceutical Compositions and Treatments".

AP21967 and AP21967-Binding FRB

In and embodiment the dimerization molecule is a rapamycin analog, e.g., AP21967, that does not bind wild-type endogenous FRAP, e.g., FRB, but that does bind a modified FRB. While not wishing to be bound by theory it is believed that the lack of binding to endogenous FRB reduces immunosuppressive activity. An exemplary modified FRB contains a single amino acid change (T2098L).

TABLE 15

Exemplary mutant FRBs.

| FRB mutant | Amino Acid Sequence | SEQ ID NO: |
|---|---|---|
| E2032I mutant | ILWHEMWHEGLIEASRLYFGERNVKGMFEVLEPLHAMMERGPQTLKETSFNQAYGR DLMEAQEWCRKYMKSGNVKDLTQAWDLYYHVFRRISKTS | 287 |
| E2032L mutant | ILWHEMWHEGLLEASRLYFGERNVKGMFEVLEPLHAMMERGPQTLKETSFNQAYGR DLMEAQEWCRKYMKSGNVKDLTQAWDLYYHVFRRISKTS | 288 |
| T2098L mutant | ILWHEMWHEGLEEASRLYFGERNVKGMFEVLEPLHAMMERGPQTLKETSFNQAYGR DLMEAQEWCRKYMKSGNVKDLLQAWDLYYHVFRRISKTS | 289 |
| E2032X, T2098X mutant | ILWHEMWHEGLXEASRLYFGERNVKGMFEVLEPLHAMMERGPQTLKETSFNQAYGR DLMEAQEWCRKYMKSGNVKDLXQAWDLYYHVFRRISKTS | 290 |
| E2032I, T2098L mutant | ILWHEMWHEGLIEASRLYFGERNVKGMFEVLEPLHAMMERGPQTLKETSFNQAYGR DLMEAQEWCRKYMKSGNVKDLLQAWDLYYHVFRRISKTS | 291 |
| E2032L, T2098L mutant | ILWHEMWHEGLLEASRLYFGERNVKGMFEVLEPLHAMMERGPQTLKETSFNQAYGR DLMEAQEWCRKYMKSGNVKDLLQAWDLYYHVFRRISKTS | 292 |

The mutant FRB allows the use of dosages of RAD001 lower than the dosage currently used in clinical settings, or lower than a dosage that induces immunosuppression in a subject, to stimulate dimerization of a FKBP-FRB based switch. In an embodiment, a dose of RAD001 that stimulates Incorporation of this mutation into the FRB component of a dimerization switch allows AP21967 to be used as a dimerization molecule.

In an embodiment, one switch domain comprises sequence from FKBP that binds a rapamycin analog, e.g., AP21967, and the other switch domain comprises sequence from FRB that binds a rapamycin analog, e.g., AP21967, binding.

FKBP (SEQ ID NO: 1)

D V P D Y A S L G G P S S P K K K R K V S R G V Q

V E T I S P G D G R T F P K R G Q T C V V H Y T G

M L E D G K K F D S S R D R N K P F K F M L G K Q

E V I R G W E E G V A Q M S V G Q R A K L T I S P

D Y A Y G A T G H P G I I P P H A T L V F D V E L

L K L E T S Y

FRB (T2098L)

(SEQ ID NO: 142)

M A S R I L W H E M W H E G L E E A S R L Y F G E

R N V K G M F E V L E P L H A M M E R G P Q T L K

E T S F N Q A Y G R D L M E A Q E W C R K Y M K S

G N V K D L L Q A W D L Y Y H V F R R I S K T S

In an embodiment, one switch domain comprises amino acid residues disclosed in SEQ ID NO: 1 and one switch domain comprises amino acid residues disclosed in SEQ ID NO: 2.

In embodiments the switch domain, or a rapamycin analog, e.g., AP21967, binding sequence of thereof, will have at least 70, 75, 80, 85, 90, 95, 96, 97, 98, or 99% identity with the FKBP sequence of SEQ ID NO: 1. In embodiments, the switch domain, or a rapamycin analog, e.g., AP21967, binding sequence thereof, will differ by no more than 30, 25, 20, 15, 10, 5, 4, 3, 2, or 1 amino acid residues from the corresponding the sequence of SEQ ID NO: 1

In embodiments the switch domain, or a rapamycin analog, e.g., AP21967, binding sequence of thereof, will have at least 70, 75, 80, 85, 90, 95, 96, 97, 98, or 99% identity with the FRB sequence of SEQ ID NO: 142. In embodiments, the switch domain, or a rapamycin analog, e.g., AP21967, binding sequence thereof, will differ by no more than 30, 25, 20, 15, 10, 5, 4, 3, 2, or 1 amino acid residues from the corresponding FRB sequence of SEQ ID NO: 142.

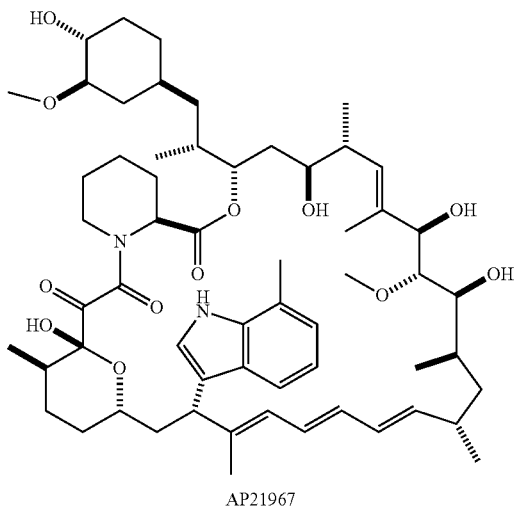

Structure 1

AP21967
Structure of A/C Heterodimerizer

Similar switches have been used to control the localization and activity of signaling domains as described above (see, e.g., Graef, I. A., Holsinger, L. J., Diver, S., Schreiber, S. L. & Crabtree, G. R. (1997) *Proximity and orientation underlie signaling by the non-receptor tyrosine kinase ZAP70*. Embo J 16: 5618-28).

Candidate sequences for use as switch domain comprising a rapamycin analog, e.g., AP21967, binding sequence from FKBP, or a rapamycin analog, e.g., AP21967, binding sequence from FRB can be evaluated by incorporating the candidate into a system such as that described herein.

Dimerization Molecules for FKPB/FRB Based Switches

Rapamycin and rapamycin analogs (sometimes referred to as rapalogs), can be used as dimerization molecules in FKBP-FRB based dimerization switches. In an embodiment the dimerization molecule can be selected from rapamycin (sirolimus), RAD001 (everolimus), zotarolimus, temsirolimus, AP-23573 (ridaforolimus), biolimus and AP21967.

Rapamycin is a known macrolide antibiotic produced by *Streptomyces hygroscopicus* having the structure shown in Formula A.

(A)

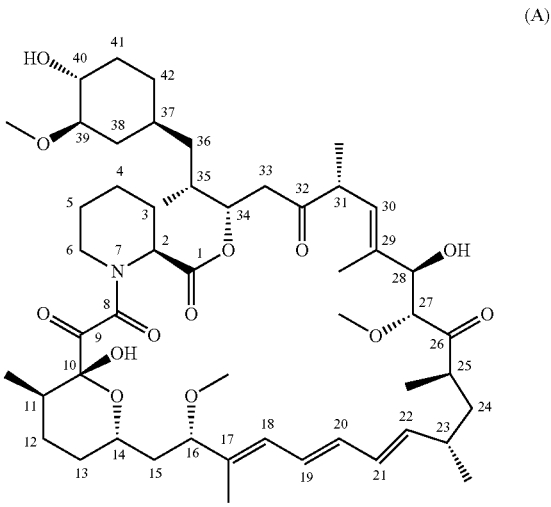 [SMILES: CO[C@H]1C[C@@H]2CC[C@@H](C)[C@@](O)(O2)C(=O)C(=O)N2CCCC[C@H]2C(=O)O[C@H]([C@H](C)C[C@@H]2CC[C@@H](O)[C@H](OC)C2)CC(=O)[C@H](C)/C=C(\C)[C@@H](O)[C@@H](OC)C(=O)[C@H](C)C[C@H](C)/C=C/C=C/C=C/1C]

See, e.g., McAlpine, J. B., et al., J. Antibiotics (1991) 44:688; Schreiber, S. L., et al., J. Am. Chem. Soc. (1991) 113:7433; U.S. Pat. No. 3,929,992. There are various numbering schemes proposed for rapamycin. To avoid confusion, when specific rapamycin analogs are named herein, the names are given with reference to rapamycin using the numbering scheme of formula A.

Numerous rapamycin analogs can be used as a heterodimerization molecule in a FKBP/FRAP-based dimerization switch. For example, O-substituted analogues in which the hydroxyl group on the cyclohexyl ring of rapamycin is replaced by OR1 in which $R_1$ is hydroxyalkyl, hydroxyalkoxyalkyl, acylaminoalkyl, or aminoalkyl; e.g. RAD001, also known as, everolimus as described in U.S. Pat. No. 5,665,772 and WO94/09010 the contents of which are incorporated by reference. Other suitable rapamycin analogs include those substituted at the 26- or 28-position. The rapamycin analog may be an epimer of an analog mentioned above, particularly an epimer of an analog substituted in position 40, 28 or 26, and may optionally be further hydrogenated, e.g. as described in U.S. Pat. No. 6,015,815, WO95/14023 and WO99/15530 the contents of which are incorporated by reference, e.g. ABT578 also known as zotarolimus or a rapamycin analog described in U.S. Pat. No. 7,091,213, WO98/02441 and WO01/14387 the contents of which are incorporated by reference, e.g. AP23573 also known as ridaforolimus.

Examples of rapamycin analogs suitable for use in the present invention from U.S. Pat. No. 5,665,772 include, but are not limited to, 40-O-benzyl-rapamycin, 40-O-(4'-hydroxymethyl)benzyl-rapamycin, 40-O-[4'-(1,2-dihydroxyethyl)]benzyl-rapamycin, 40-O-allyl-rapamycin, 40-O-[3'-(2,2-dimethyl-1,3-dioxolan-4(S)-yl)-prop-2'-en-1'-yl]-rapamycin, (2'E,4'S)-40-O-(4',5'-dihydroxypent-2'-en-1'-yl)-rapamycin, 40-O-(2-hydroxy)ethoxycarbonylmethyl-rapamycin, 40-O-(2-hydroxy)ethyl-rapamycin, 40-O-(3-hydroxy)propyl-rapamycin, 40-O-(6-hydroxy)hexyl-rapamycin, 40-O-[2-(2-hydroxy)ethoxy]ethyl-rapamycin, 40-O-[(3S)-2,2-dimethyldioxolan-3-yl]methyl-rapamycin, 40-O-[(2S)-2,3-dihydroxyprop-1-yl]-rapamycin, 40-O-(2-acetoxy)ethyl-rapamycin, 40-O-(2-nicotinoyloxy)ethyl-rapamycin, 40-O-[2-(N-morpholino)acetoxy]ethyl-rapamycin, 40-O-(2-N-imidazolylacetoxy)ethyl-rapamycin, 40-O-[2-(N-methyl-N'-piperazinyl)acetoxy]ethyl-rapamycin, 39-O-desmethyl-39,40-O,O-ethylene-rapamycin, (26R)-26-dihydro-40-O-(2-hydroxy)ethyl-rapamycin, 40-O-(2-aminoethyl)-rapamycin, 40-O-(2-acetaminoethyl)-rapamycin, 40-O-(2-nicotinamidoethyl)-rapamycin, 40-O-(2-(N-methyl-imidazo-2'-ylcarbethoxamido)ethyl)-rapamycin, 40-O-(2-ethoxycarbonylaminoethyl)-rapamycin, 40-O-(2-tolylsulfonamidoethyl)-rapamycin and 40-O-[2-(4',5'-dicarboethoxy-1',2',3'-triazol-1'-yl)-ethyl]-rapamycin.

Other examples of rapamycin analogs where the hydroxyl group on the cyclohexyl ring of rapamycin and/or the hydroxy group at the 28 position is replaced with an hydroxyester group are known, for example, rapamycin analogs found in U.S. Pat. No. RE44,768, e.g. temsirolimus.

Other rapamycin analogs include those wherein the methoxy group at the 16 position is replaced with another substituent, preferably (optionally hydroxy-substituted) alkynyloxy, benzyl, orthomethoxybenzyl or chlorobenzyl and/or wherein the mexthoxy group at the 39 position is deleted together with the 39 carbon so that the cyclohexyl ring of rapamycin becomes a cyclopentyl ring lacking the 39 position methyoxy group; e.g. as described in WO95/16691 and WO96/41807 the contents of which are incorporated by reference. The analogs can be further modified such that the hydroxy at the 40-position of rapamycin is alkylated and/or the 32-carbonyl is reduced.

Rapamycin analogs from WO95/16691 include, but are not limited to, 16-demthoxy-16-(pent-2-ynyl)oxy-rapamycin, 16-demthoxy-16-(but-2-ynyl)oxy-rapamycin, 16-demthoxy-16-(propargyl)oxy-rapamycin, 16-demethoxy-16-(4-hydroxy-but-2-ynyl)oxy-rapamycin, 16-demthoxy-16-benzyloxy-40-O-(2-hydroxyethyl)-rapamycin, 16-demthoxy-16-benzyloxy-rapamycin, 16-demethoxy-16-ortho-methoxybenzyl-rapamycin, 16-demethoxy-40-O-(2-methoxyethyl)-16-pent-2-ynyl)oxy-rapamycin, 39-demethoxy-40-desoxy-39-formyl-42-nor-rapamycin, 39-demethoxy-40-desoxy-39-hydroxymethyl-42-nor-rapamycin, 39-demethoxy-40-desoxy-39-carboxy-42-nor-rapamycin, 39-demethoxy-40-desoxy-39-(4-methyl-piperazin-1-yl)carbonyl-42-nor-rapamycin, 39-demethoxy-40-desoxy-39-(morpholin-4-yl)carbonyl-42-nor-rapamycin, 39-demethoxy-40-desoxy-39-[N-methyl, N-(2-pyridin-2-ylethyl)]carbamoyl-42-nor-rapamycin and 39-demethoxy-40-desoxy-39-(p-toluenesulfonylhydrazonomethyl)-42-nor-rapamycin.

Rapamycin analogs from WO96/41807 include, but are not limited to, 32-deoxo-rapamycin, 16-O-pent-2-ynyl-32-deoxo-rapamycin, 16-O-pent-2-ynyl-32-deoxo-40-O-(2-hydroxy-ethyl)-rapamycin, 16-O-pent-2-ynyl-32-(S)-dihydro-40-O-(2-hydroxyethyl)-rapamycin, 32(S)-dihydro-40-O-(2-methoxy)ethyl-rapamycin and 32(S)-dihydro-40-O-(2-hydroxyethyl)-rapamycin.

Another suitable rapamycin analog is biolimus as described in US2005/0101624 the contents of which are incorporated by reference.

RAD001, otherwise known as everolimus (Afinitor®), has the chemical name (1R,9S,12S,15R,16E,18R,19R,21R,23S,24E,26E,28E,30S,32S,35R)-1,18-dihydroxy-12-{(1R)-2-[(1S,3R,4R)-4-(2-hydroxyethoxy)-3-methoxycyclohexyl]-1-methylethyl}-19,30-dimethoxy-15,17,21,23,29,35-hexamethyl-11,36-dioxa-4-aza-tricyclo[30.3.1.04,9]hexatriaconta-16,24,26,28-tetraene-2,3,10,14,20-pentaone (also known as 40-O-(2-hydroxy)ethyl-rapamycin) and the following chemical structure:

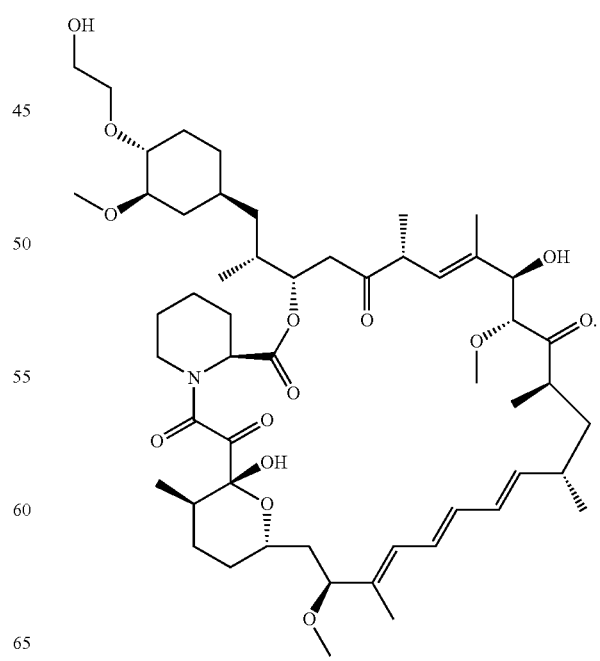

GYRB-GYRB Based Dimerization Switches

Coumermycin, a product of *Streptomyces*, binds the amino-terminal 24K subdomain of the B subunit of bacterial DNA gyrase, GyrB. Coumermycin binds two GyrB subunits, see, e.g., Rarrar et al., (1996) *Activation of the Raf-1 kinase cascade by coumermycin induced dimerization*, Nature 383: 178; Gilbert et al. (1994) *The 24 kDa N-terminal sub-domain of the DNA gyrase B protein binds coumarin drugs*, Molecular Microbiology 12: 365. Thus, coumermcyn can be used as a dimerization molecule in a homodimerization switch comprising switch domains that comprise a coumermycin binding sequence of GyrB.

In an embodiment the switch domain comprises a coumermycin binding sequence from the 24 K Da amino terminal sub-domain of GyrB.

Figure 3:
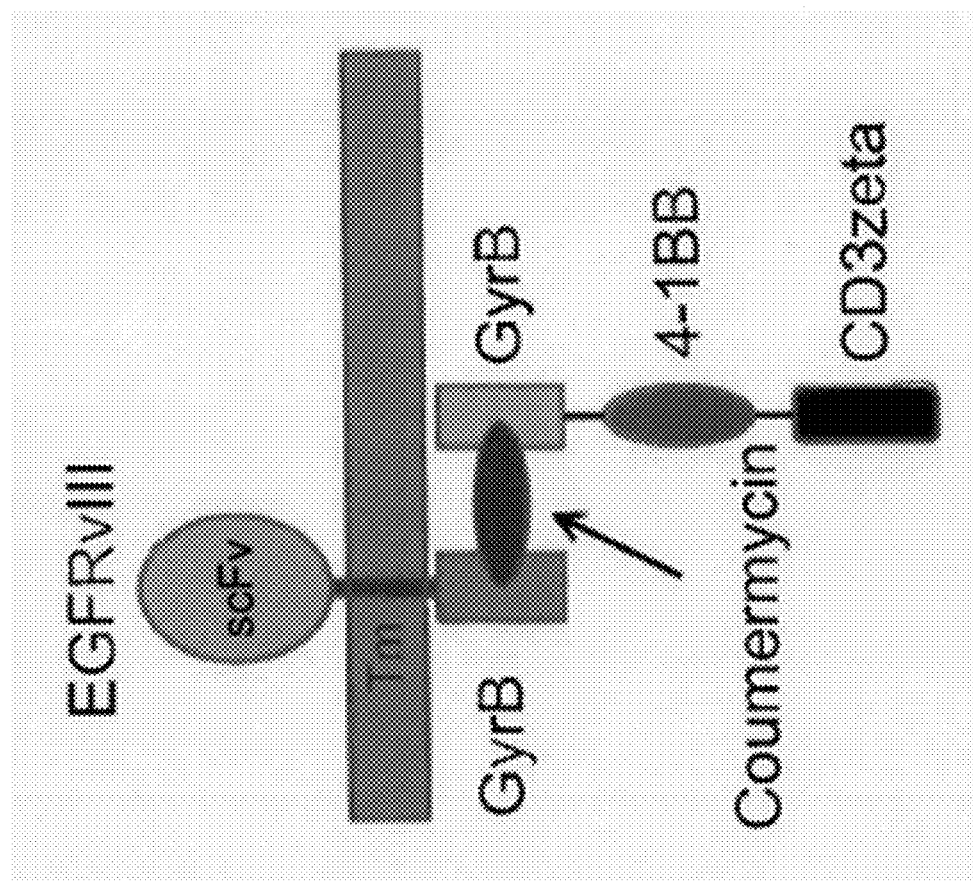
FIG. 3 depicts a RCAR having a GyrB dimerization switch induced by Coumermycin. The antigen binding domain may be an scFv, e.g., that targets EGFRvIII. The switch domains are GyrB subunits.

In embodiments the switch domain, or a coumermycin binding sequence of the switch domain thereof, will have at least 70, 75, 80, 85, 90, 95, 96, 97, 98, or 99% identity with the GyrB sequence of Rarrar et al., (1996). In embodiments, the switch domain, or a coumermycin binding sequence thereof, will differ by no more than 30, 25, 20, 15, 10, 5, 4, 3, 2, or 1 amino acid residues from the corresponding sequence of Rarrar et al., (1996). See, e.g., FIG. 3.

Candidate sequences for use as switch domain comprising coumermycin binding sequence from the 24 K Da amino terminal sub-domain of GyrB, can be evaluated by incorporating the candidate into a system such as that described in Rarrar et al., (1996).

In an embodiment one switch domain (a GAI switch domain) comprises, a sequence of GAI sufficient to bind to a gibberellin analog, e.g., $GA_3$, and once bound to the analog, e.g., $GA_3$, bind to GID1; and one switch domain (a GID1 switch domain) comprises sequence of GID1 sufficient to bind to a GAI switch domain bound to a gibberellin analog, e.g., $GA_3$.

Figure 4:
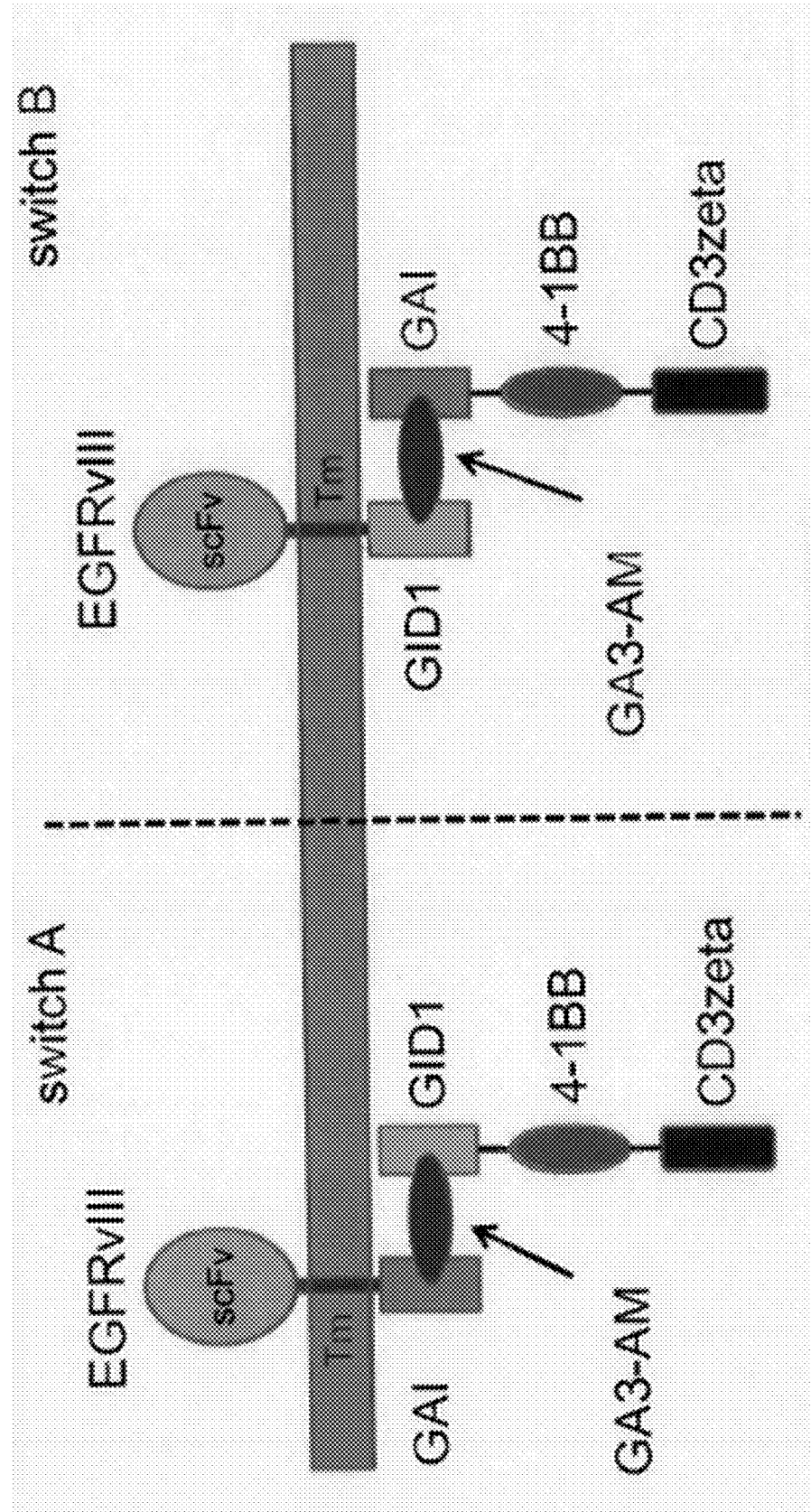
FIG. 4 depicts RCARs having a GAI/GID1 dimerization switch induced by Gibberellin. The antigen binding domain may be an scFv, e.g., that targets EGFRvIII. Switch A and switch B show the GAI and G1D1 switch domains in different orientations with respect to the antigen binding member and the intracellular signaling member.

In embodiments, a GAI switch domain, or a sequence of GAI is sufficient to bind to a gibberellin analog, e.g., $GA_3$, and once bound to the analog, e.g., $GA_3$, bind to GID1, thereof, will have at least 70, 75, 80, 85, 90, 95, 96, 97, 98, or 99% identity with a GAI sequence of Miyamoto et al. (2010); or will differ by no more than 30, 25, 20, 15, 10, 5, 4, 3, 2, or 1 amino acid residues from the corresponding a sequence of Miyamoto et al. (2010). See, e.g., FIG. 4.

In embodiments, a GID1 switch domain, or a sequence of GID1 sufficient to bind to a GAI switch domain, thereof, will have at least 70, 75, 80, 85, 90, 95, 96, 97, 98, or 99% identity with the GID sequence of Miyamoto et al. (2010); or will differ by no more than 30, 25, 20, 15, 10, 5, 4, 3, 2, or 1 amino acid residues from the corresponding of Miyamoto et al. (2010).

Candidate sequences for use as a GAI or GID1 switch domain, can be evaluated by incorporating the candidate into a system such as that described in a sequence of Miyamoto et al. (2010).

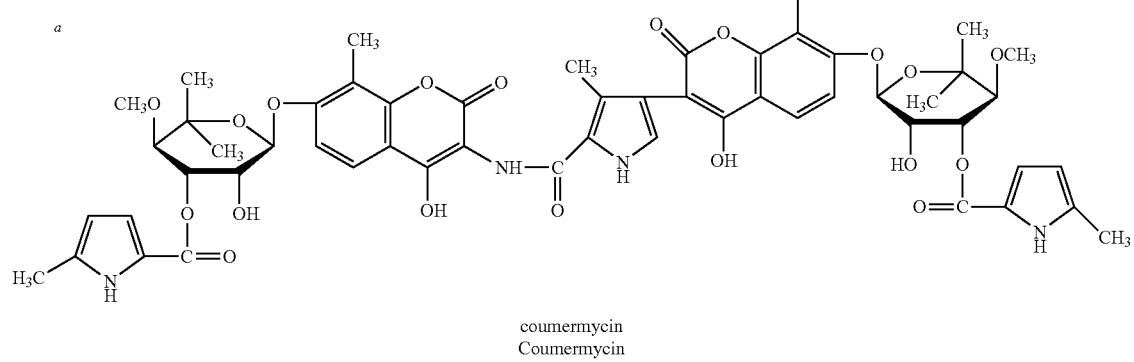

Structure 2 coumermycin
Coumermycin

Gibberellin-Based Dimerization Switches.

Gibberellins are plant hormones that regulate plant growth and development. Gibberellin binds to its receptor, gibberellin insensitive dwarf1 (GID1) and induces a conformational change in GID1. The new conformation allows GID1 to bind another protein, gibberellin insentivive (GAI). Gibberellin, or a giberellin analog, e.g., $GA_3$-AM/$GA_3$, can be used to dimerize a switch domain comprising $GA_3$ binding sequence from GID1 (a GIDI switch domain) and a switch domain comprising sequence from GAI sufficient to bind $GA_3$-bound GID1. $GA_3$-AM can cross the plasma membrane of target cells. Once inside the cells, $GA_3$-AM is cleaved by an esterase to form $GA_3$. See Miyamoto et al. (2010) *Rapid and orthogonal logic gating with a gibberellins-induced dimerization system*, Nat. Chem. Biol. 8:465.

Structure 3: $GA_3$-AM and $GA_3$

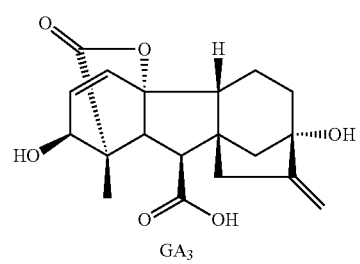

$GA_3$

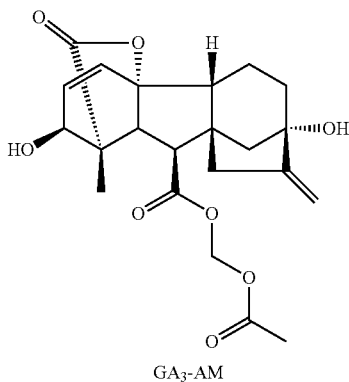

GA$_3$-AM

Tag/Binder Switches

In embodiments a dimerization switch, e.g., a homodimerization switch, e.g., an extracellular homodimerization switch, comprises switch domains that comprise tag molecules, e.g., a c-myc peptide tag, flag peptide tag, HA peptide tag or V5 peptide tag. Suitable dimerization switches include polypeptides with affinity for the switch domains, e.g., antibody molecules and non-antibody scaffold. See, e.g., FIG. 6.

Covalent Dimerization Switches

In a covalent dimerization switch, the dimerization molecule promotes a covalent interaction between the switch domains. In an embodiment, a dimerization switch comprises first and second switch domains, which, upon contact with a dimerization molecule, are covalently linked to one another. In embodiments, a covalent dimerization switch is a homodimerization switch, wherein the dimerization molecule covalently couples a first and second switch domain having the same structure. In embodiments of a covalent homodimerization switch, the linking molecule comprises a first and second moiety, each of which can bind a switch domain, thereby covalently linking the switch domains. The first and second moiety can have the same structure or different structures. In embodiments, a covalent dimerization switch is a heterodimerization switch, wherein the dimerization molecule covalently couples first and second switch domains having structures that differ from one another. In embodiments of a covalent heterodimerization switch, the linking molecule can have a first moiety that covalently binds the first switch domain, but not the second switch domain, and a second moiety that covalently binds the second switch domain, but not the first switch domain. In embodiments the dimerization molecule comprises an additional moiety that alters its solubility or cell permeability. E.g., in the case of an intracellular covalent heterodimerization switch, the dimerization molecule can comprise a moiety that optimizes the cell permeability of the dimerization molecule.

A Halotag/SNAP-tag switch is an example of a covalent heterodimerization switch. In an embodiment, the dimerization molecule comprises a first moiety, e.g., an O6-benzylguanine moiety, that reacts covalently with a SNAP-tag domain, a second moiety, e.g., a chloroalkane moiety, that reacts with a Halotag domain, and a moiety that renders the dimerization molecule cell permeable.

Covalent dimerization switches are described in Erhart et al., 2013 Chem Biol 20(4): 549-557. HaXS species described therein are useful as dimerization molecules in a Halotag/SNAP-tag switch. In embodiments, a covalent dimerization molecule minimizes potential kinetic limitations related to off rates and need for accumulation of non-covalent dimerization molecules in the cell as prerequisites to activation of the required signal cascades, e.g., for T-cell mediated killing.

In an embodiment, a Halotag/SNAP-tag dimerization comprises a first switch domain comprising a Halo-Tag moiety, e.g., SEQ ID NO: 14, or a functional derivative or fragment thereof, and a second switch domain comprising a SNAP-Tag, e.g., SEQ ID NO: 15, or a functional derivative or fragment thereof. In embodiments the dimerization molecule comprises functional groups for linking a Halo-Tag with a SNAP-Tag along with a cell penetrating core. Structure 5 depicts a dimerization molecule suitable for use in this system. See, e.g., FIG. 13.

```
A Halo-tag Domain
                                      (SEQ ID NO: 14)
Gseigtgfpfdphyvevlgermhyvdvgprdgtpvlflhgnptssyvwrn iiphvapthrciapdligmgksdkpdlgyffddhvrfmdafiealgleev vlvihdwgsalgfhwakrnpervkgiafmefirpiptwdewpefaretfq afrttdvgrkliidqnvfiegtlpmgvvrpltevemdhyrepflnpvdre plwrfpnelpiagepanivalveeymdwlhqspvpklllfwgtpgvlippa eaarlakslpnckavdigpglnllqednpdligseiarwlstleisg A SNAP-tag domain
                                      (SEQ ID NO: 15)
Mdkdcemkrttldsplgklelsgceqglhriiflgkgtsaadavevpapa avlggpeplmqatawlnayfhqpeaieefpvpalhhpvfqqesftrqvlw kllkvvkfgevisyshlaalagnpaataavktalsgnpvpilipchrvvq gdldvggyegglavkewllaheghrlgkpglg
```

Structure 5

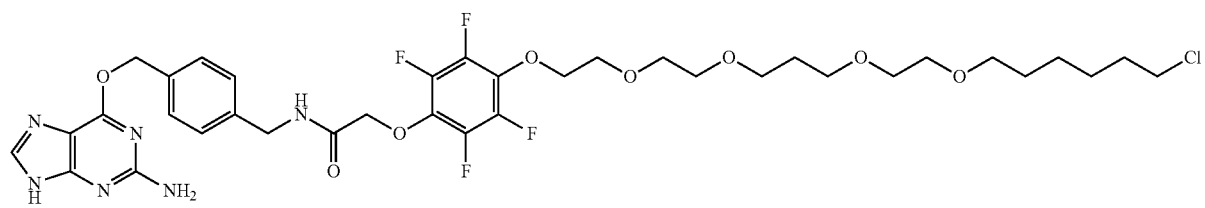

HaXS

In an embodiment, one switch domain comprises amino acid residues disclosed in SEQ ID NO: 14 and one switch domain comprises amino acid residues disclosed in SEQ ID NO: 15.

In embodiments the first switch domain, will have at least 70, 75, 80, 85, 90, 95, 96, 97, 98, or 99% identity with the sequence of SEQ ID NO: 14. In embodiments, the first switch domain, will differ by no more than 30, 25, 20, 15, 10, 5, 4, 3, 2, or 1 amino acid residues from the corresponding the sequence of SEQ ID NO: 14.

In embodiments the second switch domain, will have at least 70, 75, 80, 85, 90, 95, 96, 97, 98, or 99% identity with the sequence of SEQ ID NO: 15. In embodiments, the second switch domain, will differ by no more than 30, 25, 20, 15, 10, 5, 4, 3, 2, or 1 amino acid residues from the corresponding the sequence of SEQ ID NO: 15.

Candidate sequences for use as a switch domain, can be evaluated by incorporating the candidate into a system such as those described herein.

Multiple Switch Domains

In an embodiment, a dimerization switch described herein comprises multiple switch domains, and is sometimes referred to herein as a multi switch. A multi switch comprises a plurality of, e.g., 2, 3, 4, 5, 6, 7, 8, 9, or 10, switch domains, independently, on a first member, e.g., an antigen binding member, and a second member, e.g., an intracellular signaling member. Optionally, a linker, spacer, or hinge region, e.g., as described herein, is disposed between two switch domains on the member, e.g., the antigen binding member or the intracellular signaling member.

Figure 55A:
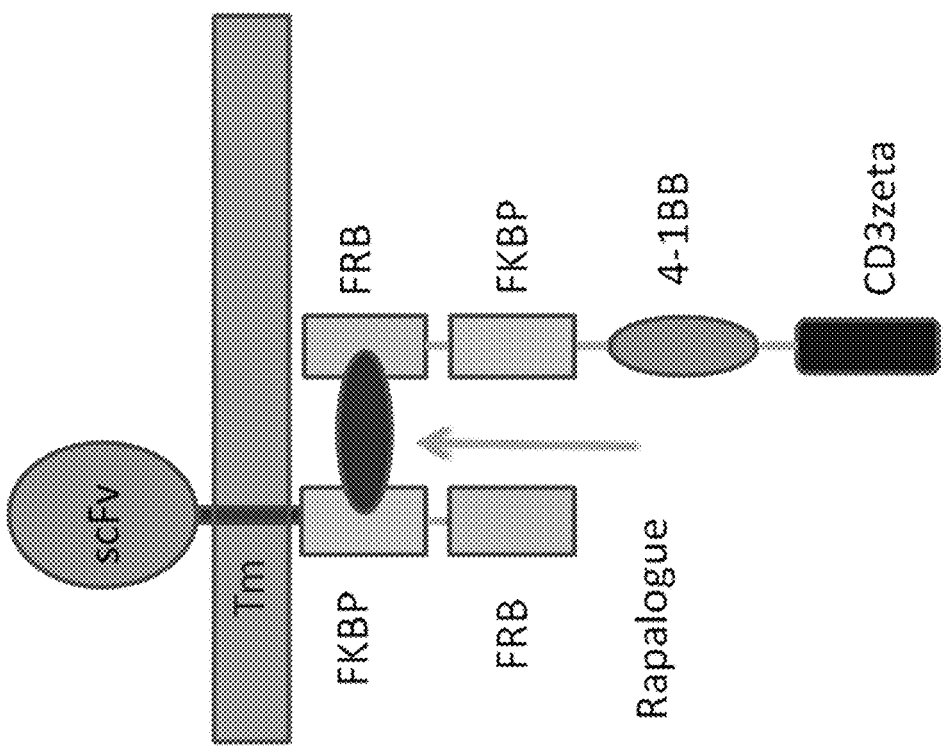
FIGS. 55A and 55B shows two structures of RCAR comprising a multi switch.

In an embodiment, the first member comprises a plurality of first switch domains, e.g., FKBP-based switch domains, and the second member can comprise a plurality of second switch domains, e.g., FRB-based switch domains. E.g., the antigen binding member comprises a plurality of first switch domains, e.g., FKBP-based switch domains, and the intracellular signaling member comprises a plurality of second switch domains, e.g., FRB-based switch domains. See, e.g., FIG. 55A.

Figure 55B:
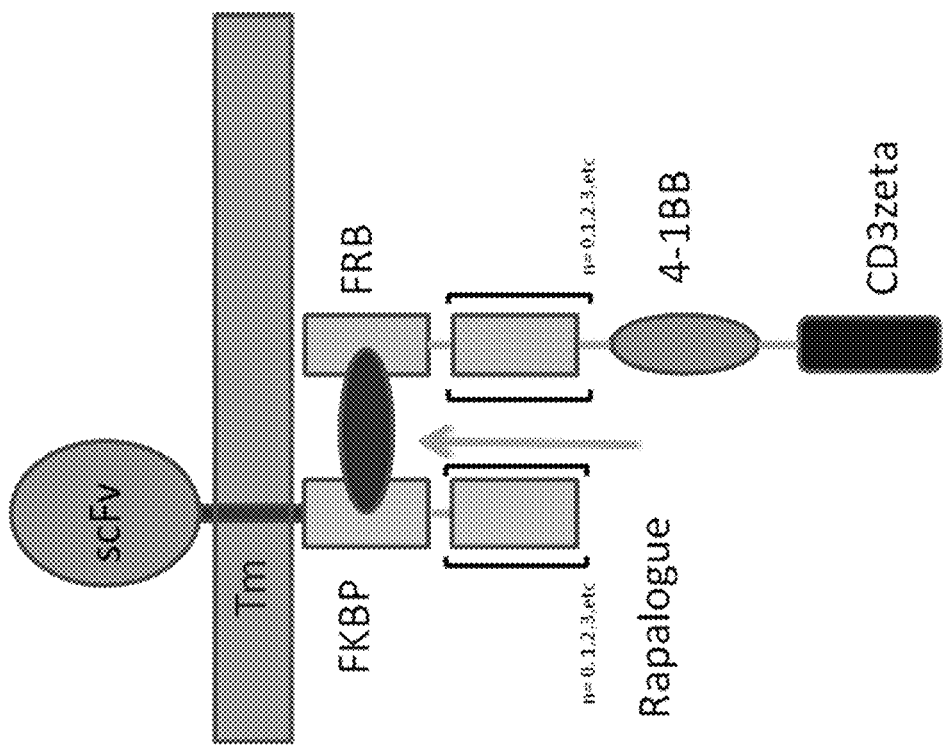
Figure 56A:
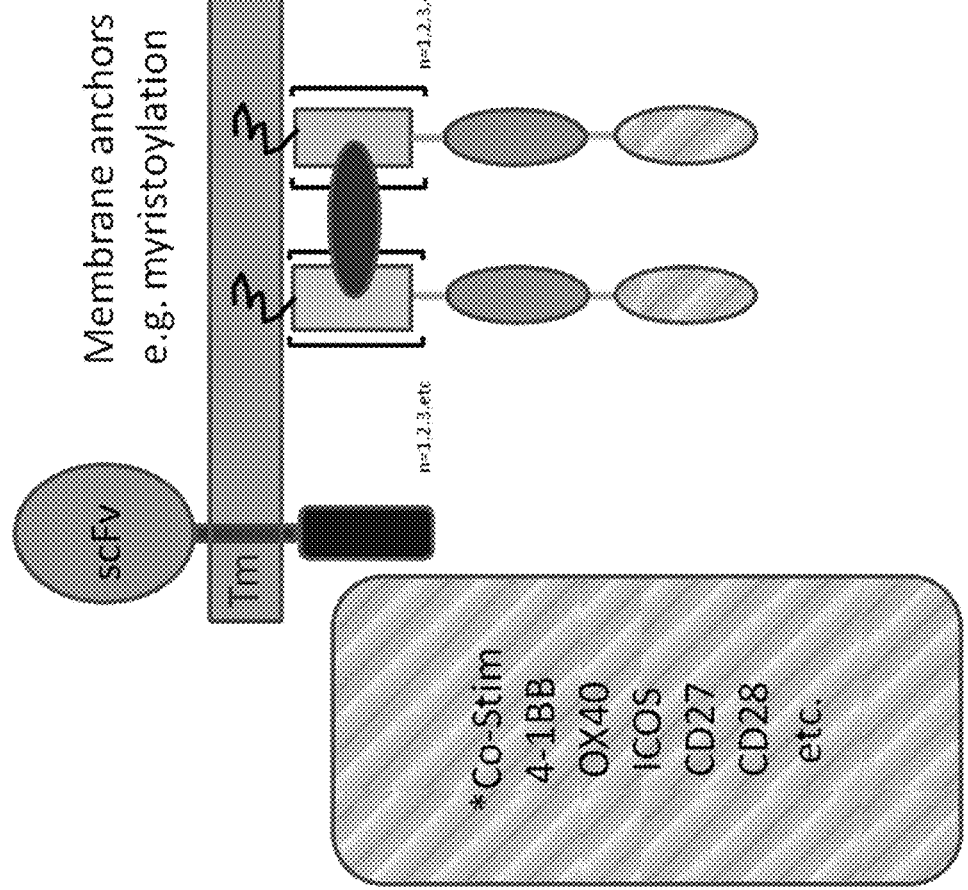
FIGS. 56A, 56B, 56C, and 56D shows four configurations of RCAR constructs that can regulate proliferation capacity. The RCAR comprises an antigen binding member comprising an antigen binding domain (e.g., scFv), a transmembrane domain, and a primary intracellular signaling domain (e.g., CD3zeta). The two intracellular signaling members both comprise at least one switch domain, e.g., FKBP and FRB switch domains, and two costimulatory domains, e.g., 2 costimulatory signaling domain 1, or costimulatory signaling domain 1 and costimulatory signaling domain 2, where the costimulatory domains 1 and 2 is selected from 4-1BB, OX40, CD27, CD28, and ICOS. The bracketed switch domains represent 1 or more additional switch domains that comprise the multi switch.
Figure 56B:
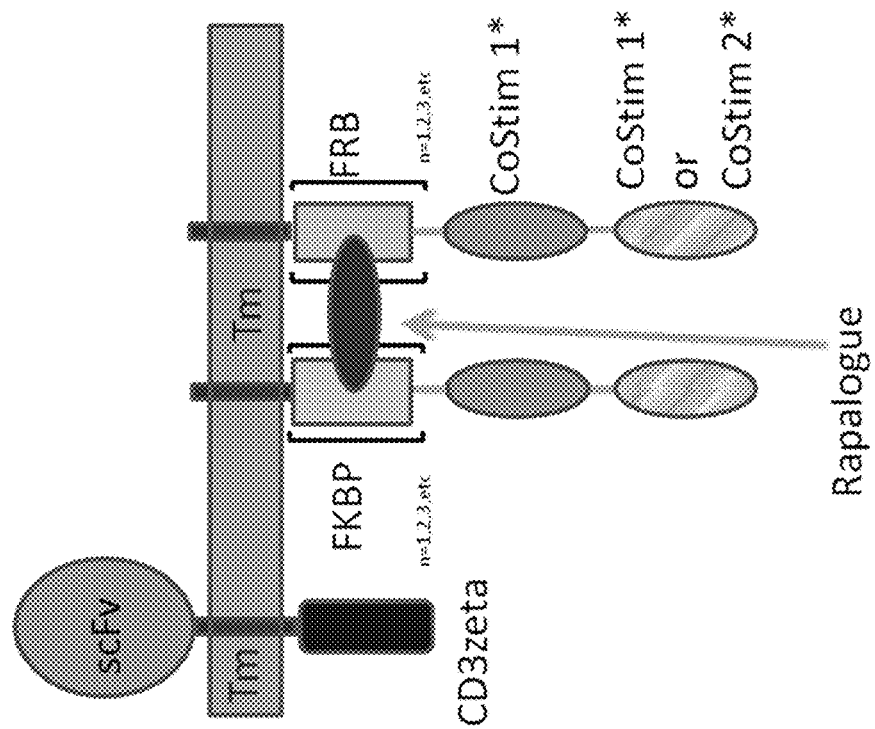
Figure 56D:
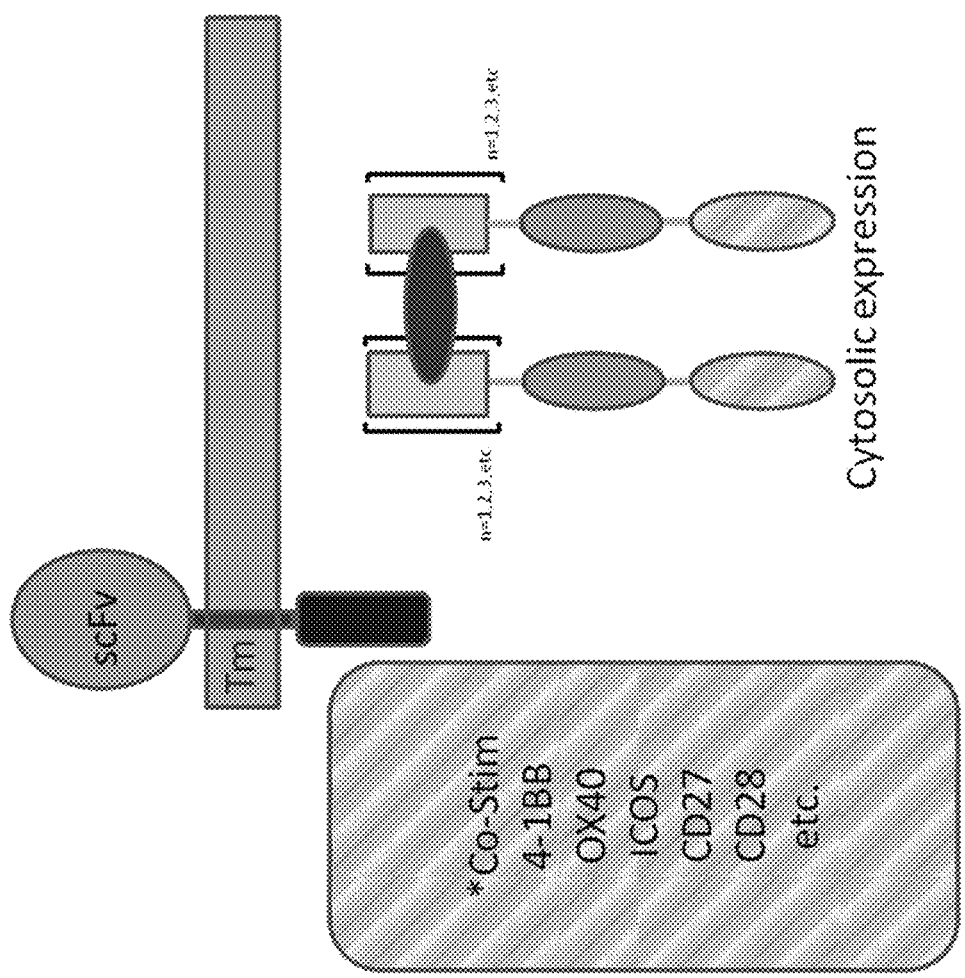
Figure 56C:
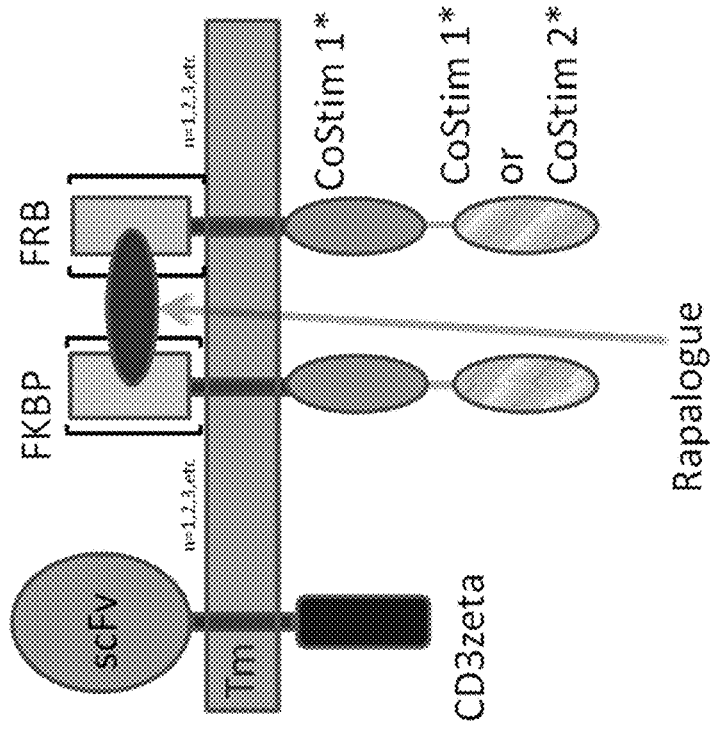

In an embodiment, the first member comprises a first and a second switch domain, e.g., a FKBP-based switch domain and a FRB-based switch domain, and the second member comprises a first and a second switch domain, e.g., a FKBP-based switch domain and aFRB-based switch domain. E.g., the antigen binding member comprises a first and a second switch domain, e.g., a FKBP-based switch domain and a FRB-based switch domain, and the intracellular signaling member comprises a first and a second switch domain, e.g., a FKBP-based switch domain and a FRB-based switch domain. See, e.g., FIG. 55B.

In an embodiment, a dimerization switch, e.g., an FKBP/FRB based dimerization switch, comprises an asymmetrical distribution of switch domains on a first and second member wherein the number of switch domains on the first member is not equal to the number of switch domains on the second member. In an embodiment one member comprises at least X switch domains, wherein X is a plurality, e.g., 2, 3, 4, 5, 6, 7, 8, 9 or 10, and the other member has fewer switch domains, e.g., 1, 2, 3, 4, or 5 fewer switch domains than the first mentioned member. In an embodiment, a member comprises two switch domains for an FKBP-FRB based dimerization switch and the other member comprises less than two switch domains for an FKBP/FRB based dimerization switch. See, e.g., FIG. 55A.

In an embodiment, the dimerization switch, e.g., an FKBP-FRB based dimerization switch, comprises a symmetrical distribution of switch domains, wherein the number of switch domains on one member is equal to the number of switch domains on the other member. See, e.g., FIGS. 55A and 55B.

In an embodiment, the first member and second member comprises a plurality of homodimerization switch domains, e.g., Gibberellin-based switch domains. E.g., the antigen binding member comprises a plurality of homodimerization switch domains, e.g., GyrB-based switch domains, and the intracellular signaling member comprises a plurality of homodimerization switch domains, e.g., GyrB-based switch domains.

Second Order Dimerization Switches

In an embodiment an RCAR comprises a first order dimerization switch which comprises a first and second switch domain. The dimerization molecule of the first order dimerization switch promotes association of the first and second switch domain. This dimerization switch can be referred to as a first order dimerization switch. In embodiments, a second order dimerization switch is also present. In the second order dimerization switch, the first order dimerization molecule serves as a second order switch domains. The second order dimerization molecule promotes the association of two or more second order switch domains (each of which comprises a first order dimerization molecule). The dimerization or clustering induces by the second order switch further increases the level of clustering of intracellular domains—in such embodiments the second order dimerization molecule results in more clustering than would be seen if only a first order switch was used. The first order dimerization molecule promotes association (or clustering) of the first order switch domains, e.g., homodimerization switch domains (and of intracellular signaling domains attached thereto). Such first order switch domains can comprise a tag molecule such as c-myc peptide tag, flag peptide tag, HA peptide tag or V5 peptide tag. In such embodiments the first order dimerization molecule can comprise an antibody, or other binder, directed to the switch domain. At the second order, the second order dimerization molecule promotes the association or clustering of the first order dimerization molecules. In other words, a second order switch comprises switch domains with comprise the first order dimerization molecule and a dimerization molecule e.g., an antibody against the first order dimerization molecule, that causes association of the second order switch domains. The first and second order does not imply any sequence to the addition of the first and second order dimerization molecules. In embodiments the first order dimerization molecule is administered first, or is contacted with its switch domains first, prior to the administration, or contacting the first order dimerization molecules with the second order dimerization molecule. In embodiments the second order dimerization molecule is administered first, or is contacted with its switch domains first, prior to the administration, or contacting the first order dimerization molecules with its switch domains.

Figure 14:
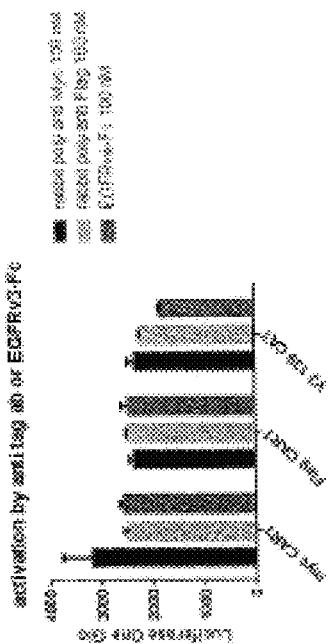
FIGS. 14A and 14B depict activation by soluble antibodies and activation by soluble antibodies+$2^{nd}$ antibodies (second order dimerization switches).

See, e.g., FIGS. 14A and 14B.

Third and higher order switch domains can also be used.

Dimerization Molecule

While not wishing to be bound by theory, it is believed that in some embodiments, referred to herein as a bi-domain binding dimerization molecule, the dimerization molecule comprises a first domain binding moiety that binds, or interacts, with a first switch domain, and a second domain binding moiety that binds, or interacts, with a second switch domain. While not wishing to be bound by theory, in some embodiments, referred to herein as a conformation-dependent dimerization molecule, the dimerization molecule binds or interacts with one of the switch domains, and alters the conformation of that switch domain such that it binds the other switch domain. Again, while not wishing to be bound by theory, it is believed that some dimerization molecules could operate by a combination or those, or other, mechanisms.

Association between the switch domains is promoted by the dimerization molecule. In the presence of dimerization molecule interaction or association between switch domains allows for signal transduction between a polypeptide associated with, e.g., fused to, a first switch domain, and a polypeptide associated with, e.g., fused to, a second switch domain. In the presence of non-limiting levels of dimerization molecule signal transduction is increased by 1.1, 1.2, 1.3, 1.4, 1.5, 1.6, 1.7, 1.8, 1.9, 2, 5, 10, 50, 100 fold, e.g., as measured in a system described herein.

In embodiments, the dimerization molecule is a small molecule, e.g., AP21967.

In embodiments the dimerization molecule is a small molecule, e.g., is other than a polypeptide.

In embodiments, the dimerization molecule is a polypeptide, e.g., a polypeptide, e.g., an antibody molecule, or a non-antibody scaffold, e.g., a fibronectin or adnectin, having specific affinity for one or both of the first and second switch domains. In embodiments, the dimerization molecule is a multimeric polypeptide, e.g., a polypeptide comprising at least one, two, three, four, five, or more protein domains linked together by a linker, e.g., a GS linker. In embodiments, the dimerization molecule is an antibody or fragment thereof. In an embodiment, the heterodimerization molecule is an antibody, e.g., a monospecific antibody, or fragment thereof or a dual specific antibody, or fragment thereof.

Figure 15:
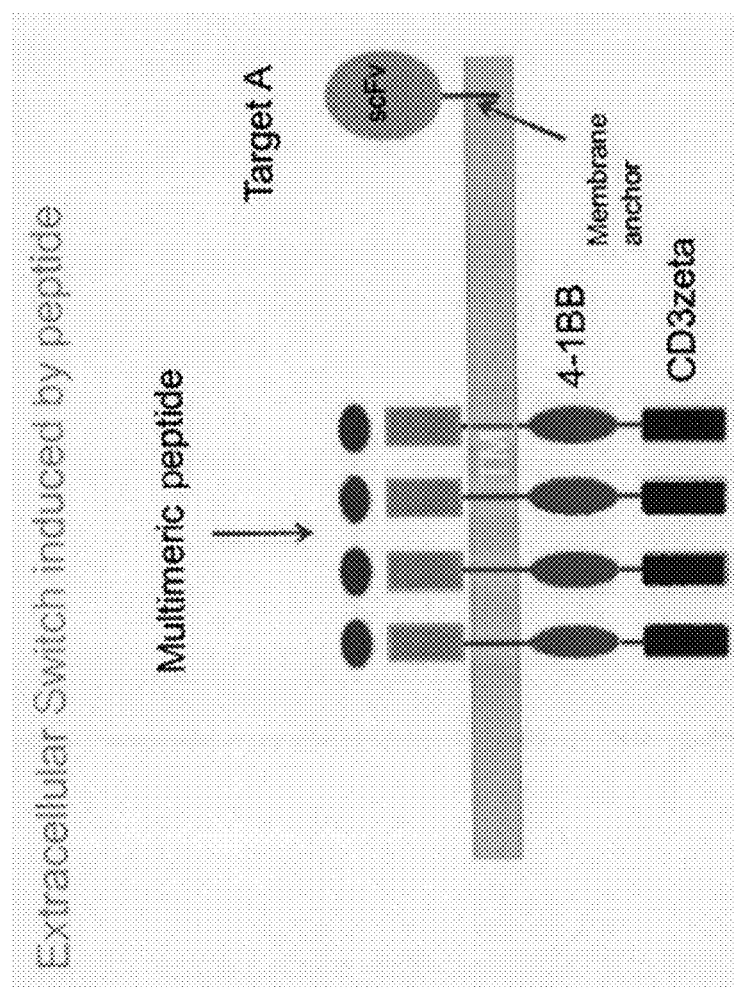
FIG. 15 depicts an RCAR having an extracellular switch and a multi-valent dimerization molecule.

In an embodiment, the dimerization switch is a heterodimerization switch i.e., has first and second switch domains that are different from one another and the dimerization molecule is a heterodimerization molecule. In an embodiment, the heterodimerization molecule is a small molecule that binds to one or both of first and second switch domains. In an embodiment, the heterodimerization molecule is a polypeptide, or fragment thereof having specific affinity for one or both of the first and second switch domains. In an embodiment, the heterodimerization molecule is a mutimeric polypeptide, or fragment thereof having specific affinity for the first and second switch domains. In an embodiment, the heterodimerization molecule is a mutimeric polypeptide, or fragment thereof having specific affinity for multiple switch domains, see, e.g., FIG. 15. In an embodiment, the heterodimerization molecule is an antibody, or fragment thereof having specific affinity for one or both of the first and second switch domains.

In an embodiment, the dimerization switch is a homodimerization switch, i.e., has first and second switch domains that are the same as one another and the dimerization molecule is a homodimerization molecule. In an embodiment, the homodimerization n molecule is a small molecule that binds to one or both of first and second switch domains. In an embodiment, the homodimerization molecule is a polypeptide, or fragment thereof having specific affinity for one or both of the first and second switch domains. In an embodiment, the homodimerization molecule is a mutimeric polypeptide, or fragment thereof having specific affinity for the first and second switch domains. In an embodiment, the homodimerization molecule is a multimeric polypeptide, or fragment thereof having specific affinity for multiple switch domains, see 5. 17. In an embodiment, the homodimerization molecule is an antibody, or fragment thereof having specific affinity for one or both of the first and second switch domains.

Dimerization molecules can be non-covalent or covalent, depending on the form of interaction between the switch domains.

In an embodiment, the dimerization molecule is poorly permeable though the plasma membrane. In an embodiment, the dimerization molecule comprises a moiety, e.g., a charged moiety that inhibits entry into cells. E.g., a dimerization molecule, e.g., rapamycin or a rapamycin analog, can be modified so as to inhibit entry into cells. Such dimerization molecules can be used with RCARs having extracellular switches. Their relatively poor entry into cells does not compromise the ability to invoke dimerization (because the switch is extracellular) but can reduce toxicity. $GA_3$, which is does not readily permeate cells, can be used with external GID1-GAI based switch. In an embodiment, a dimerization molecule that ahs been modified accumulates in a cell only 50, 40, 20, or 10% as much as the unmodified dimerization molecule.

Multi-Valent Dimerization Molecules

Generally, a dimerization molecule promotes the association of at least two switch molecules. In embodiments this association of switch domains promotes the association of intracellular domains linked to the switch domains. In embodiments the dimerization molecule has a valency of greater than two, e.g., it is multi-valent, and binds, and thus clusters or dimerizes, more than two switch domains. E.g., a dimerization molecule can comprise a plurality, e.g., at least 2, 3, 4, 5, 6, 7, 8, 9 or 10, binding domains, each of which can bind a switch domain. In embodiments, the switch domain is an antibody molecule, non-antibody scaffold, ligand, or other polypeptide having affinity for a dimerization molecule. Exemplary multi-valent dimerization molecules comprise molecules that comprise more than two domains, e.g., more than two domains each comprising a c-myc peptide tag, flag peptide tag, HA peptide tag or V5 peptide tag domain. A multi-valent dimerization molecule can be a first order or second order dimerization molecule. See, e.g., FIGS. 14A and 14B.

Intracellular Signaling Domain

In embodiments, an intracellular signaling domain produces an intracellular signal when an extracellular domain, e.g., an antigen binding domain, to which it is fused, or coupled by a dimerization switch, binds a counter ligand. Intracellular signaling domains can include primary intracellular signaling domains and costimulatory signaling domains. In an embodiment, a RCAR molecule can be constructed for expression in an immune cell, e.g., a T cell, such that the RCAR molecule comprises a domain, e.g., a primary intracellular signaling domains, costimulatory signaling domain, inhibitory domains, etc., that is derived from a polypeptide that is typically associated with the immune cell. For example, a RCAR for expression in a T cell can comprise a 41BB domain and an CD3 zeta domain. In this instance, both the 41BB and CD3 zeta domains are derived from polypeptides associated with the T cell. In another embodiment, a RCAR molecule can be constructed for expression in an immune cell e.g., a T cell, such that the RCAR molecule comprises a domain that is derived from a polypeptide that is not typically associated with the immune cell. For example, a RCAR for expression in a T cell can comprise a KIR domain derived from a NK cell. Alternatively, a RCAR for expression in a NK cell can comprise a 41BB domain and a CD3 zeta domain derived from a T cell (See e.g. WO2013/033626, incorporated herein by reference).

Primary Intracellular Signaling Domain

In an embodiments a primary intracellular signaling domain produces an intracellular signal when an extracellular domain, e.g., an antigen binding domain, to which it is fused, or coupled by a dimerization switch, binds cognate antigen. It is derived from a primary stimulatory molecule, e.g., it comprises intracellular sequence of a primary stimulatory molecule. It comprises sufficient primary stimulatory molecule sequence to produce an intracellular signal, e.g., when an antigen binding domain to which it is fused, or coupled by a dimerization switch, binds cognate antigen.

A primary stimulatory molecule, is a molecule, that upon binding cognate ligand, mediates an immune effector response, e.g., in the cell in which it is expressed. Typically, it generates an intracellular signal that is dependent on binding to a cognate ligand that comprises antigen. The TCR/CD3 complex contains exemplary primary stimulatory molecules; the complex generates an intracellular signal upon binding to cognate ligand, e.g., an MHC molecule loaded with a peptide. Typically, e.g., in the case of the TCR/CD3 primary stimulatory molecule, the generation of an intracellular signal by a primary intracellular signaling domain is dependent on binding of the primary stimulatory molecule to its ligand, e.g., antigen.

Primary stimulation can mediate altered expression of certain molecules, such as downregulation of TGF-β, and/or reorganization of cytoskeletal structures, and the like. Stimulation, can, e.g., in the presence of costimulation, result in an optimization, e.g., an increase, in an immune effector function of the RCARX cell, e.g., RCART cell. Stimulation, e.g., in the context of a RCART cell, can mediate a T cell response, e.g., proliferation, cytokine secretion, killing, activation, differentiation, and the like.

In an embodiment, the primary intracellular signaling domain comprises a signaling motif, e.g., an immunoreceptor tyrosine-based activation motif or ITAMs. A primary intracellular signaling domain can comprise ITAM containing cytoplasmic signaling sequences from TCR zeta (CD3 zeta), FcR gamma, FcR beta, CD3 gamma, CD3 delta, CD3 epsilon, CD5, CD22, CD79a, and CD79b.

Exemplary primary intracellular signaling domains are provided in Table 1.

TABLE 1

Primary Intracellular Signaling Domains In embodiments the domain comprises an ITAM FcR gamma (FCER1G)
FcR beta (FCER1B)
CD3 gamma
CD3 delta
CD3 epsilon
CD3 zeta (TCR zeta)
CD79a
CD79b
DAP10
DAP12
CD32 (Fc gamma RIIa)

A primary intracellular signaling domain comprises a functional fragment, or analog, of a primary stimulatory molecule (e.g., CD3 zeta—GenBank accno. BAG36664.1). It can comprise the entire intracellular region or a fragment of the intracellular region which is sufficient for generation of an intracellular signal when an antigen binding domain to which it is fused, or coupled by a dimerization switch, binds cognate antigen. In embodiments the primary intracellular signaling domain has at least 70, 75. 80. 85, 90, 95, 98, or 99% sequence identity with a naturally occurring primary stimulatory molecule, e.g., a human CD3 zeta (GenBank Acc No. AAY57330.1), or other mammalian, e.g., a nonhuman species, e.g., rodent, monkey, ape or murine intracellular primary stimulatory molecule. In embodiments the primary intracellular signaling domain has at least 70, 75. 80. 85, 90, 95, 98, or 99% sequence identity with SEQ ID NO: 139. In embodiments, the primary stimulatory molecule may comprise 1, 2, 3, 4, 5, 6, 7, 8, 9, or 10 mutations, e.g., in SEQ ID NO: 139.

In embodiments the primary intracellular signaling domain, has at least 70, 75, 80, 85, 90, 95, 96, 97, 98, or 99% identity with, or differs by no more than 30, 25, 20, 15, 10, 5, 4, 3, 2, or 1 amino acid residues from the corresponding residues of a naturally occurring human primary stimulatory molecule, e.g., a naturally occurring human primary stimulatory molecule disclosed herein, e.g., SEQ ID NO: 139.

Costimulatory Signaling Domain

In an embodiment, a costimulatory signaling domain produces an intracellular signal when an extracellular domain, e.g., an antigen binding domain to which it is fused, or coupled by a dimerization switch, binds cognate ligand. It is derived from a costimulatory molecule. It comprises sufficient costimulatory molecule sequence to produce an intracellular signal, e.g., when an extracellular domain, e.g., an antigen binding domain, to which it is fused, or coupled by a dimerization switch, binds cognate ligand.

Costimulatory molecules are cell surface molecules, other than antigen receptors or their counter ligands that promote an immune effector response. In some cases they are required for an efficient or enhanced immune response. Typically, a costimulatory molecule generates an intracellular signal that is dependent on binding to a cognate ligand that is, in embodiments, other than an antigen, e.g., the antigen recognized by an antigen binding domain of a RCARX cell, e.g., RCART cell. Typically, signaling from a primary stimulatory molecule and a costimulatory molecule contribute to an immune effector response, and in some cases both are required for efficient or enhanced generation of an immune effector response.

A costimulatory signaling domain comprises a functional fragment, or analog, of a costimulatory molecule (e.g., 4-1BB). It can comprise the entire intracellular region or a fragment of the intracellular region which is sufficient for generation of an intracellular signal, e.g., when an antigen binding domain to which it is fused, or coupled by a dimerization switch, binds cognate antigen. In embodiments, the costimulatory signaling domain has at least 70, 75, 80, 85, 90, 95, 98, or 99% sequence identity with a naturally occurring costimulatory molecule, e.g., a human, or other mammalian, e.g., a nonhuman species, e.g., rodent, monkey, ape or murine intracellular costimulatory molecule. In embodiments the costimulatory signaling domain has at least 70, 75, 80, 85, 90, 95, 98, or 99% sequence identity with SEQ ID NO: 138.

Exemplary costimulatory signaling domains (intracellular signaling domains) are provided in Table 2.

TABLE 2

Costimulatory Signaling Domains for RCARX (identified by the Costimulatory Molecules from which they are derived)

CD27
CD28,

TABLE 2-continued

Costimulatory Signaling Domains for RCARX (identified by
the Costimulatory Molecules from which they are derived)

4-1BB (CD137)
OX40
CD30
CD40
ICOS (CD278)
ICAM-1
LFA-1 (CD11a/CD18)
CD2
CD7
LIGHT
NKG2C
B7-H3
a ligand that specifically binds with CD83
CDS
GITR
BAFFR
HVEM (LIGHTR)
SLAMf7
NKP80 (KLRF1)
CD160 (BY55)
CD19
CD4
CD8 alpha
CD8 beta
IL2R beta
IL2R gamma
IL7R alpha
ITGA4
VLA1
CD49a
ITGA4
IA4
CD49D
ITGA6
VLA-6
C49f
ITGAD
CD11d
ITGAE
CD103
ITGAL
CD11a
LFA-1
ITGAM
CD11b
ITGAX
CD11c
ITGB1
CD29
ITGB2
CD18
ITGB7
TNFR2
TRANCE/RANKL
DNAM1 (CD226)
SLAMF4 (C244, 2B4)
CD84
CD96 (Tactile)
CEACAM1
CRTAM
Ly9 (CD229)
PSGL1
C100 (SEMA4D)
CD69
SLAMF6 (NTB-A, Ly108)
SLAM (SLAMF1, CD150, IPO-3)
BLAME (SLAMF8)
SELPLG (CD162)
LTBR
LAT
GADS
PAG/Cbp
SLP-76
NKp44
NKp30
NKp46

In embodiments the costimulatory signaling domain, has at least 70, 75, 80, 85, 90, 95, 96, 97, 98, or 99% identity with, or differs by no more than 30, 25, 20, 15, 10, 5, 4, 3, 2, or 1 amino acid residues from the corresponding residues of a naturally occurring human primary stimulatory molecule, e.g., a naturally occurring human costimulatory molecule disclosed herein.

Auxiliary Antigen Binding Member

An auxiliary antigen binding member can be included in a RCAR. In embodiments, its inclusion can increase the safety and efficacy of the RCARX cell, e.g., by increasing specificity by the binding to an additional, e.g., second target cell antigen. In embodiments, binding of both the antigen binding member, and the auxiliary antigen binding member can give greater specificity than seen with either alone. In embodiments the RCAR will include two, three, four, five, six, seven, eight, nine, or ten, auxiliary antigen binding members, all of which bind different antigens.

In an embodiment the auxiliary antigen binding domain does not comprise a switch domain that can form a dimerization switch with a switch domain on the antigen binding member or the intracellular signaling member. In embodiments the auxiliary antigen binding domain does not comprise an intracellular signaling domain. In an embodiment, the antigen binding domain is directed against a mesothelin receptor and the auxiliary antigen binding domain is directed against a folate receptor. In an embodiment, the antigen binding domain is directed against a folate receptor and the auxiliary antigen binding domain is directed against a mesothelin receptor.

Inhibitory Molecules: Inhibition

In one embodiment, the subject can be administered an agent which enhances the activity or fitness of a CAR-expressing cell. For example, in one embodiment, the agent can be an agent which inhibits a molecule that modulates or regulates, e.g., inhibits, T cell function. In some embodiments, the molecule that modulates or regulates T cell function is an inhibitory molecule. Inhibitory molecules, e.g., PD1, can, in some embodiments, decrease the ability of a RCARX cell to mount an immune effector response. Examples of inhibitory molecules are provided in Table 3. Inhibition of an inhibitory molecule that modulates or regulates, e.g., inhibits, T cell function, e.g., by inhibition at the DNA, RNA or protein level, can optimize RCARX cell performance. In embodiments an agent, e.g., an inhibitory nucleic acid, e.g., a dsRNA, e.g., an siRNA or shRNA, or e.g., an inhibitory protein or system, e.g., a clustered regularly interspaced short palindromic repeats (CRISPR), a transcription-activator like effector nuclease (TALEN), or a zinc finger endonuclease (ZFN), e.g., as described herein, can be used to inhibit expression of a molecule that modulates or regulates, e.g., inhibits, cell function in the RCARX cell. In an embodiment, the inhibitor is an shRNA. In an embodiment, the inhibitory molecule is inhibited within a RCARX cell. In these embodiments, a dsRNA molecule that inhibits expression of the inhibitory molecule is linked to the nucleic acid that encodes a component, e.g., all of the components, of the RCAR.

Exemplary inhibitory molecules, useful e.g., as shRNA targets, are provided in Table 3.

TABLE 3

Inhibitory molecules

CD160
2B4

TABLE 3-continued

Inhibitory molecules

PD1
TIM3
LAG3
TIGIT
CTLA-4
BTLA
LAIR1
PD-L1
VISTA
CEACAM (e.g., CEACAM-1,
CEACAM-3 and/or CEACAM-5)
TGFR beta In an embodiment, a nucleic acid molecule that encodes a dsRNA molecule that inhibits expression of the molecule that modulates or regulates, e.g., inhibits, T-cell function is operably linked to a promoter, e.g., a H1- or a U6-derived promoter such that the dsRNA molecule that inhibits expression of the molecule that modulates or regulates, e.g., inhibits, T-cell function is expressed, e.g., is expressed within a RCAR-expressing cell. See e.g., Tiscornia G., "Development of Lentiviral Vectors Expressing siRNA", Chapter 3, in *Gene Transfer: Delivery and Expression of DNA and RNA* (eds. Friedmann and Rossi). Cold Spring Harbor Laboratory Press, Cold Spring Harbor, N.Y., USA, 2007; Brummelkamp T R, et al. (2002) *Science* 296: 550-553; Miyagishi M, et al. (2002) *Nat. Biotechnol.* 19: 497-500. In an embodiment, the nucleic acid molecule that encodes a dsRNA molecule that inhibits expression of the molecule that modulates or regulates, e.g., inhibits, T-cell function is present on the same vector, e.g., a lentiviral vector, that comprises a nucleic acid molecule that encodes a component, e.g., all of the components, of the RCAR. In such an embodiment, the nucleic acid molecule that encodes a dsRNA molecule that inhibits expression of the molecule that modulates or regulates, e.g., inhibits, T-cell function is located on the vector, e.g., the lentiviral vector, 5'- or 3'- to the nucleic acid that encodes a component, e.g., all of the components, of the RCAR. The nucleic acid molecule that encodes a dsRNA molecule that inhibits expression of the molecule that modulates or regulates, e.g., inhibits, T-cell function can be transcribed in the same or different direction as the nucleic acid that encodes a component, e.g., all of the components, of the RCAR. In an embodiment the nucleic acid molecule that encodes a dsRNA molecule that inhibits expression of the molecule that modulates or regulates, e.g., inhibits, T-cell function is present on a vector other than the vector that comprises a nucleic acid molecule that encodes a component, e.g., all of the components, of the RCAR. In an embodiment, the nucleic acid molecule that encodes a dsRNA molecule that inhibits expression of the molecule that modulates or regulates, e.g., inhibits, T-cell function it transiently expressed within a RCAR-expressing cell. In an embodiment, the nucleic acid molecule that encodes a dsRNA molecule that inhibits expression of the molecule that modulates or regulates, e.g., inhibits, T-cell function is stably integrated into the genome of a RCAR-expressing cell. FIGS. 16A, 16B, 16C, 16D, and 16E depicts examples of vectors for expressing a component, e.g., all of the components, of the RCAR with a dsRNA molecule that inhibits expression of the molecule that modulates or regulates, e.g., inhibits, T-cell function.

Examples of dsRNA molecules useful for inhibiting expression of a molecule that modulates or regulates, e.g., inhibits, T-cell function, wherein the molecule that modulates or regulates, e.g., inhibits, T-cell function is PD-1 are provided in Example 10 and Tables 18 and 19.

Redirected Switchable Inhibitory Receptors: Inhibitory Extracellular Domains

Extracellular domains of inhibitory receptors can be coupled, e.g., by dimerization switches to intracellular signaling domains that promote an immune effector response. Thus, engagement with a counterligand of the coinhibitory molecule is redirected into an optimization of immune effector response.

In one embodiment, the extracellular domain (ECD) of an inhibitory molecule, e.g., an inhibitory molecule described herein such as, e.g., Programmed Death 1 (PD1), can be fused to a transmembrane domain and intracellular signaling domain described herein, e.g., an intracellular signaling domain comprising a costimulatory signaling domain such as, e.g., 41BB OX40, Cd28, CD27, and/or a primary signaling domain, e.g., of CD3 zeta. In one embodiment, the inhibitory molecule RCAR, e.g., PD1 RCAR, can be used alone. In one embodiment, the inhibitory molecule CAR, e.g., inhibitory molecule RCAR, e.g., PD1 RCAR, can be used in combination with another CAR, e.g., CD19CAR (e.g., a CD19RCAR). In one embodiment, the PD1 RCAR (or PD1 CAR) improves the persistence of the T cell. Examples of inhibitory molecules include PD1, PD-L1, CTLA4, TIM3, CEACAM (e.g., CEACAM-1, CEACAM-3 and/or CEACAM-5), LAG3, VISTA, BTLA, TIGIT, LAIR1, CD160, 2B4 and TGFR beta. In one embodiment, the inhibitory molecule RCAR comprises a first polypeptide, e.g., of an inhibitory molecule such as PD1, LAG3, CTLA4, CD160, BTLA, LAIR1, TIM3, CEACAM (e.g., CEACAM-1, CEACAM-3 and/or CEACAM-5), 2B4 and TIGIT, or a fragment of any of these (e.g., at least a portion of an extracellular domain of any of these), and a second polypeptide which is an intracellular signaling member described herein (e.g., comprising a costimulatory domain (e.g., 41BB, CD27 or CD28, e.g., as described herein) and/or a primary signaling domain (e.g., a CD3 zeta signaling domain described herein).

In one embodiment, the PD1 RCAR improves the persistence of the cell RCAR-expressing cell. In one embodiment, the PD1 RCAR comprises the extracellular domain of PD1 indicated as underlined in SEQ ID NO: 335. In one embodiment, the PD1 RCAR comprises, the amino acid sequence of SEQ ID NO: 335.

Malpvtalllplalllhaarppqwfldspdrpwnpptfspallvvteqdn atftcsfsntsesfvlnwvrmspsnqtdklaafpedrsqpgqdcrfrvtq lpngrdfhmsvvrarrndsgtvlcgaislapkaqikeslraelrvterra evptahpspsprpagqfqtlvttpaprpptpaptiasqplslrpeacrp aaggavhtrgldfacdiyiwaplagtcgvlllslvitlyckrgrkkllyi fkqpfmrpvqttqeedgcscrfpeeeeggcelrvkfsrsadapaykqgqn qlynelnlgrreeydvldkrrgrdpemggkprrknpqeglynelqkdkma eayseigmkgerrrgkghdglyqglstatkdtydalhmqalppr.

In one embodiment, the PD1 RCAR comprises the amino acid sequence provided below.

(SEQ ID NO: 336)
pgwfldspdrpwnpptfspallvvtegdnatftcsfsntsesfvlnwyrm spsnqtdklaafpedrsqpgqdcrfrvtqlpngrdfhmsvvrarrndsgt ylcqaislapkaqikeslraelrvterraevptahpspsprpagqfqtlv tttpaprpptpaptiasqplslrpeacrpaaggavhtrgldfacdiyiwa plagtcgvlllslvitlyckrgrkkllyifkqpfmrpvqttqeedgcscr fpeeeeggcelrvkfsrsadapaykqgqnqlynelnlgrreeydvldkrr grdpemggkprrknpqeglynelqkdkmaeayseigmkgerrrgkghdgl yqglstatkdtydalhmqalppr In one embodiment, the PD1 RCAR, e.g., the PD1 RCAR described herein, is encoded by a nucleic acid sequence shown below, or at least the comprises the nucleic acid sequence encoding the extracellular domain of PD1 (shown in underline below).

(SEQ ID NO: 337)
atggccctccctgtcactgccctgcttctcccctcgcactcctgctcca cgccgctagacca<u>cccggatggtttctggactctccggatcgcccgtgga</u>

<u>atccccaaccttctcaccggcactcttggttgtgactgagggcgataat</u>

<u>gcgaccttcacgtgctcgttctccaacacctccgaatcattcgtgctgaa</u>

<u>ctggtaccgcatgagcccgtcaaaccagaccgacaagctcgccgcgtttc</u>

<u>cggaagatcggtcgcaaccgggacaggattgtcggttccgcgtgactcaa</u>

<u>ctgccgaatggcagagacttccacatgagcgtggtccgcgctaggcgaaa</u>

<u>cgactccgggacctacctgtgcggagccatctcgctggcgcctaaggccc</u>

<u>aaatcaaagagagcttgagggccgaactgagagtgaccgagcgcagagct</u>

<u>gaggtgccaactgcacatccatccccatcgcctcggcctgcggggcagtt</u>

<u>tcagaccctggtc</u>acgaccactccggcgccgcgcccaccgactccggccc caactatcgcgagccagcccctgtcgctgaggccggaagcatgccgccct gccgccggaggtgctgtgcataccgggattggacttcgcatgcgacat ctacatttgggctcctctcgccggaacttgtggcgtgctccttctgtccc tggtcatcaccctgtactgcaagcggggtcggaaaaagcttctgtacatt ttcaagcagcccttcatgaggcccgtgcaaaccacccaggaggaggacgg ttgctcctgccggttccccgaagaggaagaaggaggttgcgagctgcgcg tgaagttctcccggagcgccgacgccccgcctataagcagggccagaac cagctgtacaacgaactgaacctgggacggcgggaagagtacgatgtgct ggacaagcggcgcggccgggacccccgaaatgggcgggaagcctagaagaa agaaccctcaggaaggcctgtataacgagctgcagaaggacaagatggcc gaggcctactccgaaattgggatgaagggagagcggcggaggggaaaggg gcacgacggcctgtaccaaggactgtccaccgccaccaaggacacatacg atgccctgcacatgcaggcccttcccctcgc.

Exemplary inhibitory extracellular domains are provided in Table 4.

TABLE 4

Extracellular counter ligand binding domains from coinhibitory molecules (identified by the Coinibitory Molecules from which they are derived)

B7-H1
B7-1
CD160
P1H
2B4
PD1
TIM3
CEACAM (e.g., CEACAM-1, CEACAM-3, and/or CEACAM-5)
LAG3
TIGIT
CTLA-4
BTLA
LAIR1
TGF-beta receptor In embodiments, the inhibitory extracellular domain, has at least 70, 75, 80, 85, 90, 95, 96, 97, 98, or 99% identity with, or differs by no more than 30, 25, 20, 15, 10, 5, 4, 3, 2, or 1 amino acid residues from the corresponding residues of a naturally occurring human inhibitory molecule, e.g., a naturally occurring human primary stimulatory molecule disclosed herein.

Costimulatory Molecule Ligand Binding Domains

Extracellular ligand binding domains of costimulatory molecules, referred to as a Costimulatory ECD domain, can be coupled, e.g., by dimerization switches, to intracellular signaling domains that promote an immune effector response. Thus, engagement with a counter ligand of the costimulatory molecule results in optimization of immune effector response.

Exemplary Costimulatory ECD domains are provided in the Table 5.

TABLE 5

Costimulatory ECD domains from costimulatory molecules (identified by the Costimulatory Molecules from which they are derived)

ICOS
CD28
CD27
HVEM
LIGHT
CD40L
4-1BB
OX40
DR3
GITR
CD30
TIM1
SLAM
CD2
CD226

In embodiments, the Costimulatory ECD domain, has at least 70, 75, 80, 85, 90, 95, 96, 97, 98, or 99% identity with, or differs by no more than 30, 25, 20, 15, 10, 5, 4, 3, 2, or 1 amino acid residues from the corresponding residues of a naturally occurring human inhibitory molecule, e.g., a naturally occurring human costimulatory molecule disclosed herein.

Transmembrane Domain

In embodiments, a RCAR comprises a transmembrane domain that is fused to an extracellular sequence, e.g., an extracellular recognition element, which can comprise an antigen binding domain, an inhibitory counter ligand binding domain, or costimulatory ECD domain. In embodiments, a RCAR comprises a transmembrane domain that is fused to an intracellular sequence, e.g. primary intracellular signaling domain, costimulatory signaling domain, or dimerization switch. In an embodiment, the transmembrane domain is one that naturally is associated with one of the domains in the RCAR. In an embodiment, the transmembrane domain is one that is not naturally associated with one of the domains in the RCAR.

In embodiments, the transmembrane domain is one which minimizes interactions with other elements, e.g., other transmembrane domains. In some instances, the transmembrane domain minimizes binding of such domains to the transmembrane domains of the same or different surface membrane proteins, e.g., to minimize interactions with other members of the receptor complex. Suitable examples can be derived by selection or modification of amino acid substitution of a known transmembrane domain. In an embodiment, the transmembrane domain is capable of promoting homodimerization with another RCAR on the cell surface.

The transmembrane domain may comprise a naturally occurring, or a non-naturally occurring synthetic sequence. Where naturally occurring, the transmembrane domain may be derived from any membrane-bound or transmembrane protein. In an embodiment, the transmembrane region is capable of signaling, via a dimerization switch, to the intracellular domain(s) whenever the RCAR has bound to a target.

Transmembrane regions suitable for use in molecules described herein may be derived from any one or more of e.g., the alpha, beta or zeta chain of the T-cell receptor, CD28, CD3 epsilon, CD45, CD4, CD5, CD8, CD9, CD16, CD22, CD33, CD37, CD64, CD80, CD86, CD134, CD137, CD154. In some embodiments, a transmembrane domain may include at least the transmembrane region(s) of, e.g., KIRDS2, OX40, CD2, CD27, LFA-1 (CD11a, CD18), ICOS (CD278), 4-1BB (CD137), GITR, CD40, BAFFR, HVEM (LIGHTR), SLAMF7, NKp80 (KLRF1), CD160, CD19, IL2R beta, IL2R gamma, IL7R α, ITGA1, VLA1, CD49a, ITGA4, IA4, CD49D, ITGA6, VLA-6, CD49f, ITGAD, CD11d, ITGAE, CD103, ITGAL, CD11a, LFA-1, ITGAM, CD11b, ITGAX, CD11c, ITGB1, CD29, ITGB2, CD18, LFA-1, ITGB7, TNFR2, DNAM1 (CD226), SLAMF4 (CD244, 2B4), CD84, CD96 (Tactile), CEACAM1, CRTAM, Ly9 (CD229), CD160 (BY55), PSGL1, CD100 (SEMA4D), SLAMF6 (NTB-A, Ly108), SLAM (SLAMF1, CD150, IPO-3), BLAME (SLAMF8), SELPLG (CD162), LTBR, PAG/Cbp. In an embodiment the transmembrane domain is derived from CD8. In an embodiment the transmembrane domain is derived from CD28. In one aspect, the transmembrane domain is a transmembrane domain from the sequence provided as SEQ ID NO: 137.

In an embodiment, a sequence, e.g., a hinge or spacer sequence, can be disposed between a transmembrane domain and another sequence or domain to which it is fused. In embodiments, a variety of human hinges (aka "spacers") can be employed as well, e.g., including but not limited to the human Ig (immunoglobulin) hinge. Optionally, a short oligo- or polypeptide linker, between 2 and 10 amino acids in length may form the linkage between the transmembrane domain and another domain, e.g., a switch or intracellular signaling domain, of a RCAR. A glycine-serine doublet provides a particularly suitable linker. In one aspect, the hinge or spacer is the amino acid sequence provided as SEQ ID NO: 136. In one aspect, the hinge or spacer comprises a KIR2DS2 hinge.

In an embodiment, the transmembrane domain may be a non-naturally occurring sequence, in which case can comprise predominantly hydrophobic residues such as leucine and valine. In an embodiment, a triplet of phenylalanine, tryptophan and valine will be found at each end of a transmembrane domain.

Domain Arrangements

In embodiments, the RCAR comprises domains can be arranged in a variety of configurations.

In an embodiment, both a primary signaling domain and a costimulatory signaling domain are separated from the antigen binding domain by a switch.

Accordingly, in one embodiment the RCAR arrangement comprises a first and second chimeric construct wherein:

(1) the first chimeric construct, e.g., an antigen binding member, comprises: an antigen binding domain; a transmembrane domain; and a first intracellular switch domain, e.g., FRB (in this embodiment the first chimeric construct does not comprise an intracellular signaling domain); and (2) a second chimeric construct, e.g., an intracellular signaling domain, (which in this embodiment does not comprise a transmembrane domain or membrane anchor) comprising: a second intracellular switch domain, e.g., FKBP; and a signaling domain, e.g., a primary or secondary signaling domain.

In an embodiment, both a primary signaling domain, e.g., a CD3zeta domain, and a costimulatory signaling domain, e.g., a 4-1BB domain, are present on the second chimeric construct. In an embodiment, the order on the second chimeric construct is: a second switch domain, primary signaling domain, e.g., a CD3zeta domain, and a costimulatory signaling domain, e.g., a 4-1BB domain. In an embodiment, the order on the second chimeric construct is a second switch domain, a costimulatory signaling domain, e.g., a 4-1BB domain, and a primary signaling domain, e.g., a CD3zeta domain. In an embodiment, the order on the second chimeric construct is a costimulatory signaling domain, e.g., a 4-1BB domain, a second switch domain, and a primary signaling domain, e.g., a CD3zeta domain. In an embodiment, the order on the second chimeric construct is a primary signaling domain, e.g., a CD3zeta domain, a second switch domain, and a costimulatory signaling domain, e.g., a 4-1BB domain.

The embodiments refer to FRB on the first chimeric constructs and FKBP on the second chimeric constructs but the placement can be reversed.

The order of the domains in the embodiments are given in the N-terminus to C-terminus direction, but especially with regard to intracellular chimeric constructs, the order can be from C-terminus to N-terminus.

In an embodiment one, but not both, of the primary signaling domain and the costimulatory signaling domain, is separated by a switch from the antigen binding domain.

Accordingly, in another embodiment, the RCAR arrangement comprises:

(1) a first chimeric construct, e.g., an antigen binding member, comprising: an antigen binding domain; a transmembrane domain; a first intracellular switch domain, e.g., FRB; and an intracellular signaling domain, e.g., a primary signaling domain, e.g., a CD3zeta domain, or a costimulatory signaling domain, e.g., a 4-1BB domain; and (2) a second chimeric construct, e.g., an intracellular signaling member, (which in this embodiment does not comprise a transmembrane domain or membrane anchor)

comprising: a second intracellular switch domain, e.g., FKBP; and an intracellular signaling domain, e.g., a primary signaling domain, e.g., a CD3zeta domain, or a costimulatory signaling domain, e.g., a 4-1BB domain.

In an embodiment, the order on the first chimeric construct is an antigen binding domain, a transmembrane domain, a first intracellular switch domain, e.g., FRB, and an intracellular signaling domain, e.g., a primary signaling domain, e.g., a CD3zeta domain, or a costimulatory signaling domain, e.g., a 4-1BB domain.

In an embodiment, the order on the first chimeric construct is an antigen binding domain, a transmembrane domain, an intracellular signaling domain, e.g., a primary signaling domain, e.g., a CD3zeta domain, or a costimulatory signaling domain, e.g., a 4-1BB domain, and a first intracellular switch domain, e.g., FRB.

In an embodiment, the first chimeric construct comprises one, but not both of, a primary signaling domain, e.g., a CD3zeta domain, and a costimulatory signaling domain, e.g., a 4-1BB domain.

In an embodiment, the order on the second chimeric construct is: a second intracellular switch domain, e.g., FKBP, and one, but not both of, a primary signaling domain, e.g., a CD3zeta domain, and a costimulatory signaling domain, e.g., a 4-1BB domain.

In an embodiment, the order on the second chimeric construct is: one, but not both of, a primary signaling domain, e.g., a CD3zeta domain, and a costimulatory signaling domain, e.g., a 4-1BB domain and a second intracellular switch domain, e.g., FKBP.

In an embodiment:

(1) the first chimeric construct, e.g., an antigen binding member, comprises: an antigen binding domain, e.g., an scFv; a transmembrane domain; a costimulatory signaling domain, e.g., a 4-1BB domain; and a first switch domain; and (2) the second chimeric construct, e.g., an intracellular signaling member, comprises a second switch domain; and a primary signaling domain, e.g., a CD3zeta domain (and in embodiments, no transmembrane domain or membrane anchor).

In an embodiment:

(1) the first chimeric construct, e.g., an antigen binding member, comprises: an antigen binding domain, e.g., an scFv; a transmembrane domain; a primary signaling domain, e.g., a CD3zeta domain; and a first switch domain; and (2) the second chimeric construct, e.g., an intracellular signaling member, comprises: a second switch domain; and a costimulatory signaling domain, e.g., a 4-1BB domain (and in embodiments, no transmembrane domain or membrane anchor).

In one embodiment the RCAR arrangement comprises a first and second chimeric construct wherein:

(1) the first chimeric construct, e.g., an antigen binding member, comprises: an antigen binding domain; a transmembrane domain; a first intracellular signaling domain, and a first intracellular switch domain, e.g., FRB; and (2) a second chimeric construct, e.g., an intracellular signaling member, (which in this embodiment does not comprise a transmembrane domain or membrane anchor) comprising: a second intracellular switch domain, e.g., FKBP; and a intracellular signaling domain, e.g., a primary or costimulatory signaling domain.

The embodiments refer to FRB on the first chimeric constructs and FKBP on the second chimeric constructs but the placement can be reversed.

The orders the embodiments are given in the N-terminus to C-terminus direction, but especially with regard to intracellular chimeric constructs, the order can be from C-terminus to N-terminus.

RCAR Members, e.g., Antigen Binding Domains or Other Extracellular Binding Domains, Having a Costimulatory Signaling Domain Persistence and expansion of T-lymphocytes expressing the chimeric antigen receptor on the surface is mediated by inclusion of various intracellular domains fused to the membrane bound receptor. E.g., an element of a RCAR having an extracellular domain that engages a target ligand on a target cell, e.g., a cancer cell, can comprise a co-stimulatory intracellular signaling domain, e.g., a costimulatory signaling domain selected from Table 2.

In embodiments, placement of a co-stimulatory intracellular signaling domain, e.g., 4-1BB, onto the first switch domain from the CD3 zeta on the second switch domain will positively modulate RCAR activity in vivo while limiting the activity of the CAR in the absence of the dimerization switch molecule.

RCAR members having an an extracellular domain that engages a target ligand on a cell, e.g., an antigen binding domain, can comprise a plurality, e.g., 2, or 3, co-stimulatory intracellular signaling domains, e.g., selected from Table 2. In an embodiment, the RCAR member comprises a plurality of costimulatory signaling domains selected from 41BB, CD28, CD27, ICOS, and OX40. By way of example, the member, e.g., an antigen binding member, comprises, from the extracellular to intracellular direction:

41BB-CD27;
CD27-41BB;
41BB-CD28;
CD28-41BB;
OX40-CD28;
CD28-OX40;
CD28-41BB; or
41BB-CD28.

An antigen binding member can comprises: a plurality, e.g., 2 or 3 costimulatory signaling domains, chosen e.g., from Table 2, e.g., selected from 41BB, CD28, CD27, ICOS, and OX40. The costimulatory signaling domains can be disposed in any order, but exemplary configurations include the following (in the direction of extracellular to intracellular):

41BB-CD27;
CD27-41BB;
41BB-CD28;
CD28-41BB;
OX40-CD28;
CD28-OX40;
CD28-41BB; or
41BB-CD28.

In an embodiment, the antigen binding member comprises the following costimulatory signaling domains: CD28-41BB.

In an embodiment, the antigen binding member comprises the following costimulatory signaling domains: CD28-OX40.

In an embodiment an antigen binding member comprises a) [an antigen binding domain]—[a transmembrane domain]—[a first costimulatory signaling domain]—[a second costimulatory signaling domain] and wherein the first and second costimulatory signaling domains:
  (i) are each independent selected from Table 2;
  (ii) are each independently selected from 41BB, CD28, CD27, ICOS, and OX40;
  (iii) comprise one of the following pairs of costimulatory signaling domains (from the extracellular to intracellular direction):
41BB-CD27;
CD27-41BB;
41BB-CD28;
CD28-41BB;
OX40-CD28;
CD28-OX40;
CD28-41BB; or
41BB-CD28.
  (iv) comprise the following pairs of costimulatory signaling domains: CD28-41BB; or
  (v) comprise the following pairs of costimulatory signaling domains: CD28-OX40; and
(b) a [switch domain],
wherein the switch domain is disposed:
  (i) between the transmembrane domain and the first costimulatory signaling domain;
  (ii) between the first costimulatory signaling domain and the second costimulatory signaling domain; or
  (iii) after the second costimulatory signaling domain,
and optionally, the switch domain comprises an FKBP binding fragment or analog of FRB, and the FKBP binding fragment or analog of FRB comprises one or more mutations which enhances the formation of a complex between an FKBP switch domain, an FRB switch domain, and the dimerization molecule, or a mutation described in the section herein entitled MODIFIED FKBP/FRB-BASED DIMERIZATION SWITCHES. E.g., the FKBP binding fragment or analog of FRB comprises: an E2032 mutation, e.g., an E2032I mutation or E2032L mutation; a T2098 mutation, e.g., a T2098L mutation; or an E2032 and a T2098 mutation, e.g., an E2032I and a T2098L or an E2032L and a T2098L mutation;

and optionally, the antigen binding member does not comprise a primary intracellular signaling domain.

In an embodiment, the antigen binding member comprises: a plurality, e.g., 2 or 3 costimulatory signaling domains, chosen e.g., from Table 2, e.g., a combination of costimulatory signaling domains described herein, and the intracellular signaling member comprises a CD3zeta domain.

Provided below are amino acid sequences of exemplary RCAR members comprising an antigen binding member comprising the following structure: [an antigen binding domain]—[a transmembrane domain]—[a first costimulatory signaling domain]—[a second costimulatory signaling domain]—[switch domain]. For the exemplary RCARs listed below, the antigen binding domain comprises an CD19 scFv (the sequence is underlined), a first costimulatory signaling domain (the sequence is italicized), a second costimulatory signaling domain (the sequence is italicized and in bold), and a switch domain (the sequence is underlined and in bold).

TABLE 16

Exemplary antigen binding members

| Antigen binding member | Amino Acid Sequence | SEQ ID NO: |
|---|---|---|
| CD19 scFv-OX40-CD28-FKBP | Malpvtalllplalllhaarpeivmtqspatlslspgeratlscrasqdiskylnwyqqkpgqapr lliyhtsrlhsqiparfsgsgsqtdytltisslqpedfavyfcqqgntlpytfgqgtkleikgqgsq gggsgggsqvqlqesgpglvkpsetlsltctvsgvslpdygvswirqppgkglewigviwg settyyssslksrvtiskdnsknqvslklssvtaadtavyycakhyyyqgsyamdywgqgtlv tvssttpaprpptpaptiasqplslrpeacrpaaggavhtrgldfacdiyiwaplagtcgvllslv itlyc *ALYLLRRDQRLPPDAHKPPGGGSFRTPIQEEQADAHSTLAKI* *RSKRSRLLHSDYMNMTPRRP**GPTRKHYQPYAPPRDFAAYRS* gvqvetispgdgrtfpkrgqtcvvhytgmledgkkfdssrdrnkpfkfmlgkqevirg weegvaqmsvgqrakltispdyaygatghpgiipphatlvfdvellkle | 293 |
| CD19 scFv-OX40-CD28-FRB E2032I/T2098L | Malpvtalllplalllhaarpeivmtqspatlslspgeratlscrasqdiskylnwyqqkpgqapr lliyhtsrlhsqiparfsgsgsqtdytltisslqpedfavyfcqqgntlpytfgqgtkleikgqgsq gggsgggsqvqlqesgpglvkpsetlsltctvsgvslpdygvswirqppgkglewigviwg settyyssslksrvtiskdnsknqvslklssvtaadtavyycakhyyyqgsyamdywgqgtlv tvssttpaprpptpaptiasqplslrpeacrpaaggavhtrgldfacdiyiwaplagtcgvllslv itlyc *ALYLLRRDQRLPPDAHKPPGGGSFRTPIQEEQADAHSTLAKI* *RSKRSRLLHSDYMNMTPRRP**GPTRKHYQPYAPPRDFAAYRS* ilwhemwheglleasrlyfgernvkgmfevleplhammergpqtlketsfnqaygrdl meaqewcrkymksgnvkdlLqawdlyyhvfrrisk | 294 |
| CD19 scFv-CD27-CD28-FKBP | Malpvtalllplalllhaarpeivmtqspatlslspgeratlscrasqdiskylnwyqqkpgqapr lliyhtsrlhsqiparfsgsgsqtdytltisslqpedfavyfcqqgntlpytfgqgtkleikgqgsq gggsgggsqvqlqesgpglvkpsetlsltctvsgvslpdygvswirqppgkglewigviwg settyyssslksrvtiskdnsknqvslklssvtaadtavyycakhyyyqgsyamdywgqgtlv tvssttpaprpptpaptiasqplslrpeacrpaaggavhtrgldfacdiyiwaplagtcgvllslv itlyc *QRRKYRSNKGESPVEPAEPCHYSCPREEEGSTIPIQEDYRKPEPACSP* *RSKRSRLLHSDYMNMTPRRP**GPTRKHYQPYAPPRDFAAYRS* gvqvetispgdgrtfpkrgqtcvvhytgmledgkkfdssrdrnkpfkfmlgkqevirg weegvaqmsvgqrakltispdyaygatghpgiipphatlvfdvellkle | 295 |

TABLE 16-continued

Exemplary antigen binding members

| Antigen binding member | Amino Acid Sequence | SEQ ID NO: |
|---|---|---|
| CD19 scFv-CD27-CD28-FRB E2032I/T2098L | Malpvtalllplalllhaarp<u>eivmtqspatlslspgeratlscrasqdiskylnwyqqkpgqapr lliyhtsrlhsqiparfsgsgsqtdytltisslqpedfavyfcqqgntlpytfgqgtkleikgqgqsq gqgsgqggsqvqlqesqpglvkpsetlsltctvsqvslpdyqvswirqppgkglewigviwg settyyssslksrvtiskdnsknqvslklssvtaadtavyycakhyyyqgsyamdywqqgtlv tvss</u>ttttpaprpptpaptiasqplslrpeacrpaaggavhtrgldfacdiyiwaplagtcgvllslv itlyc *QRRKYRSNKGESPVEPAEPCHYSCPREEEGSTIPIQEDYRKPEPACSP RSKRSRLLHSDYMNMTPRRPGPTRKHYQPYAPPRDFAAYRS* ilwhemwhegIIeasrlyfgernvkgmfevleplhammergpqtlketsfnqaygrdl meaqewcrkymksgnvkdlLqawdlyyhvfrrisk | 296 |
| CD19 scFv-41BB-CD28-FKBP | Malpvtalllplalllhaarp<u>eivmtqspatlslspgeratlscrasqdiskylnwyqqkpgqapr lliyhtsrlhsqiparfsgsgsqtdytltisslqpedfavyfcqqgntlpytfgqgtkleikgqgqsq gqgsgqggsqvqlqesqpglvkpsetlsltctvsqvslpdyqvswirqppgkglewigviwg settyyssslksrvtiskdnsknqvslklssvtaadtavyycakhyyyqgsyamdywqqgtlv tvss</u>ttttpaprpptpaptiasqplslrpeacrpaaggavhtrgldfacdiyiwaplagtcgvllslv itlyc *KRGRKKLLYIFKQPFMRPVQTTQEEDGCSCRFPEEEEGGCEL RSKRSRLLHSDYMNMTPRR PGPTRKHYQPYAPPRDFAAYRS* gvqvetispgdgrtfpkrgqtcvvhytgmledgkkfdssrdrnkpfkfmlgkgevirg weegvaqmsvggrakltispdyaygatghpgiipphatlvfdvellkle | 297 |
| CD19 scFv-41BB-CD28-FRB E2032I/T2098L | Malpvtalllplalllhaarp<u>eivmtqspatlslspgeratlscrasqdiskylnwyqqkpgqapr lliyhtsrlhsqiparfsgsgsqtdytltisslqpedfavyfcqqgntlpytfgqgtkleikgqgqsq gqgsgqggsqvqlqesqpglvkpsetlsltctvsqvslpdyqvswirqppgkglewigviwg settyyssslksrvtiskdnsknqvslklssvtaadtavyycakhyyyqgsyamdywqqgtlv tvss</u>ttttpaprpptpaptiasqplslrpeacrpaaggavhtrgldfacdiyiwaplagtcgvllslv itlyc *KRGRKKLLYIFKQPFMRPVQTTQEEDGCSCRFPEEEEGGCEL RSKRSRLLHSDYMNMTPRR PGPTRKHYQPYAPPRDFAAYRS* ilwhemwhegIIeasrlyfgernvkgmfevleplhammergpqtlketsfnqaygrdl meaqewcrkymksgnvkdlLqawdlyyhvfrrisk | 298 |

Provided below are amino acid sequences for the intracellular signaling member comprising a switch domain (the sequence is bolded and underlined) and a primary signaling domain (the sequence is italicized).

TABLE 17

Exemplary intracellular signaling domain

| Intracellular signaling member | Amino Acid Sequence | SEQ ID NO: |
|---|---|---|
| FRB E2032I/T2098L-CD3zeta | MilwhemwhegIIeasrlyfgernvkgmfevleplhammergpqtlketsfnqaygr dlmeaqewcrkymksgnvkdlLqawdlyyhvfrrisk*rvkfsrsadapaykqgqnql ynelnlgrreeydvldkrrgrdpemggkprrknpqeglynelqkdkmaeayseigmkgerr rgkghdglyqglstatkdtydalhmqalppr* | 299 |
| FKBP-CD3zeta | Mgvqvetispgdgrtfpkrgqtcvvhytgmledgkkfdssrdrnkpfkfmlgkgevir gweegvaqmsvggrakltispdyaygatghpgiipphatlvfdvellklegggggs*rvkfs rsadapaykqgqnqlynelnlgrreeydvldkrrgrdpemggkprrknpqeglynelqkdk maeayseigmkgerrrgkghdglyqglstatkdtydalhmqalppr* | 300 |

ICARs

RCARs disclosed herein can include an inhibitory CAR (iCAR) member. An iCAR member comprises: an antigen binding domain (or other extracelluar domain) that recognizes an antigen on a non-target, e.g., a noncancer, cell; a transmembrane domain; and, a domain from an inhibitory molecule, e.g., an intracellular domain from an inhibitory molecule, e.g., from PD-1, CTLA4, or from a protein listed in Table 12. In an embodiment, the iCAR member comprises a second inhibitory intracelluar signaling domain, e.g., from PD-1, CTLA4, or from a protein listed in Table 12.

Upon engagement of the antigen binding domain (or other extracelluar domain) of the iCAR member with its target antigen (or counter-ligand), the iCAR contributes to inhibiting, e.g., reversibly inhibiting, or minimizing, activation of the cell comprising the iCAR. As such, inclusion of an iCAR member in a RCAR, e.g., and RCART, cell, can limit damage to non-target, e.g., bystander, cells. While not wishing to be bound by theory, it is believed that an iCAR member, upon engagement with its antigen (or counter-ligand), limits one or more of cytokine secretion, cytotoxicity, and proliferation. In embodiments the effect is temporary, and upon subsequent engagement with a target cell the RCAR, e.g., RCART, cell is activated and attacks the target cell.

A target antigen for an iCAR member can be an antigen that has an expression profile on target cells and non-target cells such that an acceptably high level of attack on target cells and an acceptably low level of attack on non-target cells is achieved. Not only choice of antigen, but iCAR affinity for its antigen (or counter-ligand), CAR affinity for its antigen, level of expression of the iCAR, or levels of expression of the CAR can be used to optimize the ratio of on-target/off-target response.

In an embodiment, the antigen is absent, or down-regulated on tumor cells. In an embodiment the antigen comprises an HLA molecule. In an embodiment the antigen comprises a cell surface tumor suppressor antigen. In an embodiment the antigen comprises PCML (or another antigen that is down-regulated in lymphomas, breast or prostate cancer), HYAL2, DCC, or SMAR1.

In an embodiment, the antigen comprises a protein, carbohydrate, lipid, or a post-translational modification of a cell surface moiety, e.g., a mucin-type O-glycan (a core 3 O-glycan).

In an embodiment, the antigen comprises a moiety that is down-regulated by tumor cells undergoing an epithelial to mesenchymal transition.

In an embodiment, the antigen comprises E-cadherin.

In an embodiment a domain from an inhibitory molecule, e.g., an intracellular signaling domain from PD-1 or CTLA4, produces an intracellular signal when an extracellular domain, e.g., an antigen binding domain, to which it is fused binds cognate antigen (or counter ligand). The inhibitory intracellular signaling domain is derived from an inhibitory molecule, e.g., it comprises intracellular sequence of an inhibitory molecule. It comprises sufficient inhibitory molecule sequence to produce an intracellular signal, e.g., when an antigen binding domain to which it is fused binds cognate antigen.

In an embodiment, the primary intracellular signaling domain comprises a signaling motif, e.g., an immunoreceptor tyrosine-based activation motif or ITIM.

A domain from an inhibitory molecule, comprises a functional fragment, or analog, of an inhibitory molecule intracellular domain. It can comprise the entire intracellular region or a fragment of the intracellular region which is sufficient for generation of an intracellular signal when an antigen binding domain to which it is fused, binds cognate antigen. In embodiments the inhibitory intracellular signaling domain has at least 70, 75, 80, 85, 90, 95, 98, or 99% sequence identity with, or differs by no more than 30, 25, 20, 15, 10, 5, 4, 3, 2, or 1 amino acid residues from, the corresponding residues a naturally occurring inhibitory molecule, e.g., a a molecule from Table 12.

Exemplary inhibitory molecules which can provide intracellular signaling domains are provided in Table 12.

TABLE 12

| Inhibitory molecules |
| --- |
| B7-H1 |
| B7-1 |
| CD160 |
| P1H |
| 2B4 |
| PD1 |
| TIM3 |
| CEACAM (e.g., CEACAM-1, CEACAM-3, and/or CEACAM-5) |
| LAG3 |
| TIGIT |
| CTLA-4 |
| BTLA |
| LAIR1 |
| TGF-beta receptor |

Thus, in one, aspect, disclosed herein is, an RCAR comprising an iCAR member. The iCAR member comprises:

an antigen binding domain (or other extracelluar domain) that recognizes an antigen on a non-target, e.g., a noncancer cell;

a transmembrane domain; and a domain from an inhibitory molecule, e.g., from PD-1, CTLA4, or from a protein listed in Table 4.

In an embodiment, the iCAR member comprises a second inhibitory intracellular signaling domain, e.g., from PD-1, CTLA4, or from a protein listed in Table 12.

In another aspect, the invention features, a nucleic acid, e.g., an isolated nucleic acid, encoding a RCAR that comprises an iCAR member.

In an embodiment sequence encoding the iCAR member and a second member of the RCAR are present in a single nucleic acid molecule.

In an embodiment sequence encoding the iCAR member is operatively linked to a first control region and sequence encoding the second member of the RCAR is operatively linked to a second control region.

In an embodiment sequence encoding the iCAR member is translated as a first RNA and sequence encoding second member of the RCAR is translated as a second RNA.

In a another aspect, the invention features, a vector system, e.g., a vector system comprising one or more vectors, comprising nucleic acid encoding a RCAR comprising an iCAR member.

In an embodiment, all of the elements of a RCAR are encoded on a single vector.

In an embodiment, the iCAR member is encoded on a first vector and another member of the RCAR is encoded on a second vector, of the vector system.

In an embodiment, the vector system comprises a DNA, a RNA, a plasmid, a lentivirus vector, adenoviral vector, or a retrovirus vector.

In an embodiment, the vector system comprises a bi-cistronic or tri-cistronic lentivirus vector.

In an embodiment, the vector system comprises a bi-cistronic or tri-cistronic promoter.

In another aspect, the invention features, a cell, e.g., a T cell or NK cell, comprising a vector system described herein.

In another aspect, the invention features, a cell, e.g., a T cell or NK cell, an RCAR comprising an iCAR member.

iCAR member containing cells can be used in method described herein. Thus, in another aspect, the invention features, a method of treating a mammal, e.g., a method of providing an anti-tumor immunity in a mammal, comprising administering to the mammal an effective amount of a RCARX cell comprising an iCAR member.

In an embodiment the RCARX cell is an autologous T cell.

In an embodiment the RCARX cell is an allogeneic T cell.

In an embodiment the RCARX cell is an autologous NK cell.

In an embodiment the RCARX cell is an allogeneic NK cell.

In an embodiment the mammal is a human.

In a another aspect, the invention features, a method of evaluating a human who has been treated with a RCARX cell comprising an iCAR for a side effect of said treatment.

Universal RCARs

Figure 53:
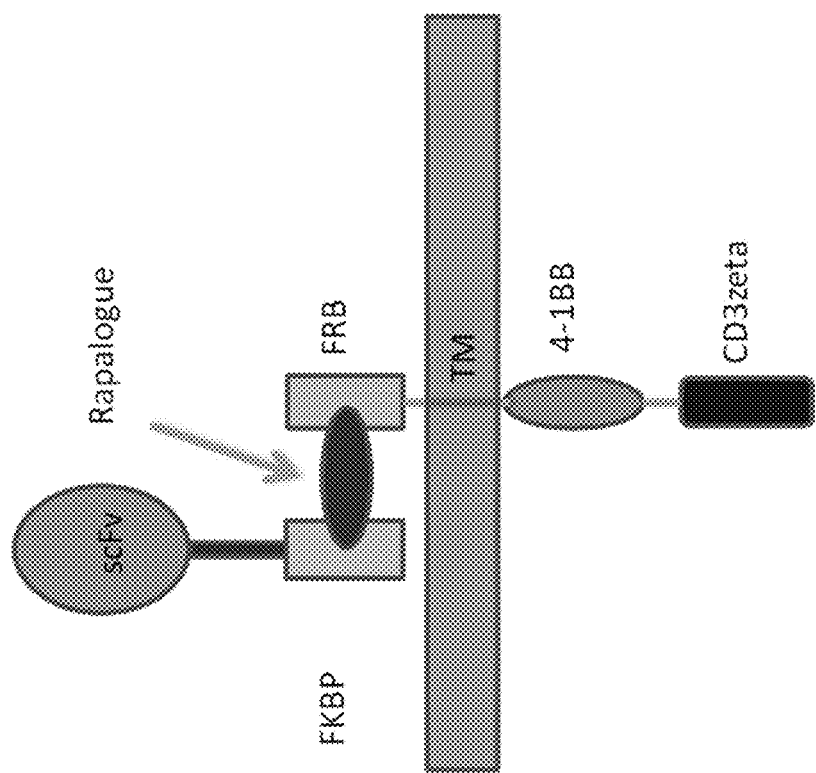
FIG. 53 shows a universal CAR construct comprising an extracellular dimerization switch, where the antigen binding member comprises a switch domain, but does not comprise a transmembrane domain or membrane anchor.
Figure 54:
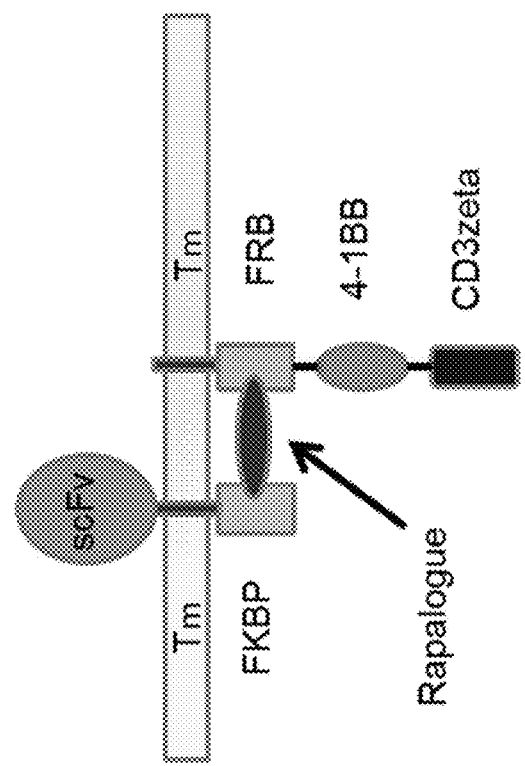
FIG. 54 shows the structure of an RCAR comprising a an antigen binding member comprising an antigen binding domain (scFv), a transmembrane domain (Tm), and a first switch domain, and an intracellular signaling member comprising a transmembrane domain (Tm), a second switch domain, a co-stimulatory signaling domain (41BB), and a primary intracellular signaling domain (CD3zeta).

An embodiment provides RCARs wherein the antigen binding member is not tethered to the surface of the RCARX, e.g., RCART, cell. Typically, such an RCARX, e.g., RCART, cell will include an intracellular signaling domain having an external or extracellular first switch domain. The cell can be contacted with an antigen binding member that comprises an antigen binding domain and a second switch domain (and no transmembrane domain or membrane tethering domain). This allows an RCARX, e.g., an RCART, cell having an intracellular signaling member to be conveniently be paired with one or more antigen binding domains, without transforming the cell with sequence that encodes the antigen binding member. An aliquot of RCARX, e.g., RCART, cells comprising the intracellular signaling member but not an antigen binding member can be provided. As needed, a RCARX, e.g., RCART, cell, e.g., having selected antigen binding properties, can be provided by adding an antigen binding member. Such a RCAR is sometimes referred to herein as universal RCAR. See, e.g., FIG. 53. E.g., an RCARX, e.g., an RCART, cell having the intracellular binding domain can be contacted, e.g., ex vivo, with the antigen binding member of a universal RCAR, and optionally a dimerization molecule. The antigen binding member can be selected from a panel of antigen binding members that comprise different antigen binding domains, e.g., that bind to different antigens. In an embodiment, based on the genotype or phenotype of a subject or subject tumor, e.g., tumor aggressiveness, tumor type, disease stage, prior treatment and the like, an antigen binding domain is selected. In an embodiment, immune effector cells, e.g., T cells, can be obtained from a subject and universal RCART cells made therefrom. A first aliquot of the RCARX cells can be combined with a first antigen binding domain. A second aliquot can be combined with a second antigen binding domain. E.g., a universal RCARX with the first antigen binding domain can be used in a first course of treatment and a universal RCARX with the second antigen binding domain can be used as a second course of treatment, e.g., administered after the initiation of the first course of treatment. In an embodiment, more than one antigen binding domain, e.g., 2, 3, or 4, antigen binding domains, are contacted with an RCARX, e.g., an RCART, cell to provide a cell having RCARs with more than one antigen specificity.

In an embodiment, the RCARX is a natural killer cell. These cells can be isolated from the subject. In an embodiment, the cells are stable cell lines of natural killer cells, e.g., a stable allogeneic NK-92 cell line available, from Conkwest. These stable NK-92 cell lines were derived from NK-92 cells that were obtained, transfected and cultured using the methods described by Gong et al (April 1994), Leukemia Macmillan Press, Ltd, 8: 652-658, and disclosed in EP1007630, incorporated herein by reference. An NK-92 cell, or a cell from a NK cell line with properties similar to the NK-92 cell line can also be used.

Screening RCARs

Modular Screening

Methods and compositions described herein allow for convenient screening and testing of CARs, e.g., RCAR, components. By way of example a panel of a plurality of CARs, e.g., RCARs, each differing at one or more elements, can be evaluated for efficacy. This allows for selection of a CAR, e.g., an RCAR, optimized for a preselected parameter, e.g., cancer type, cancer stage, patient treatment history, or a donor.

E.g., in an embodiment, each of the plurality of RCARs in the panel can have a different costimulatory signaling domain disposed on the intracellular signaling member. In this example, the plurality of RCARs are otherwise identical. Thus, the only diversity is found at the costimulatory signaling domain. Evaluation of RCARs from the panel allow for comparison of the properties RCARs having different costimulatory signaling domains. In other embodiments, diversity can also be introduced at other elements, e.g., in a primary stimulatory domain, a transmembrane domain, a linker, a switch domain, or an antigen binding domain. This allows for simultaneous evaluation and selection.

Thus, "modular" methods of screening and evaluation allow for the comparison of CARs, e.g., RCARs, having distinct variants of a domain, e.g., primary signaling domain, a costimlatory signaling domain, a transmembrane region, a switch domain or an extracellular domain, e.g., an antigen binding domain, a costimulatory extracelluar domain or an inhibitory extracelluar domain. In an embodiment, costimulatory signaling domains, e.g., selected from Table 2 can be compared. In an embodiment, primary signaling domains, e.g., selected from Table 3 can be compared.

Such methods also allow for the comparison of different placement or arrangements e.g., different order, of elements on an RCAR member.

As described herein, a panel of RCARs can be used to evaluate different combinations of intracellular signaling domains where the intracellular signaling domains are present on different members, see, e.g., FIGS. 44A and 44B. As is discussed below, provided herein are vectors which allow for the convenient insertion of diversity at one or more positions in an RCAR.

In an embodiment, a CAR, e.g., RCAR, comprises first and second member, each having a different antigen binding domain. Diversity can be introduced at one or both. In an embodiment, diversity comprises difference in affinity. In an embodiment, diversity, in terms of affinity for the cognate antigen, is introduced for one antigen binding domain. In an embodiment, diversity, in terms of affinity for the cognate antigen, is introduced for both antigen binding domains. These methods allow for selection of a combination of affinities that optimize a parameter, e.g., specificity for target cells of minimization of off target binding or killing.

Figure 11:
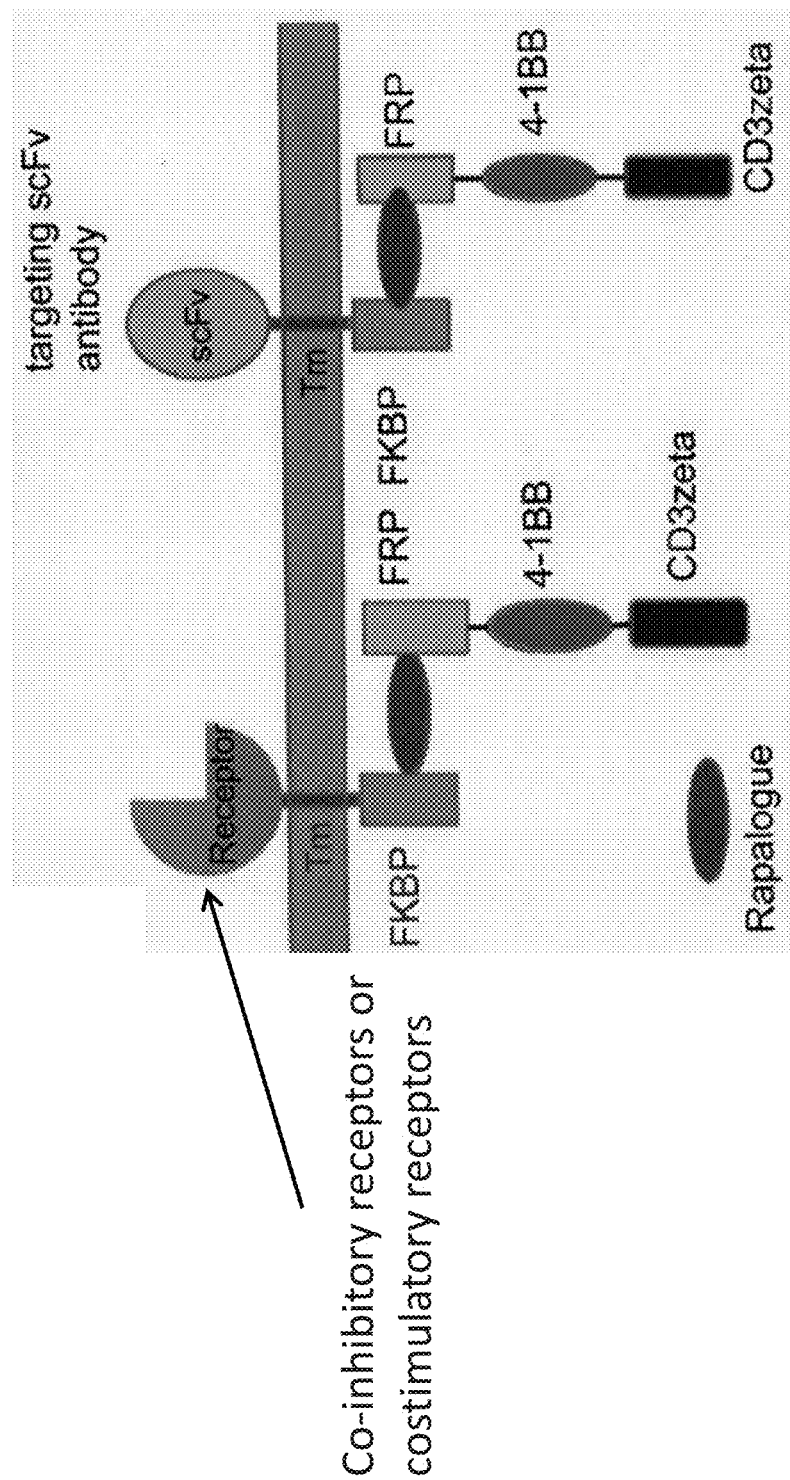
FIG. 11 depicts RCARs having context dependent elements, where the switchable receptor can be a redirected switchable co-inhibitory receptor, e.g., any one listed in Table 4, or co-stimulatory receptor, e.g., any one listed in Table 5. Optimal pairs of co-inhibitory receptors or co-stimulatory receptors and targets can be dependent on cancer types, cancer stages, donor types, etc.

FIG. 11 depicts an RCAR comprising three members, from left to right, the member comprising an inhibitory extracellular domain (ECD) or a costimulatory extracellular domain, an intracellular signaling member, an antigen binding member, and another molecule of the intracellular signaling member. The antigen binding member engages the target cell and in the presence of dimerization molecule, associates with an intracellular signaling member and contributes to the activation of the RCAR cell. The inhibitory extracellular domain member engages with an inhibitory ligand on the target cell, in the presence of dimerization molecule also engages an intracellular signaling member, contributing to activation of the RCAR cell. This system can be used to screen coinhibitory extracelluar domains from a variety of sources, e.g., from Table 4, or costimulatory receptor domains from a variety of sources, e.g., from Table 5. Embodiments allow for optimization or selection of a coinhibitory extracellular domain, or a combination of a coinhibitory extracellular domain and an antigen binding domain. A coinhibitory extracellular domain, or a combination of a coinhibitory extracellular domain and an antigen binding domain can be selected or optimized for a preselected parameter, e.g., cancer type, cancer stage, patient treatment history, or a donor.

Also provided herein are vectors that allow for efficient screening of a panel of diverse RCARs. By way of example, a vector can comprise sequence that encodes elements of an RCAR member and a site that allows for insertion of candidate sequences. E.g., a vector can comprise sequence that encodes elements of an antigen binding member, e.g., one or more of an antigen binding domain, a transmembrane domain, and a switch domain and a site for the insertion of a sequence encoding an element. By way of example, the vector can comprise sequence encoding an antigen binding domain, a transmembrane domain and a site for the insertion of another element, e.g., a costimulatory signaling domain. A plurality of sequences comprising different costimulatory signaling domains can be evaluated. The vector can further encode an intracellular signaling member. In an embodiment a second vector provides an intracellular signaling member. Populations of cells, each having one of the variant antigen binding domain members and each having the same intracellular signaling member are evaluated to identify optimized antigen binding members.

In another embodiment, a vector or vectors, provide for an insertion site in each of more than one element, e.g., an insertion site in a sequence encoding all or part of an antigen binding member and a sequence encoding all or part of an intracellular signaling member and an insertion site The evaluation can, e.g., be performed with an assay described herein, or an in vivo model.

In another aspect, disclosed herein, is a diverse panel of CARs, e.g., RCARs.

A diverse panel of CARs, e.g., RCARs, as that term is used herein, comprises a plurality of CARs, e.g., RCARs. Each CAR, e.g., RCAR, of the plurality is diverse at an element of the CAR. (An element of a CAR, or RCAR, as that term is used herein, is a functional or structural domain, e.g., an antigen binding domain, transmembrane domain, spacer, linker, costimulatory signaling domain, or primary stimulatory domain.) E.g., each CAR, e.g., RCAR, of the plurality has a member comprising a diverse element (i.e., an element that is different, e.g., in structure or position in the CAR or RCAR, from the corresponding element of the other CARs of the plurality). By way of example, the diverse element can be an extracellular binding domain, e.g., an antigen binding domain, a coinhibitory extracellular domain or a costimulatory extracellular domain. In an embodiment a diverse panel of CARs, e.g., RCARs, comprises diversity at a plurality of elements, e.g., at two elements. In an embodiment diversity comprises differences in the structure, e.g., the amino acid sequence, of the diverse elements. In an embodiment diversity comprises differences in placement of an element on a member of the CAR, e.g., RCAR.

In another aspect, disclosed herein, is a plurality of nucleic acid sequences that, collectively, encode a diverse panel of CARs, e.g., RCARs.

In another aspect, disclosed herein, is a panel comprising a plurality of cells, e.g., T cells, or preparations there of, wherein each cell, or preparation of cells, of the plurality, comprises a different CAR, e.g., a RCAR, from a diverse panel of CARs, e.g., RCARs.

In another aspect, described herein is a method of evaluating, selecting, or optimizing, a CAR, e.g., an RCAR comprising:
  providing a diverse panel of CARs, e.g., RCARs;
  evaluating each CAR of the diverse panel, e.g., for effectiveness in activation, persistence, targeting specificity, or effectiveness in cell killing,
  thereby evaluating, selecting, or optimizing, a CAR, e.g., an RCAR.

In an embodiment the method optimizes a CAR, e.g., an RCAR, for a preselected parameter, e.g., cancer type, cancer stage, or patient treatment history.

In an embodiment the CAR, e.g., RCAR, is diverse for an element selected from:
  a) an extracellular domain, e.g., an antigen binding domain, coinhibitory extracellular domain, or costimulatory extracellular domain;
  b) a transmembrane domain, e.g., a transmembrane domain on an antigen binding member;
  c) a switch domain, e.g., a switch domain on a antigen binding member;
  d) a second switch domain, e.g., a switch domain on an intracellular signaling member;
  e) a costimulatory signaling domain, e.g., disposed on an intracellular signaling member;
  f) a primary signaling domain, e.g., disposed on an intracellular signaling member; and
  g) a costimulatory signaling domain disposed on an antigen binding member.

In an embodiment diversity comprises structural diversity of the element.

In an embodiment diversity comprises positional (e.g., placement relative to other elements of the CAR, e.g., RCAR, of the element.

In an embodiment the CAR, e.g., RCAR, is diverse for a plurality of elements, e.g., two elements, e.g., elements selected from a)-g).

In an embodiment the method comprising providing a panel comprising a plurality of cells, e.g., T cells, or preparations there of, wherein each cell, or preparation of cells, of the plurality, comprises a different CAR, e.g., a RCAR, from a CAR panel comprising a plurality of CARs, e.g., RCARs, each CAR having a member comprising a different element, e.g., a different extracellular binding domain, e.g., a different coinhibitory extracellular domain or a different costimulatory extracellular domain.

Evaluation of Efficacy

Candidate RCARs can be generated using the components and methods described herein. Such candidate RCARs can be tested for efficacy in vivo by administering candidate RCARs into mouse models of cancer and monitoring and assessing anti-cancer or anti-tumor effect and overall survival of the mice.

By way of example, the efficacy of an RCAR having an antigen binding domain that comprises an anti-human CD19 antibody can be assayed in a mouse model of cancer, e.g., a CD19/ALL mouse model. Primary human acute lymphoblastic leukemia (ALL) cells are implanted, e.g., intravenously, in immune compromised mice, e.g., NOD.Cg-Prkdc$^{scid}$ Il2rg$^{tm1Wjl}$/SzJ (NSG or NOD scid gamma) mice. After a period of time sufficient for establishment of ALL, e.g., 2-3 weeks, candidate RCAR-expressing cells can be administered. Following treatment with the candidate RCAR-expressing cells, the mice are analyzed, e.g., weekly, for disease progression, tumor burden, infiltration and/or persistence of RCAR-expressing cells, using various methods known in the art. For example, the percentage of human ALL cells, e.g., human CD19+ cells in the blood, to indicate disease burden. Overall survival, e.g. morbidity, of the mice after treatment can also be assessed.

Vectors

The present invention also provides vectors which comprise RCAR encoding sequence. Vectors derived from viruses, e.g., lentivirus, are suitable tools to achieve long-term gene transfer since they allow long-term, stable integration of a transgene and its propagation in daughter cells. Lentiviral vectors have the added advantage over vectors derived from retroviruses e.g., murine leukemia viruses, in that they can transduce non-proliferating cells, such as hepatocytes. They also have the added advantage of low immunogenicity.

In an embodiment, the expression of nucleic acids encoding RCARs is achieved by a nucleic acid encoding the RCAR polypeptide or portions or components thereof operably linked to a promoter, which is incorporated into an expression vector. The vectors can be suitable for replication and integration into eukaryotes. Typical vectors contain transcription and translation terminators, initiation sequences, and promoters useful for regulation of the expression of the desired nucleic acid sequence.

In an embodiment, the vector is a viral vector. Viral vector technology is known in the art and is described, for example, in Sambrook et al., 2012, Molecular Cloning: A Laboratory Manual, volumes 1-4, Cold Spring Harbor Press, NY), and in other virology and molecular biology manuals. In an embodiment, viruses, which are useful as vectors are retroviruses, adenoviruses, adeno-associated viruses, herpes viruses, and lentiviruses. In an embodiment the vector is a lentivirus vector. In general, a suitable vector contains an origin of replication functional in at least one organism, a promoter sequence, convenient restriction endonuclease sites, and one or more selectable markers, (e.g., WO 01/96584; WO 01/29058; and U.S. Pat. No. 6,326,193).

In an embodiment, a vector which expresses two or more genes, each gene is expressed separately under the control of a different promoter region, e.g., by using bi or tri-cistronic promoters. Expression of two or more genes from the same vector can be achieved by using either a multiple promoter plasmid e.g., bi or tri-cistronic promoters. Examples of multiple promoter containing lentivirus vectors are known in the literature. For example the vector pLENTI-bi-cistronic drives the expression of two genes using the PKG promoter and the mini CMV promoter in opposite directions (Applied Biological Material Inc., Richmond, BC, Canada). Similar the tri-cistronic vector pLENTI-tri-cistronic drives expression of three genes. In this configuration one gene can be induced by the mini-CMV promoter while the second and third gene can be induced by the PGK promoter separating the two genes with a T2A peptide cleavage site.

In another embodiment, bi- or tri-cistronic vectors may also be constructed making use of internal ribosomal entry sites (IRES) such as for example the element from the encephalomyocarditis virus (EMCV) for translation of two or more open reading frames (ORFs). Such vectors are designed to drive transcription of the bi- or tri-cistronic message under control of a strong human promoter regulatory region e.g. CMV or EF1alpha. IRESs are relatively short DNA sequences that can initiate RNA translation in a 5' cap-independent fashion. Whereas the first cistron is translated in a cap-dependent manner driven by a strong mammalian promoter, the subsequent ones utilize intercistronic regions of viral origin such as the internal ribosomal entry site of poliovirus or the cap-independent translation enhancer of encephalomyocarditis virus for enhanced translation. (N Chinnasamy et al. (2009), Production of Multicistronic HIV-1 Based Lentiviral Vectors; Methods Mol Biol 515: 1-14).

Additional promoter elements, e.g., enhancers, regulate the frequency of transcriptional initiation. Typically, these are located in the region 30-110 bp upstream of the start site, although a number of promoters have been shown to contain functional elements downstream of the start site as well. The spacing between promoter elements frequently is flexible, so that promoter function is preserved when elements are inverted or moved relative to one another. In the thymidine kinase (tk) promoter, the spacing between promoter elements can be increased to 50 bp apart before activity begins to decline. Depending on the promoter, it appears that individual elements can function either cooperatively or independently to activate transcription.

Another example of a promoter is the immediate early cytomegalovirus (CMV) promoter sequence. This promoter sequence is a strong constitutive promoter sequence capable of driving high levels of expression of any polynucleotide sequence operatively linked thereto. However, other constitutive promoter sequences may also be used, including, but not limited to the simian virus 40 (SV40) early promoter, mouse mammary tumor virus (MMTV), human immunodeficiency virus (HIV) long terminal repeat (LTR) promoter, MoMuLV promoter, an avian leukemia virus promoter, an Epstein-Barr virus immediate early promoter, a Rous sarcoma virus promoter, as well as human gene promoters such as, but not limited to, the actin promoter, the myosin promoter, the elongation factor-1α promoter (EF1α), the hemoglobin promoter, and the creatine kinase promoter. Further, embodiments are not limited to the use of constitutive promoters. Embodiments comprise inducible promoters. The use of an inducible promoter provides a molecular switch capable of turning on expression of the polynucleotide sequence which it is operatively linked when such expression is desired, or turning off the expression when expression is not desired. Examples of inducible promoters include, but are not limited to a metallothionine promoter, a glucocorticoid promoter, a progesterone promoter, and a tetracycline promoter.

Sequence encoding various elements of an RCAR can be disposed on the same nucleic acid molecule, e.g., the same plasmid or vector, e.g., viral vector, e.g., lentiviral vector. E.g., both (i) sequence encoding an antigen binding member and (ii) sequence encoding an intracellular signaling member, can be present on the same nucleic acid, e.g., vector. Production of the corresponding proteins can be achieved, e.g., by the use of separate promoters, or by the use of a bicistronic transcription product (which can result in the production of two proteins by cleavage of a single translation product, the production of two proteins by ribosomal-skip during the translation from one transcription product, or by the translation of two separate protein products).

Accordingly, in an embodiment, (i) sequence encoding an antigen binding member and (ii) sequence encoding an intracellular signaling member, are present on a single nucleic acid molecule, are transcribed as a single transcription product, and are configured as follows:

a promoter, e.g., a promoter described herein, e.g., an EF1alpha promoter, is operably linked to (i), (ii), and to (iii) sequence encoding peptide, e.g., a cleavable peptide, e.g., a P2A or F2A sequence. Element (iii) is disposed between (i) and (ii). In an embodiment, (i), (ii), and (iii) are transcribed as a single RNA. In an embodiment, the order, on the nucleic acid, is (i)-(iii)-(ii). In an embodiment, the order, on the nucleic acid, is (ii)-(iii)-(i).

In an embodiment element (iii) comprises: a P2A or F2A sequence, or effective fragment thereof.

Amino acid and nucleic acid sequences for P2A and F2A are provided below:

P2A:

SEQ ID NO: 331

Ggcagcggcgccaccaacttcagcctgctgaagcaggccggcgacgtgga ggaaaaccctggcccc

-continued

GSGATNFSLLKQAGDVEENPGP
SEQ ID NO: 332

F2A:
SEQ ID NO: 333
Gtgaagcagaccctgaacttcgacctgctgaaactggccggcgacgtgga gagcaatcccggccct

VKQTLNFDLLKLAGDVESNPGP
SEQ ID NO: 334

In an embodiment (i) and (ii) form an RCAR having an intracellular switch.

In an embodiment (i) and (ii) form an RCAR having an extracellular switch.

In an embodiment (ii) comprises sequence that encode a 4-1BB domain and a CD3zeta domain.

In an embodiment (i) comprises sequence that encode a costimulatory signaling domain, e.g., a 4-1BB domain.

In an embodiment, (i) sequence encoding an antigen binding member and (ii) sequence encoding an intracellular signaling member, are present on a single nucleic acid molecule, are transcribed as a single transcription product, and are configured as follows: a promoter, e.g., a promoter described herein, e.g., an EF1alpha promoter, is operably linked to (i), (ii), and to (iii) sequence encoding an IRES, e.g., an EMCV or EV71 IRES. In an embodiment (iii) is disposed between (i) and (ii). In an embodiment, (i), (ii), and (iii) are transcribed as a single RNA. In an embodiment, the order, on the nucleic acid, is (i)-(iii)-(ii). In an embodiment, the order, on the nucleic acid, is (ii)-(iii)-(i).

In an embodiment (i) and (ii) form an RCAR having an intracellular switch.

In an embodiment (i) and (ii) form an RCAR having an extracellular switch.

In an embodiment (ii) comprises sequence that encode a 4-1BB domain and a CD3zeta domain.

In an embodiment (i) comprises sequence that encode a costimulatory signaling domain, e.g., a 4-1BB domain.

In another embodiment, (i) sequence encoding an antigen binding member and (ii) sequence encoding an intracellular signaling member, are transcribed as separate transcription products, are present on a single nucleic acid molecule, and are configured as follows: a promoter, e.g., a promoter described herein, e.g., an EF1alpha promoter, is operably linked to (i), and a second promoter, e.g., a promoter described herein, can be operable linked to (ii). In an embodiment (i) and (ii) are transcribed as separate mRNAs. In an embodiment, the order, on the nucleic acid, is first promoter-(i)-second promoter-(ii). In an embodiment, the order, on the nucleic acid, is first promoter-(ii)-second promoter-(i). In an embodiment the first promoter is a promoter described herein, e.g., an EF1alpha promoter. In an embodiment, the second promoter is a promoter described herein, e.g., a CMV or EF1 alpha promoter. In an embodiment the second promoter is a minimal promoter.

In an embodiment (i) and (ii) form an RCAR having an intracellular switch.

In an embodiment (i) and (ii) form an RCAR having an extracellular switch.

In an embodiment (ii) comprises sequence that encode a 4-1BB domain and a CD3zeta domain.

In an embodiment (i) comprises sequence that encode a costimulatory signaling domain, e.g., a 4-1BB domain.

Sequence encoding (i) an inhibitory extracellular domain member and (ii) sequence encoding an intracellular signaling member, can be present on the same nucleic acid, e.g., vector.

Accordingly, in an embodiment, (i) sequence encoding inhibitory extracellular domain member and (ii) sequence encoding an intracellular signaling member, are present on a single nucleic acid molecule, are transcribed as a single transcription product, and are configured as follows: a promoter, e.g., a promoter described herein, e.g., an EF1alpha promoter, is operably linked to (i), (ii), and to (iii) sequence encoding peptide, e.g., a cleavable peptide, e.g., a P2A or F2A sequence. Element (iii) is disposed between (i) and (ii). In an embodiment, (i), (ii), and (iii) are transcribed as a single RNA. In an embodiment, the order, on the nucleic acid, is (i)-(iii)-(ii). In an embodiment, the order, on the nucleic acid, is (ii)-(iii)-(i).

In an embodiment element (iii) comprises: a P2A or P3A sequence, or effective fragment thereof.

In an embodiment, (i) sequence encoding an inhibitory extracellular member and (ii) sequence encoding an intracellular signaling member, are present on a single nucleic acid molecule, are transcribed as a single transcription product, and are configured as follows: a promoter, e.g., a promoter described herein, e.g., an EF1alpha promoter, is operably linked to (i), (ii), and to (iii) sequence encoding an IRES, e.g., an EMCV or EV71 IRES. In an embodiment (iii) is disposed between (i) and (ii). In an embodiment, (i), (ii), and (iii) are transcribed as a single RNA. In an embodiment, the order, on the nucleic acid, is (i)-(iii)-(ii). In an embodiment, the order, on the nucleic acid, is (ii)-(iii)-(i).

In an embodiment (i) and (ii) form an RCAR having an intracellular switch.

In an embodiment (i) and (ii) form an RCAR having an extracellular switch.

In an embodiment (ii) comprises sequence that encode a 4-1BB domain and a CD3zeta domain.

In an embodiment (i) comprises sequence that encode a costimulatory signaling domain, e.g., a 4-1BB domain.

In another embodiment, (i) sequence encoding an inhibitory extracellular member and (ii) sequence encoding an intracellular signaling member, are transcribed as separate transcription products, are present on a single nucleic acid molecule, and are configured as follows: a promoter, e.g., a promoter described herein, e.g., an EF1alpha promoter, is operably linked to (i), and a second promoter, e.g., a promoter described herein, can be operable linked to (ii). In an embodiment (i) and (ii) are transcribed as separate mRNAs. In an embodiment, the order, on the nucleic acid, is first promoter-(i)-second promoter-(ii). In an embodiment, the order, on the nucleic acid, is first promoter-(ii)-second promoter-(i). In an embodiment the first promoter is a promoter described herein, e.g., an EF1alpha promoter. In an embodiment, the second promoter is a promoter described herein, e.g., a CMV or EF1 promoter. In an embodiment the second promoter is a minimal promoter.

In an embodiment (i) and (ii) form an RCAR having an intracellular switch.

In an embodiment (i) and (ii) form an RCAR having an extracellular switch.

In an embodiment (ii) comprises sequence that encode a 4-1BB domain and a CD3zeta domain.

In an embodiment (i) comprises sequence that encode a costimulatory signaling domain, e.g., a 4-1BB domain.

Sequence encoding (i) a costimulatory ECD member and (ii) sequence encoding an intracellular signaling member, can be present on the same nucleic acid, e.g., vector.

Accordingly, in an embodiment, (ia) sequence encoding costimulatory ECD member and (iai) sequence encoding an intracellular signaling member, are present on a single nucleic acid molecule, are transcribed as a single transcription product, and are configured as follows:

a promoter, e.g., a promoter described herein, e.g., an EF1alpha promoter, is operably linked to (i), (ii), and to (iii) sequence encoding peptide, e.g., a cleavable peptide, e.g., a P2A or F2A sequence. Element (iii) is disposed between (i) and (ii). In an embodiment, (i), (ii), and (iii) are transcribed as a single RNA. In an embodiment, the order, on the nucleic acid, is (i)-(iii)-(ii). In an embodiment, the order, on the nucleic acid, is (ii)-(iii)-(i).

In an embodiment element (iii) comprises: a P2A or P3A sequence, or effective fragment thereof.

In an embodiment, (ib) sequence encoding a costimulatory ECD member and (iib) sequence encoding an intracellular signaling member, are present on a single nucleic acid molecule, are transcribed as a single transcription product, and are configured as follows:

a promoter, e.g., a promoter described herein, e.g., an EF1alpha promoter, is operably linked to (ib), (iib), and to (iii) sequence encoding an IRES, e.g., an EMCV or EV71 IRES. In an embodiment (iii) is disposed between (ib) and (iib). In an embodiment, (ib), (iib), and (iii) are transcribed as a single RNA. In an embodiment, the order, on the nucleic acid, is (ib)-(iii)-(iib). In an embodiment, the order, on the nucleic acid, is (iib)-(iii)-(ib).

In an embodiment (ib) and (iib) form an RCAR having an intracellular switch.

In an embodiment (ib) and (iib) form an RCAR having an extracellular switch.

In an embodiment (iib) comprises sequence that encode a 4-1BB domain and a CD3zeta domain.

In an embodiment (ib) comprises sequence that encode a costimulatory signaling domain, e.g., a 4-1BB domain.

In another embodiment, (ib) sequence encoding an a costimulatory ECD member and (iib) sequence encoding an intracellular signaling member, are transcribed as separate transcription products, are present on a single nucleic acid molecule, and are configured as follows:

a promoter, e.g., a promoter described herein, e.g., an EF1alpha promoter, is operably linked to (ib), and a second promoter, e.g., a promoter described herein, can be operable linked to (iib). In an embodiment (ib) and (iib) are transcribed as separate mRNAs. In an embodiment, the order, on the nucleic acid, is first promoter-(ib)-second promoter-(iib). In an embodiment, the order, on the nucleic acid, is first promoter-(iib)-second promoter-(ib). In an embodiment the first promoter is a promoter described herein, e.g., an EF1alpha promoter. In an embodiment, the second promoter is a promoter described herein, e.g., a CMV or EF1 promoter. In an embodiment the second promoter is a minimal promoter.

In an embodiment (ib) and (iib) form an RCAR having an intracellular switch.

In an embodiment (ib) and (iib) form an RCAR having an extracellular switch.

In an embodiment (iib) comprises sequence that encode a 4-1BB domain and a CD3zeta domain.

In an embodiment (ib) comprises sequence that encode a costimulatory signaling domain, e.g., a 4-1BB domain.

Figure 22:
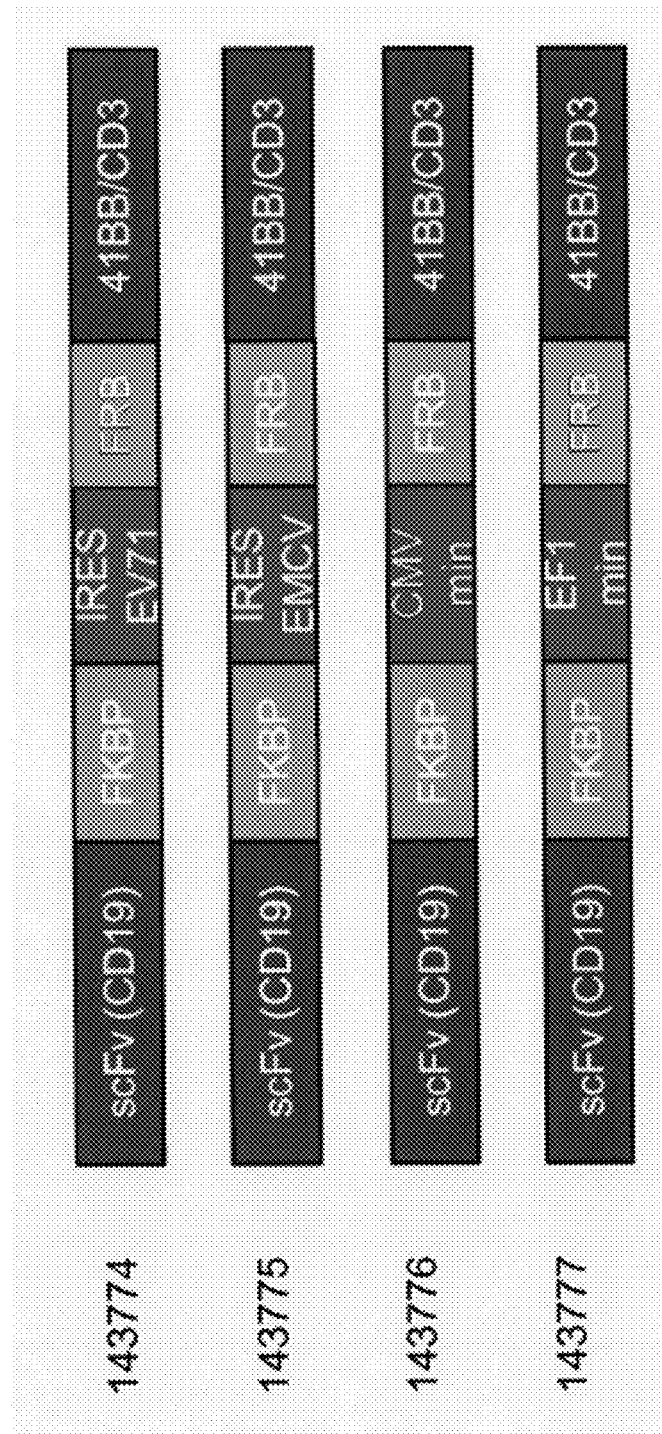
FIG. 22 depicts the arrangement of RCAR elements on a single nucleic acid vector. Constructs 143774 and 143775 utilize different IRES (e.g., IRES EV71 or IRES EMCV) between the antigen binding member (e.g., scFv linked to FKBP) and the intracellular binding member (e.g., FRB linked to 41BB/CD3zeta). Constructs 143776 and 143777 utilize two different promoters (e.g., CMV min or EF1 min) between the antigen binding member (e.g., scFv linked to FKBP) and the intracellular binding member (e.g., FRB linked to 41BB/CD3zeta).

Embodiments of single molecule constructs include those depicted in FIG. 22.

Lentiviral vector 143774 comprises: an EF1 alpha promoter operably linked to a sequence encoding an anti-CD19 scFv/CD8 TM/FKBP switch domain, an EV71 IRES, and an FRB switch domain/4-1BB domain/CD3zeta switch domain.

Lentiviral vector 143775 comprises: an EF1 alpha promoter operably linked to a sequence encoding an anti-CD19 scFv/CD8 TM/FKBP switch domain, an EMCV IRES, and an FRB switch domain/4-1BB domain/CD3zeta switch domain.

Lentiviral vector 143776 comprises: an EF1 alpha promoter operably linked to a sequence encoding an anti-CD19 scFv/CD8 TM/FKBP switch domain; and a CMV minimal promoter operably linked to a sequence encoding an FRB switch domain/4-1BB domain/CD3zeta switch domain.

Lentiviral vector 143777 comprises: an EF1 alpha promoter operably linked to a sequence encoding an anti-CD19 scFv/CD8 TM/FKBP switch domain; and an EF1 minimal promoter operably linked to a sequence encoding an FRB switch domain/4-1BB domain/CD3zeta switch domain.

In an embodiment a promoter that is capable of expressing RCAR transgene is a mammalian T cell is the EF1alpha promoter (EF1α). The native EF1α promoter drives expression of the alpha subunit of the elongation factor-1 complex, which is responsible for the enzymatic delivery of aminoacyl tRNAs to the ribosome. The EF1α promoter has been used in mammalian expression plasmids and has been shown to be effective in driving RCAR expression from transgenes cloned into a lentiviral vector. See, e.g., Milone et al., Mol. Ther. 17(8): 1453-1464 (2009). In an embodiment, the EF1α promoter comprises the sequence provided as SEQ ID NO: 140.

In order to assess the expression of a RCAR polypeptide or portions thereof, the vector to be introduced into a cell can also contain either a selectable marker gene or a reporter gene or both to facilitate identification and selection of expressing cells from the population of cells sought to be transfected or infected through viral vectors. In embodiments, the selectable marker may be carried on a separate piece of DNA and used in a co-transfection procedure. Useful selectable markers include, for example, antibiotic-resistance genes, such as neo and the like.

Reporter genes are used for identifying potentially transfected cells and for evaluating the functionality of regulatory sequences. In general, a reporter gene is a gene that is not present in or expressed by the recipient organism or tissue and that encodes a polypeptide whose expression is manifested by some easily detectable property, e.g., enzymatic activity. Expression of the reporter gene is assayed at a suitable time after the DNA has been introduced into the recipient cells. Suitable reporter genes may include genes encoding luciferase, beta-galactosidase, chloramphenicol acetyl transferase, secreted alkaline phosphatase, or the green fluorescent protein gene (e.g., Ui-Tei et al., 2000 FEBS Letters 479: 79-82). Suitable expression systems are known and may be prepared using known techniques or obtained commercially. In general, the construct with the minimal 5' flanking region showing the highest level of expression of reporter gene is identified as the promoter. Such promoter regions may be linked to a reporter gene and used to evaluate agents for the ability to modulate promoter-driven transcription.

Methods of introducing into and expressing genes in a cell are known in the art. In the context of an expression vector, the vector can be readily introduced into a host cell, e.g., mammalian, bacterial, yeast, or insect cell by any method in the art. For example, the expression vector can be transferred into a host cell by physical, chemical, or biological means. Physical methods for introducing a polynucleotide into a host cell include calcium phosphate precipitation, lipofection, particle bombardment, microinjection, electroporation, and the like.

Methods for producing cells comprising vectors and/or exogenous nucleic acids are well-known in the art. See, for example, Sambrook et al., 2012, Molecular Cloning: A Laboratory Manual, volumes 1-4, Cold Spring Harbor Press, NY).

Biological methods for introducing a polynucleotide into a host cell include the use of DNA and RNA vectors as described above. Chemical means for introducing a polynucleotide into a host cell include colloidal dispersion systems, such as macromolecule complexes, nanocapsules, microspheres, beads, and lipid-based systems including oil-in-water emulsions, micelles, mixed micelles, and liposomes. An exemplary colloidal system for use as a delivery vehicle in vitro and in vivo is a liposome (e.g., an artificial membrane vesicle). Other methods of state-of-the-art targeted delivery of nucleic acids are available, such as delivery of polynucleotides with targeted nanoparticles.

In some embodiments, the mRNA can be introduced directly to the cell or patient in a non-viral delivery system and injected directly into the patient. In the case where a non-viral delivery system is utilized, an exemplary delivery vehicle is a liposome. The use of lipid formulations is contemplated for the introduction of the nucleic acids into a host cell (in vitro, ex vivo or in vivo). In an embodiment, the nucleic acid may be associated with a lipid. The nucleic acid associated with a lipid may be encapsulated in the aqueous interior of a liposome, interspersed within the lipid bilayer of a liposome, attached to a liposome via a linking molecule that is associated with both the liposome and the oligonucleotide, entrapped in a liposome, complexed with a liposome, dispersed in a solution containing a lipid, mixed with a lipid, combined with a lipid, contained as a suspension in a lipid, contained or complexed with a micelle, or otherwise associated with a lipid. Lipid, lipid/DNA or lipid/expression vector associated compositions are not limited to any particular structure in solution. For example, they may be present in a bilayer structure, as micelles, or with a "collapsed" structure. They may also simply be interspersed in a solution, possibly forming aggregates that are not uniform in size or shape. Lipids are fatty substances which may be naturally occurring or synthetic lipids. For example, lipids include the fatty droplets that naturally occur in the cytoplasm as well as the class of compounds which contain long-chain aliphatic hydrocarbons and their derivatives, such as fatty acids, alcohols, amines, amino alcohols, and aldehydes.

Lipids suitable for use can be obtained from commercial sources. For example, dimyristyl phosphatidylcholine ("DMPC") can be obtained from Sigma, St. Louis, Mo.; dicetyl phosphate ("DCP") can be obtained from K & K Laboratories (Plainview, N.Y.); cholesterol ("Choi") can be obtained from Calbiochem-Behring; dimyristyl phosphatidylglycerol ("DMPG") and other lipids may be obtained from Avanti Polar Lipids, Inc. (Birmingham, Ala.). Stock solutions of lipids in chloroform or chloroform/methanol can be stored at about −200 C. Chloroform is used as the only solvent since it is more readily evaporated than methanol. "Liposome" is a generic term encompassing a variety of single and multilamellar lipid vehicles formed by the generation of enclosed lipid bilayers or aggregates. Liposomes can be characterized as having vesicular structures with a phospholipid bilayer membrane and an inner aqueous medium. Multilamellar liposomes have multiple lipid layers separated by aqueous medium. They form spontaneously when phospholipids are suspended in an excess of aqueous solution. The lipid components undergo self-rearrangement before the formation of closed structures and entrap water and dissolved solutes between the lipid bilayers (Ghosh et al., 1991 Glycobiology 5: 505-10). However, compositions that have different structures in solution than the normal vesicular structure are also encompassed. For example, the lipids may assume a micellar structure or merely exist as nonuniform aggregates of lipid molecules. Also contemplated are lipofectamine-nucleic acid complexes.

RCAR components can be encoded on one or more nucleic acid molecules. Exemplary nucleic acid molecules include viral vectors, e.g., lentiviral vectors, retroviral vectors, adenoviral vectors, and the like. In embodiments, the components can be provided on a single nucleic acid molecule, e.g., viral vector, e.g., lentiviral vector, retroviral vectors, adenoviral vectors, and the like, or can be disposed on more than one nucleic acid molecule, e.g., viral vector, e.g., lentiviral vector, retroviral vectors, adenoviral vectors, and the like.

Tables 6-11 below provide exemplary configurations of dimerization switches on RCARs.

TABLE 6

Nucleic Acid Configurations for RCARS comprising: an intracellular signaling member; and an antigen binding member; and optionally other components, e.g. as listed below. See, e.g., the RCARs depicted in FIGS., 2, 5, and 7.

| | A | | B | | | | | C | | | | | E | | | | | | | H |
|---|---|---|---|---|---|---|---|---|---|---|---|---|---|---|---|---|---|---|---|---|
| | a | b | a | b | c | d | e | a | b | c | d | e | a | b | c | d | e | f | g | |
| Intracellular signaling member | 1 | 1 | 1 | 1 | 2 | 2 | 1 | 1 | 1 | 2 | 2 | 1 | 1 | 1 | 1 | 1 | 1 | 1 | 1 | 1 |
| Antigen binding member | 1 | 2 | 1 | 2 | 1 | 2 | 2 | 1 | 2 | 1 | 2 | 2 | 1 | 1 | 1 | 1 | 1 | 2 | 2 | 2 |
| Auxiliary antigen binding member | | | 1 | 2 | 2 | 1 | 3 | | | | | | 1 | 1 | 2 | 2 | 2 | 1 | 2 | 3 |
| shRNA sequence | | | | | | | | 1 | 2 | 2 | 1 | 3 | 1 | 2 | 2 | 1 | 3 | 1 | 2 | 4 |

The intracellular signaling member comprises an intracellular signaling domain, a transmembrane domain and a switch domain.

The antigen binding member comprises an antigen binding domain, a transmembrane domain, and a switch domain.

The auxiliary antigen binding member comprises an antigen binding domain that binds an antigen other than the antigen bound by the antigen binding member.

The shRNA sequence encodes an shRNA that inhibits expression of an inhibitory molecule, e.g. an inhibitory molecule from Table 3. The shRNA sequence can be replaced, in embodiments, with an siRNA encoding sequence.

Each column, depicts, for a single RCAR, the listed components of that RCAR. The number in a cell indicates which nucleic acid molecule component of the RCAR is provided on. By way of example, Column Aa depicts an RCAR having two components, an intracellular signaling member and an intracellular binding member. Both components are encoded on a single nucleic acid molecule, as indicated by the number "1" in the cell for each of the two components. Column Ab depicts an RCAR having the same two components as the RCAR in column Aa. In this case, however, there are two nucleic acid molecules that encode the components. One component is encoded on the first nucleic acid (denoted by "1") and the second component is encoded on a second nucleic acid molecule (denoted by "2"). It is important to note that the numbers in the cell table do not refer to the quantity of component, but rather the number of nucleic acid molecules used to encode the components and, in cases where more than one nucleic acid is used, the nucleic acid on which a component is encoded. Thus, the "2" in the cell table of antigen binding member does not refer to two copies of the antigen binding member, but rather that the RCAR components are encoded on two nucleic acid molecules. Where more than one RCAR component is provided on a vector each component can be expressed as a separate RNA, e.g., they can be expressed from different promoters.

The switch can be intracellular or extracellular.

TABLE 7

Figure 9:
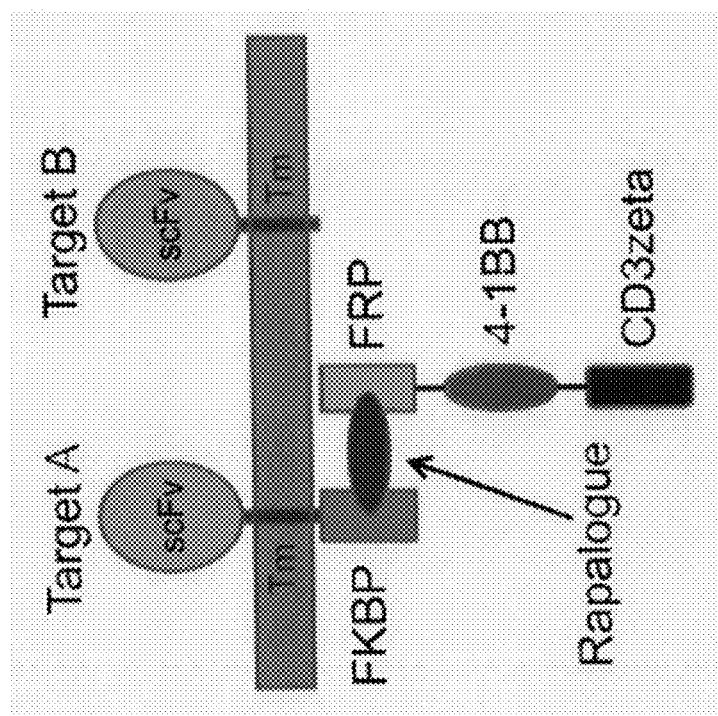
FIG. 9 depicts an RCAR comprising an auxiliary antigen binding member, wherein the auxiliary antigen binding member targets a second antigen (e.g., target B) that is different from the antigen targeted by the antigen binding member comprising a switch domain (e.g., target A). The auxiliary antigen binding member does not comprise a switch domain, and does not dimerize with the intracellular signaling member of the RCAR.

Nucleic Acid Configurations for RCARS
comprising: intracellular signaling member;
an inhibitory binding member; and
an antigen binding member, and optionally
other components, e.g. as listed below. See, e.g.,
the RCAR depicted in FIG. 9, right panel.

| | A | | B | | | C | | | | | E | | | | | | | |
|---|---|---|---|---|---|---|---|---|---|---|---|---|---|---|---|---|---|---|
| | a | b | a | b | c | d | e | a | b | c | d | e | a | b | c | d | e | f | g | H |
| Intracellular signaling member | 1 | 1 | 1 | 1 | 2 | 2 | 1 | 1 | 1 | 2 | 2 | 1 | 1 | 1 | 1 | 1 | 1 | 1 | 1 | 1 |
| Inhibitory binding member | 1 | 2 | 1 | 2 | 1 | 2 | 2 | 1 | 2 | 1 | 2 | 2 | 1 | 1 | 1 | 1 | 1 | 2 | 2 | 2 |
| Antigen binding member | | | | | 1 | 2 | 2 | 1 | 3 | | | | 1 | 1 | 2 | 2 | 2 | 1 | 2 | 3 |
| shRNA sequence | | | | | | | | | | 1 | 2 | 2 | 1 | 3 | 1 | 2 | 2 | 1 | 3 | 1 | 2 | 4 |

The interpretation is as in Table 6.

The intracellular signaling member comprises a switch domain and an intracellular binding domain.

The inhibitory binding member comprises an inhibitory extracellular domain, a transmembrane domain, and a switch domain;

The antigen binding member comprising an antigen binding domain and a transmembrane domain or membrane anchor. The antigen binding member does not comprise an intracellular signaling domain and does not comprise a switch domain that forms a dimerization switch with a switch domain on the inhibitory binding member or the switch domain on the intracellular signaling member.

The shRNA sequence encodes an shRNA that inhibits expression of an inhibitory molecule, e.g. an inhibitory molecule from Table 3. The shRNA sequence can be replaced, in embodiments, with an siRNA encoding sequence.

Where more than one RCAR component is provided on a vector each component can be expressed as a separate RNA, e.g., they can be expressed from different promoters.

The switch can be intracellular or extracellular.

TABLE 8

Nucleic Acid Configurations for RCARS
comprising: intracellular signaling member;
an inhibitory binding member; and
an antigen binding member; and optionally
other components, e.g. as listed below. See, e.g.,
the RCAR depicted in FIG. 9, middle panel.

| | A | | B | | | C | | | | | E | | | | | | | |
|---|---|---|---|---|---|---|---|---|---|---|---|---|---|---|---|---|---|---|
| | a | b | a | b | c | d | e | a | b | c | d | e | a | b | c | d | e | f | g | H |
| Intracellular signaling member | 1 | 1 | 1 | 1 | 2 | 2 | 1 | 1 | 1 | 2 | 2 | 1 | 1 | 1 | 1 | 1 | 1 | 1 | 1 | 1 |
| Inhibitory binding member | 1 | 2 | 1 | 2 | 1 | 2 | 2 | 1 | 2 | 1 | 2 | 2 | 1 | 1 | 1 | 1 | 1 | 2 | 2 | 2 |
| Antigen binding member | | | | | 1 | 2 | 2 | 1 | 3 | | | | 1 | 1 | 2 | 2 | 2 | 1 | 2 | 3 |
| shRNA sequence | | | | | | | | | | 1 | 2 | 2 | 1 | 3 | 1 | 2 | 2 | 1 | 3 | 1 | 2 | 4 |

The interpretation is as in Table 6.

The intracellular signaling member comprises a switch domain and an intracellular binding domain.

The inhibitory binding member comprises an inhibitory extracellular domain, a transmembrane domain, and a switch domain;

The antigen binding member comprises an antigen binding domain, a transmembrane domain, and an intracellular signaling domain, but does not comprise a switch domain that forms a dimerization switch with a switch domain on the inhibitory binding member or the switch domain on the intracellular signaling member.

The shRNA sequence encodes an shRNA that inhibits expression of an inhibitory molecule, e.g. an inhibitory molecule from Table 3. The shRNA sequence can be replaced, in embodiments, with an siRNA encoding sequence.

Where more than one RCAR component is provided on a vector each component can be expressed as a separate RNA, e.g., they can be expressed from different promoters.

The switch can be intracellular or extracellular.

TABLE 9

Figure 10:
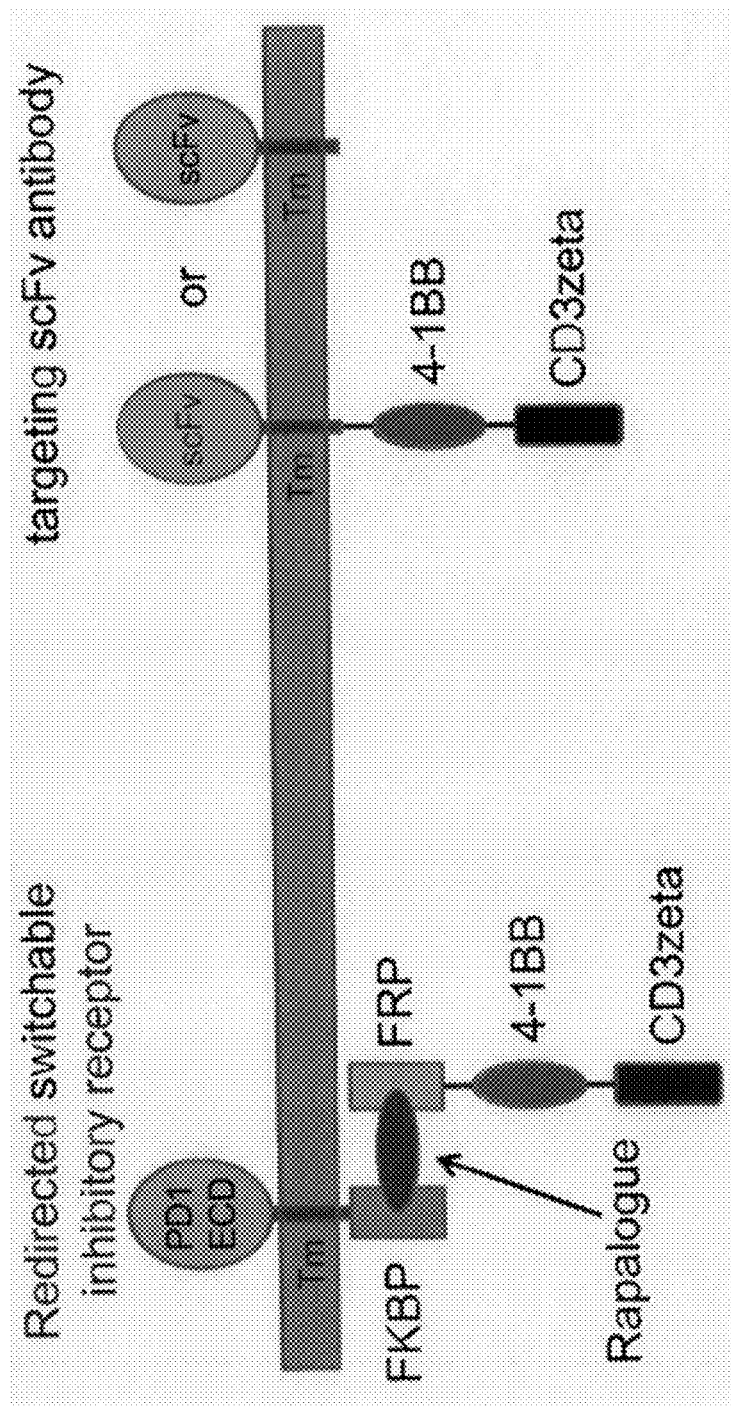
FIG. 10 depicts RCARs that redirect an inhibitory pathway.

Nucleic Acid Configurations for RCARS
comprising: an intracellular signaling member;
an inhibitory binding member; and
an antigen binding member; and optionally
other components, e.g. as listed below.
See, e.g. the CARs depicted in FIG. 10.

| | A | | B | | | C | | | | | E | | | | | | | |
|---|---|---|---|---|---|---|---|---|---|---|---|---|---|---|---|---|---|---|
| | a | b | a | b | c | d | e | a | b | c | d | e | a | b | c | d | e | f | g | H |
| Intracellular signaling member | 1 | 1 | 1 | 1 | 2 | 2 | 1 | 1 | 1 | 2 | 2 | 1 | 1 | 1 | 1 | 1 | 1 | 1 | 1 | 1 |
| Inhibitory binding member | 1 | 2 | 1 | 2 | 1 | 2 | 2 | 1 | 2 | 1 | 2 | 2 | 1 | 1 | 1 | 1 | 1 | 2 | 2 | 2 |
| Antigen binding member | | | | | 1 | 2 | 2 | 1 | 3 | | | | 1 | 1 | 2 | 2 | 2 | 1 | 2 | 3 |
| shRNA sequence | | | | | | | | | | 1 | 2 | 2 | 1 | 3 | 1 | 2 | 2 | 1 | 3 | 1 | 2 | 4 |

The interpretation is as in Table 6.

The intracellular signaling member comprises a switch domain and an intracellular binding domain.

The inhibitory binding member comprises an inhibitory extracellular domain, a transmembrane domain, and a switch domain;

The antigen binding member comprises an antigen binding domain, a transmembrane domain, and a switch domain.

The shRNA sequence encodes an shRNA that inhibits expression of an inhibitory molecule, e.g. an inhibitory molecule from Table 3. The shRNA sequence can be replaced, in embodiments, with an siRNA encoding sequence.

Where more than one RCAR component is provided on a vector each component can be expressed as a separate RNA, e.g., they can be expressed from different promoters.

The switch can be intracellular or extracellular.

TABLE 10

Nucleic Acid Configurations for RCARS
comprising: intracellular signaling member;
and an antigen binding member and optionally
other components, e.g. as listed below.
See, e.g., the RCARs depicted in FIG. 6.

| | A | | B | | | | |
|---|---|---|---|---|---|---|---|
| | a | b | a | b | c | d | e |
| Intracellular signaling member | 1 | 1 | 1 | 1 | 2 | 2 | 1 |
| Antigen binding membert | 1 | 2 | 1 | 2 | 1 | 2 | 2 |
| shRNA sequence | | | 1 | 2 | 2 | 1 | 3 |

The interpretation is as in Table 6.

The intracellular signaling member comprises a switch domain and an intracellular binding domain.

The antigen binding member comprises an antigen binding domain and a transmembrane domain or membrane anchor. The antigen binding member does not comprise an intracellular signaling domain and does not comprise a switch domain that forms a dimerization switch with a switch domain on the intracellular signaling member.

The shRNA sequence encodes an shRNA that inhibits expression of an inhibitory molecule, e.g. an inhibitory molecule from Table 3. The shRNA sequence can be replaced, in embodiments, with an siRNA encoding sequence.

Where more than one RCAR component is provided on a vector each component can be expressed as a separate RNA, e.g., they can be expressed from different promoters.

The switch can be intracellular or extracellular.

TABLE 11

Nucleic Acid Configurations for RCARS
comprising: intracellular signaling member;
a costimulatory ECD binding member; and
an antigen binding member; and optionally
other components, e.g. as listed below. See,
e.g., the RCARs depicted in FIG. 11.

| | A | | B | | | C | | | | | E | | | | | | | |
|---|---|---|---|---|---|---|---|---|---|---|---|---|---|---|---|---|---|---|
| | a | b | a | b | c | d | e | a | b | c | d | e | a | b | c | d | e | f | g | H |
| Intracellular signaling member | 1 | 1 | 1 | 1 | 2 | 2 | 1 | 1 | 1 | 2 | 2 | 1 | 1 | 1 | 1 | 1 | 1 | 1 | 1 | 1 |
| Costimulatory ECD binding member | 1 | 2 | 1 | 2 | 1 | 2 | 2 | 1 | 2 | 1 | 2 | 2 | 1 | 1 | 1 | 1 | 1 | 2 | 2 | 2 |

TABLE 11-continued

Nucleic Acid Configurations for RCARS comprising: intracellular signaling member; a costimulatory ECD binding member; and an antigen binding member; and optionally other components, e.g. as listed below. See, e.g., the RCARs depicted in FIG. 11.

| | A | | B | | | | | C | | | | | E | | | | | | |
|---|---|---|---|---|---|---|---|---|---|---|---|---|---|---|---|---|---|---|---|
| | a | b | a | b | c | d | e | a | b | c | d | e | a | b | c | d | e | f | g | H |
| Antigen binding member | | | 1 | 2 | 2 | 1 | 3 | | | | | | 1 | 1 | 2 | 2 | 2 | 1 | 2 | 3 |
| shRNA sequence | | | | | | | | 1 | 2 | 2 | 1 | 3 | 1 | 2 | 2 | 1 | 3 | 1 | 2 | 4 |

The interpretation is as in Table 6
The intracellular signaling member comprises a switch domain and an intracellular binding domain.
The Costimulatory ECD binding member comprises an a costimulatory ECD domain, a transmembrane domain, and a switch domain;
The antigen binding member comprises an antigen binding domain, a transmembrane domain, and a switch domain.
The shRNA sequence encodes an shRNA that inhibits expression of an inhibitory molecule, e.g. an inhibitory molecule from Table 3. The shRNA sequence can be replaced, in embodiments, with an siRNA encoding sequence.
Where more than one RCAR component is provided on a vector each component can be expressed as a separate RNA, e.g., they can be expressed from different promoters.
The switch can be intracellular or extracellular.

Nucleic Acid Based Inhibitors

Double Stranded RNA (dsRNA)

A nucleic acid based inhibitor useful for decreasing the expression of target gene, e.g., an inhibitory molecule gene, comprises dsRNA, such as shRNA. While not wishing to be bound by theory it is believed that the dsRNA acts by an RNAi mechanism. RNAi refers to the process of sequence-specific post-transcriptional gene silencing in animals mediated by short interfering RNAs (siRNAs). dsRNA, as used herein includes siRNA and shRNA.

The dsRNA can be chemically synthesized, expressed from a vector or enzymatically synthesized. dsRNAs can be unmodified or, e.g., in the case of dsRNAs administered as RNA, can be chemically modified. Ezymatically synthesized dsRNAs can be chemically to improve various properties of native dsRNA molecules, such as through increased resistance to nuclease degradation in vivo and/or through improved cellular uptake.

The dsRNAs targeting nucleic acid can be composed of two separate RNA molecules referred to herein as siRNA, or of one RNA molecule, which is folded to form a hairpin structure, referred to herein as shRNA. In embodiments, a suitable dsRNA for inhibiting expression of a target gene can be identified by screening an siRNA library, such as an adenoviral or lentiviral siRNA library. A dsRNA, e.g., a shRNA, can be provided to a cell as RNA, or in the form of a DNA that is transcribed to provide the dsRNA, e.g., shRNA. A dsRNA, e.g., a shRNA, gene can be expressed from a vector, e.g., viral vector, such as a lentiviral or adenoviral vector. A dsRNA, e.g., an shRNA, can be expressed by a polymerase III promoters, e.g. a U6 or H1 promoter or by a polymerase II promoter. shRNA can be expressed in the cell from a DNA construct encoding a sequence of single stranded RNA and its complement, separated by a stuffer, or linker, fragment, allowing the RNA molecule to fold back on itself, creating a dsRNA molecule with a hairpin loop. While not wishing to be bound by theory, it is believed that shRNA expressed from a DNA sequence encoding the shRNA is processed by Dicer to siRNA, which continues along the RNAi pathway via RISC to silence the target gene.

In an embodiment the inhibitor is a dsRNA .e.g., an shRNA, that comprises a duplexed region that is about 15 to about 30 base pairs in length (e.g., about 16, 17, 18, 19, 20, 21, 22, 23, 24, 25, 26, 27, 28, or 29 base pairs in length. In an embodiment the inhibitor is an shRNA, comprising a duplexed region that is about 15 to about 30 base pairs in length (e.g., about 16, 17, 18, 19, 20, 21, 22, 23, 24, 25, 26, 27, 28, or 29 base pairs in length). In an embodiment, the dsRNA, includes overhanging ends of about 1 to about 3 (e.g., about 1, 2, or 3) nucleotides. By "overhang" is meant that 3'-end of one strand of the dsRNA extends beyond the 5'-end of the other strand, or vice versa. The dsRNA can have an overhang on one or both ends of the dsRNA molecule. In some embodiments, the single-stranded overhang is located at the 3'-terminal end of the antisense strand, or, alternatively, at the 3'-terminal end of the sense strand. In some embodiments, the overhang is a TT or UU dinucleotide overhang, e.g., a TT or UU dinucleotide overhang. For example, in an embodiment, the dsRNA includes a 21-nucleotide antisense strand, a 19 base pair duplex region, and a 3'-terminal dinucleotide. In yet another embodiment, a dsRNA includes a duplex nucleic acid where both ends are blunt, or alternatively, where one of the ends is blunt.

In an embodiment the shRNA, after intracellular processing (e.g., by Dicer), results in a 19-23 nucleotide duplex siRNA with 2 nucleotide 3' overhangs.

In an embodiment, the dsRNA, e.g., a shRNA, includes a first and a second sequence, each sequence is about 18 to about 28 nucleotides in length, e.g., about 19 to about 23 nucleotides in length, wherein the first sequence of the dsRNA includes a nucleotide sequence having sufficient complementarity to the target RNA for the dsRNA to direct cleavage of the target via RNA interference, and the second sequence of the dsRNA includes a nucleotide sequence that is complementary to the first strand.

In an embodiment, an dsRNA includes a first and a second sequence that from a duplexed region, wherein each sequence of the duplexed region is about 18 to about 28 nucleotides in length, e.g., about 19 to about 23 nucleotides in length. The first sequence of the hsRNA includes a nucleotide sequence having sufficient complementarity to the target RNA for the hsRNA to direct cleavage of the target via RNA interference, and the second strand of the hsRNA includes a nucleotide sequence that is complementary to the first strand.

In an embodiment, the dsRNA (e.g., the sequences or strands of the duplexed region of an shRNA) includes an antisense sequence having a nucleotide sequence that is complementary to a nucleotide sequence of the target gene or a portion thereof, and a sense sequence having a nucleotide sequence substantially similar to the nucleotide sequence of the target gene or a portion thereof. In an embodiment, the antisense sequence and the sense sequence, independently, include about 15 to about 30 (e.g., about 15, 16, 17, 18, 19, 20, 21, 22, 23, 24, 25, 26, 27, 28, 29, or 30) nucleotides, where the antisense sequence includes about 15 to about 30 (e.g., about 15, 16, 17, 18, 19, 20, 21, 22, 23, 24, 25, 26, 27, 28, 29, or 30) nucleotides that are complementary to nucleotides of the sense sequence.

In an embodiment, a dsRNA is provided as an RNA (and not as a DNA which is transcribed to provide the dsRNA) and includes one or more chemical modifications. Non-limiting examples of such chemical modifications include without limitation phosphorothioate internucleotide linkages, 2'-deoxyribonucleotides, 2'-O-methyl ribonucleotides, 2'-deoxy-2'-fluoro ribonucleotides, "universal base" nucleotides, "acyclic" nucleotides, 5-C-methyl nucleotides, and terminal glyceryl and/or inverted deoxy abasic residue incorporation. Such chemical modifications have been shown to preserve RNAi activity in cells while at the same time, dramatically increasing the serum stability of these compounds. Furthermore, one or more phosphorothioate substitutions are well-tolerated and have been shown to confer substantial increases in serum stability for modified dsRNA constructs. The dsRNA can include modified nucleotides as a percentage of the total number of nucleotides present in the molecule. As such, the dsRNA can generally include about 5% to about 100% modified nucleotides (e.g., about 5%, 10%, 15%, 20%, 25%, 30%, 35%, 40%, 45%, 50%, 55%, 60%, 65%, 70%, 75%, 80%, 85%, 90%, 95% or 100% modified nucleotides).

Antisense

Suitable nucleic acid based inhibitors include antisense nucleic acids. While not being bound by theory it is believed that antisense inhibition is typically based upon hydrogen bonding-based hybridization of oligonucleotide strands or segments such that at least one strand or segment is cleaved, degraded, or otherwise rendered inoperable.

An antisense agent can have a chemical modification described above as being suitable for dsRNA.

Antisense agents can include, for example, from about 8 to about 80 nucleobases (i.e., from about 8 to about 80 nucleotides), e.g., about 8 to about 50 nucleobases, or about 12 to about 30 nucleobases. Antisense compounds include ribozymes, external guide sequence (EGS) oligonucleotides (oligozymes), and other short catalytic RNAs or catalytic oligonucleotides which hybridize to the target nucleic acid and modulate its expression. Anti-sense compounds can include a stretch of at least eight consecutive nucleobases that are complementary to a sequence in the target gene. An oligonucleotide need not be 100% complementary to its target nucleic acid sequence to be specifically hybridizable. An oligonucleotide is specifically hybridizable when binding of the oligonucleotide to the target interferes with the normal function of the target molecule to cause a loss of utility, and there is a sufficient degree of complementarity to avoid non-specific binding of the oligonucleotide to non-target sequences under conditions in which specific binding is desired, i.e., under physiological conditions in the case of in vivo assays or therapeutic treatment or, in the case of in vitro assays, under conditions in which the assays are conducted.

While not being bound by theory it is believed that the functions of mRNA to be interfered with include all key functions such as, for example, translocation of the RNA to the site of protein translation, translation of protein from the RNA, splicing of the RNA to yield one or more mRNA species, and catalytic activity which may be engaged in by the RNA. Binding of specific protein(s) to the RNA may also be interfered with by antisense oligonucleotide hybridization to the RNA.

Sequence Identity

Percent identity in the context of two or more nucleic acids or polypeptide sequences, refers to two or more sequences that are the same. Two sequences are "substantially identical" if two sequences have a specified percentage of amino acid residues or nucleotides that are the same (i.e., 60% identity, optionally 70%, 71%. 72%. 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% identity over a specified region, or, when not specified, over the entire sequence, e.g., of the shorter of the compared sequences), when compared and aligned for maximum correspondence over a comparison window, or designated region as measured using one of the following sequence comparison algorithms or by manual alignment and visual inspection. Optionally, the identity exists over a region that is at least about 50 nucleotides (or 10 amino acids) in length, or more preferably over a region that is 100 to 500 or 1000 or more nucleotides (or 20, 50, 200 or more amino acids) in length.

For sequence comparison, typically one sequence acts as a reference sequence, to which test sequences are compared. When using a sequence comparison algorithm, test and reference sequences are entered into a computer, subsequence coordinates are designated, if necessary, and sequence algorithm program parameters are designated. Default program parameters can be used, or alternative parameters can be designated. The sequence comparison algorithm then calculates the percent sequence identities for the test sequences relative to the reference sequence, based on the program parameters. Methods of alignment of sequences for comparison are known in the art. Optimal alignment of sequences for comparison can be conducted, e.g., by the local homology algorithm of Smith and Waterman, (1970) Adv. Appl. Math. 2:482c, by the homology alignment algorithm of Needleman and Wunsch, (1970) J. Mol. Biol. 48:443, by the search for similarity method of Pearson and Lipman, (1988) Proc. Nat'l. Acad. Sci. USA 85:2444, by computerized implementations of these algorithms (GAP, BESTFIT, FASTA, and TFASTA in the Wisconsin Genetics Software Package, Genetics Computer Group, 575 Science Dr., Madison, Wis.), or by manual alignment and visual inspection (see, e.g., Brent et al., (2003) Current Protocols in Molecular Biology).

Two examples of algorithms that are suitable for determining percent sequence identity and sequence similarity are the BLAST and BLAST 2.0 algorithms, which are described in Altschul et al., (1977) Nuc. Acids Res. 25:3389-3402; and Altschul et al., (1990) J. Mol. Biol. 215:403-410, respectively. Software for performing BLAST analyses is publicly available through the National Center for Biotechnology Information.

The percent identity between two amino acid sequences can also be determined using the algorithm of E. Meyers and W. Miller, (1988) Comput. Appl. Biosci. 4:11-17) which has been incorporated into the ALIGN program (version 2.0), using a PAM120 weight residue table, a gap length penalty of 12 and a gap penalty of 4. In addition, the percent identity between two amino acid sequences can be determined using the Needleman and Wunsch (1970) J. Mol. Biol. 48:444-453) algorithm which has been incorporated into the GAP program in the GCG software package (available at www.gcg.com), using either a Blossom 62 matrix or a PAM250 matrix, and a gap weight of 16, 14, 12, 10, 8, 6, or 4 and a length weight of 1, 2, 3, 4, 5, or 6.

In an embodiment, the present invention contemplates modifications of the antigen binding domain (e.g., svFv) amino acid sequence that generate functionally equivalent molecules. For example, the VH or VL of an scFv of RCAR can be modified to retain at least about 70%, 71%. 72%. 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% identity of the starting VH or VL sequences of the scFv.

In certain embodiments the polypeptide sequences encoded by the nucleic acid sequences are modified by replacing one or more amino acid residues with another amino acid residue from the same side chain family, i.e., conservative substitutions. Families of amino acid residues having similar side chains have been defined in the art, including basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), nonpolar side chains (e.g., alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine).

Alternative methods useful for decreasing the expression of target gene, e.g., an inhibitory molecule gene as described herein, includes a clustered regularly interspaced short palindromic repeats (CRISPR), a transcription-activator like effector nuclease (TALEN), or a zinc finger endonuclease (ZFN), e.g., as described herein.

Sources of Cells

In embodiments, prior to expansion and genetic modification or other modification, a source of cells, e.g., T cells or natural killer (NK) cells, can be obtained from a subject. The term "subject" is intended to include living organisms in which an immune response can be elicited (e.g., mammals). Examples of subjects include humans, monkeys, chimpanzees, dogs, cats, mice, rats, and transgenic species thereof. T cells can be obtained from a number of sources, including peripheral blood mononuclear cells, bone marrow, lymph node tissue, cord blood, thymus tissue, tissue from a site of infection, ascites, pleural effusion, spleen tissue, and tumors.

T Cells

In an embodiment, the cells are T cells. T cell lines available in the art, may be used. In embodiments, T cells can be obtained from a unit of blood collected from a subject using any number of techniques known to the skilled artisan, such as Ficoll™ separation. In an embodiment, cells from the circulating blood of an individual are obtained by apheresis. The apheresis product typically contains lymphocytes, including T cells, monocytes, granulocytes, B cells, other nucleated white blood cells, red blood cells, and platelets. In an embodiment, the cells collected by apheresis may be washed to remove the plasma fraction and to place the cells in an appropriate buffer or media for subsequent processing steps. In an embodiment, the cells are washed with phosphate buffered saline (PBS). In an alternative embodiment, the wash solution lacks calcium and may lack magnesium or may lack many if not all divalent cations. Surprisingly, the initial activation steps in the absence of calcium lead to magnified signal activation. A washing step may be accomplished by methods known to those in the art, such as by using a semi-automated "flow-through" centrifuge (for example, the Cobe 2991 cell processor, the Baxter CytoMate, or the Haemonetics Cell Saver 5) according to the manufacturer's instructions. After washing, the cells may be resuspended in a variety of biocompatible buffers, such as, for example, Ca-free, Mg-free PBS, PlasmaLyte A, or other saline solution with or without buffer. Alternatively, the undesirable components of the apheresis sample may be removed and the cells directly resuspended in culture media.

In an embodiment, T cells are isolated from peripheral blood lymphocytes by lysing the red blood cells and depleting the monocytes, for example, by centrifugation through a PERCOLL™ gradient or by counterflow centrifugal elutriation. A specific subpopulation of T cells, such as CD3+, CD28+, CD4+, CD8+, CD45RA+, and CD45RO+T cells, can be further isolated by positive or negative selection techniques. For example, in an embodiment, T cells are isolated by incubation with anti-CD3/anti-CD28 (i.e., 3×28)-conjugated beads, such as DYNABEADS® M-450 CD3/CD28 T, for a time period sufficient for positive selection of the desired T cells. In an embodiment, the time period is about 30 minutes. In a further embodiment, the time period ranges from 30 minutes to 36 hours or longer and all integer values there between. In a further embodiment, the time period is at least 1, 2, 3, 4, 5, or 6 hours. In yet another embodiment, the time period is 10 to 24 hours. In an embodiment, the incubation time period is 24 hours. For isolation of T cells from patients with leukemia, use of longer incubation times, such as 24 hours, can increase cell yield. Longer incubation times may be used to isolate T cells in any situation where there are few T cells as compared to other cell types, such in isolating tumor infiltrating lymphocytes (TIL) from tumor tissue or from immunocompromised individuals. Further, use of longer incubation times can increase the efficiency of capture of CD8+ T cells. Thus, by simply shortening or lengthening the time T cells are allowed to bind to the CD3/CD28 beads and/or by increasing or decreasing the ratio of beads to T cells (as described further herein), subpopulations of T cells can be preferentially selected for or against at culture initiation or at other time points during the process. Additionally, by increasing or decreasing the ratio of anti-CD3 and/or anti-CD28 antibodies on the beads or other surface, subpopulations of T cells can be preferentially selected for or against at culture initiation or at other desired time points. The skilled artisan would recognize that multiple rounds of selection can also be used. In certain embodiments, it may be desirable to perform the selection procedure and use the "unselected" cells in the activation and expansion process. "Unselected" cells can also be subjected to further rounds of selection.

Enrichment of a T cell population by negative selection can be accomplished with a combination of antibodies directed to surface markers unique to the negatively selected cells. One method is cell sorting and/or selection via negative magnetic immunoadherence or flow cytometry that uses a cocktail of monoclonal antibodies directed to cell surface markers present on the cells negatively selected. For example, to enrich for CD4+ cells by negative selection, a monoclonal antibody cocktail typically includes antibodies to CD14, CD20, CD11b, CD16, HLA-DR, and CD8. In certain embodiments, it may be desirable to enrich for or positively select for regulatory T cells which typically express CD4+, CD25+, CD62Lhi, GITR+, and FoxP3+. Alternatively, in certain embodiments, T regulatory cells are depleted by anti-C25 conjugated beads or other similar method of selection.

For isolation of a desired population of cells by positive or negative selection, the concentration of cells and surface (e.g., particles such as beads) can be varied. In certain embodiments, it may be desirable to significantly decrease the volume in which beads and cells are mixed together (i.e., increase the concentration of cells), to ensure maximum contact of cells and beads. In an embodiment, a concentration of 2 billion cells/ml is used. In an embodiment, a concentration of 1 billion cells/ml is used. In a further embodiment, greater than 100 million cells/ml is used. In a further embodiment, a concentration of cells of 10, 15, 20, 25, 30, 35, 40, 45, or 50 million cells/ml is used. In yet an embodiment, a concentration of cells from 75, 80, 85, 90, 95, or 100 million cells/ml is used. In further embodiments, concentrations of 125 or 150 million cells/ml can be used. Using high concentrations can result in increased cell yield, cell activation, and cell expansion. Further, use of high cell concentrations allows more efficient capture of cells that may weakly express target antigens of interest, such as CD28-negative T cells, or from samples where there are many tumor cells present (i.e., leukemic blood, tumor tissue, etc.). Such populations of cells may have therapeutic value and would be desirable to obtain. For example, using high concentration of cells allows more efficient selection of CD8+ T cells that normally have weaker CD28 expression.

In a related embodiment it may be desirable to use lower concentrations of cells. By significantly diluting the mixture of T cells and surface (e.g., particles such as beads), interactions between the particles and cells is minimized. This selects for cells that express high amounts of desired antigens to be bound to the particles. For example, CD4+ T cells express higher levels of CD28 and are more efficiently captured than CD8+ T cells in dilute concentrations. In an embodiment, the concentration of cells used is $5 \times 10^6$/ml. In other embodiments, the concentration used can be from about $1 \times 10^5$/ml to $1 \times 10^6$/ml, and any integer value in between. In other embodiments, the cells may be incubated on a rotator for varying lengths of time at varying speeds at either 2-10° C. or at room temperature.

T cells for stimulation can also be frozen after a washing step. Wishing not to be bound by theory, the freeze and subsequent thaw step provides a more uniform product by removing granulocytes and to some extent monocytes in the cell population. After the washing step that removes plasma and platelets, the cells may be suspended in a freezing solution. While many freezing solutions and parameters are known in the art and will be useful in this context, one method involves using PBS containing 20% DMSO and 8% human serum albumin, or culture media containing 10% Dextran 40 and 5% Dextrose, 20% Human Serum Albumin and 7.5% DMSO, or 31.25% Plasmalyte-A, 31.25% Dextrose 5%, 0.45% NaCl, 10% Dextran 40 and 5% Dextrose, 20% Human Serum Albumin, and 7.5% DMSO or other suitable cell freezing media containing for example, Hespan and PlasmaLyte A, the cells then are frozen to −80° C. at a rate of 1° per minute and stored in the vapor phase of a liquid nitrogen storage tank. Other methods of controlled freezing may be used as well as uncontrolled freezing immediately at −20° C. or in liquid nitrogen.

In certain embodiments, cryopreserved cells are thawed and washed as described herein and allowed to rest for one hour at room temperature prior to activation using the methods described herein.

In an embodiment the collection of blood samples or apheresis product from a subject is made at a time period prior to when the expanded cells might be needed. As such, the source of the cells to be expanded can be collected at any time point necessary, and desired cells, such as T cells, isolated and frozen for later use in, e.g., T cell therapy for any number of diseases or conditions that would benefit from such T cell therapy. In an embodiment a blood sample or an apheresis is taken from a generally healthy subject. In certain embodiments, a blood sample or an apheresis is taken from a generally healthy subject who is at risk of developing a disease, but who has not yet developed a disease, and the cells of interest are isolated and frozen for later use. In certain embodiments, the T cells may be expanded, frozen, and used at a later time. In certain embodiments, samples are collected from a patient shortly after diagnosis of a particular disease but prior to any treatments. In a further embodiment, the cells are isolated from a blood sample or an apheresis from a subject prior to any number of relevant treatment modalities, including but not limited to treatment with agents such as natalizumab, efalizumab, antiviral agents, chemotherapy, radiation, immunosuppressive agents, such as cyclosporin, azathioprine, methotrexate, mycophenolate, and FK506, antibodies, or other immunoablative agents such as CAMPATH, anti-CD3 antibodies, cytoxan, fludarabine, cyclosporin, FK506, rapamycin, mycophenolic acid, steroids, FR901228, and irradiation. These drugs inhibit either the calcium dependent phosphatase calcineurin (cyclosporine and FK506) or inhibit the p70S6 kinase that is important for growth factor induced signalling (rapamycin). (Liu et al., Cell 66:807-815, 1991; Henderson et al., Immun. 73:316-321, 1991; Bierer et al., Curr. Opin. Immun. 5:763-773, 1993). In a further embodiment, the cells are isolated for a patient and frozen for later use in conjunction with (e.g., before, simultaneously or following) bone marrow or stem cell transplantation, T cell ablative therapy using either chemotherapy agents such as, fludarabine, external-beam radiation therapy (XRT), cyclophosphamide, or antibodies such as OKT3 or CAMPATH. In an embodiment, the cells are isolated prior to and can be frozen for later use for treatment following B-cell ablative therapy such as agents that react with CD20, e.g., Rituxan.

In a further embodiment, T cells are obtained from a patient directly following treatment that leaves the subject with functional T cells. In this regard, it has been observed that following certain cancer treatments, in particular treatments with drugs that damage the immune system, shortly after treatment during the period when patients would normally be recovering from the treatment, the quality of T cells obtained may be optimal or improved for their ability to expand ex vivo. Likewise, following ex vivo manipulation using the methods described herein, these cells may be in a preferred state for enhanced engraftment and in vivo expansion. Thus, it is contemplated within the context of the present invention to collect blood cells, including T cells, dendritic cells, or other cells of the hematopoietic lineage, during this recovery phase. Further, in certain embodiments, mobilization (for example, mobilization with GM-CSF) and conditioning regimens can be used to create a condition in a subject wherein repopulation, recirculation, regeneration, and/or expansion of particular cell types is favored, especially during a defined window of time following therapy.

Allogeneic CAR

In embodiments described herein, the immune effector cell can be an allogeneic immune effector cell, e.g., T cell or NK cell. For example, the cell can be an allogeneic T cell, e.g., an allogeneic T cell lacking expression of a functional T cell receptor (TCR) and/or human leukocyte antigen (HLA), e.g., HLA class I and/or HLA class II.

A T cell lacking a functional TCR can be, e.g., engineered such that it does not express any functional TCR on its surface, engineered such that it does not express one or more subunits that comprise a functional TCR or engineered such that it produces very little functional TCR on its surface. Alternatively, the T cell can express a substantially impaired TCR, e.g., by expression of mutated or truncated forms of one or more of the subunits of the TCR. The term "substantially impaired TCR" means that this TCR will not elicit an adverse immune reaction in a host.

A T cell described herein can be, e.g., engineered such that it does not express a functional HLA on its surface. For example, a T cell described herein, can be engineered such that cell surface expression HLA, e.g., HLA class 1 and/or HLA class II, is downregulated.

In some embodiments, the T cell can lack a functional TCR and a functional HLA, e.g., HLA class I and/or HLA class II.

Modified T cells that lack expression of a functional TCR and/or HLA can be obtained by any suitable means, including a knock out or knock down of one or more subunit of TCR or HLA. For example, the T cell can include a knock down of TCR and/or HLA using siRNA, shRNA, clustered regularly interspaced short palindromic repeats (CRISPR) transcription-activator like effector nuclease (TALEN), or zinc finger endonuclease (ZFN). In some embodiments, the allogenic cell can be a cell which does not expresses or expresses at low levels an inhibitory molecule, e.g. by any method described herein. For example, the cell can be a cell that does not express or expresses at low levels an inhibitory molecule, e.g., that can decrease the ability of a CAR-expressing cell to mount an immune effector response. Examples of inhibitory molecules include PD1, PD-L1, CTLA4, TIM3, LAGS, VISTA, BTLA, TIGIT, LAIR1, CD160, 2B4 and TGFR beta. Inhibition of an inhibitory molecule, e.g., by inhibition at the DNA, RNA or protein level, can optimize a CAR-expressing cell performance. In embodiments, an inhibitory nucleic acid, e.g., an inhibitory nucleic acid, e.g., a dsRNA, e.g., an siRNA or shRNA, a clustered regularly interspaced short palindromic repeats (CRISPR), a transcription-activator like effector nuclease (TALEN), or a zinc finger endonuclease (ZFN), e.g., as described herein, can be used.

siRNA and shRNA to Inhibit TCR or HLA

In some embodiments, TCR expression and/or HLA expression can be inhibited using siRNA or shRNA that targets a nucleic acid encoding a TCR and/or HLA in a T cell.

Expression of siRNA and shRNAs in T cells can be achieved using any conventional expression system, e.g., such as a lentiviral expression system.

Exemplary shRNAs that downregulate expression of components of the TCR are described, e.g., in US Publication No.: 2012/0321667. Exemplary siRNA and shRNA that downregulate expression of HLA class I and/or HLA class II genes are described, e.g., in U.S. publication No.: US 2007/0036773.

CRISPR to Inhibit TCR or HLA

"CRISPR" or "CRISPR to TCR and/or HLA" or "CRISPR to inhibit TCR and/or HLA" as used herein refers to a set of clustered regularly interspaced short palindromic repeats, or a system comprising such a set of repeats. "Cas", as used herein, refers to a CRISPR-associated protein. A "CRISPR/Cas" system refers to a system derived from CRISPR and Cas which can be used to silence or mutate a TCR and/or HLA gene.

Naturally-occurring CRISPR/Cas systems are found in approximately 40% of sequenced eubacteria genomes and 90% of sequenced archaea. Grissa et al. (2007) *BMC Bioinformatics* 8: 172. This system is a type of prokaryotic immune system that confers resistance to foreign genetic elements such as plasmids and phages and provides a form of acquired immunity. Barrangou et al. (2007) Science 315: 1709-1712; Marragini et al. (2008) *Science* 322: 1843-1845.

The CRISPR/Cas system has been modified for use in gene editing (silencing, enhancing or changing specific genes) in eukaryotes such as mice or primates. Wiedenheft et al. (2012) *Nature* 482: 331-8. This is accomplished by introducing into the eukaryotic cell a plasmid containing a specifically designed CRISPR and one or more appropriate Cas.

The CRISPR sequence, sometimes called a CRISPR locus, comprises alternating repeats and spacers. In a naturally-occurring CRISPR, the spacers usually comprise sequences foreign to the bacterium such as a plasmid or phage sequence; in the TCR and/or HLA CRISPR/Cas system, the spacers are derived from the TCR or HLA gene sequence.

RNA from the CRISPR locus is constitutively expressed and processed by Cas proteins into small RNAs. These comprise a spacer flanked by a repeat sequence. The RNAs guide other Cas proteins to silence exogenous genetic elements at the RNA or DNA level. Horvath et al. (2010) *Science* 327: 167-170; Makarova et al. (2006) *Biology Direct* 1: 7. The spacers thus serve as templates for RNA molecules, analogously to siRNAs. Pennisi (2013) *Science* 341: 833-836.

As these naturally occur in many different types of bacteria, the exact arrangements of the CRISPR and structure, function and number of Cas genes and their product differ somewhat from species to species. Haft et al. (2005) *PLoS Comput. Biol.* 1: e60; Kunin et al. (2007) *Genome Biol.* 8: R61; Mojica et al. (2005) *J. Mol. Evol.* 60: 174-182; Bolotin et al. (2005) *Microbiol.* 151: 2551-2561; Pourcel et al. (2005) *Microbiol.* 151: 653-663; and Stern et al. (2010) *Trends. Genet.* 28: 335-340. For example, the Cse (Cas subtype, *E. coli*) proteins (e.g., CasA) form a functional complex, Cascade, that processes CRISPR RNA transcripts into spacer-repeat units that Cascade retains. Brouns et al. (2008) *Science* 321: 960-964. In other prokaryotes, Cas6 processes the CRISPR transcript. The CRISPR-based phage inactivation in *E. coli* requires Cascade and Cas3, but not Cas1 or Cas2. The Cmr (Cas RAMP module) proteins in *Pyrococcus furiosus* and other prokaryotes form a functional complex with small CRISPR RNAs that recognizes and cleaves complementary target RNAs. A simpler CRISPR system relies on the protein Cas9, which is a nuclease with two active cutting sites, one for each strand of the double helix. Combining Cas9 and modified CRISPR locus RNA can be used in a system for gene editing. Pennisi (2013) *Science* 341: 833-836.

The CRISPR/Cas system can thus be used to edit a TCR and/or HLA gene (adding or deleting a basepair), or introducing a premature stop which thus decreases expression of a TCR and/or HLA. The CRISPR/Cas system can alternatively be used like RNA interference, turning off TCR and/or HLA gene in a reversible fashion. In a mammalian cell, for example, the RNA can guide the Cas protein to a TCR and/or HLA promoter, sterically blocking RNA polymerases.

Artificial CRISPR/Cas systems can be generated which inhibit TCR and/or HLA, using technology known in the art, e.g., that described in U.S. Publication No. 20140068797.

TALEN to Inhibit TCR and/or HLA

"TALEN" or "TALEN to HLA and/or TCR" or "TALEN to inhibit HLA and/or TCR" refers to a transcription activator-like effector nuclease, an artificial nuclease which can be used to edit the HLA and/or TCR gene.

TALENs are produced artificially by fusing a TAL effector DNA binding domain to a DNA cleavage domain. Transcription activator-like effects (TALEs) can be engineered to bind any desired DNA sequence, including a portion of the HLA or TCR gene. By combining an engineered TALE with a DNA cleavage domain, a restriction enzyme can be produced which is specific to any desired DNA sequence, including a HLA or TCR sequence. These can then be introduced into a cell, wherein they can be used for genome editing. Boch (2011) *Nature Biotech.* 29: 135-6; and Boch et al. (2009) *Science* 326: 1509-12; Moscou et al. (2009) *Science* 326: 3501.

TALEs are proteins secreted by *Xanthomonas* bacteria. The DNA binding domain contains a repeated, highly conserved 33-34 amino acid sequence, with the exception of the 12th and 13th amino acids. These two positions are highly variable, showing a strong correlation with specific nucleotide recognition. They can thus be engineered to bind to a desired DNA sequence.

To produce a TALEN, a TALE protein is fused to a nuclease (N), which is a wild-type or mutated FokI endonuclease. Several mutations to FokI have been made for its use in TALENs; these, for example, improve cleavage specificity or activity. Cermak et al. (2011) *Nucl. Acids Res.* 39: e82; Miller et al. (2011) *Nature Biotech.* 29: 143-8; Hockemeyer et al. (2011) *Nature Biotech.* 29: 731-734; Wood et al. (2011) *Science* 333: 307; Doyon et al. (2010) *Nature Methods* 8: 74-79; Szczepek et al. (2007) *Nature Biotech.* 25: 786-793; and Guo et al. (2010) *J. Mol. Biol.* 200: 96.

The FokI domain functions as a dimer, requiring two constructs with unique DNA binding domains for sites in the target genome with proper orientation and spacing. Both the number of amino acid residues between the TALE DNA binding domain and the FokI cleavage domain and the number of bases between the two individual TALEN binding sites appear to be important parameters for achieving high levels of activity. Miller et al. (2011) *Nature Biotech.* 29: 143-8.

A HLA or TCR TALEN can be used inside a cell to produce a double-stranded break (DSB). A mutation can be introduced at the break site if the repair mechanisms improperly repair the break via non-homologous end joining. For example, improper repair may introduce a frame shift mutation. Alternatively, foreign DNA can be introduced into the cell along with the TALEN; depending on the sequences of the foreign DNA and chromosomal sequence, this process can be used to correct a defect in the HLA or TCR gene or introduce such a defect into a wt HLA or TCR gene, thus decreasing expression of HLA or TCR.

TALENs specific to sequences in HLA or TCR can be constructed using any method known in the art, including various schemes using modular components. Zhang et al. (2011) *Nature Biotech.* 29: 149-53; Geibler et al. (2011) *PLoS ONE* 6: e19509.

Zinc Finger Nuclease to Inhibit HLA and/or TCR

"ZFN" or "Zinc Finger Nuclease" or "ZFN to HLA and/or TCR" or "ZFN to inhibit HLA and/or TCR" refer to a zinc finger nuclease, an artificial nuclease which can be used to edit the HLA and/or TCR gene.

Like a TALEN, a ZFN comprises a FokI nuclease domain (or derivative thereof) fused to a DNA-binding domain. In the case of a ZFN, the DNA-binding domain comprises one or more zinc fingers. Carroll et al. (2011) *Genetics Society of America* 188: 773-782; and Kim et al. (1996) *Proc. Natl. Acad. Sci. USA* 93: 1156-1160.

A zinc finger is a small protein structural motif stabilized by one or more zinc ions. A zinc finger can comprise, for example, Cys2His2, and can recognize an approximately 3-bp sequence. Various zinc fingers of known specificity can be combined to produce multi-finger polypeptides which recognize about 6, 9, 12, 15 or 18-bp sequences. Various selection and modular assembly techniques are available to generate zinc fingers (and combinations thereof) recognizing specific sequences, including phage display, yeast one-hybrid systems, bacterial one-hybrid and two-hybrid systems, and mammalian cells.

Like a TALEN, a ZFN must dimerize to cleave DNA. Thus, a pair of ZFNs are required to target non-palindromic DNA sites. The two individual ZFNs must bind opposite strands of the DNA with their nucleases properly spaced apart. Bitinaite et al. (1998) *Proc. Natl. Acad. Sci. USA* 95: 10570-5.

Also like a TALEN, a ZFN can create a double-stranded break in the DNA, which can create a frame-shift mutation if improperly repaired, leading to a decrease in the expression and amount of HLA and/or TCR in a cell. ZFNs can also be used with homologous recombination to mutate in the HLA or TCR gene.

ZFNs specific to sequences in HLA AND/OR TCR can be constructed using any method known in the art. Cathomen et al. (2008) *Mol. Ther.* 16: 1200-7; and Guo et al. (2010) *J. Mol. Biol.* 400: 96.

NK Cells

In an embodiment, the cells are natural killer cells. These cells can be isolated from patients. In an embodiment, the cells are stable cell lines of natural killer cells, e.g., a stable allogeneic NK-92 cell line available, from Conkwest. These stable NK-92 cell lines were derived from NK-92 cells that were obtained, transfected and cultured using the methods described by Gong et al (April 1994), Leukemia Macmillan Press, Ltd, 8: 652-658, and disclosed in EP1007630, incorporated herein by reference. An NK cell line with properties similar to the NK-92 cell line can also be used. In an embodiment, NK cells from the circulating blood of an individual are obtained by apheresis. In an embodiment, NK cells are engineered to express RCAR, and these engineered RCARN cells can be used to treat a patient other than a patient from whom the NK cells were isolated. Hence, these RCARN cells are "universal" cells in that can be administered to multiple patients without adverse effects. That is to say that NK cells can be isolated from one patient and engineered to express RCAR, thereby producing RCARN cells, and these RCARN cells can then be administered to the same or different patient. NK cells, e.g., NK-92 cells, do not express killer inhibitory receptors, and therefore cannot be inactivated by evading cancer cells. Methods for isolation and use of NK cells (e.g., NK-92 cell lines or similar NK cell lines derived from peripheral blood mononuclear cells from a patient with non-Hodgkins lymphoma) have been described (See Zhang et al (2013) Retargeting NK-92 for anti-melanoma activity by a TCR-like single domain antibody; Immunol Cell Biol. 91: 615-624; Tonn et al. (2013) Treatment of patients with advanced cancer with the natural killer cell-line NK-92, Cytotherapy, 15: 1563-1570.

The NK-92 cell line was found to exhibit the $CD56^{high}$, CD2, CD7, CD11a, CD28, CD45, and CD54 surface markers It furthermore does not display the CD1, CD3, CD4, CD5, CD8, CD10, CD14, CD 16, CD19, CD20, CD23, and CD34 markers Growth of NK-92 cells in culture is dependent upon the presence of recombinant interleukin 2 (rIL-2), with a dose as low as 10 IU/mL being sufficient to maintain proliferation. NK cell lines with similar properties can also be used.

NK-92 cells are readily maintained in culture medium, such as enriched alpha minimum essential medium (MEM, Sigma Chemical Co. St Louis, Mo.) supplemented with fetal calf serum (for example, at 12 5%, Sigma, Chemical Co., St Louis, Mo.), and horse serum (for example, at 12.5%, (Sigma Chemical Co., St Louis, Mo.) Initially, 10M hydrocortisone is required, but in subsequent passages it is found that hydrocortisone may be omitted. In addition, IL-2, such as recombinant human IL-2 (500 U/mL, Chiron, Emeryville, Calif.), is required for long-term growth. When suspension cultures are maintained in this fashion with semiweekly changes of medium, the cells exhibit a doubling time of about 24 h.

NK-92 cells in vitro demonstrate lytic activity against a broad range of malignant target cells. These include cell lines derived from circulating target cells such as acute and chronic lymphoblastic and myelogenous leukemia, lymphoma, myeloma, melanoma, as well as cells from solid tumors such as prostate cancer, neuroblastoma, and breast cancer cell lines.

Other Immune Effector Cells

Figure 8:
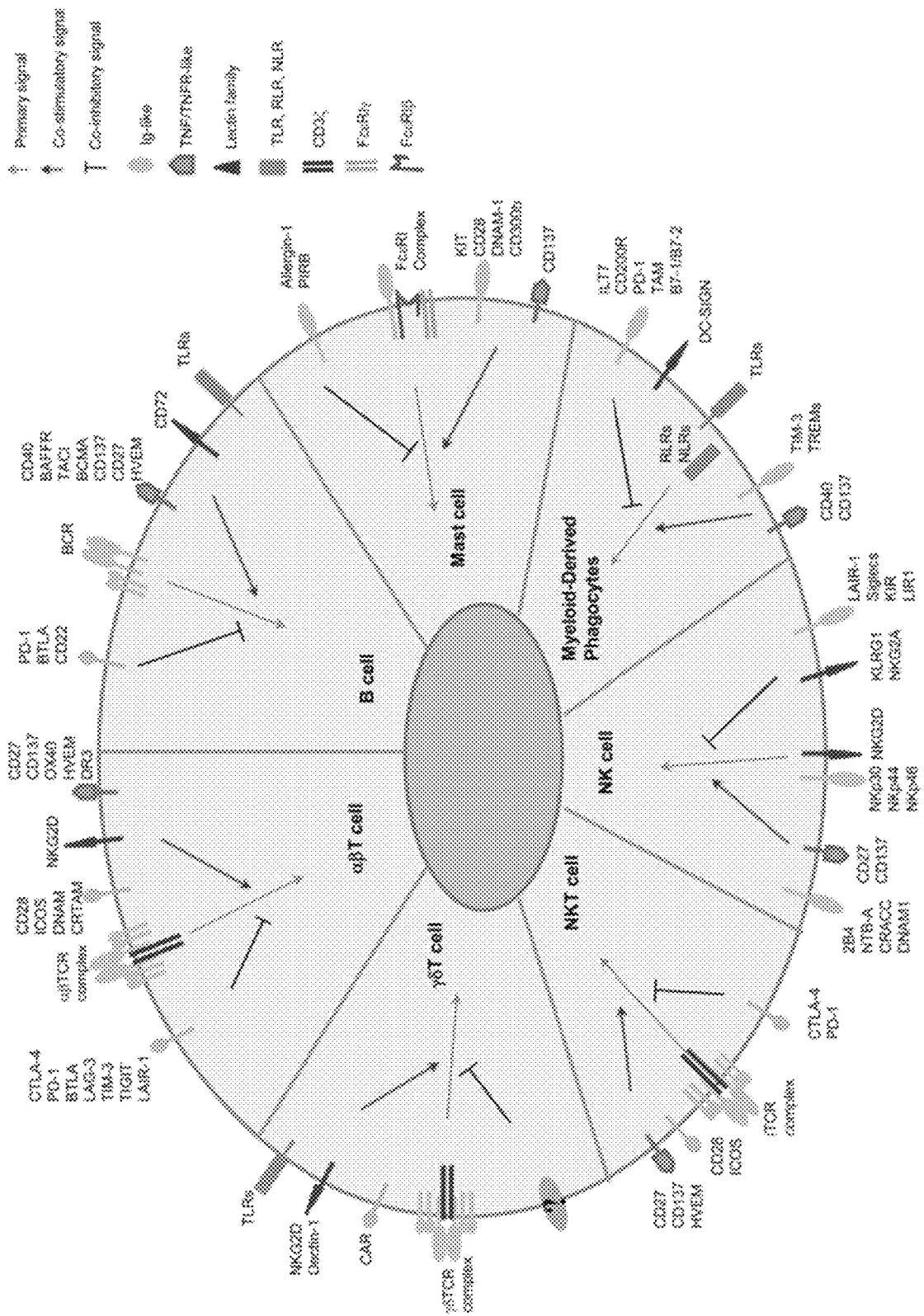
FIG. 8 provides immune effector cells that can be engineered to express RCARs.

In another embodiment, any number of immune effector cells may be isolated and engineered to express RCARs, e.g., B cell, mast cells. Myeloid derived phagocytes, NKT cells, or γδT cells. Exemplary immune effector cells are listed in FIG. 8.

Activation and Expansion of T Cells

In an embodiment, the immune effector cell is a T cell. T cells are activated and expanded generally using methods as described, for example, in U.S. Pat. Nos. 6,352,694; 6,534,055; 6,905,680; 6,692,964; 5,858,358; 6,887,466; 6,905,681; 7,144,575; 7,067,318; 7,172,869; 7,232,566; 7,175,843; 5,883,223; 6,905,874; 6,797,514; 6,867,041; and U.S. Patent Application Publication No. 20060121005.

In an embodiment, the T cells are expanded by contact with a surface having attached thereto an agent that stimulates a CD3/TCR complex associated signal and a ligand that stimulates a costimulatory molecule on the surface of the T cells. In a T cell a costimulatory molecule is a binding partner on a T cell that binds to a costimulatory ligand, mediating a costimulatory response in the T cell, i.e., an MHC class I molecule, e.g., CD28. In particular, T cell populations may be stimulated as described herein, e.g., by contact with an anti-CD3 antibody, or antigen-binding fragment thereof, or an anti-CD2 antibody immobilized on a surface, or by contact with a protein kinase C activator (e.g., bryostatin) in conjunction with a calcium ionophore. For stimulation of an accessory molecule (e.g., CD3) on the surface of the T cells, a ligand that binds the accessory molecule is used. A population of T cells can be expanded with an anti-CD3 antibody and an anti-CD28 antibody under conditions appropriate for stimulating proliferation of the T cells. To stimulate proliferation of either CD4+ T cells or CD8+ T cells, an anti-CD3 antibody and an anti-CD28 antibody would be used. Examples of an anti-CD28 antibody include 9.3, B-T3, XR-CD28 (Diaclone, Besancon, France; (Berg et al., Transplant Proc. 30(8):3975-3977, 1998; Haanen et al., J. Exp. Med. 190(9):13191328, 1999; Garland et al., J. Immunol Meth. 227(1-2):53-63, 1999).

In certain embodiments, the primary activation signal and the costimulatory signal for the T cell may be provided by different protocols. For example, the agents providing each signal may be in solution or coupled to a surface. When coupled to a surface, the agents may be coupled to the same surface (i.e., in "cis" formation) or to separate surfaces (i.e., in "trans" formation). Alternatively, one agent may be coupled to a surface and the other agent in solution. In an embodiment, the agent providing the costimulatory signal is bound to a cell surface and the agent providing the primary activation signal is in solution or coupled to a surface. In certain embodiments, both agents can be in solution. In an embodiment, the agents may be in soluble form, and then cross-linked to a surface, such as a cell expressing Fc receptors or an antibody or other binding agent which will bind to the agents. In this regard, see for example, U.S. Patent Application Publication Nos. 20040101519 and 20060034810 for artificial antigen presenting cells (aAPCs) that are contemplated for use in activating and expanding T cells.

In an embodiment, the two agents are immobilized on beads, either on the same bead, i.e., "cis," or to separate beads, i.e., "trans." By way of example, the agent providing the primary activation signal is an anti-CD3 antibody or an antigen-binding fragment thereof and the agent providing the costimulatory signal is an anti-CD28 antibody or antigen-binding fragment thereof; and both agents are co-immobilized to the same bead in equivalent molecular amounts. In an embodiment, a 1:1 ratio of each antibody bound to the beads for CD4+ T cell expansion and T cell growth is used. In certain embodiments, a ratio of anti CD3:CD28 antibodies bound to the beads is used such that an increase in T cell expansion is observed as compared to the expansion observed using a ratio of 1:1. In an embodiment an increase of from about 1 to about 3 fold is observed as compared to the expansion observed using a ratio of 1:1.

In an embodiment, the ratio of CD3:CD28 antibody bound to the beads ranges from 100:1 to 1:100 and all integer values there between. In an embodiment, more anti-CD28 antibody is bound to the particles than anti-CD3 antibody, i.e., the ratio of CD3:CD28 is less than one. In certain embodiments, the ratio of anti CD28 antibody to anti CD3 antibody bound to the beads is greater than 2:1. In an embodiment, a 1:100 CD3:CD28 ratio of antibody bound to beads is used. In an embodiment, a 1:75 CD3:CD28 ratio of antibody bound to beads is used. In a further embodiment, a 1:50 CD3:CD28 ratio of antibody bound to beads is used. In an embodiment, a 1:30 CD3:CD28 ratio of antibody bound to beads is used. In an embodiment, a 1:10 CD3:CD28 ratio of antibody bound to beads is used. In another embodiment, a 1:3 CD3:CD28 ratio of antibody bound to the beads is used. In yet another embodiment, a 3:1 CD3:CD28 ratio of antibody bound to the beads is used.

Ratios of particles to cells from 1:500 to 500:1 and any integer values in between may be used to stimulate T cells or other target cells. As those of ordinary skill in the art can readily appreciate, the ratio of particles to cells may depend on particle size relative to the target cell. For example, small sized beads could only bind a few cells, while larger beads could bind many. In certain embodiments the ratio of cells to particles ranges from 1:100 to 100:1 and any integer values in-between and in further embodiments the ratio comprises 1:9 to 9:1 and any integer values in between, can also be used to stimulate T cells. The ratio of anti-CD3- and anti-CD28-coupled particles to T cells that result in T cell stimulation can vary as noted above, however certain preferred values include 1:100, 1:50, 1:40, 1:30, 1:20, 1:10, 1:9, 1:8, 1:7, 1:6, 1:5, 1:4, 1:3, 1:2, 1:1, 2:1, 3:1, 4:1, 5:1, 6:1, 7:1, 8:1, 9:1, 10:1, and 15:1 with one preferred ratio being at least 1:1 particles per T cell. In an embodiment, a ratio of particles to cells of 1:1 or less is used. In one particular embodiment, a preferred particle: cell ratio is 1:5. In further embodiments, the ratio of particles to cells can be varied depending on the day of stimulation. For example, in an embodiment, the ratio of particles to cells is from 1:1 to 10:1 on the first day and additional particles are added to the cells every day or every other day thereafter for up to 10 days, at final ratios of from 1:1 to 1:10 (based on cell counts on the day of addition). In one particular embodiment, the ratio of particles to cells is 1:1 on the first day of stimulation and adjusted to 1:5 on the third and fifth days of stimulation. In an embodiment, particles are added on a daily or every other day basis to a final ratio of 1:1 on the first day, and 1:5 on the third and fifth days of stimulation. In an embodiment, the ratio of particles to cells is 2:1 on the first day of stimulation and adjusted to 1:10 on the third and fifth days of stimulation. In an embodiment, particles are added on a daily or every other day basis to a final ratio of 1:1 on the first day, and 1:10 on the third and fifth days of stimulation. One of skill in the art will appreciate that a variety of other ratios may be suitable for use. In particular, ratios will vary depending on particle size and on cell size and type. In an embodiment, the most typical ratios for use are in the neighborhood of 1:1, 2:1 and 3:1 on the first day.

In further embodiments, the cells, e.g., T cells, are combined with agent-coated beads, the beads and the cells are subsequently separated, and then the cells are cultured. In an alternative embodiment, prior to culture, the agent-coated beads and cells are not separated but are cultured together. In a further embodiment, the beads and cells are first concentrated by application of a force, such as a magnetic force, resulting in increased ligation of cell surface markers, thereby inducing cell stimulation.

By way of example, cell surface proteins may be ligated by allowing paramagnetic beads to which anti-CD3 and anti-CD28 are attached (3×28 beads) to contact the T cells. In an embodiment the cells (e.g., $10^4$ to $10^9$ T cells) and beads (e.g., DYNABEADS® M-450 CD3/CD28 T paramagnetic beads at a ratio of 1:1) are combined in a buffer, for example PBS (without divalent cations such as, calcium and magnesium). Again, those of ordinary skill in the art can readily appreciate any cell concentration may be used. For example, the target cell may be very rare in the sample and comprise only 0.01% of the sample or the entire sample (i.e., 100%) may comprise the target cell of interest. In certain embodiments, it may be desirable to significantly decrease the volume in which particles and cells are mixed together (i.e., increase the concentration of cells), to ensure maximum contact of cells and particles. For example, in an embodiment, a concentration of about 2 billion cells/ml is used. In an embodiment, greater than 100 million cells/ml is used. In a further embodiment, a concentration of cells of 10, 15, 20, 25, 30, 35, 40, 45, or 50 million cells/ml is used. In yet an embodiment, a concentration of cells from 75, 80, 85, 90, 95, or 100 million cells/ml is used. In further embodiments, concentrations of 125 or 150 million cells/ml can be used. Using high concentrations can result in increased cell yield, cell activation, and cell expansion. Further, use of high cell concentrations allows more efficient capture of cells that may weakly express target antigens of interest, such as CD28-negative T cells. Such populations of cells may have therapeutic value and would be desirable to obtain in certain embodiments. For example, using high concentration of cells allows more efficient selection of CD8+ T cells that normally have weaker CD28 expression.

In an embodiment, the mixture may be cultured for several hours (about 3 hours) to about 14 days or any hourly integer value in between. In an embodiment, the mixture may be cultured for 21 days. In an embodiment the beads and the T cells are cultured together for about eight days. In an embodiment, the beads and T cells are cultured together for 2-3 days. Several cycles of stimulation may also be desired such that culture time of T cells can be 60 days or more. Conditions appropriate for T cell culture include an appropriate media (e.g., Minimal Essential Media or RPMI Media 1640 or, X-vivo 15, (Lonza)) that may contain factors necessary for proliferation and viability, including serum (e.g., fetal bovine or human serum), interleukin-2 (IL-2), insulin, IFN-$\gamma$, IL-4, IL-7, GM-CSF, IL-10, IL-12, IL-15, TGF$\beta$, and TNF-$\alpha$ or any other additives for the growth of cells known to the skilled artisan. Other additives for the growth of cells include, but are not limited to, surfactant, plasmanate, and reducing agents such as N-acetyl-cysteine and 2-mercaptoethanol. Media can include RPMI 1640, AIM-V, DMEM, MEM, $\alpha$-MEM, F-12, X-Vivo 15, and X-Vivo 20, Optimizer, with added amino acids, sodium pyruvate, and vitamins, either serum-free or supplemented with an appropriate amount of serum (or plasma) or a defined set of hormones, and/or an amount of cytokine(s) sufficient for the growth and expansion of T cells. Antibiotics, e.g., penicillin and streptomycin, are included only in experimental cultures, not in cultures of cells that are to be infused into a subject. The target cells are maintained under conditions necessary to support growth for example, an appropriate temperature (e.g., 37° C.) and atmosphere (e.g., air plus 5% $CO_2$).

T cells that have been exposed to varied stimulation times may exhibit different characteristics. For example, typical blood or apheresed peripheral blood mononuclear cell products have a helper T cell population (TH, CD4+) that is greater than the cytotoxic or suppressor T cell population (TC, CD8+). Ex vivo expansion of T cells by stimulating CD3 and CD28 receptors produces a population of T cells that prior to about days 8-9 consists predominately of TH cells, while after about days 8-9, the population of T cells comprises an increasingly greater population of TC cells. Accordingly, depending on the purpose of treatment, infusing a subject with a T cell population comprising predominately of TH cells may be advantageous. Similarly, if an antigen-specific subset of TC cells has been isolated it may be beneficial to expand this subset to a greater degree.

Further, in addition to CD4 and CD8 markers, other phenotypic markers vary significantly, but in large part, reproducibly during the course of the cell expansion process. Thus, such reproducibility enables the ability to tailor an activated T cell product for specific purposes.

Various assays can be used to evaluate the activity of the RCAR molecule, such as but not limited to, the ability to expand T cells following antigen stimulation, sustain T cell expansion in the absence of re-stimulation, and anti-cancer activities in appropriate animal models. Assays to evaluate the effects of the RCAR, e.g., an EGFRvIII RCAR, are described in further detail below Western blot analysis of RCAR expression in primary T cells can be used to detect their presence using published methods for CARs. See, e.g., Milone et al., Molecular Therapy 17(8): 1453-1464 (2009). Very briefly, T cells (1:1 mixture of $CD4^+$ and $CD8^+$ T cells) expressing the RCARs are expanded in vitro for more than 10 days followed by lysis and SDS-PAGE under reducing conditions. RCARs containing the full length TCR-$\zeta$ cytoplasmic domain and the endogenous TCR-$\zeta$ chain are detected by western blotting using an antibody to the TCR-$\zeta$ chain. The same T cell subsets are used for SDS-PAGE analysis under non-reducing conditions to permit evaluation of covalent dimer formation.

In vitro expansion of RCAR T cells (i.e., RCART cells) following antigen stimulation can be measured by flow cytometry. For example, a mixture of $CD4^+$ and $CD8^+$ T cells are stimulated with $\alpha$CD3/$\alpha$CD28 aAPCs followed by transduction with lentiviral vectors expressing GFP under the control of the promoters to be analyzed. Exemplary promoters include the CMV IE gene, EF-1$\alpha$, ubiquitin C, or phosphoglycerokinase (PGK) promoters. GFP fluorescence is evaluated on day 6 of culture in the $CD4^+$ and/or $CD8^+$ T cell subsets by flow cytometry. See, e.g., Milone et al., Molecular Therapy 17(8): 1453-1464 (2009).

Alternatively, a mixture of $CD4^+$ and $CD8^+$ T cells are stimulated with $\alpha$CD3/$\alpha$CD28 coated magnetic beads on day 0, and transduced with RCAR on day 1 using a bicistronic lentiviral vector expressing RCAR along with eGFP using a 2A ribosomal skipping sequence. Cultures are re-stimulated with RCAR constructs in the presence of antiCD3 and anti-CD28 antibody (K562-BBL-3/28) following washing. Exogenous IL-2 is added to the cultures every other day at 100 IU/ml. GFP T cells are enumerated by flow cytometry using bead-based counting. See, e.g., Milone et al., Molecular Therapy 17(8): 1453-1464 (2009).

Sustained RCAR+ T cell expansion in the absence of re-stimulation can also be measured. See, e.g., Milone et al., Molecular Therapy 17(8): 1453-1464 (2009). Briefly, mean T cell volume (fl) is measured on day 8 of culture using a Coulter Multisizer III particle counter following stimulation with αCD3/αCD28 coated magnetic beads on day 0, and transduction with the indicated RCAR on day 1.

Assessment of cell proliferation and cytokine production has been previously described, e.g., at Milone et al., Molecular Therapy 17(8): 1453-1464 (2009). Briefly, assessment of RCAR-mediated proliferation is performed in microtiter plates by mixing washed T cells with target cells, such as U87MG, BHK or CHO cells expressing a tumor antigen, e.g., EGFRvIII or EGFR wildtype (wt) or CD32 and CD137 (KT32-BBL) for a final T-cell:target cell ratio of 1:1. Anti-CD3 (clone OKT3) and anti-CD28 (clone 9.3) monoclonal antibodies are added to cultures with KT32-BBL cells to serve as a positive control for stimulating T-cell proliferation since these signals support long-term CD8+ T cell expansion ex vivo. T cells are enumerated in cultures using Count-Bright™ fluorescent beads (Invitrogen, Carlsbad, Calif.) and flow cytometry as described by the manufacturer. RCAR+ T cells are identified by GFP expression using T cells that are engineered with eGFP-2A linked RCAR-expressing lentiviral vectors. For RCAR+ T cells not expressing GFP, the RCAR+ T cells are detected with biotinylated recombinant protein, e.g., EGFRvIII and a secondary avidin-PE conjugate. CD4+ and CD8+ expression on T cells are also simultaneously detected with specific monoclonal antibodies (BD Biosciences). Cytokine measurements are performed on supernatants collected 24 hours following re-stimulation using the human TH1/TH2 cytokine cytometric bead array kit (BD Biosciences, San Diego, Calif.) according to the manufacturer's instructions. Fluorescence is assessed using a FACScalibur flow cytometer, and data is analyzed according to the manufacturer's instructions.

Cytotoxicity can be assessed by a standard $^{51}$Cr-release assay. See, e.g., Milone et al., Molecular Therapy 17(8): 1453-1464 (2009). Briefly, target cells (e.g., U87MG, BHK or CHO cells expressing RCAR, e.g., EGFRvIII or EGFR wildtype (wt) are loaded with $^{51}$Cr (as NaCrO$_4$, New England Nuclear, Boston, Mass.) at 37° C. for 2 hours with frequent agitation, washed twice in complete RPMI and plated into microtiter plates. Effector T cells are mixed with target cells in the wells in complete RPMI at varying ratios of effector cell:target cell (E:T). Additional wells containing media only (spontaneous release, SR) or a 1% solution of triton-X 100 detergent (total release, TR) are also prepared. After 4 hours of incubation at 37° C., supernatant from each well is harvested. Released $^{51}$Cr is then measured using a gamma particle counter (Packard Instrument Co., Waltham, Mass.). Each condition is performed in at least triplicate, and the percentage of lysis is calculated using the formula: % Lysis=(ER−SR)/(TR−SR), where ER represents the average $^{51}$Cr released for each experimental condition. Alternative cytotoxicity assays may also be used, such as flow based cytotoxicity assays. Other assays, including those described in the Example section herein as well as those that are known in the art can also be used to evaluate the RCAR constructs.

Therapeutic Application of Target Expressing Diseases and Disorders

Methods for inhibiting the proliferation or reducing a cancer in a cancer antigen-expressing cell population, e.g., an EGFRvIII-expressing cell population, are provided herein. In certain embodiments, the immune effector cell engineered to express a RCAR (i.e., RCARX cells, e.g., RCART cells, RCARN cells, etc) reduces the quantity, number, amount or percentage of cells and/or cancer cells by at least 25%, at least 30%, at least 40%, at least 50%, at least 65%, at least 75%, at least 85%, at least 95%, or at least 99% in a subject with a cancer associated with antigen-expressing cells relative to a negative control. In an embodiment, the subject is a human.

Methods disclosed herein includes a type of cellular therapy where T cells are genetically modified to express RCAR and the resulting CARX cells (i.e., RCARX cells, e.g., RCART cells, RCARN cells, etc) is infused into a recipient in need thereof. The infused RCARX cell is able to kill or inhibit tumor cells in the recipient. Unlike antibody therapies, RCARX cells, e.g., RCART are able to replicate in vivo resulting in long-term persistence that can lead to sustained tumor control. In various embodiments, the RCARX cells e.g., RCART cells, administered to the patient, or their progeny, persist in the patient for at least four months, five months, six months, seven months, eight months, nine months, ten months, eleven months, twelve months, thirteen months, fourteen month, fifteen months, sixteen months, seventeen months, eighteen months, nineteen months, twenty months, twenty-one months, twenty-two months, twenty-three months, two years, three years, four years, or five years after administration of the RCARX cells, e.g., RCART cells, to the patient.

Without wishing to be bound by any particular theory, the anti-cancer immune response elicited by the RCARX cells, e.g., RCART cells, may be an active or a passive immune response, or alternatively may be due to a direct vs. indirect immune response. In an embodiment, the RCARX cells, e.g., RCART cells, exhibit specific proinflammatory cytokine secretion and potent cytolytic activity in response to human cancer cells expressing the target antigen, resist soluble RCAR inhibition, mediate bystander killing and mediate regression of an established human tumor. In an embodiment, the RCARX cells, e.g., RCART cells, may be a type of vaccine for ex vivo immunization and/or in vivo therapy in a mammal. In an embodiment, the mammal is a human.

In embodiments, with respect to ex vivo immunization, at least one of the following occurs in vitro prior to administering the cell into a mammal: i) expansion of the cells, ii) introducing a nucleic acid encoding a RCAR to the cells or iii) cryopreservation of the RCARX cells. Ex vivo procedures are known in the art and are discussed more fully below. Briefly, cells are isolated from a mammal (e.g., a human) and genetically modified (i.e., transduced or transfected in vitro) with a vector expressing a RCAR disclosed herein. The resulting RCARX cell, e.g., RCART cell, can be administered to a mammalian recipient to provide a therapeutic benefit. The mammalian recipient may be a human and the RCARX cell, e.g., RCART cell, can be autologous with respect to the recipient. Alternatively, the cells can be allogeneic, syngeneic or xenogeneic with respect to the recipient.

A procedure for ex vivo expansion of hematopoietic stem and progenitor cells is described in U.S. Pat. No. 5,199,942, incorporated herein by reference, can be applied to the cells described herein. Other suitable methods are known in the art therefore the methods disclosed herein are not limited to any particular method of ex vivo expansion of the cells. Briefly, ex vivo culture and expansion of T cells comprises: (1) collecting CD34+ hematopoietic stem and progenitor cells from a mammal from peripheral blood harvest or bone marrow explants; and (2) expanding such cells ex vivo. In addition to the cellular growth factors described in U.S. Pat.

No. 5,199,942, other factors such as flt3-L, IL-1, IL-3 and c-kit ligand, can be used for culturing and expansion of the cells.

In addition to using a cell-based vaccine in terms of ex vivo immunization, also provided are compositions and methods for in vivo immunization to elicit an immune response directed against an antigen in a patient.

Generally, the cells activated and expanded as described herein may be utilized in the treatment and prevention of diseases that arise in individuals who are immunocompromised. In particular, the RCARX, cells e.g., RCART cells, are used in the treatment of diseases, disorders and conditions associated with expression of a tumor antigen. In certain embodiments, the RCARX, cells e.g., RCART cells, are used in the treatment of patients at risk for developing diseases, disorders and conditions associated with expression of tumor antigen. Thus, the present disclosure provides methods for the treatment or prevention of diseases, disorders and conditions associated with expression of tumor antigen comprising administering to a subject in need thereof, a therapeutically effective amount of RCARX modified cells, e.g., RCART cells.

The RCARX cells, e.g., RCART cells, may be administered either alone, or as a pharmaceutical composition in combination with diluents and/or with other components such as IL-2 or other cytokines or cell populations.

Indications for Treatment with a Redirected Switchable Inhibitor Receptor

In one aspect, the present invention relates to treatment of a subject in vivo using a PD1 CAR such that growth of cancerous tumors is inhibited. A PD1 CAR may be used alone to inhibit the growth of cancerous tumors. Alternatively, PD1 CAR may be used in conjunction with other CARs, immunogenic agents, standard cancer treatments, or other antibodies.

In another aspect, a method of treating a subject, e.g., reducing or ameliorating, a hyperproliferative condition or disorder (e.g., a cancer), e.g., solid tumor, a soft tissue tumor, or a metastatic lesion, in a subject is provided. As used herein, the term "cancer" is meant to include all types of cancerous growths or oncogenic processes, metastatic tissues or malignantly transformed cells, tissues, or organs, irrespective of histopathologic type or stage of invasiveness. Examples of solid tumors include malignancies, e.g., sarcomas, adenocarcinomas, and carcinomas, of the various organ systems, such as those affecting liver, lung, breast, lymphoid, gastrointestinal (e.g., colon), genitourinary tract (e.g., renal, urothelial cells), prostate and pharynx. Adenocarcinomas include malignancies such as most colon cancers, rectal cancer, renal-cell carcinoma, liver cancer, non-small cell carcinoma of the lung, cancer of the small intestine and cancer of the esophagus. In one embodiment, the cancer is a melanoma, e.g., an advanced stage melanoma. Metastatic lesions of the aforementioned cancers can also be treated or prevented using the methods and compositions of the invention. Examples of other cancers that can be treated include bone cancer, pancreatic cancer, skin cancer, cancer of the head or neck, cutaneous or intraocular malignant melanoma, uterine cancer, ovarian cancer, rectal cancer, cancer of the anal region, stomach cancer, testicular cancer, uterine cancer, carcinoma of the fallopian tubes, carcinoma of the endometrium, carcinoma of the cervix, carcinoma of the vagina, carcinoma of the vulva, Hodgkin's Disease, non-Hodgkin's lymphoma, cancer of the esophagus, cancer of the small intestine, cancer of the endocrine system, cancer of the thyroid gland, cancer of the parathyroid gland, cancer of the adrenal gland, sarcoma of soft tissue, cancer of the urethra, cancer of the penis, chronic or acute leukemias including acute myeloid leukemia, chronic myeloid leukemia, acute lymphoblastic leukemia, chronic lymphocytic leukemia, solid tumors of childhood, lymphocytic lymphoma, cancer of the bladder, cancer of the kidney or ureter, carcinoma of the renal pelvis, neoplasm of the central nervous system (CNS), primary CNS lymphoma, tumor angiogenesis, spinal axis tumor, brain stem glioma, pituitary adenoma, Kaposi's sarcoma, epidermoid cancer, squamous cell cancer, T-cell lymphoma, environmentally induced cancers including those induced by asbestos, and combinations of said cancers. Treatment of metastatic cancers, e.g., metastatic cancers that express PD-L1 (Iwai et al. (2005) Int. Immunol. 17:133-144) can be effected using the antibody molecules described herein.

Exemplary cancers whose growth can be inhibited include cancers typically responsive to immunotherapy. Non-limiting examples of cancers for treatment include melanoma (e.g., metastatic malignant melanoma), renal cancer (e.g. clear cell carcinoma), prostate cancer (e.g. hormone refractory prostate adenocarcinoma), breast cancer, colon cancer and lung cancer (e.g. non-small cell lung cancer). Additionally, refractory or recurrent malignancies can be treated using the molecules described herein. In one embodiment, the subject can be administered an agent which reduces or ameliorates a side effect associated with the administration of a CAR-expressing cell. Side effects associated with the administration of a CAR-expressing cell include, but are not limited to CRS, and hemophagocytic lymphohistiocytosis (HLH), also termed Macrophage Activation Syndrome (MAS). Symptoms of CRS include high fevers, nausea, transient hypotension, hypoxia, and the like. CRS may include clinical constitutional signs and symptoms such as fever, fatigue, anorexia, myalgias, arthalgias, nausea, vomiting, and headache. CRS may include clinical skin signs and symptoms such as rash. CRS may include clinical gastrointestinal signs and symptoms such as nausea, vomiting and diarrhea. CRS may include clinical respiratory signs and symptoms such as tachypnea and hypoxemia. CRS may include clinical cardiovascular signs and symptoms such as tachycardia, widened pulse pressure, hypotension, increased cardiac output (early) and potentially diminished cardiac output (late). CRS may include clinical coagulation signs and symptoms such as elevated d-dimer, hypofibrinogenemia with or without bleeding. CRS may include clinical renal signs and symptoms such as azotemia. CRS may include clinical hepatic signs and symptoms such as transaminitis and hyperbilirubinemia. CRS may include clinical neurologic signs and symptoms such as headache, mental status changes, confusion, delirium, word finding difficulty or frank aphasia, hallucinations, tremor, dymetria, altered gait, and seizures. Accordingly, the methods described herein can comprise administering a CAR-expressing cell described herein to a subject and further administering one or more agents to manage elevated levels of a soluble factor resulting from treatment with a CAR-expressing cell. In one embodiment, the soluble factor elevated in the subject is one or more of IFN-γ, TNFα, IL-2 and IL-6. In an embodiment, the factor elevated in the subject is one or more of IL-1, GM-CSF, IL-10, IL-8, IL-5 and fraktalkine. Therefore, an agent administered to treat this side effect can be an agent that neutralizes one or more of these soluble factors. In one embodiment, the agent that neutralizes one or more of these soluble forms is an antibody or antigen binding fragment thereof. Examples of such agents include, but are not limited to a steroid (e.g., corticosteroid), an inhibitor of TNFα, and an inhibitor of IL-6.

An example of a TNFα inhibitor is an anti-TNFα antibody molecule such as, infliximab, adalimumab, certolizumab pegol, and golimumab. Another example of a TNFα inhibitor is a fusion protein such as entanercept. Small molecule inhibitor of TNFα include, but are not limited to, xanthine derivatives (e.g. pentoxifylline) and bupropion. An example of an IL-6 inhibitor is an anti-IL-6 antibody molecule such as tocilizumab (toc), sarilumab, elsilimomab, CNTO 328, ALD518/BMS-945429, CNTO 136, CPSI-2364, CDP6038, VX30, ARGX-109, FE301, and FM101. In one embodiment, the anti-IL-6 antibody molecule is tocilizumab. An example of an IL-1R based inhibitor is anakinra.

Pharmaceutical Compositions and Treatments

Pharmaceutical compositions may comprise a RCARX cells e.g., RCART cells or RCARN cells, in combination with one or more pharmaceutically or physiologically acceptable carriers, diluents or excipients. Such compositions may comprise buffers such as neutral buffered saline, phosphate buffered saline and the like; carbohydrates such as glucose, mannose, sucrose or dextrans, mannitol; proteins; polypeptides or amino acids such as glycine; antioxidants; chelating agents such as EDTA or glutathione; adjuvants (e.g., aluminum hydroxide); and preservatives. In an embodiment, the pharmaceutical compositions are formulated for intravenous administration.

Pharmaceutical compositions may be administered in a manner appropriate to the disease to be treated (or prevented). The quantity and frequency of administration will be determined by such factors as the condition of the patient, and the type and severity of the patient's disease, although appropriate dosages may be determined by clinical trials.

When "an immunologically effective amount," "an anti-cancer effective amount," "a cancer-inhibiting effective amount," or "therapeutic amount" is indicated, the precise amount of the compositions to be administered can be determined by a physician with consideration of individual differences in age, weight, disease state, e.g., tumor size, extent of infection or metastasis, and condition of the patient (subject). In embodiments, a pharmaceutical composition comprising the RCARX cells, e.g., RCART cells, described herein may be administered at a dosage of $10^4$ to $10^9$ cells/kg body weight, in some instances $10^5$ to $10^6$ cells/kg body weight, including all integer values within those ranges. T cell compositions may also be administered multiple times at these dosages.

In certain embodiments RCARX cells, e.g., RCART are activated and expanded to therapeutic levels, and are administered to a patient by using infusion techniques that are commonly known in immunotherapy (see, e.g., Rosenberg et al., New Eng. J. of Med. 319:1676, 1988). The optimal dosage and treatment regime for a particular patient can be determined by one skilled in the art of medicine by monitoring the patient for signs of disease and adjusting the treatment accordingly.

In embodiments, the RCARX cells with RCARs comprising one or more switch domains, generate an intracellular signal that promotes an immune effector response in the presence of a dimerization molecule, e.g., a small molecule heterodimerization molecule, e.g., RAD001 or AP21967.

The administration of the dimerization molecule may be carried out in any convenient manner, including by aerosol inhalation, injection, ingestion, transfusion, or implantation. In an embodiment the dimerization molecule is administered orally. The dimerization molecule may be administered to a patient transarterially, subcutaneously, intradermally, intratumorally, intranodally, intramedullary, intramuscularly, by intravenous (i.v.) injection, or intraperitoneally. In an embodiment, the dimerization molecule is administered orally, e.g., in tablet form. In an embodiment, the dimerization molecule is administered by intradermal or subcutaneous injection. In an embodiment, an embodiment the dimerization molecule is administered by i.v. injection.

In an embodiment, the dimerization molecule is administered after the RCARX cells, e.g., RCART cells, have been infused into the patient. In one embodiment, the dimerization molecule is administered one day after the RCARX cells, e.g., RCART cells, have been infused into the patient. In one embodiment, the dimerization molecule is administered 2, 3, 4, 5, 6, 7, 8, 9, 10, 11, 12, 13, 14, 15, 16, 17, 18, 19, 20, 21, 22, 23, 24, 25, 26, 27, 28, 29, or 30 days after the RCARX cells, e.g., RCART cells, have been infused into the patient. In an embodiment the dimerization molecule is administered after administration of the RCARX cells, e.g., on or after 1, 2, 3, 4, 5, 6, 7, 8, 9, 10, 11, 12, 16, 17, 18, 19, 20, 21, 22, or 23 hours, or on or after 1, 2, 3, 4, 5, 6, 7 or 8 days, after administration of the RCARX cells. In one embodiment, the dimerization molecule is administered more than once to the after the RCARX cells, e.g., RCART cells, have been infused into the patient, e.g., based on a dosing schedule tailored for the patient, e.g., administration of the dimerization molecule on a bi-weekly, weekly, monthly, 6-monthly, yearly basis. In an embodiment, dosing of the dimerization molecule will be daily, every other day, twice a week, or weekly, but in embodiments will not exceed 5 mg, 10 mg, 15 mg, 20 mg, 30 mg, 40 mg, or 50 mg, weekly. In an embodiment, the dimerization molecule is dosed continuously, e.g. by use of a pump, e.g., a wearable pump. In an embodiment continuous administration lasts for at least 4 hours, 12 hours, 24 hours, 2 days, 3 days, 4 days or 5 days. In an embodiment, a FKBP-FRB heterodimerization molecule, e.g., rapamycin, or a rapalog, e.g., AP21967 or RAD001, is administered at a dose of no greater than about 0.5 mg in a 24 hr period.

In an embodiment a dimerization molecule is administered at the same time, e.g., on the same day, as the administration of the RCARX cells.

In an embodiment, the patient is monitored after the dimerization molecule has been administered for a decrease in cancer. If the cancer reappears, the dimerization molecule can be readministered at that time. In an embodiment, a subject will undergo additional or subsequent, e.g., second, third or fourth, RCART cell infusions, e.g., at weekly or monthly intervals, or as determined to be needed. In an embodiment, a subsequent administration is accompanied with, or followed by, administration of the dimerization molecule. In an embodiment subsequent administration of RCARX, or dimerization molecule continues, e.g., until tumor burden is cleared, no additional benefit is perceived, or a preselected criterion is met. In an embodiment, a method disclosed herein comprises administration of cellular therapy wherein T cells are genetically modified to express a chimeric antigen receptor (CAR). The CAR T cell is infused to a recipient in need thereof. The infused cell is able to kill tumor cells in the recipient but only in the presence of the dimerization molecule. In addition, in the presence of the dimerization molecule, RCART cells will expand and replicate in vivo upon engagement of their target antigen which will lead to sustained tumor control. Cytokine release during tumor cell killing may also be measured in the serum. This expansion and cytokine production can be measured in the patient by routine blood draws and subsequent analysis of CAR expression and serum cytokine levels. This method will also inform one skilled in the art to modify dosing strategy of the dimerization molecule to maintain the functional RCART cell population. It is envisioned that dosing of the dimerization molecule will continue as long as tumor burden is being reduced.

Dosages of dimerization molecules depend on the type of dimerization molecule being used and the PK properties of the individual dimerization molecules.

Also provided herein are compositions comprising a FKBP-FRB heterodimerization molecule, e.g., rapamycin, or a rapalog, e.g., AP21967 or RAD001 at a concentration of about 0.005-1.5 mg, about 0.005-1.5 mg, about 0.01-1 mg, about 0.01-0.7 mg, about 0.01-0.5 mg, or about 0.1-0.5 mg. In a further aspect the present invention provides compositions comprising a FKBP-FRB heterodimerization molecule, e.g., rapamycin, or a rapalog, e.g., AP21967 or RAD001 at a concentration of 0.005-1.5 mg, 0.005-1.5 mg, 0.01-1 mg, 0.01-0.7 mg, 0.01-0.5 mg, or 0.1-0.5 mg. More particularly, in one aspect, the invention provides compositions comprising a FKBP-FRB heterodimerization molecule, e.g., rapamycin, or a rapalog, e.g., AP21967 or RAD001 at a dose of about 0.005 mg, 0.006 mg, 0.007 mg, 0.008 mg, 0.009 mg, 0.01 mg, 0.02 mg, 0.03 mg, 0.04 mg, 0.05 mg, 0.06 mg, 0.07 mg, 0.08 mg, 0.09 mg, 0.1 mg, 0.2 mg, 0.3 mg, 0.4 mg, 0.5 mg, 0.6 mg, 0.7 mg, 0.8 mg, 0.9 mg, or 1.0 mg. In one aspect, the FKBP-FRB heterodimerization molecule, e.g., rapamycin, or a rapalog, e.g., AP21967 or RAD001 is at a dose of 0.5 mg or less. In a still further aspect, a FKBP-FRB heterodimerization molecule, e.g., rapamycin, or a rapalog, e.g., AP21967 or RAD001 is at a dose of about 0.5 mg. In a further aspect, the invention provides compositions comprising a FKBP-FRB heterodimerization molecule, e.g., rapamycin, or a rapalog, e.g., AP21967 or RAD001 at a dose of 0.005 mg, 0.006 mg, 0.007 mg, 0.008 mg, 0.009 mg, 0.01 mg, 0.02 mg, 0.03 mg, 0.04 mg, 0.05 mg, 0.06 mg, 0.07 mg, 0.08 mg, 0.09 mg, 0.1 mg, 0.2 mg, 0.3 mg, 0.4 mg, 0.5 mg, 0.6 mg, 0.7 mg, 0.8 mg, 0.9 mg, or 1.0 mg. In one aspect, a FKBP-FRB heterodimerization molecule, e.g., rapamycin, or a rapalog, e.g., AP21967 or RAD001 is at a dose of 0.5 mg or less. In a still further aspect, a FKBP-FRB heterodimerization molecule, e.g., rapamycin, or a rapalog, e.g., AP21967 or RAD001 is at a dose of 0.5 mg. In a further aspect, the invention relates to compositions comprising an rapamycin, or a rapamycin analog, that is not RAD001, in an amount that is bioequivalent to the specific amounts or doses specified for RAD001. In a further aspect, the invention relates to compositions comprising a FKBP-FRB heterodimerization molecule, e.g., rapamycin, or a rapalog, e.g., AP21967 or RAD001 in an amount sufficient to promote RCART activation following target engagement, as measured by NFAT activation, tumor cell killing or cytokine production. In an embodiment the dose of the a FKBP-FRB heterodimerization molecule, e.g., rapamycin, or a rapalog, e.g., AP21967 or RAD001 is not immunosuppressive. In an embodiment a dose provided here is designed to produce only partial or minimal inhibition of mTOR activity.

Also within the invention are unit dosage forms of a heterodimerization molecule, e.g., rapamycin, or a rapalog, e.g., AP21967 or RAD001, that contain 25%, 50%, 100%, 150% or 200% of any daily dosage referred to herein.

A FKBP-FRB heterodimerization molecule, e.g., rapamycin, or a rapalog, e.g., AP21967 or RAD001, can be administered at a dose that results in a therapeutic effect.

In an embodiment, rapamycin, or a rapalog, e.g., AP21967 or RAD001, is administered at a dose of about 0.005-1.5 mg daily, about 0.01-1 mg daily, about 0.01-0.7 mg daily, about 0.01-0.5 mg daily, or about 0.1-0.5 mg daily.

In an embodiment, rapamycin, or a rapalog, e.g., AP21967 or RAD001, is administered at a dose of 0.005-1.5 mg daily, 0.005-1.5 mg daily, 0.01-1 mg daily, 0.01-0.7 mg daily, 0.01-0.5 mg daily, or 0.1-0.5 mg daily.

In an embodiment, rapamycin, or a rapalog, e.g., AP21967 or RAD001, is administered at a dose of about: 0.005 mg daily, 0.006 mg daily, 0.007 mg daily, 0.008 mg daily, 0.009 mg daily, 0.01 mg daily, 0.02 mg daily, 0.03 mg daily, 0.04 mg daily, 0.05 mg daily, 0.06 mg daily, 0.07 mg daily, 0.08 mg daily, 0.09 mg daily, 0.1 mg daily, 0.2 mg daily, 0.3 mg daily, 0.4 mg daily, 0.5 mg daily, 0.6 mg daily, 0.7 mg daily, 0.8 mg daily, 0.9 mg daily, or 1.0 mg daily.

In an embodiment, rapamycin, or a rapalog, e.g., AP21967 or RAD001, is administered at a dose of 0.5 mg daily, or less than 0.5 mg daily.

In an embodiment, rapamycin, or a rapalog, e.g., AP21967 or RAD001, is administered at a dose of about 0.1-20 mg weekly, about 0.5-15 mg weekly, about 1-10 mg weekly, or about 3-7 mg weekly.

In an embodiment, rapamycin, or a rapalog, e.g., AP21967 or RAD001, is administered at a dose of 0.1-20 mg weekly, 0.5-15 mg weekly, 1-10 mg weekly, or 3-7 mg weekly.

In an embodiment, rapamycin, or a rapalog, e.g., AP21967 or RAD001, is administered at a dose of no greater than about: 0.7 mg in a 24 hour period; 0.5 mg in a 24 hour period. In some embodiments, rapamycin, or a rapalog, e.g., AP21967 or RAD001, can be administered at a dose of or 0.5 mg, or less daily. In some embodiments, rapamycin, or a rapalog, e.g., AP21967 or RAD001,01 can be administered at a dose of 0.5 mg daily.

In an embodiment, rapamycin, or a rapalog, e.g., AP21967 or RAD001, is administered at a dose of about: 0.1 mg weekly, 0.2 mg weekly, 0.3 mg weekly, 0.4 mg weekly, 0.5 mg weekly, 0.6 mg weekly, 0.7 mg weekly, 0.8 mg weekly, 0.9 mg weekly, 1 mg weekly, 2 mg weekly, 3 mg weekly, 4 mg weekly, 5 mg weekly, 6 mg weekly, 7 mg weekly, 8 mg weekly, 9 mg weekly, 10 mg weekly, 11 mg weekly, 12 mg weekly, 13 mg weekly, 14 mg weekly, 15 mg weekly, 16 mg weekly, 17 mg weekly, 18 mg weekly, 19 mg weekly, or 20 mg weekly.

In an embodiment, the invention can utilize an FKBP-FRB heterodimerization molecule other than RAD001 in an amount that is bioequivalent, in terms of its ability to activate a RCAR, to the specific amounts or doses specified for RAD001.

In an embodiment, rapamycin, or a rapalog, e.g., AP21967 or RAD001, is administered at a dosage of about: 30 pM to 4 nM; 50 pM to 2 nM; 100 pM to 1.5 nM; 200 pM to 1 nM; 300 pM to 500 pM; 50 pM to 2 nM; 100 pM to 1.5 nM; 200 pM to 1 nM; or 300 pM to 500 pM.

In an embodiment, rapamycin, or a rapalog, e.g., AP21967 or RAD001, is administered at a dosage of about: 30 pM, 40 pM, 50 pM, 60 pM, 70 pM, 80 pM, 90 pM, 100 pM, 150 pM, 200 pM, 250 pM, 300 pM, 350 pM, 400 pM, 450 pM, 500 pM, 550 pM, 600 pM, 650 pM, 700 pM, 750 pM, 800 pM, 850 pM, 900 pM, 950 pM, 1 nM, 1.5 nM, 2 nM, 2.5 nM, 3 nM, 3.5 nM, or 4 nM.

In an embodiment, rapamycin, or a rapalog, e.g., AP21967 or RAD001, is administered to a subject at a dosage that provides a target trough level. As used herein, the term "trough level" refers to the concentration of a drug in plasma just before the next dose, or the minimum drug concentration between two doses. In an embodiment, the trough level is significantly lower than trough levels associated with dosing regimens used in organ transplant and cancer patients. In an embodiment rapamycin, or a rapalog, e.g., AP21967 or RAD001, is administered to result in a trough level that is less than ½, ¼, 1/10, or 1/20 of the trough level that results in immunosuppression or an anticancer effect. In an embodiment rapamycin, or a rapalog, e.g., AP21967 or RAD001, is administered to result in a trough level that is less than ½, ¼, 1/10, or 1/20 of the trough level provided on the FDA approved packaging insert for use in immunosuppression or an anticancer indications.

In an embodiment, a heterodimerization molecule, e.g., rapamycin, or a rapalog, e.g., AP21967 or RAD001, is administered in sufficient amounts to provide a trough level in a selected range. In an embodiment the range is selected from between: 0.1 and 4.9 ng/ml; 2.4 and 4.9 ng/ml; about 0.1 and 2.4 ng/ml; about 0.1 and 1.5 ng/ml.

In an embodiment, a heterodimerization molecule, e.g., rapamycin, or a rapalog, e.g., AP21967 or RAD001, is administered in sufficient amounts to provide a trough level of about: is 0.1 ng/ml; 0.2 ng/ml; 0.3 ng/ml; 0.4 ng/ml; 0.5 ng/ml; 0.6 ng/ml; 0.7 ng/ml; 0.8 ng/ml; 0.9 ng/ml; 1.0 ng/ml; 1.1 ng/ml; 1.2 ng/ml; 1.3 ng/ml; 1.4 ng/ml; and 1.5 ng/ml.

In an embodiment, a heterodimerization molecule, e.g., rapamycin, or a rapalog, e.g., AP21967 or RAD001, is administered in sufficient amounts to provide a trough level of less than: 5 ng/ml. 2.5 ng/ml; 2 ng/ml; 1.9 ng/ml; 1.8 ng/ml; 1.7 ng/ml; 1.6 ng/ml; 1.5 ng/ml; 1.4 ng/ml; 1.3 ng/ml, 1.2 ng/ml; 1.1 ng/ml; 1.0 ng/ml; 0.9 ng/ml; 0.8 ng/ml; 0.7 ng/ml; 0.6 ng/ml; 0.5 ng/ml; 0.4 ng/ml; 0.3 ng/ml; 0.2 ng/ml; or 0.1 ng/ml.

Also within the invention are unit dosage forms of a heterodimerization molecule, e.g., rapamycin, or a rapalog, e.g., AP21967 or RAD001, that contain any daily dosage referred to herein.

In an embodiment, an RCAR, e.g., an RCART, cell is treated with dimerization molecule after removal from the body but before introduction into the subject.

In an embodiment, an RCAR, e.g., an RCART, cell is treated with dimerization molecule after ex vivo generation of the RCAR and prior to introduction into the subject.

In an embodiment the RCAR comprises a GyrB-GyrB based switch, e.g., an GyrB-GyrB based switch described herein, e.g., an GyrB-GyrB based switch as described herein, e.g., in the Dimerization Switch Module.

In an embodiment the RCAR comprises a GAI-GID1 based switch, e.g., an GAI-GID1 based switch described herein, e.g., an GAI-GID1 based switch as described herein, e.g., in the Dimerization Switch Module.

In an embodiment the RCAR comprises a Halotag/SNAP-tag based switch, e.g., a Halotag/SNAP-tag based switch described herein, e.g., a Halotag/SNAP-tag based switch as described herein, e.g., in the Dimerization Switch Module.

In an embodiment, the RCARX, e.g., RCART, cell is contacted with dimerization molecule at a concentration selected from the following:

2,000-0.01 nM; 2,000-100 nM; 1000-0.01 nM; 500-0.01 nM; 100-0.01 nM; 100-0.05 nM; 100-0.5 nM; 100-1 nM 100-10 nM; 25-0.01 nM; 20 to 0.01 nM; 10-0.01 nM; 10-0.1 nM; or 10-1.0 nM.

In an embodiment, the RCAR comprises a FKBP-FRAP based switch, e.g., an FKBP-FRAP based switch described herein, e.g., an FKBP-FRAP based switch as described herein, e.g., in the Dimerization Switch Module.

In an embodiment, the RCARX, e.g., RCART, comprises an FKBP-FRAP dimerization switch and the dimerization molecule is rapamycin or a rapamycin analog, e.g., a rapamycin analog disclosed herein, e.g., RAD001 or AP21967, and is the RCARX cell is contacted with dimerization molecule at a concentration selected from the following:

2,000-0.01 nM; 2,000-100 nM; 1000-0.01 nM; 500-0.01 nM; 100-0.01 nM; 100-0.05 nM; 100-0.5 nM; 100-1 nM 100-10 nM; 25-0.01 nM; 20 to 0.01 nM; 10-0.01 nM; 10-0.1 nM; or 10-1.0 nM.

In further embodiments, the RCARX cells, e.g., RCART cells may be used in a treatment regimen in combination with chemotherapy, radiation, immunosuppressive agents, such as cyclosporin, azathioprine, methotrexate, mycophenolate, and FK506, antibodies, or other immunoablative agents such as CAMPATH, anti-CD3 antibodies or other antibody therapies, cytoxin, fludarabine, cyclosporin, FK506, rapamycin, mycophenolic acid, steroids, FR901228, cytokines, and irradiation. Drugs that inhibit either the calcium dependent phosphatase calcineurin (cyclosporine and FK506) or inhibit the p70S6 kinase that is important for growth factor induced signalling (rapamycin). (Liu et al., Cell 66:807-815, 1991; Henderson et al., Immun. 73:316-321, 1991; Bierer et al., Curr. Opin. Immun. 5:763-773, 1993) can also be used.

In a further embodiment, the cell compositions are administered to a patient in conjunction with (e.g., before, simultaneously or following) bone marrow transplantation, T cell ablative therapy using either chemotherapy agents such as, fludarabine, external-beam radiation therapy (XRT), cyclophosphamide, or antibodies such as OKT3 or CAMPATH. In an embodiment, the cell compositions are administered following B-cell ablative therapy such as agents that react with CD20, e.g., Rituxan. For example, in an embodiment, subjects may undergo standard treatment with high dose chemotherapy followed by peripheral blood stem cell transplantation. In certain embodiments, following the transplant, subjects receive an infusion of the expanded immune cells described herein. In an embodiment where RCARX cells, e.g., RCART cells, are administered post-transplant, the immune effector cells, e.g., T cells, used to make the RCARX cells, e.g., RCART cells, are obtained from the subject after transplant. In an embodiment, the immune effector cells, e.g., T cells, used to make the RCARX, e.g., RCART cell, are of donor origin, e.g., they are derived from donor cells implanted in the subject.

In an additional embodiment, expanded cells are administered before or following surgery. In an embodiment, RCARX, e.g., RCART cells, are administered to the subject after surgery that debulks the tumor.

In a particular exemplary embodiment, subjects may undergo leukapheresis, wherein leukocytes are collected, enriched, or depleted ex vivo to select and/or isolate the cells of interest, e.g., T cells. These T cell isolates may be expanded by methods known in the art and treated such that one or more RCAR constructs of the disclosed herein may be introduced, thereby creating RCART cell. Subjects in need thereof may subsequently undergo standard treatment with high dose chemotherapy followed by peripheral blood stem cell transplantation. In certain embodiments, following or concurrent with the transplant, subjects receive an infusion of the expanded RCART cells disclosed herein. In an additional embodiment, expanded cells are administered before or following surgery.

Adjunctive Treatment with a Low, Immune Enhancing, Dose of an mTOR Inhibitor.

As used herein, the term "mTOR inhibitor" refers to a compound or ligand, or a pharmaceutically acceptable salt thereof, which inhibits the mTOR kinase in a cell. In an embodiment an mTOR inhibitor is an allosteric inhibitor. In an embodiment an mTOR inhibitor is a catalytic inhibitor.

The administration of a low, immune enhancing dose of an mTOR inhibitor can be combined with the administration of RCAR cells described herein, e.g., immune effector cells (e.g., T cells or NK cells) engineered to express a Regulatable Chimeric Antigen Receptor (RCAR).

Administration of a low, immune enhancing, dose of an mTOR inhibitor can optimize the performance of immune effector cells in the subject. Depending on the timing and dosage of the mTOR inhibitor, the performance of harvested T cells, non-harvested T cells, or both can be optimized.

While not wishing to be bound by theory, it is believed that treatment with a low, immune enhancing, dose (e.g., a dose that is insufficient to completely suppress the immune system but sufficient to improve immune function) is accompanied by a decrease in PD-1 positive T cells or an increase in PD-1 negative cells, at least transiently, as compared to a non-treated subject. PD-1 positive T cells, but not PD-1 negative T cells, can be exhausted by engagement with cells which express a PD-1 ligand, e.g., PD-L1 or PD-L2. In addition or alternatively, again while not wishing to be bound by theory, it is believed that a low, immune enhancing, dose of an mTOR inhibitor can increase naive T cell numbers, e.g., at least transiently, e.g., as compared to a non-treated subject. Alternatively or additionally, again while not wishing to be bound by theory, it is believed that treatment with an mTOR inhibitor after a sufficient amount of time or sufficient dosing results in one or more of the following:

an increase in the expression of one or more of the following markers: $CD62L^{high}$, $CD127^{high}$, $CD27^+$, and BCL2, e.g., on memory T cells, e.g., memory T cell precursors;

a decrease in the expression of KLRG1, e.g., on memory T cells, e.g., memory T cell precursors; and an increase in the number of memory T cell precursors, e.g., cells with any one or combination of the following characteristics: increased $CD62L^{high}$, increased $CD127^{high}$, increased $CD27^+$, decreased KLRG1, and increased BCL2;

and wherein any of the changes described above occurs, e.g., at least transiently, e.g., as compared to a non-treated subject.

Memory T cell precursors are memory T cells that are early in the differentiation program. For example, memory T cells have one or more of the following characteristics: increased $CD62L^{high}$, increased $CD127^{high}$, increased $CD27^+$, decreased KLRG1, and/or increased BCL2.

In an embodiment, administration of a low, immune enhancing dose of an mTOR inhibitor, e.g., an allosteric inhibitor, e.g., RAD001, or a catalytic inhibitor, is initiated prior to administration (e.g., prior to harvest or after harvest of the immune effector cells, e.g., T cells engineered to express a RCAR, but prior to administration of the RCAR cells) of a RCAR cell described herein, e.g., an immune effector cells, e.g., T cells, engineered to express a RCAR. While not wishing to be bound by theory, it is believed that in an embodiment, one or more of the following occurs:

a decrease in the number of PD-1 positive immune effector cells;

an increase in the number of PD-1 negative immune effector cells;

an increase in the ratio of PD-1 negative immune effector cells/PD-1 positive immune effector cells;

an increase in the number of naive T cells;

an increase in the expression of one or more of the following markers: $CD62L^{high}$, $CD127^{high}$, $CD27^+$, and BCL2, e.g., on memory T cells, e.g., memory T cell precursors;

a decrease in the expression of KLRG1, e.g., on memory T cells, e.g., memory T cell precursors; or an increase in the number of memory T cell precursors, e.g., cells with any one or combination of the following characteristics: increased $CD62L^{high}$, increased $CD127^{high}$, increased $CD27^+$, decreased KLRG1, and increased BCL2;

and wherein any of the changes described above occurs, e.g., at least transiently, e.g., as compared to a non-treated subject.

Administration of a low, immune enhancing dose of an mTOR inhibitor can enhance the performance of immune effector cells, e.g., T cells, to be engineered to express a RCAR. In an embodiment, a low, immune enhancing dose of an mTOR inhibitor is administered prior to harvesting immune effector cells, e.g., T cells, to be engineered to express a RCAR.

In one embodiment, the immune effector cell, e.g., T cell, to be engineered to express a RCAR, is harvested at least 5, 10, 15, 20, 25, 30, 35, 40, 45, 50, 55, or 60 days after initiation, or completion, of dosing with the low, immune enhancing, dose of an mTOR inhibitor.

In an embodiment, the low, immune enhancing, dosing of an mTOR inhibitor is initiated, or completed, sufficiently prior to harvest of immune effector cells, e.g., T cells, to be engineered to express a RCAR such that performance is enhanced. While not wishing to be bound by theory, it is believed that in an embodiment, one or more of the following occurs, e.g., occurs in the harvested cells or in the engineered cells (or in non-harvested cells, or in both):

a decrease in the number of PD-1 positive immune effector cells;

an increase in the number of PD-1 negative immune effector cells;

an increase in the ratio of PD-1 negative immune effector cells/PD-1 positive immune effector cells;

an increase in the number of naive T cells;

an increase in the expression of one or more of the following markers: $CD62L^{high}$, $CD127^{high}$, $CD27^+$, and BCL2, e.g., on memory T cells, e.g., memory T cell precursors;

a decrease in the expression of KLRG1, e.g., on memory T cells, e.g., memory T cell precursors; or an increase in the number of memory T cell precursors, e.g., cells with any one or combination of the following characteristics: increased $CD62L^{high}$, increased $CD127^{high}$, increased $CD27^+$, decreased KLRG1, and increased BCL2;

and wherein any of the changes described above occurs, e.g., at least transiently, e.g., as compared to a non-treated subject.

In an embodiment, administration of a low, immune enhancing, dose of an mTOR inhibitor, e.g., an allosteric inhibitor, e.g., RAD001, or a catalytic inhibitor, is initiated after harvest of immune effector cells, e.g., T cells, engineered to express a RCAR. While not wishing to be bound by theory, it is believed that in an embodiment, one or more of the following occurs:

a decrease in the number of PD-1 positive immune effector cells;

an increase in the number of PD-1 negative immune effector cells;

an increase in the ratio of PD-1 negative immune effector cells/PD-1 positive immune effector cells;

an increase in the number of naive T cells;

an increase in the expression of one or more of the following markers: $CD62L^{high}$, $CD127^{high}$, $CD27^+$, and BCL2, e.g., on memory T cells, e.g., memory T cell precursors;

a decrease in the expression of KLRG1, e.g., on memory T cells, e.g., memory T cell precursors; or an increase in the number of memory T cell precursors, e.g., cells with any one or combination of the following characteristics: increased $CD62L^{high}$, increased $CD127^{high}$, increased $CD27^+$, decreased KLRG1, and increased BCL2;

and wherein any of the changes described above occurs, e.g., at least transiently, e.g., as compared to a non-treated subject.

In an embodiment, administration of a low, immune enhancing, dose of an mTOR inhibitor, e.g., an allosteric inhibitor, e.g., RAD001, or a catalytic inhibitor, is initiated after administration of immune effector cells, e.g., T cells, engineered to express a RCAR. While not wishing to be bound by theory, it is believed that in an embodiment, one or more of the following occurs:

a decrease in the number of PD-1 positive immune effector cells;

an increase in the number of PD-1 negative immune effector cells;

an increase in the ratio of PD-1 negative immune effector cells/PD-1 positive immune effector cells;

an increase in the number of naive T cells;

an increase in the expression of one or more of the following markers: $CD62L^{high}$, $CD127^{high}$, $CD27^+$, and BCL2, e.g., on memory T cells, e.g., memory T cell precursors;

a decrease in the expression of KLRG1, e.g., on memory T cells, e.g., memory T cell precursors; or an increase in the number of memory T cell precursors, e.g., cells with any one or combination of the following characteristics: increased $CD62L^{high}$, increased $CD127^{high}$, increased $CD27^+$, decreased KLRG1, and increased BCL2;

and wherein any of the changes described above occurs, e.g., at least transiently, e.g., as compared to a non-treated subject.

In other embodiments, immune effector cells, e.g., T cells, which have, or will be engineered to express a RCAR, are treated ex vivo by contact with an amount of an mTOR inhibitor that optimizes performance. While not wishing to be bound by theory, it is believed that in an embodiment, one or more of the following occurs:

a decrease in the number of PD-1 positive immune effector cells;

an increase in the number of PD-1 negative immune effector cells;

an increase in the ratio of PD-1 negative immune effector cells/PD-1 positive immune effector cells;

an increase in the number of naive T cells;

an increase in the expression of one or more of the following markers: $CD62L^{high}$, $CD127^{high}$, $CD27^+$, and BCL2, e.g., on memory T cells, e.g., memory T cell precursors;

a decrease in the expression of KLRG1, e.g., on memory T cells, e.g., memory T cell precursors; or an increase in the number of memory T cell precursors, e.g., cells with any one or combination of the following characteristics: increased $CD62L^{high}$, increased $CD127^{high}$, increased $CD27^+$, decreased KLRG1, and increased BCL2;

and wherein any of the changes described above occurs, e.g., at least transiently, e.g., as compared to a non-treated cell.

The term "bioequivalent" refers to an amount of an agent other than the reference compound (e.g., RAD001), required to produce an effect equivalent to the effect produced by the reference dose or reference amount of the reference compound (e.g., RAD001). In an embodiment the effect is the level of mTOR inhibition, e.g., as measured by P70 S6 kinase inhibition, e.g., as evaluated in an in vivo or in vitro assay, e.g., as measured by an assay described herein, e.g., the Boulay assay or measurement of phosphorylated S6 substrate levels by western blot. In an embodiment, the effect is alteration of the ratio of PD-1 positive/PD-1 negative T cells, as measured by cell sorting. In an embodiment a bioequivalent amount or dose of an mTOR inhibitor is the amount or dose that achieves the same level of P70 S6 kinase inhibition as does the reference dose or reference amount of a reference compound. In an embodiment, a bioequivalent amount or dose of an mTOR inhibitor is the amount or dose that achieves the same level of alteration in the ratio of PD-1 positive/PD-1 negative T cells or in the level of naive T cells as does the reference dose or reference amount of a reference compound.

The term "immunosenescence" refers to a decrease in immune function resulting in impaired immune response, e.g., to cancer, vaccination, infectious pathogens, among others. It involves both the host's capacity to respond to infections and the development of long-term immune memory, especially by vaccination. This immune deficiency is ubiquitous and found in both long- and short-lived species as a function of their age relative to life expectancy rather than chronological time. It is considered a major contributory factor to the increased frequency of morbidity and mortality among the elderly. Immunosenescence is not a random deteriorative phenomenon, rather it appears to inversely repeat an evolutionary pattern and most of the parameters affected by immunosenescence appear to be under genetic control. Immunosenescence can also be sometimes envisaged as the result of the continuous challenge of the unavoidable exposure to a variety of antigens such as viruses and bacteria. Immunosenescence is a multifactoral condition leading to many pathologically significant health problems, e.g., in the aged population. Age-dependent biological changes such as depletion of hematopoietic stem cells, decline in the total number of phagocytes and NK cells and a decline in humoral immunity contribute to the onset of immunosenescence. In one aspect, immunosenescence can be measured in an individual by measuring telomere length in immune cells (See, e.g., U.S. Pat. No. 5,741,677). Immunosenescence can also be determined by documenting in an individual a lower than normal number of naïve CD4 and/or CD8 T cells, T cell repertoire, or response to vaccination in a subject greater than or equal to 65 years of age.

The term "impaired immune response" refers to a state in which a subject does not have an appropriate immune response, e.g., to cancer, vaccination, pathogen infection, among others. In some embodiments, a subject having an impaired immune response is predicted not to get protective antibody titer levels following prophylactic vaccination, or in which a subject does not have a decrease in disease burden after therapeutic vaccination. A subject can also have an impaired immune response if the subject is a member of a population known to have decreased immune function or that has a history of decreased immune function such as the elderly, subjects undergoing chemotherapy treatment, asplenic subjects, immunocompromised subjects, or subjects having HIV/AIDS. Methods described herein allow for the treatment of an impaired immune response by administration of a low, immune enhancing, dose of an mTOR inhibitor, e.g., an allosteric mTOR inhibitor, such as RAD001.

The term 'low, immune enhancing, dose" when used in conjunction with an mTOR inhibitor, e.g., an allosteric mTOR inhibitor, e.g., RAD001 or rapamycin, or a catalytic mTOR inhibitor, refers to a dose of mTOR inhibitor that partially, but not fully, inhibits mTOR activity, e.g., as measured by the inhibition of P70 S6 kinase activity. Methods for evaluating mTOR activity, e.g., by inhibition of P70 S6 kinase, are discussed herein. The dose is insufficient to result in complete immune suppression but is sufficient to enhance the immune response. In an embodiment, the low, immune enhancing, dose of mTOR inhibitor results in a decrease in the number of PD-1 positive T cells and/or an increase in the number of PD-1 negative T cells, an increase in the ratio of PD-1 negative T cells/PD-1 positive T cells, or an increase in the number of naive T cells.

In an embodiment, a dose of an mTOR inhibitor is associated with, or provides, mTOR inhibition of at least 5 but no more than 90%, at least 10 but no more than 90%, at least 15, but no more than 90%, at least 20 but no more than 90%, at least 30 but no more than 90%, at least 40 but no more than 90%, at least 50 but no more than 90%, at least 60 but no more than 90%, or at least 70 but no more than 90%.

In an embodiment, a dose of an mTOR inhibitor is associated with, or provides, mTOR inhibition of at least 5 but no more than 80%, at least 10 but no more than 80%, at least 15, but no more than 80%, at least 20 but no more than 80%, at least 30 but no more than 80%, at least 40 but no more than 80%, at least 50 but no more than 80%, or at least 60 but no more than 80%.

In an embodiment, a dose of an mTOR inhibitor is associated with, or provides, mTOR inhibition of at least 5 but no more than 70%, at least 10 but no more than 70%, at least 15, but no more than 70%, at least 20 but no more than 70%, at least 30 but no more than 70%, at least 40 but no more than 70%, or at least 50 but no more than 70%.

In an embodiment, a dose of an mTOR inhibitor is associated with, or provides, mTOR inhibition of at least 5 but no more than 60%, at least 10 but no more than 60%, at least 15, but no more than 60%, at least 20 but no more than 60%, at least 30 but no more than 60%, or at least 40 but no more than 60%.

In an embodiment, a dose of an mTOR inhibitor is associated with, or provides, mTOR inhibition of at least 5 but no more than 50%, at least 10 but no more than 50%, at least 15, but no more than 50%, at least 20 but no more than 50%, at least 30 but no more than 50%, or at least 40 but no more than 50%.

In an embodiment, a dose of an mTOR inhibitor is associated with, or provides, mTOR inhibition of at least 5 but no more than 40%, at least 10 but no more than 40%, at least 15, but no more than 40%, at least 20 but no more than 40%, at least 30 but no more than 40%, or at least 35 but no more than 40%.

In an embodiment, a dose of an mTOR inhibitor is associated with, or provides, mTOR inhibition of at least 5 but no more than 30%, at least 10 but no more than 30%, at least 15, but no more than 30%, at least 20 but no more than 30%, or at least 25 but no more than 30%.

In an embodiment, a dose of an mTOR inhibitor is associated with, or provides, mTOR inhibition of at least 1, 2, 3, 4 or 5 but no more than 20%, at least 1, 2, 3, 4 or 5 but no more than 30%, at least 1, 2, 3, 4 or 5, but no more than 35, at least 1, 2, 3, 4 or 5 but no more than 40%, or at least 1, 2, 3, 4 or 5 but no more than 45%.

In an embodiment, a dose of an mTOR inhibitor is associated with, or provides, mTOR inhibition of at least 1, 2, 3, 4 or 5 but no more than 90%.

As is discussed herein, the extent of mTOR inhibition can be expressed as the extent of P70 S6 inhibition, e.g., the extent of mTOR inhibition can be determined by the level of decrease in P70 S6 activity, e.g., by the decrease in phosphorylation of a P70 S6 substrate. The level of mTOR inhibition can be evaluated by a method described herein, e.g. by the Boulay assay.

mTOR Inhibitors

Allosteric mTOR inhibitors include the neutral tricyclic compound rapamycin (sirolimus), rapamycin-related compounds, that is compounds having structural and functional similarity to rapamycin including, e.g., rapamycin derivatives, rapamycin analogs (also referred to as rapalogs) and other macrolide compounds that inhibit mTOR activity.

Rapamycin is a known macrolide antibiotic produced by *Streptomyces hygroscopicus* having the structure shown in Formula A.

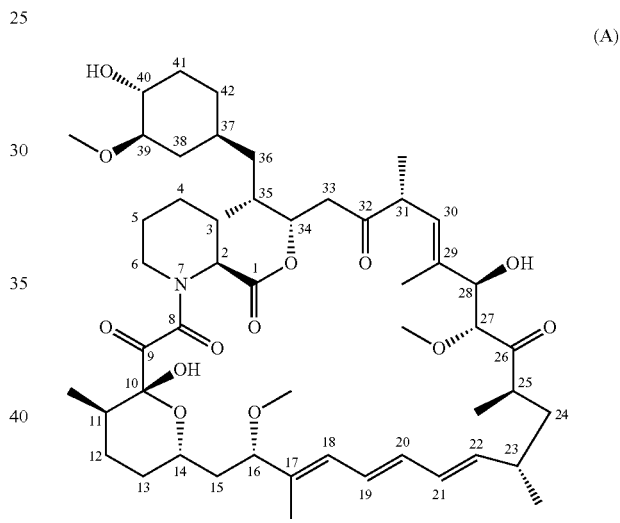

(A)

See, e.g., McAlpine, J. B., et al., J. Antibiotics (1991) 44: 688; Schreiber, S. L., et al., J. Am. Chem. Soc. (1991) 113: 7433; U.S. Pat. No. 3,929,992. There are various numbering schemes proposed for rapamycin. To avoid confusion, when specific rapamycin analogs are named herein, the names are given with reference to rapamycin using the numbering scheme of formula A.

Rapamycin analogs useful in the invention are, for example, O-substituted analogs in which the hydroxyl group on the cyclohexyl ring of rapamycin is replaced by $OR_1$ in which $R_1$ is hydroxyalkyl, hydroxyalkoxyalkyl, acylaminoalkyl, or aminoalkyl; e.g. RAD001, also known as, everolimus as described in U.S. Pat. No. 5,665,772 and WO94/09010 the contents of which are incorporated by reference. Other suitable rapamycin analogs include those substituted at the 26- or 28-position. The rapamycin analog may be an epimer of an analog mentioned above, particularly an epimer of an analog substituted in position 40, 28 or 26, and may optionally be further hydrogenated, e.g. as described in U.S. Pat. No. 6,015,815, WO95/14023 and WO99/15530 the contents of which are incorporated by reference, e.g. ABT578 also known as zotarolimus or a rapamycin analog described in U.S. Pat. No. 7,091,213, WO98/02441 and WO01/14387 the contents of which are incorporated by reference, e.g. AP23573 also known as ridaforolimus.

Examples of rapamycin analogs suitable for use in the present invention from U.S. Pat. No. 5,665,772 include, but are not limited to, 40-O-benzyl-rapamycin, 40-O-(4'-hydroxymethyl)benzyl-rapamycin, 40-O-[4'-(1,2-dihydroxyethyl)]benzyl-rapamycin, 40-O-allyl-rapamycin, 40-O[3'-(2,2-dimethyl-1,3-dioxolan-4(S)-yl)-prop-2'-en-1'-yl]-rapamycin, (2'E,4'S)-40-O-(4',5'-dihydroxypent-2'-en-1'-yl)-rapamycin, 40-O-(2-hydroxy)ethoxycarbonylmethyl-rapamycin, 40-O-(2-hydroxy)ethyl-rapamycin, 40-O-(3-hydroxy)propyl-rapamycin, 40-O-(6-hydroxy)hexyl-rapamycin, 40-O-[2-(2-hydroxy)ethoxy]ethyl-rapamycin, 40-O-[(3S)-2,2-dimethyldioxolan-3-yl]methyl-rapamycin, 40-O-[(2S)-2,3-dihydroxyprop-1-yl]-rapamycin, 40-O-(2-acetoxy)ethyl-rapamycin, 40-O-(2-nicotinoyloxy)ethyl-rapamycin, 40-O-[2-(N-morpholino)acetoxy]ethyl-rapamycin, 40-O-(2-N-imidazolylacetoxy)ethyl-rapamycin, 40-O-[2-(N-methyl-N'-piperazinyl)acetoxy]ethyl-rapamycin, 39-O-desmethyl-39,40-0,O-ethylene-rapamycin, (26R)-26-dihydro-40-O-(2-hydroxy)ethyl-rapamycin, 40-O-(2-aminoethyl)-rapamycin, 40-O-(2-acetaminoethyl)-rapamycin, 40-O-(2-nicotinamidoethyl)-rapamycin, 40-O-(2-(N-methyl-imidazo-2'-ylcarbethoxamido)ethyl)-rapamycin, 40-O-(2-ethoxycarbonylaminoethyl)-rapamycin, 40-O-(2-tolylsulfonamidoethyl)-rapamycin and 40-O-[2-(4',5'-dicarboethoxy-1',2',3'-triazol-1'-yl)-ethyl]-rapamycin.

Other rapamycin analogs useful in the present invention are analogs where the hydroxyl group on the cyclohexyl ring of rapamycin and/or the hydroxy group at the 28 position is replaced with an hydroxyester group are known, for example, rapamycin analogs found in U.S. RE44,768, e.g. temsirolimus.

Other rapamycin analogs useful in the preset invention include those wherein the methoxy group at the 16 position is replaced with another substituent, preferably (optionally hydroxy-substituted) alkynyloxy, benzyl, orthomethoxybenzyl or chlorobenzyl and/or wherein the mexthoxy group at the 39 position is deleted together with the 39 carbon so that the cyclohexyl ring of rapamycin becomes a cyclopentyl ring lacking the 39 position methyoxy group; e.g. as described in WO95/16691 and WO96/41807 the contents of which are incorporated by reference. The analogs can be further modified such that the hydroxy at the 40-position of rapamycin is alkylated and/or the 32-carbonyl is reduced.

Rapamycin analogs from WO95/16691 include, but are not limited to, 16-demthoxy-16-(pent-2-ynyl)oxy-rapamycin, 16-demthoxy-16-(but-2-ynyl)oxy-rapamycin, 16-demthoxy-16-(propargyl)oxy-rapamycin, 16-demethoxy-16-(4-hydroxy-but-2-ynyl)oxy-rapamycin, 16-demthoxy-16-benzyloxy-40-O-(2-hydroxyethyl)-rapamycin, 16-demthoxy-16-benzyloxy-rapamycin, 16-demethoxy-16-ortho-methoxybenzyl-rapamycin, 16-demethoxy-40-O-(2-methoxyethyl)-16-pent-2-ynyl)oxy-rapamycin, 39-demethoxy-40-desoxy-39-formyl-42-nor-rapamycin, 39-demethoxy-40-desoxy-39-hydroxymethyl-42-nor-rapamycin, 39-demethoxy-40-desoxy-39-carboxy-42-nor-rapamycin, 39-demethoxy-40-desoxy-39-(4-methyl-piperazin-1-yl)carbonyl-42-nor-rapamycin, 39-demethoxy-40-desoxy-39-(morpholin-4-yl)carbonyl-42-nor-rapamycin, 39-demethoxy-40-desoxy-39-[N-methyl, N-(2-pyridin-2-yl-ethyl)]carbamoyl-42-nor-rapamycin and 39-demethoxy-40-desoxy-39-(p-toluenesulfonylhydrazonomethyl)-42-nor-rapamycin.

Rapamycin analogs from WO96/41807 include, but are not limited to, 32-deoxo-rapamycin, 16-O-pent-2-ynyl-32-deoxo-rapamycin, 16-O-pent-2-ynyl-32-deoxo-40-O-(2-hydroxy-ethyl)-rapamycin, 16-O-pent-2-ynyl-32-(S)-dihydro-40-O-(2-hydroxyethyl)-rapamycin, 32(S)-dihydro-40-O-(2-methoxy)ethyl-rapamycin and 32(S)-dihydro-40-O-(2-hydroxyethyl)-rapamycin.

Another suitable rapamycin analog is umirolimus as described in US2005/0101624 the contents of which are incorporated by reference.

In mammalian cells, the target of rapamycin (mTOR) kinase exists as a multiprotein complex described as the mTORC1 complex or mTORC2 complex, which senses the availability of nutrients and energy and integrates inputs from growth factors and stress signaling. The mTORC1 complex is sensitive to allosteric mTOR inhibitors such as rapamycin, is composed of mTOR, GβL, and regulatory associated proteins of mTOR (raptor), and binds to the peptidyl-prolyl isomerase FKBP12 protein (a FK506-binding protein 1A, 12 kDa). In contrast, the mTORC2 complex is composed of mTOR, GβL, and rapamycin-insensitive companion proteins of mTOR (rictor), and does not bind to the FKBP12 protein in vitro.

The mTORC1 complex has been shown to be involved in protein translational control, operating as a growth factor and nutrient sensitive apparatus for growth and proliferation regulation. mTORC1 regulates protein translation via two key downstream substrates: P70 S6 kinase, which in turn phosphorylates ribosomal protein P70 S6, and eukaryotic translation initiation factor 4E binding protein 1 (4EBP1), which plays a key role in modulating eIF4E regulated cap-dependent translation. The mTORC1 complex regulates cell growth in response to the energy and nutrient homeostasis of the cell, and the deregulation of mTORC1 is common in a wide variety of human cancers. The function of mTORC2 involves the regulation of cell survival via phosphorylation of Akt and the modulation of actin cytoskeleton dynamics.

The mTORC1 complex is sensitive to allosteric mTOR inhibitors such as rapamycin and derivatives in large part due to rapamycin's mode of action, which involves the formation of an intracellular complex with the FKBP12 and binding to the FKBP12-rapamycin binding (FRB) domain of mTOR. This results in a conformational change in mTORC1 which is believed to alter and weaken the interaction with its scaffolding protein raptor, in turn impeding substrates such as P70 S6K1 from accessing mTOR and being phosphorylated. Rapamycin and rapalogues such as RAD001 have gained clinical relevance by inhibiting hyperactivation of mTOR associated with both benign and malignant proliferation disorders.

RAD001, otherwise known as everolimus (Afinitor®), has the chemical name (1R,9S,12S,15R,16E,18R,19R,21R,23S,24E,26E,28E,30S,32S,35R)-1,18-dihydroxy-12-{(1R)-2-[(1S,3R,4R)-4-(2-hydroxyethoxy)-3-methoxycyclohexyl]-1-methylethyl}-19,30-dimethoxy-15,17,21,23,29,35-hexamethyl-11,36-dioxa-4-aza-tricyclo[30.3.1.04,9]hexatriaconta-16,24,26,28-tetraene-2,3,10,14,20-pentaone and the following chemical structure

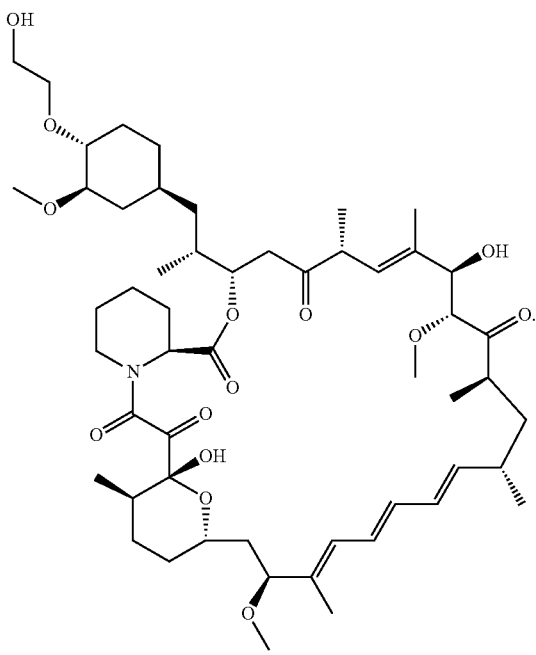 [SMILES: CO[C@H]1C[C@@H]2CC[C@@H](C)[C@@](O)(O2)C(=O)C(=O)N2CCCC[C@H]2C(=O)O[C@H]([C@H](C)C[C@@H]2CC[C@@H](OCCO)[C@H](OC)C2)CC(=O)[C@H](C)/C=C(\C)[C@@H](O)[C@@H](OC)C(=O)[C@H](C)C[C@H](C)/C=C/C=C/C=C/1C]

Everolimus is an FDA approved drug for the treatment of advanced kidney cancer and is being investigated in several other phase III clinical trials in oncology. Preclinical studies have shown that Everolimus is able to inhibit the proliferation of a wide variety of tumor cell lines both in vitro and in vivo, presumably through the suppression of rapamycin sensitive mTORC1 function. Everolimus, as a derivative of rapamycin, is an allosteric mTOR inhibitor that is highly potent at inhibiting part of the mTORC1 function, namely P70 S6 kinase (P70 S6K) and the downstream P70 S6K substrate P70 S6. Allosteric mTOR inhibitors like everolimus (and other rapamycin analogs) have little or no effect at inhibiting the mTORC2 pathway, or its resulting activation of Akt signaling. Further examples of allosteric mTOR inhibitors include sirolimus (rapamycin, AY-22989), 40-[3-hydroxy-2-(hydroxymethyl)-2-methylpropanoate]-rapamycin (also called temsirolimus or CCI-779) and ridaforolimus (AP-23573/MK-8669). Other examples of allosteric mTor inhibitors include zotarolimus (ABT578) and umirolimus.

Alternatively or additionally, catalytic, ATP-competitive mTOR inhibitors have been found to target the mTOR kinase domain directly and target both mTORC1 and mTORC2. These are also more complete inhibitors of mTORC1 than such allosteric mTOR inhibitors as rapamycin, because they modulate rapamycin-resistant mTORC1 outputs such as 4EBP1-T37/46 phosphorylation and cap-dependent translation.

BEZ235 is a catalytic mTOR inhibitor, having the chemical name 2-methyl-2-[4-(3-methyl-2-oxo-8-quinolin-3-yl-2,3-dihydro-imidazo[4,5-c]quinolin-1-yl)-phenyl]-propionitrile and the following chemical structure

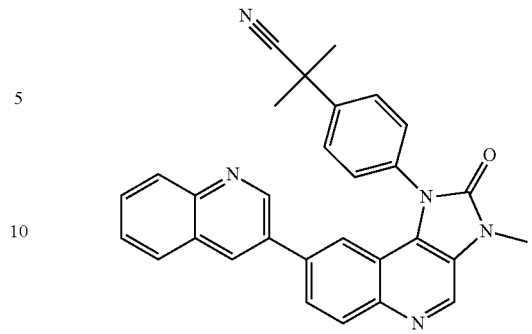

BEZ235 may also be used in its monotosylate salt form. The synthesis of BEZ235 is described in WO2006/122806.

As a catalytic mTOR inhibitor BEZ235 is capable of shutting down the complete function of mTORC1 complex, including both the rapamycin sensitive (phosphorylation of P70 S6K, and subsequently phosphorylation of P70 S6) and rapamycin insensitive (phosphorylation of 4EBP1) functions. BEZ235 has a differential effect according to the drug concentration used, whereby mTOR inhibition predominates at a low concentration (less than 100 nmol/L) but dual PI3K/mTOR inhibition at relatively higher concentrations (approximately 500 nmol/L), Serra et al., 2008.

Another catalytic mTOR inhibitor described in the literature is CCG168 (otherwise known as AZD-8055, Chresta, C. M., et al., Cancer Res, 2010, 70(1), 288-298) which has the chemical name {5-[2,4-bis-((S)-3-methyl-morpholin-4-yl)-pyrido[2,3d]pyrimidin-7-yl]-2-methoxy-phenyl}-methanol and the following chemical structure

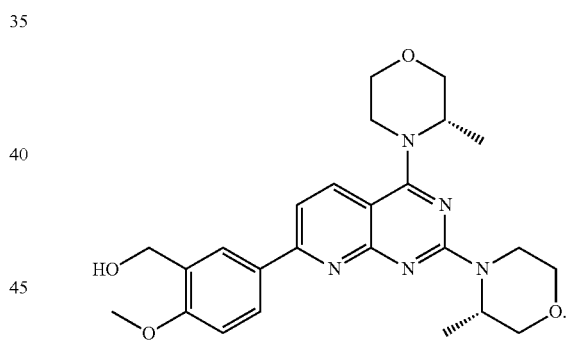

Another catalytic mTOR inhibitor described in the literature is 3-[2,4-bis[(3S)-3-methylmorpholin-4-yl]pyrido[2,3-d]pyrimidin-7-yl]-N-methylbenzamide (WO09104019) having the following chemical structure:

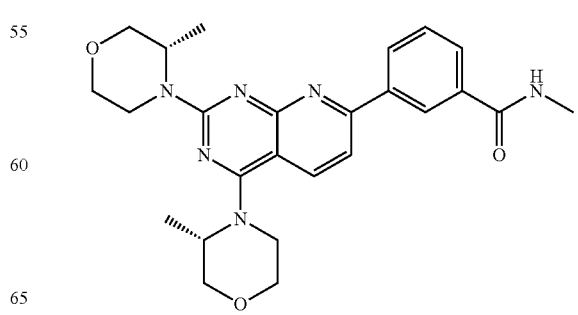

Another catalytic mTOR inhibitor described in the literature is 3-(2-aminobenzo[d]oxazol-5-yl)-1-isopropyl-1H-pyrazolo[3,4-d]pyrimidin-4-amine (WO10051043 and WO2013023184) having following chemical structure:

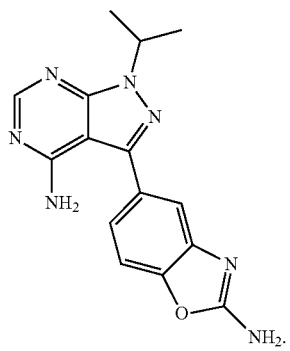 [SMILES: CC(C)n1nc(-c2ccc3oc(N)nc3c2)c2c(N)ncnc21]

Another catalytic mTOR inhibitor described in the literature is N-(3-(N-(3-((3,5-dimethoxyphenyl)amino)quinoxaline-2-yl)sulfamoyl)phenyl)-3-methoxy-4-methylbenzamide (WO07044729 and WO12006552) having the following chemical structure:

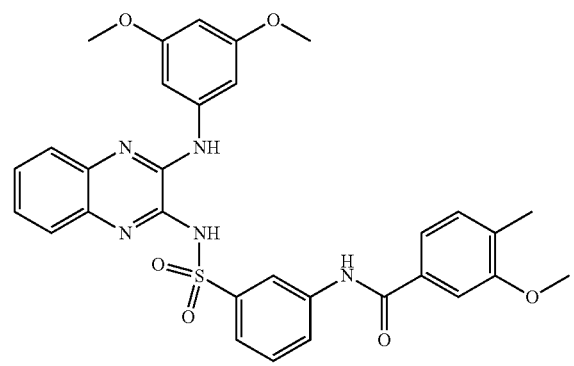

Another catalytic mTOR inhibitor described in the literature is PKI-587 (Venkatesan, A. M., J. Med. Chem., 2010, 53, 2636-2645) which has the chemical name 1-[4-[4-(dimethylamino)piperidine-1-carbonyl]phenyl]-3-[4-(4,6-dimorpholino-1,3,5-triazin-2-yl)phenyl]urea and having the following chemical structure

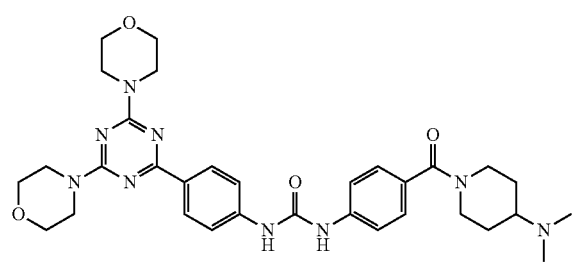

Another catalytic mTOR inhibitor described in the literature is GSK-2126458 (ACS Med. Chem. Lett., 2010, 1, 39-43) which has the chemical name 2,4-difluoro-N-{2-methoxy-5-[4-(4-pyridazinyl)-6-quinolinyl]-3-pyridinyl}benzenesulfonamide and having the following chemical structure:

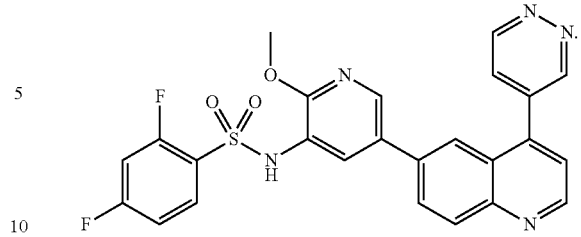

Another catalytic mTOR inhibitor described in the literature is 5-(9-isopropyl-8-methyl-2-morpholino-9H-purin-6-yl)pyrimidin-2-amine (WO10114484) having the following chemical structure:

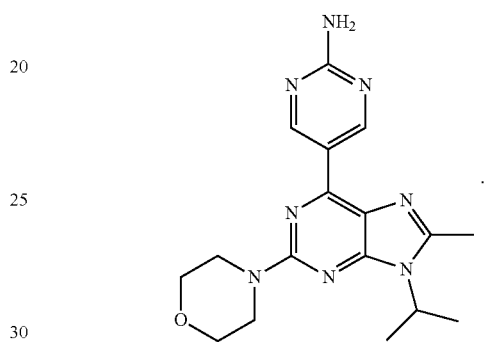

Another catalytic mTOR inhibitor described in the literature is (E)-N-(8-(6-amino-5-(trifluoromethyl)pyridin-3-yl)-1-(6-(2-cyanopropan-2-yl)pyridin-3-yl)-3-methyl-1H-imidazo[4,5-c]quinolin-2(3H)-ylidene)cyanamide (WO12007926) having the following chemical structure:

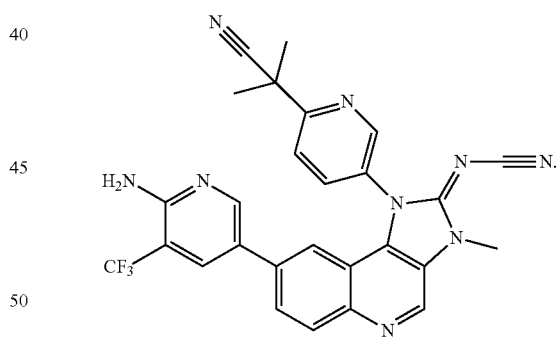

Further examples of catalytic mTOR inhibitors include 8-(6-methoxy-pyridin-3-yl)-3-methyl-1-(4-piperazin-1-yl-3-trifluoromethyl-phenyl)-1,3-dihydro-imidazo[4,5-c]quinolin-2-one (WO2006/122805) and Ku-0063794 (Garcia-Martinez J M, et al., Biochem J., 2009, 421(1), 29-42. Ku-0063794 is a specific inhibitor of the mammalian target of rapamycin (mTOR).) WYE-354 is another example of a catalytic mTor inhibitor (Yu K, et al. (2009). Biochemical, Cellular, and In vivo Activity of Novel ATP-Competitive and Selective Inhibitors of the Mammalian Target of Rapamycin. Cancer Res. 69(15): 6232-6240).

mTOR inhibitors useful according to the present invention also include prodrugs, derivatives, pharmaceutically acceptable salts, or analogs thereof of any of the foregoing.

mTOR inhibitors, such as RAD001, may be formulated for delivery based on well-established methods in the art based on the particular dosages described herein. In particular, U.S. Pat. No. 6,004,973 (incorporated herein by reference) provides examples of formulations useable with the mTOR inhibitors described herein.

Downstream Inhibitors

Many of the methods described herein rely on the use of a low, immune enhancing, dose of an mTOR inhibitors, e.g., to increase the level of PD1 negative immune effector cells, e.g., T cells, to decrease the level of PD1 positive immune effector cells, e.g., T cells, to increase the ratio of PD1 negative immune effector cells, e.g., T cells/PD1 positive immune effector cells, e.g., T cells, or increase the level of naive T cells. Any of these methods can also be practiced with, in place of the low, immune enhancing, dose of an mTOR inhibitors, the administration of an inhibitor of a downstream element in the pathway, e.g., P70 S6K or mTORC1. Examples of inhibitors of P70 S6K include PF-4708671 or LY2584702 tosylate. Examples of inhibitors of mTORC1 are allosteric inhibitors of mTOR, e.g., mTOR inhibitors that specifically inhibit mTORC1 activity but not mTORC2 activity. In an embodiment, a downstream inhibitor is adminered at a dose effective to increase the level of PD1 negative immune effector cells, e.g., T cells, to decrease the level of PD1 positive immune effector cells, e.g., T cells, to increase the ratio of PD1 negative immune effector cells, e.g., T cells/PD1 positive immune effector cells, e.g., T cells, or increase the level of naive T cells.

Evaluation of mTOR Inhibition mTOR phosphorylates the kinase P70 S6 (also known as P70 S6K or S6K), thereby activating P70 S6K and allowing it to phosphorylate its substrate. The extent of mTOR inhibition can be expressed as the extent of P70 S6K inhibition, e.g., the extent of mTOR inhibition can be determined by the level of decrease in P70 S6K activity, e.g., by the decrease in phosphorylation of a P70 S6K substrate. One can determine the level of mTOR inhibition, by evaluating P70 S6K activity (the ability of P70 S6 to phsophorylate a substrate), in the absence of inhibitor, e.g., prior to administration of inhibitor, and in the presences of inhibitor, or after the administration of inhibitor. The level of inhibition of P70 S6K gives the level of mTOR inhibition. Thus, if P70 S6K is inhibited by 40%, mTOR activity, as measured by P70 S6K activity, is inhibited by 40%. The extent or level of inhibition referred to herein is the average level of inhibition over the dosage interval. By way of example, if the inhibitor is given once per week, the level of inhibition is given by the average level of inhibition over that interval, namely a week.

Boulay et al., *Cancer Res,* 2004, 64:252-61, hereby incorporated by reference, teaches an assay that can be used to assess the level of mTOR inhibition (referred to herein as the Boulay assay). In an embodiment, the assay relies on the measurement of P70 S6 kinase activity from biological samples before and after administration of an mTOR inhibitor, e.g., RAD001. Samples can be taken at preselected times after treatment with an mTOR inhibitor, e.g., 24, 48, and 72 hours after treatment. Biological samples, e.g., from skin or peripheral blood mononuclear cells (PBMCs) can be used. Total protein extracts are prepared from the samples. P70 S6 kinase is isolated from the protein extracts by immunoprecipitation using an antibody that specifically recognizes the P70 S6 kinase. Activity of the isolated P70 S6 kinase can be measured in an in vitro kinase assay. The isolated kinase can be incubated with 40S ribosomal subunit substrates (which is an endogenous substrate of P70 S6K) and gamma-$^{32}$P under conditions that allow phosphorylation of the substrate. Then the reaction mixture can be resolved on an SDS-PAGE gel, and $^{32}$P signal analyzed using a PhosphorImager. A $^{32}$P signal corresponding to the size of the 40S ribosomal subunit indicates phosphorylated substrate and the activity of P70 S6K. Increases and decreases in kinase activity can be calculated by quantifying the area and intensity of the $^{32}$P signal of the phosphorylated substrate (e.g., using ImageQuant, Molecular Dynamics), assigning arbitrary unit values to the quantified signal, and comparing the values from after administration with values from before administration or with a reference value. For example, percent inhibition of kinase activity can be calculated with the following formula: 1-(value obtained after administration/value obtained before administration)×100. As described above, the extent or level of inhibition referred to herein is the average level of inhibition over the dosage interval.

Methods for the evaluation of kinase activity, e.g., P70 S6 kinase activity, are also provided in U.S. Pat. No. 7,727,950, hereby incorporated by reference.

The level of mTOR inhibition can also be evaluated by a change in the ratio of PD1 negative to PD1 positive T cells. T cells from peripheral blood can be identified as PD1 negative or positive by art-known methods.

Low-Dose mTOR Inhibitors

Methods described herein use low, immune enhancing, dose mTOR inhibitors, doses of mTOR inhibitors, e.g., allosteric mTOR inhibitors, including rapalogs such as RAD001. In contrast, levels of inhibitor that fully or near fully inhibit the mTOR pathway are immunosuppressive and are used, e.g., to prevent organ transplant rejection. In addition, high doses of rapalogs that fully inhibit mTOR also inhibit tumor cell growth and are used to treat a variety of cancers (See, e.g., Antineoplastic effects of mammalian target of rapamycine inhibitors. Salvadori M. World J Transplant. 2012 Oct. 24; 2(5):74-83; Current and Future Treatment Strategies for Patients with Advanced Hepatocellular Carcinoma: Role of mTOR Inhibition. Finn RS. Liver Cancer. 2012 November; 1(3-4):247-256; Emerging Signaling Pathways in Hepatocellular Carcinoma. Moeini A, Cornelia H, Villanueva A. Liver Cancer. 2012 September; 1(2):83-93; Targeted cancer therapy—Are the days of systemic chemotherapy numbered? Joo W D, Visintin I, Mor G. Maturitas. 2013 Sep. 20; Role of natural and adaptive immunity in renal cell carcinoma response to VEGFR-TKIs and mTOR inhibitor. Santoni M, Berardi R, Amantini C, Burattini L, Santini D, Santoni G, Cascinu S. Int J Cancer. 2013 Oct. 2).

The present invention is based, at least in part, on the surprising finding that doses of mTOR inhibitors well below those used in current clinical settings had a superior effect in increasing an immune response in a subject and increasing the ratio of PD-1 negative T cells/PD-1 positive T cells. It was surprising that low doses of mTOR inhibitors, producing only partial inhibition of mTOR activity, were able to effectively improve immune responses in human subjects and increase the ratio of PD-1 negative T cells/PD-1 positive T cells.

Accordingly, in one aspect, the present invention provides compositions, e.g., provides as a unit dosage form, comprising an mTOR inhibitor, e.g., a allosteric mTOR inhibitor, e.g., RAD001, at a concentration of about 0.005-1.5 mg, about 0.005-1.5 mg, about 0.01-1 mg, about 0.01-0.7 mg, about 0.01-0.5 mg, or about 0.1-0.5 mg. In a further aspect the present invention provides compositions comprising an mTOR inhibitor, e.g., RAD001, at a concentration of 0.005-1.5 mg, 0.005-1.5 mg, 0.01-1 mg, 0.01-0.7 mg, 0.01-0.5 mg, or 0.1-0.5 mg. More particularly, in one aspect, the invention provides compositions comprising an mTOR inhibitor, e.g., RAD001, at a dose of about 0.005 mg, 0.006 mg, 0.007 mg, 0.008 mg, 0.009 mg, 0.01 mg, 0.02 mg, 0.03 mg, 0.04 mg, 0.05 mg, 0.06 mg, 0.07 mg, 0.08 mg, 0.09 mg, 0.1 mg, 0.2 mg, 0.3 mg, 0.4 mg, 0.5 mg, 0.6 mg, 0.7 mg, 0.8 mg, 0.9 mg, or 1.0 mg. In one aspect, the mTOR inhibitor, e.g., RAD001, is at a dose of 0.5 mg or less. In a still further aspect, the mTOR inhibitor, e.g., RAD001, is at a dose of about 0.5 mg. In a further aspect, the invention provides compositions comprising an mTOR inhibitor, e.g., RAD001, at a dose of 0.005 mg, 0.006 mg, 0.007 mg, 0.008 mg, 0.009 mg, 0.01 mg, 0.02 mg, 0.03 mg, 0.04 mg, 0.05 mg, 0.06 mg, 0.07 mg, 0.08 mg, 0.09 mg, 0.1 mg, 0.2 mg, 0.3 mg, 0.4 mg, 0.5 mg, 0.6 mg, 0.7 mg, 0.8 mg, 0.9 mg, or 1.0 mg. In one aspect, the mTOR inhibitor, e.g., RAD001, is at a dose of 0.5 mg or less. In a still further aspect, the mTOR inhibitor, e.g., RAD001, is at a dose of 0.5 mg.

In a further aspect, the invention relates to compositions comprising an mTOR inhibitor that is not RAD001, in an amount that is bioequivalent to the specific amounts or doses specified for RAD001.

a further aspect, the invention relates to compositions comprising an mTOR inhibitor in an amount sufficient to inhibit P70 S6 kinase by no greater than 80%. In a further aspect the compositions described herein comprise an mTOR inhibitor in an amount sufficient to inhibit P70 S6 kinase by no greater than 38%.

In an embodiment, the invention relates to a composition, or dosage form, of an mTOR inhibitor, e.g., an allosteric mTOR inhibitor, e.g., a rapalog, rapamycin, or RAD001, or a catalytic mTOR inhibitor, which, when administered on a selected dosing regimen, e.g., once daily or once weekly, is associated with: a level of mTOR inhibition that is not associated with complete, or significant immune suppression, but is associated with enhancement of the immune response.

In a further aspect, the invention provides methods for enhancing immune response, e.g., treating immunosenescence, comprising a step of administering to a subject an mTOR inhibitor. In some embodiments, an mTOR inhibitor, e.g., an allosteric mTOR inhibitor, e.g., RAD001, can be administered at a dose of about 0.005-1.5 mg daily, about 0.01-1 mg daily, about 0.01-0.7 mg daily, about 0.01-0.5 mg daily, or about 0.1-0.5 mg daily. In a further aspect, an mTOR inhibitor, e.g., RAD001, can be administered at a dose of about 0.1-20 mg weekly, about 0.5-15 mg weekly, about 1-10 mg weekly, or about 3-7 mg weekly. In some embodiments, an mTOR inhibitor, e.g., RAD001, can be administered at a dose of 0.005-1.5 mg daily, 0.01-1 mg daily, 0.01-0.7 mg daily, 0.01-0.5 mg daily, or 0.1-0.5 mg daily. In some embodiments, an mTOR inhibitor, e.g., RAD001, can be administered at a dose of about 0.1-20 mg weekly, 0.5-15 mg weekly, 1-10 mg weekly, 3-7 mg weekly, or 5 mg weekly.

In a further aspect, the invention relates to methods for enhancing immune response, e.g., treating immunosenescence, comprising the step of administering an mTOR inhibitor that is not RAD001, in an amount that is bioequivalent to the specific amounts or doses described herein for RAD001.

In some embodiments, an mTOR inhibitor, e.g., a allosteric mTOR inhibitor, eg., e.g., RAD001, can be administered at a dose of about 0.005 mg daily, 0.006 mg daily, 0.007 mg daily, 0.008 mg daily, 0.009 mg daily, 0.01 mg daily, 0.02 mg daily, 0.03 mg daily, 0.04 mg daily, 0.05 mg daily, 0.06 mg daily, 0.07 mg daily, 0.08 mg daily, 0.09 mg daily, 0.1 mg daily, 0.2 mg daily, 0.3 mg daily, 0.4 mg daily, 0.5 mg daily, 0.6 mg daily, 0.7 mg daily, 0.8 mg daily, 0.9 mg daily, or 1.0 mg daily. In some embodiments, RAD001 can be administered at a dose of no greater than about 0.7 mg in a 24 hour period. In some embodiments, an mTOR inhibitor, e.g., an allosteric mTOR inhibitor, e.g., RAD001, can be administered at a dose of no greater than about 0.5 mg in a 24 hour period. In some embodiments, RAD001 can be administered at a dose of 0.5 mg or less daily. In some embodiments, RAD001 can be administered at a dose of 0.5 mg daily.

In a further aspect, the invention can utilize an mTOR inhibitor other than RAD001 in an amount that is bioequivalent to the specific amounts or doses specified for RAD001. In some embodiments, an mTOR inhibitor, e.g., an allosteric mTOR inhibitor, e.g., RAD001, can be administered at a dose of 0.1 mg weekly, 0.2 mg weekly, 0.3 mg weekly, 0.4 mg weekly, 0.5 mg weekly, 0.6 mg weekly, 0.7 mg weekly, 0.8 mg weekly, 0.9 mg weekly, 1 mg weekly, 2 mg weekly, 3 mg weekly, 4 mg weekly, 5 mg weekly, 6 mg weekly, 7 mg weekly, 8 mg weekly, 9 mg weekly, 10 mg weekly, 11 mg weekly, 12 mg weekly, 13 mg weekly, 14 mg weekly, 15 mg weekly, 16 mg weekly, 17 mg weekly, 18 mg weekly, 19 mg weekly, or 20 mg weekly. In some embodiments, an mTOR inhibitor, e.g., an allosteric mTOR inhibitor, e.g., RAD001, is administered at a dose of 5 mg or less weekly. In some embodiments, an mTOR inhibitor, e.g., an allosteric mTOR inhibitor, e.g., RAD001, is administered at a dose of 5 mg weekly.

In some embodiments, the invention can utilize an mTOR inhibitor other than RAD001 in an amount that is bioequivalent to the specific amounts or doses specified for RAD001.

An mTOR inhibitor, e.g., an allosteric mTOR inhibitor, e.g., a rapalog, rapamycin, or RAD001, or a catalytic mTOR inhibitor, can be provided in a sustained release formulation. Any of the compositions or unit dosage forms described herein can be provided in a sustained release formulation. In some embodiments, a sustained release formulation will have lower bioavailability than an immediate release formulation. E.g., in embodiments, to attain a similar therapeutic effect of an immediate release formulation a sustained release formulation will have from about 2 to about 5, about 2.5 to about 3.5, or about 3 times the amount of inhibitor provided in the immediate release formulation.

In an embodiment, immediate release forms, e.g., of RAD001, typically used for one administration per week, having 0.1 to 20, 0.5 to 10, 2.5 to 7.5, 3 to 6, or about 5, mgs per unit dosage form, are provided. For once per week administrations, these immediate release formulations correspond to sustained release forms, having, respectively, 0.3 to 60, 1.5 to 30, 7.5 to 22.5, 9 to 18, or about 15 mgs of an mTOR inhibitor, e.g., an allosteric mTOR inhibitor, e.g., rapamycin or RAD001. In embodiments both forms are administered on a once/week basis.

In an embodiment, immediate release forms, e.g., of RAD001, typically used for one administration per day, having having 0.005 to 1.5, 0.01 to 1.5, 0.1 to 1.5, 0.2 to 1.5, 0.3 to 1.5, 0.4 to 1.5, 0.5 to 1.5, 0.6 to 1.5, 0.7 to 1.5, 0.8 to 1.5, 1.0 to 1.5, 0.3 to 0.6, or about 0.5 mgs per unit dosage form, are provided. For once per day administrations, these immediate release forms correspond to sustained release forms, having, respectively, 0.015 to 4.5, 0.03 to 4.5, 0.3 to 4.5, 0.6 to 4.5, 0.9 to 4.5, 1.2 to 4.5, 1.5 to 4.5, 1.8 to 4.5, 2.1 to 4.5, 2.4 to 4.5, 3.0 to 4.5, 0.9 to 1.8, or about 1.5 mgs of an mTOR inhibitor, e.g., an allosteric mTOR inhibitor, e.g., rapamycin or RAD001. For once per week administrations, these immediate release forms correspond to sustained release forms, having, respectively, 0.1 to 30, 0.2 to 30, 2 to 30, 4 to 30, 6 to 30, 8 to 30, 10 to 30, 1.2 to 30, 14 to 30, 16 to 30, 20 to 30, 6 to 12, or about 10 mgs of an mTOR inhibitor, e.g., an allosteric mTOR inhibitor, e.g., rapamycin or RAD001.

In an embodiment, immediate release forms, e.g., of RAD001, typically used for one administration per day, having having 0.01 to 1.0 mgs per unit dosage form, are provided. For once per day administrations, these immediate release forms correspond to sustained release forms, having, respectively, 0.03 to 3 mgs of an mTOR inhibitor, e.g., an allosteric mTOR inhibitor, e.g., rapamycin or RAD001. For once per week administrations, these immediate release forms correspond to sustained release forms, having, respectively, 0.2 to 20 mgs of an mTOR inhibitor, e.g., an allosteric mTOR inhibitor, e.g., rapamycin or RAD001.

In an embodiment, immediate release forms, e.g., of RAD001, typically used for one administration per week, having having 0.5 to 5.0 mgs per unit dosage form, are provided. For once per week administrations, these immediate release forms correspond to sustained release forms, having, respectively, 1.5 to 15 mgs of an mTOR inhibitor, e.g., an allosteric mTOR inhibitor, e.g., rapamycin or RAD001.

As described above, one target of the mTOR pathway is the P70 S6 kinase. Thus, doses of mTOR inhibitors which are useful in the methods and compositions described herein are those which are sufficient to achieve no greater than 80% inhibition of P70 S6 kinase activity relative to the activity of the P70 S6 kinase in the absence of an mTOR inhibitor, e.g., as measured by an assay described herein, e.g., the Boulay assay. In a further aspect, the invention provides an amount of an mTOR inhibitor sufficient to achieve no greater than 38% inhibition of P70 S6 kinase activity relative to P70 S6 kinase activity in the absence of an mTOR inhibitor, e.g., as measured by an assay described herein, e.g., the Boulay assay In one aspect the dose of mTOR inhibitor useful in the methods and compositions of the invention is sufficient to achieve, e.g., when administered to a human subject, 90%, 89%, 88%, 87%, 86%, 85%, 84%, 83%, 82%, 81%, 80%, 79%, 78%, 77%, 76%, 75%, 74%, 73%, 72%, 71%, 70%, 69%, 68%, 67%, 66%, 65%, 64%, 63%, 62%, 61%, 60%, 59%, 58%, 57%, 56%, 55%, 54%, 54%, 53%, 52%, 51%, 50%, 49%, 48%, 47%, 46%, 45%, 44%, 43%, 42%, 41%, 40%, 39%, 38%, 37%, 36%, 35%, 34%, 33%, 32%, 31%, 30%, 29%, 28%, 27%, 26%, 25%, 24%, 23%, 22%, 21%, 20%, 19%, 18%, 17%, 16%, 15%, 14%, 13%, 12%, 11%, or 10% or less inhibition of P70 S6 kinase activity, e.g., as measured by an assay described herein, e.g., the Boulay assay.

In one aspect the dose of mTOR inhibitor useful in the methods and compositions of the invention is sufficient to achieve, e.g., when administered to a human subject, 90+/−5% (i.e., 85-95%), 89+/−5%, 88+/−5%, 87+/−5%, 86+/−5%, 85+/−5%, 84+/−5%, 83+/−5%, 82+/−5%, 81+/−5%, 80+/−5%, 79+/−5%, 78+/−5%, 77+/−5%, 76+/−5%, 75+/−5%, 74+/−5%, 73+/−5%, 72+/−5%, 71+/−5%, 70+/−5%, 69+/−5%, 68+/−5%, 67+/−5%, 66+/−5%, 65+/−5%, 64+/−5%, 63+/−5%, 62+/−5%, 61+/−5%, 60+/−5%, 59+/−5%, 58+/−5%, 57+/−5%, 56+/−5%, 55+/−5%, 54+/−5%, 54+/−5%, 53+/−5%, 52+/−5%, 51+/−5%, 50+/−5%, 49+/−5%, 48+/−5%, 47+/−5%, 46+/−5%, 45+/−5%, 44+/−5%, 43+/−5%, 42+/−5%, 41+/−5%, 40+/−5%, 39+/−5%, 38+/−5%, 37+/−5%, 36+/−5%, 35+/−5%, 34+/−5%, 33+/−5%, 32+/−5%, 31+/−5%, 30+/−5%, 29+/−5%, 28+/−5%, 27+/−5%, 26+/−5%, 25+/−5%, 24+/−5%, 23+/−5%, 22+/−5%, 21+/−5%, 20+/−5%, 19+/−5%, 18+/−5%, 17+/−5%, 16+/−5%, 15+/−5%, 14+/−5%, 13+/−5%, 12+/−5%, 11+/−5%, or 10+/−5%, inhibition of P70 S6 kinase activity, e.g., as measured by an assay described herein, e.g., the Boulay assay.

P70 S6 kinase activity in a subject may be measured using methods known in the art, such as, for example, according to the methods described in U.S. Pat. No. 7,727,950, by immunoblot analysis of phosphoP70 S6K levels and/or phosphoP70 S6 levels or by in vitro kinase activity assays.

In a further aspect, the invention relates to compositions comprising an mTOR inhibitor such as an mTOR inhibitor, e.g., an allosteric mTOR inhibitor, e.g., RAD001. Doses of an mTOR inhibitor, e.g., an allosteric mTOR inhibitor, e.g., RAD001, in such compositions can be in the range of about 30 pM to 4 nM. In one aspect, the dose of an mTOR inhibitor, e.g., an allosteric mTOR inhibitor, e.g., RAD001, is in the range of about 50 pM to 2 nM, about 100 pM to 1.5 nM, about 200 pM to 1 nM, or about 300 pM to 500 pM. In one aspect, the dose of RAD001 is in the range of 50 pM to 2 nM, 100 pM to 1.5 nM, 200 pM to 1 nM, or 300 pM to 500 pM. In a further aspect the dose of RAD001 is about 30 pM, 40 pM, 50 pM, 60 pM, 70 pM, 80 pM, 90 pM, 100 pM, 150 pM, 200 pM, 250 pM, 300 pM, 350 pM, 400 pM, 450 pM, 500 pM, 550 pM, 600 pM, 650 pM, 700 pM, 750 pM, 800 pM, 850 pM, 900 pM, 950 pM, 1 nM, 1.5 nM, 2 nM, 2.5 nM, 3 nM, 3.5 nM, or 4 nM.

In a further aspect, the invention can utilize an mTOR inhibitor other than RAD001 in an amount that is bioequivalent to the specific amounts or doses specified for RAD001.

The invention further relates to methods comprising the administration of an mTOR inhibitor to a subject. Such methods may employ doses of the mTOR inhibitor RAD001 in the range of about 30 pM to 4 nM. In a further aspect, the dose of RAD001 can be in the range of about 50 pM to 2 nM, about 100 pM to 1.5 nM, about 200 pM to 1 nM, or about 300 pM to 500 pM. In one aspect, the dose of RAD001 is in the range of 50 pM to 2 nM, 100 pM to 1.5 nM, 200 pM to 1 nM, or 300 pM to 500 pM. In a further aspect the dose of RAD001 is about 30 pM, 40 pM, 50 pM, 60 pM, 70 pM, 80 pM, 90 pM, 100 pM, 150 pM, 200 pM, 250 pM, 300 pM, 350 pM, 400 pM, 450 pM, 500 pM, 550 pM, 600 pM, 650 pM, 700 pM, 750 pM, 800 pM, 850 pM, 900 pM, 950 pM, 1 nM, 1.5 nM, 2 nM, 2.5 nM, 3 nM, 3.5 nM, or 4 nM.

In a further aspect, the methods of the invention can utilize an mTOR inhibitor other than RAD001 in an amount that is bioequivalent to the specific amounts or doses specified for RAD001.

As used herein, the term "about" in reference to a dose of mTOR inhibitor refers to up to a +/−10% variability in the amount of mTOR inhibitor, but can include no variability around the stated dose.

In some embodiments, the invention provides methods comprising administering to a subject an mTOR inhibitor, e.g., an allosteric inhibitor, e.g., RAD001, at a dosage within a target trough level. In some embodiments, the trough level is significantly lower than trough levels associated with dosing regimens used in organ transplant and cancer patients. In an embodiment mTOR inhibitor, e.g., RAD001, or rapamycin, is administered to result in a trough level that is less than ½, ¼, 1/10, or 1/20 of the trough level that results in immunosuppression or an anticancer effect. In an embodiment mTOR inhibitor, e.g., RAD001, or rapamycin, is administered to result in a trough level that is less than ½, ¼, 1/10, or 1/20 of the trough level provided on the FDA approved packaging insert for use in immunosuppression or an anticancer indications.

In an embodiment a method disclosed herein comprises administering to a subject an mTOR inhibitor, e.g., an allosteric inhibitor, e.g., RAD001, at a dosage that provides a target trough level of 0.1 to 10 ng/ml, 0.1 to 5 ng/ml, 0.1 to 3 ng/ml, 0.1 to 2 ng/ml, or 0.1 to 1 ng/ml. In an embodiment a method disclosed herein comprises administering to a subject an mTOR inhibitor, e.g., an allosteric inhibitor, e.g., RAD001, at a dosage that provides a target trough level of 0.2 to 10 ng/ml, 0.2 to 5 ng/ml, 0.2 to 3 ng/ml, 0.2 to 2 ng/ml, or 0.2 to 1 ng/ml.

In an embodiment a method disclosed herein comprises administering to a subject an mTOR inhibitor, e.g. an, allosteric inhibitor, e.g., RAD001, at a dosage that provides a target trough level of 0.3 to 10 ng/ml, 0.3 to 5 ng/ml, 0.3 to 3 ng/ml, 0.3 to 2 ng/ml, or 0.3 to 1 ng/ml.

In an embodiment a method disclosed herein comprises administering to a subject an mTOR inhibitor, e.g., an allosteric inhibitor, e.g., RAD001, at a dosage that provides a target trough level of 0.4 to 10 ng/ml, 0.4 to 5 ng/ml, 0.4 to 3 ng/ml, 0.4 to 2 ng/ml, or 0.4 to 1 ng/ml.

In an embodiment a method disclosed herein comprises administering to a subject an mTOR inhibitor, e.g., an allosteric inhibitor, e.g., RAD001, at a dosage that provides a target trough level of 0.5 to 10 ng/ml, 0.5 to 5 ng/ml, 0.5 to 3 ng/ml, 0.5 to 2 ng/ml, or 0.5 to 1 ng/ml.

In an embodiment a method disclosed herein comprises administering to a subject an mTOR inhibitor, e.g., an allosteric inhibitor, e.g., RAD001, at a dosage that provides a target trough level of 1 to 10 ng/ml, 1 to 5 ng/ml, 1 to 3 ng/ml, or 1 to 2 ng/ml.

As used herein, the term "trough level" refers to the concentration of a drug in plasma just before the next dose, or the minimum drug concentration between two doses.

In some embodiments, a target trough level of RAD001 is in a range of between about 0.1 and 4.9 ng/ml. In an embodiment, the target trough level is below 3 ng/ml, e.g., is between 0.3 or less and 3 ng/ml. In an embodiment, the target trough level is below 3 ng/ml, e.g., is between 0.3 or less and 1 ng/ml. In some embodiments, a target trough level of RAD001 is in a range of between about 2.4 and 4.9 ng/ml. In some embodiments, a target trough level of RAD001 is in a range of between about 0.1 and 2.4 ng/ml. In some embodiments, a target trough level of RAD001 is in a range of between about 0.1 and 1.5 ng/ml. In some embodiments, a target trough level of RAD001 is in a range of between 0.1 and 4.9 ng/ml. In some embodiments, a target trough level of RAD001 is in a range of between 2.4 and 4.9 ng/ml. In some embodiments, a target trough level of RAD001 is in a range of between 0.1 and 2.4 ng/ml. In some embodiments, a target trough level of RAD001 is in a range of between 0.1 and 1.5 ng/ml. In some embodiments, a target trough level of RAD001 is 0.1 ng/ml. In some embodiments, a target trough level of RAD001 is 0.2 ng/ml. In some embodiments, a target trough level of RAD001 is 0.3 ng/ml. In some embodiments, a target trough level of RAD001 is 0.4 ng/ml. In some embodiments, a target trough level of RAD001 is 0.5 ng/ml. In some embodiments, a target trough level of RAD001 is 0.6 ng/ml. In some embodiments, a target trough level of RAD001 is 0.7 ng/ml. In some embodiments, a target trough level of RAD001 is 0.8 ng/ml. In some embodiments, a target trough level of RAD001 is 0.9 ng/ml. In some embodiments, a target trough level of RAD001 is 1.0 ng/ml. In some embodiments, a target trough level of RAD001 is 1.1 ng/ml. In some embodiments, a target trough level of RAD001 is 1.2 ng/ml. In some embodiments, a target trough level of RAD001 is 1.3 ng/ml. In some embodiments, a target trough level of RAD001 is 1.4 ng/ml. In some embodiments, a target trough level of RAD001 is 1.5 ng/ml. In some embodiments, a target trough level of RAD001 is less than 5 ng/ml. In some embodiments, a target trough level of RAD001 is less than 2.5 ng/ml. In some embodiments, a target trough level of RAD001 is less than 2 ng/ml, 1.9 ng/ml, 1.8 ng/ml, 1.7 ng/ml, 1.6 ng/ml, 1.5 ng/ml, 1.4 ng/ml, 1.3 ng/ml, 1.2 ng/ml, 1.1 ng/ml, 1.0 ng/ml, 0.9 ng/ml, 0.8 ng/ml, 0.7 ng/ml, 0.6 ng/ml, 0.5 ng/ml, 0.4 ng/ml, 0.3 ng/ml, 0.2 ng/ml, or 0.1 ng/ml.

In a further aspect, the invention can utilize an mTOR inhibitor other than RAD001 in an amount that is associated with a target trough level that is bioequivalent to the specified target trough level for RAD001. In an embodiment, the target trough level for an mTOR inhibitor other than RAD001, is a level that gives the same level of mTOR inhibition (e.g., as measured by a method described herein, e.g., the inhibition of P70 S6 kinase) as does a trough level of RAD001 described herein.

Pharmaceutical Compositions: mTOR Inhibitors

In one aspect, the present invention relates to pharmaceutical compositions comprising an mTOR inhibitor, e.g., an mTOR inhibitor as described herein, formulated for use in combination with CAR cells described herein.

In some embodiments, the mTOR inhibitor is formulated for administration in combination with an additional, e.g., as described herein.

In general, compounds of the invention will be administered in therapeutically effective amounts as described above via any of the usual and acceptable modes known in the art, either singly or in combination with one or more therapeutic agents.

The pharmaceutical formulations may be prepared using conventional dissolution and mixing procedures. For example, the bulk drug substance (e.g., an mTOR inhibitor or stabilized form of the compound (e.g., complex with a cyclodextrin derivative or other known complexation agent) is dissolved in a suitable solvent in the presence of one or more of the excipients described herein. The mTOR inhibitor is typically formulated into pharmaceutical dosage forms to provide an easily controllable dosage of the drug and to give the patient an elegant and easily handleable product.

Compounds of the invention can be administered as pharmaceutical compositions by any conventional route, in particular enterally, e.g., orally, e.g., in the form of tablets or capsules, or parenterally, e.g., in the form of injectable solutions or suspensions, topically, e.g., in the form of lotions, gels, ointments or creams, or in a nasal or suppository form. Where an mTOR inhibitor is administered in combination with (either simultaneously with or separately from) another agent as described herein, in one aspect, both components can be administered by the same route (e.g., parenterally). Alternatively, another agent may be administered by a different route relative to the mTOR inhibitor. For example, an mTOR inhibitor may be administered orally and the other agent may be administered parenterally. Pharmaceutical compositions comprising an mTOR inhibitor in free form or in a pharmaceutically acceptable salt form in association with at least one pharmaceutically acceptable carrier or diluent can be manufactured in a conventional manner by mixing, granulating or coating methods. For example, oral compositions can be tablets or gelatin capsules comprising the active ingredient together with a) diluents, e.g., lactose, dextrose, sucrose, mannitol, sorbitol, cellulose and/or glycine; b) lubricants, e.g., silica, talcum, stearic acid, its magnesium or calcium salt and/or polyethyleneglycol; for tablets also c) binders, e.g., magnesium aluminum silicate, starch paste, gelatin, tragacanth, methylcellulose, sodium carboxymethylcellulose and or polyvinylpyrrolidone; if desired d) disintegrants, e.g., starches, agar, alginic acid or its sodium salt, or effervescent mixtures; and/or e) absorbents, colorants, flavors and sweeteners. Oral formulations can also comprise the active ingredient along with 20-60% Eudragit EPO, Hydroxypropyl cellulose EF, Hydroxypropyl methylcellulose, or Kollidon VA64, and up to 5% of pluronic F68, Cremophor EL, or Gelucire 44/14. Injectable compositions can be aqueous isotonic solutions or suspensions, and suppositories can be prepared from fatty emulsions or suspensions. The compositions may be sterilized and/or contain adjuvants, such as preserving, stabilizing, wetting or emulsifying agents, solution promoters, salts for regulating the osmotic pressure and/or buffers. In addition, they may also contain other therapeutically valuable substances. Suitable formulations for transdermal applications include an effective amount of a compound of the present invention with a carrier. A carrier can include absorbable pharmacologically acceptable solvents to assist passage through the skin of the host. For example, transdermal devices are in the form of a bandage comprising a backing member, a reservoir containing the compound optionally with carriers, optionally a rate controlling barrier to deliver the compound to the skin of the host at a controlled and predetermined rate over a prolonged period of time, and means to secure the device to the skin. Matrix transdermal formulations may also be used. In a further aspect, the mTOR inhibitors described herein may be administered via a microneedle patch. Microneedle based drug delivery is well known in the art (See, e.g., U.S. Pat. No. 8,162,901) and these technologies and methods may be adapted by one of skill in the art for administration of an mTOR inhibitor as described herein. Suitable formulations for topical application, e.g., to the skin and eyes, are preferably aqueous solutions, ointments, creams or gels well-known in the art. Such formulations may contain solubilizers, stabilizers, tonicity enhancing agents, buffers and preservatives.

The term "pharmaceutical combination" as used herein means a product that results from the mixing or combining of more than one active ingredient and includes both fixed and non-fixed combinations of the active ingredients. The term "fixed combination" means that the active ingredients, e.g. an mTOR inhibitor and other agent, are both administered to a patient simultaneously in the form of a single entity or dosage. The term "non-fixed combination" means that the active ingredients, e.g. an mTOR inhibitor and other agent, are both administered to a patient as separate entities either simultaneously, concurrently or sequentially with no specific time limits, wherein such administration provides therapeutically effective levels of the 2 compounds in the body of the patient. The latter also applies to cocktail therapy, e.g. the administration of 3 or more active ingredients.

Sustained Release mTOR inhibitors, e.g., allosteric mTOR inhibitors or catalytic mTOR inhibitors, disclosed herein can be provided as pharmaceutical formulations in form of oral solid dosage forms comprising an mTOR inhibitor disclosed herein, e.g., rapamycin or RAD001, which satisfy product stability requirements and/or have favorable pharmacokinetic properties over the immediate release (IR) tablets, such as reduced average plasma peak concentrations, reduced inter- and intra-patient variability in the extent of drug absorption and in the plasma peak concentration, reduced $C_{max}/C_{min}$ ratio and/or reduced food effects. Provided pharmaceutical formulations may allow for more precise dose adjustment and/or reduce frequency of adverse events thus providing safer treatments for patients with an mTOR inhibitor disclosed herein, e.g., rapamycin or RAD001.

In some embodiments, the present disclosure provides stable extended release formulations of an mTOR inhibitor disclosed herein, e.g., rapamycin or RAD001, which are multi-particulate systems and may have functional layers and coatings.

The term "extended release, multi-particulate formulation as used herein refers to a formulation which enables release of an mTOR inhibitor disclosed herein, e.g., rapamycin or RAD001, over an extended period of time e.g. over at least 1, 2, 3, 4, 5 or 6 hours. The extended release formulation may contain matrices and coatings made of special excipients, e.g., as described herein, which are formulated in a manner as to make the active ingredient available over an extended period of time following ingestion.

The term "extended release" can be interchangeably used with the terms "sustained release" (SR) or "prolonged release". The term "extended release" relates to a pharmaceutical formulation that does not release active drug substance immediately after oral dosing but over an extended in accordance with the definition in the pharmacopoeias Ph. Eur. ($7^{th}$ edition) mongraph for tablets and capsules and USP general chapter <1151> for pharmaceutical dosage forms. The term "Immediate Release" (IR) as used herein refers to a pharmaceutical formulation which releases 85% of the active drug substance within less than 60 minutes in accordance with the definition of "Guidance for Industry: "Dissolution Testing of Immediate Release Solid Oral Dosage Forms" (FDA CDER, 1997). In some embodiments, the term "immediate release" means release of everolismus from tablets within the time of 30 minutes, e.g., as measured in the dissolution assay described herein.

Stable extended release formulations of an mTOR inhibitor disclosed herein, e.g., rapamycin or RAD001, can be characterized by an in-vitro release profile using assays known in the art, such as a dissolution assay as described herein: a dissolution vessel filled with 900 mL phosphate buffer pH 6.8 containing sodium dodecyl sulfate 0.2% at 37° C. and the dissolution is performed using a paddle method at 75 rpm according to USP by according to USP testing monograph 711, and Ph. Eur. testing monograph 2.9.3. respectively.

In some embodiments, stable extended release formulations of an mTOR inhibitor disclosed herein, e.g., rapamycin or RAD001, release the mTOR inhibitor in the in-vitro release assay according to following release specifications:

0.5h: <45%, or <40, e.g., <30%
1h: 20-80%, e.g., 30-60%
2h: >50%, or >70%, e.g., >75%
3h: >60%, or >65%, e.g., >85%, e.g., >90%.

In some embodiments, stable extended release formulations of an mTOR inhibitor disclosed herein, e.g., rapamycin or RAD001, release 50% of the mTOR inhibitor not earlier than 45, 60, 75, 90, 105 min or 120 min in the in-vitro dissolution assay.

In one embodiment, stable extended release formulations of an mTOR inhibitor disclosed herein, e.g., rapamycin or RAD001, comprise an mTOR inhibitor in a fast dissolving or disintegrating carrier matrix in combination with coatings wherein at least one of the coatings is an extended release coating. In another embodiment, stable extended release formulations of an mTOR inhibitor disclosed herein, e.g., rapamycin or RAD001, comprise an mTOR inhibitor in a non-disintegrating carrier matrix with extended release properties, which can be combined optionally with additional coatings.

In some embodiments, a carrier matrix comprises matrix formers, typically matrix forming polymers, and may contain additional excipients, such as fillers, e.g., lactose, mannitol, maltodextrine, pregelatinized starch, calcium phosphate, or microcrystallline cellulose, and disintegrants, e.g., corn starch, croscamellose, sodium starch glycolate, or crospovidone, antioxidants, e.g., butylhydroxy anisol, butylhydroxy toluol, ascorbyl palmitate, tocopherol, vitamin E polyethylene glycol succinate, and process enhancing agents, such as lubricants and glidants, e.g., colloidal silicon dioxide, talc, glyceryl monostearate, magnesium stearate, calcium stearate, or sodium stearyl fumarate. The term "matrix former" typically relates to a pharmaceutically inert material which provides physical stability, such as e.g., mechanical or binding stability.

Suitable matrix forming polymers used for fast dissolving or disintegrating carrier matrices are known in the art include for instance cellulose or starch, for instance microcrystalline cellulose ("MCC"), for example Avicel PH 101 (FMC BioPolymer), acacia, sodium alginate, gelatine, starch, pregeliatinised starch, methylcellulose, hydroxypropyl methylcellulose ("HPMC"), hydroxypropylcellulose, hydroxyethylcellulose, polyethylene glycol or polyvinylpyrrolidone ("PVP"), carrageenan, such as Gelcarin GP 812 or combinations thereof.

Suitable matrix forming excipients for non-disintegrating carrier matrices with extended release properties are known in the art include for instance acacia, sodium alginate, gelatine, carboxmethylcellulose sodium, (or "CMC sodium"), methylcellulose, ethylcellulose and cellulose acetate or polyacrylates, e.g., ammonio methacrylate copolymers (Eudragit RS/RL), hydroxypropyl methylcellulose ("HPMC"), hydroxypropylcellulose, hydroxyethylcellulose, polyvinylacetate, polyethylene glycol or polyvinylpyrrolidone ("PVP"), e.g., carrageenan, such as Gelcarin GP 812, glyceryl monostearate, stearylalcohol, stearic acid, glyceryl behenate, Vitamin E polyethylen glycol succinate, or combinations thereof.

In one embodiment, the extended release coating is a layer formed with water insoluble, non-disintegrating polymers, controlling the release by permeation of the drug through this layer.

The extended release coating may also contain one or more of pore formers, plasticizers, and processing enhancing agents, such as lubricants and anti tacking agents. Suitable extended release coating forming polymers which enable diffusion controlled release are known in the art include for instance ethylcellulose and cellulose acetate or polyacrylates, e.g., ammonio methacrylate copolymers (Eudragit RS/RL), polyvinylacetate or combinations thereof. In a particular embodiment, the extended release coating forming polymer is ethylcellulose or cellulose acetate or polyacrylates, e.g., ammoniomethacrylate copolymer Type A (Eudragit RS) or ammonio-methacrylate copolymer Type B (Eudragit RL) or combinations thereof. Moreover, the extended release coating may include plasticizer, such as triacetine, triethyl citrate, dibutylsebacate, diethylsebacate, polyethylene glycol 3000, 4000 or 6000, acetyltriethylcitrate, acetyltributylcitrate, or diethylphthalate, and/or antitacking agents such Syloid 244 FP, talc, glyceryl monostearate, or titanium dioxide. In some embodiments, the amount of plasticizer may be between 5 to 40%, preferably 10 to 25%, relative to the amount of sustained release polymer.

In an embodiment, an extended release coating is a pore forming system which comprises a water insoluble coating forming polymer and a pore former. The term "pore former" relates to a readily soluble excipient which allows pores to be introduced or permeability of the coating to be increased, and a diffusion controlled release of the active ingredient. Suitable pore formers are known in the art include for instance hydroxypropylcellulose (HPC (e.g., Klucel™ EF, EXF, LF), or hydroxypropyl methylcellulose (HPMC, e.g., Methocel™ E3/E5, Pharmacoat 603™), polyethylen glycol (e.g., Macrogol 1500, 3500, 4000, 6000), poloxamer 188 (Pluronic F68™) or povidone (PVP, e.g., Kollidon K25/K30), a saccharide, e.g., a monosaccharide, such as dextrose, mannose, fructose, a disaccharide, such as sucrose or glucodifructose or combinations thereof. Preferably the pore former is hydroxypropylcellulose (HPC (Klucel™ EF, EXF, LF), or hydroxypropyl methylcellulose (HPMC, Methocel™ E3/E5, Pharmacoat 603™), polyethylen glycol (Macrogol 1500, 3500, 4000, 6000), poloxamer 188 (Pluronic F68™) or povidone (PVP, Kollidon K25/K30) or combinations thereof. In some embodiments, suitable amounts of pore formers included in coating are equal to ratios of coating polymer to pore former of e.g. 100:20 to 100:50, or 100:20 to 100:100, preferably ratios of 100:35 to 100:45, particularly ratios of 100:35 to 100:50 relative to the amount of coating forming polymer. In some embodiments, suitable amounts of coating forming polymers included are equal to percentages of polymer weight increase of e.g., 4% to 15%, 5% to 15%, preferably 5% to 12%, more preferably 6% to 12% weight of total weight of pharmaceutical formulation.

In another embodiment, a non-disintegrating extended release carrier matrix comprises matrix forming polymers which enable diffusion controlled release of the active ingredient by hydration of the polymer. The extended carrier matrix may contain further excipients, such as binders and or fillers and process enhancing agents, such as lubricants and glidants, etc.

The following exemplary matrix forming polymers may be used for diffusion controlled release: sodium alginate, polyacrylic acids (or "carbomers"), carboxmethylcellulose sodium, (or "CMC sodium"), methylcellulose, ethylcellulose and cellulose acetate or polyacrylates, e.g., ammonio methacrylate copolymers (Eudragit RS/RL), hydroxypropyl methylcellulose ("HPMC") of different viscosity grades (i.e., average polymer chain lengths) and combinations thereof, e.g., Methocel™ CR grades, hydroxypropyl cellulose, e.g. Klucel™ HF/MF, polyoxyethylene, e.g., Polyox™ or polyvinylpyrrolidone ("PVP"), e.g., PVP K60, K90, carrageenan, such as Viscarin™ GP-209/GP-379, or combinations thereof. Combining of matrix forming polymers allows adjusting the dissolution rate of the active ingredient according to the need.

In some embodiments, a non-disintegrating extended release matrix is formed with excipients, which enable release of the active ingredient by a controlled erosion. The erosion controlled matrices may contain lipophilic matrix formers, and also further excipients, such as fillers, disintegrants and process enhancing agents, such as lubricants and glidants. Exemplary lipophilic matrix forming excipients related to this matrix type include lipophilic excipients, such as glyceryl monostearate, e.g., Cutina GMS, glyceryl behenate, e.g., Compritol 888 ATO, stearyl alcohol, stearic acid, hart fat, e.g., Gelucire™, or Vitamin E polyethylen glycol succinate, e.g., Speziol TPGS or combinations thereof.

Exemplary suitable binders, fillers or further excipients include, but are not limited to, mannitol, pregelatinized starch, microcrystalline cellulose, lactose, calcium phosphate, talc, titanium dioxide, triethylcitrate, Aerosil, antioxidants such as e.g., BHT, desiccants and disintegrant such as e.g., crospovidone or sodium starch glycolate, starch, or croscarmellose. In an embodiment, a stable extended release formulation comprises an mTOR inhibitor disclosed herein, e.g., rapamycin or RAD001, in a fast dissolving/disintegrating matrix, e.g., in form of a solid dispersion as described herein, in combination with functional layers or coatings wherein at least one of the functional layer(s) or coating(s) has release controlling behavior enabling extended release of the active ingredient. In another embodiment, a stable extended release formulation comprises an mTOR inhibitor disclosed herein, e.g., rapamycin or RAD001, in the extended release matrix which, optionally, can further contain functional layers or coatings, such as protective or sustained release layers or coatings. In some embodiments, the coating, e.g., the extended release coating may have a thickness in the range of 10 to 100 µm, e.g., 10 to 50 µm (assessed by confocal RAMAN spectroscopy).

In some embodiments, the formulation of an mTOR inhibitor disclosed herein, e.g., rapamycin or RAD001, is in form of a multi-particulate delivery system. In some embodiments, a multi-particulate drug delivery system is an oral dosage form consisting of multiple, small discrete dose units. In such systems, the dosage form of the drug substances such as capsule, tablets, sachet or stickpack, may contain a plurality of subunits, typically consisting of tens to hundreds or even up to thousands of spherical particles with diameter of 0.05-2.00 mm. Formulations of the size 1.5-3 mm, e.g., minitablets, present another alternative. The dosage form may be designed to disintegrate rapidly in the stomach releasing the multi-particulates. Without wishing to be bound by a particular theory, it is thought that the multi-particulates are spread in the gastro-intestinal lumen and will be emptied gradually from the stomach releasing the drug substance in a controlled manner.

In one embodiment, the formulation of an mTOR inhibitor disclosed herein, e.g., rapamycin or RAD001, e.g., in form of multi-particulate delivery system, comprises an mTOR inhibitor as active ingredient, e.g., dissolved or dispersed in the core of the particle, (e.g., a bead, pellet, granule or minitablet), or in a layer surrounding an inert core of the particle. The active ingredient can be for instance be embedded in an extended release matrix, preferably comprising a hydrophilic or lipophilic matrix forming excipients, or embedded in a fast disintegrating and/or dissolving matrix in combination with functional layer(s) and top coating(s) wherein at least one of the functional layer(s) or top coating(s) comprises a coating forming polymer enabling diffusion controlled extended release of the active ingredient. Optionally, a protection layer for improving stability of the active ingredient separates the matrix containing the active substance from functional layers or top coatings, to ensure stability of the drug product.

In a another embodiment, the formulation of an mTOR inhibitor disclosed herein, e.g., rapamycin or RAD001, e.g., in form of a multi-particulate delivery system, comprises an mTOR inhibitor as active ingredient and an outer coating layer comprising an insoluble polymer and a soluble component as pore former, and optionally further functional layers. For the purpose of the present invention the terms "outer layer" is a layer located towards to the outside of a particle and may be coated with a further layer(s) or may be a top coating. The terms "outer layer", "coating layer" or "top coat" may be used interchangeably depending on the context in which the terms are used.

In one embodiment, the particles comprise one or several top coats enabling extended release of the active ingredient. Top coats typically are final layers with release controlling behavior, which are enclosing each particle of the multi-particulates separately.

In an embodiment, the formulation of an mTOR inhibitor disclosed herein, e.g., rapamycin or RAD001, comprises an outer layer or a top coating that controls the release by the diffusion of the drug through the coating layer which is permeable, optionally by the formation of pores in the insoluble polymer layer, or alternatively solely by the hydration of the insoluble polymer, or that controls the release by a combination of a pore former and hydration of the insoluble polymer. The polymer is insoluble independently from pH, and optionally contains water soluble pore former. The release rate is affected by the extent of pore formation after the pore former is dissolved. The insoluble coating polymer can be cellulose ethers such as ethylcellulose and cellulose acetate or polyacrylates, e.g., ammonio methacrylate copolymers (Eudragit RS/RL). Suitable pore formers include water soluble cellulose ethers, for instance hydroxypropylcellulose (HPC (Klucel™ EF, EXF, LF) or hydroxypropyl methylcellulose (HPMC, Methocel™ E3/E5, Pharmacoat 603™), polyethylen glycol (Macrogol 1500, 3500, 4000, 6000), poloxamer 188 (Pluronic F68™) or povidone (PVP, Kollidon K12, K25, K30). For instance, water soluble pore former can be mixed with insoluble polymer in a ratio of 2:1 to 1:10, e.g. 1:1 to 1:5, 1:3 or 1:5. In an embodiment, the pore former to insoluble polymer ratio is HPC, e.g Klucel™ EF, EXF, LF or HMPC 3 cP, e.g., Methocel™ E3, in a ratio of 1:1 to 1:4, e.g., about 1:1, 1:1.2, 1:1.5 or 1:2. Exemplary insoluble polymers include, but are not limited to ethylcellulose (EC, Aqualon EC N10™) in combination with a pore former. In some embodiments, without the use of a pore former, the combination of the insoluble polymers ammoniomethacrylate copolymer Type A (Eudragit RS) and ammonio-methacrylate copolymer Type B (Eudragit RL) may be at ratios of 1:2 to 9:1, preferably 1:1 to 4:1.

A sustained release top coat(s) may achieve release of majority of the active substance into the small intestine and allows protection of the active substance from stomach fluids and minimizes the exposure of the active substance to the mouth, esophagus and stomach.

In one embodiment, the formulation of an mTOR inhibitor disclosed herein, e.g., rapamycin or RAD001, comprise a drug substance containing matrix, e.g., fast disintegrating and/or dissolving matrix layer or in an extended release matrix layer, e.g., on a starter core such as beads, pellets or granules, which can consist of one or more components, and in which the active ingredient is dispersed or dissolved. For instance, amorphous or crystalline mTOR inhibitor, e.g., rapamycin or RAD001, can be dispersed or dissolved in the matrix in a ratio from 1:100 to 100:1 in the matrix, e.g., 1:50 to 5:1; or 1:50 to 1:1 by weight, or 1:5 to 2:3, or 1:10 to 1:5 by weight (as to the matrix former).

In an embodiment, the drug substance containing matrix is layered onto the surface of starter cores. The layer may be built by spraying a dispersion or solution of the matrix components and the drug substance on to particles of uniform, regular size and shape in a fluid bed process. Alternatively, powder mixtures of the matrix components can be layered using a rotating disk processor. Starter cores have an average particle size 0.1 to 2.5 mm. They can be single crystals, e.g., sucrose, or granular agglomerates manufactured by fluid bed granulation, a rotorgranulation, extrusion and spheronization, or a compaction process. In some embodiments, minitablets can be used as starter cores. In particular embodiments, the starter cores have a spherical shape and consist of inert material such as sucrose and starch (Sugar Spheres, Suglets™, Non-pareils), mannitol (e.g. MCells™), lactose (e.g., spray dried lactose) or microcrystalline cellulose (e.g., Cellets™).

In another embodiment, the drug substance containing matrix is incorporated in the cores of the particles. The matrix forming excipients, fillers, and other ingredients for enhancing the process are mixed together with the drug substance. The powder mixtures obtained can be formulated as particles by using wet extrusion or melt extrusion and subsequent spheronization, or by compacting the mixtures to minitablets. The matrices formed could be either fast disintegrating/dissolving matrices, or non-disintegrating matrices with extended release properties built with hydrophilic or lipophilic matrix forming excipients.

In an embodiment, multi-particulates consisting of a hydrophilic, non-disintegrating matrix which contains the drug substance or a solid dispersion thereof, are prepared by mixing the active ingredient, a filler, e.g., lactose, together with hydrophilic, hydrogel forming polymers with different viscosities, a glidant, and a lubricant. In some embodiments, the hydrophilic, hydrogel forming polymer may be, for example hydroxypropyl methylcellulose, with low viscosity grade of less than 20 mPas for a 2% by weight aqueous solution, e.g., Methocel E5, combined with hydroxypropyl methylcellulose grade with high viscosity of more than 100 mPas for a 2% by weight aqueous solution, e.g., Methocel K100. The powder mixture is then compressed on the tabletting machine to obtain minitablets. Alternatively, the powder mixture can be wetted with organic solvent, e.g., ethanol, and then extruded and spheronized for obtaining multi-particulates.

In another embodiment, multi-particulates consisting of a lipophilic, non-disintegrating matrix which contains the drug substance or a solid dispersion thereof are prepared by mixing the active ingredient, lipophilic, meltable, matrix forming excipients, and fillers. The mixture is processed by melting and mixing in an extruder. The obtained extudate strands are cut into particles and are optionally spheronized. The lipophilic excipients used are for example Vitamin E polyethylen glycol succinate (Vit E TPGS, e.g., Kolliphor TPGS Pharma from BASF) solely, or in combination with glycerol monostearate (GMS, e.g., Kolliwax GMS from-BASF) at ratios of 9:1 to 1:9.

In some embodiments, an extended release formulation of an mTOR inhibitor disclosed herein, e.g., rapamycin or RAD001, reduces the peak concentration ($C_{max}$) to concentration at 24 hours post-dose ($C_{24h}$) ratio after a single dose administration in 24 healthy subjects, as compared to an immediate release tablet, e.g., a rapamycin or RAD001 immediate release tablet available to patients (Final Market Image or "FMI" tablets). In some embodiments, the $C_{max}/C_{24h}$ ratio is decreased, e.g., as measured by pharmacokinetic model simulations. An advantage of a reduced $C_{max}/C_{min}$ ratio is that, with the appropriate dose based on the bioavailability of the mTOR inhibitor relative to an FMI formulation, the concentration of mTOR inhibitor may be maintained above the lower therapeutic range of drug (for sufficient efficacy) and at the same time distance away from the upper therapeutic range of drug (concentration region of toxicity). Thus, in some embodiments, an extended release formulation of an mTOR inhibitor disclosed herein, e.g., rapamycin or RAD001, is able to improve the safety profile of the mTOR inhibitor without affecting its efficacy. In an embodiment, a $C_{max}/C_{24h}$ (thus $C_{max}/C_{min}$) ratio in patients having been administered an extended release formulation of an mTOR inhibitor disclosed herein, e.g., rapamycin or RAD001, is <5 or <4, e.g. 3.5±1 or 3±0.5.

In an embodiment, an mTOR inhibitor disclosed herein, e.g., rapamycin or RAD001, is contained in a layer separate from the functional layer or top coat controlling the extended release properties of the formulation. Such layer may be made of any substance which is suitable for dispersing or dissolving the mTOR inhibitor. In an embodiment, the layer comprising the mTOR inhibitor is made of a hydrophilic carrier matrix. The carrier matrix may be embedding the active ingredient and protecting it against degradation. Suitable matrix formers include, but are not limited to, hydrophilic polymers, e.g. HPMC type 2910 or type 2280, HPC, HEC, MEC, MHEC, povidone, which can be dissolved or rapidly dispersed in water. In one embodiment, the matrix layer is in form of a solid dispersion, for instance as described in WO97/03654 or WO03/028705, the entire contents of each of which are incorporated herein by reference.

In an embodiment, the fast dissolving/disintegrating carrier matrix for an mTOR inhibitor disclosed herein, e.g., rapamycin or RAD001, is in form of a solid dispersion. In some embodiments, the solid dispersion comprises a carrier, e.g., a water-soluble polymer, for example one or a mixture of the following polymers may be used:

hydroxypropylmethylcellulose (HPMC), e.g., Hypromellose type 2910, which is available as Methocel™ E from Dow Chemicals or Pharmacoat™ from Shin Etsu. Good results may be obtained using HPMC with a low apparent viscosity, e.g., below 100 cps as measured at 20° C. for a 2% by weight aqueous solution, e.g. below 50 cps, preferably below 20 cps, for example HPMC 3 cps;

polyvinylpyrrolidone (povidone, PVP), e.g., PVP K25, K30 or PVP K12. PVP is available commercially, for example, as Kollidon® from the BASF company or as Plasdone® from ISP company. A PVP having an average molecular weight between about 8,000 and about 50,000 Daltons is preferred, e.g., PVP K30;

hydroxypropylcellulose (HPC), e.g., Klucel EF/LF/JFor a derivative thereof.

Examples of HPC derivatives include those having low dynamic viscosity in aqueous media, e.g., water, e.g. below about 400 cps as measured in a 5% aqueous solution at 25° C. Preferred HPC derivatives an average molecular weight below about 200,000 Daltons, e.g., between 80,000 and 140,000 Daltons. Examples of HPC available commercially include Klucel® LF, Klucel® EF and Klucel® JF from the Hercules Aqualon company; and Nisso® HPC-L available from Nippon Soda Ltd;

a polyethylene glycol (PEG). Examples include PEGs having an average molecular weight between 1000 and 9000 Daltons, e.g. between about 1800 and 7000, for example PEG 2000, PEG 4000, or PEG 6000 (Handbook of Pharmaceutical Excipients, p. 355-361);

a saturated polyglycolised glyceride, available for example, as Gelucire®, e.g., Gelucire® 44/14, 53/10, 50/13, 42/12, or 35/10 from the Gattefossé company; or a cyclodextrin, for example a β-cyclodextrin or an α-cyclodextrin. Examples of suitable β-cyclodextrins include, but are not limited to, methyl-β-cyclodextrin; dimethyl-β-cyclodextrin; hydroxyproypl-β-cyclodextrin; glycosyl-β-cyclodextrin; maltosyl-β-cyclodextrin; sulfo-β-cyclodextrin; a sulfo-alkylethers of β-cyclodextrin, e.g. sulfo-$C_{1-4}$-alkyl ethers. Examples of α-cyclodextrins include, but are not limited to, glucosyl-α-cyclodextrin and maltosyl-α-cyclodextrin.

In one embodiment, an mTOR inhibitor-containing layer contains antioxidant in a ratio of 1:1000 to 1:1 related to the amount of drug substance. The antioxidant may also be present in other functional layers, e.g., at concentration of 0.1 to 10%, preferably 0.1 to 1%. Suitable antioxidants include, but are not limited to, butyl hydroxyl toluol, butyl hydroxy anisol, ascorbyl palmitate, tocopherol, vitamin E polyethylene glycol succinate. In a particular embodiment, the antioxidant is butyl hydroxyl toluol.

In one embodiment, a protection layer separates the layer containing the active substance from other functional layers, such as e.g., the top coating, to enhance stability of the of the drug product. The drug substance is stabilized by excluding any direct contact with the top coating. The protection layer also acts as diffusion barrier preventing any components in the top coating, e.g., polymer by-products or plasticizers, which can migrate through the layers, from getting in direct contact with the active. Beside the polymers, which are used also as matrix formers (e.g., the matrix formers described above), high content, of inorganic pigments or anti-tacking agents such as talc and/or titanium dioxide, e.g., 10 to 100%, e.g., 20 to 50%, relative to the applied amount of polymer, contribute to the barrier function. The protection layer thickness can be adjusted to gain optimized drug product stability.

In another embodiment, the mTOR inhibitor, e.g., rapamycin or RAD001, is directly embedded in the extended release carrier matrix.

In some embodiments, a formulation comprising an mTOR inhibitor disclosed herein, e.g., rapamycin or RAD001, contains strongly hygroscopic excipients, which are able to bind water moisture enclosed in the formulation working as an internal desiccant. Adsorbents such as e.g., crospovidone, croscarmellose sodium, sodium starch glycolate, or starch can be used. For example, in some embodiments, crospovidone is used as tablet disintegrant, e.g., at 2% to 25% crospovidone. The adsorbent, e.g., crospovidone, may be part of the powder mixtures used for wet and melt extrusion, part of the powder blend for compressing the minitablets, part of powder blend for tabletting the multi-particulates, and/or directly added to the multi-particulates in a sachet or capsule filling process.

In one aspect, an mTOR inhibitor disclosed herein, e.g., rapamycin or RAD001, is present in a particle (e.g., 0.1 to 0.5 mm), bead, pellet (e.g., 0.2 to 2 mm) or mini-tablet (e.g., 1.5 to 3 mm), with a low water moisture content of less than 5% in total, e.g., less than 3% or less than 2.5% in total.

In some embodiments, a pharmaceutical compositions, e.g., a multi-particulate delivery system of an mTOR inhibitor disclosed herein, e.g., rapamycin or RAD001, can be formulated into a drug product such as e.g., capsules (e.g., HPMC or Hart Gelatine capsules), or filled into sachets or stick-packs, or formulated as tablets which release the particles upon disintegration.

In some embodiments, the primary packaging, such as sachets, stickpacks, blisters or bottles may include an water sorbing ingredient, e.g., silica gel, which reduces or stabilizes the water moisture content of the drug product during shelf life storage and/or in during in-use time.

Provided formulations may comprise and/or release multiple pellets, granules or minitablets.

In some embodiments, provided formulations, e.g., multi-particulates formulations, can be prepared by extruding and spheronizing a mixture of the matrix forming excipients together with the drug substance with the aid of heat or wetting liquids, or by compacting minitablets with drug containing mixtures, or by layering the drug containing matrix layer onto cores in a fluid bed or rotogranulation process.

In some embodiments, the layer containing the active substance can be prepared by spraying a spray dispersion with organic solvents in which the hydrophilic components and the active substance are dispersed or dissolved onto the core material, while concurrently the solvents are continuously removed by the aid of heated, dry air. By this process a matrix layer surrounding the cores is formed, e.g., the layer formed is a solid dispersion of the active in polymers such as e.g., HPMC, HPC, HEC.

In one aspect, a provided pharmaceutical formulation may be prepared as follows: An organic feed mixture for spraying in which the hydrophilic polymer is dispersed in colloidal manner and an mTOR inhibitor disclosed herein, e.g., rapamycin or RAD001, is dispersed or dissolved, which precipitate together as a uniform, smooth layer of solid dispersion upon removal of the solvent in such a way that they can be coated with modified release coats. In some embodiments, the obtained drug containing multi-particulates can be coated with additional functional layers and top coatings. A spray dispersion containing coating polymers, lubricants, anti tack agents, pore formers and plastisizers, which are dissolved, dispersed and suspended in organic solvents and mixtures thereof, is sprayed onto the drug containing multi-particulates. During processing the multi-particulates are kept continuously in a controlled motion or fluidization, while dry, heated process gas is applied to the product bed for evaporating the solvents from the surface of the multi-particulates, where the film layer is formed at a defined temperature. The film layer thickness can be controlled by the amount of coating dispersion sprayed. Final drying is applied for minimizing the residual solvent content in the layered and coated multi-particulates.

another aspect, an mTOR inhibitor disclosed herein, e.g., rapamycin or RAD001, may be formulated as part of a high drug load part of an extended release formulation. In some embodiments, the formulation further comprises a surfactant. The term "surfactant" can be used interchangeably with a "wetting agent" or "detergent" and refers to a non-ionic, ionic, anionic, cationic or amphoteric surfactant, e.g., a non-ionic, ionic, anionic, or amphoteric surfactant. Examples of suitable surfactants/wetting agents include, but are not limited to, polyoxyethylene-polyoxypropylene co-polymers and block co-polymers known, for example, under the trademarks Pluronic or Poloxamer (e.g. poloxamer 188 (Pluronic F68), polyoxyethylene, sorbitan fatty acid esters including mono and tri lauryl, palmityl, stearyl and oleyl esters of the type known under the trade name Tween, polyoxyethylene fatty acid esters including polyoxyethylene stearic acid esters of the type known under the trade name Myrj, poly-oxyethylene alkyl ethers known under the trade mark Brij, sodium alkyl sulfates like Soldium lauryl sulphate (SDS) and sulfonates, and sodium alkyl aryl sulfonates, water soluble tocopheryl polyethylene glycol succinic acid esters (TPGS), polyglycerol fatty acid esters, alkylene polyol ethers or esters, polyethylene glycol glyceryl fatty acid esters, sterols and derivatives thereof, trans-esterified, polyoxyethylated caprylic-capric acid glycerides, sugar fatty acid esters, PEG sterol ethers, phospholipids, salts of fatty acids, fatty acid sulfates and sulfonates, salts of fatty acids, fatty acid sulfates and sulfonates, medium or long-chain alkyl, e.g., $C_6$-$C_{18}$, ammonium salts, bile acid or salt thereof; for example cholic acid, glycolic acid or a salt, e.g., sodium cholate and polyoxyethylene mono esters of a saturated $C_{10}$ to $C_{22}$ fatty acid. In a particular embodiment the surfactant is polyoxyethylene-polyoxypropylene co-polymer or block co-polymer, or a water soluble tocopheryl polyethylene glycol succinic acid ester, e.g., a water soluble tocopheryl polyethylene glycol succinic acid ester, e.g., Vitamin E polyethylene glycol 1000 succinate (TPGS). In another embodiment the surfactant in the present pharmaceutical formulation is polyoxyethylene-polyoxypropylene co-polymer, e.g., poloxamer 188. In yet another embodiment, the pharmaceutical formulation comprises the surfactant sodium alkyl sulfate, e.g., sodium lauryl sulfate.

The surfactant or wetting agent may be present in a formulation in a ratio to mTOR inhibitor, e.g., rapamycin or RAD001, from 10:1 to 1:200 by weight, e.g., 1:1 to 1:100 by weight, 1:2 to 1:8 by weight, 1:4 to 1:6 by weight.

In some embodiments, the mTOR inhibitor, e.g., rapamycin or RAD001, is in a high drug load containing first layer, and a surfactant in a second layer, wherein the second layer is beneath the first layer, optionally with additional extended release coating. In some such embodiments, the surfactant is not poloxamer 188 and TPGS. In some embodiments, the surfactant or wetting agent in a second layer can form a protection layer which separates the active ingredient containing layer from the coating covering the formulation. The coating covering the formulation may be an extended release coating.

The dosage of the above treatments to be administered to a patient will vary with the precise nature of the condition being treated and the recipient of the treatment. The scaling of dosages for human administration can be performed according to art-accepted practices. In an embodiment, the dose for CAMPATH, for example, will generally be in the range 1 to about 100 mg for an adult patient, usually administered daily for a period between 1 and 30 days. The preferred daily dose is 1 to 10 mg per day although in some instances larger doses of up to 40 mg per day may be used (described in U.S. Pat. No. 6,120,766).

EXAMPLES

The invention is further described in detail by reference to the following experimental examples. These examples are provided for purposes of illustration only, and are not intended to be limiting unless otherwise specified. Thus, the invention should in no way be construed as being limited to the following examples, but rather, should be construed to encompass any and all variations which become evident as a result of the teaching provided herein.

Without further description, it is believed that one of ordinary skill in the art can, using the preceding description and the following illustrative examples, make and utilize the compounds of the present invention and practice the claimed methods. The following working examples specifically point out various aspects of the present invention, and are not to be construed as limiting in any way the remainder of the disclosure.

Example 1: Regulatable CAR Using a Rapalogue Switch

This example illustrates an important general concept underlying embodiments of regulatable chimeric antigen receptors (RCARs), that is based on the separation of an antigen binding member ("binding event") from an intracellular signaling member ("signaling event"). In the presence of a dimerization molecule, e.g., a small molecule, the switch domains of the antigen binding member and the intracellular signaling member associate and trigger signal transduction in the now associated RCAR molecule. By way of example, an extracellular antigen binding domain, such as a scFv, is fused to a transmembrane domain and a first switch domain (e.g., a switch domain from FKBP or FRB) of the dimerization switch (e.g., a heterodimerization switch). The intracellular signaling domain comprises a second switch domain (e.g., FRB or FKBP) of the heterodimerization switch and one or more intracellular signaling domains such as 4-1BB and CD3zeta. Dimerization and initiation of the signaling cascade was achieved by the addition of a small molecule heterodimerizer ("heterodimerization molecule" because the switch domains are not the same) which links the extracellular binding domain to the intracellular signaling domain. In this example the small molecule inducing dimerization can be rapamycin or analogs thereof (termed "rapalogue"). The rapamycin or rapalogues function by binding with high affinity to FKBP and to the FRB domain of mTOR, thereby acting as a heterodimerizer to induce complex formation Choi, J., et al (1996) *Structure of the FKBP*12-*rapamycin complex interacting with the binding domain of human FRAP* Science 273: 239-42).

The following examples illustrate that the dimerization switch can be on the inside or the outside of the cell.

For illustrative purposes only, the EGFRvIII scFv fragment termed "139" was used as an extracellular antigen binding domain to generate the RCARs. This scFv is derived from a human antibody to EGFRvIII (Morgan et al., 2012 Hum Gene Ther 23(10): 1043-53). To generate a RCAR, a pair of constructs was generated and co-expressed in the target immune effector cell. The various switch domains of the heterodimerization switch can be linked to different domains of the RCAR construct.

"Switch 1" comprises a pair of constructs. The first construct was designed in which the antigen binding domain (139 scFv) was constructed by fusing a leader sequence to the 139 scFv followed by a hinge region, a transmembrane region, a linker and the first intracellular switch domain—FRB (SEQ ID NO: 3). The second construct was designed by fusing the second switch domain—FKBP to a second linker and the signaling domains 4-1BB followed by CD3zeta (SEQ ID NO: 4).

"Switch 2" comprises a pair of constructs. The first construct was designed in which the antigen binding domain was constructed by fusing a leader sequence to the 139 scFv followed by a hinge region, a transmembrane region, a linker, and the first intracellular switch domain—FKBP (SEQ ID NO: 5). The corresponding intracellular signaling construct was designed by fusing the second switch domain—FRB to a second linker and the intracellular signaling domains 4-1BB followed by CD3zeta (SEQ ID NO: 6).

The EGFRvIII CAR sequence for 139 scFv was cloned with the signaling domains for 4-1BB and CD3 zeta. The non-regulatable CAR construct (139scFv-BBZ, SEQ ID NO: 7) is expressed from the pELNS vector for lentivirus production and is used in the subsequent experiments as a control.

EGFRvIII clone 139-CD8alphaTM-FRB (SEQ ID NO: 3)

Malpvtalllplalllhaarpdiqmtqspsslsasvgdrvtitcrasqgi rnnlawyqqkpgkapkrliyaasnlqsgvpsrftgsgsgteftlivsslq pedfatyyclqhhsypltsgggtkveikrtgstsgsgkpgsgegsevqvl esgggvlqpggslrlscaasgftfssyamswvrqapgkglewvsaisgsg gstnyadsvkgrftisrdnskntlylqmnslraedtavyycagssgwsey wgqgtlvtvsstttpaprpptpaptiasqplslrpeacrpaaggavhtrg ldfacdiyiwaplagtcgvlllslvitlyc<u>krgrkkllqgggsgqgggs</u>as -continued
rilwhemwhegleeasrlyfgernvkgmfevleplhammergpqtlkets fnqaygrdlmeaqewcrkymksgnvkdllqawdlyyhvfrrisktsFKBP-4-1BB-CD3zeta (SEQ ID NO: 4)
mgvqvetispgdgrtfpkrgqtcvvhytgmledgkkfdssrdrnkpfkfm lgkqevirgweegvaqmsvgqrakltispdyaygatghpgiipphatlvf dvellkletsggggsggggskrgrkkllyifkqpfmrpvqttqeedgcsc rfpeeeeggcelrvkfsrsadapaykqgqnqlynelnlgrreeydvldkr rgrdpemggkprrknpqeglynelqkdkmaeayseigmkgerrrgkghdg lyqglstatkdtydalhmqalppr EGFRvIII clone 139-CD8alphaTM-FKBP
(SEQ ID NO: 5)
Malpvtalllplalllhaarpdiqmtqspsslsasvgdrvtitcrasqgi rnnlawyqqkpgkapkrliyaasnlqsgvpsrftgsgsgteftlivsslq pedfatyyclqhhsypltsgggtkveikrtgstsgsgkpgsgegsevqvl esggglvqpggslrlscaasgftfssyamswvrqapgkglewvsaisgsg gstnyadsvkgrftisrdnskntlylqmnslraedtavyycagssgwsey wgqgtlvtvsstttpaprpptpaptiasqplslrpeacrpaaggavhtrg ldfacdiyiwaplagtcgvlllslvitlyckrgrkkllgqqgsqqqgsgv qvetispgdgrtfpkrgqtcvvhytgmledgkkfdssrdrnkpfkfmlgk qevirgweegvaqmsvgqrakltispdyaygatghpgiipphatlvfdve llklets FRB-4-1BB-CD3zeta
(SEQ ID NO: 6)
Masrilwhemwhegleeasrlyfgernvkgmfevleplhammergpqtlk etsfnqaygrdlmeaqewcrkymksgnvkdllqawdlyyhvfrrisktsg gggsggggskrgrkkllyifkqpfmrpvqttqeedgcscrfpeeeeggce lrvkfsrsadapaykqgqnqlynelnlgrreeydvldkrrgrdpemggkp rrknpqeglynelqkdkmaeayseigmkgerrrgkghdglyqglstatkd tydalhmqalppr 139scFv-BBz (Control)
(SEQ ID NO: 7)
MALPVTALLLPLALLLHAARPGSDIQMTQSPSSLSASVGDRVTITCRASQ

GIRNNLAWYQQKPGKAPKRLIYAASNLQSGVPSRFTGSGSGTEFTLIVSS

LQPEDFATYYCLQHHSYPLTSGGGTKVEIKRTGSTSGSGKPGSGEGSEVQ

VLESGGGLVQPGGSLRLSCAASGFTFSSYAMSWVRQAPGKGLEWVSAISG

SGGSTNYADSVKGRFTISRDNSKNTLYLQMNSLRAEDTAVYYCAGSSGWS

EYWGQGTLVTVSSASTTTPAPRPPTPAPTIASQPLSLRPEACRPAAGGAV

HTRGLDFACDIYIWAPLAGTCGVLLLSLVITLYCKRGRKKLLYIFKQPFM

RPVQTTQEEDGCSCRFPEEEEGGCELRVKFSRSADAPAYKQGQNQLYNEL

NLGRREEYDVLDKRRGRDPEMGGKPRRKNPQEGLYNELQKDKMAEAYSEI

GMKGERRRGKGHDGLYQGLSTATKDTYDALHMQALPPR

Structure 1: AP21967

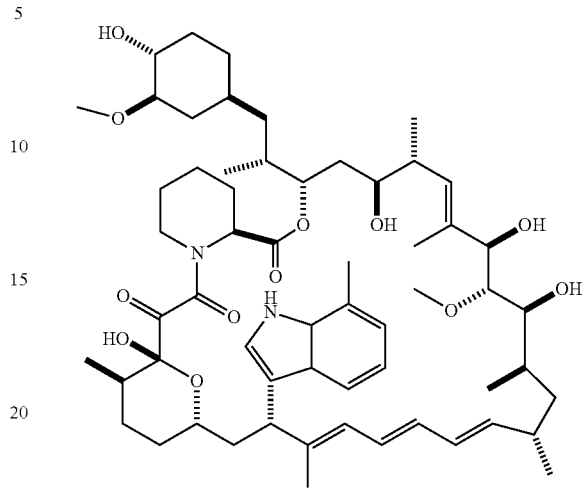

Structure of A/C Heterodimerizer

Materials and Methods
Surface Expression of EGFRvIII CAR Constructs and Staining by FACS Jurkat E6 cells were electroporated with the various EGFRvIII CAR constructs or the 139 CAR control vector using Amaxa Cell Line Nucleofector Kit V (Lonza, Colgne AG, Germany) and program X-001. One day after the transfection, $0.5 \times 10^6$ cells were placed into each well of a V-shape 96 well plate (Greiner Bio-One, Germany) in 0.2 ml FACS buffer (DPBS buffer containing 5% FBS) and incubated for 10 minutes at room temperature. Cells were then spun down and resuspended in 0.2 ml of the FACS buffer with 100 nM of EGFRvIII-Fc and incubated at 4° C. for 60 minutes. Cells were then washed with FACS buffer two times, and incubated with 0.2 ml of the FACS buffer with 1 µl of PE anti-human IgG Fc (Jackson ImmunoResearch Laboratories, West Grove, Pa.) for 30 minutes at 4° C. in the dark. After washing with 0.2 ml of FACS buffer two times, cells were analyzed on a LSRII (BD Biosciences, San Jose, Calif.) machine using the FACSDiva software (BD Biosciences, San Jose, Calif.). Immunofluorescence staining was analyzed as the relative log fluorescence of live cells, and the percentage of the PE positive cells were measured.

Generation of Jurkat Reporter Cell Line for Initial Characterization of CAR Function As an alternative to primary T cell transduction and activation, a Jurkat-NFAT reporter cell line can be used to evaluate the functional activity of CAR constructs. The Jurkat T cell line (E6-1) was transfected with a NFAT-luciferase reporter construct and a stable, clonal cell line Jurket cells with NFAT-LUC reporter (JNL), was selected for further characterization based on strong induction of the NFAT reporter following PMA and ionomycin stimulation.

Transfection of Jurkat Reporter Cell Line and Activation of NFAT by Switch 1 or Switch 2

Jurkat cells with NFAT-LUC reporter (JNL) were grown to the density of $0.5 \times 10^6$/ml in Jurkat cell growth media with puromycin at 0.5 µg/ml. For each transfection $2.5 \times 10^6$ cells were spin down at 100 g for 10 minutes. Two μg of DNA per construct were used per transfection. Amaxa Nucleofector solution V and supplement I was mixed and 100 μl was added into the tube with DNA construct. The mixture was then added to the cells and transferred to the electroporation cuvette. Electroporation was done under setting X-001 using Amaxa Nucleofector II Device. 0.5 ml of growth media was added immediately after electroporation and the mixture were transferred into 2 ml growth media in one well of the 6-well plate. After one hour, A/Z compound was applied at the final concentration of 500 nM. The cells were incubated in the 37° C. incubator with 5% $CO_2$ overnight for 18 hrs. Tissue culture plate was coated with 5 μg/ml of EGFRvIII-Fc or IgG1-Fc for 2 hrs, blocked with the blocking buffer (DPBS with 5% serum) for 1 hour. The transfected cells with or without A/Z compound were resuspended and added to the target plate with 100 μl per well and incubated for 18 hrs. Luciferase One Glo reagent 100 μl was added per well. The samples were incubated for 5 min at 37° C. and then luminescence is measured using a luminometer.

Dose Response of Rapalogue on NFAT Activation

The ability of RCAR constructs to demonstrate rapalogue dependent signal activation following target antigen engagement of the antigen binding domain was measured with the Jurket cells with NFAT-LUC reporter (JNL) reporter cell line. Specifically, JNL were grown to the density of $0.5 \times 10^6$/ml in Jurket cell growth media with puromycin at 0.5 μg/ml. For each transfection $2.5 \times 10^6$ cells were spin down at 100 g for 10 minutes. Two μg of DNA per construct were used per transfection. Amaxa Nucleofector solution V and supplement I was mixed and 100 μl was added into the tube with DNA construct. The mixture was then added to the cells and transferred to the electroporation cuvette. Electroporation was done under setting X-001 using Amaxa Nucleofector II Device. 0.5 ml of growth media was added immediately after electroporation and the mixture were transferred into 2 ml growth media in one well of the 6-well plate. After one hour, the rapalogue compound at various concentrations was added to cells. The cells were incubated in the 37° C. incubator with 5% $CO_2$ overnight for 18 hrs. Tissue culture plate was coated with 5 μg/ml of EGFRvIII-Fc or IgG1-Fc for 2 hrs, blocked with the blocking buffer (DPBS with 5% serum) for 1 hour. The transfected cells were added to the target plate with 100 μl per well and incubated further for 18 hrs. Luciferase One Glo reagent 100 μl was added per well. The samples were incubated for 5 min at 37° C. and then luminescence is measured using a luminometer.

Results

Jurkat Reporter Assay to Test Target Mediated Activity of the Rapalogue Regulated CAR-EGFRvIII Collectively, these experiments demonstrate that various components of a RCAR can be engineered separately and combined in the presence of a dimerization molecule to activate signaling in the RCAR. Surface expression of the scFv was assessed by flow cytometry and was shown to be about ~50% for all the constructs (data not shown). The JNL-RCAR-EGFRvIII cells were then stimulated with or without rapalogue (heterodimerization molecule) demonstrating that the RCAR constructs expressed on the surface of the cells. JNL parental cells and JNL cells expressing a control CAR were included as additional controls. FIG. 12A shows the results from studies designed to investigate the signaling events between the RCAR expressing the antigen binding domain, e.g., scFv, and RCAR expressing the intracellular signaling domains in the presence of a heterodimerization molecule. The data shows significant target regulated activation upon stimulation with the rapalogue equal to the control RCAR. Furthermore, no significant on-target activation was observed in the absence of the rapalogue, indicating a switch mediated by the small molecule regulated heterodimerization of the switch domains (FKBP and FRB). Finally, no activation was observed against a control target (IgG1-Fc only) (open bars). These data demonstrate specificity of the RCAR constructs for EGFRvIII target in the presence of the rapalogue only, and lack of cross-reactivity to control target or in the absence of rapalogue. These data show for the first time that RCAR constructs can be regulated with a heterodimerization switch.

To determine the dose response, rapaloque ("A/C heterodimerizer" AP21967), at various concentrations, was applied to the transfected cells that were cotransfected with EGFRvIII clone 139-CD8alpha™-FKBP (SEQ ID NO: 5, construct 66) and FRB-4-1BB-CD3zeta (SEQ ID NO: 6, construct 67) and NFAT activation was measured. EGFRvIII 139scFv-BBz (SEQ ID NO: 7) was used as a control.

As shown in FIG. 12B, the fold activation of NFAT remained relatively constant from a concentration of 500 nM to as low as 20 nM. Surprisingly, even at 0.8 nM concentration of rapalogue, there is still 2-3 fold of induction of NFAT mediated by the target. The decrease in fold activation was likely due to a decrease in the extent of dimerized 4-1BB-CD3 zeta, while the expression was quite comparable throughout the various concentrations of the rapalogue treatment. This result indicated that rapalogue is potent in mediating the dimerization of FKRP and FBP in the context of a heterodimerization switch used in RCARs. One would expect to see similar results when the switches are reversed such that the FKBP is on the intracellular signaling domain and the FRB is on the 139 scFv antigen binding domain. As in FIG. 12A, there was no activation observed against a control target IgG1-Fc (second set of bars for each pair of bars).

Example 2: Regulatable CAR Using a Coumermycin Switch

The following example illustrates the use of coumermycin regulated dimerization (Farrar, M. A. et al, 1996, nature. 383: 178-181) to activate a RCAR construct. In this example the switch is designed by fusing a leader sequence to the 139 scFv followed by a hinge region, a transmembrane region, a linker and the first intracellular switch domain—GyrB (SEQ ID NO: 8). The second construct was designed by fusing the second switch domain GyrB to a second linker and the intracellular signaling domains 4-1BB followed by CD3zeta (SEQ ID NO: 9). As the switch domain are the same, this dimerization switch is referred to as "homodimerization switch." Signal activation of the T cell will be regulated by addition of the small molecule coumermycin (Structure 2).

Structure 2

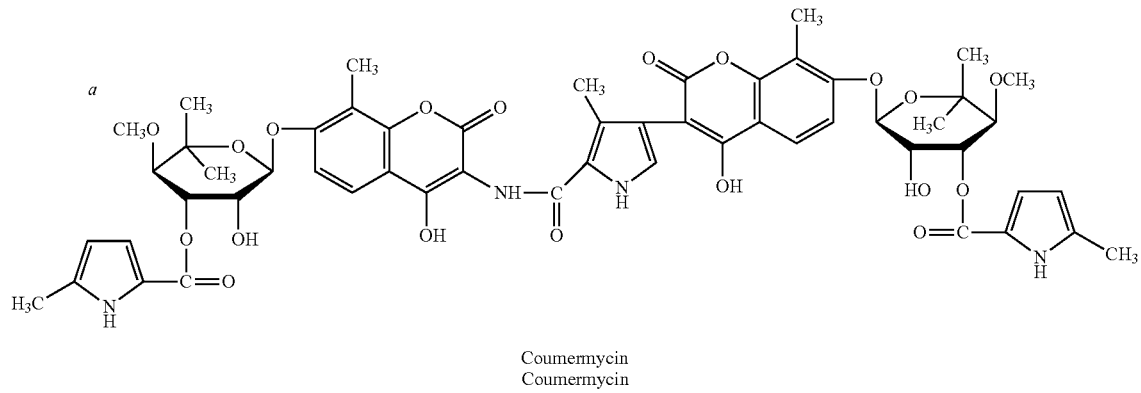

Coumermycin
Coumermycin

EGFRvIII clone 139-CD8alphaTM-gyrB
(SEQ ID NO: 8)
Malpvtalllplalllhaarpdiqmtqspsslsasvgdrvtitcrasqgi rnnlawyqqkpgkapkrliyaasnlqsgvpsrftgsgsgteftlivsslq pedfatyyclqhhsypltsgggtkveikrtgstsgsgkpgsgegsevqvl esggglvqpggslrlscaasgftfssyamswvrqapgkglewvsaisgsg gstnyadsvkgrftisrdnskntlylqmnslraedtavyycagssgwsey wgqgtlvtvsstttpaprpptpaptiasqplslrpeacrpaaggavhtrg ldfacdiyiwaplagtcgvlllslvitlyckrqrkkllqqqqsqqqqsSN

SYDSSSIKVLKGLDAVRKRPGMYIGDTDDGTGLHHMVFEVVDNAIDEALA

GHCKEIIVTIHADNSVSVQDDGRGIPTGIHPEEGVSAAEVIMTVLHAGGK

FDDNSYKVSGGLHGVGVSVVNALSQKLELVIQREGKIHRQIYEHGVPQAP

LAVTGETEKTGTMVRFWPSLETFTNVTEFEYEILAKRLRELSFLNSGVSI

RLRDKRDGKEDHFHYEG

GyrB-4-1BB-CD3zeta
(SEQ ID NO: 9)
MSNSYDSSSIKVLKGLDAVRKRPGMYIGDTDDGTGLHHMVFEVVDNAIDE

ALAGHCKEIIVTIHADNSVSVQDDGRGIPTGIHPEEGVSAAEVIMTVLHA

GGKFDDNSYKVSGGLHGVGVSVVNALSQKLELVIQREGKIHRQIYEHGVP

QAPLAVTGETEKTGTMVRFWPSLETFTNVTEFEYEILAKRLRELSFLNSG

VSIRLRDKRDGKEDHFHYEGggggsggggskrgrkkllyifkqpfmrpvq ttqeedgcscrfpeeeeggcelrvkfsrsadapaykqgqnqlynelnlgr reeydvldkrrgrdpemggkprrknpqeglynelqkdkmaeayseigmkg errrgkghdglyqglstatkdtydalhmqalppr Materials and Methods
Synthesis of DNA for Regulatable CAR Using the Coumermycin Switch Coumermycin is commercially available from several vendors. The sequence for the 139 scFv was cloned with the signaling domains for 4-1BB and CD3 zeta. The non-regulatable CAR construct, 139scFv-BBZ, SEQ ID: 7, can be used as a control. For the coumermycin RCAR, the 139 scFv was cloned with a transmembrane domain followed by the GyrB switch domain at the c-terminus (SEQ ID NO:8) and the corresponding activation construct made by fusing GyrB to a linker and the signaling domains 4-1BB followed by CD3zeta (SEQ ID NO:9). Jurkat assays were performed essentially as described in Example 1, with the exception that the final step involves incubating the transfected cells for 18 hrs in the presence of varying concentrations of coumermycin. Luciferase One Glo reagent 100 µl was added per well. The samples were incubated for 5 min at 37° C. and then luminescence was measured using a luminometer.

Figures 20A, 20B:
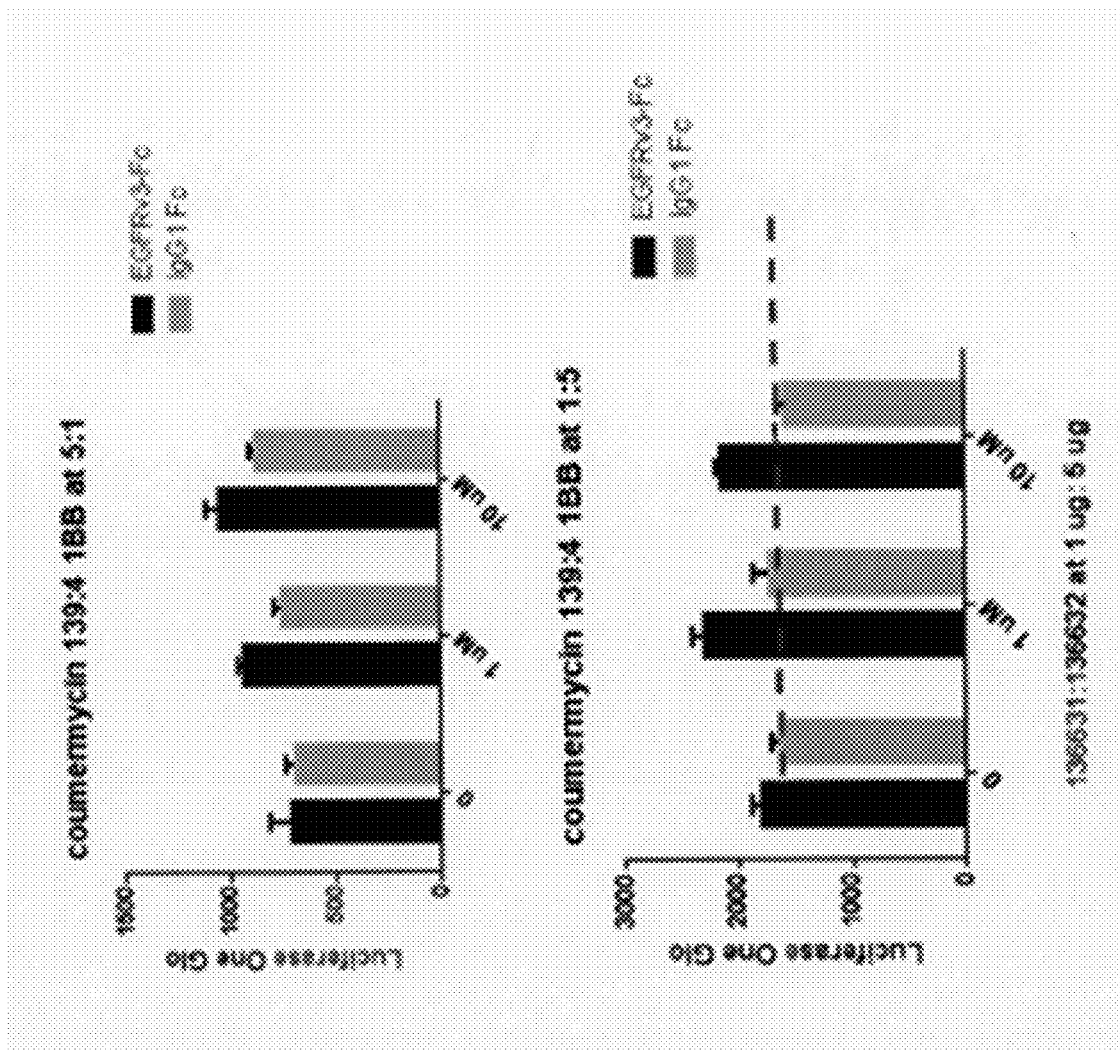
FIGS. 20A and 20B show the activity of an RCAR having a GyrB-GyrB based intracellular switch, e.g., as shown in FIG. 3.

FIGS. 20A and 20B depict the effect of addition of coumermycin on signal at two different ratios of antigen binding member:intracellular signaling member (5:1 and 1:5). Addition of coumerycin resulted in a significant increase in signal at both 1 mM and 10 mM, at both ratios.

Example 3: Regulatable CAR Using a Gibberellin Switch

The following example illustrates the use of gibberellin mediated heterodimerization to activate a RCAR construct (Takafumi M et al, 2012. Nat Chem Biol; 8(5):465-470). To generate a RCAR, a pair of constructs was generated and co-expressed in the target cell. The various heterodimerization domains of the switch domains can be linked to different domains of the RCAR construct.

"Switch 1" comprises a pair of constructs. The first construct was designed in by fusing a leader sequence to the 139 scFv followed by a hinge region, a transmembrane region, a linker and the first intracellular switch domain—GAI (SEQ ID NO: 10). The corresponding second construct was designed by fusing the second switch domain—GID1, to a second linker and the signaling domains 4-1BB followed by CD3zeta (SEQ ID NO: 11).

"Switch 2" comprises a pair of constructs. The first construct was designed by fusing a leader sequence to the scFv followed by a hinge region, a transmembrane region, a linker and the first intracellular switch domain—GID1 (SEQ ID NO: 12). The corresponding second construct was designed by fusing the second switch domain—GAI, to a second linker and the intracellular signaling domains 4-1BB followed by CD3zeta (SEQ ID NO: 13).

Induction of heterodimerization switch is achieved by addition of Gibberellic Acid Acetoxymethyl Ester (structure 3, commercially available from Toronto Research Chemicals, Inc)

Structure 3

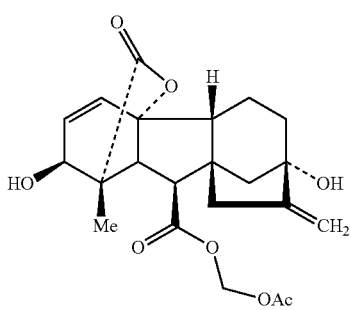

Gibberellic Acid Acetoxymethyl Ester

EGFRvIII clone 139-CD8alphaTM-GAI  (SEQ ID NO: 10)
Malpvtalllplalllhaarpdiqmtqspsslsasvgdrvtitcrasqgirnnlawyqqkpgkapkrliyaasnlqsgvpsrftgsgsgte
ftlivsslqpedfatyyclqhhsypltsgggtkveikrtgstsgsgkpgsgegsevqvlesggglvqpggslrlscaasgftfssyamsw
vrqapgkglewvsaisgsggstnyadsvkgrftisrdnskntlylqmnslraedtavyycagssgwseywgqgtlvtvssttttpaprp
ptpaptiasqplslrpeacrpaaggavhtrgldfacdiyiwaplagtcgvlllslvitlyc<u>krgrkkllgggsgggqs</u>KRDHHHH
HHQDKKTMMMNEEDDGNGMDELLAVLGYKVRSSEMADVAQKLEQLEVMMSNVQE
DDLSQLATETVHYNPAELYTWLDSMLTDLN GID1-4-1BB-CD3zeta  (SEQ ID NO: 11)
MAASDEVNLIESRTVVPLNTWVLISNFKVAYNILRRPDGTFNRHLAEYLDRKVTANAN
PVDGVFSFDVLIDRRINLLSRVYRPAYADQEQPPSILDLEKPVDGDIVPVILFFHGGSFA
HSSANSAIYDTLCRRLVGLCKCVVVSVNYRRAPENPYPCAYDDGWIALNWVNSRSWL
KSKKDSKVHIFLAGDSSGGNIAHNVALRAGESGIDVLGNILLNPMFGGNERTESEKSLD
GKYFVTVRDRDWYWKAFLPEGEDREHPACNPFSPRGKSLEGVSFPKSLVVVAGLDLIR
DWQLAYAEGLKKAGQEVKLMHLEKATVGFYLLPNNNHFHNVMDEISAFVNAECgggg
sggggskrgrkkllyifkqpfmrpvqttqeedgcscrfpeeeeggcelrvkfsrsadapaykqgqnqlynelnlgrreeydvldkrrg
rdpemggkprrknpqeglynelqkdkmaeayseigmkgerrrgkghdglyqglstatkdtydalhmqalppr EGFRvIII clone 139-CD8alphaTM-GID1  (SEQ ID NO: 12)
Malpvtalllplalllhaarpdiqmtqspsslsasvgdrvtitcrasqgirnnlawyqqkpgkapkrliyaasnlqsgvpsrftgsgsgte
ftlivsslqpedfatyyclqhhsypltsgggtkveikrtgstsgsgkpgsgegsevqvlesggglvqpggslrlscaasgftfssyamsw
vrqapgkglewvsaisgsggstnyadsvkgrftisrdnskntlylqmnslraedtavyycagssgwseywgqgtlvtvssttttpaprp
ptpaptiasqplslrpeacrpaaggavhtrgldfacdiyiwaplagtcgvlllslvitlyc<u>krgrkkllgggsgggqs</u>AASDEVNL
IESRTVVPLNTWVLISNFKVAYNILRRPDGTFNRHLAEYLDRKVTANANPVDGVFSFD
VLIDRRINLLSRVYRPAYADQEQPPSILDLEKPVDGDIVPVILFFHGGSFAHSSANSAIYD
TLCRRLVGLCKCVVVSVNYRRAPENPYPCAYDDGWIALNWVNSRSWLKSKKDSKVH
IFLAGDSSGGNIAHNVALRAGESGIDVLGNILLNPMFGGNERTESEKSLDGKYFVTVRD
RDWYWKAFLPEGEDREHPACNPFSPRGKSLEGVSFPKSLVVVAGLDLIRDWQLAYAE
GLKKAGQEVKLMHLEKATVGFYLLPNNNHFHNVMDEISAFVNAEC GAI-4-1BB-CD3zeta  (SEQ ID NO: 13)
MKRDHHHHHHQDKKTMMMNEEDDGNGMDELLAVLGYKVRSSEMADVAQKLEQLE
VMMSNVQEDDLSQLATETVHYNPAELYTWLDSMLTDLNgggggsggggskrgrkkllyifkqpfmr -continued

```
pvqttqeedgcscrfpeeeeggcelrvkfsrsadapaykqgqnqlynelnlgrreeydvldkrrgrdpemggkprrknpqeglynel qkdkmaeayseigmkgerrrgkghdglyqglstatkdtydalhmqalppr
```

Materials and Methods
Synthesis of DNA for Regulatable CAR Using the Coumermycin Switch Gibberellic Acid Acetoxymethyl Ester is commercially available from Toronto Research Chemicals, Inc. The sequence for the 139 scFv will be cloned with the signaling domains for 4-1BB and CD3 zeta. The non-regulatable CAR construct, 139scFv-BBZ, SEQ ID: 7, can be used as a control. For the Gibberellin RCAR, "Switch 1" comprises a pair of constructs. In the first construct the 139 scFv will be cloned with the GAI-switch domain at the c-terminus (SEQ ID NO:10) and the corresponding second construct designed by fusing the GID1-switch domain to a linker and the intracellular signaling domains 4-1BB followed by CD3zeta (SEQ ID NO:11).

"Switch 2" comprises a pair of constructs. In the first construct, the 139 scFv will be cloned with the GID1-switch domain at the c-terminus (SEQ ID NO:12) and the corresponding second construct designed by fusing the GAI-switch domain to a linker and the intracellular signaling domains 4-1BB followed by CD3zeta (SEQ ID NO:13).

Jurkat assays were performed as described in Example 1, with the exception that the final step involved incubating the transfected cells for 18 hrs in the presence of varying concentrations of gibberellic acid acetoxymethyl ester or giberellic acid. Luciferase One Glo reagent 100 µl was added per well. The samples were incubated for 5 min at 37° C. and then luminescence was measured using a luminometer.

Figure 21A:
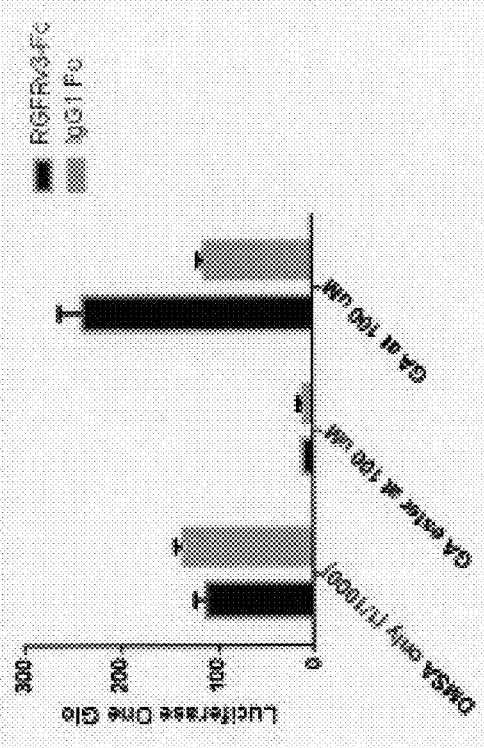
FIGS. 21A and 21B show the activity of an RCAR having a GAI-GID1 based intracellular switch, e.g., as shown in FIG. 4.

FIG. 21A shows the effect of DMSA, gibberellic acid acetoxymethyl ester, and giberellic acid on NFAT expression.

Figure 21B:
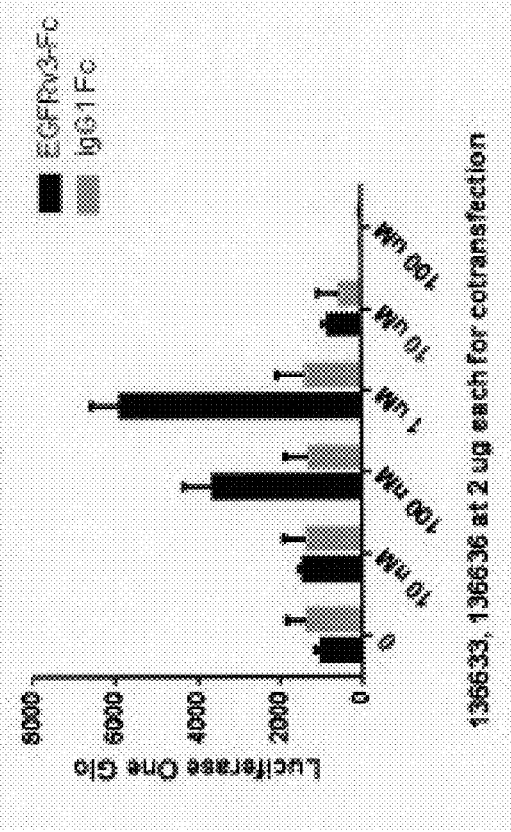

FIG. 21B shows the response of NFAT expression to increasing dose of gibberellic acid acetoxymethyl ester.

Example 4: Internal Covalent Switch

The use of specific covalent cross-linking agents as alternatives for heterodimerization has recently been described (Erhart et al., 2013 Chem Biol 20(4): 549-557), although not in the context of RCARs. In embodiments, these agents, designated HaXS, can overcome potential kinetic limitations related to off rates and need for accumulation of non-covalent molecules in the cell as prerequisites to activation of the required signal cascades for T-cell mediated killing. HaXS contain functional groups for linking a Halo-Tag (see, e.g., SEQ ID NO:14) with a SNAP-Tag (see e.g., SEQ ID NO:15) along with a cell penetrating core. Evaluation of HaXS molecules in the context of regulatable RCARs will be performed using EGFRvIII RCAR (139 scFv) as a model system. See, e.g., FIG. 13.

Materials and Methods
Synthesis of HaXS and DNA for Regulatable CAR

A representative HaXS (Structure 5) will be chemically synthesized as described by Erhart et. Al supra. The sequence for the 139 scFv will be cloned with the intracellular signaling domains for 4-1BB and CD3 zeta. The non-regulatable CAR construct, 139scFv-BBZ, SEQ ID: 7, will be used as a control. For the HaXs RCAR, the various heterodimerization domains of the switch domains can be linked to different domains of the RCAR construct.

"Switch 1" comprises a pair of constructs. In the first construct, the 139 scFV will be cloned with the SNAP-tag at the c-terminus (SEQ ID NO:16) and the corresponding second construct designed by fusing the Halo-Tag to a linker and the intracellular signaling domains 4-1BB followed by CD3zeta (SEQ ID NO:17). "Switch 2" comprises a pair of constructs. In the first construct, the 139 scFV will be cloned with the SNAP-tag at the c-terminus (SEQ ID NO:18) and the corresponding second construct designed by fusing the Halo-Tag to a linker and the intracellular signaling domains 4-1BB followed by CD3zeta (SEQ ID NO:19). Jurkat assays will be performed as described in Example 1, with the exception that the final step will involve incubating the transfected cells for 18 hrs in the presence of varying concentrations of HaXS. Luciferase One Glo reagent 100 µl will be added per well. The samples will be incubated for 5 min at 37° C. and then luminescence will be measured using a luminometer.

```
Halo-tag
                                                          (SEQ ID NO: 14)
Gseigtgfpfdphyvevlgermhyvdvgprdgtpvlflhgnptssyvwrniiphvapthrciapdligmgksdkpdlgyffddh vrfmdafiealgleevvlvihdwgsalgfhwakrnpervkgiafmefirpiptwdewpefaretfqafrttdvgrkliidqnvfieg tlpmgvvrpltevemdhyrepflnpvdreplwrfpnelpiagepanivalveeymdwlhqspvpkllfwgtpgvlippaeaarl akslpnckavdigpglnllqednpdligseiarwlstleisg SNAP-tag
                                                          (SEQ ID NO: 15)
Mdkdcemkrttldsplgklelsgceqglhriiflgkgtsaadavevpapaavlggpeplmqatawlnayfhqpeaieefpvpalh hpvfqqesftrqvlwkllkvvkfgevisyshlaalagnpaataavktalsgnpvpilipchrvvqgdldvggyegglavkewllah eghrlgkpglg 139scFV-CD8alphaTM-SNAP
                                                          (SEQ ID NO: 16)
Malpvtalllplalllhaarpdiqmtqspsslsasvgdrvtitcrasqgirnnlawyqqkpgkapkrliyaasnlqsgvpsrftgsgs gteftlivsslqpedfatyyclqhhsypltsgggtkveikrtgstsgsgkpgsgegsevqvlesggglvqpggslrlscaasgftfssy
```

-continued

```
amswvrqapgkglewvsaisgsggstnyadsvkgrftisrdnskntlylqmnslraedtavyycagssgwseywgqgtlvtvss
tttpaprpptpaptiasqplslrpeacrpaaggavhtrgldfacdiyiwaplagtcgvlllslvitlyckrgrkkllggggsggggsdkd
cemkrttldsplgklelsgceqglhriiflgkgtsaadavevpapaavlggpeplmqatawlnayfhqpeaieefpvpalhhpvfq
qesftrqvlwkllkvvkfgevisyshlaalagnpaataavktalsgnpvpilipchrvvqgdldvggyegglavkewllaheghrl
gkpglg
```

Halo-4-1BB-CD3zeta                                              (SEQ ID NO: 17)

```
MGseigtgfpfdphyvevlgermhyvdvgprdgtpvlflhgnptssyvwrniiphvapthrciapdligmgksdkpdlgyffd
dhvrfmdafiealgleevvlvihdwgsalgfhwakrnpervkgiafmefirpiptwdewpefaretfqafrttdvgrkliidqnvfi
egtlpmgvvrpltevemdhyrepflnpvdreplwrfpnelpiagepanivalveeymdwlhqspvpkllfwgtpgvlippaea
arlakslpnckavdigpglnllqednpdligseiarwlstleisggggsggggskrgrkkllyifkqpfmrpvqttqeedgcscrfp
eeeeggcelrvkfsrsadapaykqgqnqlynelnlgrreeydvldkrrgrdpemggkprrknpqeglynelqkdkmaeaysei
gmkgerrrgkghdglyqglstatkdtydalhmqalppr
```

139scFV-CD8alphaTM-halo                                         (SEQ ID NO: 18)

```
Malpvtalllplalllhaarpdiqmtqspsslsasvgdrvtitcrasqgirnnlawyqqkpgkapkrliyaasnlqsgvpsrftgsgs
gteftlivsslqpedfatyyclqhhsypltsgggtkveikrtgstsgsgkpgsgegsevqvlesgglvqpggslrlscaasgftfssy
amswvrqapgkglewvsaisgsggstnyadsvkgrftisrdnskntlylqmnslraedtavyycagssgwseywgqgtlvtvss
tttpaprpptpaptiasqplslrpeacrpaaggavhtrgldfacdiyiwaplagtcgvlllslvitlyckrgrkkllggggsggggsGse
igtgfpfdphyvevlgermhyvdvgprdgtpvlflhgnptssyvwrniiphvapthrciapdligmgksdkpdlgyffddhvrf
mdafiealgleevvlvihdwgsalgfhwakrnpervkgiafmefirpiptwdewpefaretfqafrttdvgrkliidqnvfiegtlp
mgvvrpltevemdhyrepflnpvdreplwrfpnelpiagepanivalveeymdwlhqspvpkllfwgtpgvlippaeaarlak
slpnckavdigpglnllqednpdligseiarwlstleisg
```

SNAP-4-1BB-CD3zeta                                              (SEQ ID NO: 19)

```
Mdkdcemkrttldsplgklelsgceqglhriiflgkgtsaadavevpapaavlggpeplmqatawlnayfhqpeaieefpvpalh
hpvfqqesftrqvlwkllkvvkfgevisyshlaalagnpaataavktalsgnpvpilipchrvvqgdldvggyegglavkewllah
eghrlgkpglggggsggggskrgrkkllyifkqpfmrpvqttqeedgcscrfpeeeeggcelrvkfsrsadapaykqgqnqlyn
elnlgrreeydvldkrrgrdpemggkprrknpqeglynelqkdkmaeayseigmkgerrrgkghdglyqglstatkdtydalh
mqalppr
```

Structure 5

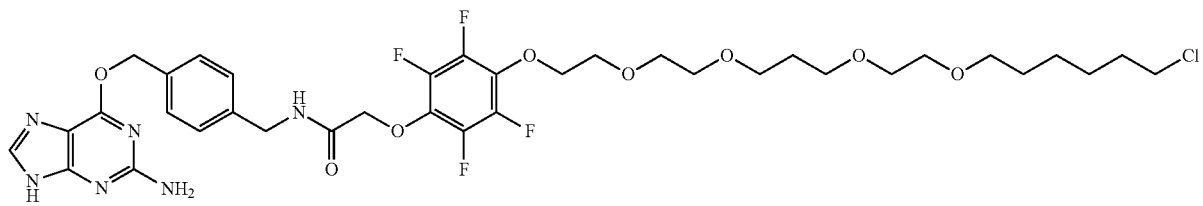

HaXS

Example 5: Peptide Based Dimerization Switch—Myc Tag

Figure 6:
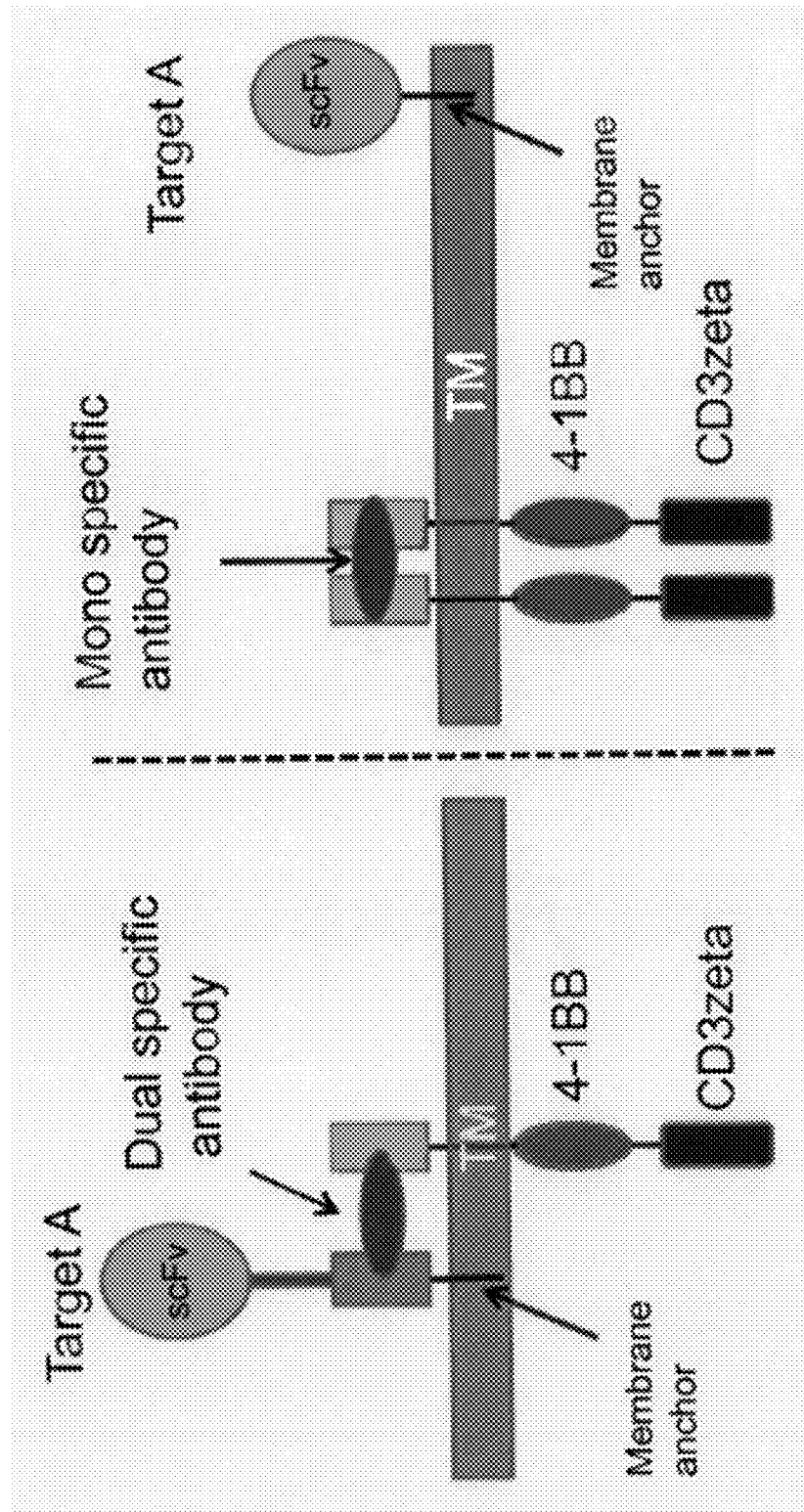
FIG. 6 depicts RCARs having extracellular switches induced by antibody molecule, non-antibody scaffold, or polypeptide. In the RCAR system on the left, the two heterodimerization switch domains are brought together by a dual specific antibody. In the RCAR system on the right, two intracellular signaling members can be brought together by a mono specific antibody to initiate CAR signaling.
Figure 7:
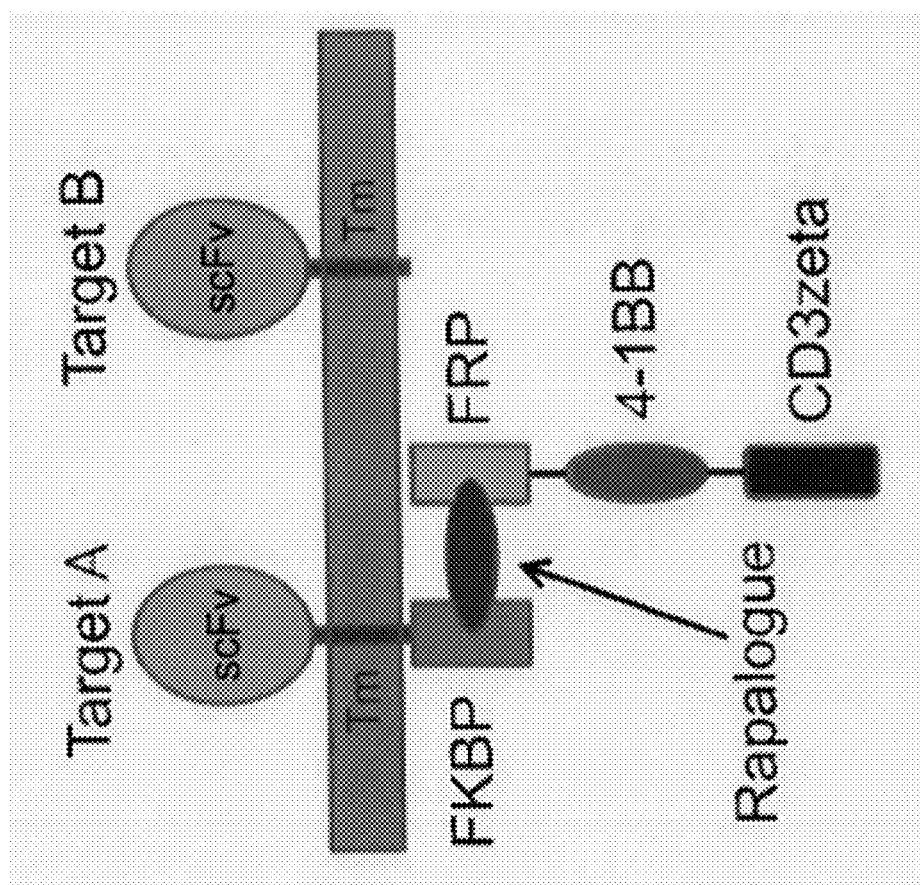
FIG. 7 depicts a dual RCAR system, where two different targets (Target A and Target B) can be targeted.

In embodiments, T cell-mediated cell death requires the linking of an external binding event to the signaling activation cascade in the intracellular space, see, e.g., FIG. 6. Co-localization and clustering of these intracellular signaling domains via an externally displayed switch domain (e.g., c-myc peptide tag) and a soluble ligand with the target cell bound receptor/scFv (e.g., anti-myc antibody) is allows for induction of the desired signaling response. The extracellular switch domain can be any tag molecule such as c-myc peptide tag, flag peptide tag, HA peptide tag or V5 peptide tag, that interacts with the appropriate dimerization molecule. In these cases the dimerization molecule acts as a crosslinking reagent, and can include antibodies against the peptide tag molecules comprised by the switch domain. The extracellular domain can also be scFvs against cancer antigens, such as scFv (e.g., 139) against EGFRvIII antigen. In this case the crosslinking reagent can be antigen itself such as EGFRvIII-Fc molecule. When a switch domain acting as a single crosslinking reagent, such as an anti-tag antibody, is insufficient to form clusters and activate a signal, a further crosslinking reagent can be used. This can be antibodies against anti-tag antibodies, or antibodies against Fc to further crosslink EGFRvIII-Fc. Specifically, in this example, the switch is an external homodimerization switch and the first and second switch domains are myc tag peptides that are linked to the intracellular transmembrane and intracellular signaling domains. The antigen binding domain, e.g., 139 scFv, does not have a switch domain and serves only to bind to the target cancer cell. In this example, signaling is initiated by the addition of a crosslinking rabbit polyclonal myc antibody (i.e., a homodimerization molecule) that binds to the each of the external first and second myc peptide switch domains causing them to cluster. This clustering of the external homodimerization switch causes the intracellular signaling domains to cluster and activate signaling—see FIG. 14A. Further enhancement of the intracellular signaling event is achieved by increasing the external co-clustering with the addition of further cross-linking antibodies. In this example, further clustering is achieved by the addition of an anti-rabbit antibody against the rabbit polyclonal myc antibody as shown in FIG. 14B.

Methods and Materials

RCAR with flag or c-myc peptide tag displayed on the cell surface will be designed by fusing the corresponding sequences to a linker and the intracellular signaling domains 4-1BB followed by CD3zeta (SEQ ID NO: 20 and 21, respectively). The non-regulatable CAR construct, 139scFv-BBZ, SEQ ID: 7, will be used as a control. Jurket cells with NFAT-LUC reporter (JNL) were grown to the density of 0.5×10⁶/ml in Jurket cell growth media with puromycin at 0.5 μg/ml. For each transfection 2.5×10⁶ cells were spun down at 100 g for 10 minutes. Two μg of DNA per construct was used per transfection. Amaxa Nucleofector solution V and supplement I were mixed and 100 μl was added into the tube with DNA construct. The mixture was then added to the cells and transferred to the electroporation cuvette. Electroporation was done under setting X-001 using Amaxa Nucleofector II Device. 0.5 ml of growth media was added immediately after electroporation and the mixture were transferred into 2 ml growth media in one well of the 6-well plate. The cells were incubated in the 37° C. incubator with 5% $CO_2$ overnight. Rabbit polyclonal antibody against myc tag was added to the cells which were transfected with RCAR construct with myc tag as the extracellular domain. The concentration of the polyclonal antibody was at 100 nM. One and half hour later, 100 nM of anti rabbit antibody was added in order to enhance cluster formation. The cell mixture was incubated at 37° C. for 18 hrs. Luciferase One Glo reagent 100 μl was added per well. The samples were incubated for 5 min at 37° C. and then luminescence was measured using a luminometer.

Similarly, a construct with Flag peptide tag as the extracellular domain was used to transfect reporter cells. Rabbit polyclonal antibody against Flag peptide tag was used at 100 nM; and to facilitate further clustering, an antibody against the rabbit polyclonal antibody was used at 100 nM. In addition, a construct with scFv 139 as the extracellular domain was used to transfect reporter cells, and EGFRvIII-Fc at 100 nM was used, and one and half hour later anti-Fc antibody was used.

flag tag CAR (SEQ ID NO: 20)
Malpvtalllplalllhaarpgsdykddddkggggsggggstttpaprpp tpaptiasqplslrpeacrpaaggavhtrgldfacdiyiwaplagtcgvl llslvitlyckrgrkkllyifkqpfmrpvqttqeedgcscrfpeeeeggc elrvkfsrsadapaykqgqnqlynelnlgrreeydvldkrrgrdpemggk prrknpqeglynelqkdkmaeayseigmkgerrrgkghdglyqglstatk dtydalhmqalppr myc tag CAR (SEQ ID NO: 21)
Malpvtalllplalllhaarpgseqkliseedlggggsggggstttpapr pptpaptiasqplslrpeacrpaaggavhtrgldfacdiyiwaplagtcg vlllslvitlyckrgrkkllyifkqpfmrpvqttqeedgcscrfpeeeeg gcelrvkfsrsadapaykqgqnqlynelnlgrreeydvldkrrgrdpemg gkprrknpqeglynelqkdkmaeayseigmkgerrrgkghdglyqglsta tkdtydalhmqalppr As shown in FIG. 14A, RCAR with c-myc peptide tag as the extracellular domain showed higher NFAT activity when incubated with rabbit polyclonal anti-myc antibody as compared to other antibodies. This indicated that the activation was specifically due to crosslinking of c-myc peptide tag on the cell surface forming clusters. The activation was further enhanced by the addition of anti rabbit antibody, as show in FIG. 14A.

RCAR with Flag tag only showed activation when both crosslinking reagents were added, i.e., both the rabbit polyclonal anti-Flag antibody and anti-rabbit antibody. Similarly, RCAR with 139 scFv as the extracellular domain showed activation when EGRFvIII-Fc and anti-Fc antibody were added. See FIGS. 14A and 14B.

Example 6: Peptide-Based Multimerization of Activation Signaling Domains

In embodiments, T cell-mediated cell death requires the linking of an external binding event to the signaling activation cascade in the intracellular space. Co-localization and clustering of these intracellular signaling domains via an external displayed molecule, a switch domain, and a dimerization molecule that comprises a multimerized soluble ligand in combination with a target cell bound receptor/scFv can be used to induce the desired response. See, e.g., FIG. 15. Exemplification of this principle in the context of regulatable CARs can be performed using EGFRvIII RCAR (139sFv) as a model system with an additional scFv (as switch domains) displayed to various multimers of the c-myc peptide tag (as the dimerization molecule).

Materials and Methods

Synthesis of c-Myc Peptide Multimers and DNA for Regulatable RCAR

Monomers, dimers, trimers and tetramers of c-myc peptide (SEQ ID NO:22-25) will be synthesized via standard solid-phase peptide synthesis and used as multimeric dimerization switches. Each of the c-myc peptide monomers is linked by a GS linker. The sequence for the 139 scFv will be cloned with the intracellular signaling domains for 4-1BB and CD3 zeta. The non-regulatable CAR construct, 139scFv-BBZ, SEQ ID: 7, will be used as a control. For the c-myc regulatable CAR, the 139 scFv will be cloned with the CD8 alpha transmembrane domain (SEQ ID NO: 26) and the corresponding intracellular signaling construct designed by fusing the 9E10 anti-myc scFv to linker and the intracellular signaling domains 4-1BB followed by CD3zeta (9e10 scFv-BBZ, SEQ ID NO: 27).

```
c-myc monomer peptide
                                            (SEQ ID NO: 22)
EEQKLISEEDL c-myc dimer peptide
                                            (SEQ ID NO: 23)
EEQKLISEEDLGGGGSGGGGSGGGGSEEQKLISEEDL c-myc trimer peptide
                                            (SEQ ID NO: 24)
EEQKLISEEDLGGGGSGGGGSGGGGSEEQKLISEEDLGGGGSGGGGSGGG
GSEEQKLISEEDL c-myc tetramer peptide
                                            (SEQ ID NO: 25)
EEQKLISEEDLGGGGSGGGGSGGGGSEEQKLISEEDLGGGGSGGGGSGGG
GSEEQKLISEEDLGGGGSGGGGSGGGGSEEQKLISEEDL 139scFV-CD8alphaTM
                                            (SEQ ID NO: 26)
Malpvtalllplalllhaarpdiqmtqspsslsasvgdrvtitcrasqgi rnnlawyqqkpgkapkrliyaasnlqsgvpsrftgsgsgteftlivsslq pedfatyyclqhhsypltsgggtkveikrtgstsgsgkpgsgegsevqvl esgggglvqpggslrlscaasgftfssyamswvrqapgkglewvsaisgsg gstnyadsvkgrftisrdnskntlylqmnslraedtavyycagssgwsey wgqgtlvtvsstttpaprpptpaptiasqplslrpeacrpaaggavhtrg ldfacdiyiwaplagtcgvlllslvitlyckrgrkkll 9E10scFv-BBz
                                            (SEQ ID NO: 27)
MALPVTALLLPLALLLHAARPGSDIVLTQSPASLAVSLGQRATISCRASE

SVDNYGFSFMNWFQQKPGQPPKLLIYAISNRGSGVPARFSGSGSGTDFSL

NIHPVEEDDPAMYFCQQTKEVPWTFGGGTKLEIKGGGGSGGGGSGGGGSE

VHLVESGGDLVKPGGSLKLSCAASGFTFSHYGMSWVRQTPDKRLEWVATI

GSRGTYTHYPDSVKGRFTISRDNDKNALYLQMNSLKSEDTAMYYCARRSE

FYYYGNTYYYSAMDYWGQGASVTVSSASTTTPAPRPPTPAPTIASQPLSL

RPEACRPAAGGAVHTRGLDFACDIYIWAPLAGTCGVLLLSLVITLYCKRG

RKKLLYIFKQPFMRPVQTTQEEDGCSCRFPEEEEGGCELRVKFSRSADAP

AYKQGQNQLYNELNLGRREEYDVLDKRRGRDPEMGGKPRRKNPQEGLYNE

LQKDKMAEAYSEIGMKGERRRGKGHDGLYQGLSTATKDTYDALHMQAL

PPR
```

NFAT Activation Assay

Jurkat cells with NFAT-LUC reporter (JNL) were grown to the density of $0.5 \times 10^6$/ml in Jurkat cell growth media with puromycin at 0.5 μg/ml. For each transfection $2.5 \times 10^6$ cells were spin down at 100 g for 10 minutes. Two μg of DNA per construct were used per transfection. Amaxa Nucleofector solution V and supplement I was mixed and 100 μl was added into the tube with DNA construct. The mixture was then added to the cells and transferred to the electroporation cuvette. Electroporation was done under setting X-001 using Amaxa Nucleofector II Device. 0.5 ml of growth media was added immediately after electroporation and the mixture were transferred into 2 ml growth media in one well of the 6-well plate and incubated for two hours. For myc tags in solution, the cells were distributed into 96-wells, monomer, dimer, trimer or tetramer myc tags or IgG1 Fc were applied at 100 nM. The cells were incubated for 18 hr. Alternatively, tissue culture plate was coated with 100 nM of various myc tags or IgG1 Fc for two hours, blocked with the blocking buffer (DPBS with 5% serum) for 1 hour. The transfected cells were added to the target plate with 100 μl per well and incubated for 18 hrs. Luciferase One Glo reagent 100 μl was added per well. The samples were incubated for 5 min at 37° C. and then luminescence is measured using Envision plate reader.

Results

Figure 57:
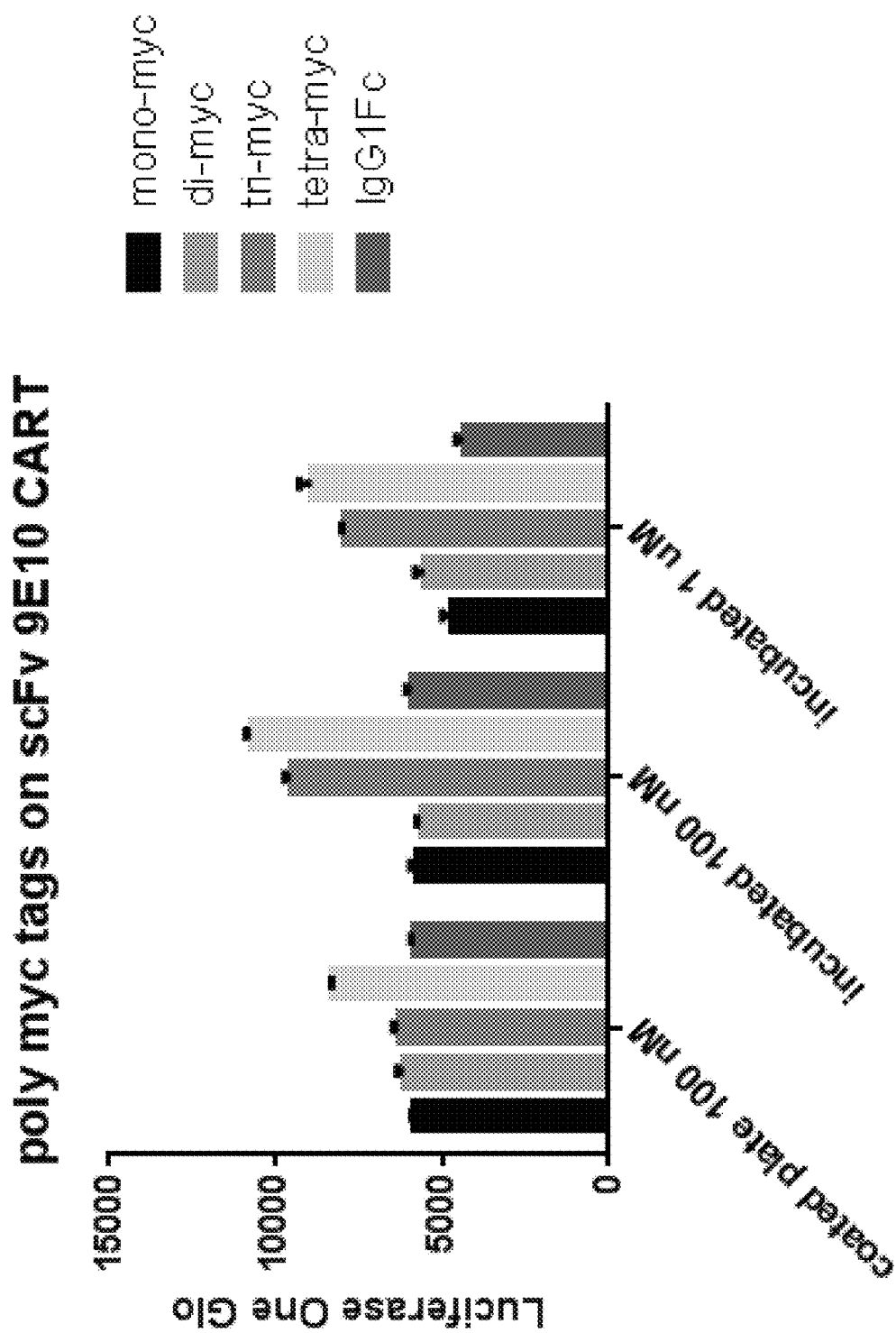
FIG. 57 is a graphic representation showing NFAT activation of 9E10scFv-containing intracellular members with myc-tag multimer dimerization molecules. Single myc tag (mono-myc), dimer myc tag (di-myc), trime myc tag (tri-myc), tetramer myc tag (tetra-myc), and control (IgG1 Fc) was administered at 100 nm and 1 µM.

As shown in the FIG. 57, NFAT activation depended on the number of multimers of the myc tags. Higher NFAT activation was observed when higher multimer, e.g., trimer or tetramer, myc tags were used for the transfected cells. The poly myc tag in solution at 100 nM resulted in increased NFAT activation compared to activation from the coated plate with 100 nM myc tag. These results show that multimers of myc tags can be used to switch on extracellular switch RCARs.

Example 7: Redirected Inhibitory RCAR

A general principle of the immune system is that T cells sense their microenvironment, and then either are activated or inhibited, depending on the signals that they sense. This finely tuned balance is transmitted by several activating receptors such as CD28 and ICOS and several inactivating receptors e.g. CTLA4, PD-1 and BTLA (Riley et al., 2005, Blood 105:13-21). The ligands for PD-1 are PDL1 and PDL2. PD-1 ligands are often expressed in the tumor microenvironment, and the engagement of PD-1 (programmed cell death 1) on T cells by PDL1 or PDL2, can lead to T cell inactivation. Limitations in treatment options to overcome this T cell inactivation in the tumor microenvironment would therefore be beneficial. Methods disclosed herein redirect the inhibitory signal using adoptive T cell therapy thereby rendering the negative regulatory signal, for example triggered through activation of PD1 receptor, into a positive signal that enhances the T cell activity when engaged. The general concept as outlined here is based on the regulatable switch RCAR as previously described. However in this embodiment, the RCAR comprises a cancer targeting moiety comprising an extracellular domain of an inhibitory receptor such as PD1. Additionally, the RCAR, may or may not display a standard CAR or a scFv tethered to the membrane used as a homing reagent for a particular cancer cell. See, e.g., the RCARs depicted in FIG. 9. In this example the switch is designed by fusing a leader sequence to the extracellular domain of PD1 followed by a hinge region, a transmembrane region, a linker and the first intracellular switch domain—FKBP (SEQ ID NO: 28). The second construct was designed by fusing the second switch domain FRB to a second linker and the internal signaling domains 4-1BB followed by CD3zeta (SEQ ID NO: 6). Activation of the T cell will be regulated by engagement of the PD1 ligands PDL1 or PDL2 in the presence of dimerization molecule, e.g., rapalogue, only. Co-expression of standard CAR or a targeting scFv may also be included in the RCAR to enhance specificity of the chimeric T cell.

Materials and Methods

Synthesis of DNA for Redirecting Inhibitory RCAR

The sequence for the extracellular domain of human PD1 receptor will be cloned with the FRB-domain at the c-terminus (SEQ ID NO:28) and the corresponding activation construct designed by fusing the FKBP-domain to a linker and the activation domains 4-1BB followed by CD3zeta (SEQ ID NO:6). In another embodiment, the extracellular domain of human PD1 receptor will be cloned with the FRBP domain at the c-terminus (SEQ ID NO:29) and the corresponding activation construct designed by fusing the FRB-domain to a linker and the activation domains 4-1BB followed by CD3zeta (SEQ ID NO:4). Jurkat assays will be performed as described in Example 1. Stimulation of the redirected inhibitory CAR can be achieved by addition of extracellular ligand PD1L or PD2L or by co-incubation of cells expressing PD1L or PD2L. Luciferase One Glo reagent 100 μl will be added per well. The samples will be incubated for 5 min at 37° C. and then luminescence will be measured using a luminometer.

human PD1 switch CART FRB
(SEQ ID NO: 29)
MalpvtalllplalllhaarpPGWFLDSPDRPWNPPTFSPALLVVTEGDN

ATFTCSFSNTSESFVLNWYRMSPSNQTDKLAAFPEDRSQPGQDCRFRVTQ

LPNGRDFHMSVVRARRNDSGTYLCGAISLAPKAQIKESLRAELRVTERRA

EVPTAHPSPSPRPAGQFQTLVtttpaprpptpaptiasqplslrpeacrp aaggavhtrgldfacdiyiwaplagtcgvlllslvitlyckrgrkkllqq qqsqqqqsasrilwhemwhegleeasrlyfgernvkgmfevleplhamme rgpqtlketsfnqaygrdlmeaqewcrkymksgnvkdllqawdlyyhvfr riskts human PD1 switch CART FKBP
(SEQ ID NO: 28)
MalpvtalllplalllhaarpPGWFLDSPDRPWNPPTFSPALLVVTEGDN

ATFTCSFSNTSESFVLNWYRMSPSNQTDKLAAFPEDRSQPGQDCRFRVTQ

LPNGRDFHMSVVRARRNDSGTYLCGAISLAPKAQIKESLRAELRVTERRA

EVPTAHPSPSPRPAGQFQTLVtttpaprpptpaptiasqplslrpeacrp aaggavhtrgldfacdiyiwaplagtcgvlllslvitlyckrgrkkllqq qqsqqqqsgvqvetispgdgrtfpkrgqtcvvhytgmledgkkfdssrdr nkpfkfmlgkqevirgweegvaqmsvgqrakltispdyaygatghpgiip phatlvfdvellklets Activation Assay of Redirected Inhibitory RCAR Jurkat cells with NFAT-LUC reporter (JNL) were grown to the density of 0.5×10$^6$/ml in Jurkat cell growth media with puromycin at 0.5 μg/ml. For each transfection 3×10$^6$ cells were spin down at 100 g for 10 minutes. Four μg DNA per construct were used per transfection. Amaxa Nucleofector solution V and supplement I was mixed and 100 μl was added into the tube with DNA construct. The mixture was then added to the cells and transferred to the electroporation cuvette. Electroporation was done under setting X-001 using Amaxa Nucleofector II Device. 0.5 ml of growth media was added immediately after electroporation and the mixture were transferred into 2 ml growth media in one well of the 6-well plate. After two hours, the rapalogue compound at various concentrations was added to cells. The cells were applied to tissue culture plate wells that were coated by the target. Tissue culture plate was coated with 5 μg/ml of PDL1-Fc or IgG1-Fc or any target for 2 hrs at 37° C., then blocked with the blocking buffer (DPBS with 5% serum) for 30 minutes. The transfected cells were added to the target plate with 100 μl per well and incubated further for 16 hrs. Luciferase One Glo reagent 100 μl was added per well. The samples were incubated for 5 min at 37° C. and then luminescence is measured using Envision plate reader.

The PD1 CAR construct comprises PD1-ECD-TM-41BB-CD3zeta. This construct may improve the persistence of cells transfected with the construct, e.g., CART cells transfected with PD1 CAR.

The PD1 RCAR (switchable PD1 CAR) construct uses the FRB-FKBP heterodimerization switch and the rapalogue hetermodimerization molecule AP21967. Specifically, the PD1 RCAR comprises a PD1-ECD-TM-FRB construct; and FKBP-41BB-CD3 zeta construct, that were co-transfected into Jurkat cells. These constructs may improve the persistence of cells transfected with the construct, e.g., RCART cells transfected with PD1 RCAR.

Figures 17A, 17B:
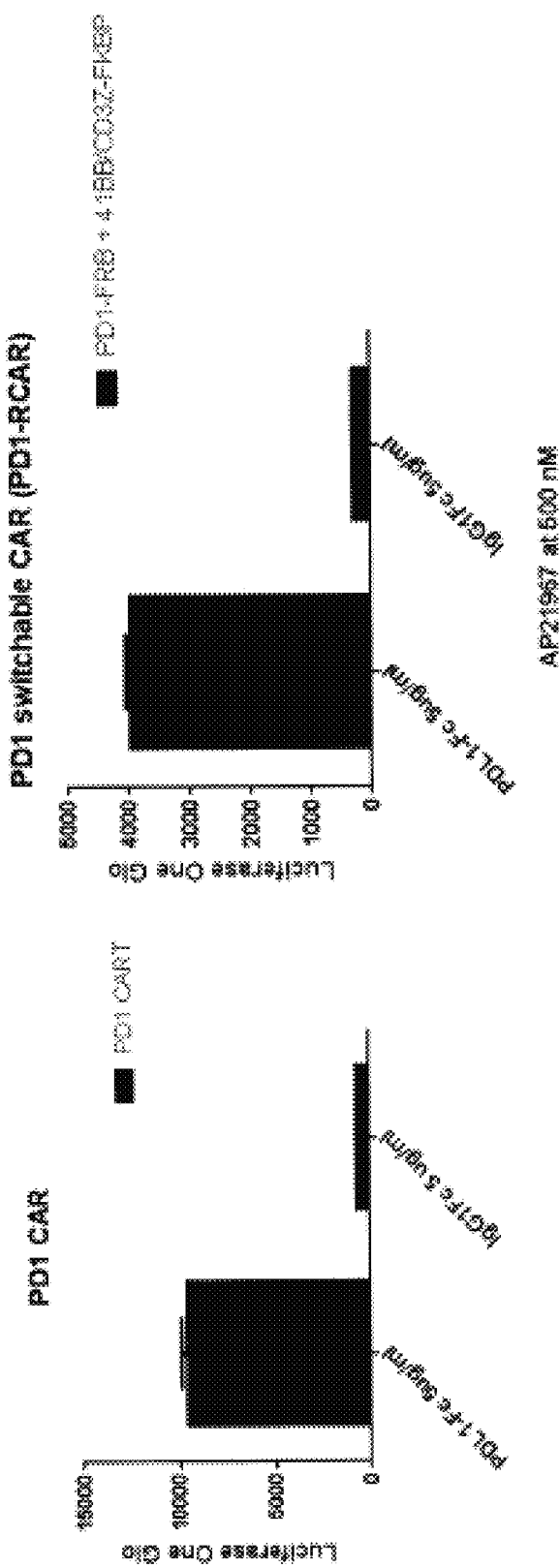
FIGS. 17A and 17B depicts activation of a PD1 CAR and a PD1 RCAR.
Figure 18:
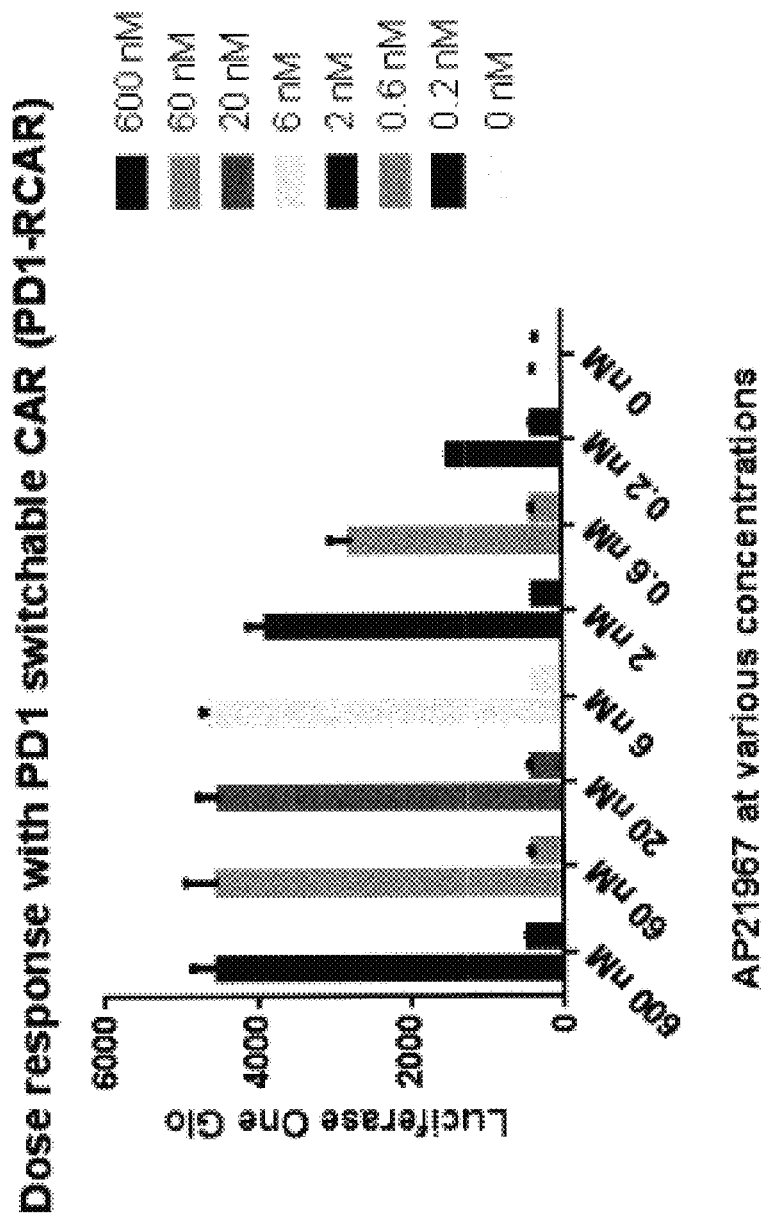
FIG. 18 demonstrates a dose response with AP21967 treatment. The bar on the left for each tested dosage is the PD1 RCAR, while the bar the right for each tested dosage is PD1 CAR control.

As shown in FIG. 17A: PD1 CAR showed significant PD1 induced activation of NFAT inducible promoter driven luciferase activity, as compared to the control treatment by IgG1-Fc. This suggest that PD1 interaction with PDL-1 is sufficient in causing clustering of PD1 on Jurket cell surface and triggers the strong activation of the NFAT pathway. This PD1 CAR was used as a control for the PD1 RCAR experiments. In FIG. 17B, when Jurket reporter cells were co-transfected by the PD1 RCAR which include PD1-ECD-TM-FRB and FKBP-4 1BB-CD3 zeta, and incubated with 500 nM AP21967 heterodimerization molecule, there was significant induction of signaling by PDL-1 target, which indicate that AP21967 heterodimerization molecule induced dimerization of PD1 from one construct with 4 1BB-CD3 zeta of another construct, and this resulted activation of NFAT signaling. To further investigate the effect of AP21967 heterodimerization molecule on the RCAR, varying concentrations of the AP21967 heterodimerization molecule were added to the cells. As shown in FIG. 18, there was a dose response with AP21967 treatment. Each bar on the left is the PD1 RCAR, while each bar on is PD1 CAR control at different concentrations of AP21967. The AP21967 was potent even at sub nM concentration in inducing the dimerization of the heterodimerization switch resulting in activation of NFAT signaling.

Example 8: Switchable CART Activation by Co-Cluster Receptors Including PD1

Cancer cells not only abnormally express cancer antigens but can also express PD1 ligands, which provide for escape from immune attack by effector T-cells. PD1, upon ligand binding, forms micro-clusters with TCR and directly inhibits T-cell activation. The formation of clusters by co-stimulators or co-inhibitors is used by nature to enhance or inhibit an immune response similar to a digital event, i.e., it is either "on" or "off". In other words, the immune response is turned on when multiple factors align. This differentiates "real" signals from "noise," which can be harmful. See FIG. 10.

The phenomenon of co-stimulator/co-inhibitor clusters can be used for CART therapy to ensure the targeting/killing specificity. This can be combined with small molecule (rapalogue) as the dimerization switch for RCAR cell activity. In embodiment this will increase the therapeutic window and reduce toxic side effects.

Recognition and binding of cancer cells by T-cells represent the important initial step to establish the killing specificity. Co-targeting of cancer cells by cancer cell specific antigen which is recognized by low affinity scFv and PDL1/2 by PD1 can be achieved through low affinity interactions: PD1 with PDL1 or PDL2 from cancer cells, and low affinity interaction of scFv with cancer antigens on cancer cells. This dual binding event is amplified through the avidity effect, and is further amplified through micro-cluster formation of scFv and PD1. These recognition and binding events will enable the immune synapse formation between target cells and RCART cells, the first step for RCART regulated cancer cell killing. The addition of rapalogue will dimerize/cluster 4-1BB/CD3 zeta, which will further activate RCART cells for cancer cell killing.

Experimental Procedure

Mouse or human PD1 ECD will be fused with a transmembrane domain followed by an FKBP switch domain. Low affinity scFv against one of the tumor antigens such as mesothelin will be fused with a transmembrane domain followed by a FKBP switch domain. The FRB switch domain will be fused with intracellular signaling domains 4-1BB and CD3 zeta. See, e.g., the RCAR depicted in FIG. 10. Jurket T-cells with NFAT driven luciferase reporter will be co-transfected with the three constructs: PD1-TM-FKBP, scFv-TM-FKPB and FRB-4-1BB-CD3 zeta. Transfection will be done with Amaxa nucleofactor with 3×10$^6$ Jurket cells per transfection with 2 μg DNA per construct. The cells will be incubated at 37° C. with 8% $CO_2$ for one day incubation after co-transfection. The Jurket cells will then be applied to the wells that are coated with 5 μg/ml of human mesothelin and 5 μg/ml of mouse PD-L1 or PD-L2. After one day of incubation at 37° C., luciferase activity will be measured by One-Glo reagent from Promega.

In addition, the co-transfected cells will be mixed with cancer cells that express both mesothelin and PDL1 or PDL2, as well as normal cells at 1:0.3 ratio of effector CART cells: target cells. After one day of incubation, luciferase activity will be measured.

The target cancer cells that show overexpression of PDL1 or PDL2 will be tested.

Example 9: Small Molecule Regulated CAR Activation—Extracellular Switch

Figure 5:
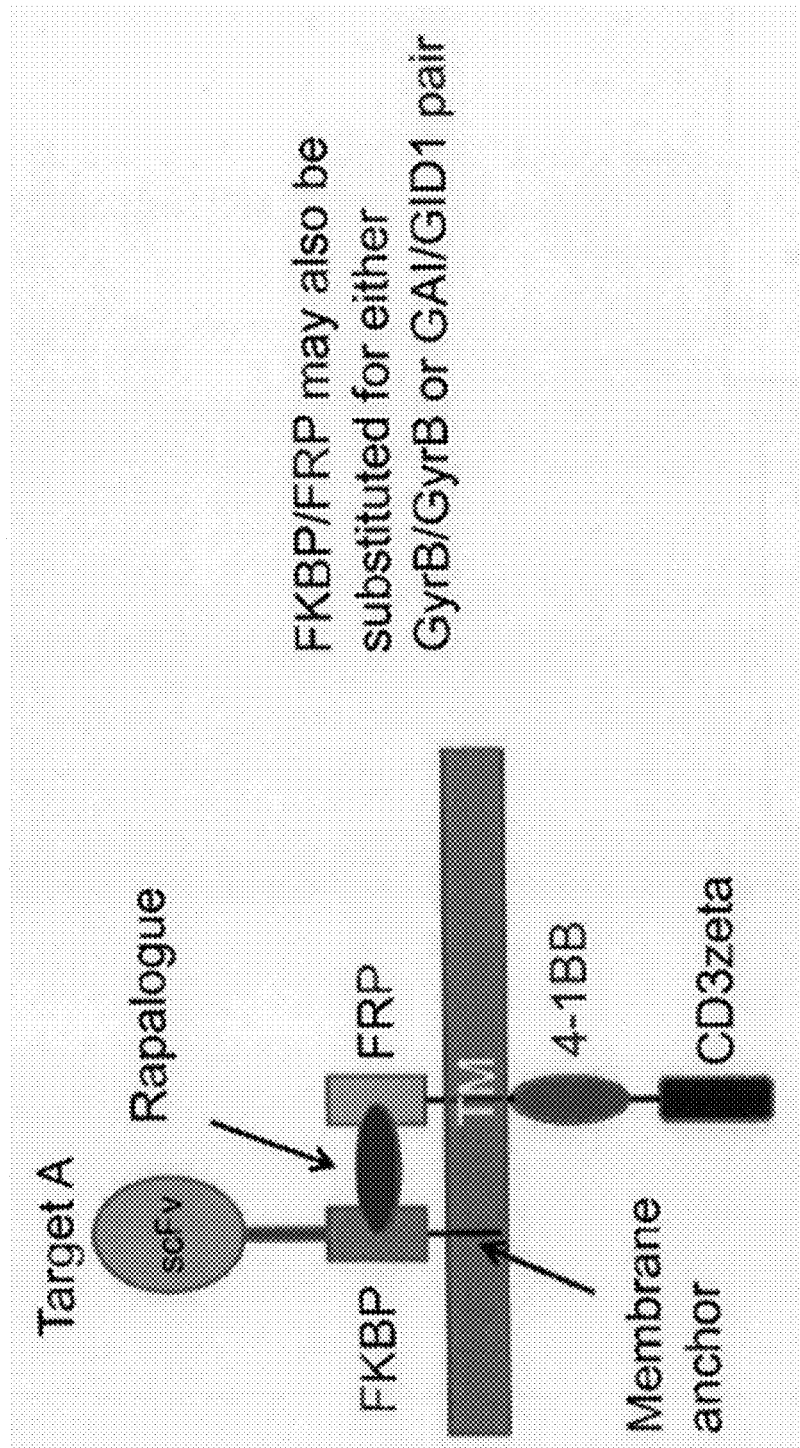
FIG. 5 depicts an RCAR having an extracellular switch induced by small molecule drug. The extracellular dimerization switch can be an FKBP/FRB switch, a GyrB/GyrB switch, or a GAI/G1D1 switch.

T cell-mediated cell death requires the linking of the external binding event to the signaling activation cascade in the intracellular space. In an embodiment, a RCAR comprises and extracellular dimerization switch, e.g., an extracellular heterodimerization switch activated by a small molecule heterodimerization molecule. See, e.g., the RCAR depicted in FIG. 5. The following example illustrates the design of such an "extracellular small molecule" switch.

In this example, the switch is designed by fusing a leader sequence to the 139 scFv followed by linker and the first switch domain—FKBP, a hinge region and a transmembrane region (SEQ ID NO: 31). The second construct is designed by fusing a leader sequence to the FRB switch domain, a transmembrane region and the intracellular signaling domains 4-1BB followed by CD3zeta (SEQ ID NO: 32).

Alternatively a pair of constructs with the following design (139-FRB-TM (SEQ ID NO: 30) FKBP-TM-41BB-CD3zeta (SEQ ID NO: 33) may also be used.

Co-transfection of the T cell of the pair of construct will yield a tuneable extracellular activation switch regulated by addition of the small molecule rapalogue (Structure 1).

EGFRvIII clone 139-FRB-CD8alphaTM
(SEQ ID NO: 30)
Malpvtalllplalllhaarpdiqmtqspsslsasvgdrvtitcrasqgi rnnlawyqqkpgkapkrliyaasnlqsgvpsrftgsgsgteftlivsslq pedfatyyclqhhsypltsgggtkveikrtgstsgsgkpgsgegsevqvl esggglvqpggslrlscaasgftfssyamswvrqapgkglewvsaisgsg gstnvadsvkgrftisrdnskntlvlqmnslraedtavyycagssgwsey wgqgtlvtsskrqrkkllgqqgsqqqgsasrilwhemwhegleeasrly fgernvkgmfevleplhammergpqtlketsfnqaygrdlmeaqewcrky mksgnvkdllqawdlyyhvfrrisktstttpaprpptpaptiasqplslr peacrpaaggavhtrgldfacdiyiwaplagtcgvlllslvitlyc EGFRvIII clone 139-FKBP-CD8alphaTM
(SEQ ID NO: 31)
Malpvtalllplalllhaarpdiqmtqspsslsasvgdrvtitcrasqgi rnnlawyqqkpgkapkrliyaasnlqsgvpsrftgsgsgteftlivsslq pedfatyyclqhhsypltsgggtkveikrtgstsgsgkpgsgegsevqvl esggglvqpggslrlscaasgftfssyamswvrqapgkglewvsaisgsg gstnyadsvkgrftisrdnskntlylqmnslraedtavyycagssgwsey wgqgtlvtsskrqrkkllgqqgsqqqgsgvqvetispgdgrtfpkrgqt cvvhytgmledgkkfdssrdrnkpfkfmlgkqevirgweegvaqmsvgqr akltispdyaygatghpgiipphatlvfdvellkletstttpaprpptpa ptiasqplslrpeacrpaaggavhtrgldfacdiyiwaplagtcgvllls lvitlyc FRB-hinge-CD8alphaTM-4-1BB-CD3zeta
(SEQ ID NO: 32)
Malpvtalllplalllhaarasrilwhemwhegleeasrlyfgernvkgm fevleplhammergpqtlketsfnqaygrdlmeaqewcrkymksgnvkdl lqawdlyyhvfrrisktsTTTPAPRPPTPAPTIASQPLSLRPEACRPAAG GAVHTRGLDFACDIYIWAPLAGTCGVLLLSLVITLYCggggsggggskrg rkkllyifkqpfmrpvqttqeedgcscrfpeeeeggcelrvkfsrsadap aykqgqnqlynelnlgrreeydvldkrrgrdpemggkprrknpqeglyne lqkdkmaeayseigmkgerrrgkghdglyqglstatkdtydalhmqalpp rFKBP-hinge-CD8alphaTM-4-1BB-CD3zeta
(SEQ ID NO: 33)
Malpvtalllplalllhaargvqvetispgdgrtfpkrgqtcvvhytgml edgkkfdssrdrnkpfkfmlgkqevirgweegvaqmsvgqrakltispdy aygatghpgiipphatlvfdvellkletsTTTPAPRPPTPAPTIASQPLS LRPEACRPAAGGAVHTRGLDFACDIYIWAPLAGTCGVLLLSLVITLYCgg ggsggggskrgrkkllyifkqpfmrpvqttqeedgcscrfpeeeeggcel rvkfsrsadapaykqgqnqlynelnlgrreeydvldkrrgrdpemggkpr rknpqeglynelqkdkmaeayseigmkgerrrgkghdglyqglstatkdt ydalhmqalppr The extracellular switch transfections and activations were carried out essentially as described for the intracellular switches in Example 1.

Figure 19:
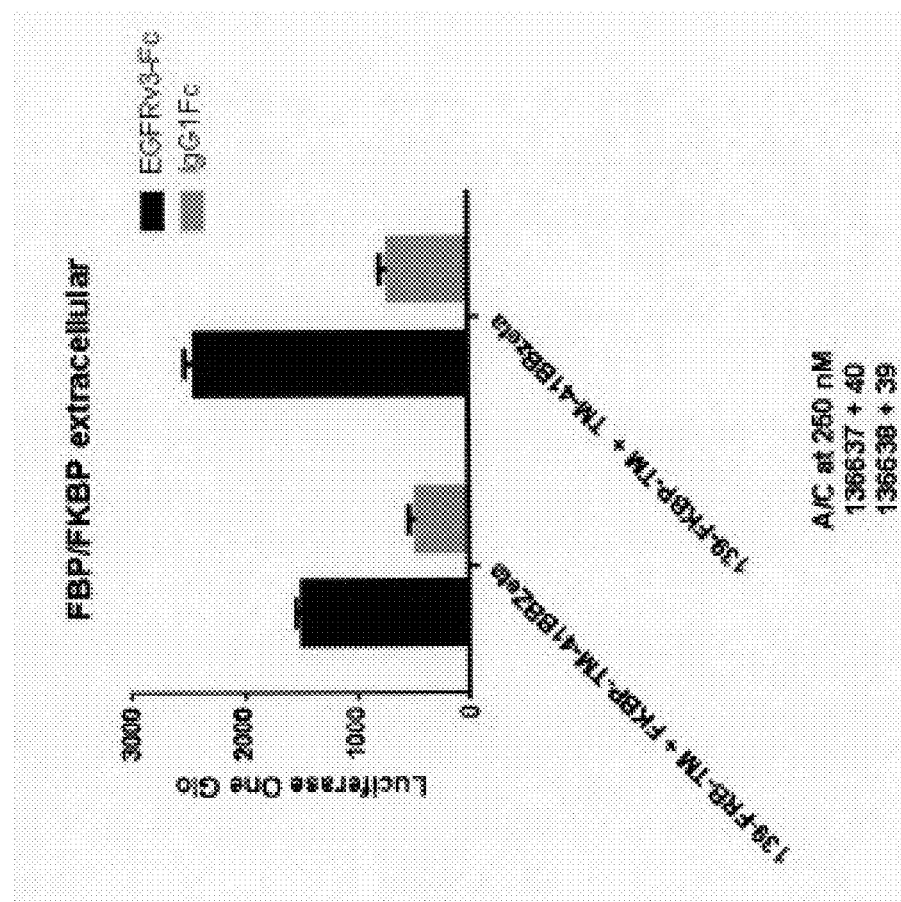
FIG. 19 the activity of an RCAR having an FKBP-FRB based extracellular switch, e.g., as shown in FIG. 5.

FIG. 19 shows the results from studies designed to investigate the signaling events between an RCAR expressing the antigen binding domain, e.g., scFv, and an RCAR expressing the intracellular signaling domains, wherein the heterodimerization switch domains are external, in the presence of a heterodimerization molecule. The data shows significant target regulated activation upon stimulation with the rapalogue at 250 nM. Furthermore, no significant on-target activation was observed in the absence of the rapalogue, indicating an external switch mediated by the small molecule regulated heterodimerization of the switch domains (FKBP and FRB). Finally, no activation was observed against a control target (IgG1-Fc only). These data demonstrate specificity of an externally-switched RCAR constructs for EGFRvIII target in the presence of the rapalogue only, and lack of cross-reactivity to control target or in the absence of rapalogue.

Additional RCAR constructs comprising extracellular switches and functional analysis thereof are described in Example 22.

Example 10: Targeting Mouse and Human Programmed Cell Death 1 (PDCD1) Gene Using shRNA In addition to the RCAR constructs described in Examples 1-9, further regulation can be provided by engineering shRNA into the nucleic acids encoding the RCAR Commonly used promoters such as U6 and H1 may be placed downstream of the RCAR lentivirus constructs. PDCD1, TIM3, or other negative regulators of T cell activity may be attenuated by the expression of suitable shRNA constructs. A generic map showing different configurations of constructs encoding the regulatable CAR with a shRNA for coexpression of RCAR and an shRNA is provided in FIGS. 16A, 16B, 16C, 16D, and 16E.

Figures 16A, 16B, 16C, 16D, 16E:
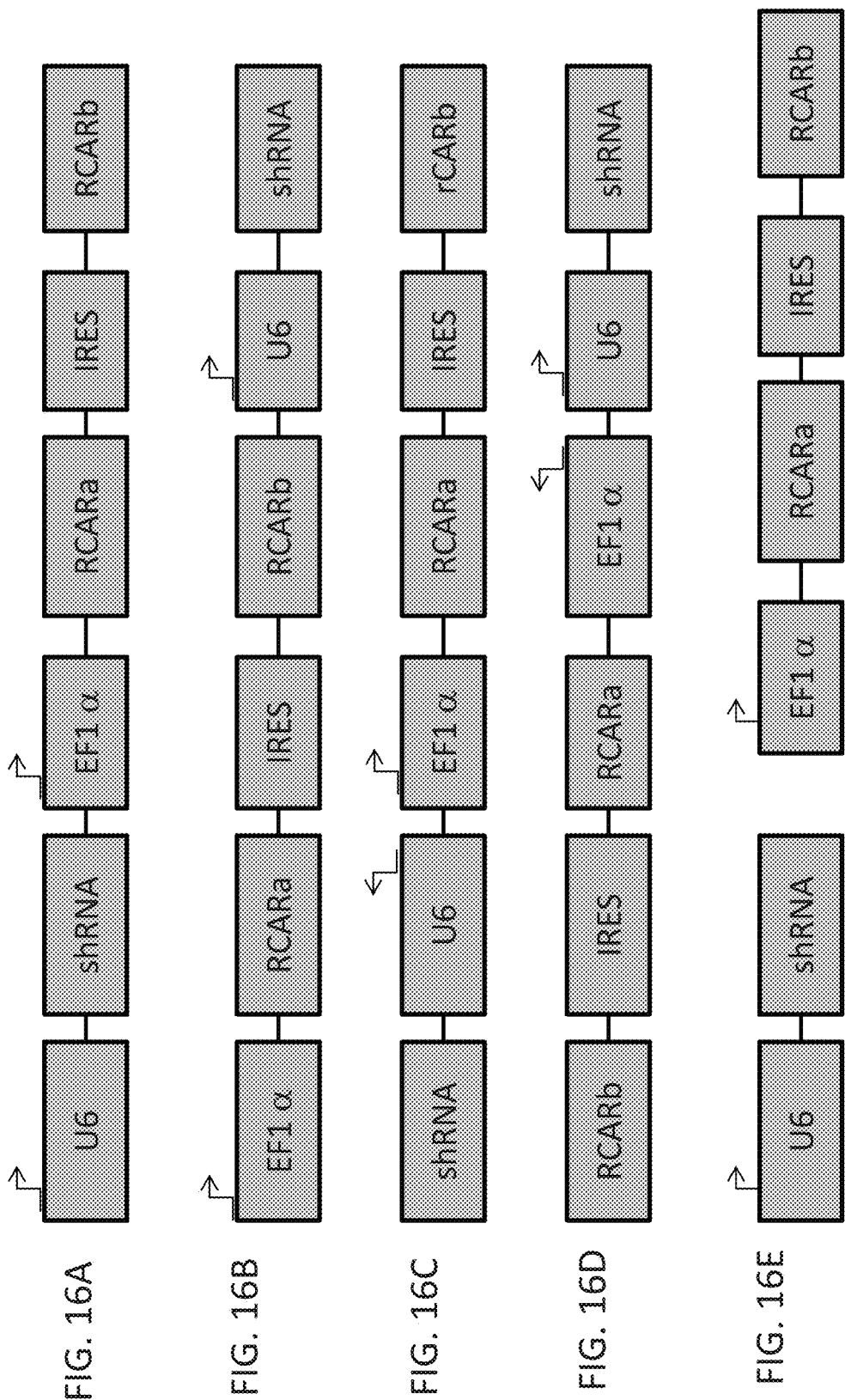
FIGS. 16A, 16B, 16C, 16D, and 16E depict a vector for expressing a RCAR.

The two switch domain containing members (RCARa and RCARb), e.g., an antigen binding member and an intracellular signaling member, are regulated by a combination of the EF1alpha promoter and a suitable IRES element such as the EMCV. As shown in FIGS. 16A, 16B, 16C, 16D, and 16E, the EF1 alpha promoter is located upstream of a first RCAR member, e.g., RCARa, which is followed by an IRES element, and finally the second RCAR member, e.g., RCARb. In embodiments, the shRNA is regulated by the U6 promoter. In embodiments, the shRNA and RCAR encoding elements are present on a single vector. FIG. 16A-16D show the various configurations on a single vector, e.g., where the U6 regulated shRNA is upstream or or downstream of the EF1 alpha regulated RCAR encoding elements. In the exemplary constructs depicted in FIGS. 16A and 16B, the transcription occurs through the U6 and EF1 alpha promoters in the same direction. In the exemplary constructs depicted in FIGS. 16C and 16D, the transcription occurs through the U6 and EF1 alpha promoters in different directions. In another embodiment, the shRNA (and corresponding U6 promoter) is on a first vector, and the RCAR (and corresponding EF1 alpha promoter) is on a second vector (FIG. 16E). Constitutive attenuation of inhibitory receptors such as PD1 in T cells specifically targeting cancer cells should overcome PD1 pathway mediated immune suppression in the tumor microenvironment.

Computational Analysis for Sequence Selection shRNA design was carried out to identify shRNAs targeting the mouse and human gene Programmed Cell Death 1 (PDCD1) gene. The design used the NM_008798.2 (mouse) and NM_005018.2 transcript from the NCBI RefSeq collection, respectively. The predicted potency and specificity of all possible 19 mers was predicted from each sequence. For potency prediction, 19 mer sequences that contained a BioPred score >0.8, and a Dharmacon score >4 were selected. For specificity, 19 mer sequences that lacked repeats longer than 4 nucleotides and that did not contain seed-region matches to multiple (>10) known human miR-NAs were selected. In addition, 19 mer sequences when searched against the human and mouse transcriptome, respectively (defined as the set of NM_ and XM_ records within the human, mouse NCBI Refseq set) using the BLAST algorithm were discarded when either the antisense or the sense strand (including position 1 or 2 counting from the 5'end of the guide strand) had >15 consecutive nucleotides in common with any other mRNA transcript in NCBI Refseq. Furthermore, sequences containing motifs reported to potentially induce innate immune as well as cytotoxic response were discarded.

In a final step, the acceptable 19 mer sequences were sorted according to the predicted potency score and the top twelve sequences were selected in form of their corresponding 21-mer sequences for shRNA synthesis.

Provided in Table 18 below are the names of PDCD1 (PD1) RNAi agents (derived from their position in the mouse PDCD1 gene sequence NM_008798.2), along with the SEQ ID NOs: 34-81 representing the DNA sequence. Both sense (S) and antisense (AS) sequences are presented as 19 mer and 21 mer sequences are in this table. Also note that the position (PoS, e.g., 176) is derived from the position number in the mouse PDCD1 gene sequence NM_008798.2. SEQ ID NOs are indicated in groups of 12 that correspond with "sense 19" SEQ ID NOs: 34-45; "sense 21" SEQ ID NOs: 46-57; "asense 21" SEQ ID NOs: 58-69; "asense 19" SEQ ID NOs: 70-81.

TABLE 18

Mouse PDCD1 (PD1) shRNA sequences

| Position on Target NM_008798.2 | region | Sense19 | Sense21 | Asense21 | Asense19 |
|---|---|---|---|---|---|
| 176 | CDS | GGAGGTCCCTCACC TTCTA (SEQ ID NO: 34) | CTGGAGGTCCCTCA CCTTCTA (SEQ ID NO: 46) | TAGAAGGTGAGGG ACCTCCAG (SEQ ID NO: 58) | TAGAAGGTGAGGG ACCTCC (SEQ ID NO: 70) |
| 260 | CDS | CGGAGGATCTTATG CTGAA (SEQ ID NO: 35) | GTCGGAGGATCTTA TGCTGAA (SEQ ID NO: 47) | TTCAGCATAAGATC CTCCGAC (SEQ ID NO: 59) | TTCAGCATAAGATC CTCCG (SEQ ID NO: 71) |
| 359 | CDS | CCCGCTTCCAGATC ATACA (SEQ ID NO: 36) | TGCCCGCTTCCAGA TCATACA (SEQ ID NO: 48) | TGTATGATCTGGAA GCGGGCA (SEQ ID NO: 60) | TGTATGATCTGGAA GCGGG (SEQ ID NO: 72) |

TABLE 18-continued

Mouse PDCD1 (PD1) shRNA sequences

| Position on Target NM_008798.2 | region | Sense19 | Sense21 | Asense21 | Asense19 |
|---|---|---|---|---|---|
| 528 | CDS | GGAGACCTCAACAAGATAT (SEQ ID NO: 37) | CTGGAGACCTCAACAAGATAT (SEQ ID NO: 49) | ATATCTTGTTGAGGTCTCCAG (SEQ ID NO: 61) | ATATCTTGTTGAGGTCTCC (SEQ ID NO: 73) |
| 581 | CDS | AAGGCATGGTCATTGGTAT (SEQ ID NO: 38) | TCAAGGCATGGTCATTGGTAT (SEQ ID NO: 50) | ATACCAATGACCATGCCTTGA (SEQ ID NO: 62) | ATACCAATGACCATGCCTT (SEQ ID NO: 74) |
| 584 | CDS | GCATGGTCATTGGTATCAT (SEQ ID NO: 39) | AGGCATGGTCATTGGTATCAT (SEQ ID NO: 51) | ATGATACCAATGACCATGCCT (SEQ ID NO: 63) | ATGATACCAATGACCATGC (SEQ ID NO: 75) |
| 588 | CDS | GGTCATTGGTATCATGAGT (SEQ ID NO: 40) | ATGGTCATTGGTATCATGAGT (SEQ ID NO: 52) | ATGGTCATTGGTATCATGAGT (SEQ ID NO: 64) | ATGGTCATTGGTATCATGA (SEQ ID NO: 76) |
| 609 | CDS | CCTAGTGGGTATCCCTGTA (SEQ ID NO: 41) | GCCCTAGTGGGTATCCCTGTA (SEQ ID NO: 53) | GCCCTAGTGGGTATCCCTGTA (SEQ ID NO: 65) | GCCCTAGTGGGTATCCCTG (SEQ ID NO: 77) |
| 919 | CDS | GAGGATGGACATTGTTCTT (SEQ ID NO: 42) | ATGAGGATGGACATTGTTCTT (SEQ ID NO: 54) | ATGAGGATGGACATTGTTCTT (SEQ ID NO: 66) | ATGAGGATGGACATTGTTC (SEQ ID NO: 78) |
| 1021 | 3'UTR | GCATGCAGGCTACAGTTCA (SEQ ID NO: 43) | GAGCATGCAGGCTACAGTTCA (SEQ ID NO: 55) | GAGCATGCAGGCTACAGTTCA (SEQ ID NO: 67) | GAGCATGCAGGCTACAGTT (SEQ ID NO: 79) |
| 1097 | 3'UTR | CCAGCACATGCACTGTTGA (SEQ ID NO: 44) | TTCCAGCACATGCACTGTTGA (SEQ ID NO: 56) | TTCAGCACATGCACTGTTGA (SEQ ID NO: 68) | TTCCAGCACATGCACTGTT (SEQ ID NO: 80) |
| 1101 | 3'UTR | CACATGCACTGTTGAGTGA (SEQ ID NO: 45) | AGCACATGCACTGTTGAGTGA (SEQ ID NO: 57) | AGCACATGCACTGTTGAGTGA (SEQ ID NO: 69) | AGCACATGCACTGTTGAGT (SEQ ID NO: 81) |

Provided in Table 19 below are the names of PDCD1 (PD1) RNAi agents (derived from their position in the human PDCD1 gene sequence, along with the SEQ ID NOs. 82-129 representing the DNA sequence. Both sense (S) and antisense (AS) sequences are presented as 19 mer and 21 mer sequences. SEQ ID NOs are indicated in groups of 12 that correspond with "sense 19" SEQ ID NOs: 82-93; "sense 21" SEQ ID NOs: 94-105; "asense 21" SEQ ID NOs: 106-117; "asense 19" SEQ ID NOs: 118-129.

TABLE 19

Human PDCD1 (PD1) shRNA sequences

| Position on Target NM_005018.2 | region | Sense19 | Asense19 | Sense21 | Asense21 |
|---|---|---|---|---|---|
| 145 | CDS | GGCCAGGATGGTTCTTGA (SEQ ID NO: 82) | TCTAAGAACCATCCTGGCC (SEQ ID NO: 94) | GCGGCCAGGATGGTTCTTAGA (SEQ ID NO: 106) | TCTAAGAACCATCCTGGCCGC (SEQ ID NO: 118) |
| 271 | CDS | GCTTCGTGCTAAACTGGTA (SEQ ID NO: 83) | TACCAGTTTAGCACGAAGC (SEQ ID NO: 95) | GAGCTTCGTGCTAAACTGGTA (SEQ ID NO: 107) | TACCAGTTTAGCACGAAGCTC (SEQ ID NO: 119) |
| 393 | CDS | GGGCGTGACTTCCACATGA (SEQ ID NO: 84) | TCATGTGGAAGTCACGCCC (SEQ ID NO: 96) | ACGGGCGTGACTTCCACATGA (SEQ ID NO: 108) | TCATGTGGAAGTCACGCCCGT (SEQ ID NO: 120) |

TABLE 19-continued

Human PDCD1 (PD1) shRNA sequences

| Position on Target NM_005018.2 | region | Sense19 | Asense19 | Sense21 | Asense21 |
|---|---|---|---|---|---|
| 1497 | 3'UTR | CAGGCCTAG AGAAGTTTCA (SEQ ID NO: 85) | TGAAACTTC TCTAGGCCTG (SEQ ID NO: 97) | TGCAGGCCT AGAGAAGTT TCA (SEQ ID NO: 109) | TGAAACTTC TCTAGGCCT GCA (SEQ ID NO: 121) |
| 1863 | 3'UTR | CTTGGAACC CATTCCTGAA (SEQ ID NO: 86) | TTCAGGAAT GGGTTCCAAG (SEQ ID NO: 98) | TCCTTGGAA CCCATTCCT GAA (SEQ ID NO: 110) | TTCAGGAAT GGGTTCCAA GGA (SEQ ID NO: 122) |
| 1866 | 3'UTR | GGAACCCAT TCCTGAAATT (SEQ ID NO: 87) | AATTTCAGG AATGGGTTCC (SEQ ID NO: 99) | TTGGAACCC ATTCCTGAA ATT (SEQ ID NO: 111) | AATTTCAGG AATGGGTTC CAA (SEQ ID NO: 123) |
| 1867 | 3'UTR | GAACCCATT CCTGAAATTA (SEQ ID NO: 88) | TAATTTCAG GAATGGGTTC (SEQ ID NO: 100) | TGGAACCCA TTCCTGAAA TTA (SEQ ID NO: 112) | TAATTTCAG GAATGGGTT CCA (SEQ ID NO: 124) |
| 1868 | 3'UTR | AACCCATTC CTGAAATTAT (SEQ ID NO: 89) | ATAATTTCA GGAATGGGTT (SEQ ID NO: 101) | GGAACCCAT TCCTGAAAT TAT (SEQ ID NO: 113) | ATAATTTCA GGAATGGGT TCC (SEQ ID NO: 125) |
| 1869 | 3'UTR | ACCCATTCC TGAAATTATT (SEQ ID NO: 90) | AATAATTTC AGGAATGGGT (SEQ ID NO: 102) | GAACCCATT CCTGAAATT ATT (SEQ ID NO: 114) | AATAATTTC AGGAATGGG TTC (SEQ ID NO: 126) |
| 1870 | 3'UTR | CCCATTCCT GAAATTATTT (SEQ ID NO: 91) | AAATAATTT CAGGAATGGG (SEQ ID NO: 103) | AACCCATTC CTGAAATTA TTT (SEQ ID NO: 115) | AAATAATTT CAGGAATGG GTT (SEQ ID NO: 127) |
| 2079 | 3'UTR | CTGTGGTTC TATTATATTA (SEQ ID NO: 92) | TAATATAAT AGAACCACAG (SEQ ID NO: 104) | CCCTGTGGT TCTATTATAT TA (SEQ ID NO: 116) | TAATATAAT AGAACCACA GGG (SEQ ID NO: 128) |
| 2109 | 3'UTR | AAATATGA GAGCATGCT AA (SEQ ID NO: 93) | TTAGCATGC TCTCATATTT (SEQ ID NO: 105) | TTAAATATG AGAGCATGC TAA (SEQ ID NO: 117) | TTAGCATGC TCTCATATTT AA (SEQ ID NO: 129) |

Validation of shRNA-Mediated PD1 Knockdown shRNA sequences targeting human and mouse PD1 were validated by an in vitro knockdown assay. The human 21 mer shRNA sequences listed in Table 20 (SEQ ID NOs: 106-117) and the mouse 21 mer shRNA sequences listed in Table 19 (SEQ ID NOs: 46-57) were were synthesized according to the following design scheme.

(SEQ ID NO: 325)
5'-G xxxxxxxxxxxxxxxxxxxxx TTCAAGAGA yyyyyyyyyyyyyyyyyyyyy TTTTTT-3'

A single 5' G was added to the target sense sequence depicted above, with the target sense sequence designated by x (provided in Tables 19 or 20), followed by a hairpin loop of the sequence TTCAAGAGA (SEQ ID NO: 326), the corresponding target anti-sense sequence (designated by y) and a 3' poly-T terminator sequence (underlined above). To facilitate cloning each construct was also flanked by a 5' BamHI and a 3' EcoRI site. Finally the synthesized constructs were sub-cloned into pLVX-shRNA2 (Clontech) using recombinant DNA techniques.

The human PD1 knockdown assay was performed as follows. Two million Jurkat JNL cells were nucleofected with 1-2 μg shRNA plasmid DNA (depending on stock concentration) using Lonza's SE Cell Line 4D Kit and pulse code CL-116, according to the manufacturer's recommendations. Cells were immediately resuspended and plated in Antibiotic Free Growth Media to a density of 1×10$^6$/mL. Nucleofected Jurkat JNL cells were incubated at 37° C., 5%

CO$_2$, 24 hours, 48 hours or 72 hours. At the end of each time point cell lysis was performed using QIAGEN's FastLane Cell Multiplex kit according to the manufacturer's recommendations. Multiplex qPCR was performed on diluted cell lysates using hPDCD1 Taqman probe, Hs01550088_m1, and hGAPDH Taqman probe, 4326317E. Percent transcript remaining was determined using the delta delta Ct method relative to the PBS nucleofection control. Error bars are standard deviation of technical and biological replicates.

Figure 40:
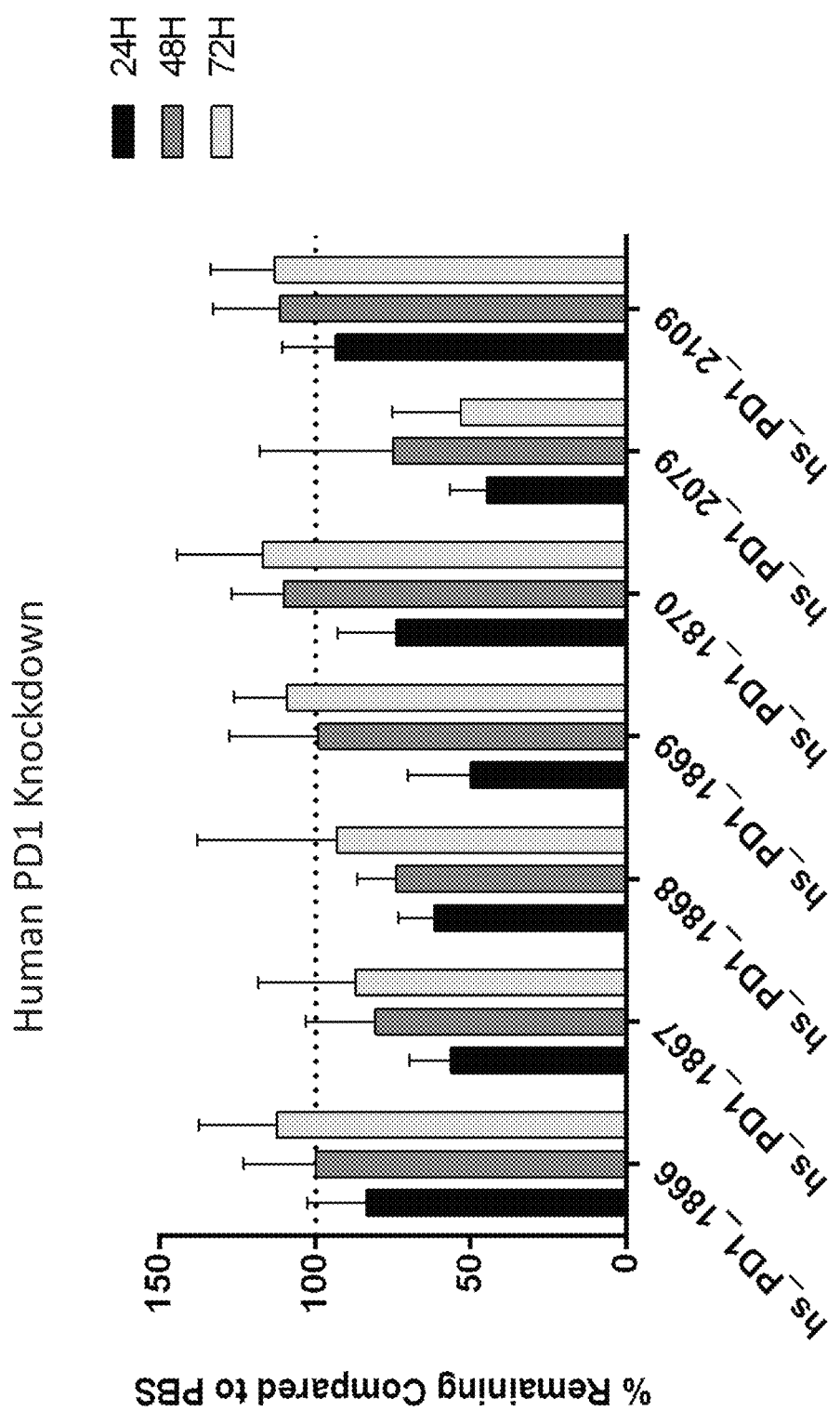
FIG. 40 depicts human PD1 knockdown at 24, 48 and 72 hours, by the human PD1 shRNA sequences indicated on the x-axis. Knockdown is represented by percentage of PD1 transcript remaining (y-axis). Human PD1 shRNA sequences are provided in Table 19.

As shown in FIG. 40, all tested human PD1 shRNA constructs knocked down PD1 expression, as represented by lower than 100% of PD1 transcript remaining, e.g., at 24 hours after nucleofection. The shRNAs targeting positions 1867, 1868, 1869, 1870, and 2079 demonstrated reduced PD1 expression to less than 75% of normal expression levels, with the shRNA targeting position 2079 having the most robust knockdown at all three tested timepoints, 24, 48, and 72 hours.

The mouse PD1 knockdown assay was performed as follows. Two hundred thousand EL4 cells were nucleofected with 0.5-1 µg shRNA plasmid DNA (depending on stock concentration) using Lonza's SF Cell Line 4D Kit and pulse code CM-120-AA, according to the manufacturer's recommendations. Cells were immediately resuspended and plated in Antibiotic Free Growth Media to a density of 2.5×10$^6$/mL. Nucleofected EL4 cells were incubated at 37° C., 5% CO$_2$, 24 hours or 48 hours. At the end of each time point cell lysis was performed using QIAGEN's FastLane Cell Multiplex kit according to the manufacturer's recommendations. Multiplex qPCR was performed on diluted cell lysates using mPDCD1 Taqman probe, Mm01285676_m1, and mβ-actin Taqman probe, 4352341E. Percent transcript remaining was determined using the delta delta Ct method relative to the PBS nucleofection control. Error bars are standard deviation of technical and biological replicates.

Figure 41:
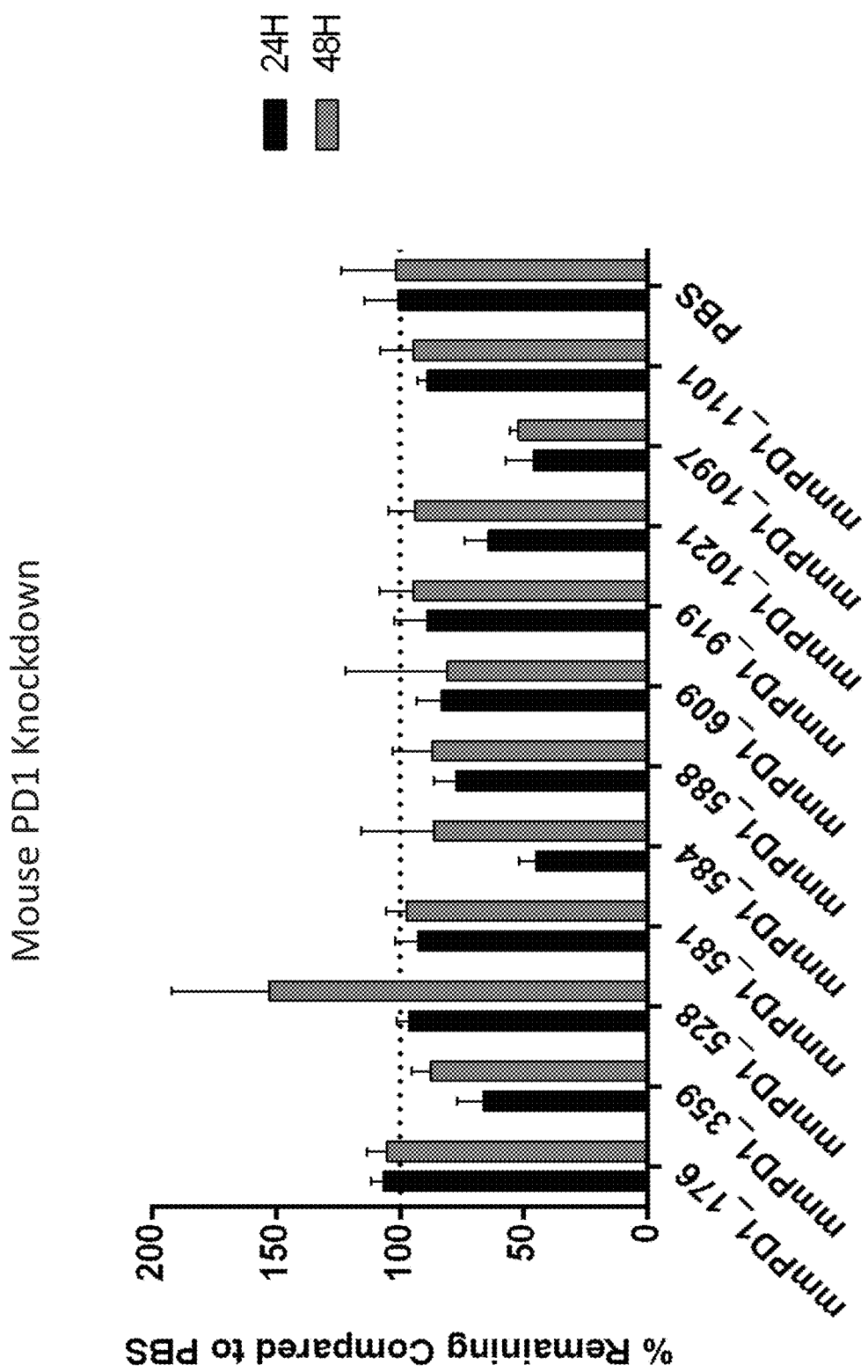
FIG. 41 depicts mouse PD1 knockdown at 24 and 48 hours, by the mouse PD1 shRNA sequences indicated on the x-axis. Knockdown is represented by percentage of PD1 transcript remaining (y-axis). Mouse PD1 shRNA sequences are provided in Table 18.

As shown in FIG. 41, the different shRNA constructs tested exhibited varying levels of PD1 knockdown. The shRNA constructs targeting positions 584 (mmPD1_584) and 1097 (mmPD1_1097) demonstrated the most robust PD1 knockdown of all of the constructs.

Example 11: Analysis of Regulatable CAR Constructs in T Cells

To evaluate the feasibility of regulating CAR technology, the regulatable CARs will be cloned into a lentiviral CAR expression vector with the CD3zeta chain and the 4-1BB costimulatory molecule in different configurations under the control of an EF1 alpha promoter. Sequence encoding an antigen binding domain, e.g., an scFv described herein, can be inserted between the leader and hinge sequences described below.

RCAR Components—Nucleic Acid Sequences

```
leader (nucleic acid sequence);
                                  (SEQ ID NO: 130)
ATGGCCTTACCAGTGACCGCCTTGCTCCTGCCGCTGGCCTTGCTGCTCCA

CGCCGCCAGGCCG hinge (nucleic acid sequence);
                                  (SEQ ID NO: 131)
ACCACGACGCCAGCGCCGCGACCACCAACACCGGCGCCCACCATCGCGTC

GCAGCCCCTGTCCCTGCGCCCAGAGGCGTGCCGGCCAGCGGCGGGGGCG

CAGTGCACACGAGGGGGCTGGACTTCGCCTGTGAT transmembrane (nucleic acid sequence);
                                  (SEQ ID NO: 132)
ATCTACATCTGGGCGCCCTTGGCCGGGACTTGTGGGGTCCTTCTCCTGTC

ACTGGTTATCACCCTTTACTGC 4-1BB Intracellular domain
(nucleic acid sequence);
                                  (SEQ ID NO: 133)
AAACGGGGCAGAAAGAAACTCCTGTATATATTCAAACAACCATTTATGAG

ACCAGTACAAACTACTCAAGAGGAAGATGGCTGTAGCTGCCGATTTCCAG

AAGAAGAAGAAGGAGGATGTGAACTG

CD3 zeta (nucleic acid sequence);
                                  (SEQ ID NO: 134)
AGAGTGAAGTTCAGCAGGAGCGCAGACGCCCCCGCGTACAAGCAGGGCCA

GAACCAGCTCTATAACGAGCTCAATCTAGGACGAAGAGAGGAGTACGATG

TTTTGGACAAGAGACGTGGCCGGGACCCTGAGATGGGGGGAAAGCCGAGA

AGGAAGAACCCTCAGGAAGGCCTGTACAATGAACTGCAGAAAGATAAGAT

GGCGGAGGCCTACAGTGAGATTGGGATGAAAGGCGAGCGCCGGAGGGGCA

AGGGGCACGATGGCCTTTACCAGGGTCTCAGTACAGCCACCAAGGACACC

TACGACGCCCTTCACATGCAGGCCCTGCCCCCTCGC
```

RCAR Components—Amino Acid Sequences

```
leader (amino acid sequence)
                                  (SEQ ID NO: 135)
MALPVTALLLPLALLLHAARP hinge (amino acid sequence)
                                  (SEQ ID NO: 136)
TTTPAPRPPTPAPTIASQPLSLRPEACRPAAGGAVHTRGLDFACD transmembrane (amino acid sequence)
                                  (SEQ ID NO: 137)
IYIWAPLAGTCGVLLLSLVITLYC 4-1BB Intracellular domain
(amino acid sequence)
                                  (SEQ ID NO: 138)
KRGRKKLLYIFKQPFMRPVQTTQEEDGCSCRFPEEEEGGCEL CD3 zeta domain (amino acid sequence)
                                  (SEQ ID NO: 139)
RVKFSRSADAPAYKQGQNQLYNELNLGRREEYDVLDKRRGRDPEMGGKPR

RKNPQEGLYNELQKDKMAEAYSEIGMKGERRRGKGHDGLYQGLSTATKDT

YDALHMQALPPR

EF1 alpha promoter.
                                  (SEQ ID NO: 140)
CGTGAGGCTCCGGTGCCCGTCAGTGGGCAGAGCGCACATCGCCCACAGTC

CCCGAGAAGTTGGGGGAGGGGTCGGCAATTGAACCGGTGCCTAGAGAAG

GTGGCGCGGGGTAAACTGGGAAAGTGATGTCGTGTACTGGCTCCGCCTTT

TTCCCGAGGGTGGGGAGAACCGTATATAAGTGCAGTAGTCGCCGTGAAC

GTTCTTTTTCGCAACGGGTTTGCCGCCAGAACACAGGTAAGTGCCGTGTG

TGGTTCCCGCGGGCCTGGCCTCTTTACGGGTTATGGCCCTTGCGTGCCTT

GAATTACTTCCACCTGGCTGCAGTACGTGATTCTTGATCCCGAGCTTCGG

GTTGGAAGTGGGTGGGAGAGTTCGAGGCCTTGCGCTTAAGGAGCCCCTTC

GCCTCGTGCTTGAGTTGAGGCCTGGCCTGGGCGCTGGGGCCGCCGCGTGC
```

```
-continued
GAATCTGGTGGCACCTTCGCGCCTGTCTCGCTGCTTTCGATAAGTCTCTA

GCCATTTAAAATTTTTGATGACCTGCTGCGACGCTTTTTTTCTGGCAAGA

TAGTCTTGTAAATGCGGGCCAAGATCTGCACACTGGTATTTCGGTTTTTG

GGGCCGCGGGCGGCGACGGGGCCCGTGCGTCCCAGCGCACATGTTCGGCG

AGGCGGGGCCTGCGAGCGCGGCCACCGAGAATCGGACGGGGGTAGTCTCA

AGCTGGCCGGCCTGCTCTGGTGCCTGGCCTCGCGCCGCCGTGTATCGCCC

CGCCCTGGGCGGCAAGGCTGGCCCGGTCGGCACCAGTTGCGTGAGCGGAA

AGATGGCCGCTTCCCGGCCCTGCTGCAGGGAGCTCAAAATGGAGGACGCG

GCGCTCGGGAGAGCGGGCGGGTGAGTCACCCACACAAAGGAAAAGGGCCT

TTCCGTCCTCAGCCGTCGCTTCATGTGACTCCACGGAGTACCGGCGCCG

TCCAGGCACCTCGATTAGTTCTCGAGCTTTTGGAGTACGTCGTCTTTAGG

TTGGGGGAGGGGTTTTATGCGATGGAGTTTCCCCACACTGAGTGGGTGG

AGACTGAAGTTAGGCCAGCTTGGCACTTGATGTAATTCTCCTTGGAATTT

GCCCTTTTTGAGTTTGGATCTTGGTTCATTCTCAAGCCTCAGACAGTGGT

TCAAAGTTTTTTCTTCCATTTCAGGTGTCGTGA
```

The optimal construct will be selected based on the quantity and quality of the effector T cell response regulatable RCAR transduced T cells in response to EGFRvIII+ and EGFR wild type targets. Effector T cell responses include, but are not limited to, cellular expansion, proliferation, doubling, cytokine production and target cell killing or cytolytic activity (degranulation).

Generation of Regulatable CAR T Cells

The RCAR lentiviral transfer vectors are used to produce the genomic material packaged into the VSVg psuedotyped lentiviral particles. Lentiviral transfer vector DNA is mixed with the three packaging components of VSVg, gag/pol and rev in combination with lipofectamine reagent to transfect them together in to 293T cells. After 24 and 48 hr, the media is collected, filtered and concentrated by ultracentrifugation. The resulting viral preparation is stored at −80 C. The number of transducing units is determined by titration on SupT1 cells.

For example, redirected EGFRvIII-specific RCART cells are produced by activating fresh T cells by engaging with CD3×28 beads for 24 hrs and then adding the appropriate number of transducing units to obtain the desired percentage of transduced T cells. These modified T cells are allowed to expand until they become rested and come down in size (~300 fl) at which point they are cryopreserved for later analysis. The cell numbers and sizes are measured using a Coulter multisizer III. Before cryopreserving, percentage of cells transduced (expressing the EGFRvIII-specific CAR on the cell surface) and their relative fluorescence intensity of that expression are determined by flow cytometric analysis on an LSRII. From the histogram plots, the relative expression levels of the CARs can be examined by comparing percentage transduced with their relative fluorescent intensity.

Evaluating Cytolytic Activity, Proliferation Capabilities and Cytokine Secretion of EGFRvIII Redirected, Regulatable CAR T Cells.

To evaluate the functional abilities of EGFRvIII-specific RCAR T cells to kill, proliferate and secrete cytokines, the cells are thawed and allowed to recover overnight. In addition to the RCAR constructs, the standard second generation EGFRvIII-clone 139-BBz CAR is used for comparative purposes while SS1-BBz (mesothelin-specific) is used as non-targeting expressed CAR for background CAR/T cell effect. For this flow based cytotoxicity assay, the target cells are stained with CSFE to quantitate their presence. The target cells are also stained for EGFRvIII expression to confirm similar target antigens levels. The cytolytic activities of EGFRvIII CAR T cells are measured at a titration of effector:target cell ratios of 10:1, 3:1, 1:1, 0.3:1 and 0:1 where effectors were defined as T cells expressing the anti-EGFRvIII chimeric receptor. Assays were initiated by mixing an appropriate number of T cells with a constant number of targets cells. A dose titration of the dimerization molecule is also added to the cultures, from 0-1000 nM concentrations for the rapalogue or anti-Myc antibody. After 4 or 16 hrs, total volume of each mixture is removed and each well washed. The T cells are stained for CD3 and all cells stained with live/dead marker 7AAD. After the final wash, the pelleted cells are re-suspended in a specific volume with a predetermined number of counting beads. Cell staining data is collected by LSRII flow cytometry and analyzed with FlowJo software using beads to quantitate results.

For measuring cell proliferation and cytokine production of RCAR-EGFRvIII T cells, cells are thawed and allowed to recover overnight. In addition to the RCAR constructs, the standard second generation EGFRvIII-clone 139-BBz CAR is used for comparative purposes while SS1-BBz (mesothelin-specific) is used as non-targeting expressed CAR for background CAR/T cell effect. The T cells are directed towards U87, a glioblastoma, astrocytoma cell line expressing or not expressing EGFRvIII. In addition, CD3×28 beads are used to evaluate the potential of T cells to respond to the second round of endogenous immunological signals. A dose titration of the dimerization molecule is also added to the cultures, from 0-1000 nM concentrations for the rapalogue or anti-Myc antibody. To analyze proliferation, T cells are stained with CSFE. The proliferation is the dilution of the CSFE stain reflecting the separation of the parental markings now into two daughter cells. The assay tests only an effector: target ratios of 1:1 and 1:0 where effectors were defined as total T cells (CD4 and 8) normalized to express the anti-EGFRvIII chimeric receptor at a common percentage. The assay is done in duplicate and 24 hrs after mixing of the cells, supernatant is removed for cytokine production. After 5 days, T cells are stained for live/dead with Live/Dead Violet (Invitrogen), then stained for CAR expression and phenotyped as either CD4 or CD8 cells. After the final wash, the pelleted cells are re-suspended in a specific volume with a predetermined number of BD counting beads. Cell staining data is collected by LSRII flow cytometry and analyzed with FlowJo software using beads to quantitate results. Total cell counts are determined by number of cells counted relative to a specific number of beads multiplied by the fraction of beads yet to be counted.

Evaluation of Regulatable CARTs In Vivo

The following experiments were designed to address whether the function of the regulatable CARTs can be modulated in vivo. Experiments are designed to test the in vivo delivery and function of the dimerization molecule in the context of a tumor model. Parameters to be measured include, but are not limited to, CART expansion, activation status of CART cells in the periphery as measured by FACS of peripheral blood samples, and tumor cell killing. Three different in vivo experiments are envisioned to address the utility of the RCAR and the dimerization molecule. These experiments will include assessment of 1) the basic function of the RCAR with the dimerization molecule, 2) a PD-1 dependent tumor model with the redirected switchable inhibitory RCAR, and 3) a PD-1 dependent tumor model with a RCAR and co-expression of a shRNA to PD-1.

The immunodeficient NOD/scid/γcnull (NSG) mouse is a suitable xenotransplantation model to engraft human tumor cell lines or primary tumors and human T cells. Following engraftment, the human T cells can be maintained in NSG mice for approximately 2 months, or until fatal xenogeneic GVHD (xGVHD) develops, which depends on the dose of human T cells infused. The administration of the dimerization molecule may be carried out in any convenient manner, based on the pharmacokinetic properties of the molecule and the optimized dosage and treatment regimen previously determined.

Example 12: In Vivo Analysis of the Basic RCAR with a Dimerization Molecule

To evaluate turning on RCART function in vivo with the dimerization molecule, human T cells expressing either switch 1 or switch 2 with a human CD19-specific scFv (FMC63) will be tested in an ALL tumor model using the NALM6-Luciferase (NALM6-Luc) tumor cell line which expresses human CD19. The FMC63 scFv has been validated extensively as part of a second generation CAR construct (CD19-41BB-zeta) that mediates complete tumor regression in preclinical models (Milone et al., Molecular Therapy 17(8): 1453-1464 (2009)). In brief, lentiviral constructs will be generated with switch 1 or switch 2 using the FMC63 scFv and these constructs will be transduced into primary human T cells. The T cells will be expanded ex vivo for 10-12 days and then cryopreserved by methods previously described. NSG mice will be implanted with NALM6-Luc tumor cell line by intravenous inoculation and tumor burden allowed to establish for 5-8 days. Tumor burden can be measured by standard imaging for luciferase activity. Mice are randomized as to treatment groups which include the following groups: 1) Mock/PBS, 2) Untransduced T cells, 3) CART19 ($2^{nd}$ generation intact CAR), 4) CD19-Switch 1, 5) CD19-Switch 1 plus rapalogue or RAD001 and 6) Rapalogue or RAD001 alone. Treatment groups will receive either PBS (groups 1 and 6) or 5×10$^6$ CART cells/mouse 5-8 days post tumor implantation. At a predetermined time following T cell infusion, e.g. 1-3 days, mice will be dosed with the rapalogue or RAD001. Dosage and schedule will be based on doses of the dimerization molecule which does not inhibit tumor cell growth by itself. Throughout the course of the study, mice will be imaged for tumor burden every other day or as frequently as needed to accurately assess the impact on tumor growth. At various intervals, blood samples will be collected for immunophenotyping analysis and peripheral T cell counts.

Dose-dependent effects of the rapalogue or RAD001 can be further assessed in additional experiments with treated groups receiving different doses of the rapalogue or RAD001 and/or alternative dosing regimens. The time course of tumor regression as well as degree of tumor regression can both be quantitated based on the imaging analysis.

Example 13: In Vivo Analysis of the Basic RCAR Along while Targeting a Checkpoint Inhibitor with a shRNA To evaluate the redirected switchable inhibitoryR CAR, human T cells expressing the RCAR will be evaluated in a mesothelin xenograft tumor model which expresses PD-L1. T cells will be generated which co-express switch 1 with a human mesothelin-specific scFv (SS1) along with a shRNA to PD-1. The SS1 scFv has been extensively validated as part of a second generation CAR construct that mediates tumor regression in preclinical models (Carpenito et al, PNAS, 106: 3360-3365, 2009). In brief, tumor cells expressing mesothelin and PD-L1 will be injected in to the flanks of NSG mice. These tumor cells may derive from a primary tumor such as M108 or from a tumor cell line such as OvCAR8. For OvCAR8, the cell line may be engineered to express PD-L1 if it does not express endogenous levels of the protein. Once tumors are established and the tumor burden is about 200-300 mm$^3$, mice will be randomized into the following treatment groups: 1) Mock/PBS, 2) Untransduced T cells, 3) SS1-BBz ($2^{nd}$ generation intact CAR), 4) Meso-Switch 1 plus rapalogue, 5) Meso-Switch 1 with PD-1 shRNA and rapalogue, and 6) Rapalogue alone. Treatment groups will receive either PBS (groups 1 and 6) or 5×105 CART cells/mouse. At a predetermined time following T cell infusion, e.g. 1-3 days, mice will be dosed with the rapalogue. Throughout the course of the study, tumor volume will be measured with callipers. At various intervals, blood samples will be collected for immunophenotyping analysis and peripheral T cell counts. Levels of PD-1 expression on the RCART cells will also be measured to assess the level of target knockdown by the shRNA.

Dose-dependent effects of the rapalogue can be further assessed in additional experiments with treated groups receiving different doses of the rapalogue and/or alternative dosing regimens. The time course of tumor regression as well as degree of tumor regression can both be quantitated based on the tumor volume.

Example 14: Expression of Single Vector Constructs

Lenti viral vectors were constructed that encode two elements of an RCAR.

Construct 143775 is a single nucleic acid vector which comprises an EF1 alpha promoter operably linked to sequence encoding an CD19 scFV-based antigen binding member, an IRES, and an intracellular signaling member comprising a 4-1BB domain and a CD3zeta domain. It expresses a single transcript from which the two products are separately transcribed.

Construct 143776 is a single nucleic acid vector which comprises an EF1 alpha promoter operably linked to sequence encoding an CD19 scFV-based antigen binding member, and a CMV minimal promoter operably linked to a sequence encoding an intracellular signaling member comprising a 4-1BB domain and a CD3zeta domain.

Construct 143777 is a single nucleic acid vector which comprises an EF1 alpha promoter operably linked to sequence encoding an CD19 scFV-based antigen binding member, and a CMV minimal promoter operably linked to a sequence encoding an intracellular signaling member comprising a 4-1BB domain and a CD3zeta domain.

The constructs and viral particles were made and tested essentially as described in Example 11. Viral particles were introduced into JNL cells and evaluated for activity essentially as described in Example 1 except that the target was CD19 (as opposed to EGFRviii).

Figure 23:
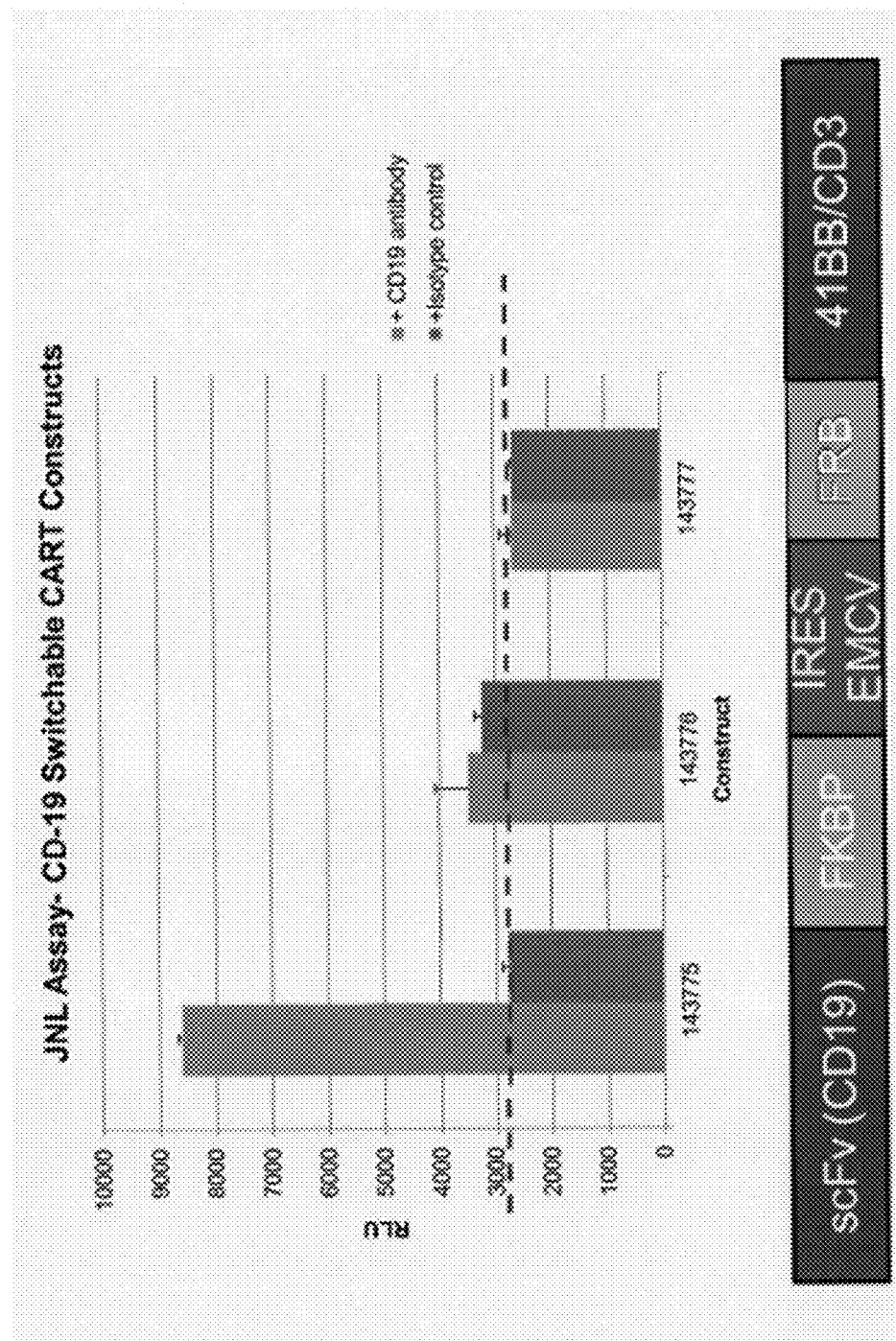
FIG. 23 shows RCAR activity from single vector encoded RCARs, where the arrangement of the single vectors are shown in FIG. 22.

FIG. 23 shows the ability of RCART constructs expressed from the single vector construct to activate the RCART. The dimerization molecule was RAD001. The graph shows that elements of an RCAR encoded by a single vector are expressed and respond to dimerization molecule to activate cells, as measured by expression of a reporter promoter under NFAT control.

Example 15: Dimerization Molecule Dose Response

Construct 143775 was introduced into cells and the affect of dimerization molecule concentration on activation evaluated essentially as described in Example 14.

Figure 24A:
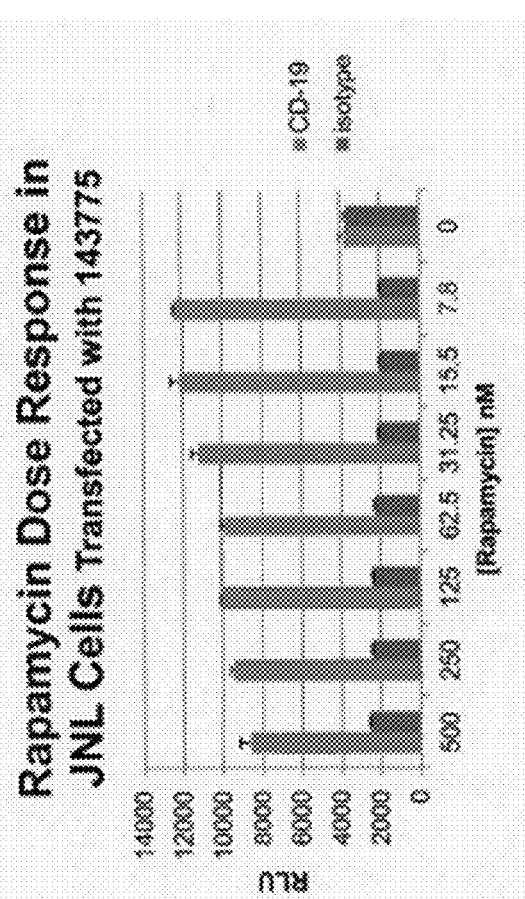
FIGS. 24A and 24B show activation of a CD19 RCAR by different heterodimerization molecule, RAD001 (FIG. 24A) or rapamycin (FIG. 24B) at the indicated nM concentrations. The RCAR is encoded by the construct 143775, as shown in FIG. 22.
Figure 24B:
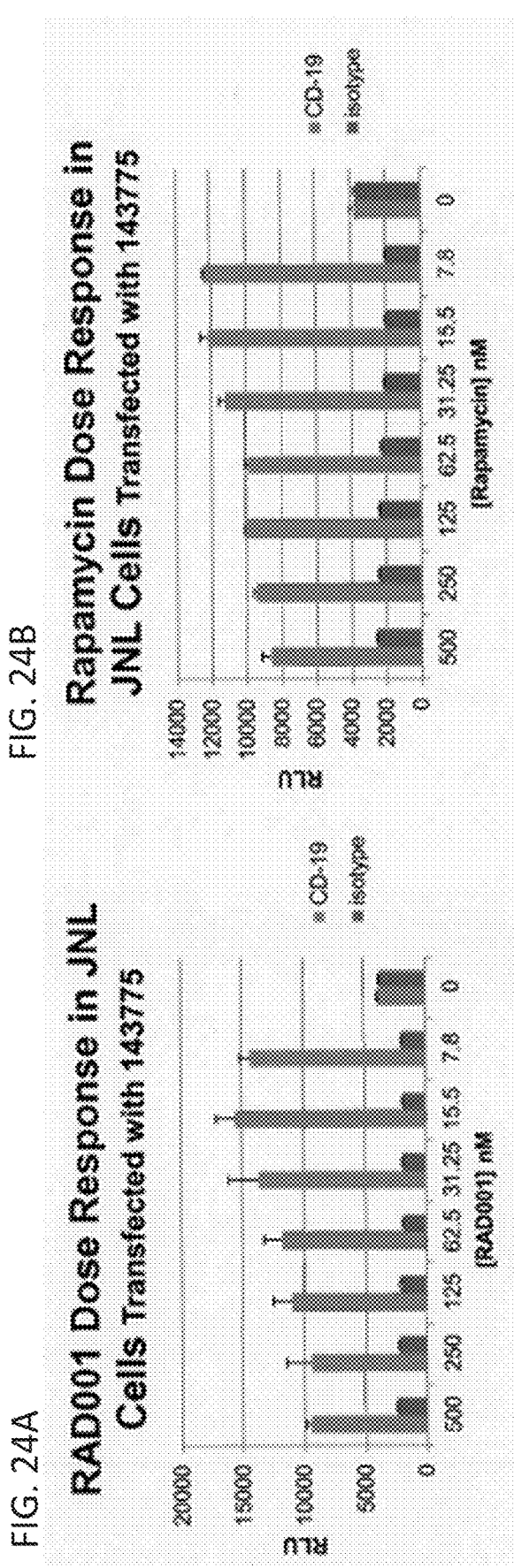

FIG. 24A shows the effect of nM doses of RAD001 on activation. FIG. 24B shows the effect of nM doses of rapamycin on activation.

Figure 25A:
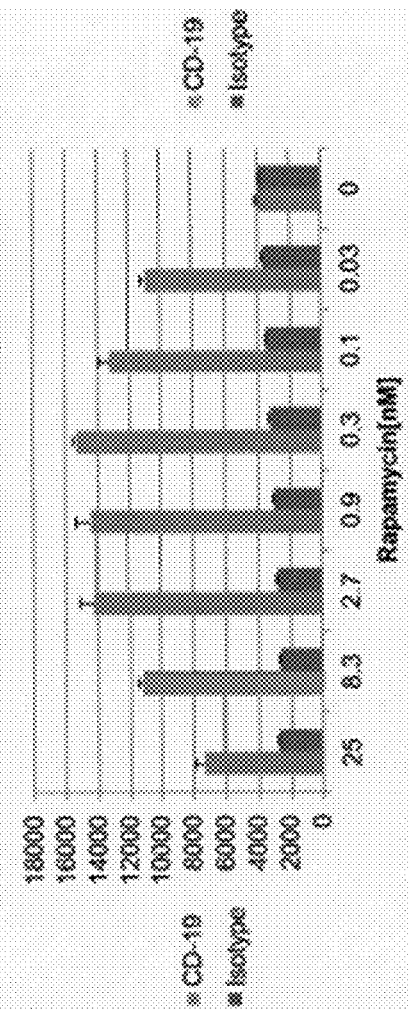
FIGS. 25A and 25B show activation of a CD19 RCAR by different heterodimerization molecule, RAD001 (FIG. 24A) or rapamycin (FIG. 24B) at the indicated nM concentrations. The RCAR is encoded by the construct 143775, as shown in FIG. 22.
Figure 25B:
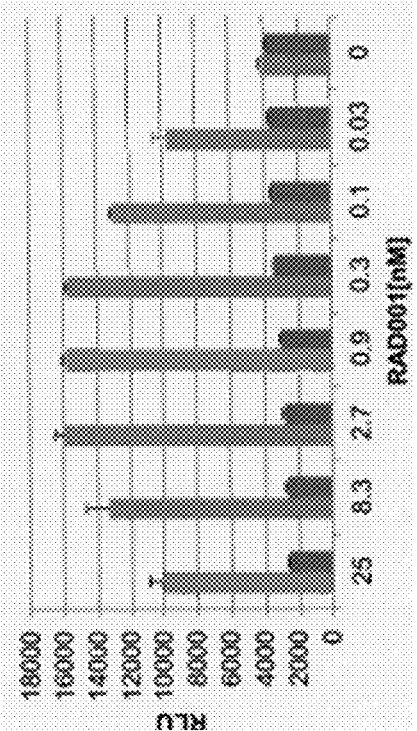
Figure 26:
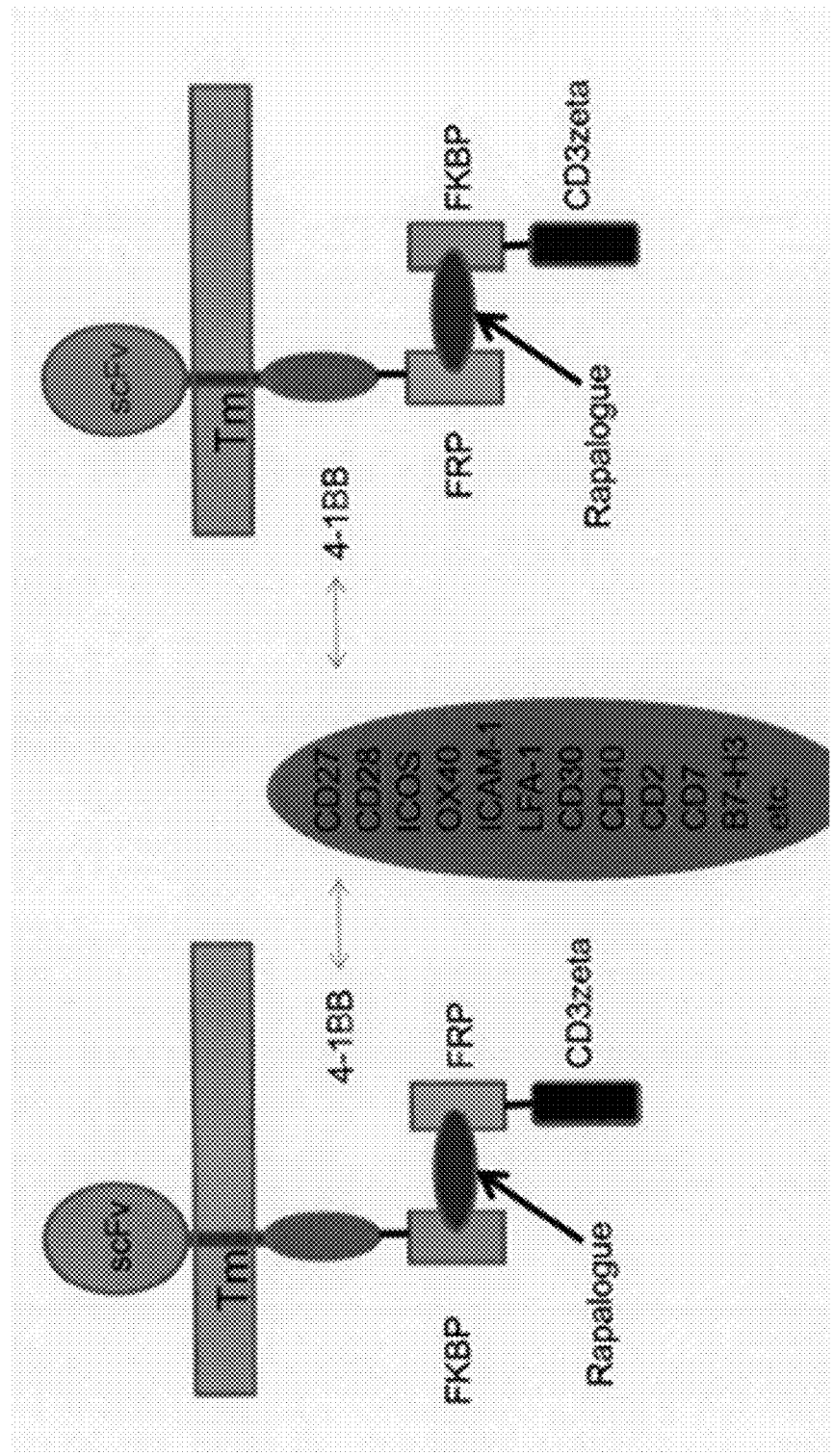
FIG. 26 depicts a half RCAR structure having a costimulatory signaling domain on the antigen binding member. The costimulatory signaling domain can be any of those listed, or from Table 2.

FIG. 25A shows the effect of nM to sub-nM doses of RAD001 on activation. FIG. 25B shows the effect of nM to sub-nM doses of rapamycin on activation. The data show that both RAD001 and rapamycin are effective at a broad range of concentrations.

Example 16: Optimized Members Having an Antigen Binding Domain or Other Extracellular Binding Domain Construction The DNA encoding for the amino acid sequence of the anti-human EGFRvIII 139 scFv will be cloned with a CD8 hinge and transmembrane domain followed by the endodomain for 4-1BB and the first intracellular switch domain FKBP. The DNA corresponding to the intracellular signaling member having the second switch domain FRB and CD3 zeta will also be synthesized. Additionally, DNA will be synthesized whereby the FRB and FKBP domains are exchanged for one another. Additional switches may also be cloned substituting the co-stimulatory endodomains shown in Table 2 for 4-1BB.

Generation of Jurkat Reporter Cell Line for Initial Characterization of CAR Function As an alternative to primary T cell transduction and activation, a Jurkat-NFAT reporter cell line can be used to evaluate the functional activity of CAR constructs. The Jurkat T cell line (E6-1) is transfected with a NFAT-luciferase reporter construct and a stable, clonal cell line (JNL) is selected for further characterization based on strong induction of the NFAT reporter following PMA and ionomycin stimulation.

Transfection of Jurkat Cell with NFAT-LUC Reporter and the Functional Assay Using Purified Proteins Jurkat cells with NFAT-LUC reporter (JNL) will be grown to the density of $5 \times 10^5$ cells per mL in Jurkat cell growth media with puromycin at 0.5 ug/ml. For each transfection $2.5 \times 10^6$ cells will be spin down at 100 g for 10 minutes. Two ug of DNA per construct will be used per transfection. Amaxa Nucleofector solution V and supplement I will be mixed and 100 ul will be added into the tube with each DNA construct. The mixture will be then added to the cells and transferred to the electroporation cuvette. Electroporation will be done under setting X-001 using Amaxa Nucleofector II Device. 500 uL Growth media shall be added immediately after electroporation and the mixture subsequently transferred into an additional 2 ml growth media in one well of the 6-well plate. The cells will be incubated in the 37C incubator with 5% CO2 for 24 hours. Tissue culture plate will be coated with 5 ug/ml of EGFRvIII-Fc or 5 ug/ml of IgG1-Fc for 2 hrs and blocked with 5% serum in DPBS for 1 hour. The transfected cells will be added to the target plate with 100 ul per well and incubated further for 18 hrs in the presence of varying concentrations of a suitable rapalogue. Luciferase One Glo reagent 100 ul will be added per well. The samples shall be incubated for 5 min at 37 C and then luminescence will be measured using a luminometer.

The degree to which the construct improves persistence can be evaluated by methods described herein.

Example 17: Effects of mTOR Inhibition on Immunosenescence in the Elderly

One of the pathways most clearly linked to aging is the mTOR pathway. The mTOR inhibitor rapamycin has been shown to extend lifespan in mice and improve a variety of aging-related conditions in old mice (Harrison, D E et al. (2009) Nature 460:392-395; Wilkinson J E et al. (2012) Aging Cell 11:675-682; and Flynn, J M et al. (2013) Aging Cell 12:851-862). Thus, these findings indicate that mTOR inhibitors may have beneficial effects on aging and aging-related conditions in humans.

An age-related phenotype that can be studied in a short clinical trial timeframe is immunosenescence. Immunosenescence is the decline in immune function that occurs in the elderly, leading to an increased susceptibility to infection and a decreased response to vaccination, including influenza vaccination. The decline in immune function with age is due to an accumulation of immune defects, including a decrease in the ability of hematopoietic stem cells (HSCs) to generate naïve lymphocytes, and an increase in the numbers of exhausted PD-1 positive lymphocytes that have defective responses to antigenic stimulation (Boraschi, D et al. (2013) Sci. Transl. Med. 5:185ps8; Lages, C S et al. (2010) Aging Cell 9:785-798; and Shimatani, K et al., (2009) Proc. Natl. Acad. Sci. USA 106:15807-15812). Studies in elderly mice showed that 6 weeks of treatment with the mTOR inhibitor rapamycin rejuvenated HSC function leading to increased production of naïve lymphocytes, improved response to influenza vaccination, and extended lifespan (Chen, C et al. (2009) Sci. Signal. 2:ra75).

To assess the effects of mTOR inhibition on human aging-related phenotypes and whether the mTOR inhibitor RAD001 ameliorates immunosenescence, the response to influenza vaccine in elderly volunteers receiving RAD001 or placebo was evaluated. The findings presented herein suggest that RAD001 enhanced the response to influenza vaccine in elderly volunteers at doses that were well tolerated. RAD001 also reduced the percentage of programmed death (PD)-1 positive CD4 and CD8 T lymphocytes that accumulate with age. These results show that mTOR inhibition has beneficial effects on immunosenescence in elderly volunteers.

As described herein, a 6 week treatment with the mTOR inhibitor RAD001, an analog of rapamycin, improved the response to influenza vaccination in elderly human volunteers.

Methods

Study Population

Elderly volunteers >=65 years of age without unstable underlying medical diseases were enrolled at 9 sites in New Zealand and Australia. Exclusion criteria at screening included hemoglobin <9.0 g/dL, white blood cell count <3,500/mm$^3$, neutrophil count <2,000/mm$^3$, or platelet count <125,000/mm$^3$, uncontrolled diabetes, unstable ischemic heart disease, clinically significant underlying pulmonary disease, history of an immunodeficiency or receiving immunosuppressive therapy, history of coagulopathy or medical condition requiring long-term anticoagulation, estimated glomerular filtration rate <30 ml/min, presence of severe uncontrolled hypercholesterolemia (>350 mg/dL, 9.1 mmol/L) or hypertriglyceridemia (>500 mg/dL, 5.6 mmol/L).

Baseline demographics between the treatment arms were similar (Table 20). Of the 218 subjects enrolled, 211 completed the study. Seven subjects withdrew from the study. Five subjects withdrew due to adverse events (AEs), one subject withdrew consent, and one subject left the study as a result of a protocol violation.

TABLE 20

Demographic and Baseline characteristics of the Study Patients

|  |  | RAD001 0.5 mg daily | RAD001 5 mg weekly | RAD001 20 mg weekly | Placebo pooled | Total |
|---|---|---|---|---|---|---|
|  |  | Population |  |  |  |  |
|  |  | N = 53 | N = 53 | N = 53 | N = 59 | N = 218 |
| Age (Years) | Mean | 70.8 | 72.0 | 71.4 | 71.1 | 71.3 |
|  | (SD) | (5.0) | (5.3) | (5.2) | (5.1) | (5.2) |
| Gender | Male—n | 34 | 27 | 32 | 31 | 124 |
|  | (%) | (64%) | (51%) | (60%) | (53%) | (57%) |
| BMI* (kg/m2) | Mean | 27.4 | 28.8 | 28.0 | 28.0 | 28.0 |
|  | (SD) | (4.2) | (5.0) | (4.1) | (4.2) | (4.4) |
| Race—n (%) | Caucasian | 48 | 50 | 46 | 54 | 198 |
|  |  | (91%) | (94%) | (87%) | (92%) | (91%) |
|  | Other | 5 | 3 | 7 | 5 | 20 |
|  |  | (9%) | (6%) | (13%) | (8%) | (9%) |

*The body-mass index is weight in kilograms divided by the square of the height in meters Study Design and Conduct From December 2011 to April 2012, 218 elderly volunteers were enrolled in a randomized, observer-blind, placebo-controlled trial. The subjects were randomized to treatment arms using a validated automated randomization system with a ratio of RAD001 to placebo of 5:2 in each treatment arm. The treatment arms were:

RAD001 0.5 mg daily or placebo
RAD001 5 mg weekly or placebo
RAD001 20 mg weekly or placebo The trial was observer-blind because the placebo in the RAD001 0.5 mg daily and 20 mg weekly cohorts differed slightly from the RAD001 tablets in those cohorts. The study personnel evaluating the subjects did not see the study medication and therefore were fully blinded. The treatment duration for all cohorts was 6 weeks during which time subjects underwent safety evaluations in the clinic every 2 weeks. After subjects had been dosed for 4 weeks, RAD001 steady state levels were measured pre-dose and at one hour post dose. After completing the 6 week course of study drug, subjects were given a 2 week drug free break to reverse any possible RAD001-induced immunosuppression, and then were given a 2012 seasonal influenza vaccination (Agrippal®, Novartis Vaccines and Diagnostics, Siena, Italy) containing the strains H1N1 A/California/07/2009, H3N2 A/Victoria/210/2009, B/Brisbane/60/2008. Four weeks after influenza vaccination, subjects had serum collected for influenza titer measurements. Antibody titers to the 3 influenza vaccine strains as well as to 2 heterologous strains (A/H1N1 strain A/New Jersey/8/76 and A/H3N2 strain A/Victoria/361/11) were measured by standard hemagglutination inhibition assay (Kendal, A P et al. (1982) *Concepts and procedures for laboratory-based influenza surveillance. Atlanta: Centers for Disease Control and Prevention* B17-B35).

Levels of IgG and IgM specific for the A/H1N1/California/07/2009 were measured in serum samples taken before and 4 weeks after influenza vaccination as described previously (Spensieri, F. et al. (2013) *Proc. Natl. Acad. Sci. USA* 110:14330-14335). Results were expressed as fluorescence intensity.

All subjects provided written informed consent. The study was conducted in accordance with the principals of Good Clinical Practice and was approved by the appropriate ethics committees and regulatory agencies.

Safety

Adverse event assessment and blood collection for hematologic and biochemical safety assessments were performed during study visits. Adverse event information was also collected in diaries that subjects filled out at home during the 6 weeks they were on study drug. Data on all adverse events were collected from the time of informed consent until 30 days after the last study visit. Events were classified by the investigators as mild, moderate or severe.

Statistical Analysis

The primary analysis of geometric mean titer ratios was done using a normal Bayesian regression model with non-informative priors. This model was fitted to each antibody titer on the log scale. The primary outcome in each model was the Day 84 measurement. The Day 63 measurement was included in the outcome vector. The model fitted using SAS 9.2 proc mixed with the prior statement. The covariance structure of the matrix was considered as unstructured (option type=UN). A flat prior was used. For the secondary analysis of seroconversion rates, logistic regression was used.

The intention to treat population was defined as all subjects who received at least one full dose of study drug and who had no major protocol deviations impacting efficacy data. 199 out of the total of 218 subjects enrolled in the study were in the intention to treat population.

Immunophenotyping

Peripheral blood mononuclear cells were isolated from whole blood collected at 3 time points: baseline; after 6 weeks of study drug treatment; and at the end of study when subjects had been off study drug for 6 weeks and 4 weeks after influenza vaccination. Seventy-six PBMC subsets were analyzed by flow cytometry using 8-color immunophenotyping panels at the Human Immune Monitoring Center at Stanford University, CA, USA as described previously (Maecker, H T et al. (2012) *Nat Rev Immunol.* 12:191-200). Seventy-six PBMC subsets were analyzed by flow cytometry using 8-color lyophilized immunophenotyping panels (BD Lyoplate, BD Biosciences, San Diego, Calif.). PBMC samples with viability >80% and yield of $2\times10^6$ cells or greater were included in the analysis.

Relative changes of the immunophenotypes from baseline to Week 6 of study drug treatment and from baseline to the end of study (Week 12) were calculated for each of the RAD001 dosing cohorts. Student T test was conducted to examine if the relative change of the immunophenotypes from baseline to the two blood sampling time points was significantly different from zero, respectively, within each dosing group after adjusting for placebo effect. Missing data imputation in treatment effect analysis was not conducted. Therefore if a patient has a missing phenotype data at baseline, this patient was not be included in the analysis for this phenotype. If a patient had a missing phenotype data at 6 or 12 weeks, then this patient did not contribute to the analysis of this phenotype for the affected timepoint.

608 tests in 76 phenotypes under 3 dosing groups were conducted to compare the treatment effect against the placebo effect. Stratified false discovery rate (FDR) control methodology was implemented to control the occurrence of false positives associated with multiple testing yet provide considerably better power. The cell type group was taken as the stratification factor and conducted FDR (q-value) calculation within each stratum respectively. All null-hypotheses were rejected at 0.05 significance level with corresponding q-value ≤0.1. The multiple testing adjustment strategy with rejecting at 0.05 significance level and corresponding q<0.1 ensured that less than 10% of the findings are false.

In a second analysis, the immunophenotype changes between pooled treatment and placebo groups, where all three RAD001 dosing groups were combined. To determine which immunophenotype changes differed between the treated and placebo groups, within-patient cell count ratios for each measured phenotype were calculated between baseline and Week 6 of study drug treatment and between baseline and the end of study (Week 12). The ratios were log transformed, and analyzed by analysis of covariance at each time point in order to detect a difference between the pooled treatment and placebo groups. 152 tests in 76 phenotypes were performed to compare the pooled treatment effect against the placebo effect. Stratified false discovery rate (FDR) control methodology was implemented to control the occurrence of false positives associated with multiple testing yet provide considerably better power (Benjamini, Y. et al. (1995) *J. Roy. Statist.* 57:289-300; and Sun, L. et al. (2006) *Genet. Epidemiol.* 30:519-530). The cell type group was taken as the stratification factor and FDR (q-value) calculation was conducted within each stratum respectively. All null-hypotheses at 0.05 significance level and q-value less than 20% were rejected. This can be interpreted as rejecting only those hypotheses with P values less than 0.05 and less than 20% probability that the each observed significant result is due to multiple testing.

Results

In general, RAD001 was well tolerated, particularly the 0.5 mg daily and 5 mg weekly dosing regimens. No deaths occurred during the study. Three subjects experienced four serious adverse events (SAEs) that were assessed as unrelated to RAD001. The 4 SAEs were retinal hemorrhage of the left eye with subsequent blindness in a subject with normal platelet counts who had completed a 6 week course of 5 mg weekly RAD001 6 weeks previously; severe back pain in a subject treated with placebo and severe gastroenteritis in a subject treated with placebo. A list of treatment-related adverse events (AEs) with an incidence >2% in any treatment group is provided in Table 21. The most common RAD001-related AE was mouth ulcer that, in the majority of cases, was of mild severity. Overall, subjects who received RAD001 had a similar incidence of severe AEs as those treated with placebo. Only one severe AE was assessed as related to RAD001 mouth ulcers in a subject treated with 20 mg weekly RAD001.

TABLE 21

Incidence of treatment-related AEs >2% in any treatment group by preferred term

|  | RAD001 0.5 mg daily N = 53 n (%) | RAD001 5 mg weekly N = 53 n (%) | RAD001 20 mg weekly N = 53 n (%) | Placebo, pooled N = 59 n (%) | Total N = 218 n (%) |
|---|---|---|---|---|---|
| Total AE(s) | 35 | 46 | 109 | 21 | 211 |
| Patients with AE(s) | 22 (41.5%) | 20 (37.7%) | 27 (50.9%) | 12 (20.3%) | 81 (37.2%) |
| Mouth ulceration | 6 (11.3%) | 2 (3.8%) | 9 (17.0%) | 3 (5.1%) | 20 (9.2%) |
| Headache | 0 | 2 (3.8%) | 9 (17.0%) | 1 (1.7%) | 12 (5.5%) |
| Blood cholesterol increased | 2 (3.8%) | 2 (3.8%) | 2 (3.8%) | 0 | 6 (2.8%) |
| Diarrhea | 1 (1.9%) | 4 (7.5%) | 1 (1.9%) | 0 | 6 (2.8%) |
| Dyspepsia | 0 | 3 (5.7%) | 2 (3.8%) | 1 (1.7%) | 6 (2.8%) |
| Fatigue | 0 | 2 (3.8%) | 4 (7.5%) | 0 | 6 (2.8%) |
| Low density lipoprotein increased | 2 (3.8%) | 1 (1.9%) | 2 (3.8%) | 0 | 5 (2.3%) |
| Tongue ulceration | 3 (5.7%) | 1 (1.9%) | 0 | 1 (1.7%) | 5 (2.3%) |
| Insomnia | 1 (1.9%) | 2 (3.8%) | 1 (1.9%) | 0 | 4 (1.8%) |
| Dry mouth | 0 | 0 | 2 (3.8%) | 1 (1.7%) | 3 (1.4%) |
| Neutropenia | 0 | 0 | 3 (5.7%) | 0 | 3 (1.4%) |
| Oral pain | 0 | 2 (3.8%) | 1 (1.9%) | 0 | 3 (1.4%) |
| Pruritus | 0 | 2 (3.8%) | 1 (1.9%) | 0 | 3 (1.4%) |
| Conjunctivitis | 0 | 2 (3.8%) | 0 | 0 | 2 (0.9%) |
| Erythema | 0 | 2 (3.8%) | 0 | 0 | 2 (0.9%) |
| Limb discomfort | 0 | 2 (3.8%) | 0 | 0 | 2 (0.9%) |
| Mucosal inflammation | 0 | 0 | 2 (3.8%) | 0 | 2 (0.9%) |
| Paresthesia oral | 2 (3.8%) | 0 | 0 | 0 | 2 (0.9%) |
| Stomatitis | 0 | 0 | 2 (3.8%) | 0 | 2 (0.9%) |
| Thrombocytopenia | 0 | 0 | 2 (3.8%) | 0 | 2 (0.9%) |
| Urinary tract infection | 0 | 0 | 2 (3.8%) | 0 | 2 (0.9%) |

The ability of RAD001 to improve immune function in elderly volunteers was evaluated by measuring the serologic response to the 2012 seasonal influenza vaccine. The hemagglutination inhibition (HI) geometric mean titers (GMT) to each of the 3 influenza vaccine strains at baseline and 4 weeks after influenza vaccination are provided in Table 22. The primary analysis variable was the HI GMT ratio (4 weeks post vaccination/baseline). The study was powered to be able to demonstrate that in at least 2 out of 3 influenza vaccine strains there was 1) a >1.2-fold GMT increase relative to placebo; and 2) a posterior probability no lower than 80% that the placebo-corrected GMT ratio exceeded 1. This endpoint was chosen because a 1.2-fold increase in the influenza GMT ratio induced by the MF-59 vaccine adjuvant was associated with a decrease in influenza illness (Iob, A et al. (2005) *Epidemiol Infect* 133:687-693).

TABLE 22

HI GMTs for each influenza vaccine strain at baseline and at 4 weeks after influenza vaccination

| Influenza Vaccine Strain | | Time | RAD001 0.5 mg daily N = 50 | RAD001 5 mg weekly N = 49 | RAD001 20 mg weekly N = 49 | Placebo N = 55 |
|---|---|---|---|---|---|---|
| A/H1N1 | GMT (CV %) | Baseline | 102.8 (186.9) | 84.2 (236.4) | 90.1 (188.4) | 103.2 (219.7) |
| | | Week 4 | 190.2 (236.9) | 198.73 (195.6) | 129.7 (175.9) | 169.4 (259.8) |
| | GMT ratio (CV %) | | 2.6 (302.5) | 2.5 (214.3) | 1.8 (201.5) | 2.0 (132.7) |
| A/H3N2 | GMT (CV %) | Baseline | 106.8 (168.2) | 126.04 (162.6) | 137.1 (211.5) | 131.7 (162.3) |
| | | Week 4 | 194.4 (129.1) | 223.0 (118.8) | 223.0 (163.6) | 184.3 (153.2) |
| | GMT ratio (CV %) | | 2.1 (152.6) | 2.0 (189.2) | 2.1 (277.3) | 1.6 (153.6) |
| B | GMT (CV %) | Baseline | 44.2 (96.6) | 64.8 (87.3) | 58.0 (156.0) | 57.0 (112.6) |
| | | Week 4 | 98.4 (94.8) | 117.3 (99.9) | 99.2 (124.1) | 114.6 (136.7) |
| | GMT ratio (CV %) | | 2.5 (111.2) | 2.2 (112.8) | 2.1 (126.5) | 2.2 (109.2) |

Figure 27A:
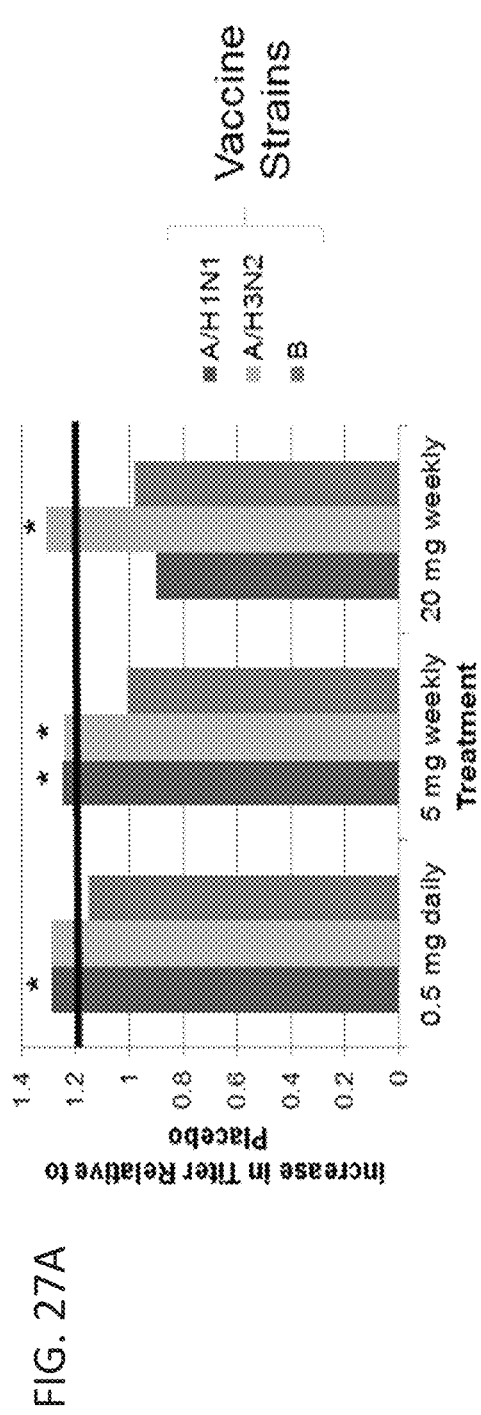
FIGS. 27A and 27B are graphs showing an increase in titers to influenza vaccine strains as compared to placebo.

Baseline indicates 2 weeks prior to influenza vaccination
Week 4 indicates 4 weeks after influenza vaccination
N is number of subjects per cohort
GMT is geometric mean titer
GMT ratio is the GMT at week 4 post vaccination/GMT at baseline
CV % indicates coefficient of variation In the intent-to-treat (ITT) population, the low, immune enhancing, dose RAD001 (0.5 mg daily or 5 mg weekly) cohorts but not higher dose (20 mg weekly) cohort met the primary endpoint of the study (FIG. 27A). This demonstrates that there is a distinct immunomodulatory mechanism of RAD001 at the lower doses, and that at the higher dose the known immunosuppressive effects of mTOR inhibition may come into play. Furthermore, the results suggest a trend toward improved immune function in the elderly after low, immune enhancing, dose RAD001 treatment.

Figure 27B:
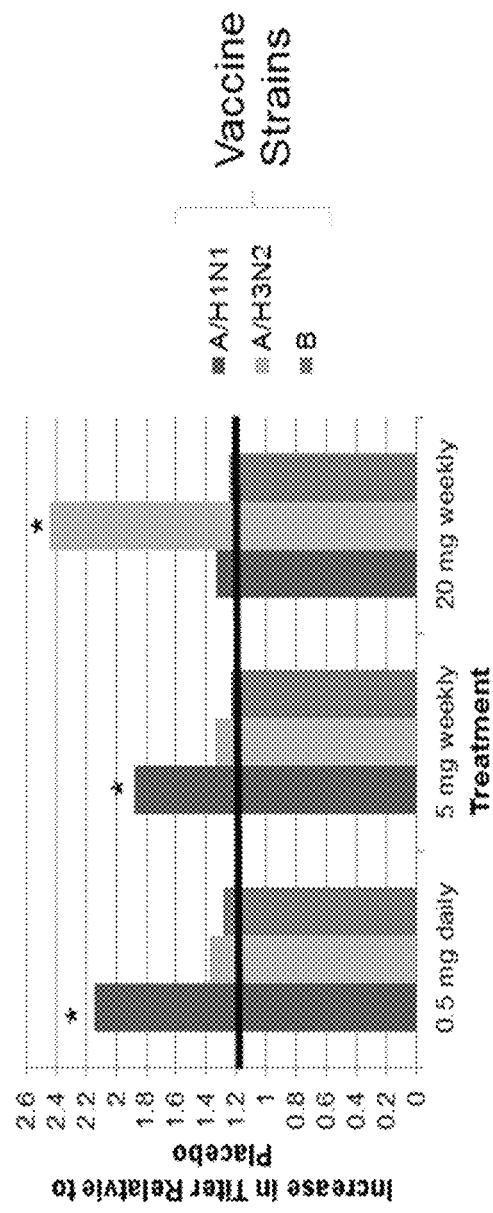

In a subgroup analysis, the subset of subjects with low baseline influenza titers (<1:40) experienced a greater RAD001-associated increase in titers than did the ITT population (FIG. 27B). These data show that RAD001 is particularly effective at enhancing the influenza vaccine response of subjects who did not have protective (>1:40) titers at baseline, and therefore were at highest risk of influenza illness.

Figure 28:
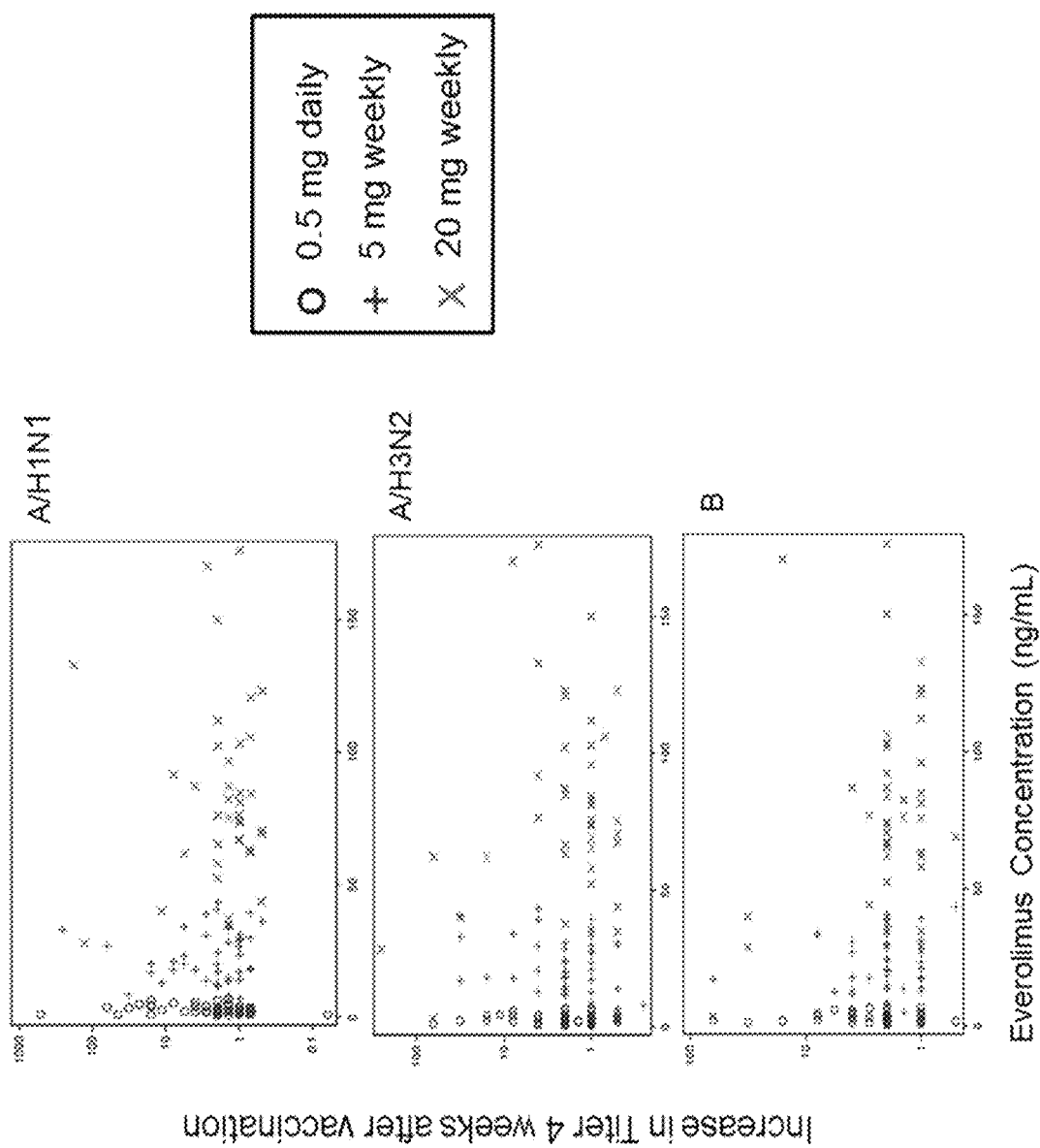
FIG. 28 shows a scatter plot of RAD001 concentration versus fold increase in geometric mean titer to each influenza vaccine strain 4 weeks after vaccination. RAD001 concentrations (1 hour post dose) were measured after subjects had been dosed for 4 weeks. All subjects who had pharmacokinetic measurements were included in the analysis set. The fold increase in geometric mean titers at 4 weeks post vaccination relative to baseline is shown on the y axis.

Scatter plots of RAD001 concentration versus increase in titer to each influenza vaccine strain show an inverse exposure/response relationship (FIG. 28). Modeling and simulation based on mTOR mediated phosphorylation of S6 kinase (S6K) predicts that the 20 mg weekly dosing regimen inhibits mTOR-mediated S6K activity almost completely, the 5 mg weekly dosing regimen inhibits S6K activity by over 50%, and the 0.5 mg daily dosing regiment inhibits S6K phosphorylation by approximately 38% during the dosing interval (Tanaka, C et al. (2008) *J. Clin. Oncol* 26:1596-1602). Thus, partial mTOR inhibition, e.g., mTOR-mediated S6K phosphorylation, with low, immune enhancing, dose RAD001 may be as, if not more effective, than near complete mTOR inhibition with high dose RAD001 at enhancing the immune response of the elderly.

Rates of seroconversion 4 weeks after influenza vaccination were also evaluated. Seroconversion was defined as the change from a negative pre-vaccination titer (i.e., HI titer <1:10) to post-vaccination HI titer ≥1:40 or at least 4-fold increase from a non-negative (≥1:10) pre-vaccination HI titer. In the intention-to-treat population, seroconversion rates for the H3N2 and B strains were increased in the RAD001 as compared to the placebo cohorts although the increases did not meet statistical significance (Table 23). In the subpopulation of subjects with baseline influenza titers <=1:40, RAD001 treatment also increased the rates of seroconversion to the H3N2 and B strains, and these results reached statistical significance for the B strain in the 0.5 mg daily dosing cohort. These data further show that RAD001 enhanced the serologic response to influenza vaccination in the elderly.

TABLE 23

Percent of subjects with seroconversion to influenza 4 weeks after vaccination

| | Placebo N = 54 | 0.5 mg N = 48 | 5 mg N = 49 | 20 mg N = 48 |
|---|---|---|---|---|
| Intention to Treat Population | | | | |
| H1N1 | 24 | 27 | 27 | 17 |
| H3N2 | 17 | 27 | 24 | 25 |
| B | 17 | 27 | 22 | 19 |
| Subjects with Baseline Titers <=40 | | | | |
| H1N1 | 40 | 42 | 45 | 36 |
| H3N2 | 42 | 64 | 53 | 71 |
| B | 16 | 40* | 33 | 28 |

*Odds ratio for seroconversion between RAD001 and Placebo significantly different than 1 (two-sided p-value < 0.05 obtained by logistic regression with treatment as fixed effect)

Current seasonal influenza vaccines often provide inadequate protection against continuously emerging strains of influenza that present as variants of previously circulating viruses. However, mice vaccinated against influenza in the presence of the mTOR inhibitor rapamycin, as compared to placebo, developed a broader serologic response to influenza. The broader serologic response included antibodies to conserved epitopes expressed by multiple subtypes of influenza that provided protection against infection with heterologous strains of influenza not contained in the vaccine (Keating, R et al. (2013) *Nat Immunology* 14:2166-2178). To determine if RAD001 broadened the serologic response to influenza in the elderly volunteers, HI titers to 2 heterologous strains of influenza not contained in the influenza vaccine (A/H1N1 strain A/New Jersey/8/76 and A/H3N2 strain A/Victoria/361/11) were measured. The increase in the HI GMT ratios for the heterologous strains was higher in the RAD001 as compared to placebo cohorts (FIG. 29). In addition, seroconversion rates for the heterologous strains were higher in the RAD001 as compared to placebo cohorts. The increase in seroconversion rates in the 5 and 20 mg weekly RAD001 dosing cohorts was statistically significant for the H3N2 heterologous strain (Table 24). The H3N2 seroconversion rate for the pooled RAD001 cohorts was 39% versus 20% for the placebo cohort (p=0.007). The results presented herein suggest that mTOR inhibition broadens the serologic response of elderly volunteers to influenza vaccination, and increases antibody titers to heterologous strains of influenza not contained in the seasonal influenza vaccine.

Figure 30A:
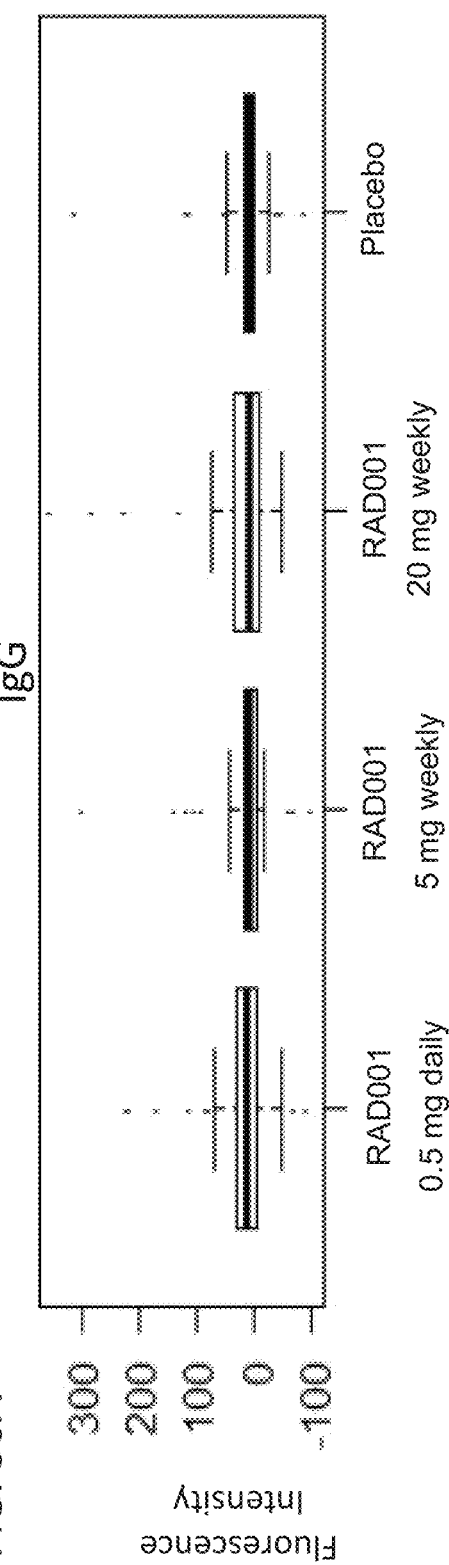
FIGS. 30A and 30B are graphic representations of IgG and IgM levels before and after influenza vaccination. Levels of anti-A/H1N1/California/07/2009 influenza IgG and IgM were measured in serum obtained from subjects before and 4 weeks post influenza vaccination. No significant difference in the change from baseline to 4 weeks post vaccination in anti-H1N1 influenza IgG and IgM levels were detected between the RAD001 and placebo cohorts (all p values >0.05 by Kruskal-Wallis rank sum test).
Figure 30B:
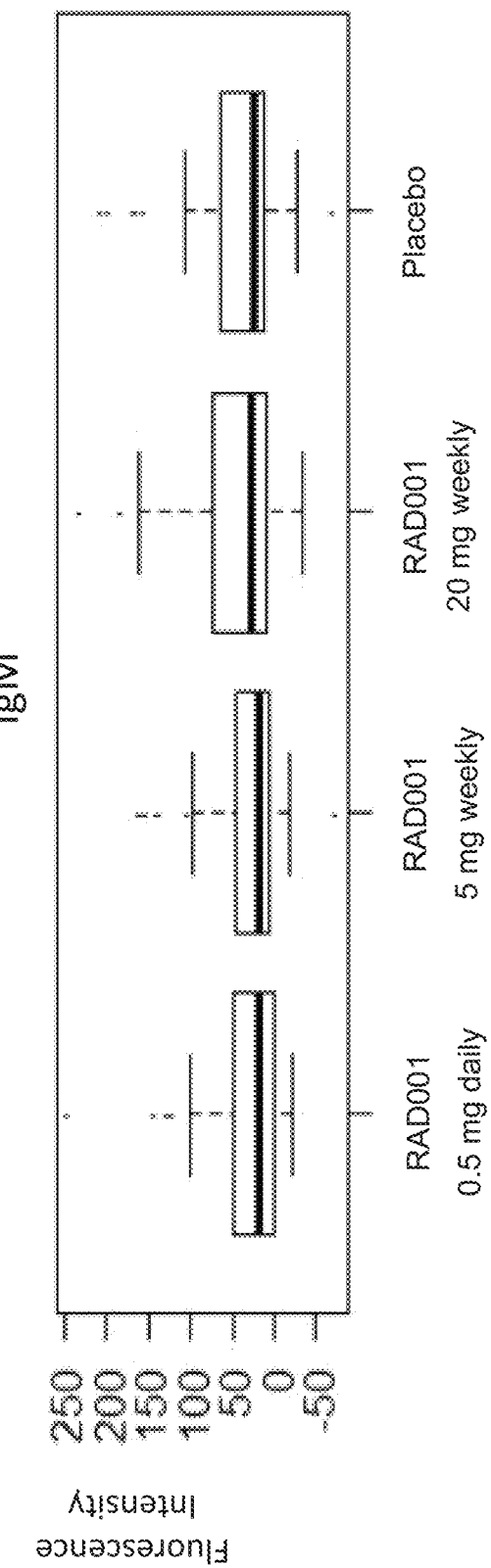

Broadened serologic response to heterologous strains of influenza in mice treated with rapamycin has been associated with an inhibition of class switching in B cells and an increase in anti-influenza IgM levels (Keating, R. et al. (2013) *Nat Immunol* 14:2166-2178). However, inhibition of class switching may not be involved in the broadened serologic response in humans treated with RAD001 because the post-vaccination anti-influenza IgM and IgG levels did not differ between RAD001 and placebo treated cohorts (FIGS. 30A and 30B).

TABLE 24

Percentage of subjects who seroconvert to heterologous strains of influenza 4 weeks after seasonal influenza vaccination

|  | Placebo, pooled | RAD001 0.5 mg daily | RAD001 5 mg weekly | RAD001 20 mg weekly |
|---|---|---|---|---|
| A/H1N1 strain: A/New Jersey/8/76 | 7% | 17% | 16% | 8% |
| A/H3N2 strain: A/Victoria/361/11 | 20% | 38% | 39%* | 40%* |

*Odds ratio for seroconversion between RAD001 and Placebo significantly different than 1 (two-sided p-value < 0.05 obtained by logistic regression with treatment as fixed effect)

Figure 31A:
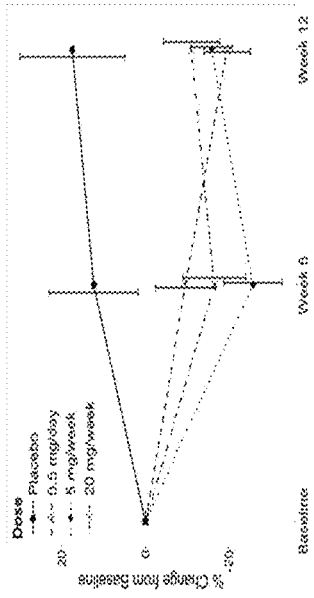
FIGS. 31A, 31B, and 31C are graphic representations of the decrease in percent of PD-1-positive CD4 and CD8 and increase in PD-1-negative CD4 T cells after RAD001 treatment. The percent of PD-1-positive CD4, CD8 and PD-1-negative CD4 T cells was determined by FACS analysis of PBMC samples at baseline, after 6 weeks of study drug treatment (Week 6) and 6 weeks after study drug discontinuation and 4 weeks after influenza vaccination (Week 12).
Figure 31B:
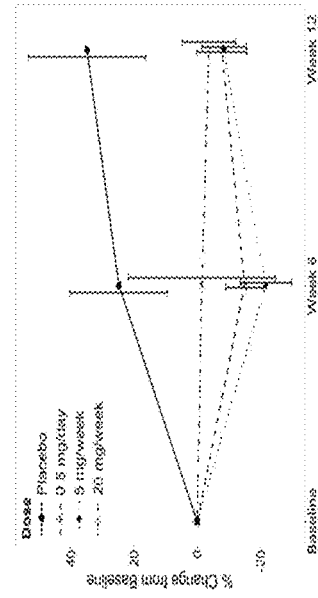
Figure 31C:
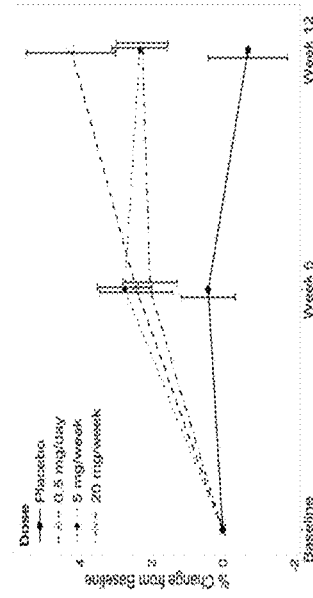

To address the mechanism by which RAD001 enhanced immune function in elderly volunteers, immunophenotyping was performed on PBMC samples obtained from subjects at baseline, after 6 weeks of study drug treatment and 4 weeks after influenza vaccination (6 weeks after study drug discontinuation). Although the percentage of most PBMC subsets did not differ between the RAD001 and placebo cohorts, the percentage of PD-1 positive CD4 and CD8 cells was lower in the RAD001 as compared to placebo cohorts (FIGS. 31A, 31B and 31C). PD-1 positive CD4 and CD8 cells accumulate with age and have defective responses to antigen stimulation because PD-1 inhibits T cell receptor-induced T cell proliferation, cytokine production and cytolytic function (Lages, C S et al. (2010) *Aging Cell* 9:785-798). There was an increase in percentage of PD-1 positive T cells over time in the placebo cohort. At week 12 (4 weeks post-vaccination) this increase may have been due to influenza vaccination since influenza virus has been shown to increase PD-1 positive T cells (Erikson, J J et al. (2012) *JCI* 122:2967-2982). However the percentage of CD4 PD-1 positive T cells decreased from baseline at week 6 and 12 in all RAD001 cohorts (FIG. 31A). The percentage of CD8 PD-1 positive cells also decreased from baseline at both week 6 and 12 in the two lower dose RAD001 cohorts (FIG. 31B). The percentage of PD-1 negative CD4 T cells was evaluated and increased in the RAD001 cohorts as compared to the placebo cohorts (FIG. 31C).

Figure 32A:
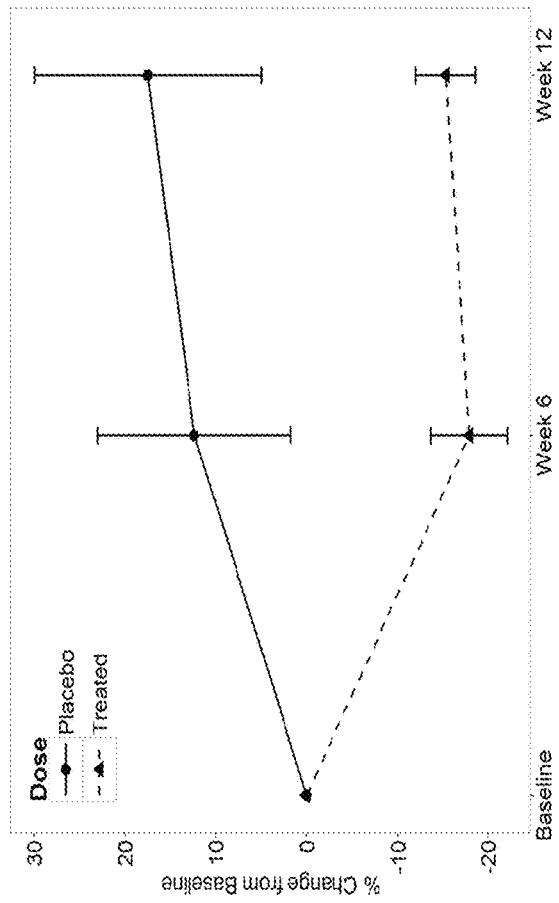
FIGS. 32A and 32B are graphic representations of the decrease in percent of PD-1-positive CD4 and CD8 and increase in PD-1-negative CD4 T cells after RAD001 treatment adjusted for differences in baseline PD-1 expression. The percent of PD-1-positive CD4, CD8 and PD-1-negative CD4 T cells was determined by FACS analysis of PBMC samples at baseline, after 6 weeks of study drug treatment (Week 6) and 6 weeks after study drug discontinuation and 4 weeks after influenza vaccination (Week 12).
Figure 32B:
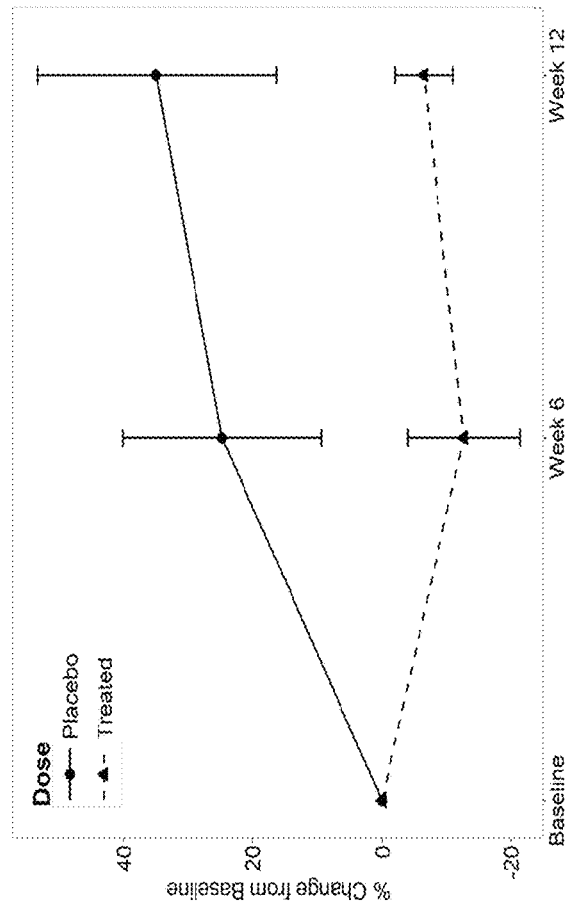

Under more stringent statistical analysis, where the results from the RAD001 cohorts were pooled and adjusted for differences in baseline PD-1 expression, there was a statistically significant decrease of 30.2% in PD-1 positive CD4 T cells at week 6 in the pooled RAD cohort (n=84) compared to placebo cohort (n=25) with p=0.03 (q=0.13) (FIG. 32A). The decrease in PD-1 positive CD4 T cells at week 12 in the pooled RAD as compared to the placebo cohort is 32.7% with p=0.05 (q=0.19). FIG. 32B shows a statistically significant decrease of 37.4% in PD-1 positive CD8 T cells at week 6 in the pooled RAD001 cohort (n=84) compared to placebo cohort (n=25) with p=0.008 (q=0.07). The decrease in PD-1 positive CD8 T cells at week 12 in the pooled RAD001 as compared to the placebo cohort is 41.4% with p=0.066 (q=0.21). Thus, the results from FIGS. 31A-C and 32A-B together suggest that the RAD001-associated decrease in the percentage of PD-1 positive CD4 and CD8 T cells may contribute to enhanced immune function.

Conclusion

In conclusion, the data presented herein show that the mTOR inhibitor RAD001 ameliorates the age-related decline in immunological function of the human elderly as assessed by response to influenza vaccination, and that this amelioration is obtained with an acceptable risk/benefit balance. In a study of elderly mice, 6 weeks treatment with the mTOR inhibitor rapamycin not only enhanced the response to influenza vaccination but also extended lifespan, suggesting that amelioration of immunosenescence may be a marker of a more broad effect on aging-related phenotypes.

Since RAD001 dosing was discontinued 2 weeks prior to vaccination, the immune enhancing effects of RAD001 may be mediated by changes in a relevant cell population that persists after discontinuation of drug treatment. The results presented herein show that RAD001 decreased the percentage of exhausted PD-1 positive CD4 and CD8 T cells as compared to placebo. PD-1 expression is induced by TCR signaling and remains high in the setting of persistent antigen stimulation including chronic viral infection. While not wishing to be bound by theory, is possible that RAD001 reduced chronic immune activation in elderly volunteers and thereby led to a decrease in PD-1 expression. RAD001 may also directly inhibit PD-1 expression as has been reported for the immunophilin cyclosporine A (Oestreich, K J et al. (2008) *J Immunol.* 181:4832-4839). A RAD001-induced reduction in the percentage of PD-1 positive T cells is likely to improve the quality of T cell responses. This is consistent with previous studies showing that mTOR inhibition improved the quality of memory CD8 T cell response to vaccination in mice and primates (Araki, K et al. (2009) *Nature* 460:108-112). In aged mice, mTOR inhibition has also been shown to increase the number of hematopoietic stem cells, leading to increased production of naïve lymphocytes (Chen, C et al. (2009) *Sci Signal* 2:ra75). Although significant differences in the percentages of naïve lymphocytes in the RAD001 versus placebo cohorts were not detected in this example, this possible mechanism may be further investigated.

The mechanism by which RAD001 broadened the serologic response to heterologous strains of influenza may be further investigated. Rapamycin has also been shown to inhibit class switching in B cells after influenza vaccination. As a result, a unique repertoire of anti-influenza antibodies was generated that promoted cross-strain protection against lethal infection with influenza virus subtypes not contained in the influenza vaccine (Keating, R et al. (2013) *Nat Immunol.* 14:2166-2178). The results described herein did not show that RAD001 altered B cell class switching in the elderly subjects who had discontinued RAD001 2 weeks prior to influenza vaccination. Although the underlying mechanism requires further elucidation, the increased serologic response to heterologous influenza strains described herein may confer enhanced protection to influenza illness in years when there is a poor match between the seasonal vaccine and circulating strains of influenza in the community.

The effect of RAD001 on influenza antibody titers was comparable to the effect of the MF59 vaccine adjuvant that is approved to enhance the response of the elderly to influenza vaccination (Podda, A (2001) *Vaccine* 19:2673-2680). Therefore, RAD001-driven enhancement of the antibody response to influenza vaccination may translate into clinical benefit as demonstrated with MF59-adjuvanted influenza vaccine in the elderly (Iob, A et al. (2005) *Epide-*

*miol Infect.* 133:687-693). However, RAD001 is also used to suppress the immune response of organ transplant patients. These seemingly paradoxical findings raise the possibility that the immunomodulatory effects of mTOR inhibitors may be dose and/or antigen-dependent (Ferrer, I R et al. (2010) *J Immunol.* 185:2004-2008). A trend toward an inverse RAD001 exposure/vaccination response relationship was seen herein. It is possible that complete mTOR inhibition suppresses immune function through the normal cyclophilin-rapamycin mechanism, whereas partial mTOR inhibition, at least in the elderly, enhances immune function due to a distinct aging-related phenotype inhibition. Of interest, mTOR activity is increased in a variety of tissues including hematopoietic stem cells in aging animal models (Chen C. et al. (2009) *Sci Signal* 2:ra75 and Barns, M. et al. (2014) *Int J Biochem Cell Biol.* 53:174-185). Thus, turning down mTOR activity to levels seen in young tissue, as opposed to more complete suppression of mTOR activity, may be of clinical benefit in aging indications.

The safety profile of mTOR inhibitors such as RAD001 in the treatment of aging-related indications has been of concern. The toxicity of RAD001 at doses used in oncology or organ transplant indications includes rates of stomatitis, diarrhea, nausea, cytopenias, hyperlipidemia, and hyperglycemia that would be unacceptable for many aging-related indications. However, these AEs are related to the trough levels of RAD001 in blood. Therefore the RAD001 dosing regimens used in this study were chosen to minimize trough levels. The average RAD001 trough levels of the 0.5 mg daily, 5 mg weekly and 20 mg weekly dosing cohorts were 0.9 ng/ml, below 0.3 ng/ml (the lower limit of quantification), and 0.7 ng/ml, respectively. These trough levels are significantly lower than the trough levels associated with dosing regimens used in organ transplant and cancer patients. In addition, the limited 6 week course of treatment decreased the risk of adverse events. These findings suggest that the dosing regimens used in this study may have an acceptable risk/benefit for some conditions of the elderly. Nonetheless, significant numbers of subjects in the experiments described herein developed mouth ulcers even when dosed as low as 0.5 mg daily. Therefore the safety profile of low, immune enhancing, dose RAD001 warrants further study. Development of mTOR inhibitors with cleaner safety profiles than currently available rapalogs may provide better therapeutic options in the future for aging-associated conditions.

Example 18: Enhancement of Immune Response to Vaccine in Elderly Subjects

Immune function declines in the elderly, leading to an increase incidence of infection and a decreased response to vaccination. As a first step in determining if mTOR inhibition has anti-aging effects in humans, a randomized placebo-controlled trial was conducted to determine if the mTOR inhibitor RAD001 reverses the aging-related decline in immune function as assessed by response to vaccination in elderly volunteers. In all cases, appropriate patent consents were obtained and the study was approved by national health authorities.

The following 3 dosing regimens of RAD001 were used in the study:
 20 mg weekly (trough level: 0.7 ng/ml)
 5 mg weekly (trough level was below detection limits)
 0.5 mg daily (trough level: 0.9 ng/ml)

These dosing regimens were chosen because they have lower trough levels than the doses of RAD001 approved for transplant and oncology indications. Trough level is the lowest level of a drug in the body. The trough level of RAD001 associated with the 10 mg daily oncology dosing regimen is approximately 20 ng/ml. The trough level associated with the 0.75-1.5 mg bid transplant dosing regimen is approximately 3 ng/ml. In contrast, the trough level associated with the dosing regimens used in our immunization study were 3-20 fold lower. Since RAD001-related AEs are associated with trough levels, the 3 dosing regimens were predicted to have adequate safety for normal volunteers. In addition, the 3 doses were predicted to give a range of mTOR inhibition. P70 S6 Kinase (P70 S6K) is a downstream target that is phosphorylated by mTOR. Levels of P70 S6K phosphorylation serve as a measure of mTOR activity. Based on modeling and simulation of P70 S6K phosphorylation data obtained in preclinical and clinical studies of RAD001, 20 mg weekly was predicted to almost fully inhibit mTOR activity for a full week, whereas 5 mg weekly and 0.5 mg daily were predicted to partially inhibit mTOR activity.

Elderly volunteers >=65 years of age were randomized to one of the 3 RAD001 treatment groups (50 subjects per arm) or placebo (20 subjects per arm). Subjects were treated with study drug for 6 weeks, given a 2 week break, and then received influenza (Aggrippal, Novartis) and pneumoccal (Pneumovax 23, Merck), vaccinations. Response to influenza vaccination was assessed by measuring the geometric mean titers (GMTs) by hemagglutination inhibition assay to the 3 influenza strains (H1N1, H3N2 and B influenza subtypes) in the influenza vaccine 4 weeks after vaccination. The primary endpoints of the study were (1) safety and tolerability and (2) a 1.2 fold increase in influenza titers as compared to placebo in ⅔ of the influenza vaccine strains 4 weeks after vaccination. This endpoint was chosen because a 1.2 fold increase in influenza titers is associated with a decrease in influenza illness post vaccination, and therefore is clinically relevant. The 5 mg weekly and 0.5 mg daily doses were well tolerated and unlike the 20 mg weekly dose, met the GMT primary endpoint (FIG. 27A). Not only did RAD001 improve the response to influenza vaccination, it also improved the response to pneumococcal vaccination as compared to placebo in elderly volunteers. The pneumococcal vaccine contains antigens from 23 pneumococcal serotypes. Antibody titers to 7 of the serotypes were measured in our subjects. Antibody titers to 6/7 serotypes were increased in all 3 RAD cohorts compared to placebo.

The combined influenza and pneumococcal titer data suggest that partial (less than 80-100%) mTOR inhibition is more effective at reversing the aging-related decline in immune function than more complete mTOR inhibition.

Example 19: Low Dose mTOR Inhibition Increases Energy and Exercise

Figure 33:
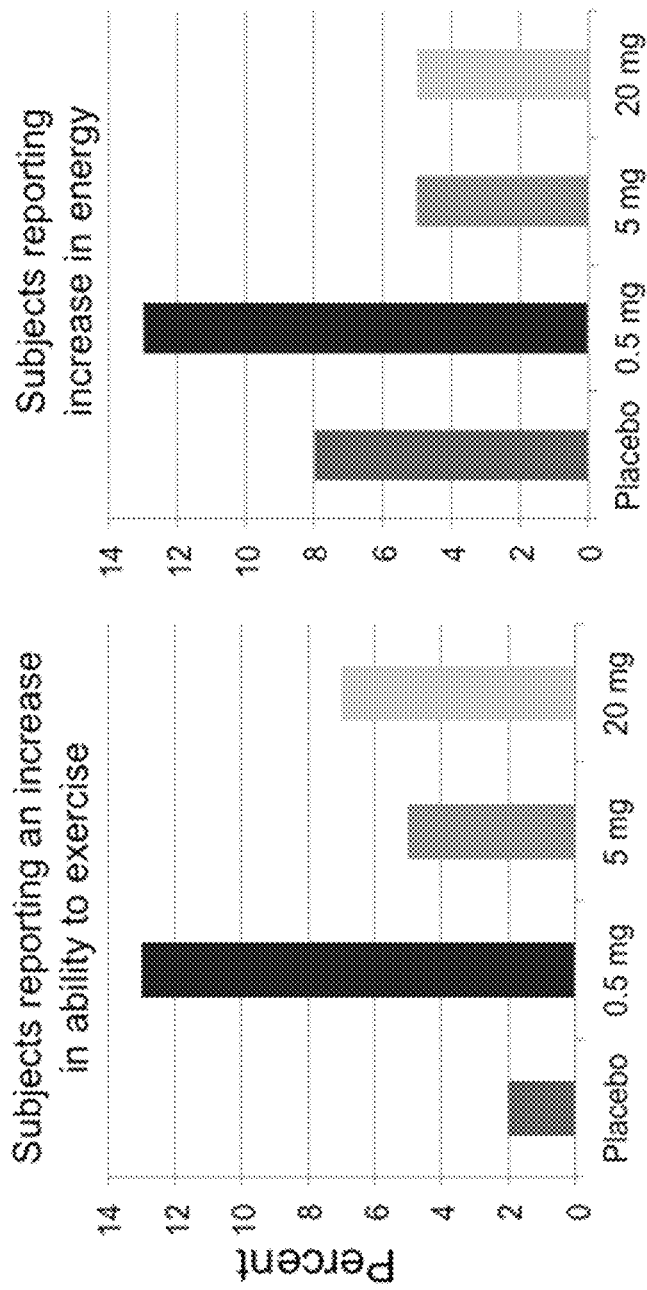
FIG. 33 depicts increases in exercise and energy in elderly subjects in response to RAD001.

In preclinical models, mTOR inhibition with the rapalog rapamycin increases spontaneous physical activity in old mice (Wilkinson et al. Rapamycin slows aging in mice. (2012) Aging Cell; 11:675-82). Of interest, subjects in the 0.5 mg daily dosing cohort described in Example 18 also reported increased energy and exercise ability as compared to placebo in questionnaires administered one year after dosing (FIG. 33). These data suggest that partial mTOR inhibition with rapalogs may have beneficial effects on aging-related morbidity beyond just immune function.

Example 20: P70 S6 Kinase Inhibition with RAD001

Figure 34A:
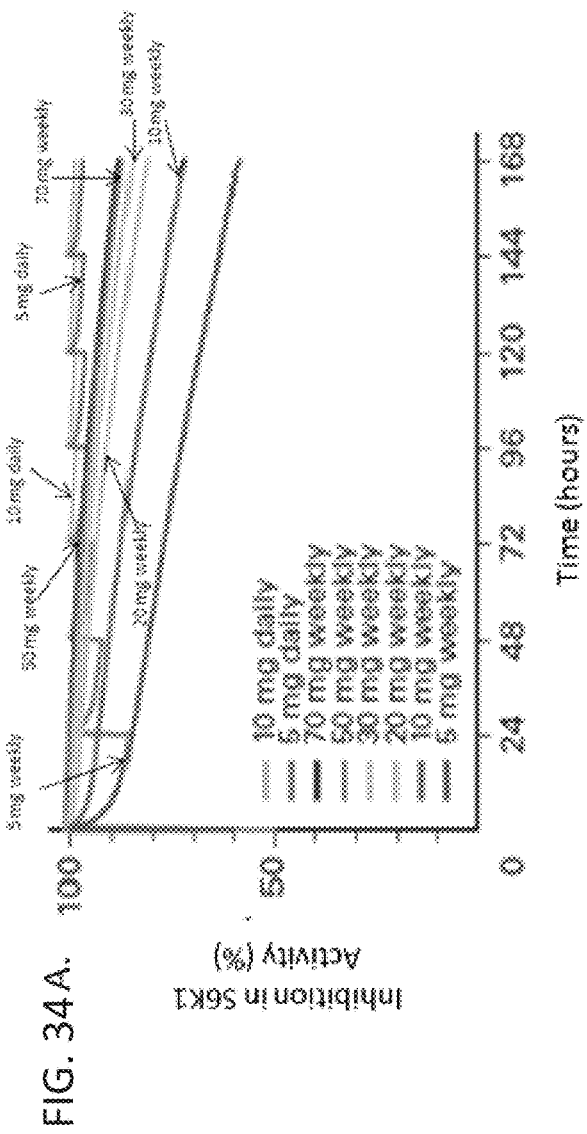
FIGS. 34A and 34B depict the predicted effect of RAD001 on P70 S6K activity in cells.
Figure 34B:
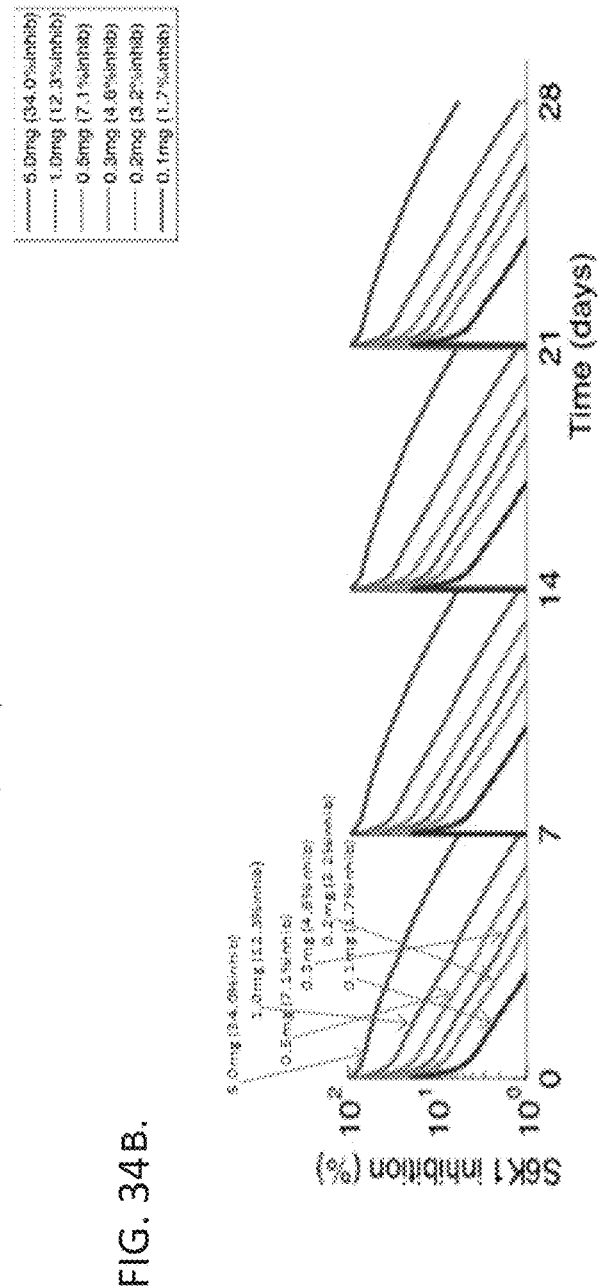

Modeling and simulation were performed to predict daily and weekly dose ranges of RAD001 that are predicted to partially inhibit mTOR activity. As noted above, P70 S6K is phosphorylated by mTOR and is the downstream target of mTOR that is most closely linked to aging because knockout of P70 S6K increases lifespan. Therefore modeling was done of doses of RAD001 that partially inhibit P70 S6K activity. Weekly dosing in the range of >=0.1 mg and <20 mg are predicted to achieve partial inhibition of P70 S6K activity (FIGS. 34A and 34B).

For daily dosing, concentrations of RAD001 from 30 pM to 4 nM partially inhibited P70 S6K activity in cell lines (Table 25). These serum concentrations are predicted to be achieved with doses of RAD001 >=0.005 mg to <1.5 mg daily.

TABLE 25

Percent inhibition of P70 S6K activity in HeLa cells in vitro

| | RAD001 concentration | | | | | |
|---|---|---|---|---|---|---|
| | 0 | 6 pM | 32 pM | 160 pM | 800 pM | 4 nM | 20 nM |
| % P70 S6K inhibition | 0 | 0 | 18 | 16 | 62 | 90 | 95 |

Conclusion

Methods of treating aging-related morbidity, or generally enhancing an immune response, with doses of mTOR inhibitors that only partially inhibit P70 S6K. The efficacy of partial mTOR inhibition with low doses of RAD001 in aging indications is an unexpected finding. RAD001 dose ranges between >=0.1 mg to <20 mg weekly and >=0.005 mg to <1.5 mg daily will achieve partial mTOR inhibition and therefore are expected to have efficacy in aging-related morbidity or in the enhancement of the immune response.

Example 21: Generation and Characterization of Mutant FKBP/FRB Dimerization Switches In this example, mutation of the residues involved in binding between the switch domains, e.g., FRB or FKBP, with the dimerization molecule was performed to identify mutations that enhance formation of a complex between FKBP, FRB, and the dimerization molecule, e.g., rapamycin or a rapalog, e.g., RAD001. Libraries of candidate mutant FKBP and FRB switch domains were generated and screened as described herein. Mutant FKBP or FRB allows the use of circulating concentrations of the dimerization molecule, e.g., RAD001, which are less than the concentrations used to mediate immunosuppression.

Figure 35:
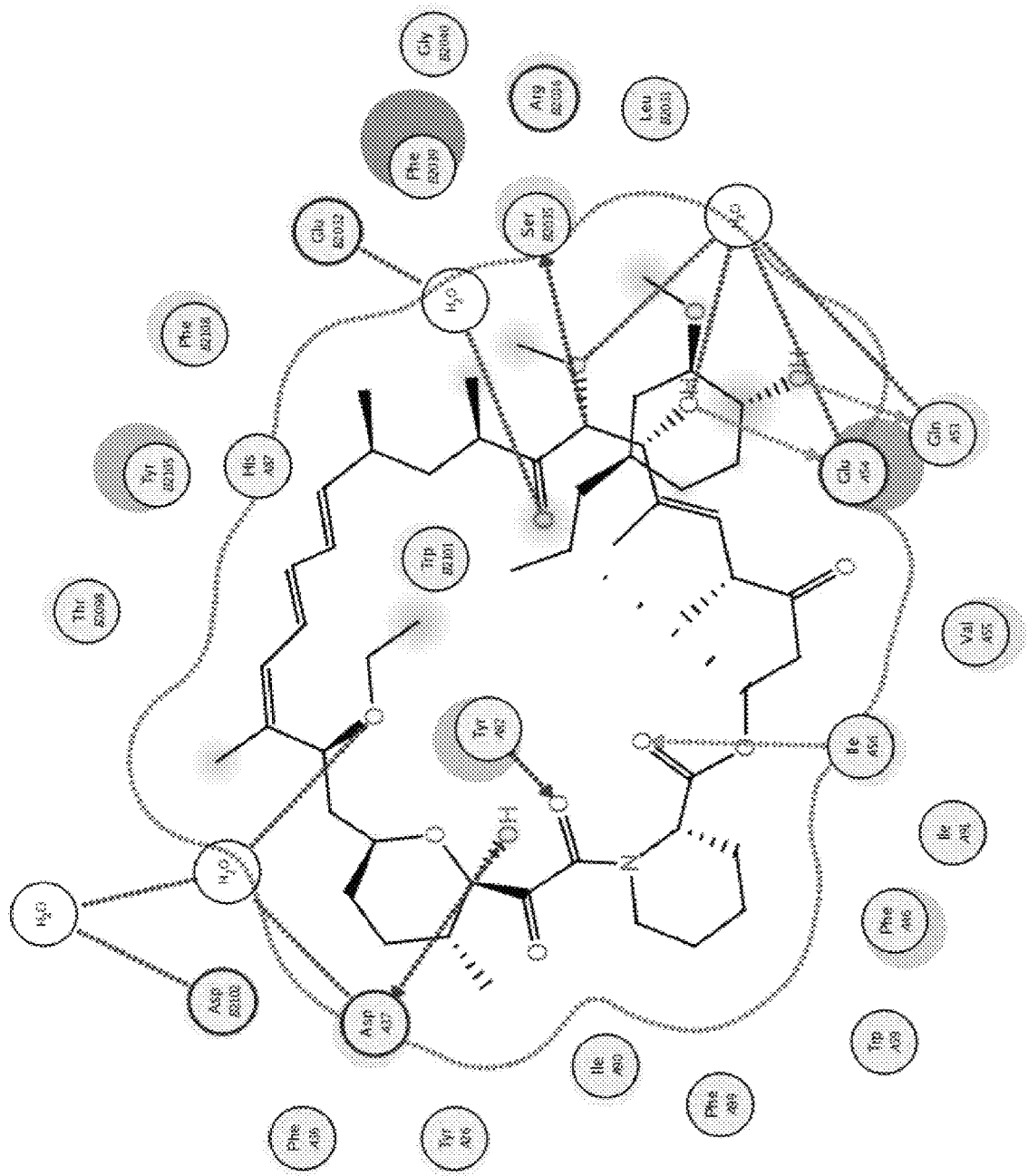
FIG. 35 is a graphic representation FRAP binding with RAD001. The dotted area represents the pocket that binds to RAD001. Residues that are in proximity of RAD001 or mediate interaction with RAD001 are circled and the amino acid position on FRAP.

The interface between FKBP, FRB, and rapamycin is clearly defined allowing for inspection of the FRB/rapamycin and FRB/FKBP interface. In the 2.2 Å x-ray structure of the ternary FKBP/FRB/rapamycin complex, FRB residues Leu2031, Glu2032, Ser2035, Arg2036, Phe2039, Gly2040, Thr2098, Trp2101, Tyr2015, and Phe2108 make 38 direct contacts with rapamycin and FRB residues Arg2042 and Asp2102 make water mediated contacts with the compound (Liang et al., 1999, *J. Acta Cryst.* D55:736-744). FIG. 35 shows the rapamycin interaction with FKBP and FRB which were determined in the x-ray structure of the ternary complex, RCSB code 2FAP, generated using the Molecular Operating Environment (MOE) (Clark et al., 2007, *J. Chem. Inf. Model.* 47(5):1933-1944). The FRB molecule is chain B in the structure.

Figure 36:
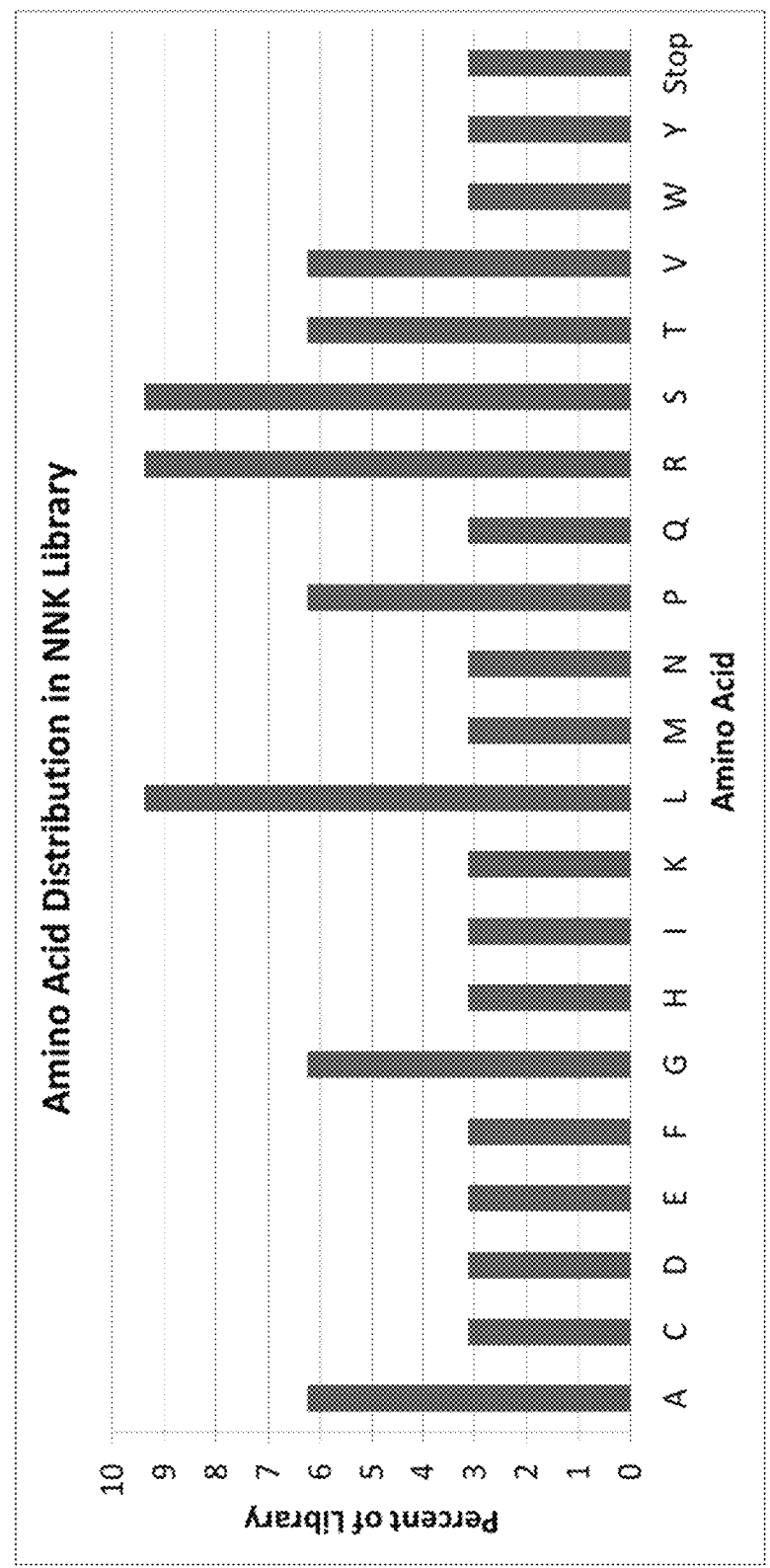
FIG. 36 shows the amino acid istribution of the NKK library used to generate libraries of FRB mutants. The different amino acids are listed on the x-axis, and the percent represented in the library is shown on the y-axis.

The FRB residues chosen for mutation included: L2031, E2032, S2035, R2036, F2039, G2040, T2098, W2101, D2102, Y2105, and F2108. Each point mutant library was generated by randomizing the codon at the desired position using an NNK library, where N can be adenine (A), cytosine (C), guanine (G), or thymine (T), and K can be guanine (G) or thymine (T). Table 13 shows the codon distribution of an NNK library and the corresponding amino acids. FIG. 36 shows the distributions of the amino acids produced from the codons in the NNK library, ranging from a low of 3.1% to a high 9.4%. Each point mutant library was cloned into the pNAT43 vector with a N-terminal histidine tag. SEQ ID NOs: 301-311 give the amino acid composition of each point mutant library, where X indicates the position of the NNK library. The DNA for each library was transformed into Acella chemically competent *E. coli*, plated onto 100 mm LB agar plates with 50 µg/mL kanamycin sulfate, and incubated overnight at 37° C. 94 colonies from each library plate were transferred to Costar 2 mL pyramidal bottom 96-well plates with 1 mL of ZYP-5052 auto induction medium containing 75 µg/mL kanamycin sulfate. The plates were incubated for 40 hours at 800 rpm at 30° C. in a micro plate incubator.

The candidate FRB clones were isolated as follows. First, the cells were lysed. The cells were pelleted by centrifugation at 2,000×g at 4° C. for 30 minutes. The supernatant was discarded and the cell pellets were stored at −80° C. The 96-well plates containing the cell pellets were removed from storage at −80° C. and thawed at room temperature for 1 hour. 0.5 mL of 50 mM HEPES pH 7.5, 150 mM NaCl, 5 mM EDTA, 0.25% (v/v) Triton X-100, 2.5 mg/mL lysozyme were added to each well. The pellets were resuspended by pipetting 180 µL 60 times. The samples were incubated at room temperature for 0.1 to 1 hour. 0.5 mL of 50 mM HEPES pH 7.5, 150 mM NaCl, 20 mM CaCl$_2$, 20 mM MgCl$_2$, 0.5 mg/mL DNase I were added to each well. The samples were mixed by pipetting 180 µL 10 times. The plates were incubated for 30 minutes at room temperature. The lysed cells were pelleted by centrifugation at 2,000×g at 4° C. for 30 minutes. The supernatant was discarded from each plate by inversion followed by gentle tapping. The plates were stored overnight at −80° C.

Figure 37A:
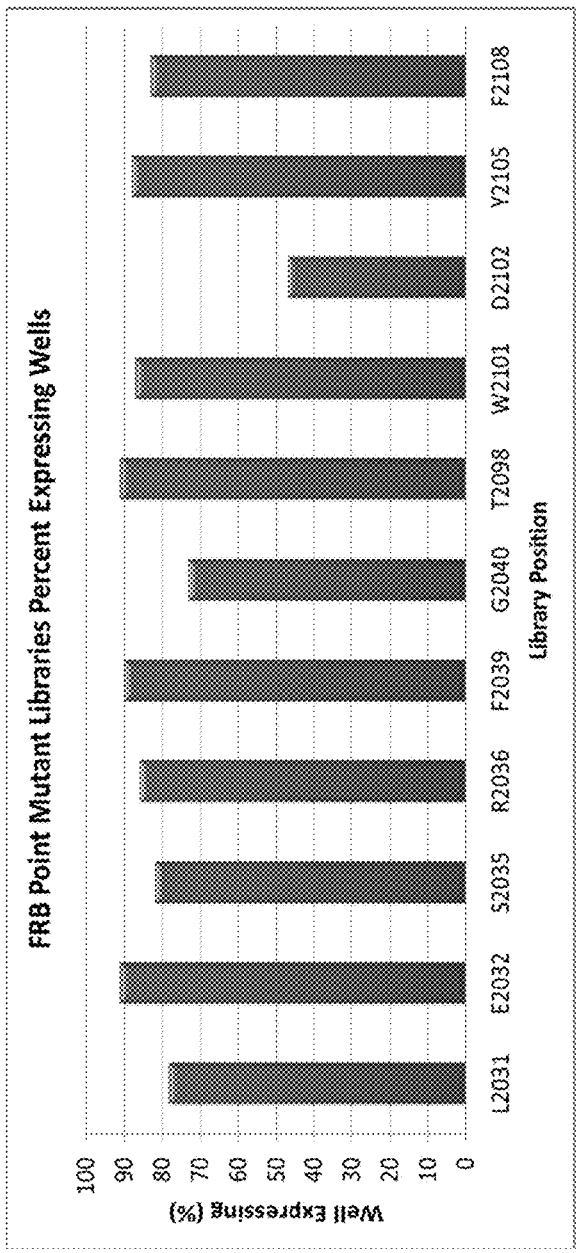
FIGS. 37A and 37B show the protein expression results from each of the different mutant FRB libraries. The 11 different mutant FRB libraries are listed on the x-axis.
Figure 37B:
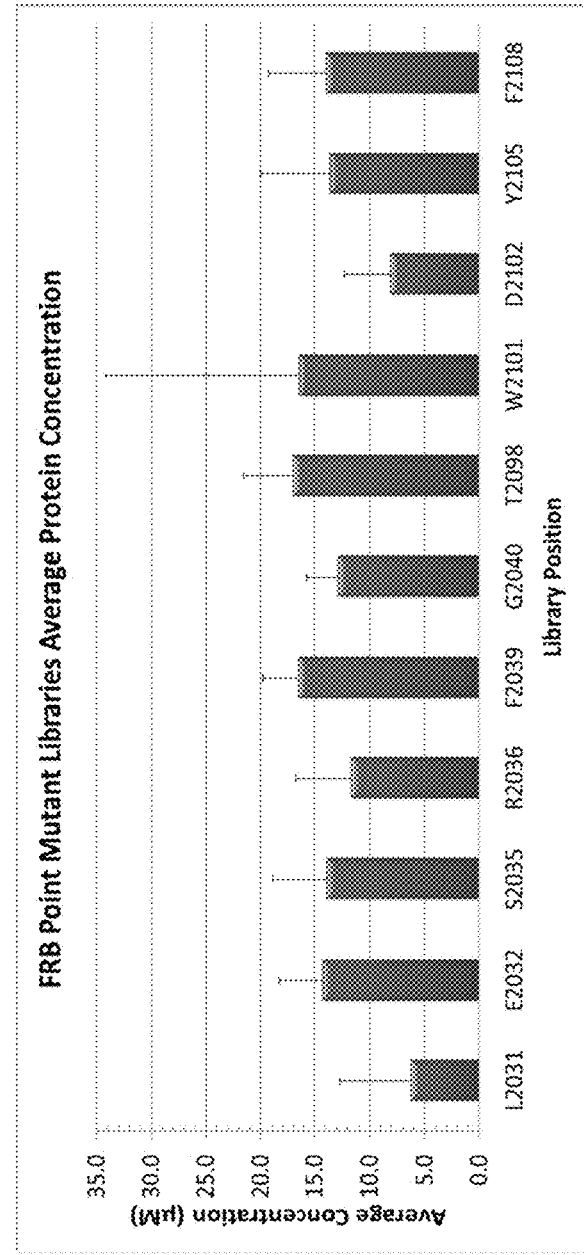

Next, the stored lysates were processed by affinity purification to isolate the mutant FRB as follows. The following morning, the plates were removed from storage at −80° C. and thawed at room temperature for 1 hour. 0.7 mL of 50 mM HEPES, 500 mM NaCl, 5 mM TCEP, 5% (v/v) Triton X-100, pH 7.5 were added to each well. The pellets were resuspended by pipetting 180 µL 50 times, followed by a 1 hour incubation at room temperature. The plates were centrifuged for 30 minutes at 2,000×g at 4° C. and the supernatant for each was discarded. 0.5 mL of 50 mM HEPES pH 7.5, 1 mM TCEP, 60% ethanol were added to each well. The pellets were resuspended by pipetting 180 µL 50 times, followed by a 1 hour incubation at room temperature. The plates were centrifuged for 30 minutes at 2,000×g at 4° C. and the supernatant for each was discarded. 0.5 mL of 50 mM HEPES pH 7.5, 500 mM NaCl, 1 mM TCEP, 8 M urea were added to each well. The pellets were resuspended by pipetting 180 µL 50 times and incubated overnight at room temperature. The following morning, the samples were transferred to 20 µm fritted 96-well plates. The samples were filtered through the plates into new 2 mL Costar 96-well plates by centrifugation for 5 minutes at 1,500×g at 4° C. A 25% slurry of Ni Sepharose 6 Fast Flow resin in 50 mM HEPES pH 7.5, 500 mM NaCl, 1 mM TCEP, 8 M urea was prepared. 100 µL of slurry, 25 µL of resin, were added to each well. The resin was incubated with the samples for 1 hour at room temperature. The resin was then transferred to 20 µm fritted 96-well plates and the column flow-through was removed by vacuum. 500 µL of 50 mM HEPES pH 7.5, 150 mM NaCl, 1 mM TCEP, 4 M urea was added to each well, incubated for 5 minutes, and removed by vacuum. 500 µL of 50 mM HEPES pH 7.5, 150 mM NaCl, 1 mM TCEP, 2 M urea was added to each well, incubated for 5 minutes, and removed by vacuum. 500 µL of 50 mM HEPES pH 7.5, 150 mM NaCl, 1 mM TCEP, 1 M urea was added to each well, incubated for 5 minutes, and removed by vacuum. 500 µL of 50 mM HEPES pH 7.5, 150 mM NaCl, 1 mM TCEP, 25 mM imidazole was added to each well, incubated for 5 minutes, and removed by vacuum. 200 µL of 50 mM HEPES pH 7.5, 150 mM NaCl, 1 mM TCEP, 500 mM imidazole was added to each and incubated for 5 minutes. The bound protein was eluted by centrifugation for 2 minutes at 500×g at 4° C. into a new 300 µL BD Falcon 96-well plate. The protein concentration in mg/mL for each well was measured using the Bradford assay with BSA as the standard. The protein concentrations were converted to µM by using the molecular weight for wild type FRB. The point mutant libraries had expression in a least 50% of the wells except for FRB D2102, which was 47%. FIG. 37A shows the expression levels of each library and FIG. 37B shows the average concentration for the expressing wells.

The inhibition for each well expressing protein for each library was calculated by using the well known to contain no protein as blank measurements. For each library plate, the average for the blank wells was calculated. Expressing wells with values greater than the average for the blank wells were defined to have 0% inhibition. The percent inhibition for wells with values less than or equal to the average for the blank wells was calculated by subtracting the average for the blank wells from the well value, dividing by −1 multiplied by the average for the blank wells, and multiplying by 100. When the well value was 0, there was 100% inhibition and when the well value was equal to the average of the blank wells, there was 0% inhibition. Wells with inhibition greater than or equal to 75% were chosen for re-array. Table 26 shows the number of wells selected for each library and the number of wells expected to be wild type FRB. 320 out of 1034 wells were chosen, 31.3%. The selected wells were grown, purified, and analyzed as described. The DNA for each of the selected wells was sequenced to identify the individual mutations. The protein concentration for each of the mutants was assessed by the Bradford assay. The activity of each mutant was compared with the ability of wild type FRB to bind to everolimus, e.g., RAD001, in multiple assay formats.

TABLE 26

Wells selected for retesting for each point mutant library in the initial screen

| Library | Wells Selected | Expected Wild Type Wells |
|---|---|---|
| L2031 | 41 | 9 |
| E2032 | 82 | 3 |
| S2035 | 33 | 9 |
| R2036 | 9 | 9 |
| F2039 | 15 | 3 |
| G2040 | 49 | 6 |
| T2098 | 57 | 6 |
| W2101 | 1 | 3 |
| D2102 | 11 | 3 |
| Y2105 | 6 | 3 |
| F2108 | 16 | 3 |

Figure 38A:
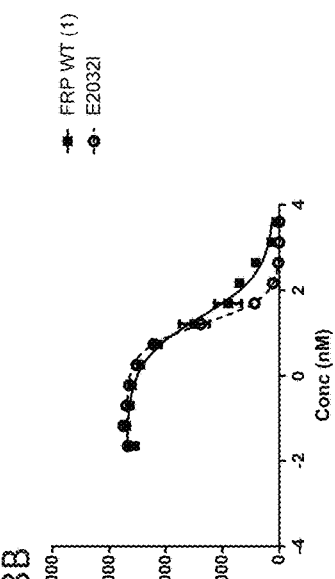
FIGS. 38A, 38B, 38C, 38D, and 38E show the binding curves for the EC50 competition binding assay for FRB mutants: E2032L (FIG. 38A), E2032I (FIG. 38B), T2098L (FIG. 38C), E2032L, T2098L (FIG. 38D), and E2032I, T2098L (FIG. 38E).
Figure 38B:
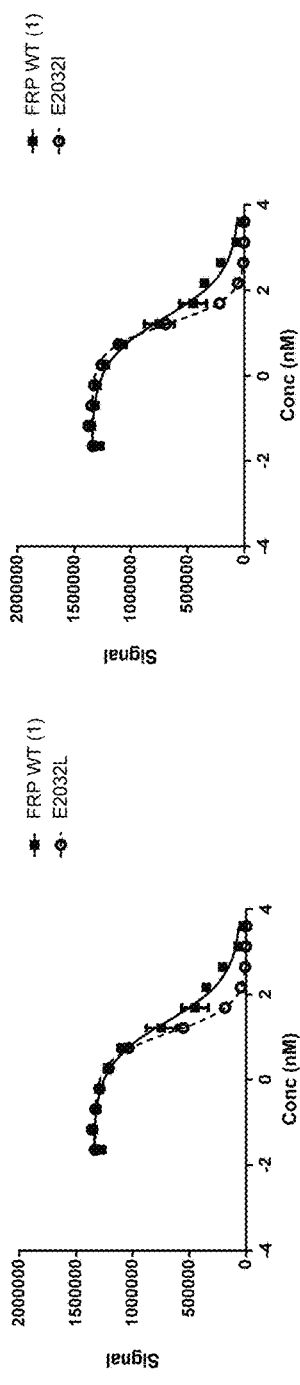
Figure 38C:
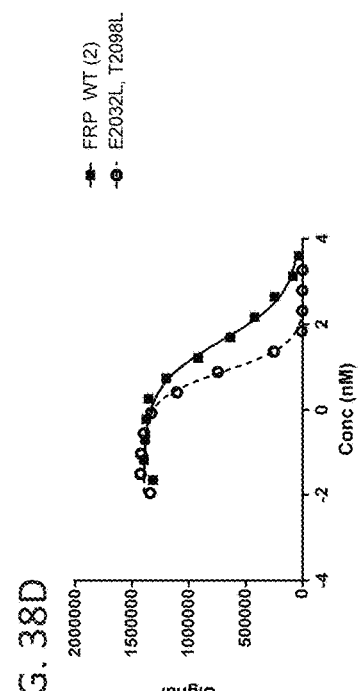
Figure 38D:
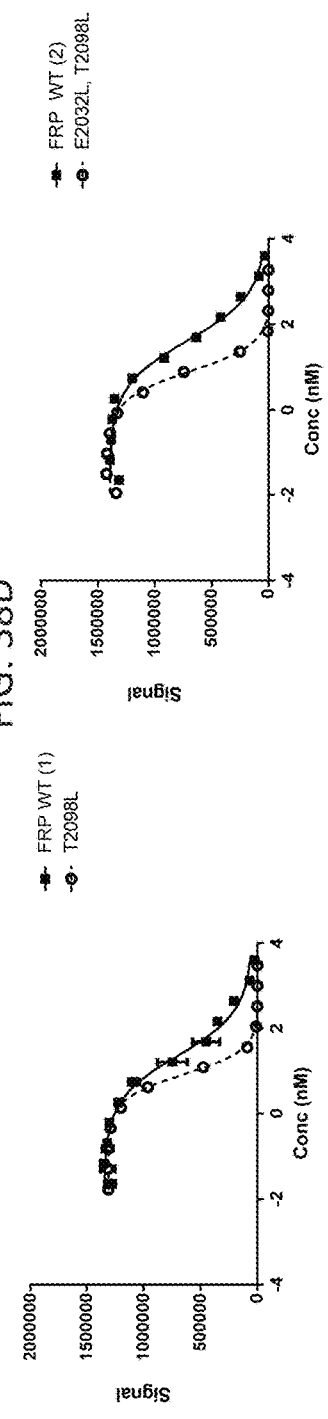
Figure 38E:
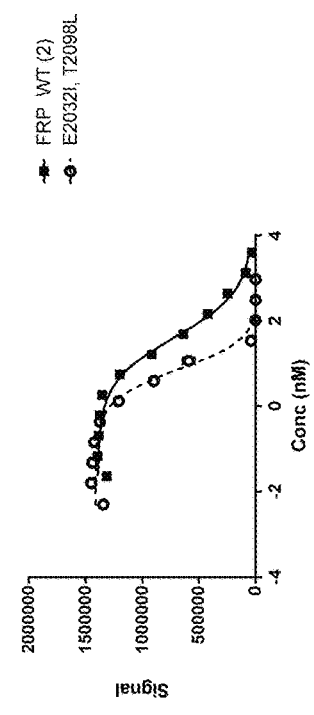

For the competition assay, FRB mutations of interest are ranked compared to wild type FRB. Unlabeled FRB proteins of interest (SEQ ID NOs: 313-317) and unlabeled wild type FRB (SEQ ID NO: 312) were serial diluted 1:3 from a starting final concentration of between 0.9 and 4 uM dependent upon expression and added in solution with 30 nM (final) wild type Flag-FRB (SEQ ID NO: 318) and 30 nM (final) biotinylated wild-type FKBP (SEQ ID NO: 24) in the presence of 60 nM (final) everolimus in a 96 well ½ surface flat-bottom plate (PerkinElmer). All dilutions were made in 1× AlphaLISA Immunoassay buffer (PerkinElmer). The plate was incubated for one hour at room temperature with mild shaking. Anti-Flag acceptor beads (PerkinElmer) were then added at 10ug/ml final concentration and incubated for one hour at room temperature with mild shaking. Streptavidin donor beads (PerkinElmer), were then added at a final concentration of 40ug/ml and the plate was protected from light for a 30 minute room temperature incubation with mild shaking. The plate was then read on the PerkinElmer EnVision Multiplate reader equipped with the Alpha Module using excitation of 680 nm and a 570 nm Emission filter. The EC50s of each FRB sequence from the competition assay are shown in Table 27 in comparison to WT FRB analyzed in the same plate. Single point mutations E2032L (SEQ ID NO: 314) and E2032I (SEQ ID NO: 313) were approximately 2-fold better than wild type (FIGS. 38A and 38B; T2098L (SEQ ID NO: 315) was 3-fold improved (FIG. 38C). FRB proteins incorporating mutations at both sites (SEQ ID NOs: 316 and 317) demonstrated 5-fold relative improvement (FIGS. 38D and 38E).

TABLE 27

EC50 Values from Competition Assay

| Mutation | Ec50 (nM) |
|---|---|
| Wild type FRB (1) | 23.33 |
| E2032L | 12.94 |
| E2032I | 16.61 |
| T2098L | 8.255 |
| Wild type FRB (2) | 42.62 |
| E2032L, T2098L | 8.047 |
| E2032I, T2098L | 7.138 |

Figure 39A:
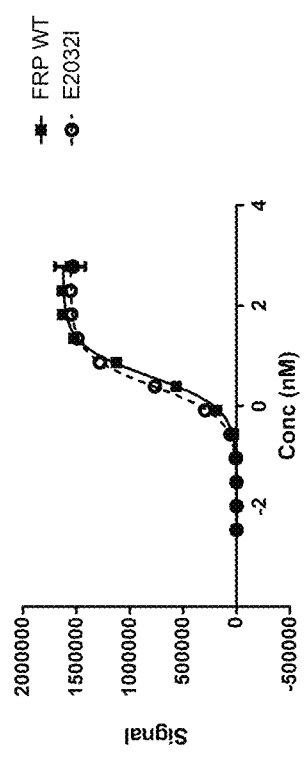
FIGS. 39A, 39B, and 39C show the binding curves for the EC50 direct binding assay for fRB mutants: E2032L (FIG. 39A), E2032I (FIG. 39B), and T2098L (FIG. 39C).
Figure 39B:
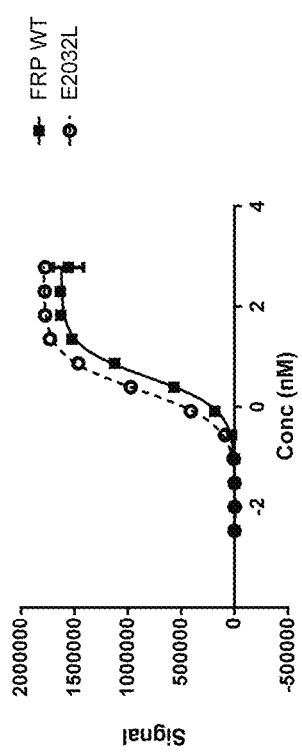
Figure 39C:
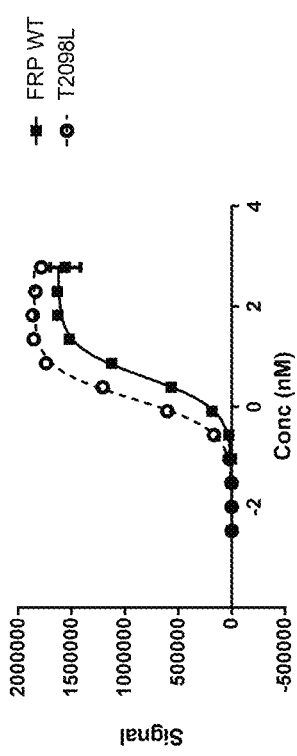

FRB mutations were also ranked in an alternative assay format. Briefly, FRB proteins incorporating single and double mutations (SEQ ID NO: 319-323) were produced as FLAG tagged constructs in E. coli as described previously. 30 nM (final) of biotinylated FKBP (SEQ ID NO: 324) and each FLAG FRB protein were combined in the presence of everolimus serial diluted 1:3 from a starting final concentration of 600 nM into a 96 well ½ surface flat-bottom plate (PerkinElmer) and incubated for one hour at room temperature. All dilutions were made in 1× AlphaLISA Immunoassay buffer (PerkinElmer). Anti-Flag acceptor beads (PerkinElmer) were added at 10ug/ml final concentration and incubated for one hour at room temperature. Streptavidin donor beads (PerkinElmer), were then added at a final concentration of 40ug/ml and the plate was protected from light and incubated for 30 minutes at room temperature. The plate was then read on the PerkinElmer EnVision Multiplate reader equipped with the Alpha Module using excitation of 680 nm and a 570 nm Emission filter. The EC50s of each FRB sequence from this assay are shown in Table 28. Single point mutations E2032I (SEQ ID NO: 319) and E2032L (SEQ ID NO: 320) were approximately 1.5-2-fold better than wild type (FIGS. 39A and 39B); T2098L (SEQ ID NO: 321) was 3-fold improved (FIG. 39C). Flag-tagged FRB proteins which incorporated the double mutations (SEQ ID NO: 322 and 323) demonstrated limited dynamic range in this assay and therefore could not be evaluated.

TABLE 28

EC50 Values from Direct Binding Assay

| Mutation | Ec50 (nM) |
|---|---|
| Wild type FRB | 3.899 |
| E2032L | 2.146 |
| E2032I | 2.461 |
| T2098L | 1.442 |

TABLE 29

Sequences of candidate mutant FRB and FRB used in binding assays

| Name | Amino Acid Sequence | SEQ ID NO: |
|---|---|---|
| L2031 library | MGHHHHHHHHGSASRILWHEMWHEGXEEASRLYFGERNVKGMFEVLEPLHAMMER GPQTLKETSFNQAYGRDLMEAQEWCRKYMKSGNVKDLTQAWDLYYHVFRRISKTS | 301 |
| E2032 library | MGHHHHHHHHGSASRILWHEMWHEGLXEASRLYFGERNVKGMFEVLEPLHAMMER GPQTLKETSFNQAYGRDLMEAQEWCRKYMKSGNVKDLTQAWDLYYHVFRRISKTS | 302 |
| S2035 library | MGHHHHHHHHGSASRILWHEMWHEGLEEAXRLYFGERNVKGMFEVLEPLHAMMER GPQTLKETSFNQAYGRDLMEAQEWCRKYMKSGNVKDLTQAWDLYYHVFRRISKTS | 303 |
| R2036 library | MGHHHHHHHHGSASRILWHEMWHEGLEEASXLYFGERNVKGMFEVLEPLHAMMER GPQTLKETSFNQAYGRDLMEAQEWCRKYMKSGNVKDLTQAWDLYYHVFRRISKTS | 304 |
| F2039 library | MGHHHHHHHHGSASRILWHEMWHEGLEEASRLYXGERNVKGMFEVLEPLHAMMER GPQTLKETSFNQAYGRDLMEAQEWCRKYMKSGNVKDLTQAWDLYYHVFRRISKTS | 305 |
| G2040 library | MGHHHHHHHHGSASRILWHEMWHEGLEEASRLYFXERNVKGMFEVLEPLHAMMER GPQTLKETSFNQAYGRDLMEAQEWCRKYMKSGNVKDLTQAWDLYYHVFRRISKTS | 306 |
| T2098 library | MGHHHHHHHHGSASRILWHEMWHEGLEEASRLYFGERNVKGMFEVLEPLHAMMER GPQTLKETSFNQAYGRDLMEAQEWCRKYMKSGNVKDLXQAWDLYYHVFRRISKTS | 307 |
| W2101 library | MGHHHHHHHHGSASRILWHEMWHEGLEEASRLYFGERNVKGMFEVLEPLHAMMER GPQTLKETSFNQAYGRDLMEAQEWCRKYMKSGNVKDLTQAXDLYYHVFRRISKTS | 308 |
| D2102 library | MGHHHHHHHHGSASRILWHEMWHEGLEEASRLYFGERNVKGMFEVLEPLHAMMER GPQTLKETSFNQAYGRDLMEAQEWCRKYMKSGNVKDLTQAWXLYYHVFRRISKTS | 309 |
| Y2105 library | MGHHHHHHHHGSASRILWHEMWHEGLEEASRLYFGERNVKGMFEVLEPLHAMMER GPQTLKETSFNQAYGRDLMEAQEWCRKYMKSGNVKDLTQAWDLYXHVFRRISKTS | 310 |
| F2108 library | MGHHHHHHHHGSASRILWHEMWHEGLEEASRLYFGERNVKGMFEVLEPLHAMMER GPQTLKETSFNQAYGRDLMEAQEWCRKYMKSGNVKDLTQAWDLYYHVXRRISKTS | 311 |
| His-FRB (wild-type FRB) | MGHHHHHHHHGSASRILWHEMWHEGLEEASRLYFGERNVKGMFEVLEPLHAMMER GPQTLKETSFNQAYGRDLMEAQEWCRKYMKSGNVKDLTQAWDLYYHVFRRISKTS | 312 |
| His-FRB E2032I | MGHHHHHHHHGSASRILWHEMWHEGLIEASRLYFGERNVKGMFEVLEPLHAMMER GPQTLKETSFNQAYGRDLMEAQEWCRKYMKSGNVKDLTQAWDLYYHVFRRISKTS | 313 |
| His-FRB E2032L | MGHHHHHHHHGSASRILWHEMWHEGLLEASRLYFGERNVKGMFEVLEPLHAMMER GPQTLKETSFNQAYGRDLMEAQEWCRKYMKSGNVKDLTQAWDLYYHVFRRISKTS | 314 |
| His-FRB T 2098L | MGHHHHHHHHGSASRILWHEMWHEGLEEASRLYFGERNVKGMFEVLEPLHAMMER GPQTLKETSFNQAYGRDLMEAQEWCRKYMKSGNVKDLLQAWDLYYHVFRRISKTS | 315 |
| His-FRB E2032I, T2098L | MGHHHHHHHHGSASRILWHEMWHEGLIEASRLYFGERNVKGMFEVLEPLHAMMER GPQTLKETSFNQAYGRDLMEAQEWCRKYMKSGNVKDLLQAWDLYYHVFRRISKTS | 316 |
| His-FRB E2032L, T2098L | MGHHHHHHHHGSASRILWHEMWHEGLLEASRLYFGERNVKGMFEVLEPLHAMMER GPQTLKETSFNQAYGRDLMEAQEWCRKYMKSGNVKDLLQAWDLYYHVFRRISKTS | 317 |
| His-FLAG-FRB (wild-type FRB) | MGHHHHHHHHGSDYKDDDDKGSASRILWHEMWHEGLEEASRLYFGERNVKGMFEV LEPLHAMMERGPQTLKETSFNQAYGRDLMEAQEWCRKYMKSGNVKDLTQAWDLYY HVFRRISKTS | 318 |
| His-FLAG-FRB E2032I | MGHHHHHHHHGSDYKDDDDKGSASRILWHEMWHEGLIEASRLYFGERNVKGMFEV LEPLHAMMERGPQTLKETSFNQAYGRDLMEAQEWCRKYMKSGNVKDLTQAWDLYY HVFRRISKTS | 319 |
| His-FLAG-FRB E2032L | MGHHHHHHHHGSDYKDDDDKGSASRILWHEMWHEGLLEASRLYFGERNVKGMFEV LEPLHAMMERGPQTLKETSFNQAYGRDLMEAQEWCRKYMKSGNVKDLTQAWDLYY HVFRRISKTS | 320 |

TABLE 29-continued

Sequences of candidate mutant FRB and FRB used in binding assays

| Name | Amino Acid Sequence | SEQ ID NO: |
|---|---|---|
| His-FLAG-FRB T2098L | MGHHHHHHHHGSDYKDDDDKGSASRILWHEMWHEGLEEASRLYFGERNVKGMFEV LEPLHAMMERGPQTLKETSFNQAYGRDLMEAQEWCRKYMKSGNVKDLLQAWDLYY HVFRRISKTS | 321 |
| His-FLAG-FRB E2032I, T2098L | MGHHHHHHHHGSDYKDDDDKGSASRILWHEMWHEGLIEASRLYFGERNVKGMFEV LEPLHAMMERGPQTLKETSFNQAYGRDLMEAQEWCRKYMKSGNVKDLLQAWDLYY HVFRRISKTS | 322 |
| His-FLAG-FRB E2032L, T2098L | MGHHHHHHHHGSDYKDDDDKGSASRILWHEMWHEGLLEASRLYFGERNVKGMFEV LEPLHAMMERGPQTLKETSFNQAYGRDLMEAQEWCRKYMKSGNVKDLLQAWDLYY HVFRRISKTS | 323 |
| His-Avidin-FKBP (wild-type FKBP) | MGHHHHHHHHGSGLNDIFEAQKIEWHEGSGVQVETISPGDGRTFPKRGQTCVVHY TGMLEDGKKFDSSRDRNKPFKFMLGKQEVIRGWEEGVAQMSVGQRAKLTISPDYA YGATGHPGIIPPHATLVFDVELLKLE | 324 |

Example 22: Activation of RCAR with an Extracellular Switch

In this example, the activation of RCAR with an extracellular switch was evaluated in the presence of the dimerization molecule RAD001. Four RCARs were tested: two half switch constructs, e.g., with the dimerization switch in both orientations (FIG. 42A), and two full switch constructs, e.g., with the dimerization switch in both orientations (FIG. 42B), where the dimerization switch is an extracellular FKBP/FRB dimerization, as depicted in FIGS. 42A and 42B. In the half-switch constructs, the antigen binding member comprises a scFV domain, an extracellular switch domain, a transmembrane domain, an intracellular costimulatory signaling domain 4-1BB, and the intracellular signaling member comprises an extracellular switch domain, a transmembrane domain, and an intracellular primary signaling domain, CD3zeta (FIG. 42A). In the full-switch constructs, the antigen binding member comprises a scFv domain, an extracellular switch domain, and a transmembrane domain, and the intracellular signaling member comprises an extracellular switch domain, a transmembrane domain, an intracellular costimulatory signaling domain, 4-1BB, and an intracellular primary signaling domain, CD3zeta (FIG. 42B).

Materials and Methods

The RCAR constructs were expressed in a Jurkat reporter cell line. Jurkat cells with NFAT-LUC reporter (JNL) were grown to the density of $0.5 \times 10^6$/ml in Jurkat cell growth media with puromycin at 0.5 μg/ml. For each transfection $2.5 \times 10^6$ cells were spin down at 100 g for 10 minutes. Two μg of DNA per RCAR construct were used per transfection. Amaxa Nucleofector solution V and supplement I was mixed and 100 μl was added into the tube with DNA construct. The mixture was then added to the cells and transferred to the electroporation cuvette. Electroporation was done under setting X-001 using Amaxa Nucleofector II Device. 0.5 ml of growth media was added immediately after electroporation and the mixture were transferred into 2 ml growth media in one well of the 6-well plate.

After one hour, RAD001 compound was applied at various concentrations: 0 nM, 0.01 nM, 0.03 nM, 0.1 nM, 0.3 nM, 1 nM, 5 nM, and 50 nM. Tissue culture plate was coated with 5 μg/ml of anti anti-CD19 antibody or isotype control for 2 hrs, blocked with the blocking buffer (DPBS with 5% serum) for 1 hour. The transfected cells with or without Rad001 were resuspended and added to the target plate with 100 μl per well and incubated for 18 hrs. Luciferase One Glo reagent 100 μl was added per well. The samples were incubated for 5 min at 37° C. and then luminescence was measured using Envision plate reader.

Results

Figure 43A:
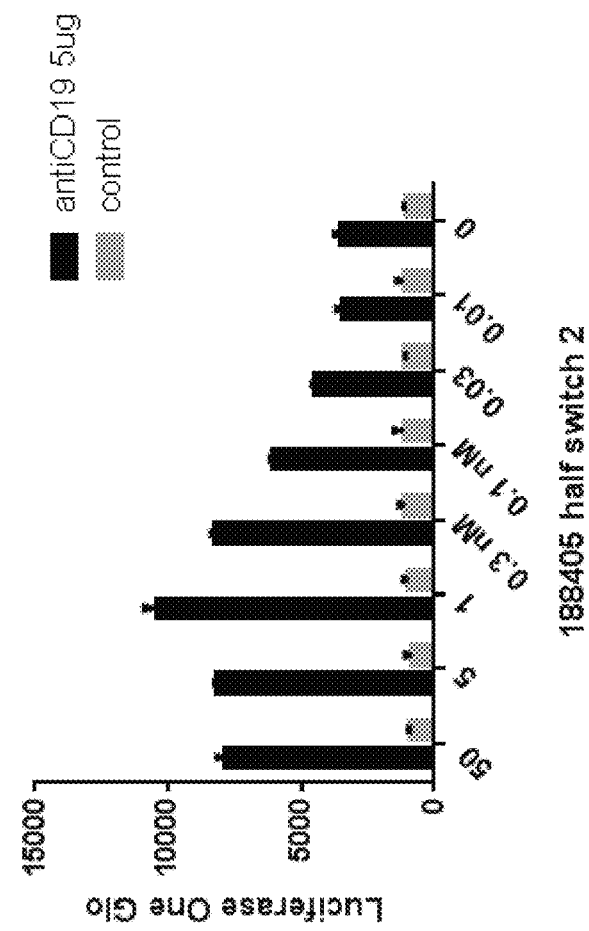
FIGS. 43A, 43B, 43C, and 43D show the activation of the RCAR half switch constructs of FIGS. 42A and 42B with varying concentrations of RAD001.
Figure 43B:
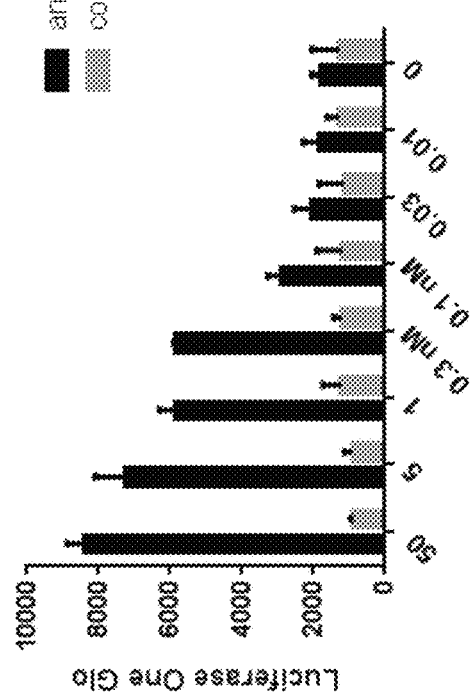

As shown FIGS. 43A and 43B, increasing the concentration of RAD001 correlated with increase in NFAT activity for both extracellular half switches, as represented by the luminescence detected. A dose-dependent response was observed for both RCAR half switch constructs. For the half switch 2, NFAT activity peaked at the 1 nM RAD001 dose, while NFAT activity decreased at the higher Rad001 dosages (5 nM and 50 nM). The observed decrease in activation may be due to general immune suppression by the higher dosages of RAD001. For the half switch 1, no inhibition of activity was observed with the higher dosages of RAD001, e.g., 5 nM and 50 nM.

Figure 43C:
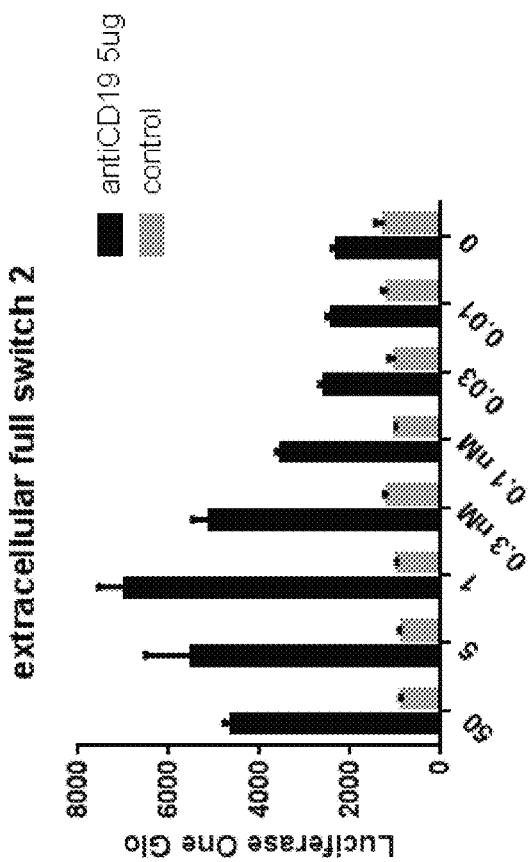
Figure 43D:
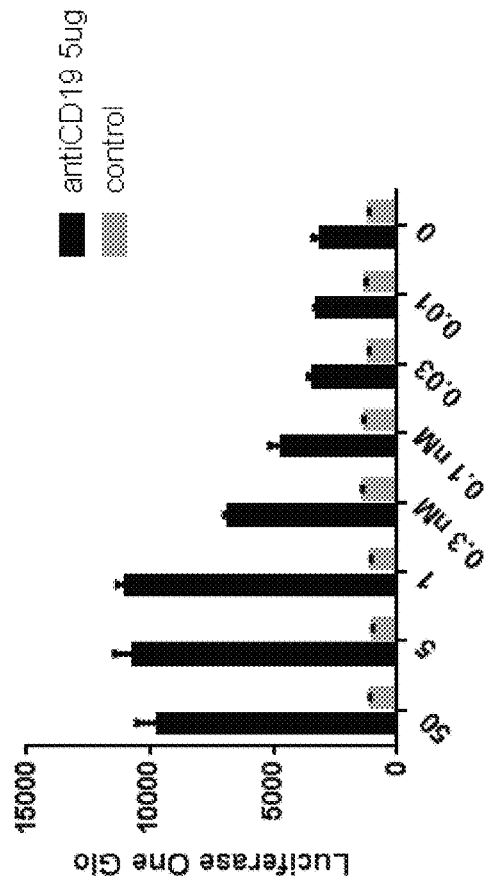

As shown FIGS. 43C and 43D, increasing the concentration of RAD001 also correlated with increase in NFAT activity for both extracellular full switches, as represented by the luminescence detected. The pattern of activation for the RCAR full switches was similar to that of the RCAR half switch 2 (FIG. 42B), where NFAT activity peaked at the 1 nM RAD001 dose and decreased at the higher Rad001 dosages, e.g., 5 nM and 50 nM.

These data show that RAD001 triggers dimerization of the extracellular FKBP/FRB switch domains present in the RCAR half switch and full switch constructs and target-dependent NFAT activation.

Example 23: Activation of RCAR Half Switches

In this example, the activation of a RCAR half switch was evaluated in the presence of the dimerization molecule RAD001. Two RCAR constructs were tested where the dimerization switch is an intracellular FKBP/FRB dimerization switch, and the switch domains are located in both orientations with respect to the antigen binding member and the intracellular member. For example, the antigen binding member comprises a scFV domain, a transmembrane domain, an intracellular switch domain, and an intracellular costimulatory signaling domain; and the intracellular signaling member comprises an extracellular switch domain, a transmembrane domain, and an intracellular primary signaling domain, e.g., CD3zeta (FIG. 44A).

Materials and Methods

Jurkat cells with NFAT-LUC reporter (JNL) were grown to the density of 0.5×10⁶/ml in Jurkat cell growth media with puromycin at 0.5 μg/ml. For each transfection 2.5×10⁶ cells were spin down at 100 g for 10 minutes. Two μg of DNA per construct were used per transfection. Amaxa Nucleofector solution V and supplement I was mixed and 100 μl was added into the tube with DNA construct. The mixture was then added to the cells and transferred to the electroporation cuvette. Electroporation was done under setting X-001 using Amaxa Nucleofector II Device. 0.5 ml of growth media was added immediately after electroporation and the mixture were transferred into 2 ml growth media in one well of the 6-well plate.

Figure 45A:
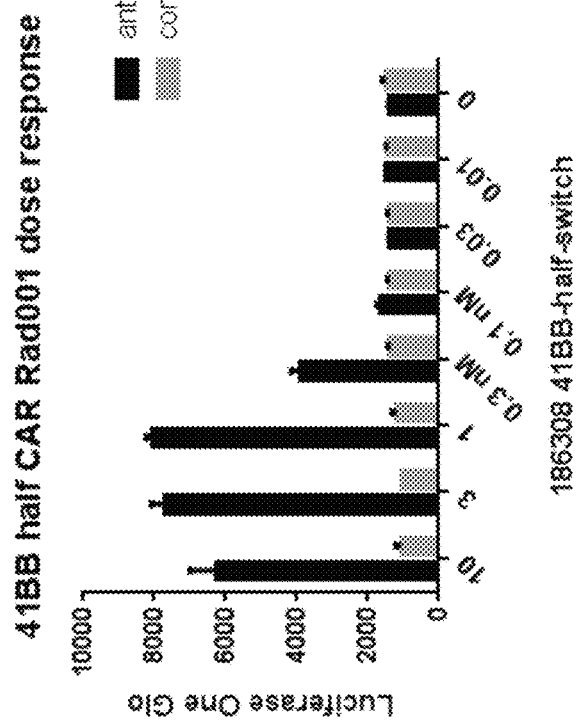
FIGS. 45A and 45B show the activation of two half RCAR constructs with varying concentrations of RAD001. Activation of half RCAR with a CD28 costimulatory signaling domain is shown in FIG. 45A. Activation of half RCAR with a 41BB costimulatory signaling domain is shown in FIG. 45B. NFAT activation is represented by luminescence detected by Luciferase One Glo (y-axis) and the different RAD001 concentrations are listed on the x-axis.
Figure 45B:
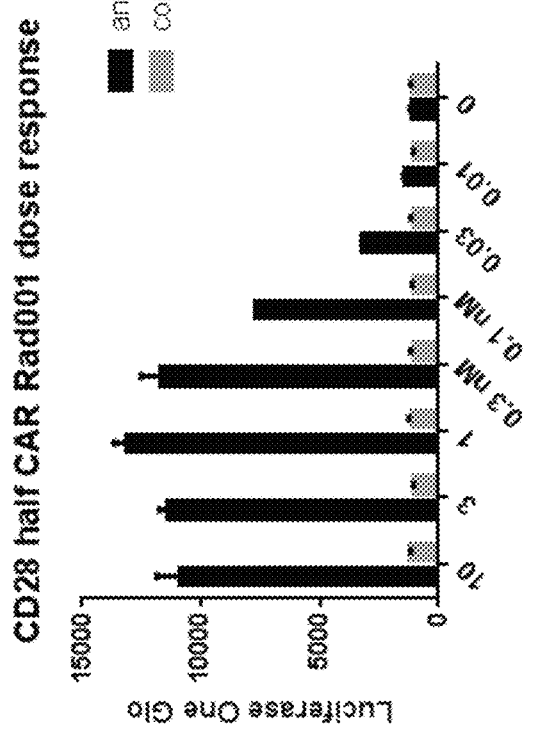

After one hour, RAD001 compound was delivered at 50 nM when testing RCARs with different costimulatory signaling domains (FIGS. 44A and 44B), or various concentrations: 0 nM, 0.01 nM, 0.03 nM, 0.1 nM, 0.3 nM, 1 nM, 3 nM, and 10 nM (FIGS. 45A and 45B). Tissue culture plate was coated with 5 μg/ml of anti anti-CD19 antibody or isotype control for 2 hrs, blocked with the blocking buffer (DPBS with 5% serum) for 1 hour. The transfected cells with or without RAD001 were resuspended and added to the target plate with 100 μl per well and incubated for 18 hrs. Luciferase One Glo reagent 100 μl was added per well. The samples were incubated for 5 min at 37° C. and then luminescence is measured using Envision plate reader.

Results

Five different RCAR half switch constructs were generated with different costimulatory signaling domains: CD27, CD28, ICOS, OX40, and 4-1BB; and NFAT activation after incubation with Rad001 was evaluated. As shown in FIG. 44B, RCARs containing CD27, CD28, ICOS, OX40 and 41BB as the costimulatory domain, with CD3zeta as the primary signaling domain, were all able to activate the target-dependent NFAT activity after addition of RAD001. The RCAR with CD28-CD3 zeta and OX40-CD3 zeta dimmers were demonstrated to have the most robust activation as compared to the other costimulatory signaling domain-CD3 zeta dimers (e.g., 4-1BB-CD3 zeta, ICOS-CD3zeta, and OX40-CD3zeta).

Two RCAR half switches, containing either CD28 or 4-1BB costimulatory signaling domains, were also assessed for NFAT activity in response to increasing doses of RAD001. As shown in FIGS. 45A and 45B, both half switches generally exhibited dose-dependent NFAT activity, where increased RAD001 concentrations correlated with increased luminescence, or NFAT activity. For both half switches, NFAT activity peaked at the 1 nM RAD001 concentration, with NFAT activity decreasing at the higher RAD001 concentrations (e.g., 3 nM and 10 nM).

These results show that RAD001 triggers dimerization of RCAR half switches with various different costimulatory signaling domains and target-dependent NFAT activation.

Example 24: Analysis of Half-Switch Constructs

To evaluate the feasibility of the half-switch technology, lentiviruses were produced for all of the half-switch constructs and T cells were transduced. The constructs tested were composed of two genes, coexpressed from one vector using the EMCV IRES. The genes encoded two proteins, which were a) the anti-CD19 scFv fused to the CD8 hinge and transmembrane domain, a costimulatory signaling domain and the FKBP heterodimerizing domain and b) the FRB heterodimerizing fused to the CD3z cytoplasmic domain. The costimulatory signaling domains tested were 41BB, CD28, CD27, ICOS and OX40. The half-switches were compared to a 41BB full-switch CAR and the non-regulatable 41BB CAR. All CAR-transduced T cells (CARTs) were tested for effector T cell responses, namely target cell killing and target cell-induced proliferation and cytokine production.

Materials and Methods

Generation of CAR-Transduced T Cells (CARTs)

The CAR lentiviral transfer vectors are used to produce the genomic material packaged into the VSVg pseudotyped lentiviral particles. Lentiviral transfer vector DNA is mixed with the three packaging components VSVg env, gag/pol and rev in combination with lipofectamine reagent to transfect Lenti-X 293T cells. Medium is changed after 24h and after another 24h, the media is collected, filtered and stored at −80° C. CARTs are generated by transduction of fresh or frozen naïve T cells obtained by negative magnetic selection of healthy donor blood. T cells are activated by incubation with anti-CD3/anti-CD28 beads for 24h, after which 1 mL of viral supernatant or concentrated virus (moi=10) is added to the cultures. These modified T cells are allowed to expand for about 10 days. The percentage of cells transduced (expressing the CARs on the cell surface) and the level of CAR expression (relative fluorescence intensity, Geo Mean) are determined by flow cytometric analysis between days 7 and 9. The combination of slowing growth rate and T cell size approaching ~300 fL determines the state for T cells to be cryopreserved for later analysis.

Evaluating Cytolytic Activity, Proliferation and Cytokine Secretion of CARTs

To evaluate the functionality of CARTs, the T cells are thawed, counted and viability assessed by Cellometer. The number of CAR-positive cells in each culture is normalized using non-transduced T cells. The induction of the regulatable CARTs was tested in titrations with RAD001, starting at 50 nM. The target cell line used in all co-culture experiments is Nalm-6, a human pre-B cell acute lymphoblastic leukemia (ALL) cell line expressing CD19 and transduced to express luciferase. The human glioblastoma line U87MG expressing luciferase serves as negative control.

The cytolytic activities of CARTs are measured at an effector:target ratio of 4:1, where effectors were defined as total T cells and targets the respective positive or negative cancer lines. After 20h of co-culture, cultures are lysed and a substrate for luciferase is added (BrightGlo) to quantify surviving target cells. Plates are read out on the luminometer (EnVision) and specific lysis (%) is calculated as lum (sample)/lum(max)*100.

For measuring cytokine production by CARTs, T cells are cultured with target cells at a ratio of 1:1. In addition, PMA/Ionomycin is used to evaluate the maximal secretion of the CART populations and CAR T cells alone give a read-out of basal activity. The assay is run for 24h, when the media is removed for cytokine analysis using the CBA kit for human cytokine detection; the amounts of IFNγ, IL2 and TNFα were measured.

For measuring the proliferation of CARTs, T cells are cultured with target cells at a ratio of 1:1. The assay is run for 4 days, when cells are stained for CD3, CD4, CD8 and CAR expression. The number of T cells is assessed by flow cytometry using counting beads as reference.

Results

Figure 46:
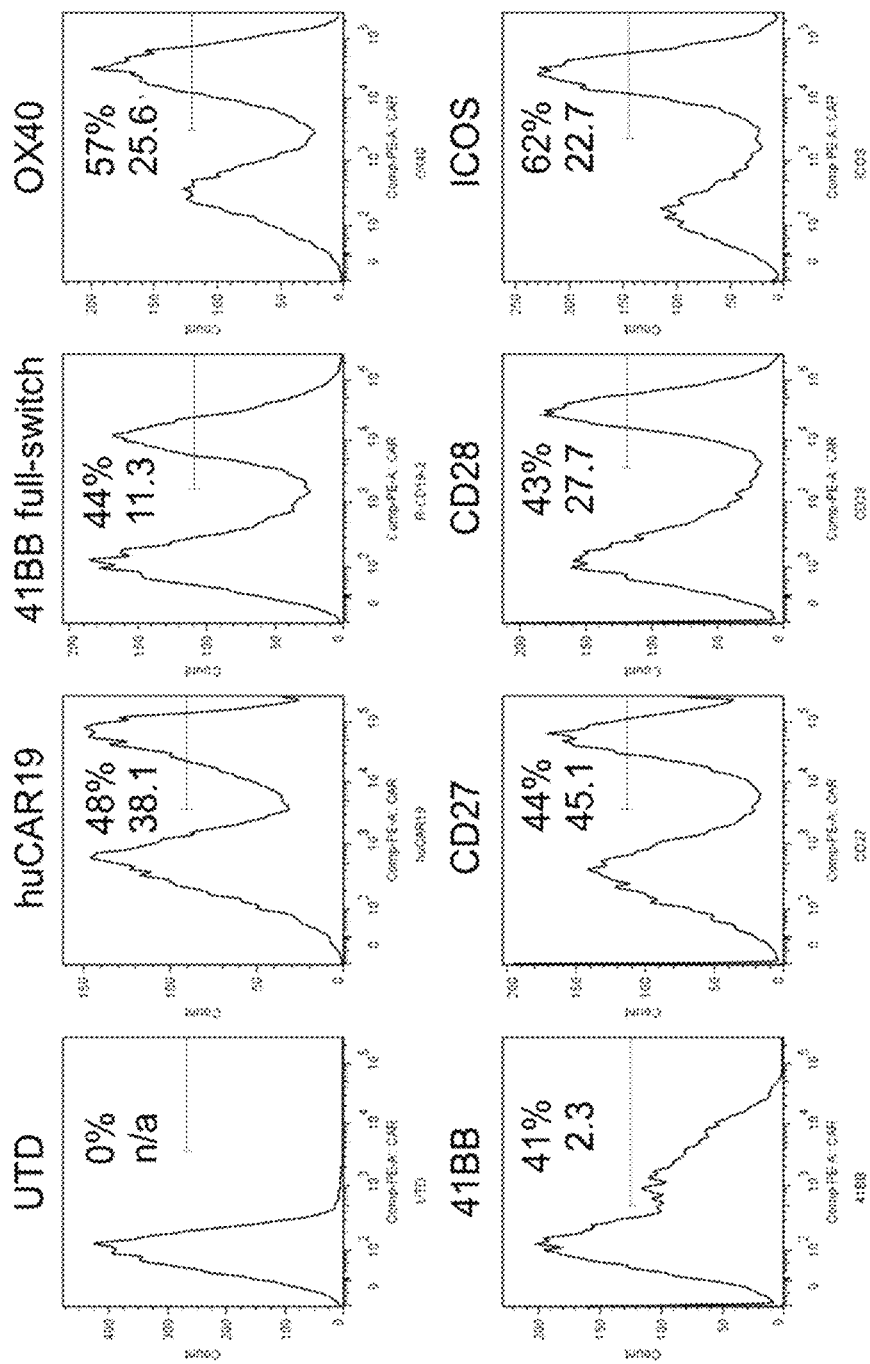
FIG. 46 shows the expression of half RCARs on transduced primary T cells. Numbers indicate the percentage of half RCAR-positive T cells (%) and the mean fluorescence intensity of the CAR-positive population ($10^3$ GeoMean).

Most CARs used for this experiment showed very similar surface expression; the standard huCART19, the 41BB full-switch as well as the OX40, CD27, CD28 and ICOS half-switches are well expressed and comparable regarding percent CAR+ population and number of CAR molecules per cell (GeoMean). Only the 41BB half-switch showed lower expression on a per-cell basis, while the population of CAR-positive cells is similar to the other CARTs (FIG. 46).

Figure 47:
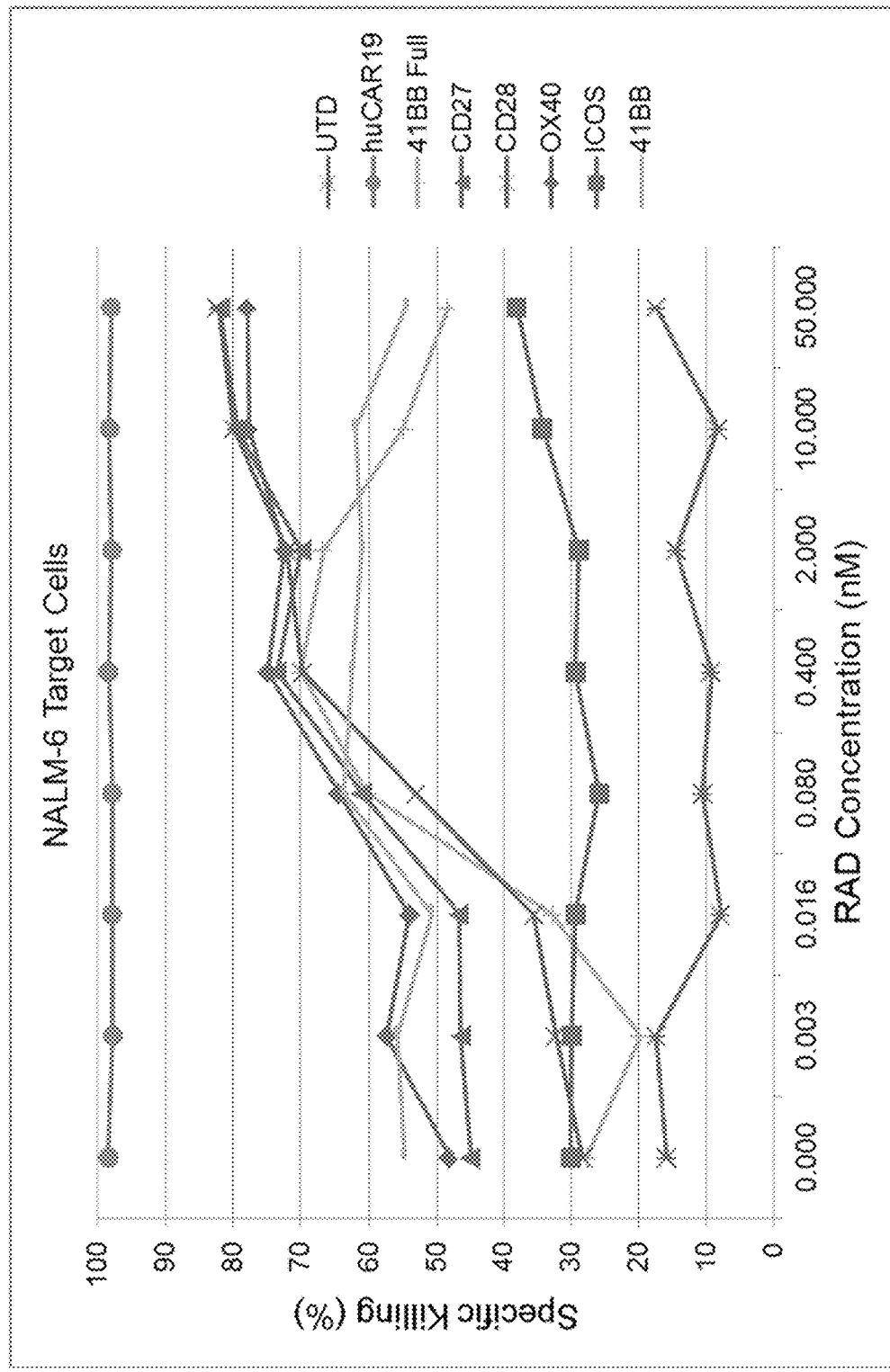
FIG. 47 shows the cytotoxicity of half RCAR expressing, transduced T cells. RCARTs were co-cultured with Nalm6 cells expressing luciferase in the presence of different concentration of RAD001.

The potential of these CARs to kill CD19-positive target cells (Nalm6-Luc) in the presence of different concentrations of RAD001 was tested in a 20h assay. Almost 100% killing was seen for the non-inducible huCART19, while non-transduced T cells (UTD) showed background killing (FIG. 47). The 41BB full-switch CARTs showed an induction of killing with increasing RAD concentrations, with a maximum at 0.4 nM RAD001, and a decrease in killing at higher concentrations. CD28, CD27 and OX40 half-switch CARTs showed an increase in killing, with a maximum at the highest concentration of RAD001. The maximal killing seen for these half-switches was higher than seen for the full-switch. The 41BB and ICOS half-switch CARTs showed non-inducible killing at moderate and low levels, respectively.

Figure 48:
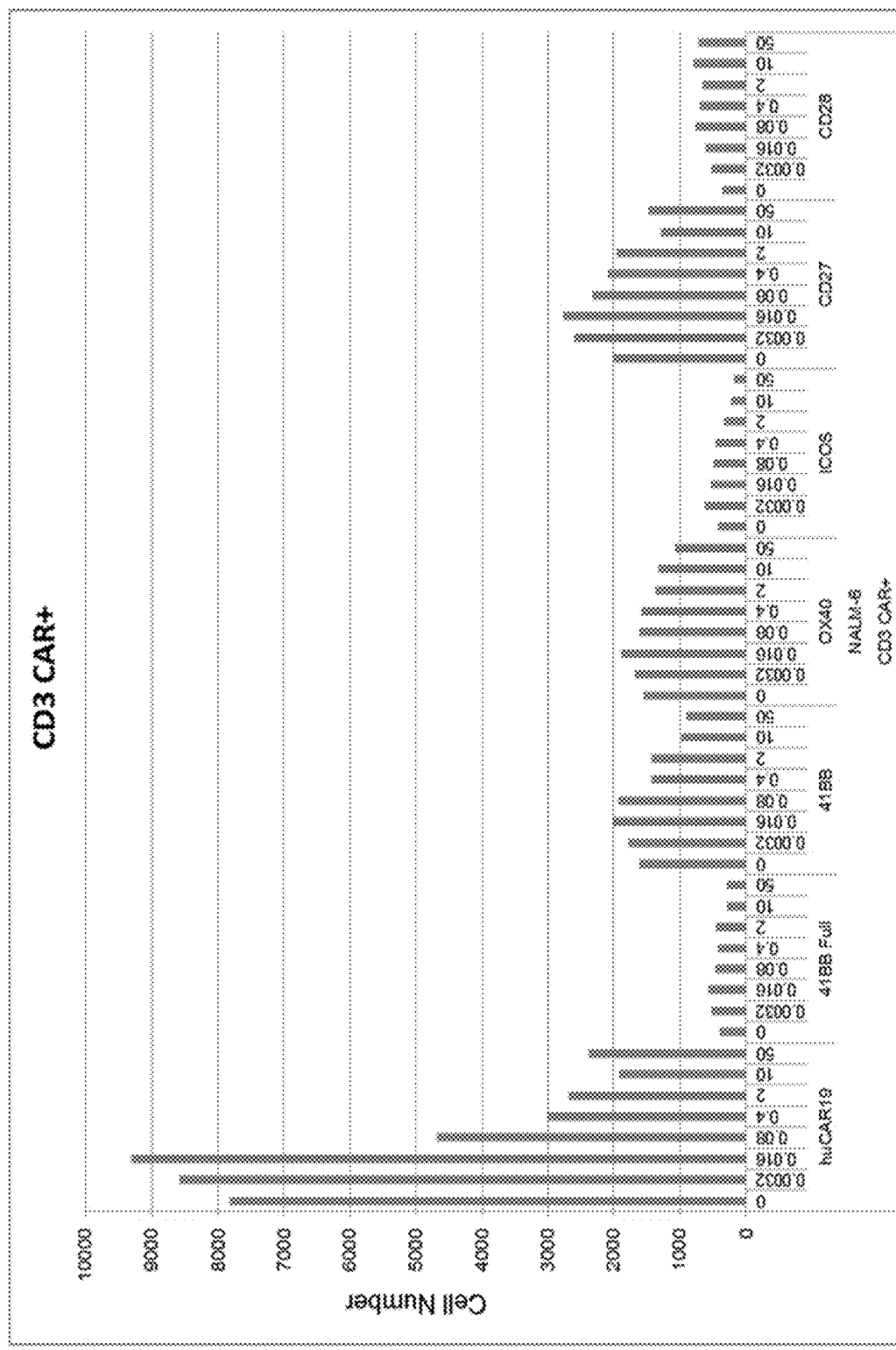
FIG. 48 shows the proliferation of half RCAR expressing, transduced T cells. RCARTs were co-cultured with Nalm6 cells in the presence of different concentration of RAD001. The number of RCAR-positive CD3-positive T cells was assessed after 4 days of co-culture.

The proliferative capacity of CART cells was tested in a 4 day co-culture assay. Number of CAR-positive CD3-positive T cells was assessed after culturing the differently transduced T cells with Nalm6 (FIG. 48). huCART19 cells expanded dramatically when cultured in the presence of less than 0.016 nM of RAD001, and to a lesser extent at higher concentrations of the compound. Half-switches 41BB, OX40 and CD27 expanded to similar, lower levels, showing a maximum at 0.016 nM RAD001. The ICOS and CD28 half-switches and the 41BB full-switch did not show detectable expansion.

Figure 49:
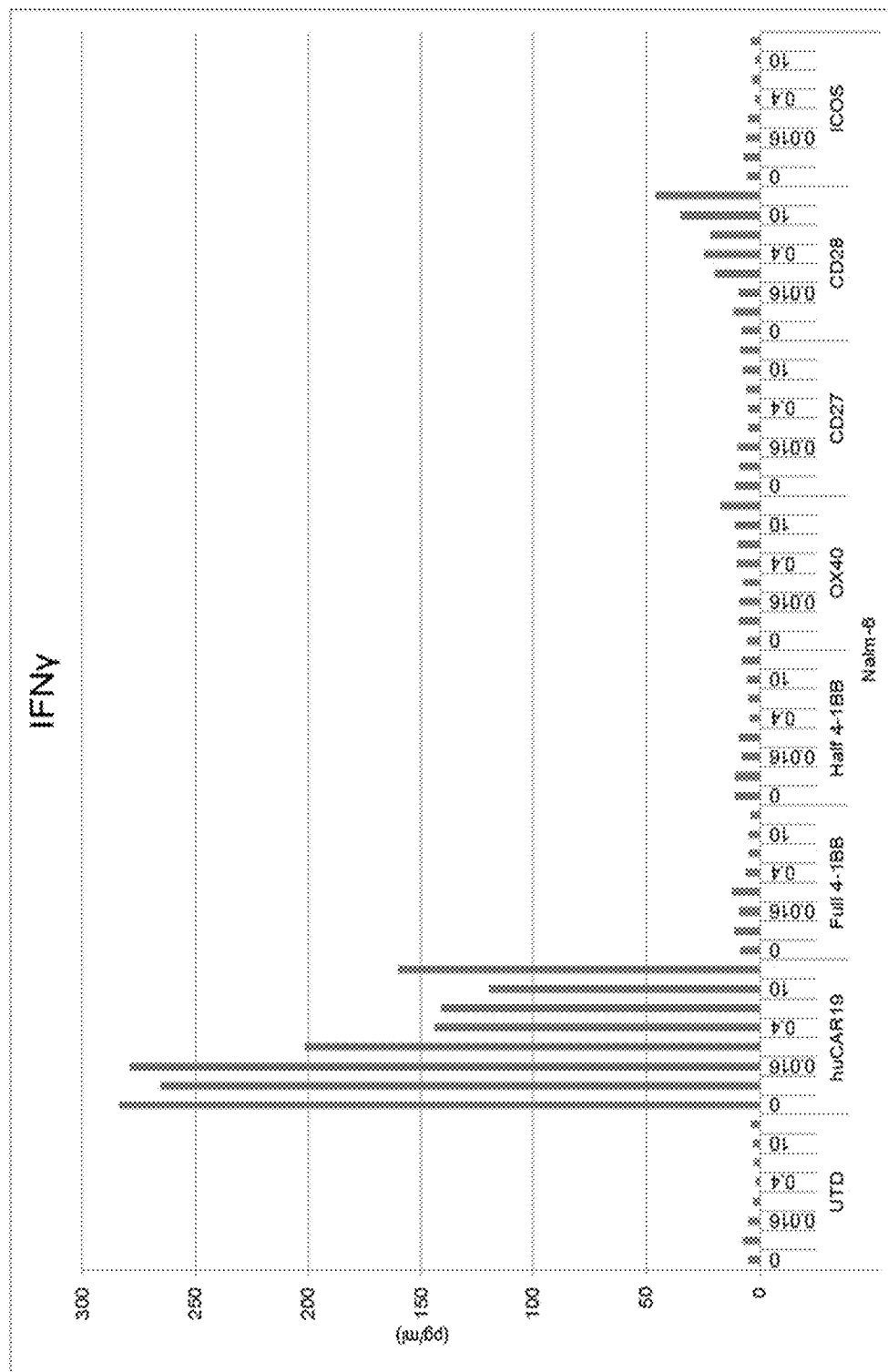
FIG. 49 shows the secretion of IFNγ by CAR expressing, transduced T cells. CARTs were co-cultured with Nalm6 cells in the presence of different concentration of RAD001. The concentration of IFNγ in the cell culture supernatant was determined after 20h of co-cultivation.

The capabilities of the regulatable CARTs to produce cytokine were tested in a similar assay, where CART cells were cultured with Nalm6 cells at a ratio of 1:1 for 20h. The supernatant was harvested and concentrations of IFNγ were measured. Again, we saw the strongest function by huCART19 and an inhibition at higher RAD001 levels (FIG. 49). Among the switch CARTs, the CD28 half-switch was the only showing a clear increase in secreted IFN. The highest induction was seen for the highest levels of RAD001.

Example 25: Covalent Dimerization Switch by Halo/Snap Tag

Figure 13:
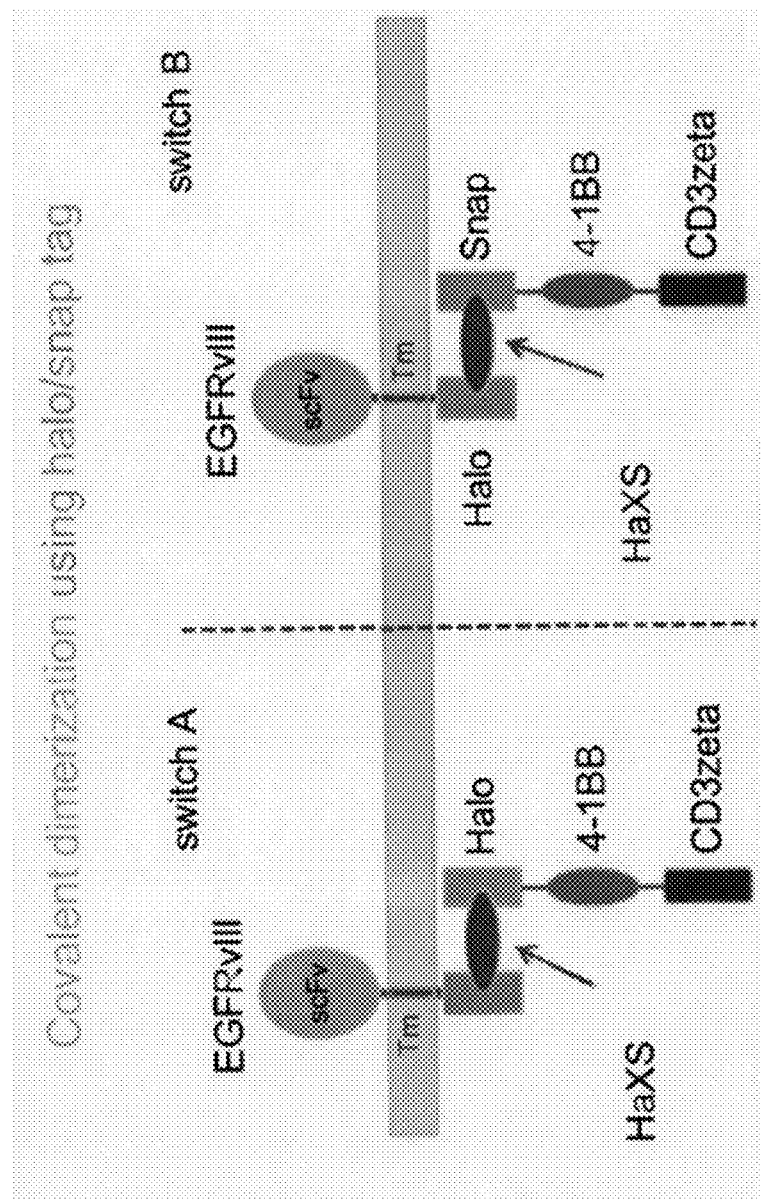
FIG. 13 depicts RCARs having a halo/snap tag dimerization switch. The antigen binding domain may be an scFv, e.g., that targets EGFRvIII. Switch A and switch B show the Halo-tag and Snap-tag switch domains in different orientations with respect to the antigen binding member and the intracellular signaling member.

In this example, the activation of a RCAR with a covalent dimerization switch was evaluated after addition of the dimerization molecule NVP-HAL421. Examples of RCAR constructs with covalent dimerization switches are shown in FIG. 13.
Materials and Methods
Jurkat cells with NFAT-LUC reporter (JNL) were grown to the density of $0.5 \times 10^6$/ml in Jurkat cell growth media with puromycin at 0.5 μg/ml. For each transfection $2.5 \times 10^6$ cells were spin down at 100 g for 10 minutes. Two μg of DNA per construct were used per transfection. Amaxa Nucleofector solution V and supplement I was mixed and 100 μl was added into the tube with DNA construct. The mixture was then added to the cells and transferred to the electroporation cuvette. Electroporation was done under setting X-001 using Amaxa Nucleofector II Device. 0.5 ml of growth media was added immediately after electroporation and the mixture were transferred into 2 ml growth media in one well of the 6-well plate.

Figure 50:
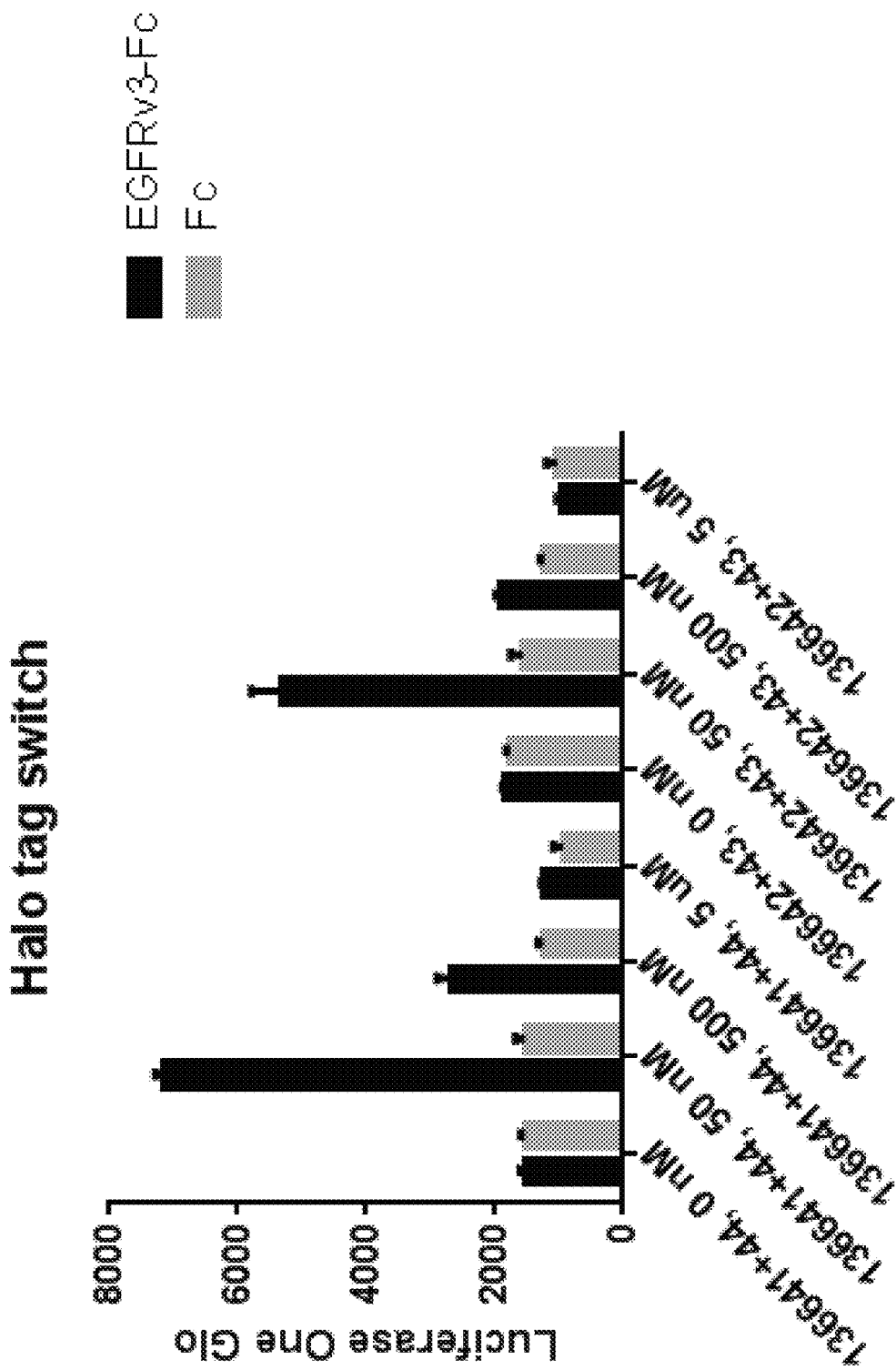
FIG. 50 shows the activation of RCAR with a covalent halo/snap tag switch. NFAT activation is represented by luminescence detected by Luciferase One Glo (y-axis) and the different NVP-HAL421 concentrations are listed on the x-axis.

After one hour, NVP-HAL421 was applied at various concentrations, e.g., 0 nM, 50 nM, 500 nM, and 5 μM; or 0 nM, 0.06 nM, 0.2 nM, 0.6 nM, 2 nM, 6 nM, 20 nM, and 60 nM. Tissue culture plate was coated with 5 m/ml of EGFRVIII-Fc or IgG1 Fc control for 2 hrs, blocked with the blocking buffer (DPBS with 5% serum) for 1 hour. The transfected cells with or without were re-suspended and added to the target plate with 100 μl per well and incubated for 18 hrs. Luciferase One Glo reagent 100 μl was added per well. The samples were incubated for 5 min at 37° C. and then luminescence is measured using Envision plate reader.
Results The concept of a RCAR with halo-tag and snap-tag as the switch domains is illustrated in FIG. 13. JNL cells were co-transfected with an RCAR construct comprising halo-tag and snap-tag switch domains. The addition of NVP-HAL421 at 50 nM resulted in covalent linkage between the halo-tag and snap-tag switch domains, which in term lead to NFAT activation, as shown in FIG. 50. The level of NFAT activity peaked at 50 nM of NVP-HAL421, while NFAT activation was decreased at the higher concentrations of NVP-HAL421 (500 nM and 5 μM), as compared to the activity at 50 nM. This decrease in target-specific activation could be due to the toxicity of the compound.

Figure 51:
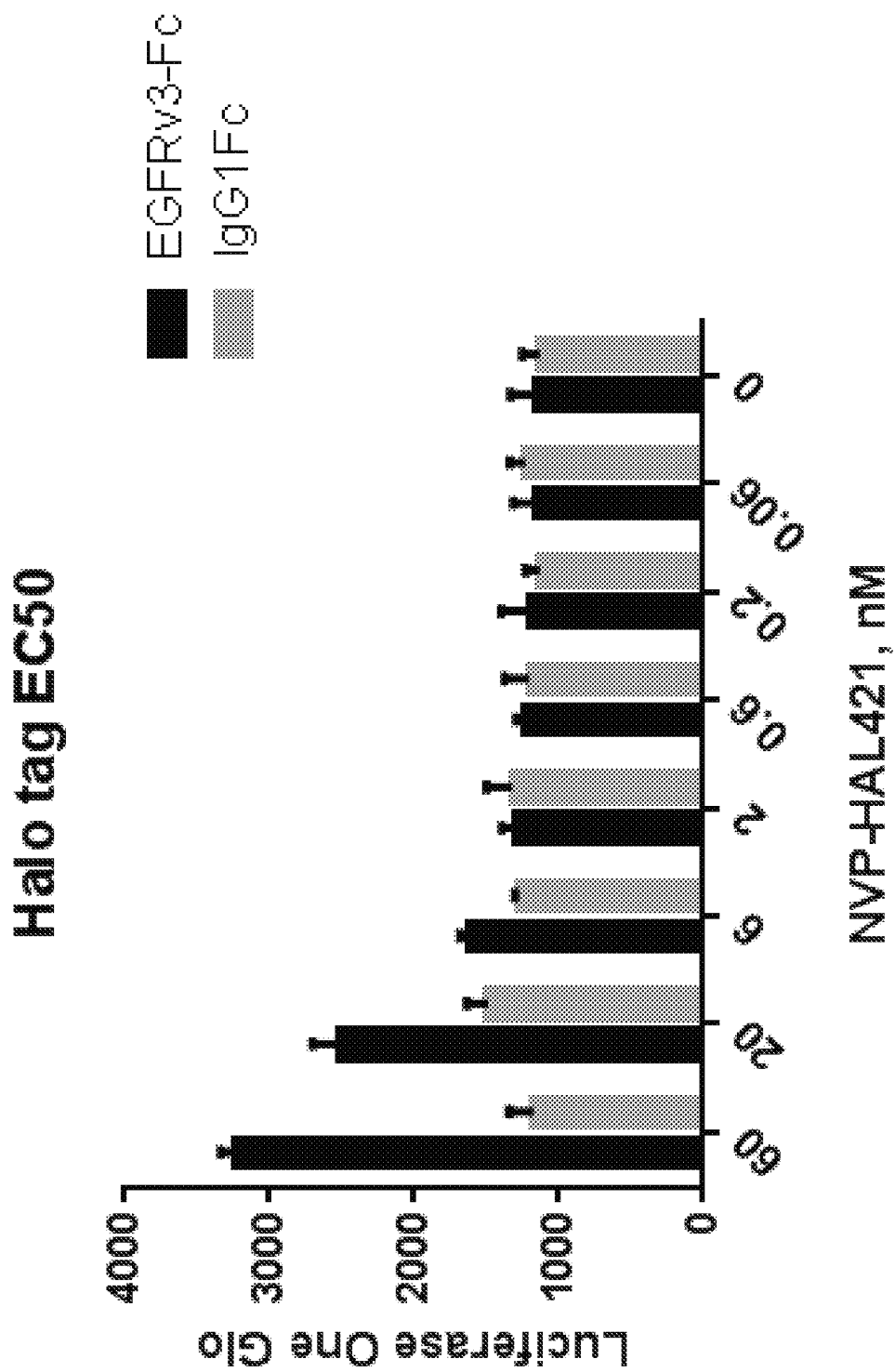
FIG. 51 shows the activation of RCAR with a covalent halo/snap tag switch, in the presence of the indicated NVP-HAL421 concentrations. NFAT activation is represented by luminescence detected by Luciferase One Glo (y-axis) and the different NVP-HAL421 concentrations are listed on the x-axis.
Figure 52:
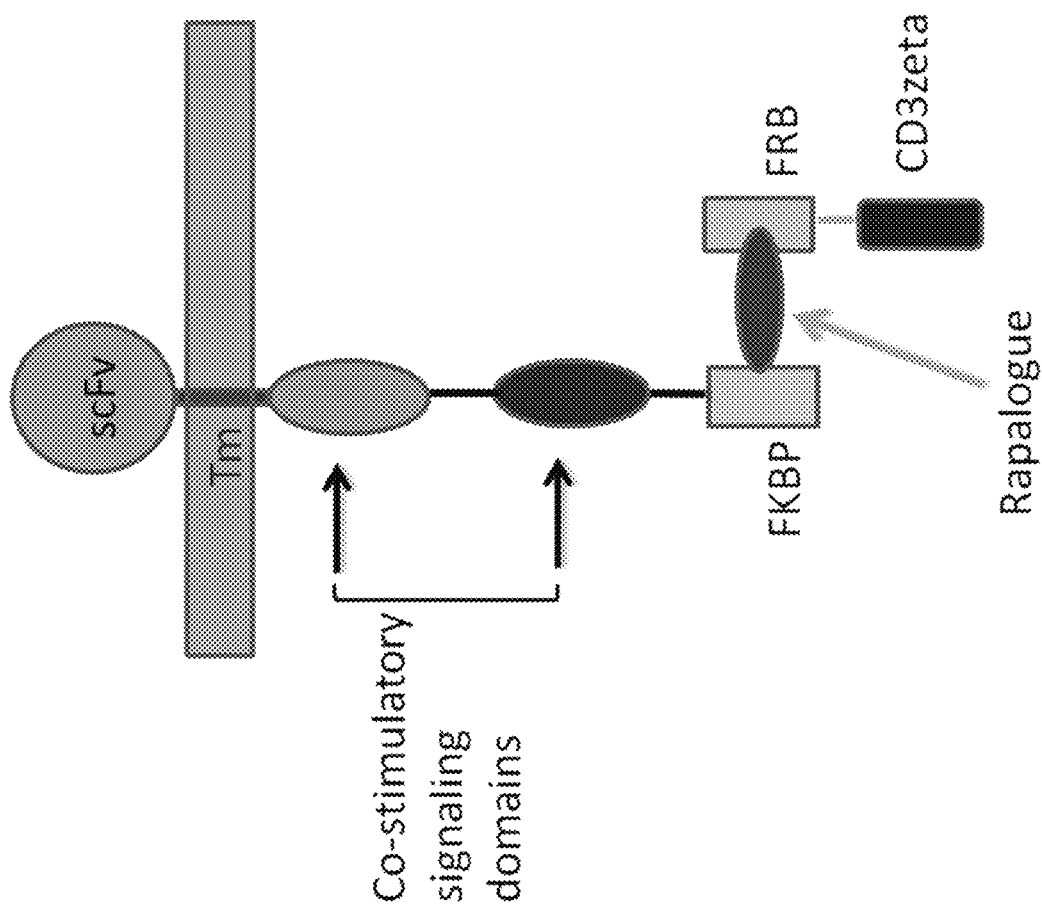
FIG. 52 shows a double half RCAR construct, where two costimulatory signaling domains are present on the antigen binding member.

A second assay was performed to evaluate the NFAT activity for varying dosages of NVP-HAL421 between 0 nM and 60 nM. As shown in FIG. 51, NFAT activity increased as dosage of dimerization molecule NVP-HAL421 increased, with the highest level of NFAT activity detected at the highest tested dosage, 60 nM.

EQUIVALENTS

The disclosures of each and every patent, patent application, and publication cited herein are hereby incorporated herein by reference in their entirety. While this invention has been disclosed with reference to specific aspects, it is apparent that other aspects and variations of this invention may be devised by others skilled in the art without departing from the true spirit and scope of the invention. The appended claims are intended to be construed to include all such aspects and equivalent variations.

What is claimed is:

1. A regulatable chimeric antigen receptor (RCAR), wherein the RCAR comprises:

a) an intracellular signaling member comprising:
   an intracellular signaling domain, and
   a first switch domain of an FKBP-FRB based switch;

b) an antigen binding member comprising:
   an antigen binding domain,
   a transmembrane domain or a membrane anchoring domain, and
   a second switch domain of an FKBP-FRB based switch; and
   wherein the first and second switch domains form an intracellular switch, wherein the first switch domain comprises an FRB binding fragment or analog of FKBP and the second switch domain comprises an FKBP binding fragment or analog of FRB, or the first switch domain comprises an FKBP binding fragment or analog of FRB and the second switch domain comprises an FRB binding fragment or analog of FKBP, and wherein the FKBP binding fragment or analog of FRB comprises one or more mutations chosen from an E2032 mutation, a T2098 mutation, or an E2032 and a T2098 mutation.

2. The RCAR of claim 1, wherein the intracellular signaling domain on the intracellular signaling member comprises a primary intracellular signaling domain from a molecule chosen from FcR gamma, FcR beta, CD3 gamma, CD3 delta, CD3 epsilon, CD3 zeta, CD79a, CD79b, DAP10, DAP12, or CD32.

3. The RCAR of claim 1, wherein the intracellular signaling domain on the intracellular signaling member comprises a costimulatory signaling domain chosen from CD27, CD28, 4-1BB, OX40, CD30, CD40, ICOS, ICAM-1, LFA-1, CD2, CD7, LIGHT, NKG2C, B7-H3, a ligand that specifically binds with CD83, CDS, GITR, BAFFR, HVEM, SLAMf7, NKP80, CD160, CD19, CD4, CD8 alpha, CD8 beta, IL2R beta, IL2R gamma, IL7R alpha, ITGA4, VLA1, CD49a, ITGA4, IA4, CD49D, ITGA6, VLA-6, C49f, ITGAD, CD11d, ITGAE, CD103 ITGAL, CD11a, LFA-1, ITGAM, CD11b, ITGAX, CD11c, ITGB1, CD29, ITGB2, CD18, ITGB7, TNFR2, TRANCE/RANKL, DNAM1, SLAMF4, CD84, CD96, CEACAM1, CRTAM, Ly9, PSGL1, C100, CD69, SLAMF6, SLAM, BLAME, SELPLG, LTBR, LAT, GADS, PAG/Cbp, SLP-76, NKp44, NKp30, or NKp46.

4. The RCAR of claim 1, wherein the antigen binding member comprises: a costimulatory signaling domain chosen from CD27, CD28, 4-1BB, OX40, CD30, CD40, ICOS, ICAM-1, LFA-1, CD2, CD7, LIGHT, NKG2C, B7-H3, a ligand that specifically binds with CD83, CDS, GITR, BAFFR, HVEM, SLAMf7, NKP80, CD160, CD19, CD4, CD8 alpha, CD8 beta, IL2R beta, IL2R gamma, IL7R alpha, ITGA4, VLA1, CD49a, ITGA4, IA4, CD49D, ITGA6, VLA-6, C49f, ITGAD, CD11d, ITGAE, CD103 ITGAL, CD11a, LFA-1, ITGAM, CD11b, ITGAX, CD11c, ITGB1, CD29, ITGB2, CD18, ITGB7, TNFR2, TRANCE/RANKL, DNAM1, SLAMF4, CD84, CD96, CEACAM1, CRTAM, Ly9, PSGL1, C100, CD69, SLAMF6, SLAM, BLAME, SELPLG, LTBR, LAT, GADS, PAG/Cbp, SLP-76, NKp44, NKp30, or NKp46.

5. A cell comprising an RCAR of claim 1.

6. A method of providing a cell comprising an RCAR to a subject, comprising:
(a) administering to the subject the cell of claim 5; and
(b) administering a dimerization molecule to the subject, thereby providing the cell.

7. The method of claim 6, wherein the cell is an autologous T cell, an allogeneic T cell, an autologous NK cell, or an allogeneic NK cell.

8. The method of claim 6, wherein the subject is a human having a cancer.

9. A method of treating a subject, comprising:
(a) administering to the subject an effective amount of a RCARX cell, wherein the RCARX cell comprises: the RCAR of claim 1 or a nucleic acid encoding the RCAR; and
(b) administering to the subject a dimerization molecule, thereby treating the subject.

10. The method of claim 9, wherein the RCARX cell is an autologous T cell, an allogeneic T cell, an autologous NK cell, or an allogeneic NK cell.

11. The method of claim 9, comprising treating the subject for cancer, wherein the subject is a human.

12. A method of providing an RCARX cell comprising:
providing an immune effector cell to a recipient entity; and
receiving from said entity, an RCARX cell derived from said immune effector cell, or a daughter cell thereof, wherein the RCARX comprises an RCAR of claim 1, or a nucleic acid or vector encoding the RCAR.

13. The RCAR of claim 1, wherein the antigen binding member comprises a plurality of costimulatory signaling domains comprising the costimulatory signaling domains of CD28 and 4-1BB, and no primary intracellular signaling domain.

14. The RCAR of claim 1, wherein the antigen binding member comprises a plurality of costimulatory signaling domains comprising the costimulatory signaling domains of CD28 and OX40, and no primary intracellular signaling domain.

15. The RCAR of claim 1, wherein the intracellular signaling member comprises a plurality of costimulatory signaling domains comprising the costimulatory signaling domains of CD28 and 4-1BB, and no primary intracellular signaling domain.

16. The RCAR of claim 1, wherein the intracellular signaling member comprises a plurality of costimulatory signaling domains comprising the costimulatory signaling domains of CD28 and OX40, and no primary intracellular signaling domain.

17. The RCAR of claim 1, wherein the one or more mutations comprise an E2032 mutation.

18. The RCAR of claim 1, wherein the one or more mutations comprise a T2098 mutation.

19. The RCAR of claim 1, wherein the one or more mutations comprises an E2032 mutation and a T2098 mutation.

20. The RCAR of claim 1, wherein the first or second switch domain that comprises an FRB binding fragment or analog of FKBP comprises a sequence having at least 80% identity with the FKBP sequence of SEQ ID NO: 1 or 141.

21. The RCAR of claim 1, wherein the second or first switch domain that comprises an FKBP binding fragment or analog of FRB comprises a sequence having at least 80% identity with the FRB sequence of SEQ ID NO: 2.

22. The RCAR of claim 1, wherein the first or second switch domain that comprises an FRB binding fragment or analog of FKBP comprises a sequence having at least 90% identity with the FKBP sequence of SEQ ID NO: 1 or 141.

23. The RCAR of claim 1, wherein the second or first switch domain that comprises an FKBP binding fragment or analog of FRB comprises a sequence having at least 90% identity with the FRB sequence of SEQ ID NO: 2.

24. The RCAR of claim 1, wherein the first or second switch domain that comprises an FRB binding fragment or analog of FKBP comprises a sequence having at least 95% identity with the FKBP sequence of SEQ ID NO: 1 or 141.

25. The RCAR of claim 1, wherein the second or first switch domain that comprises an FKBP binding fragment or analog of FRB comprises a sequence having at least 95% identity with the FRB sequence of SEQ ID NO: 2.

26. The RCAR of claim 1, wherein the E2032 mutation is chosen from E2032I or E2032L, and the T2098 mutation is T2098L.

27. A nucleic acid encoding a RCAR, wherein the RCAR comprises:
a) an intracellular signaling member comprising:
an intracellular signaling domain, and
a first switch domain of an FKBP-FRB based switch;
b) an antigen binding member comprising:
an antigen binding domain,
a transmembrane domain or a membrane anchoring domain, and
a second switch domain of an FKBP-FRB based switch; and
wherein the first and second switch domains form an intracellular switch,
wherein the first switch domain comprises an FRB binding fragment or analog of FKBP and the second switch domain comprises an FKBP binding fragment or analog of FRB, or the first switch domain comprises an FKBP binding fragment or analog of FRB and the second switch domain comprises an FRB binding fragment or analog of FKBP, and
wherein the FKBP binding fragment or analog of FRB comprises one or more mutations chosen from an E2032 mutation, a T2098 mutation, or an E2032 and a T2098 mutation.

28. A vector system comprising a nucleic acid of claim 27.

29. A method of making a cell comprising an RCAR, comprising introducing a nucleic acid of claim 27 into a cell, and culturing the cell, thereby making the cell.

30. A nucleic acid encoding an RCAR, comprising:
(a) a sequence encoding an antigen binding member comprising:
an antigen binding domain,
a transmembrane domain or a membrane anchoring domain, and
a first switch domain of an FKBP-FRB based switch;
(b) a sequence encoding an intracellular signaling member comprising:
an intracellular signaling domain, and
a second switch domain of an FKBP-FRB based switch; and
(c) a sequence encoding a cleavable peptide or an IRES,
wherein the first and second switch domains form an intracellular switch,
wherein the first switch domain comprises an FRB binding fragment or analog of FKBP and the second switch domain comprises an FKBP binding fragment or analog of FRB, or the first switch domain comprises an FKBP binding fragment or analog of FRB and the second switch domain comprises an FRB binding fragment or analog of FKBP,
wherein the FKBP binding fragment or analog of FRB comprises one or more mutations chosen from an E2032 mutation, a T2098 mutation, or an E2032 and a T2098 mutation, and
wherein:
i) (a), (b), and (c) are present on a single nucleic acid molecule, are transcribed as a single transcription product, and are configured as follows:
a promoter is operably linked to (a), (b), and (c), wherein (c) encodes a cleavable peptide, and (c) is disposed between (a) and (b); or
ii) (a), (b), and (c) are present on a single nucleic acid molecule, are transcribed as a single transcription product, and are configured as follows:
a promoter is operably linked to (a), (b), and (c), wherein (c) encodes an IRES, and (c) is disposed between (a) and (b).

* * * * *

SEQUENCE LISTING

```
<160> NUMBER OF SEQ ID NOS: 337

<210> SEQ ID NO 1
<211> LENGTH: 132
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 1
```

```
Asp Val Pro Asp Tyr Ala Ser Leu Gly Gly Pro Ser Ser Pro Lys Lys
1               5                   10                  15

Lys Arg Lys Val Ser Arg Gly Val Gln Val Glu Thr Ile Ser Pro Gly
            20                  25                  30

Asp Gly Arg Thr Phe Pro Lys Arg Gly Gln Thr Cys Val Val His Tyr
        35                  40                  45

Thr Gly Met Leu Glu Asp Gly Lys Lys Phe Asp Ser Ser Arg Asp Arg
    50                  55                  60

Asn Lys Pro Phe Lys Phe Met Leu Gly Lys Gln Glu Val Ile Arg Gly
65                  70                  75                  80

Trp Glu Glu Gly Val Ala Gln Met Ser Val Gly Gln Arg Ala Lys Leu
                85                  90                  95

Thr Ile Ser Pro Asp Tyr Ala Tyr Gly Ala Thr Gly His Pro Gly Ile
            100                 105                 110

Ile Pro Pro His Ala Thr Leu Val Phe Asp Val Glu Leu Leu Lys Leu
        115                 120                 125

Glu Thr Ser Tyr
    130

<210> SEQ ID NO 2
<211> LENGTH: 93
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 2

Ile Leu Trp His Glu Met Trp His Glu Gly Leu Glu Glu Ala Ser Arg
1               5                   10                  15

Leu Tyr Phe Gly Glu Arg Asn Val Lys Gly Met Phe Glu Val Leu Glu
            20                  25                  30

Pro Leu His Ala Met Met Glu Arg Gly Pro Gln Thr Leu Lys Glu Thr
        35                  40                  45

Ser Phe Asn Gln Ala Tyr Gly Arg Asp Leu Met Glu Ala Gln Glu Trp
    50                  55                  60

Cys Arg Lys Tyr Met Lys Ser Gly Asn Val Lys Asp Leu Thr Gln Ala
65                  70                  75                  80

Trp Asp Leu Tyr Tyr His Val Phe Arg Arg Ile Ser Lys
                85                  90

<210> SEQ ID NO 3
<211> LENGTH: 446
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 3

Met Ala Leu Pro Val Thr Ala Leu Leu Leu Pro Leu Ala Leu Leu Leu
1               5                   10                  15

His Ala Ala Arg Pro Asp Ile Gln Met Thr Gln Ser Pro Ser Ser Leu
            20                  25                  30

Ser Ala Ser Val Gly Asp Arg Val Thr Ile Thr Cys Arg Ala Ser Gln
        35                  40                  45

Gly Ile Arg Asn Asn Leu Ala Trp Tyr Gln Gln Lys Pro Gly Lys Ala
    50                  55                  60
```

Pro Lys Arg Leu Ile Tyr Ala Ala Ser Asn Leu Gln Ser Gly Val Pro
65                  70                  75                  80

Ser Arg Phe Thr Gly Ser Gly Ser Gly Thr Glu Phe Thr Leu Ile Val
                85                  90                  95

Ser Ser Leu Gln Pro Glu Asp Phe Ala Thr Tyr Tyr Cys Leu Gln His
            100                 105                 110

His Ser Tyr Pro Leu Thr Ser Gly Gly Thr Lys Val Glu Ile Lys
            115                 120                 125

Arg Thr Gly Ser Thr Ser Gly Ser Lys Pro Gly Ser Gly Glu Gly
130                 135                 140

Ser Glu Val Gln Val Leu Glu Ser Gly Gly Leu Val Gln Pro Gly
145                 150                 155                 160

Gly Ser Leu Arg Leu Ser Cys Ala Ala Ser Gly Phe Thr Phe Ser Ser
                165                 170                 175

Tyr Ala Met Ser Trp Val Arg Gln Ala Pro Gly Lys Gly Leu Glu Trp
            180                 185                 190

Val Ser Ala Ile Ser Gly Ser Gly Gly Ser Thr Asn Tyr Ala Asp Ser
            195                 200                 205

Val Lys Gly Arg Phe Thr Ile Ser Arg Asp Asn Ser Lys Asn Thr Leu
210                 215                 220

Tyr Leu Gln Met Asn Ser Leu Arg Ala Glu Asp Thr Ala Val Tyr Tyr
225                 230                 235                 240

Cys Ala Gly Ser Ser Gly Trp Ser Glu Tyr Trp Gly Gln Gly Thr Leu
                245                 250                 255

Val Thr Val Ser Ser Thr Thr Thr Pro Ala Pro Arg Pro Pro Thr Pro
            260                 265                 270

Ala Pro Thr Ile Ala Ser Gln Pro Leu Ser Leu Arg Pro Glu Ala Cys
            275                 280                 285

Arg Pro Ala Ala Gly Gly Ala Val His Thr Arg Gly Leu Asp Phe Ala
290                 295                 300

Cys Asp Ile Tyr Ile Trp Ala Pro Leu Ala Gly Thr Cys Gly Val Leu
305                 310                 315                 320

Leu Leu Ser Leu Val Ile Thr Leu Tyr Cys Lys Arg Gly Arg Lys Lys
                325                 330                 335

Leu Leu Gly Gly Gly Gly Ser Gly Gly Gly Ser Ala Ser Arg Ile
            340                 345                 350

Leu Trp His Glu Met Trp His Glu Gly Leu Glu Glu Ala Ser Arg Leu
                355                 360                 365

Tyr Phe Gly Glu Arg Asn Val Lys Gly Met Phe Glu Val Leu Glu Pro
            370                 375                 380

Leu His Ala Met Met Glu Arg Gly Pro Gln Thr Leu Lys Glu Thr Ser
385                 390                 395                 400

Phe Asn Gln Ala Tyr Gly Arg Asp Leu Met Glu Ala Gln Glu Trp Cys
            405                 410                 415

Arg Lys Tyr Met Lys Ser Gly Asn Val Lys Asp Leu Leu Gln Ala Trp
            420                 425                 430

Asp Leu Tyr Tyr His Val Phe Arg Arg Ile Ser Lys Thr Ser
            435                 440                 445

<210> SEQ ID NO 4
<211> LENGTH: 274
<212> TYPE: PRT
<213> ORGANISM: Artificial Sequence
<220> FEATURE:

<223> OTHER INFORMATION: Description of Artificial Sequence: Synthetic
      polypeptide

<400> SEQUENCE: 4

Met Gly Val Gln Val Glu Thr Ile Ser Pro Gly Asp Gly Arg Thr Phe
1               5                   10                  15

Pro Lys Arg Gly Gln Thr Cys Val Val His Tyr Thr Gly Met Leu Glu
            20                  25                  30

Asp Gly Lys Lys Phe Asp Ser Ser Arg Asp Arg Asn Lys Pro Phe Lys
        35                  40                  45

Phe Met Leu Gly Lys Gln Glu Val Ile Arg Gly Trp Glu Glu Gly Val
    50                  55                  60

Ala Gln Met Ser Val Gly Gln Arg Ala Lys Leu Thr Ile Ser Pro Asp
65                  70                  75                  80

Tyr Ala Tyr Gly Ala Thr Gly His Pro Gly Ile Ile Pro Pro His Ala
                85                  90                  95

Thr Leu Val Phe Asp Val Glu Leu Leu Lys Leu Glu Thr Ser Gly Gly
            100                 105                 110

Gly Gly Ser Gly Gly Gly Ser Lys Arg Gly Arg Lys Lys Leu Leu
        115                 120                 125

Tyr Ile Phe Lys Gln Pro Phe Met Arg Pro Val Gln Thr Thr Gln Glu
    130                 135                 140

Glu Asp Gly Cys Ser Cys Arg Phe Pro Glu Glu Glu Glu Gly Gly Cys
145                 150                 155                 160

Glu Leu Arg Val Lys Phe Ser Arg Ser Ala Asp Ala Pro Ala Tyr Lys
                165                 170                 175

Gln Gly Gln Asn Gln Leu Tyr Asn Glu Leu Asn Leu Gly Arg Arg Glu
            180                 185                 190

Glu Tyr Asp Val Leu Asp Lys Arg Arg Gly Arg Asp Pro Glu Met Gly
        195                 200                 205

Gly Lys Pro Arg Arg Lys Asn Pro Gln Glu Gly Leu Tyr Asn Glu Leu
    210                 215                 220

Gln Lys Asp Lys Met Ala Glu Ala Tyr Ser Glu Ile Gly Met Lys Gly
225                 230                 235                 240

Glu Arg Arg Arg Gly Lys Gly His Asp Gly Leu Tyr Gln Gly Leu Ser
                245                 250                 255

Thr Ala Thr Lys Asp Thr Tyr Asp Ala Leu His Met Gln Ala Leu Pro
            260                 265                 270

Pro Arg

<210> SEQ ID NO 5
<211> LENGTH: 457
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 5

Met Ala Leu Pro Val Thr Ala Leu Leu Leu Pro Leu Ala Leu Leu Leu
1               5                   10                  15

His Ala Ala Arg Pro Asp Ile Gln Met Thr Gln Ser Pro Ser Ser Leu
            20                  25                  30

Ser Ala Ser Val Gly Asp Arg Val Thr Ile Thr Cys Arg Ala Ser Gln
        35                  40                  45

Gly Ile Arg Asn Asn Leu Ala Trp Tyr Gln Gln Lys Pro Gly Lys Ala

```
              50                  55                  60
Pro Lys Arg Leu Ile Tyr Ala Ala Ser Asn Leu Gln Ser Gly Val Pro
 65                  70                  75                  80

Ser Arg Phe Thr Gly Ser Gly Ser Gly Thr Glu Phe Thr Leu Ile Val
                     85                  90                  95

Ser Ser Leu Gln Pro Glu Asp Phe Ala Thr Tyr Tyr Cys Leu Gln His
                    100                 105                 110

His Ser Tyr Pro Leu Thr Ser Gly Gly Thr Lys Val Glu Ile Lys
                115                 120                 125

Arg Thr Gly Ser Thr Ser Gly Ser Gly Lys Pro Gly Ser Gly Glu Gly
            130                 135                 140

Ser Glu Val Gln Val Leu Glu Ser Gly Gly Leu Val Gln Pro Gly
145                 150                 155                 160

Gly Ser Leu Arg Leu Ser Cys Ala Ala Ser Gly Phe Thr Phe Ser Ser
                165                 170                 175

Tyr Ala Met Ser Trp Val Arg Gln Ala Pro Gly Lys Gly Leu Glu Trp
                180                 185                 190

Val Ser Ala Ile Ser Gly Ser Gly Gly Ser Thr Asn Tyr Ala Asp Ser
                195                 200                 205

Val Lys Gly Arg Phe Thr Ile Ser Arg Asp Asn Ser Lys Asn Thr Leu
210                 215                 220

Tyr Leu Gln Met Asn Ser Leu Arg Ala Glu Asp Thr Ala Val Tyr Tyr
225                 230                 235                 240

Cys Ala Gly Ser Ser Gly Trp Ser Glu Tyr Trp Gly Gln Gly Thr Leu
                245                 250                 255

Val Thr Val Ser Ser Thr Thr Thr Pro Ala Pro Arg Pro Pro Thr Pro
                260                 265                 270

Ala Pro Thr Ile Ala Ser Gln Pro Leu Ser Leu Arg Pro Glu Ala Cys
                275                 280                 285

Arg Pro Ala Ala Gly Gly Ala Val His Thr Arg Gly Leu Asp Phe Ala
                290                 295                 300

Cys Asp Ile Tyr Ile Trp Ala Pro Leu Ala Gly Thr Cys Gly Val Leu
305                 310                 315                 320

Leu Leu Ser Leu Val Ile Thr Leu Tyr Cys Lys Arg Gly Arg Lys Lys
                325                 330                 335

Leu Leu Gly Gly Gly Ser Gly Gly Gly Ser Val Gln Val
                340                 345                 350

Glu Thr Ile Ser Pro Gly Asp Gly Arg Thr Phe Pro Lys Arg Gly Gln
                355                 360                 365

Thr Cys Val Val His Tyr Thr Gly Met Leu Glu Asp Gly Lys Lys Phe
370                 375                 380

Asp Ser Ser Arg Asp Arg Asn Lys Pro Phe Lys Phe Met Leu Gly Lys
385                 390                 395                 400

Gln Glu Val Ile Arg Gly Trp Glu Glu Gly Val Ala Gln Met Ser Val
                405                 410                 415

Gly Gln Arg Ala Lys Leu Thr Ile Ser Pro Asp Tyr Ala Tyr Gly Ala
                420                 425                 430

Thr Gly His Pro Gly Ile Ile Pro Pro His Ala Thr Leu Val Phe Asp
                435                 440                 445

Val Glu Leu Leu Lys Leu Glu Thr Ser
450                 455

<210> SEQ ID NO 6
```

```
<211> LENGTH: 263
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 6

Met Ala Ser Arg Ile Leu Trp His Glu Met Trp His Glu Gly Leu Glu
1               5                   10                  15

Glu Ala Ser Arg Leu Tyr Phe Gly Glu Arg Asn Val Lys Gly Met Phe
            20                  25                  30

Glu Val Leu Glu Pro Leu His Ala Met Met Glu Arg Gly Pro Gln Thr
        35                  40                  45

Leu Lys Glu Thr Ser Phe Asn Gln Ala Tyr Gly Arg Asp Leu Met Glu
    50                  55                  60

Ala Gln Glu Trp Cys Arg Lys Tyr Met Lys Ser Gly Asn Val Lys Asp
65                  70                  75                  80

Leu Leu Gln Ala Trp Asp Leu Tyr Tyr His Val Phe Arg Arg Ile Ser
                85                  90                  95

Lys Thr Ser Gly Gly Gly Ser Gly Gly Gly Ser Lys Arg Gly
            100                 105                 110

Arg Lys Lys Leu Leu Tyr Ile Phe Lys Gln Pro Phe Met Arg Pro Val
            115                 120                 125

Gln Thr Thr Gln Glu Glu Asp Gly Cys Ser Cys Arg Phe Pro Glu Glu
    130                 135                 140

Glu Glu Gly Gly Cys Glu Leu Arg Val Lys Phe Ser Arg Ser Ala Asp
145                 150                 155                 160

Ala Pro Ala Tyr Lys Gln Gly Gln Asn Gln Leu Tyr Asn Glu Leu Asn
                165                 170                 175

Leu Gly Arg Arg Glu Glu Tyr Asp Val Leu Asp Lys Arg Arg Gly Arg
            180                 185                 190

Asp Pro Glu Met Gly Gly Lys Pro Arg Arg Lys Asn Pro Gln Glu Gly
        195                 200                 205

Leu Tyr Asn Glu Leu Gln Lys Asp Lys Met Ala Glu Ala Tyr Ser Glu
    210                 215                 220

Ile Gly Met Lys Gly Glu Arg Arg Arg Gly Lys Gly His Asp Gly Leu
225                 230                 235                 240

Tyr Gln Gly Leu Ser Thr Ala Thr Lys Asp Thr Tyr Asp Ala Leu His
                245                 250                 255

Met Gln Ala Leu Pro Pro Arg
            260

<210> SEQ ID NO 7
<211> LENGTH: 488
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 7

Met Ala Leu Pro Val Thr Ala Leu Leu Leu Pro Leu Ala Leu Leu Leu
1               5                   10                  15

His Ala Ala Arg Pro Gly Ser Asp Ile Gln Met Thr Gln Ser Pro Ser
            20                  25                  30

Ser Leu Ser Ala Ser Val Gly Asp Arg Val Thr Ile Thr Cys Arg Ala
        35                  40                  45
```

```
Ser Gln Gly Ile Arg Asn Asn Leu Ala Trp Tyr Gln Gln Lys Pro Gly
    50                  55                  60

Lys Ala Pro Lys Arg Leu Ile Tyr Ala Ala Ser Asn Leu Gln Ser Gly
 65              70                  75                  80

Val Pro Ser Arg Phe Thr Gly Ser Gly Ser Gly Thr Glu Phe Thr Leu
                 85                  90                  95

Ile Val Ser Ser Leu Gln Pro Glu Asp Phe Ala Thr Tyr Tyr Cys Leu
            100                 105                 110

Gln His His Ser Tyr Pro Leu Thr Ser Gly Gly Thr Lys Val Glu
            115                 120                 125

Ile Lys Arg Thr Gly Ser Thr Ser Gly Ser Gly Lys Pro Gly Ser Gly
        130                 135                 140

Glu Gly Ser Glu Val Gln Val Leu Glu Ser Gly Gly Gly Leu Val Gln
145                 150                 155                 160

Pro Gly Gly Ser Leu Arg Leu Ser Cys Ala Ala Ser Gly Phe Thr Phe
                165                 170                 175

Ser Ser Tyr Ala Met Ser Trp Val Arg Gln Ala Pro Gly Lys Gly Leu
            180                 185                 190

Glu Trp Val Ser Ala Ile Ser Gly Ser Gly Gly Ser Thr Asn Tyr Ala
        195                 200                 205

Asp Ser Val Lys Gly Arg Phe Thr Ile Ser Arg Asp Asn Ser Lys Asn
210                 215                 220

Thr Leu Tyr Leu Gln Met Asn Ser Leu Arg Ala Glu Asp Thr Ala Val
225                 230                 235                 240

Tyr Tyr Cys Ala Gly Ser Ser Gly Trp Ser Glu Tyr Trp Gly Gln Gly
                245                 250                 255

Thr Leu Val Thr Val Ser Ser Ala Ser Thr Thr Thr Pro Ala Pro Arg
            260                 265                 270

Pro Pro Thr Pro Ala Pro Thr Ile Ala Ser Gln Pro Leu Ser Leu Arg
        275                 280                 285

Pro Glu Ala Cys Arg Pro Ala Ala Gly Gly Ala Val His Thr Arg Gly
290                 295                 300

Leu Asp Phe Ala Cys Asp Ile Tyr Ile Trp Ala Pro Leu Ala Gly Thr
305                 310                 315                 320

Cys Gly Val Leu Leu Leu Ser Leu Val Ile Thr Leu Tyr Cys Lys Arg
                325                 330                 335

Gly Arg Lys Lys Leu Leu Tyr Ile Phe Lys Gln Pro Phe Met Arg Pro
            340                 345                 350

Val Gln Thr Thr Gln Glu Glu Asp Gly Cys Ser Cys Arg Phe Pro Glu
        355                 360                 365

Glu Glu Glu Gly Gly Cys Glu Leu Arg Val Lys Phe Ser Arg Ser Ala
370                 375                 380

Asp Ala Pro Ala Tyr Lys Gln Gly Gln Asn Gln Leu Tyr Asn Glu Leu
385                 390                 395                 400

Asn Leu Gly Arg Arg Glu Glu Tyr Asp Val Leu Asp Lys Arg Arg Gly
                405                 410                 415

Arg Asp Pro Glu Met Gly Gly Lys Pro Arg Arg Lys Asn Pro Gln Glu
            420                 425                 430

Gly Leu Tyr Asn Glu Leu Gln Lys Asp Lys Met Ala Glu Ala Tyr Ser
        435                 440                 445

Glu Ile Gly Met Lys Gly Glu Arg Arg Arg Gly Lys Gly His Asp Gly
450                 455                 460
```

Leu Tyr Gln Gly Leu Ser Thr Ala Thr Lys Asp Thr Tyr Asp Ala Leu
465                 470                 475                 480

His Met Gln Ala Leu Pro Pro Arg
                485

<210> SEQ ID NO 8
<211> LENGTH: 567
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 8

Met Ala Leu Pro Val Thr Ala Leu Leu Leu Pro Leu Ala Leu Leu Leu
1               5                   10                  15

His Ala Ala Arg Pro Asp Ile Gln Met Thr Gln Ser Pro Ser Ser Leu
                20                  25                  30

Ser Ala Ser Val Gly Asp Arg Val Thr Ile Thr Cys Arg Ala Ser Gln
            35                  40                  45

Gly Ile Arg Asn Asn Leu Ala Trp Tyr Gln Gln Lys Pro Gly Lys Ala
    50                  55                  60

Pro Lys Arg Leu Ile Tyr Ala Ala Ser Asn Leu Gln Ser Gly Val Pro
65                  70                  75                  80

Ser Arg Phe Thr Gly Ser Gly Ser Gly Thr Glu Phe Thr Leu Ile Val
                85                  90                  95

Ser Ser Leu Gln Pro Glu Asp Phe Ala Thr Tyr Tyr Cys Leu Gln His
            100                 105                 110

His Ser Tyr Pro Leu Thr Ser Gly Gly Gly Thr Lys Val Glu Ile Lys
        115                 120                 125

Arg Thr Gly Ser Thr Ser Gly Ser Gly Lys Pro Gly Ser Gly Glu Gly
    130                 135                 140

Ser Glu Val Gln Val Leu Glu Ser Gly Gly Gly Leu Val Gln Pro Gly
145                 150                 155                 160

Gly Ser Leu Arg Leu Ser Cys Ala Ala Ser Gly Phe Thr Phe Ser Ser
                165                 170                 175

Tyr Ala Met Ser Trp Val Arg Gln Ala Pro Gly Lys Gly Leu Glu Trp
            180                 185                 190

Val Ser Ala Ile Ser Gly Ser Gly Gly Ser Thr Asn Tyr Ala Asp Ser
        195                 200                 205

Val Lys Gly Arg Phe Thr Ile Ser Arg Asp Asn Ser Lys Asn Thr Leu
    210                 215                 220

Tyr Leu Gln Met Asn Ser Leu Arg Ala Glu Asp Thr Ala Val Tyr Tyr
225                 230                 235                 240

Cys Ala Gly Ser Ser Gly Trp Ser Glu Tyr Trp Gly Gln Gly Thr Leu
                245                 250                 255

Val Thr Val Ser Ser Thr Thr Thr Pro Ala Pro Arg Pro Pro Thr Pro
            260                 265                 270

Ala Pro Thr Ile Ala Ser Gln Pro Leu Ser Leu Arg Pro Glu Ala Cys
        275                 280                 285

Arg Pro Ala Ala Gly Gly Ala Val His Thr Arg Gly Leu Asp Phe Ala
    290                 295                 300

Cys Asp Ile Tyr Ile Trp Ala Pro Leu Ala Gly Thr Cys Gly Val Leu
305                 310                 315                 320

Leu Leu Ser Leu Val Ile Thr Leu Tyr Cys Lys Arg Gly Arg Lys Lys
                325                 330                 335

Leu Leu Gly Gly Gly Gly Ser Gly Gly Gly Ser Ser Asn Ser Tyr
            340                 345                 350

Asp Ser Ser Ile Lys Val Leu Lys Gly Leu Asp Ala Val Arg Lys
            355                 360                 365

Arg Pro Gly Met Tyr Ile Gly Asp Thr Asp Gly Thr Gly Leu His
370                 375                 380

His Met Val Phe Glu Val Val Asp Asn Ala Ile Asp Glu Ala Leu Ala
385                 390                 395                 400

Gly His Cys Lys Glu Ile Ile Val Thr Ile His Ala Asp Asn Ser Val
            405                 410                 415

Ser Val Gln Asp Asp Gly Arg Gly Ile Pro Thr Gly Ile His Pro Glu
            420                 425                 430

Glu Gly Val Ser Ala Ala Glu Val Ile Met Thr Val Leu His Ala Gly
            435                 440                 445

Gly Lys Phe Asp Asp Asn Ser Tyr Lys Val Ser Gly Gly Leu His Gly
            450                 455                 460

Val Gly Val Ser Val Val Asn Ala Leu Ser Gln Lys Leu Glu Leu Val
465                 470                 475                 480

Ile Gln Arg Glu Gly Lys Ile His Arg Gln Ile Tyr Glu His Gly Val
            485                 490                 495

Pro Gln Ala Pro Leu Ala Val Thr Gly Glu Thr Glu Lys Thr Gly Thr
            500                 505                 510

Met Val Arg Phe Trp Pro Ser Leu Glu Thr Phe Thr Asn Val Thr Glu
            515                 520                 525

Phe Glu Tyr Glu Ile Leu Ala Lys Arg Leu Arg Glu Leu Ser Phe Leu
            530                 535                 540

Asn Ser Gly Val Ser Ile Arg Leu Arg Asp Lys Arg Asp Gly Lys Glu
545                 550                 555                 560

Asp His Phe His Tyr Glu Gly
            565

<210> SEQ ID NO 9
<211> LENGTH: 384
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 9

Met Ser Asn Ser Tyr Asp Ser Ser Ile Lys Val Leu Lys Gly Leu
1               5                   10                  15

Asp Ala Val Arg Lys Arg Pro Gly Met Tyr Ile Gly Asp Thr Asp Asp
            20                  25                  30

Gly Thr Gly Leu His His Met Val Phe Glu Val Val Asp Asn Ala Ile
            35                  40                  45

Asp Glu Ala Leu Ala Gly His Cys Lys Glu Ile Ile Val Thr Ile His
            50                  55                  60

Ala Asp Asn Ser Val Ser Val Gln Asp Asp Gly Arg Gly Ile Pro Thr
65                  70                  75                  80

Gly Ile His Pro Glu Glu Gly Val Ser Ala Ala Glu Val Ile Met Thr
            85                  90                  95

Val Leu His Ala Gly Gly Lys Phe Asp Asp Asn Ser Tyr Lys Val Ser
            100                 105                 110

Gly Gly Leu His Gly Val Gly Val Ser Val Val Asn Ala Leu Ser Gln

```
                    115                 120                 125
Lys Leu Glu Leu Val Ile Gln Arg Glu Gly Lys Ile His Arg Gln Ile
    130                 135                 140

Tyr Glu His Gly Val Pro Gln Ala Pro Leu Ala Val Thr Gly Glu Thr
145                 150                 155                 160

Glu Lys Thr Gly Thr Met Val Arg Phe Trp Pro Ser Leu Glu Thr Phe
                165                 170                 175

Thr Asn Val Thr Glu Phe Glu Tyr Glu Ile Leu Ala Lys Arg Leu Arg
                180                 185                 190

Glu Leu Ser Phe Leu Asn Ser Gly Val Ser Ile Arg Leu Arg Asp Lys
                195                 200                 205

Arg Asp Gly Lys Glu Asp His Phe His Tyr Glu Gly Gly Gly Gly Gly
    210                 215                 220

Ser Gly Gly Gly Gly Ser Lys Arg Gly Arg Lys Lys Leu Leu Tyr Ile
225                 230                 235                 240

Phe Lys Gln Pro Phe Met Arg Pro Val Gln Thr Thr Gln Glu Glu Asp
                245                 250                 255

Gly Cys Ser Cys Arg Phe Pro Glu Glu Glu Gly Gly Cys Glu Leu
            260                 265                 270

Arg Val Lys Phe Ser Arg Ser Ala Asp Ala Pro Ala Tyr Lys Gln Gly
                275                 280                 285

Gln Asn Gln Leu Tyr Asn Glu Leu Asn Leu Gly Arg Arg Glu Glu Tyr
    290                 295                 300

Asp Val Leu Asp Lys Arg Arg Gly Arg Asp Pro Glu Met Gly Gly Lys
305                 310                 315                 320

Pro Arg Arg Lys Asn Pro Gln Glu Gly Leu Tyr Asn Glu Leu Gln Lys
                325                 330                 335

Asp Lys Met Ala Glu Ala Tyr Ser Glu Ile Gly Met Lys Gly Glu Arg
                340                 345                 350

Arg Arg Gly Lys Gly His Asp Gly Leu Tyr Gln Gly Leu Ser Thr Ala
                355                 360                 365

Thr Lys Asp Thr Tyr Asp Ala Leu His Met Gln Ala Leu Pro Pro Arg
    370                 375                 380

<210> SEQ ID NO 10
<211> LENGTH: 439
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 10

Met Ala Leu Pro Val Thr Ala Leu Leu Leu Pro Leu Ala Leu Leu Leu
1               5                   10                  15

His Ala Ala Arg Pro Asp Ile Gln Met Thr Gln Ser Pro Ser Ser Leu
                20                  25                  30

Ser Ala Ser Val Gly Asp Arg Val Thr Ile Thr Cys Arg Ala Ser Gln
            35                  40                  45

Gly Ile Arg Asn Asn Leu Ala Trp Tyr Gln Lys Pro Gly Lys Ala
    50                  55                  60

Pro Lys Arg Leu Ile Tyr Ala Ala Ser Asn Leu Gln Ser Gly Val Pro
65                  70                  75                  80

Ser Arg Phe Thr Gly Ser Gly Ser Gly Thr Glu Phe Thr Leu Ile Val
                85                  90                  95
```

```
Ser Ser Leu Gln Pro Glu Asp Phe Ala Thr Tyr Tyr Cys Leu Gln His
            100                 105                 110

His Ser Tyr Pro Leu Thr Ser Gly Gly Gly Thr Lys Val Glu Ile Lys
        115                 120                 125

Arg Thr Gly Ser Thr Ser Gly Ser Gly Lys Pro Gly Ser Gly Glu Gly
    130                 135                 140

Ser Glu Val Gln Val Leu Glu Ser Gly Gly Gly Leu Val Gln Pro Gly
145                 150                 155                 160

Gly Ser Leu Arg Leu Ser Cys Ala Ala Ser Gly Phe Thr Phe Ser Ser
                165                 170                 175

Tyr Ala Met Ser Trp Val Arg Gln Ala Pro Gly Lys Gly Leu Glu Trp
            180                 185                 190

Val Ser Ala Ile Ser Gly Ser Gly Gly Ser Thr Asn Tyr Ala Asp Ser
        195                 200                 205

Val Lys Gly Arg Phe Thr Ile Ser Arg Asp Asn Ser Lys Asn Thr Leu
    210                 215                 220

Tyr Leu Gln Met Asn Ser Leu Arg Ala Glu Asp Thr Ala Val Tyr Tyr
225                 230                 235                 240

Cys Ala Gly Ser Ser Gly Trp Ser Glu Tyr Trp Gly Gln Gly Thr Leu
                245                 250                 255

Val Thr Val Ser Ser Thr Thr Thr Pro Ala Pro Arg Pro Pro Thr Pro
            260                 265                 270

Ala Pro Thr Ile Ala Ser Gln Pro Leu Ser Leu Arg Pro Glu Ala Cys
        275                 280                 285

Arg Pro Ala Ala Gly Gly Ala Val His Thr Arg Gly Leu Asp Phe Ala
    290                 295                 300

Cys Asp Ile Tyr Ile Trp Ala Pro Leu Ala Gly Thr Cys Gly Val Leu
305                 310                 315                 320

Leu Leu Ser Leu Val Ile Thr Leu Tyr Cys Lys Arg Gly Arg Lys Lys
                325                 330                 335

Leu Leu Gly Gly Gly Gly Ser Gly Gly Gly Ser Lys Arg Asp His
            340                 345                 350

His His His His His Gln Asp Lys Lys Thr Met Met Met Asn Glu Glu
        355                 360                 365

Asp Asp Gly Asn Gly Met Asp Glu Leu Leu Ala Val Leu Gly Tyr Lys
    370                 375                 380

Val Arg Ser Ser Glu Met Ala Asp Val Ala Gln Lys Leu Glu Gln Leu
385                 390                 395                 400

Glu Val Met Met Ser Asn Val Gln Glu Asp Asp Leu Ser Gln Leu Ala
                405                 410                 415

Thr Glu Thr Val His Tyr Asn Pro Ala Glu Leu Tyr Thr Trp Leu Asp
            420                 425                 430

Ser Met Leu Thr Asp Leu Asn
        435

<210> SEQ ID NO 11
<211> LENGTH: 509
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 11

Met Ala Ala Ser Asp Glu Val Asn Leu Ile Glu Ser Arg Thr Val Val
1               5                   10                  15
```

```
Pro Leu Asn Thr Trp Val Leu Ile Ser Asn Phe Lys Val Ala Tyr Asn
            20                  25                  30

Ile Leu Arg Arg Pro Asp Gly Thr Phe Asn Arg His Leu Ala Glu Tyr
        35                  40                  45

Leu Asp Arg Lys Val Thr Ala Asn Ala Asn Pro Val Asp Gly Val Phe
50                      55                  60

Ser Phe Asp Val Leu Ile Asp Arg Arg Ile Asn Leu Leu Ser Arg Val
65                      70                  75                  80

Tyr Arg Pro Ala Tyr Ala Asp Gln Glu Gln Pro Ser Ile Leu Asp
                85                  90                  95

Leu Glu Lys Pro Val Asp Gly Asp Ile Val Pro Val Ile Leu Phe Phe
            100                 105                 110

His Gly Gly Ser Phe Ala His Ser Ser Ala Asn Ser Ala Ile Tyr Asp
                115                 120                 125

Thr Leu Cys Arg Arg Leu Val Gly Leu Cys Lys Cys Val Val Ser
    130                 135                 140

Val Asn Tyr Arg Arg Ala Pro Glu Asn Pro Tyr Pro Cys Ala Tyr Asp
145                     150                 155                 160

Asp Gly Trp Ile Ala Leu Asn Trp Val Asn Ser Arg Ser Trp Leu Lys
                165                 170                 175

Ser Lys Lys Asp Ser Lys Val His Ile Phe Leu Ala Gly Asp Ser Ser
            180                 185                 190

Gly Gly Asn Ile Ala His Asn Val Ala Leu Arg Ala Gly Glu Ser Gly
        195                 200                 205

Ile Asp Val Leu Gly Asn Ile Leu Leu Asn Pro Met Phe Gly Gly Asn
    210                 215                 220

Glu Arg Thr Glu Ser Glu Lys Ser Leu Asp Gly Lys Tyr Phe Val Thr
225                     230                 235                 240

Val Arg Asp Arg Asp Trp Tyr Trp Lys Ala Phe Leu Pro Glu Gly Glu
            245                 250                 255

Asp Arg Glu His Pro Ala Cys Asn Pro Phe Ser Pro Arg Gly Lys Ser
            260                 265                 270

Leu Glu Gly Val Ser Phe Pro Lys Ser Leu Val Val Ala Gly Leu
        275                 280                 285

Asp Leu Ile Arg Asp Trp Gln Leu Ala Tyr Ala Glu Gly Leu Lys Lys
    290                 295                 300

Ala Gly Gln Glu Val Lys Leu Met His Leu Glu Lys Ala Thr Val Gly
305                     310                 315                 320

Phe Tyr Leu Leu Pro Asn Asn Asn His Phe His Asn Val Met Asp Glu
                325                 330                 335

Ile Ser Ala Phe Val Asn Ala Glu Cys Gly Gly Gly Ser Gly Gly
            340                 345                 350

Gly Gly Ser Lys Arg Gly Arg Lys Lys Leu Leu Tyr Ile Phe Lys Gln
            355                 360                 365

Pro Phe Met Arg Pro Val Gln Thr Thr Gln Glu Glu Asp Gly Cys Ser
        370                 375                 380

Cys Arg Phe Pro Glu Glu Glu Gly Gly Cys Glu Leu Arg Val Lys
385                     390                 395                 400

Phe Ser Arg Ser Ala Asp Ala Pro Ala Tyr Lys Gln Gly Gln Asn Gln
            405                 410                 415

Leu Tyr Asn Glu Leu Asn Leu Gly Arg Arg Glu Glu Tyr Asp Val Leu
        420                 425                 430
```

```
Asp Lys Arg Arg Gly Arg Asp Pro Glu Met Gly Gly Lys Pro Arg Arg
            435                 440                 445

Lys Asn Pro Gln Glu Gly Leu Tyr Asn Glu Leu Gln Lys Asp Lys Met
        450                 455                 460

Ala Glu Ala Tyr Ser Glu Ile Gly Met Lys Gly Glu Arg Arg Arg Gly
465                 470                 475                 480

Lys Gly His Asp Gly Leu Tyr Gln Gly Leu Ser Thr Ala Thr Lys Asp
                485                 490                 495

Thr Tyr Asp Ala Leu His Met Gln Ala Leu Pro Pro Arg
            500                 505
```

<210> SEQ ID NO 12
<211> LENGTH: 692
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 12

```
Met Ala Leu Pro Val Thr Ala Leu Leu Leu Pro Leu Ala Leu Leu Leu
1               5                   10                  15

His Ala Ala Arg Pro Asp Ile Gln Met Thr Gln Ser Pro Ser Ser Leu
                20                  25                  30

Ser Ala Ser Val Gly Asp Arg Val Thr Ile Thr Cys Arg Ala Ser Gln
            35                  40                  45

Gly Ile Arg Asn Asn Leu Ala Trp Tyr Gln Gln Lys Pro Gly Lys Ala
        50                  55                  60

Pro Lys Arg Leu Ile Tyr Ala Ala Ser Asn Leu Gln Ser Gly Val Pro
65                  70                  75                  80

Ser Arg Phe Thr Gly Ser Gly Ser Gly Thr Glu Phe Thr Leu Ile Val
                85                  90                  95

Ser Ser Leu Gln Pro Glu Asp Phe Ala Thr Tyr Tyr Cys Leu Gln His
            100                 105                 110

His Ser Tyr Pro Leu Thr Ser Gly Gly Gly Thr Lys Val Glu Ile Lys
        115                 120                 125

Arg Thr Gly Ser Thr Ser Gly Ser Gly Lys Pro Gly Ser Gly Glu Gly
130                 135                 140

Ser Glu Val Gln Val Leu Glu Ser Gly Gly Gly Leu Val Gln Pro Gly
145                 150                 155                 160

Gly Ser Leu Arg Leu Ser Cys Ala Ala Ser Gly Phe Thr Phe Ser Ser
                165                 170                 175

Tyr Ala Met Ser Trp Val Arg Gln Ala Pro Gly Lys Gly Leu Glu Trp
            180                 185                 190

Val Ser Ala Ile Ser Gly Ser Gly Gly Ser Thr Asn Tyr Ala Asp Ser
        195                 200                 205

Val Lys Gly Arg Phe Thr Ile Ser Arg Asp Asn Ser Lys Asn Thr Leu
210                 215                 220

Tyr Leu Gln Met Asn Ser Leu Arg Ala Glu Asp Thr Ala Val Tyr Tyr
225                 230                 235                 240

Cys Ala Gly Ser Ser Gly Trp Ser Glu Tyr Trp Gly Gln Gly Thr Leu
                245                 250                 255

Val Thr Val Ser Ser Thr Thr Thr Pro Ala Pro Arg Pro Pro Thr Pro
            260                 265                 270

Ala Pro Thr Ile Ala Ser Gln Pro Leu Ser Leu Arg Pro Glu Ala Cys
        275                 280                 285
```

```
Arg Pro Ala Ala Gly Gly Ala Val His Thr Arg Gly Leu Asp Phe Ala
    290                 295                 300

Cys Asp Ile Tyr Ile Trp Ala Pro Leu Ala Gly Thr Cys Gly Val Leu
305                 310                 315                 320

Leu Leu Ser Leu Val Ile Thr Leu Tyr Cys Lys Arg Gly Arg Lys Lys
                325                 330                 335

Leu Leu Gly Gly Gly Gly Ser Gly Gly Gly Ser Ala Ala Ser Asp
                340                 345                 350

Glu Val Asn Leu Ile Glu Ser Arg Thr Val Val Pro Leu Asn Thr Trp
                355                 360                 365

Val Leu Ile Ser Asn Phe Lys Val Ala Tyr Asn Ile Leu Arg Arg Pro
370                 375                 380

Asp Gly Thr Phe Asn Arg His Leu Ala Glu Tyr Leu Asp Arg Lys Val
385                 390                 395                 400

Thr Ala Asn Ala Asn Pro Val Asp Gly Val Phe Ser Phe Asp Val Leu
                405                 410                 415

Ile Asp Arg Arg Ile Asn Leu Leu Ser Arg Val Tyr Arg Pro Ala Tyr
                420                 425                 430

Ala Asp Gln Glu Gln Pro Pro Ser Ile Leu Asp Leu Glu Lys Pro Val
                435                 440                 445

Asp Gly Asp Ile Val Pro Val Ile Leu Phe Phe His Gly Gly Ser Phe
450                 455                 460

Ala His Ser Ser Ala Asn Ser Ala Ile Tyr Asp Thr Leu Cys Arg Arg
465                 470                 475                 480

Leu Val Gly Leu Cys Lys Cys Val Val Val Ser Val Asn Tyr Arg Arg
                485                 490                 495

Ala Pro Glu Asn Pro Tyr Pro Cys Ala Tyr Asp Asp Gly Trp Ile Ala
                500                 505                 510

Leu Asn Trp Val Asn Ser Arg Ser Trp Leu Lys Ser Lys Lys Asp Ser
                515                 520                 525

Lys Val His Ile Phe Leu Ala Gly Asp Ser Ser Gly Gly Asn Ile Ala
530                 535                 540

His Asn Val Ala Leu Arg Ala Gly Glu Ser Gly Ile Asp Val Leu Gly
545                 550                 555                 560

Asn Ile Leu Leu Asn Pro Met Phe Gly Gly Asn Glu Arg Thr Glu Ser
                565                 570                 575

Glu Lys Ser Leu Asp Gly Lys Tyr Phe Val Thr Val Arg Asp Arg Asp
                580                 585                 590

Trp Tyr Trp Lys Ala Phe Leu Pro Glu Gly Glu Asp Arg Glu His Pro
                595                 600                 605

Ala Cys Asn Pro Phe Ser Pro Arg Gly Lys Ser Leu Glu Gly Val Ser
610                 615                 620

Phe Pro Lys Ser Leu Val Val Ala Gly Leu Asp Leu Ile Arg Asp
625                 630                 635                 640

Trp Gln Leu Ala Tyr Ala Glu Gly Leu Lys Lys Ala Gly Gln Glu Val
                645                 650                 655

Lys Leu Met His Leu Glu Lys Ala Thr Val Gly Phe Tyr Leu Leu Pro
                660                 665                 670

Asn Asn Asn His Phe His Asn Val Met Asp Glu Ile Ser Ala Phe Val
                675                 680                 685

Asn Ala Glu Cys
                690
```

```
<210> SEQ ID NO 13
<211> LENGTH: 256
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 13

Met Lys Arg Asp His His His His His Gln Asp Lys Lys Thr Met
1               5                   10                  15

Met Met Asn Glu Glu Asp Asp Gly Asn Gly Met Asp Glu Leu Leu Ala
            20                  25                  30

Val Leu Gly Tyr Lys Val Arg Ser Ser Glu Met Ala Asp Val Ala Gln
        35                  40                  45

Lys Leu Glu Gln Leu Glu Val Met Met Ser Asn Val Gln Glu Asp Asp
50                  55                  60

Leu Ser Gln Leu Ala Thr Glu Thr Val His Tyr Asn Pro Ala Glu Leu
65                  70                  75                  80

Tyr Thr Trp Leu Asp Ser Met Leu Thr Asp Leu Asn Gly Gly Gly
                85                  90                  95

Ser Gly Gly Gly Gly Ser Lys Arg Gly Arg Lys Lys Leu Leu Tyr Ile
                100                 105                 110

Phe Lys Gln Pro Phe Met Arg Pro Val Gln Thr Thr Gln Glu Glu Asp
            115                 120                 125

Gly Cys Ser Cys Arg Phe Pro Glu Glu Glu Gly Gly Cys Glu Leu
130                 135                 140

Arg Val Lys Phe Ser Arg Ser Ala Asp Ala Pro Ala Tyr Lys Gln Gly
145                 150                 155                 160

Gln Asn Gln Leu Tyr Asn Glu Leu Asn Leu Gly Arg Arg Glu Glu Tyr
                165                 170                 175

Asp Val Leu Asp Lys Arg Arg Gly Arg Asp Pro Glu Met Gly Gly Lys
            180                 185                 190

Pro Arg Arg Lys Asn Pro Gln Glu Gly Leu Tyr Asn Glu Leu Gln Lys
        195                 200                 205

Asp Lys Met Ala Glu Ala Tyr Ser Glu Ile Gly Met Lys Gly Glu Arg
    210                 215                 220

Arg Arg Gly Lys Gly His Asp Gly Leu Tyr Gln Gly Leu Ser Thr Ala
225                 230                 235                 240

Thr Lys Asp Thr Tyr Asp Ala Leu His Met Gln Ala Leu Pro Pro Arg
                245                 250                 255

<210> SEQ ID NO 14
<211> LENGTH: 297
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 14

Gly Ser Glu Ile Gly Thr Gly Phe Pro Phe Asp Pro His Tyr Val Glu
1               5                   10                  15

Val Leu Gly Glu Arg Met His Tyr Val Asp Val Gly Pro Arg Asp Gly
            20                  25                  30

Thr Pro Val Leu Phe Leu His Gly Asn Pro Thr Ser Ser Tyr Val Trp
        35                  40                  45
```

Arg Asn Ile Ile Pro His Val Ala Pro Thr His Arg Cys Ile Ala Pro
    50                  55                  60

Asp Leu Ile Gly Met Gly Lys Ser Asp Lys Pro Asp Leu Gly Tyr Phe
65                  70                  75                  80

Phe Asp Asp His Val Arg Phe Met Asp Ala Phe Ile Glu Ala Leu Gly
                85                  90                  95

Leu Glu Glu Val Val Leu Val Ile His Asp Trp Gly Ser Ala Leu Gly
                100                 105                 110

Phe His Trp Ala Lys Arg Asn Pro Glu Arg Val Lys Gly Ile Ala Phe
            115                 120                 125

Met Glu Phe Ile Arg Pro Ile Pro Thr Trp Asp Glu Trp Pro Glu Phe
130                 135                 140

Ala Arg Glu Thr Phe Gln Ala Phe Arg Thr Thr Asp Val Gly Arg Lys
145                 150                 155                 160

Leu Ile Ile Asp Gln Asn Val Phe Ile Glu Gly Thr Leu Pro Met Gly
                165                 170                 175

Val Val Arg Pro Leu Thr Glu Val Glu Met Asp His Tyr Arg Glu Pro
            180                 185                 190

Phe Leu Asn Pro Val Asp Arg Glu Pro Leu Trp Arg Phe Pro Asn Glu
        195                 200                 205

Leu Pro Ile Ala Gly Glu Pro Ala Asn Ile Val Ala Leu Val Glu Glu
210                 215                 220

Tyr Met Asp Trp Leu His Gln Ser Pro Val Pro Lys Leu Leu Phe Trp
225                 230                 235                 240

Gly Thr Pro Gly Val Leu Ile Pro Pro Ala Glu Ala Ala Arg Leu Ala
                245                 250                 255

Lys Ser Leu Pro Asn Cys Lys Ala Val Asp Ile Gly Pro Gly Leu Asn
            260                 265                 270

Leu Leu Gln Glu Asp Asn Pro Asp Leu Ile Gly Ser Glu Ile Ala Arg
        275                 280                 285

Trp Leu Ser Thr Leu Glu Ile Ser Gly
    290                 295

<210> SEQ ID NO 15
<211> LENGTH: 182
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 15

Met Asp Lys Asp Cys Glu Met Lys Arg Thr Thr Leu Asp Ser Pro Leu
1               5                   10                  15

Gly Lys Leu Glu Leu Ser Gly Cys Glu Gln Gly Leu His Arg Ile Ile
            20                  25                  30

Phe Leu Gly Lys Gly Thr Ser Ala Ala Asp Ala Val Glu Val Pro Ala
        35                  40                  45

Pro Ala Ala Val Leu Gly Gly Pro Glu Pro Leu Met Gln Ala Thr Ala
    50                  55                  60

Trp Leu Asn Ala Tyr Phe His Gln Pro Glu Ala Ile Glu Glu Phe Pro
65                  70                  75                  80

Val Pro Ala Leu His His Pro Val Phe Gln Gln Glu Ser Phe Thr Arg
                85                  90                  95

Gln Val Leu Trp Lys Leu Leu Lys Val Val Lys Phe Gly Glu Val Ile
            100                 105                 110

```
Ser Tyr Ser His Leu Ala Ala Leu Ala Gly Asn Pro Ala Thr Ala
            115                 120                 125

Ala Val Lys Thr Ala Leu Ser Gly Asn Pro Val Pro Ile Leu Ile Pro
130                 135                 140

Cys His Arg Val Val Gln Gly Asp Leu Asp Val Gly Gly Tyr Glu Gly
145                 150                 155                 160

Gly Leu Ala Val Lys Glu Trp Leu Leu Ala His Glu Gly His Arg Leu
                165                 170                 175

Gly Lys Pro Gly Leu Gly
            180

<210> SEQ ID NO 16
<211> LENGTH: 529
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 16

Met Ala Leu Pro Val Thr Ala Leu Leu Leu Pro Leu Ala Leu Leu Leu
1               5                   10                  15

His Ala Ala Arg Pro Asp Ile Gln Met Thr Gln Ser Pro Ser Ser Leu
            20                  25                  30

Ser Ala Ser Val Gly Asp Arg Val Thr Ile Thr Cys Arg Ala Ser Gln
        35                  40                  45

Gly Ile Arg Asn Asn Leu Ala Trp Tyr Gln Gln Lys Pro Gly Lys Ala
50                  55                  60

Pro Lys Arg Leu Ile Tyr Ala Ala Ser Asn Leu Gln Ser Gly Val Pro
65                  70                  75                  80

Ser Arg Phe Thr Gly Ser Gly Ser Gly Thr Glu Phe Thr Leu Ile Val
                85                  90                  95

Ser Ser Leu Gln Pro Glu Asp Phe Ala Thr Tyr Tyr Cys Leu Gln His
            100                 105                 110

His Ser Tyr Pro Leu Thr Ser Gly Gly Thr Lys Val Glu Ile Lys
        115                 120                 125

Arg Thr Gly Ser Thr Ser Gly Ser Gly Lys Pro Gly Ser Gly Glu Gly
130                 135                 140

Ser Glu Val Gln Val Leu Glu Ser Gly Gly Gly Leu Val Gln Pro Gly
145                 150                 155                 160

Gly Ser Leu Arg Leu Ser Cys Ala Ala Ser Gly Phe Thr Phe Ser Ser
                165                 170                 175

Tyr Ala Met Ser Trp Val Arg Gln Ala Pro Gly Lys Gly Leu Glu Trp
            180                 185                 190

Val Ser Ala Ile Ser Gly Ser Gly Gly Ser Thr Asn Tyr Ala Asp Ser
        195                 200                 205

Val Lys Gly Arg Phe Thr Ile Ser Arg Asp Asn Ser Lys Asn Thr Leu
210                 215                 220

Tyr Leu Gln Met Asn Ser Leu Arg Ala Glu Asp Thr Ala Val Tyr Tyr
225                 230                 235                 240

Cys Ala Gly Ser Ser Gly Trp Ser Glu Tyr Trp Gly Gln Gly Thr Leu
                245                 250                 255

Val Thr Val Ser Ser Thr Thr Thr Pro Ala Pro Arg Pro Pro Thr Pro
            260                 265                 270

Ala Pro Thr Ile Ala Ser Gln Pro Leu Ser Leu Arg Pro Glu Ala Cys
```

```
            275                 280                 285
Arg Pro Ala Ala Gly Ala Val His Thr Arg Gly Leu Asp Phe Ala
    290                 295                 300
Cys Asp Ile Tyr Ile Trp Ala Pro Leu Ala Gly Thr Cys Gly Val Leu
305                 310                 315                 320
Leu Leu Ser Leu Val Ile Thr Leu Tyr Cys Lys Arg Gly Arg Lys Lys
                325                 330                 335
Leu Leu Gly Gly Gly Ser Gly Gly Gly Ser Asp Lys Asp Cys
                340                 345                 350
Glu Met Lys Arg Thr Thr Leu Asp Ser Pro Leu Gly Lys Leu Glu Leu
                355                 360                 365
Ser Gly Cys Glu Gln Gly Leu His Arg Ile Ile Phe Leu Gly Lys Gly
        370                 375                 380
Thr Ser Ala Ala Asp Ala Val Glu Val Pro Ala Pro Ala Ala Val Leu
385                 390                 395                 400
Gly Gly Pro Glu Pro Leu Met Gln Ala Thr Ala Trp Leu Asn Ala Tyr
                405                 410                 415
Phe His Gln Pro Glu Ala Ile Glu Glu Phe Pro Val Pro Ala Leu His
                420                 425                 430
His Pro Val Phe Gln Gln Glu Ser Phe Thr Arg Gln Val Leu Trp Lys
            435                 440                 445
Leu Leu Lys Val Val Lys Phe Gly Glu Val Ile Ser Tyr Ser His Leu
    450                 455                 460
Ala Ala Leu Ala Gly Asn Pro Ala Ala Thr Ala Ala Val Lys Thr Ala
465                 470                 475                 480
Leu Ser Gly Asn Pro Val Pro Ile Leu Ile Pro Cys His Arg Val Val
                485                 490                 495
Gln Gly Asp Leu Asp Val Gly Gly Tyr Glu Gly Gly Leu Ala Val Lys
                500                 505                 510
Glu Trp Leu Leu Ala His Glu Gly His Arg Leu Gly Lys Pro Gly Leu
        515                 520                 525
Gly

<210> SEQ ID NO 17
<211> LENGTH: 462
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 17

Met Gly Ser Glu Ile Gly Thr Gly Phe Pro Phe Asp Pro His Tyr Val
1               5                   10                  15
Glu Val Leu Gly Glu Arg Met His Tyr Val Asp Val Gly Pro Arg Asp
                20                  25                  30
Gly Thr Pro Val Leu Phe Leu His Gly Asn Pro Thr Ser Ser Tyr Val
            35                  40                  45
Trp Arg Asn Ile Ile Pro His Val Ala Pro Thr His Arg Cys Ile Ala
    50                  55                  60
Pro Asp Leu Ile Gly Met Gly Lys Ser Asp Lys Pro Asp Leu Gly Tyr
65                  70                  75                  80
Phe Phe Asp Asp His Val Arg Phe Met Asp Ala Phe Ile Glu Ala Leu
                85                  90                  95
Gly Leu Glu Glu Val Val Leu Val Ile His Asp Trp Gly Ser Ala Leu
```

```
            100                 105                 110
Gly Phe His Trp Ala Lys Arg Asn Pro Glu Arg Val Lys Gly Ile Ala
            115                 120                 125

Phe Met Glu Phe Ile Arg Pro Ile Pro Thr Trp Asp Glu Trp Pro Glu
130                 135                 140

Phe Ala Arg Glu Thr Phe Gln Ala Phe Arg Thr Thr Asp Val Gly Arg
145                 150                 155                 160

Lys Leu Ile Ile Asp Gln Asn Val Phe Ile Glu Gly Thr Leu Pro Met
                165                 170                 175

Gly Val Val Arg Pro Leu Thr Glu Val Glu Met Asp His Tyr Arg Glu
                180                 185                 190

Pro Phe Leu Asn Pro Val Asp Arg Glu Pro Leu Trp Arg Phe Pro Asn
                195                 200                 205

Glu Leu Pro Ile Ala Gly Glu Pro Ala Asn Ile Val Ala Leu Val Glu
                210                 215                 220

Glu Tyr Met Asp Trp Leu His Gln Ser Pro Val Pro Lys Leu Leu Phe
225                 230                 235                 240

Trp Gly Thr Pro Gly Val Leu Ile Pro Pro Ala Glu Ala Ala Arg Leu
                245                 250                 255

Ala Lys Ser Leu Pro Asn Cys Lys Ala Val Asp Ile Gly Pro Gly Leu
                260                 265                 270

Asn Leu Leu Gln Glu Asp Asn Pro Asp Leu Ile Gly Ser Glu Ile Ala
                275                 280                 285

Arg Trp Leu Ser Thr Leu Glu Ile Ser Gly Gly Gly Gly Ser Gly
                290                 295                 300

Gly Gly Gly Ser Lys Arg Gly Arg Lys Lys Leu Leu Tyr Ile Phe Lys
305                 310                 315                 320

Gln Pro Phe Met Arg Pro Val Gln Thr Thr Gln Glu Glu Asp Gly Cys
                325                 330                 335

Ser Cys Arg Phe Pro Glu Glu Glu Glu Gly Gly Cys Glu Leu Arg Val
                340                 345                 350

Lys Phe Ser Arg Ser Ala Asp Ala Pro Ala Tyr Lys Gln Gly Gln Asn
                355                 360                 365

Gln Leu Tyr Asn Glu Leu Asn Leu Gly Arg Arg Glu Glu Tyr Asp Val
                370                 375                 380

Leu Asp Lys Arg Arg Gly Arg Asp Pro Glu Met Gly Gly Lys Pro Arg
385                 390                 395                 400

Arg Lys Asn Pro Gln Glu Gly Leu Tyr Asn Glu Leu Gln Lys Asp Lys
                405                 410                 415

Met Ala Glu Ala Tyr Ser Glu Ile Gly Met Lys Gly Glu Arg Arg Arg
                420                 425                 430

Gly Lys Gly His Asp Gly Leu Tyr Gln Gly Leu Ser Thr Ala Thr Lys
                435                 440                 445

Asp Thr Tyr Asp Ala Leu His Met Gln Ala Leu Pro Pro Arg
                450                 455                 460

<210> SEQ ID NO 18
<211> LENGTH: 645
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 18
```

```
Met Ala Leu Pro Val Thr Ala Leu Leu Leu Pro Leu Ala Leu Leu Leu
1               5                   10                  15

His Ala Ala Arg Pro Asp Ile Gln Met Thr Gln Ser Pro Ser Ser Leu
                20                  25                  30

Ser Ala Ser Val Gly Asp Arg Val Thr Ile Thr Cys Arg Ala Ser Gln
            35                  40                  45

Gly Ile Arg Asn Asn Leu Ala Trp Tyr Gln Gln Lys Pro Gly Lys Ala
        50                  55                  60

Pro Lys Arg Leu Ile Tyr Ala Ala Ser Asn Leu Gln Ser Gly Val Pro
65                  70                  75                  80

Ser Arg Phe Thr Gly Ser Gly Ser Gly Thr Glu Phe Thr Leu Ile Val
                85                  90                  95

Ser Ser Leu Gln Pro Glu Asp Phe Ala Thr Tyr Tyr Cys Leu Gln His
            100                 105                 110

His Ser Tyr Pro Leu Thr Ser Gly Gly Thr Lys Val Glu Ile Lys
        115                 120                 125

Arg Thr Gly Ser Thr Ser Gly Ser Gly Lys Pro Gly Ser Gly Glu Gly
    130                 135                 140

Ser Glu Val Gln Val Leu Glu Ser Gly Gly Leu Val Gln Pro Gly
145                 150                 155                 160

Gly Ser Leu Arg Leu Ser Cys Ala Ala Ser Gly Phe Thr Phe Ser Ser
                165                 170                 175

Tyr Ala Met Ser Trp Val Arg Gln Ala Pro Gly Lys Gly Leu Glu Trp
            180                 185                 190

Val Ser Ala Ile Ser Gly Ser Gly Gly Ser Thr Asn Tyr Ala Asp Ser
        195                 200                 205

Val Lys Gly Arg Phe Thr Ile Ser Arg Asp Asn Ser Lys Asn Thr Leu
210                 215                 220

Tyr Leu Gln Met Asn Ser Leu Arg Ala Glu Asp Thr Ala Val Tyr Tyr
225                 230                 235                 240

Cys Ala Gly Ser Ser Gly Trp Ser Glu Tyr Trp Gly Gln Gly Thr Leu
                245                 250                 255

Val Thr Val Ser Ser Thr Thr Thr Pro Ala Pro Arg Pro Pro Thr Pro
            260                 265                 270

Ala Pro Thr Ile Ala Ser Gln Pro Leu Ser Leu Arg Pro Glu Ala Cys
        275                 280                 285

Arg Pro Ala Ala Gly Gly Ala Val His Thr Arg Gly Leu Asp Phe Ala
    290                 295                 300

Cys Asp Ile Tyr Ile Trp Ala Pro Leu Ala Gly Thr Cys Gly Val Leu
305                 310                 315                 320

Leu Leu Ser Leu Val Ile Thr Leu Tyr Cys Lys Arg Gly Arg Lys Lys
                325                 330                 335

Leu Leu Gly Gly Gly Gly Ser Gly Gly Gly Gly Ser Gly Ser Glu Ile
            340                 345                 350

Gly Thr Gly Phe Pro Phe Asp Pro His Tyr Val Glu Val Leu Gly Glu
        355                 360                 365

Arg Met His Tyr Val Asp Val Gly Pro Arg Asp Gly Thr Pro Val Leu
    370                 375                 380

Phe Leu His Gly Asn Pro Thr Ser Ser Tyr Val Trp Arg Asn Ile Ile
385                 390                 395                 400

Pro His Val Ala Pro Thr His Arg Cys Ile Ala Pro Asp Leu Ile Gly
            405                 410                 415

Met Gly Lys Ser Asp Lys Pro Asp Leu Gly Tyr Phe Phe Asp Asp His
```

```
             420                 425                 430
Val Arg Phe Met Asp Ala Phe Ile Glu Ala Leu Gly Leu Glu Glu Val
            435                 440                 445

Val Leu Val Ile His Asp Trp Gly Ser Ala Leu Gly Phe His Trp Ala
        450                 455                 460

Lys Arg Asn Pro Glu Arg Val Lys Gly Ile Ala Phe Met Glu Phe Ile
465                 470                 475                 480

Arg Pro Ile Pro Thr Trp Asp Glu Trp Pro Glu Phe Ala Arg Glu Thr
                485                 490                 495

Phe Gln Ala Phe Arg Thr Thr Asp Val Gly Arg Lys Leu Ile Ile Asp
            500                 505                 510

Gln Asn Val Phe Ile Glu Gly Thr Leu Pro Met Gly Val Val Arg Pro
        515                 520                 525

Leu Thr Glu Val Glu Met Asp His Tyr Arg Glu Pro Phe Leu Asn Pro
    530                 535                 540

Val Asp Arg Glu Pro Leu Trp Arg Phe Pro Asn Glu Leu Pro Ile Ala
545                 550                 555                 560

Gly Glu Pro Ala Asn Ile Val Ala Leu Val Glu Glu Tyr Met Asp Trp
                565                 570                 575

Leu His Gln Ser Pro Val Pro Lys Leu Leu Phe Trp Gly Thr Pro Gly
            580                 585                 590

Val Leu Ile Pro Pro Ala Glu Ala Ala Arg Leu Ala Lys Ser Leu Pro
        595                 600                 605

Asn Cys Lys Ala Val Asp Ile Gly Pro Gly Leu Asn Leu Leu Gln Glu
    610                 615                 620

Asp Asn Pro Asp Leu Ile Gly Ser Glu Ile Ala Arg Trp Leu Ser Thr
625                 630                 635                 640

Leu Glu Ile Ser Gly
                645

<210> SEQ ID NO 19
<211> LENGTH: 346
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 19

Met Asp Lys Asp Cys Glu Met Lys Arg Thr Thr Leu Asp Ser Pro Leu
1               5                   10                  15

Gly Lys Leu Glu Leu Ser Gly Cys Glu Gln Gly Leu His Arg Ile Ile
            20                  25                  30

Phe Leu Gly Lys Gly Thr Ser Ala Ala Asp Ala Val Glu Val Pro Ala
        35                  40                  45

Pro Ala Ala Val Leu Gly Gly Pro Glu Pro Leu Met Gln Ala Thr Ala
    50                  55                  60

Trp Leu Asn Ala Tyr Phe His Gln Pro Glu Ala Ile Glu Glu Phe Pro
65                  70                  75                  80

Val Pro Ala Leu His His Pro Val Phe Gln Gln Glu Ser Phe Thr Arg
                85                  90                  95

Gln Val Leu Trp Lys Leu Leu Lys Val Val Lys Phe Gly Glu Val Ile
            100                 105                 110

Ser Tyr Ser His Leu Ala Ala Leu Ala Gly Asn Pro Ala Ala Thr Ala
        115                 120                 125
```

```
Ala Val Lys Thr Ala Leu Ser Gly Asn Pro Val Pro Ile Leu Ile Pro
    130                 135                 140

Cys His Arg Val Val Gln Gly Asp Leu Asp Val Gly Tyr Glu Gly
145                 150                 155                 160

Gly Leu Ala Val Lys Glu Trp Leu Leu Ala His Glu Gly His Arg Leu
                165                 170                 175

Gly Lys Pro Gly Leu Gly Gly Gly Gly Ser Gly Gly Gly Gly Ser
            180                 185                 190

Lys Arg Gly Arg Lys Lys Leu Leu Tyr Ile Phe Lys Gln Pro Phe Met
            195                 200                 205

Arg Pro Val Gln Thr Thr Gln Glu Glu Asp Gly Cys Ser Cys Arg Phe
210                 215                 220

Pro Glu Glu Glu Glu Gly Gly Cys Glu Leu Arg Val Lys Phe Ser Arg
225                 230                 235                 240

Ser Ala Asp Ala Pro Ala Tyr Lys Gln Gly Gln Asn Gln Leu Tyr Asn
                245                 250                 255

Glu Leu Asn Leu Gly Arg Arg Glu Glu Tyr Asp Val Leu Asp Lys Arg
            260                 265                 270

Arg Gly Arg Asp Pro Glu Met Gly Gly Lys Pro Arg Arg Lys Asn Pro
            275                 280                 285

Gln Glu Gly Leu Tyr Asn Glu Leu Gln Lys Asp Lys Met Ala Glu Ala
            290                 295                 300

Tyr Ser Glu Ile Gly Met Lys Gly Glu Arg Arg Arg Gly Lys Gly His
305                 310                 315                 320

Asp Gly Leu Tyr Gln Gly Leu Ser Thr Ala Thr Lys Asp Thr Tyr Asp
                325                 330                 335

Ala Leu His Met Gln Ala Leu Pro Pro Arg
                340                 345

<210> SEQ ID NO 20
<211> LENGTH: 264
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 20

Met Ala Leu Pro Val Thr Ala Leu Leu Leu Pro Leu Ala Leu Leu Leu
1               5                   10                  15

His Ala Ala Arg Pro Gly Ser Asp Tyr Lys Asp Asp Asp Asp Lys Gly
                20                  25                  30

Gly Gly Ser Gly Gly Gly Gly Ser Thr Thr Thr Pro Ala Pro Arg
            35                  40                  45

Pro Pro Thr Pro Ala Pro Thr Ile Ala Ser Gln Pro Leu Ser Leu Arg
            50                  55                  60

Pro Glu Ala Cys Arg Pro Ala Ala Gly Gly Ala Val His Thr Arg Gly
65                  70                  75                  80

Leu Asp Phe Ala Cys Asp Ile Tyr Ile Trp Ala Pro Leu Ala Gly Thr
                85                  90                  95

Cys Gly Val Leu Leu Leu Ser Leu Val Ile Thr Leu Tyr Cys Lys Arg
                100                 105                 110

Gly Arg Lys Lys Leu Leu Tyr Ile Phe Lys Gln Pro Phe Met Arg Pro
            115                 120                 125

Val Gln Thr Thr Gln Glu Glu Asp Gly Cys Ser Cys Arg Phe Pro Glu
            130                 135                 140
```

```
Glu Glu Glu Gly Gly Cys Glu Leu Arg Val Lys Phe Ser Arg Ser Ala
145                 150                 155                 160

Asp Ala Pro Ala Tyr Lys Gln Gly Gln Asn Gln Leu Tyr Asn Glu Leu
                165                 170                 175

Asn Leu Gly Arg Arg Glu Glu Tyr Asp Val Leu Asp Lys Arg Arg Gly
            180                 185                 190

Arg Asp Pro Glu Met Gly Gly Lys Pro Arg Arg Lys Asn Pro Gln Glu
        195                 200                 205

Gly Leu Tyr Asn Glu Leu Gln Lys Asp Lys Met Ala Glu Ala Tyr Ser
    210                 215                 220

Glu Ile Gly Met Lys Gly Glu Arg Arg Arg Gly Lys Gly His Asp Gly
225                 230                 235                 240

Leu Tyr Gln Gly Leu Ser Thr Ala Thr Lys Asp Thr Tyr Asp Ala Leu
                245                 250                 255

His Met Gln Ala Leu Pro Pro Arg
            260

<210> SEQ ID NO 21
<211> LENGTH: 266
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 21

Met Ala Leu Pro Val Thr Ala Leu Leu Leu Pro Leu Ala Leu Leu Leu
1               5                   10                  15

His Ala Ala Arg Pro Gly Ser Glu Gln Lys Leu Ile Ser Glu Glu Asp
            20                  25                  30

Leu Gly Gly Gly Gly Ser Gly Gly Gly Gly Ser Thr Thr Thr Pro Ala
        35                  40                  45

Pro Arg Pro Pro Thr Pro Ala Pro Thr Ile Ala Ser Gln Pro Leu Ser
    50                  55                  60

Leu Arg Pro Glu Ala Cys Arg Pro Ala Ala Gly Gly Ala Val His Thr
65                  70                  75                  80

Arg Gly Leu Asp Phe Ala Cys Asp Ile Tyr Ile Trp Ala Pro Leu Ala
                85                  90                  95

Gly Thr Cys Gly Val Leu Leu Leu Ser Leu Val Ile Thr Leu Tyr Cys
            100                 105                 110

Lys Arg Gly Arg Lys Lys Leu Leu Tyr Ile Phe Lys Gln Pro Phe Met
        115                 120                 125

Arg Pro Val Gln Thr Thr Gln Glu Glu Asp Gly Cys Ser Cys Arg Phe
    130                 135                 140

Pro Glu Glu Glu Glu Gly Gly Cys Glu Leu Arg Val Lys Phe Ser Arg
145                 150                 155                 160

Ser Ala Asp Ala Pro Ala Tyr Lys Gln Gly Gln Asn Gln Leu Tyr Asn
                165                 170                 175

Glu Leu Asn Leu Gly Arg Arg Glu Glu Tyr Asp Val Leu Asp Lys Arg
            180                 185                 190

Arg Gly Arg Asp Pro Glu Met Gly Gly Lys Pro Arg Arg Lys Asn Pro
        195                 200                 205

Gln Glu Gly Leu Tyr Asn Glu Leu Gln Lys Asp Lys Met Ala Glu Ala
    210                 215                 220

Tyr Ser Glu Ile Gly Met Lys Gly Glu Arg Arg Arg Gly Lys Gly His
```

```
            225                 230                 235                 240

Asp Gly Leu Tyr Gln Gly Leu Ser Thr Ala Thr Lys Asp Thr Tyr Asp
                245                 250                 255

Ala Leu His Met Gln Ala Leu Pro Pro Arg
            260                 265

<210> SEQ ID NO 22
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 22

Glu Glu Gln Lys Leu Ile Ser Glu Glu Asp Leu
1               5                   10

<210> SEQ ID NO 23
<211> LENGTH: 37
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 23

Glu Glu Gln Lys Leu Ile Ser Glu Glu Asp Leu Gly Gly Gly Gly Ser
1               5                   10                  15

Gly Gly Gly Gly Ser Gly Gly Gly Gly Ser Glu Glu Gln Lys Leu Ile
            20                  25                  30

Ser Glu Glu Asp Leu
        35

<210> SEQ ID NO 24
<211> LENGTH: 63
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 24

Glu Glu Gln Lys Leu Ile Ser Glu Glu Asp Leu Gly Gly Gly Gly Ser
1               5                   10                  15

Gly Gly Gly Gly Ser Gly Gly Gly Gly Ser Glu Glu Gln Lys Leu Ile
            20                  25                  30

Ser Glu Glu Asp Leu Gly Gly Gly Gly Ser Gly Gly Gly Gly Ser Gly
        35                  40                  45

Gly Gly Gly Ser Glu Glu Gln Lys Leu Ile Ser Glu Glu Asp Leu
    50                  55                  60

<210> SEQ ID NO 25
<211> LENGTH: 89
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 25

Glu Glu Gln Lys Leu Ile Ser Glu Glu Asp Leu Gly Gly Gly Gly Ser
1               5                   10                  15
```

Gly Gly Gly Gly Ser Gly Gly Gly Ser Glu Glu Gln Lys Leu Ile
            20                  25                  30

Ser Glu Glu Asp Leu Gly Gly Gly Ser Gly Gly Gly Gly Ser Gly
        35                  40                  45

Gly Gly Gly Ser Glu Glu Gln Lys Leu Ile Ser Glu Glu Asp Leu Gly
65              55                  60

Gly Gly Gly Ser Gly Gly Gly Ser Gly Gly Gly Ser Glu Glu
65                  70                  75                  80

Gln Lys Leu Ile Ser Glu Glu Asp Leu
                85

<210> SEQ ID NO 26
<211> LENGTH: 338
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 26

Met Ala Leu Pro Val Thr Ala Leu Leu Leu Pro Leu Ala Leu Leu
1               5                   10                  15

His Ala Ala Arg Pro Asp Ile Gln Met Thr Gln Ser Pro Ser Ser Leu
                20                  25                  30

Ser Ala Ser Val Gly Asp Arg Val Thr Ile Thr Cys Arg Ala Ser Gln
            35                  40                  45

Gly Ile Arg Asn Asn Leu Ala Trp Tyr Gln Gln Lys Pro Gly Lys Ala
        50                  55                  60

Pro Lys Arg Leu Ile Tyr Ala Ala Ser Asn Leu Gln Ser Gly Val Pro
65                  70                  75                  80

Ser Arg Phe Thr Gly Ser Gly Ser Gly Thr Glu Phe Thr Leu Ile Val
                85                  90                  95

Ser Ser Leu Gln Pro Glu Asp Phe Ala Thr Tyr Tyr Cys Leu Gln His
            100                 105                 110

His Ser Tyr Pro Leu Thr Ser Gly Gly Gly Thr Lys Val Glu Ile Lys
        115                 120                 125

Arg Thr Gly Ser Thr Ser Gly Ser Gly Lys Pro Gly Ser Gly Glu Gly
    130                 135                 140

Ser Glu Val Gln Val Leu Glu Ser Gly Gly Gly Leu Val Gln Pro Gly
145                 150                 155                 160

Gly Ser Leu Arg Leu Ser Cys Ala Ala Ser Gly Phe Thr Phe Ser Ser
                165                 170                 175

Tyr Ala Met Ser Trp Val Arg Gln Ala Pro Gly Lys Gly Leu Glu Trp
            180                 185                 190

Val Ser Ala Ile Ser Gly Ser Gly Gly Ser Thr Asn Tyr Ala Asp Ser
        195                 200                 205

Val Lys Gly Arg Phe Thr Ile Ser Arg Asp Asn Ser Lys Asn Thr Leu
    210                 215                 220

Tyr Leu Gln Met Asn Ser Leu Arg Ala Glu Asp Thr Ala Val Tyr Tyr
225                 230                 235                 240

Cys Ala Gly Ser Ser Gly Trp Ser Glu Tyr Trp Gly Gln Gly Thr Leu
                245                 250                 255

Val Thr Val Ser Ser Thr Thr Thr Pro Ala Pro Arg Pro Pro Thr Pro
            260                 265                 270

Ala Pro Thr Ile Ala Ser Gln Pro Leu Ser Leu Arg Pro Glu Ala Cys
        275                 280                 285

Arg Pro Ala Ala Gly Gly Ala Val His Thr Arg Gly Leu Asp Phe Ala
            290                 295                 300

Cys Asp Ile Tyr Ile Trp Ala Pro Leu Ala Gly Thr Cys Gly Val Leu
305                 310                 315                 320

Leu Leu Ser Leu Val Ile Thr Leu Tyr Cys Lys Arg Gly Arg Lys Lys
                325                 330                 335

Leu Leu

<210> SEQ ID NO 27
<211> LENGTH: 501
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 27

Met Ala Leu Pro Val Thr Ala Leu Leu Leu Pro Leu Ala Leu Leu Leu
1               5                   10                  15

His Ala Ala Arg Pro Gly Ser Asp Ile Val Leu Thr Gln Ser Pro Ala
            20                  25                  30

Ser Leu Ala Val Ser Leu Gly Gln Arg Ala Thr Ile Ser Cys Arg Ala
        35                  40                  45

Ser Glu Ser Val Asp Asn Tyr Gly Phe Ser Phe Met Asn Trp Phe Gln
50                  55                  60

Gln Lys Pro Gly Gln Pro Pro Lys Leu Leu Ile Tyr Ala Ile Ser Asn
65                  70                  75                  80

Arg Gly Ser Gly Val Pro Ala Arg Phe Ser Gly Ser Gly Ser Gly Thr
                85                  90                  95

Asp Phe Ser Leu Asn Ile His Pro Val Glu Asp Asp Pro Ala Met
            100                 105                 110

Tyr Phe Cys Gln Gln Thr Lys Glu Val Pro Trp Thr Phe Gly Gly Gly
        115                 120                 125

Thr Lys Leu Glu Ile Lys Gly Gly Gly Gly Ser Gly Gly Gly Gly Ser
130                 135                 140

Gly Gly Gly Gly Ser Glu Val His Leu Val Glu Ser Gly Gly Asp Leu
145                 150                 155                 160

Val Lys Pro Gly Gly Ser Leu Lys Leu Ser Cys Ala Ala Ser Gly Phe
                165                 170                 175

Thr Phe Ser His Tyr Gly Met Ser Trp Val Arg Gln Thr Pro Asp Lys
            180                 185                 190

Arg Leu Glu Trp Val Ala Thr Ile Gly Ser Arg Gly Thr Tyr Thr His
        195                 200                 205

Tyr Pro Asp Ser Val Lys Gly Arg Phe Thr Ile Ser Arg Asp Asn Asp
210                 215                 220

Lys Asn Ala Leu Tyr Leu Gln Met Asn Ser Leu Lys Ser Glu Asp Thr
225                 230                 235                 240

Ala Met Tyr Tyr Cys Ala Arg Arg Ser Glu Phe Tyr Tyr Tyr Gly Asn
                245                 250                 255

Thr Tyr Tyr Tyr Ser Ala Met Asp Tyr Trp Gly Gln Gly Ala Ser Val
            260                 265                 270

Thr Val Ser Ser Ala Ser Thr Thr Thr Pro Ala Pro Arg Pro Pro Thr
        275                 280                 285

Pro Ala Pro Thr Ile Ala Ser Gln Pro Leu Ser Leu Arg Pro Glu Ala
290                 295                 300

```
Cys Arg Pro Ala Ala Gly Gly Ala Val His Thr Arg Gly Leu Asp Phe
305                 310                 315                 320

Ala Cys Asp Ile Tyr Ile Trp Ala Pro Leu Ala Gly Thr Cys Gly Val
                325                 330                 335

Leu Leu Leu Ser Leu Val Ile Thr Leu Tyr Cys Lys Arg Gly Arg Lys
            340                 345                 350

Lys Leu Leu Tyr Ile Phe Lys Gln Pro Phe Met Arg Pro Val Gln Thr
        355                 360                 365

Thr Gln Glu Glu Asp Gly Cys Ser Cys Arg Phe Pro Glu Glu Glu Glu
    370                 375                 380

Gly Gly Cys Glu Leu Arg Val Lys Phe Ser Arg Ser Ala Asp Ala Pro
385                 390                 395                 400

Ala Tyr Lys Gln Gly Gln Asn Gln Leu Tyr Asn Glu Leu Asn Leu Gly
                405                 410                 415

Arg Arg Glu Glu Tyr Asp Val Leu Asp Lys Arg Arg Gly Arg Asp Pro
            420                 425                 430

Glu Met Gly Gly Lys Pro Arg Arg Lys Asn Pro Gln Glu Gly Leu Tyr
        435                 440                 445

Asn Glu Leu Gln Lys Asp Lys Met Ala Glu Ala Tyr Ser Glu Ile Gly
    450                 455                 460

Met Lys Gly Glu Arg Arg Arg Gly Lys Gly His Asp Gly Leu Tyr Gln
465                 470                 475                 480

Gly Leu Ser Thr Ala Thr Lys Asp Thr Tyr Asp Ala Leu His Met Gln
                485                 490                 495

Ala Leu Pro Pro Arg
            500

<210> SEQ ID NO 28
<211> LENGTH: 367
<212> TYPE: PRT
<213> ORGANISM: Homo sapiens

<400> SEQUENCE: 28

Met Ala Leu Pro Val Thr Ala Leu Leu Leu Pro Leu Ala Leu Leu Leu
1               5                   10                  15

His Ala Ala Arg Pro Pro Gly Trp Phe Leu Asp Ser Pro Asp Arg Pro
            20                  25                  30

Trp Asn Pro Pro Thr Phe Ser Pro Ala Leu Leu Val Val Thr Glu Gly
        35                  40                  45

Asp Asn Ala Thr Phe Thr Cys Ser Phe Ser Asn Thr Ser Glu Ser Phe
    50                  55                  60

Val Leu Asn Trp Tyr Arg Met Ser Pro Ser Asn Gln Thr Asp Lys Leu
65                  70                  75                  80

Ala Ala Phe Pro Glu Asp Arg Ser Gln Pro Gly Gln Asp Cys Arg Phe
                85                  90                  95

Arg Val Thr Gln Leu Pro Asn Gly Arg Asp Phe His Met Ser Val Val
            100                 105                 110

Arg Ala Arg Arg Asn Asp Ser Gly Thr Tyr Leu Cys Gly Ala Ile Ser
        115                 120                 125

Leu Ala Pro Lys Ala Gln Ile Lys Glu Ser Leu Arg Ala Glu Leu Arg
    130                 135                 140

Val Thr Glu Arg Arg Ala Glu Val Pro Thr Ala His Pro Ser Pro Ser
145                 150                 155                 160

Pro Arg Pro Ala Gly Gln Phe Gln Thr Leu Val Thr Thr Thr Pro Ala
```

```
            165                 170                 175
Pro Arg Pro Pro Thr Pro Ala Pro Thr Ile Ala Ser Gln Pro Leu Ser
            180                 185                 190

Leu Arg Pro Glu Ala Cys Arg Pro Ala Gly Gly Ala Val His Thr
        195                 200                 205

Arg Gly Leu Asp Phe Ala Cys Asp Ile Tyr Ile Trp Ala Pro Leu Ala
    210                 215                 220

Gly Thr Cys Gly Val Leu Leu Ser Leu Val Ile Thr Leu Tyr Cys
225                 230                 235                 240

Lys Arg Gly Arg Lys Lys Leu Leu Gly Gly Gly Ser Gly Gly Gly
                245                 250                 255

Gly Ser Gly Val Gln Val Glu Thr Ile Ser Pro Gly Asp Gly Arg Thr
            260                 265                 270

Phe Pro Lys Arg Gly Gln Thr Cys Val Val His Tyr Thr Gly Met Leu
        275                 280                 285

Glu Asp Gly Lys Lys Phe Asp Ser Ser Arg Asp Arg Asn Lys Pro Phe
    290                 295                 300

Lys Phe Met Leu Gly Lys Gln Glu Val Ile Arg Gly Trp Glu Glu Gly
305                 310                 315                 320

Val Ala Gln Met Ser Val Gly Gln Arg Ala Lys Leu Thr Ile Ser Pro
                325                 330                 335

Asp Tyr Ala Tyr Gly Ala Thr Gly His Pro Gly Ile Ile Pro Pro His
            340                 345                 350

Ala Thr Leu Val Phe Asp Val Glu Leu Leu Lys Leu Glu Thr Ser
        355                 360                 365

<210> SEQ ID NO 29
<211> LENGTH: 356
<212> TYPE: PRT
<213> ORGANISM: Homo sapiens

<400> SEQUENCE: 29

Met Ala Leu Pro Val Thr Ala Leu Leu Leu Pro Leu Ala Leu Leu Leu
1               5                   10                  15

His Ala Ala Arg Pro Pro Gly Trp Phe Leu Asp Ser Pro Asp Arg Pro
                20                  25                  30

Trp Asn Pro Pro Thr Phe Ser Pro Ala Leu Leu Val Val Thr Glu Gly
            35                  40                  45

Asp Asn Ala Thr Phe Thr Cys Ser Phe Ser Asn Thr Ser Glu Ser Phe
        50                  55                  60

Val Leu Asn Trp Tyr Arg Met Ser Pro Ser Asn Gln Thr Asp Lys Leu
65                  70                  75                  80

Ala Ala Phe Pro Glu Asp Arg Ser Gln Pro Gly Gln Asp Cys Arg Phe
                85                  90                  95

Arg Val Thr Gln Leu Pro Asn Gly Arg Asp Phe His Met Ser Val Val
            100                 105                 110

Arg Ala Arg Arg Asn Asp Ser Gly Thr Tyr Leu Cys Gly Ala Ile Ser
        115                 120                 125

Leu Ala Pro Lys Ala Gln Ile Lys Glu Ser Leu Arg Ala Glu Leu Arg
    130                 135                 140

Val Thr Glu Arg Arg Ala Glu Val Pro Thr Ala His Pro Ser Pro Ser
145                 150                 155                 160

Pro Arg Pro Ala Gly Gln Phe Gln Thr Leu Val Thr Thr Thr Pro Ala
                165                 170                 175
```

```
Pro Arg Pro Pro Thr Pro Ala Pro Thr Ile Ala Ser Gln Pro Leu Ser
            180                 185                 190

Leu Arg Pro Glu Ala Cys Arg Pro Ala Ala Gly Gly Ala Val His Thr
        195                 200                 205

Arg Gly Leu Asp Phe Ala Cys Asp Ile Tyr Ile Trp Ala Pro Leu Ala
    210                 215                 220

Gly Thr Cys Gly Val Leu Leu Leu Ser Leu Val Ile Thr Leu Tyr Cys
225                 230                 235                 240

Lys Arg Gly Arg Lys Lys Leu Leu Gly Gly Gly Ser Gly Gly Gly
                245                 250                 255

Gly Ser Ala Ser Arg Ile Leu Trp His Glu Met Trp His Glu Gly Leu
        260                 265                 270

Glu Glu Ala Ser Arg Leu Tyr Phe Gly Glu Arg Asn Val Lys Gly Met
    275                 280                 285

Phe Glu Val Leu Glu Pro Leu His Ala Met Met Glu Arg Gly Pro Gln
    290                 295                 300

Thr Leu Lys Glu Thr Ser Phe Asn Gln Ala Tyr Gly Arg Asp Leu Met
305                 310                 315                 320

Glu Ala Gln Glu Trp Cys Arg Lys Tyr Met Lys Ser Gly Asn Val Lys
                325                 330                 335

Asp Leu Gln Ala Trp Asp Leu Tyr Tyr His Val Phe Arg Arg Ile
            340                 345                 350

Ser Lys Thr Ser
        355

<210> SEQ ID NO 30
<211> LENGTH: 446
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 30

Met Ala Leu Pro Val Thr Ala Leu Leu Leu Pro Leu Ala Leu Leu Leu
1               5                   10                  15

His Ala Ala Arg Pro Asp Ile Gln Met Thr Gln Ser Pro Ser Ser Leu
            20                  25                  30

Ser Ala Ser Val Gly Asp Arg Val Thr Ile Thr Cys Arg Ala Ser Gln
        35                  40                  45

Gly Ile Arg Asn Asn Leu Ala Trp Tyr Gln Gln Lys Pro Gly Lys Ala
    50                  55                  60

Pro Lys Arg Leu Ile Tyr Ala Ala Ser Asn Leu Gln Ser Gly Val Pro
65                  70                  75                  80

Ser Arg Phe Thr Gly Ser Gly Ser Gly Thr Glu Phe Thr Leu Ile Val
                85                  90                  95

Ser Ser Leu Gln Pro Glu Asp Phe Ala Thr Tyr Tyr Cys Leu Gln His
            100                 105                 110

His Ser Tyr Pro Leu Thr Ser Gly Gly Gly Thr Lys Val Glu Ile Lys
        115                 120                 125

Arg Thr Gly Ser Thr Ser Gly Ser Gly Lys Pro Gly Ser Gly Glu Gly
    130                 135                 140

Ser Glu Val Gln Val Leu Glu Ser Gly Gly Gly Leu Val Gln Pro Gly
145                 150                 155                 160

Gly Ser Leu Arg Leu Ser Cys Ala Ala Ser Gly Phe Thr Phe Ser Ser
                165                 170                 175
```

Tyr Ala Met Ser Trp Val Arg Gln Ala Pro Gly Lys Gly Leu Glu Trp
            180                 185                 190

Val Ser Ala Ile Ser Gly Ser Gly Gly Ser Thr Asn Tyr Ala Asp Ser
            195                 200                 205

Val Lys Gly Arg Phe Thr Ile Ser Arg Asp Asn Ser Lys Asn Thr Leu
210                 215                 220

Tyr Leu Gln Met Asn Ser Leu Arg Ala Glu Asp Thr Ala Val Tyr Tyr
225                 230                 235                 240

Cys Ala Gly Ser Ser Gly Trp Ser Glu Tyr Trp Gln Gly Thr Leu
                245                 250                 255

Val Thr Val Ser Ser Lys Arg Gly Arg Lys Lys Leu Leu Gly Gly
            260                 265                 270

Gly Ser Gly Gly Gly Ser Ala Ser Arg Ile Leu Trp His Glu Met
            275                 280                 285

Trp His Glu Gly Leu Glu Glu Ala Ser Arg Leu Tyr Phe Gly Glu Arg
            290                 295                 300

Asn Val Lys Gly Met Phe Glu Val Leu Glu Pro Leu His Ala Met Met
305                 310                 315                 320

Glu Arg Gly Pro Gln Thr Leu Lys Glu Thr Ser Phe Asn Gln Ala Tyr
                325                 330                 335

Gly Arg Asp Leu Met Glu Ala Gln Glu Trp Cys Arg Lys Tyr Met Lys
            340                 345                 350

Ser Gly Asn Val Lys Asp Leu Leu Gln Ala Trp Asp Leu Tyr Tyr His
            355                 360                 365

Val Phe Arg Arg Ile Ser Lys Thr Ser Thr Thr Thr Pro Ala Pro Arg
370                 375                 380

Pro Pro Thr Pro Ala Pro Thr Ile Ala Ser Gln Pro Leu Ser Leu Arg
385                 390                 395                 400

Pro Glu Ala Cys Arg Pro Ala Ala Gly Gly Ala Val His Thr Arg Gly
                405                 410                 415

Leu Asp Phe Ala Cys Asp Ile Tyr Ile Trp Ala Pro Leu Ala Gly Thr
            420                 425                 430

Cys Gly Val Leu Leu Leu Ser Leu Val Ile Thr Leu Tyr Cys
            435                 440                 445

<210> SEQ ID NO 31
<211> LENGTH: 457
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 31

Met Ala Leu Pro Val Thr Ala Leu Leu Leu Pro Leu Ala Leu Leu Leu
1               5                   10                  15

His Ala Ala Arg Pro Asp Ile Gln Met Thr Gln Ser Pro Ser Ser Leu
            20                  25                  30

Ser Ala Ser Val Gly Asp Arg Val Thr Ile Thr Cys Arg Ala Ser Gln
        35                  40                  45

Gly Ile Arg Asn Asn Leu Ala Trp Tyr Gln Gln Lys Pro Gly Lys Ala
    50                  55                  60

Pro Lys Arg Leu Ile Tyr Ala Ala Ser Asn Leu Gln Ser Gly Val Pro
65                  70                  75                  80

Ser Arg Phe Thr Gly Ser Gly Ser Gly Thr Glu Phe Thr Leu Ile Val

```
                    85                  90                  95
Ser Ser Leu Gln Pro Glu Asp Phe Ala Thr Tyr Tyr Cys Leu Gln His
                100                 105                 110

His Ser Tyr Pro Leu Thr Ser Gly Gly Thr Lys Val Glu Ile Lys
            115                 120                 125

Arg Thr Gly Ser Thr Ser Gly Ser Gly Lys Pro Gly Ser Gly Glu Gly
        130                 135                 140

Ser Glu Val Gln Val Leu Glu Ser Gly Gly Leu Val Gln Pro Gly
145                 150                 155                 160

Gly Ser Leu Arg Leu Ser Cys Ala Ala Ser Gly Phe Thr Phe Ser Ser
                165                 170                 175

Tyr Ala Met Ser Trp Val Arg Gln Ala Pro Gly Lys Gly Leu Glu Trp
            180                 185                 190

Val Ser Ala Ile Ser Gly Ser Gly Gly Ser Thr Asn Tyr Ala Asp Ser
                195                 200                 205

Val Lys Gly Arg Phe Thr Ile Ser Arg Asp Asn Ser Lys Asn Thr Leu
    210                 215                 220

Tyr Leu Gln Met Asn Ser Leu Arg Ala Glu Asp Thr Ala Val Tyr Tyr
225                 230                 235                 240

Cys Ala Gly Ser Ser Gly Trp Ser Glu Tyr Trp Gly Gln Gly Thr Leu
                245                 250                 255

Val Thr Val Ser Ser Lys Arg Gly Arg Lys Leu Leu Gly Gly Gly
            260                 265                 270

Gly Ser Gly Gly Gly Gly Ser Gly Val Gln Val Glu Thr Ile Ser Pro
        275                 280                 285

Gly Asp Gly Arg Thr Phe Pro Lys Arg Gly Gln Thr Cys Val Val His
    290                 295                 300

Tyr Thr Gly Met Leu Glu Asp Gly Lys Lys Phe Asp Ser Ser Arg Asp
305                 310                 315                 320

Arg Asn Lys Pro Phe Lys Phe Met Leu Gly Lys Gln Glu Val Ile Arg
                325                 330                 335

Gly Trp Glu Glu Gly Val Ala Gln Met Ser Val Gly Gln Arg Ala Lys
            340                 345                 350

Leu Thr Ile Ser Pro Asp Tyr Ala Tyr Gly Ala Thr Gly His Pro Gly
        355                 360                 365

Ile Ile Pro Pro His Ala Thr Leu Val Phe Asp Val Glu Leu Leu Lys
    370                 375                 380

Leu Glu Thr Ser Thr Thr Thr Pro Ala Pro Arg Pro Pro Thr Pro Ala
385                 390                 395                 400

Pro Thr Ile Ala Ser Gln Pro Leu Ser Leu Arg Pro Glu Ala Cys Arg
                405                 410                 415

Pro Ala Ala Gly Gly Ala Val His Thr Arg Gly Leu Asp Phe Ala Cys
            420                 425                 430

Asp Ile Tyr Ile Trp Ala Pro Leu Ala Gly Thr Cys Gly Val Leu Leu
        435                 440                 445

Leu Ser Leu Val Ile Thr Leu Tyr Cys
450                 455
```

<210> SEQ ID NO 32
<211> LENGTH: 351
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 32

```
Met Ala Leu Pro Val Thr Ala Leu Leu Pro Leu Ala Leu Leu Leu
1               5                   10                  15

His Ala Ala Arg Ala Ser Arg Ile Leu Trp His Glu Met Trp His Glu
            20                  25                  30

Gly Leu Glu Glu Ala Ser Arg Leu Tyr Phe Gly Glu Arg Asn Val Lys
                35                  40                  45

Gly Met Phe Glu Val Leu Glu Pro Leu His Ala Met Met Glu Arg Gly
    50                  55                  60

Pro Gln Thr Leu Lys Glu Thr Ser Phe Asn Gln Ala Tyr Gly Arg Asp
65                  70                  75                  80

Leu Met Glu Ala Gln Glu Trp Cys Arg Lys Tyr Met Lys Ser Gly Asn
                85                  90                  95

Val Lys Asp Leu Leu Gln Ala Trp Asp Leu Tyr Tyr His Val Phe Arg
                100                 105                 110

Arg Ile Ser Lys Thr Ser Thr Thr Pro Ala Pro Arg Pro Pro Thr
                115                 120                 125

Pro Ala Pro Thr Ile Ala Ser Gln Pro Leu Ser Leu Arg Pro Glu Ala
    130                 135                 140

Cys Arg Pro Ala Ala Gly Gly Ala Val His Thr Arg Gly Leu Asp Phe
145                 150                 155                 160

Ala Cys Asp Ile Tyr Ile Trp Ala Pro Leu Ala Gly Thr Cys Gly Val
                165                 170                 175

Leu Leu Leu Ser Leu Val Ile Thr Leu Tyr Cys Gly Gly Gly Ser
                180                 185                 190

Gly Gly Gly Gly Ser Lys Arg Gly Arg Lys Lys Leu Leu Tyr Ile Phe
            195                 200                 205

Lys Gln Pro Phe Met Arg Pro Val Gln Thr Thr Gln Glu Glu Asp Gly
    210                 215                 220

Cys Ser Cys Arg Phe Pro Glu Glu Glu Glu Gly Gly Cys Glu Leu Arg
225                 230                 235                 240

Val Lys Phe Ser Arg Ser Ala Asp Ala Pro Ala Tyr Lys Gln Gly Gln
                245                 250                 255

Asn Gln Leu Tyr Asn Glu Leu Asn Leu Gly Arg Arg Glu Glu Tyr Asp
                260                 265                 270

Val Leu Asp Lys Arg Arg Gly Arg Asp Pro Glu Met Gly Gly Lys Pro
                275                 280                 285

Arg Arg Lys Asn Pro Gln Glu Gly Leu Tyr Asn Glu Leu Gln Lys Asp
    290                 295                 300

Lys Met Ala Glu Ala Tyr Ser Glu Ile Gly Met Lys Gly Glu Arg Arg
305                 310                 315                 320

Arg Gly Lys Gly His Asp Gly Leu Tyr Gln Gly Leu Ser Thr Ala Thr
                325                 330                 335

Lys Asp Thr Tyr Asp Ala Leu His Met Gln Ala Leu Pro Pro Arg
                340                 345                 350
```

<210> SEQ ID NO 33
<211> LENGTH: 362
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 33

```
Met Ala Leu Pro Val Thr Ala Leu Leu Leu Pro Leu Ala Leu Leu Leu
1               5                   10                  15

His Ala Ala Arg Gly Val Gln Val Glu Thr Ile Ser Pro Gly Asp Gly
            20                  25                  30

Arg Thr Phe Pro Lys Arg Gly Gln Thr Cys Val Val His Tyr Thr Gly
        35                  40                  45

Met Leu Glu Asp Gly Lys Lys Phe Asp Ser Ser Arg Asp Arg Asn Lys
50                  55                  60

Pro Phe Lys Phe Met Leu Gly Lys Gln Glu Val Ile Arg Gly Trp Glu
65                  70                  75                  80

Glu Gly Val Ala Gln Met Ser Val Gly Gln Arg Ala Lys Leu Thr Ile
                85                  90                  95

Ser Pro Asp Tyr Ala Tyr Gly Ala Thr Gly His Pro Gly Ile Ile Pro
            100                 105                 110

Pro His Ala Thr Leu Val Phe Asp Val Glu Leu Leu Lys Leu Glu Thr
        115                 120                 125

Ser Thr Thr Thr Pro Ala Pro Arg Pro Pro Thr Pro Ala Pro Thr Ile
130                 135                 140

Ala Ser Gln Pro Leu Ser Leu Arg Pro Glu Ala Cys Arg Pro Ala Ala
145                 150                 155                 160

Gly Gly Ala Val His Thr Arg Gly Leu Asp Phe Ala Cys Asp Ile Tyr
                165                 170                 175

Ile Trp Ala Pro Leu Ala Gly Thr Cys Gly Val Leu Leu Leu Ser Leu
            180                 185                 190

Val Ile Thr Leu Tyr Cys Gly Gly Gly Ser Gly Gly Gly Ser
            195                 200                 205

Lys Arg Gly Arg Lys Lys Leu Leu Tyr Ile Phe Lys Gln Pro Phe Met
210                 215                 220

Arg Pro Val Gln Thr Thr Gln Glu Glu Asp Gly Cys Ser Cys Arg Phe
225                 230                 235                 240

Pro Glu Glu Glu Glu Gly Gly Cys Glu Leu Arg Val Lys Phe Ser Arg
                245                 250                 255

Ser Ala Asp Ala Pro Ala Tyr Lys Gln Gly Gln Asn Gln Leu Tyr Asn
            260                 265                 270

Glu Leu Asn Leu Gly Arg Arg Glu Glu Tyr Asp Val Leu Asp Lys Arg
        275                 280                 285

Arg Gly Arg Asp Pro Glu Met Gly Gly Lys Pro Arg Arg Lys Asn Pro
290                 295                 300

Gln Glu Gly Leu Tyr Asn Glu Leu Gln Lys Asp Lys Met Ala Glu Ala
305                 310                 315                 320

Tyr Ser Glu Ile Gly Met Lys Gly Glu Arg Arg Arg Gly Lys Gly His
                325                 330                 335

Asp Gly Leu Tyr Gln Gly Leu Ser Thr Ala Thr Lys Asp Thr Tyr Asp
            340                 345                 350

Ala Leu His Met Gln Ala Leu Pro Pro Arg
        355                 360

<210> SEQ ID NO 34
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide
```

```
<400> SEQUENCE: 34
ggaggtccct caccttcta                                                   19

<210> SEQ ID NO 35
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 35
cggaggatct tatgctgaa                                                   19

<210> SEQ ID NO 36
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 36
cccgcttcca gatcataca                                                   19

<210> SEQ ID NO 37
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 37
ggagacctca acaagatat                                                   19

<210> SEQ ID NO 38
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 38
aaggcatggt cattggtat                                                   19

<210> SEQ ID NO 39
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 39
gcatggtcat tggtatcat                                                   19

<210> SEQ ID NO 40
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 40
```

-continued

```
ggtcattggt atcatgagt                                              19

<210> SEQ ID NO 41
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 41
cctagtgggt atccctgta                                              19

<210> SEQ ID NO 42
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 42
gaggatggac attgttctt                                              19

<210> SEQ ID NO 43
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 43
gcatgcaggc tacagttca                                              19

<210> SEQ ID NO 44
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 44
ccagcacatg cactgttga                                              19

<210> SEQ ID NO 45
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 45
cacatgcact gttgagtga                                              19

<210> SEQ ID NO 46
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 46
```
ctggaggtcc ctcaccttct a                        21

<210> SEQ ID NO 47
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 47
gtcggaggat cttatgctga a                        21

<210> SEQ ID NO 48
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 48
tgcccgcttc cagatcatac a                        21

<210> SEQ ID NO 49
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 49
ctggagacct caacaagata t                        21

<210> SEQ ID NO 50
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 50
tcaaggcatg gtcattggta t                        21

<210> SEQ ID NO 51
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 51
aggcatggtc attggtatca t                        21

<210> SEQ ID NO 52
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 52
atggtcattg gtatcatgag t                        21

<210> SEQ ID NO 53
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 53
gccctagtgg gtatccctgt a                                              21

<210> SEQ ID NO 54
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 54
atgaggatgg acattgttct t                                              21

<210> SEQ ID NO 55
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 55
gagcatgcag gctacagttc a                                              21

<210> SEQ ID NO 56
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 56
ttccagcaca tgcactgttg a                                              21

<210> SEQ ID NO 57
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 57
agcacatgca ctgttgagtg a                                              21

<210> SEQ ID NO 58
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 58
tagaaggtga gggacctcca g                                              21

<210> SEQ ID NO 59
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 59
ttcagcataa gatcctccga c                                              21

<210> SEQ ID NO 60
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 60
tgtatgatct ggaagcgggc a                                              21

<210> SEQ ID NO 61
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 61
atatcttgtt gaggtctcca g                                              21

<210> SEQ ID NO 62
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 62
ataccaatga ccatgccttg a                                              21

<210> SEQ ID NO 63
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 63
atgataccaa tgaccatgcc t                                              21

<210> SEQ ID NO 64
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 64
atggtcattg gtatcatgag t                                              21

```
<210> SEQ ID NO 65
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 65
gccctagtgg gtatccctgt a                                              21

<210> SEQ ID NO 66
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 66
atgaggatgg acattgttct t                                              21

<210> SEQ ID NO 67
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 67
gagcatgcag gctacagttc a                                              21

<210> SEQ ID NO 68
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 68
ttccagcaca tgcactgttg a                                              21

<210> SEQ ID NO 69
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 69
agcacatgca ctgttgagtg a                                              21

<210> SEQ ID NO 70
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 70
tagaaggtga gggacctcc                                                 19

<210> SEQ ID NO 71
```

```
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 71
ttcagcataa gatcctccg                                                     19

<210> SEQ ID NO 72
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 72
tgtatgatct ggaagcggg                                                     19

<210> SEQ ID NO 73
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 73
atatcttgtt gaggtctcc                                                     19

<210> SEQ ID NO 74
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 74
ataccaatga ccatgcctt                                                     19

<210> SEQ ID NO 75
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 75
atgataccaa tgaccatgc                                                     19

<210> SEQ ID NO 76
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 76
atggtcattg gtatcatga                                                     19

<210> SEQ ID NO 77
<211> LENGTH: 19
```

```
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 77
gccctagtgg gtatccctg                                               19

<210> SEQ ID NO 78
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 78
atgaggatgg acattgttc                                               19

<210> SEQ ID NO 79
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 79
gagcatgcag gctacagtt                                               19

<210> SEQ ID NO 80
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 80
ttccagcaca tgcactgtt                                               19

<210> SEQ ID NO 81
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 81
agcacatgca ctgttgagt                                               19

<210> SEQ ID NO 82
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 82
ggccaggatg gttcttaga                                               19

<210> SEQ ID NO 83
<211> LENGTH: 19
<212> TYPE: DNA
```

<213> ORGANISM: Artificial Sequence
<220> FEATURE:
<223> OTHER INFORMATION: Description of Artificial Sequence: Synthetic oligonucleotide

<400> SEQUENCE: 83
gcttcgtgct aaactggta                                            19

<210> SEQ ID NO 84
<211> LENGTH: 19
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 84
gggcgtgact tccacatga                                            19

<210> SEQ ID NO 85
<211> LENGTH: 19
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 85
caggcctaga gaagtttca                                            19

<210> SEQ ID NO 86
<211> LENGTH: 19
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 86
cttggaaccc attcctgaa                                            19

<210> SEQ ID NO 87
<211> LENGTH: 19
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 87
ggaacccatt cctgaaatt                                            19

<210> SEQ ID NO 88
<211> LENGTH: 19
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 88
gaacccattc ctgaaatta                                            19

<210> SEQ ID NO 89
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 89
aacccattcc tgaaattat                                                19

<210> SEQ ID NO 90
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 90
acccattcct gaaattatt                                                19

<210> SEQ ID NO 91
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 91
cccattcctg aaattattt                                                19

<210> SEQ ID NO 92
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 92
ctgtggttct attatatta                                                19

<210> SEQ ID NO 93
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 93
aaatatgaga gcatgctaa                                                19

<210> SEQ ID NO 94
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 94
tctaagaacc atcctggcc                                                19

<210> SEQ ID NO 95
<211> LENGTH: 19
<212> TYPE: DNA
<213> ORGANISM: Artificial Sequence
<220> FEATURE:

```
<223> OTHER INFORMATION: Description of Artificial Sequence: Synthetic
      oligonucleotide

<400> SEQUENCE: 95
taccagttta gcacgaagc                                                        19

<210> SEQ ID NO 96
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 96
tcatgtggaa gtcacgccc                                                        19

<210> SEQ ID NO 97
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 97
tgaaacttct ctaggcctg                                                        19

<210> SEQ ID NO 98
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 98
ttcaggaatg ggttccaag                                                        19

<210> SEQ ID NO 99
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 99
aatttcagga atgggttcc                                                        19

<210> SEQ ID NO 100
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 100
taatttcagg aatgggttc                                                        19

<210> SEQ ID NO 101
<211> LENGTH: 19
<212> TYPE: DNA
<213> ORGANISM: Artificial Sequence
<220> FEATURE:
<223> OTHER INFORMATION: Description of Artificial Sequence: Synthetic
``` oligonucleotide

<400> SEQUENCE: 101
ataatttcag gaatgggtt                                              19

<210> SEQ ID NO 102
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 102
aataatttca ggaatgggt                                              19

<210> SEQ ID NO 103
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 103
aaataatttc aggaatggg                                              19

<210> SEQ ID NO 104
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 104
taatataata gaaccacag                                              19

<210> SEQ ID NO 105
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 105
ttagcatgct ctcatattt                                              19

<210> SEQ ID NO 106
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 106
gcggccagga tggttcttag a                                           21

<210> SEQ ID NO 107
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 107
gagcttcgtg ctaaactggt a                                              21

<210> SEQ ID NO 108
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 108
acgggcgtga cttccacatg a                                              21

<210> SEQ ID NO 109
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 109
tgcaggccta gagaagtttc a                                              21

<210> SEQ ID NO 110
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 110
tccttggaac ccattcctga a                                              21

<210> SEQ ID NO 111
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 111
ttggaaccca ttcctgaaat t                                              21

<210> SEQ ID NO 112
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 112
tggaacccat tcctgaaatt a                                              21

<210> SEQ ID NO 113
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

```
<400> SEQUENCE: 113
ggaacccatt cctgaaatta t                                              21

<210> SEQ ID NO 114
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 114
gaacccattc ctgaaattat t                                              21

<210> SEQ ID NO 115
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 115
aacccattcc tgaaattatt t                                              21

<210> SEQ ID NO 116
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 116
ccctgtggtt ctattatatt a                                              21

<210> SEQ ID NO 117
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 117
ttaaatatga gagcatgcta a                                              21

<210> SEQ ID NO 118
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 118
tctaagaacc atcctggccg c                                              21

<210> SEQ ID NO 119
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 119
```
taccagttta gcacgaagct c                                              21

<210> SEQ ID NO 120
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 120
tcatgtggaa gtcacgcccg t                                              21

<210> SEQ ID NO 121
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 121
tgaaacttct ctaggcctgc a                                              21

<210> SEQ ID NO 122
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 122
ttcaggaatg ggttccaagg a                                              21

<210> SEQ ID NO 123
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 123
aatttcagga atgggttcca a                                              21

<210> SEQ ID NO 124
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 124
taatttcagg aatgggttcc a                                              21

<210> SEQ ID NO 125
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 125
ataatttcag gaatgggttc c                                           21

<210> SEQ ID NO 126
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 126
aataatttca ggaatgggtt c                                           21

<210> SEQ ID NO 127
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 127
aaataatttc aggaatgggt t                                           21

<210> SEQ ID NO 128
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 128
taatataata gaaccacagg g                                           21

<210> SEQ ID NO 129
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 129
ttagcatgct ctcatattta a                                           21

<210> SEQ ID NO 130
<211> LENGTH: 63
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 130
atggccttac cagtgaccgc cttgctcctg ccgctggcct tgctgctcca cgccgccagg    60
ccg                                                                 63

<210> SEQ ID NO 131
<211> LENGTH: 135
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 131

```
accacgacgc cagcgccgcg accaccaaca ccggcgccca ccatcgcgtc gcagccctg      60 tccctgcgcc cagaggcgtg ccggccagcg gcgggggggcg cagtgcacac gagggggctg    120
gacttcgcct gtgat                                                      135
```

<210> SEQ ID NO 132
<211> LENGTH: 72
<212> TYPE: DNA
<213> ORGANISM: Artificial Sequence
<220> FEATURE:
<223> OTHER INFORMATION: Description of Artificial Sequence: Synthetic
     oligonucleotide

<400> SEQUENCE: 132

```
atctacatct gggcgcccttt ggccgggact tgtggggtcc ttctcctgtc actggttatc    60
accctttact gc                                                          72
```

<210> SEQ ID NO 133
<211> LENGTH: 126
<212> TYPE: DNA
<213> ORGANISM: Artificial Sequence
<220> FEATURE:
<223> OTHER INFORMATION: Description of Artificial Sequence: Synthetic
     polynucleotide

<400> SEQUENCE: 133

```
aaacggggca gaaagaaact cctgtatata ttcaaacaac catttatgag accagtacaa    60
actactcaag aggaagatgg ctgtagctgc cgatttccag aagaagaaga aggaggatgt    120
gaactg                                                               126
```

<210> SEQ ID NO 134
<211> LENGTH: 336
<212> TYPE: DNA
<213> ORGANISM: Artificial Sequence
<220> FEATURE:
<223> OTHER INFORMATION: Description of Artificial Sequence: Synthetic
     polynucleotide

<400> SEQUENCE: 134

```
agagtgaagt tcagcaggag cgcagacgcc cccgcgtaca agcagggcca gaaccagctc    60
tataacgagc tcaatctagg acgaagagag gagtacgatg ttttggacaa gagacgtggc    120
cgggaccctg agatgggggg aaagccgaga aggaagaacc ctcaggaagg cctgtacaat    180
gaactgcaga aagataagat ggcggaggcc tacagtgaga ttgggatgaa aggcgagcgc    240 cggagggggca aggggcacga tggcctttac cagggtctca gtacagccac caaggacacc    300
tacgacgccc ttcacatgca ggccctgccc cctcgc                              336
```

<210> SEQ ID NO 135
<211> LENGTH: 21
<212> TYPE: PRT
<213> ORGANISM: Artificial Sequence
<220> FEATURE:
<223> OTHER INFORMATION: Description of Artificial Sequence: Synthetic
     peptide

<400> SEQUENCE: 135

```
Met Ala Leu Pro Val Thr Ala Leu Leu Leu Pro Leu Ala Leu Leu Leu
1               5                   10                  15

His Ala Ala Arg Pro
            20
```

```
<210> SEQ ID NO 136
<211> LENGTH: 45
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 136

Thr Thr Thr Pro Ala Pro Arg Pro Pro Thr Pro Ala Pro Thr Ile Ala
1               5                   10                  15

Ser Gln Pro Leu Ser Leu Arg Pro Glu Ala Cys Arg Pro Ala Ala Gly
                20                  25                  30

Gly Ala Val His Thr Arg Gly Leu Asp Phe Ala Cys Asp
            35                  40                  45

<210> SEQ ID NO 137
<211> LENGTH: 24
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 137

Ile Tyr Ile Trp Ala Pro Leu Ala Gly Thr Cys Gly Val Leu Leu Leu
1               5                   10                  15

Ser Leu Val Ile Thr Leu Tyr Cys
                20

<210> SEQ ID NO 138
<211> LENGTH: 42
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 138

Lys Arg Gly Arg Lys Lys Leu Leu Tyr Ile Phe Lys Gln Pro Phe Met
1               5                   10                  15

Arg Pro Val Gln Thr Thr Gln Glu Glu Asp Gly Cys Ser Cys Arg Phe
                20                  25                  30

Pro Glu Glu Glu Glu Gly Gly Cys Glu Leu
            35                  40

<210> SEQ ID NO 139
<211> LENGTH: 112
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 139

Arg Val Lys Phe Ser Arg Ser Ala Asp Ala Pro Ala Tyr Lys Gln Gly
1               5                   10                  15

Gln Asn Gln Leu Tyr Asn Glu Leu Asn Leu Gly Arg Arg Glu Glu Tyr
                20                  25                  30

Asp Val Leu Asp Lys Arg Arg Gly Arg Asp Pro Glu Met Gly Gly Lys
            35                  40                  45

Pro Arg Arg Lys Asn Pro Gln Glu Gly Leu Tyr Asn Glu Leu Gln Lys
        50                  55                  60
```

Asp Lys Met Ala Glu Ala Tyr Ser Glu Ile Gly Met Lys Gly Glu Arg
65                  70                  75                  80

Arg Arg Gly Lys Gly His Asp Gly Leu Tyr Gln Gly Leu Ser Thr Ala
            85                  90                  95

Thr Lys Asp Thr Tyr Asp Ala Leu His Met Gln Ala Leu Pro Pro Arg
        100                 105                 110

<210> SEQ ID NO 140
<211> LENGTH: 1184
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 140
cgtgaggctc cggtgcccgt cagtgggcag agcgcacatc gcccacagtc cccgagaagt    60
tgggggagg ggtcggcaat tgaaccggtg cctagagaag gtggcgcggg gtaaactggg    120
aaagtgatgt cgtgtactgg ctccgccttt ttcccgaggg tgggggagaa ccgtatataa    180
gtgcagtagt cgccgtgaac gttctttttc gcaacgggtt tgccgccaga acacaggtaa    240
gtgccgtgtg tggttcccgc gggcctggcc tctttacggg ttatggccct tgcgtgcctt    300
gaattacttc cacctggctg cagtacgtga ttcttgatcc cgagcttcgg gttgaagtg    360
ggtgggagag ttcgaggcct tgcgcttaag gagccccttc gcctcgtgct tgagttgagg    420
cctggcctgg gcgctgggc cgccgcgtgc gaatctggtg gcaccttcgc gcctgtctcg    480
ctgctttcga taagtctcta gccatttaaa attttgatg acctgctgcg acgctttttt    540
tctggcaaga tagtcttgta aatgcgggcc aagatctgca cactggtatt cggtttttg    600
gggccgcggg cggcgacggg gcccgtgcgt cccagcgcac atgttcggcg aggcggggcc    660
tgcgagcgcg gccaccgaga tcggacggg ggtagtctca agctggccgg cctgctctgg    720
tgcctggcct cgcgccgccg tgtatcgccc cgccctgggc ggcaaggctg gcccggtcgg    780
caccagttgc gtgagcggaa agatggccgc ttccggcc tgctgcaggg agctcaaaat    840
ggaggacgcg gcgctcggga gagcgggcgg gtgagtcacc cacacaaagg aaaagggcct    900
ttccgtcctc agccgtcgct tcatgtgact ccacggagta ccgggcgccg tccaggcacc    960
tcgattagtt ctcgagcttt tggagtacgt cgtctttagg ttggggggag gggttttatg   1020
cgatggagtt tcccacact gagtgggtgg agactgaagt taggccagct tggcacttga   1080
tgtaattctc cttggaattt gccctttttg agtttggatc ttggttcatt ctcaagcctc   1140
agacagtggt tcaaagtttt tttcttccat ttcaggtgtc gtga                   1184

<210> SEQ ID NO 141
<211> LENGTH: 108
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 141

Val Gln Val Glu Thr Ile Ser Pro Gly Asp Gly Arg Thr Phe Pro Lys
1               5                   10                  15

Arg Gly Gln Thr Cys Val Val His Tyr Thr Gly Met Leu Glu Asp Gly
            20                  25                  30

Lys Lys Phe Asp Ser Ser Arg Asp Arg Asn Lys Pro Phe Lys Phe Met

```
                35                  40                  45
Leu Gly Lys Gln Glu Val Ile Arg Gly Trp Glu Glu Gly Val Ala Gln
         50                  55                  60
Met Ser Val Gly Gln Arg Ala Lys Leu Thr Ile Ser Pro Asp Tyr Ala
 65                  70                  75                  80
Tyr Gly Ala Thr Gly His Pro Gly Ile Ile Pro Pro His Ala Thr Leu
                 85                  90                  95
Val Phe Asp Val Glu Leu Leu Lys Leu Glu Thr Ser
                100                 105

<210> SEQ ID NO 142
<211> LENGTH: 99
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 142

Met Ala Ser Arg Ile Leu Trp His Glu Met Trp His Glu Gly Leu Glu
 1               5                  10                  15
Glu Ala Ser Arg Leu Tyr Phe Gly Glu Arg Asn Val Lys Gly Met Phe
                20                  25                  30
Glu Val Leu Glu Pro Leu His Ala Met Met Glu Arg Gly Pro Gln Thr
                35                  40                  45
Leu Lys Glu Thr Ser Phe Asn Gln Ala Tyr Gly Arg Asp Leu Met Glu
         50                  55                  60
Ala Gln Glu Trp Cys Arg Lys Tyr Met Lys Ser Gly Asn Val Lys Asp
 65                  70                  75                  80
Leu Leu Gln Ala Trp Asp Leu Tyr Tyr His Val Phe Arg Arg Ile Ser
                 85                  90                  95
Lys Thr Ser

<210> SEQ ID NO 143
<211> LENGTH: 242
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 143

Glu Ile Val Met Thr Gln Ser Pro Ala Thr Leu Ser Leu Ser Pro Gly
 1               5                  10                  15
Glu Arg Ala Thr Leu Ser Cys Arg Ala Ser Gln Asp Ile Ser Lys Tyr
                20                  25                  30
Leu Asn Trp Tyr Gln Gln Lys Pro Gly Gln Ala Pro Arg Leu Leu Ile
                35                  40                  45
Tyr His Thr Ser Arg Leu His Ser Gly Ile Pro Ala Arg Phe Ser Gly
         50                  55                  60
Ser Gly Ser Gly Thr Asp Tyr Thr Leu Thr Ile Ser Ser Leu Gln Pro
 65                  70                  75                  80
Glu Asp Phe Ala Val Tyr Phe Cys Gln Gln Gly Asn Thr Leu Pro Tyr
                 85                  90                  95
Thr Phe Gly Gln Gly Thr Lys Leu Glu Ile Lys Gly Gly Gly Gly Ser
                100                 105                 110
Gly Gly Gly Gly Ser Gly Gly Gly Ser Gln Val Gln Leu Gln Glu
            115                 120                 125
```

Ser Gly Pro Gly Leu Val Lys Pro Ser Glu Thr Leu Ser Leu Thr Cys
            130                 135                 140

Thr Val Ser Gly Val Ser Leu Pro Asp Tyr Gly Val Ser Trp Ile Arg
145                 150                 155                 160

Gln Pro Pro Gly Lys Gly Leu Glu Trp Ile Gly Val Ile Trp Gly Ser
                165                 170                 175

Glu Thr Thr Tyr Tyr Ser Ser Ser Leu Lys Ser Arg Val Thr Ile Ser
            180                 185                 190

Lys Asp Asn Ser Lys Asn Gln Val Ser Leu Lys Leu Ser Ser Val Thr
                195                 200                 205

Ala Ala Asp Thr Ala Val Tyr Tyr Cys Ala Lys His Tyr Tyr Tyr Gly
            210                 215                 220

Gly Ser Tyr Ala Met Asp Tyr Trp Gly Gln Gly Thr Leu Val Thr Val
225                 230                 235                 240

Ser Ser

<210> SEQ ID NO 144
<211> LENGTH: 242
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 144

Glu Ile Val Met Thr Gln Ser Pro Ala Thr Leu Ser Leu Ser Pro Gly
1               5                   10                  15

Glu Arg Ala Thr Leu Ser Cys Arg Ala Ser Gln Asp Ile Ser Lys Tyr
            20                  25                  30

Leu Asn Trp Tyr Gln Gln Lys Pro Gly Gln Ala Pro Arg Leu Leu Ile
        35                  40                  45

Tyr His Thr Ser Arg Leu His Ser Gly Ile Pro Ala Arg Phe Ser Gly
    50                  55                  60

Ser Gly Ser Gly Thr Asp Tyr Thr Leu Thr Ile Ser Ser Leu Gln Pro
65                  70                  75                  80

Glu Asp Phe Ala Val Tyr Phe Cys Gln Gln Gly Asn Thr Leu Pro Tyr
                85                  90                  95

Thr Phe Gly Gln Gly Thr Lys Leu Glu Ile Lys Gly Gly Gly Gly Ser
            100                 105                 110

Gly Gly Gly Gly Ser Gly Gly Gly Ser Gln Val Gln Leu Gln Glu
        115                 120                 125

Ser Gly Pro Gly Leu Val Lys Pro Ser Glu Thr Leu Ser Leu Thr Cys
            130                 135                 140

Thr Val Ser Gly Val Ser Leu Pro Asp Tyr Gly Val Ser Trp Ile Arg
145                 150                 155                 160

Gln Pro Pro Gly Lys Gly Leu Glu Trp Ile Gly Val Ile Trp Gly Ser
                165                 170                 175

Glu Thr Thr Tyr Tyr Gln Ser Ser Leu Lys Ser Arg Val Thr Ile Ser
            180                 185                 190

Lys Asp Asn Ser Lys Asn Gln Val Ser Leu Lys Leu Ser Ser Val Thr
                195                 200                 205

Ala Ala Asp Thr Ala Val Tyr Tyr Cys Ala Lys His Tyr Tyr Tyr Gly
            210                 215                 220

Gly Ser Tyr Ala Met Asp Tyr Trp Gly Gln Gly Thr Leu Val Thr Val
225                 230                 235                 240

Ser Ser

<210> SEQ ID NO 145
<211> LENGTH: 242
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 145

```
Gln Val Gln Leu Gln Glu Ser Gly Pro Gly Leu Val Lys Pro Ser Glu
1               5                   10                  15

Thr Leu Ser Leu Thr Cys Thr Val Ser Gly Val Ser Leu Pro Asp Tyr
            20                  25                  30

Gly Val Ser Trp Ile Arg Gln Pro Pro Gly Lys Gly Leu Glu Trp Ile
        35                  40                  45

Gly Val Ile Trp Gly Ser Glu Thr Thr Tyr Tyr Ser Ser Ser Leu Lys
    50                  55                  60

Ser Arg Val Thr Ile Ser Lys Asp Asn Ser Lys Asn Gln Val Ser Leu
65                  70                  75                  80

Lys Leu Ser Ser Val Thr Ala Ala Asp Thr Ala Val Tyr Tyr Cys Ala
                85                  90                  95

Lys His Tyr Tyr Tyr Gly Gly Ser Tyr Ala Met Asp Tyr Trp Gly Gln
            100                 105                 110

Gly Thr Leu Val Thr Val Ser Ser Gly Gly Gly Gly Ser Gly Gly Gly
        115                 120                 125

Gly Ser Gly Gly Gly Gly Ser Glu Ile Val Met Thr Gln Ser Pro Ala
    130                 135                 140

Thr Leu Ser Leu Ser Pro Gly Glu Arg Ala Thr Leu Ser Cys Arg Ala
145                 150                 155                 160

Ser Gln Asp Ile Ser Lys Tyr Leu Asn Trp Tyr Gln Gln Lys Pro Gly
                165                 170                 175

Gln Ala Pro Arg Leu Leu Ile Tyr His Thr Ser Arg Leu His Ser Gly
            180                 185                 190

Ile Pro Ala Arg Phe Ser Gly Ser Gly Ser Gly Thr Asp Tyr Thr Leu
        195                 200                 205

Thr Ile Ser Ser Leu Gln Pro Glu Asp Phe Ala Val Tyr Phe Cys Gln
    210                 215                 220

Gln Gly Asn Thr Leu Pro Tyr Thr Phe Gly Gln Gly Thr Lys Leu Glu
225                 230                 235                 240

Ile Lys
```

<210> SEQ ID NO 146
<211> LENGTH: 242
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 146

```
Gln Val Gln Leu Gln Glu Ser Gly Pro Gly Leu Val Lys Pro Ser Glu
1               5                   10                  15

Thr Leu Ser Leu Thr Cys Thr Val Ser Gly Val Ser Leu Pro Asp Tyr
            20                  25                  30

Gly Val Ser Trp Ile Arg Gln Pro Pro Gly Lys Gly Leu Glu Trp Ile
```

```
            35                  40                  45
Gly Val Ile Trp Gly Ser Glu Thr Thr Tyr Tyr Gln Ser Ser Leu Lys
 50                  55                  60

Ser Arg Val Thr Ile Ser Lys Asp Asn Ser Lys Asn Gln Val Ser Leu
 65                  70                  75                  80

Lys Leu Ser Ser Val Thr Ala Ala Asp Thr Ala Val Tyr Tyr Cys Ala
                 85                  90                  95

Lys His Tyr Tyr Tyr Gly Gly Ser Tyr Ala Met Asp Tyr Trp Gly Gln
                100                 105                 110

Gly Thr Leu Val Thr Val Ser Ser Gly Gly Gly Ser Gly Gly Gly
            115                 120                 125

Gly Ser Gly Gly Gly Ser Glu Ile Val Met Thr Gln Ser Pro Ala
130                 135                 140

Thr Leu Ser Leu Ser Pro Gly Glu Arg Ala Thr Leu Ser Cys Arg Ala
145                 150                 155                 160

Ser Gln Asp Ile Ser Lys Tyr Leu Asn Trp Tyr Gln Gln Lys Pro Gly
                165                 170                 175

Gln Ala Pro Arg Leu Leu Ile Tyr His Thr Ser Arg Leu His Ser Gly
                180                 185                 190

Ile Pro Ala Arg Phe Ser Gly Ser Gly Ser Gly Thr Asp Tyr Thr Leu
                195                 200                 205

Thr Ile Ser Ser Leu Gln Pro Glu Asp Phe Ala Val Tyr Phe Cys Gln
210                 215                 220

Gln Gly Asn Thr Leu Pro Tyr Thr Phe Gly Gln Gly Thr Lys Leu Glu
225                 230                 235                 240

Ile Lys

<210> SEQ ID NO 147
<211> LENGTH: 247
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 147

Glu Ile Val Met Thr Gln Ser Pro Ala Thr Leu Ser Leu Ser Pro Gly
 1               5                  10                  15

Glu Arg Ala Thr Leu Ser Cys Arg Ala Ser Gln Asp Ile Ser Lys Tyr
                 20                  25                  30

Leu Asn Trp Tyr Gln Gln Lys Pro Gly Gln Ala Pro Arg Leu Leu Ile
             35                  40                  45

Tyr His Thr Ser Arg Leu His Ser Gly Ile Pro Ala Arg Phe Ser Gly
 50                  55                  60

Ser Gly Ser Gly Thr Asp Tyr Thr Leu Thr Ile Ser Ser Leu Gln Pro
 65                  70                  75                  80

Glu Asp Phe Ala Val Tyr Phe Cys Gln Gln Gly Asn Thr Leu Pro Tyr
                 85                  90                  95

Thr Phe Gly Gln Gly Thr Lys Leu Glu Ile Lys Gly Gly Gly Gly Ser
                100                 105                 110

Gly Gly Gly Gly Ser Gly Gly Gly Gly Gly Gly Ser Gln
            115                 120                 125

Val Gln Leu Gln Glu Ser Gly Pro Gly Leu Val Lys Pro Ser Glu Thr
130                 135                 140

Leu Ser Leu Thr Cys Thr Val Ser Gly Val Ser Leu Pro Asp Tyr Gly
```

```
145                 150                 155                 160
Val Ser Trp Ile Arg Gln Pro Pro Gly Lys Gly Leu Glu Trp Ile Gly
                165                 170                 175

Val Ile Trp Gly Ser Glu Thr Thr Tyr Tyr Ser Ser Ser Leu Lys Ser
            180                 185                 190

Arg Val Thr Ile Ser Lys Asp Asn Ser Lys Asn Gln Val Ser Leu Lys
        195                 200                 205

Leu Ser Ser Val Thr Ala Ala Asp Thr Ala Val Tyr Tyr Cys Ala Lys
    210                 215                 220

His Tyr Tyr Tyr Gly Gly Ser Tyr Ala Met Asp Tyr Trp Gly Gln Gly
225                 230                 235                 240

Thr Leu Val Thr Val Ser Ser
                245

<210> SEQ ID NO 148
<211> LENGTH: 247
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 148

Glu Ile Val Met Thr Gln Ser Pro Ala Thr Leu Ser Leu Ser Pro Gly
1               5                   10                  15

Glu Arg Ala Thr Leu Ser Cys Arg Ala Ser Gln Asp Ile Ser Lys Tyr
            20                  25                  30

Leu Asn Trp Tyr Gln Gln Lys Pro Gly Gln Ala Pro Arg Leu Leu Ile
        35                  40                  45

Tyr His Thr Ser Arg Leu His Ser Gly Ile Pro Ala Arg Phe Ser Gly
    50                  55                  60

Ser Gly Ser Gly Thr Asp Tyr Thr Leu Thr Ile Ser Ser Leu Gln Pro
65                  70                  75                  80

Glu Asp Phe Ala Val Tyr Phe Cys Gln Gln Gly Asn Thr Leu Pro Tyr
                85                  90                  95

Thr Phe Gly Gln Gly Thr Lys Leu Glu Ile Lys Gly Gly Gly Gly Ser
            100                 105                 110

Gly Gly Gly Gly Ser Gly Gly Gly Ser Gly Gly Gly Gly Ser Gln
        115                 120                 125

Val Gln Leu Gln Glu Ser Gly Pro Gly Leu Val Lys Pro Ser Glu Thr
    130                 135                 140

Leu Ser Leu Thr Cys Thr Val Ser Gly Val Ser Leu Pro Asp Tyr Gly
145                 150                 155                 160

Val Ser Trp Ile Arg Gln Pro Pro Gly Lys Gly Leu Glu Trp Ile Gly
                165                 170                 175

Val Ile Trp Gly Ser Glu Thr Thr Tyr Tyr Gln Ser Ser Leu Lys Ser
            180                 185                 190

Arg Val Thr Ile Ser Lys Asp Asn Ser Lys Asn Gln Val Ser Leu Lys
        195                 200                 205

Leu Ser Ser Val Thr Ala Ala Asp Thr Ala Val Tyr Tyr Cys Ala Lys
    210                 215                 220

His Tyr Tyr Tyr Gly Gly Ser Tyr Ala Met Asp Tyr Trp Gly Gln Gly
225                 230                 235                 240

Thr Leu Val Thr Val Ser Ser
                245
```

```
<210> SEQ ID NO 149
<211> LENGTH: 247
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 149

Gln Val Gln Leu Gln Glu Ser Gly Pro Gly Leu Val Lys Pro Ser Glu
1               5                   10                  15

Thr Leu Ser Leu Thr Cys Thr Val Ser Gly Val Ser Leu Pro Asp Tyr
            20                  25                  30

Gly Val Ser Trp Ile Arg Gln Pro Pro Gly Lys Gly Leu Glu Trp Ile
        35                  40                  45

Gly Val Ile Trp Gly Ser Glu Thr Thr Tyr Tyr Ser Ser Ser Leu Lys
    50                  55                  60

Ser Arg Val Thr Ile Ser Lys Asp Asn Ser Lys Asn Gln Val Ser Leu
65                  70                  75                  80

Lys Leu Ser Ser Val Thr Ala Ala Asp Thr Ala Val Tyr Tyr Cys Ala
                85                  90                  95

Lys His Tyr Tyr Tyr Gly Gly Ser Tyr Ala Met Asp Tyr Trp Gly Gln
            100                 105                 110

Gly Thr Leu Val Thr Val Ser Ser Gly Gly Gly Ser Gly Gly Gly
        115                 120                 125

Gly Ser Gly Gly Gly Ser Gly Gly Gly Ser Glu Ile Val Met
    130                 135                 140

Thr Gln Ser Pro Ala Thr Leu Ser Leu Ser Pro Gly Glu Arg Ala Thr
145                 150                 155                 160

Leu Ser Cys Arg Ala Ser Gln Asp Ile Ser Lys Tyr Leu Asn Trp Tyr
                165                 170                 175

Gln Gln Lys Pro Gly Gln Ala Pro Arg Leu Leu Ile Tyr His Thr Ser
            180                 185                 190

Arg Leu His Ser Gly Ile Pro Ala Arg Phe Ser Gly Ser Gly Ser Gly
        195                 200                 205

Thr Asp Tyr Thr Leu Thr Ile Ser Ser Leu Gln Pro Glu Asp Phe Ala
    210                 215                 220

Val Tyr Phe Cys Gln Gln Gly Asn Thr Leu Pro Tyr Thr Phe Gly Gln
225                 230                 235                 240

Gly Thr Lys Leu Glu Ile Lys
            245

<210> SEQ ID NO 150
<211> LENGTH: 247
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 150

Gln Val Gln Leu Gln Glu Ser Gly Pro Gly Leu Val Lys Pro Ser Glu
1               5                   10                  15

Thr Leu Ser Leu Thr Cys Thr Val Ser Gly Val Ser Leu Pro Asp Tyr
            20                  25                  30

Gly Val Ser Trp Ile Arg Gln Pro Pro Gly Lys Gly Leu Glu Trp Ile
        35                  40                  45
```

```
Gly Val Ile Trp Gly Ser Glu Thr Thr Tyr Tyr Gln Ser Ser Leu Lys
    50                  55                  60

Ser Arg Val Thr Ile Ser Lys Asp Asn Ser Lys Asn Gln Val Ser Leu
65                  70                  75                  80

Lys Leu Ser Ser Val Thr Ala Ala Asp Thr Ala Val Tyr Tyr Cys Ala
                85                  90                  95

Lys His Tyr Tyr Tyr Gly Gly Ser Tyr Ala Met Asp Tyr Trp Gly Gln
            100                 105                 110

Gly Thr Leu Val Thr Val Ser Gly Gly Gly Ser Gly Gly Gly
            115                 120                 125

Gly Ser Gly Gly Gly Gly Ser Gly Gly Gly Ser Glu Ile Val Met
    130                 135                 140

Thr Gln Ser Pro Ala Thr Leu Ser Leu Ser Pro Gly Glu Arg Ala Thr
145                 150                 155                 160

Leu Ser Cys Arg Ala Ser Gln Asp Ile Ser Lys Tyr Leu Asn Trp Tyr
                165                 170                 175

Gln Gln Lys Pro Gly Gln Ala Pro Arg Leu Leu Ile Tyr His Thr Ser
            180                 185                 190

Arg Leu His Ser Gly Ile Pro Ala Arg Phe Ser Gly Ser Gly Ser Gly
        195                 200                 205

Thr Asp Tyr Thr Leu Thr Ile Ser Ser Leu Gln Pro Glu Asp Phe Ala
210                 215                 220

Val Tyr Phe Cys Gln Gln Gly Asn Thr Leu Pro Tyr Thr Phe Gly Gln
225                 230                 235                 240

Gly Thr Lys Leu Glu Ile Lys
            245

<210> SEQ ID NO 151
<211> LENGTH: 247
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 151

Glu Ile Val Met Thr Gln Ser Pro Ala Thr Leu Ser Leu Ser Pro Gly
1               5                   10                  15

Glu Arg Ala Thr Leu Ser Cys Arg Ala Ser Gln Asp Ile Ser Lys Tyr
            20                  25                  30

Leu Asn Trp Tyr Gln Gln Lys Pro Gly Gln Ala Pro Arg Leu Leu Ile
        35                  40                  45

Tyr His Thr Ser Arg Leu His Ser Gly Ile Pro Ala Arg Phe Ser Gly
    50                  55                  60

Ser Gly Ser Gly Thr Asp Tyr Thr Leu Thr Ile Ser Ser Leu Gln Pro
65                  70                  75                  80

Glu Asp Phe Ala Val Tyr Phe Cys Gln Gln Gly Asn Thr Leu Pro Tyr
                85                  90                  95

Thr Phe Gly Gln Gly Thr Lys Leu Glu Ile Lys Gly Gly Gly Gly Ser
            100                 105                 110

Gly Gly Gly Gly Ser Gly Gly Gly Ser Gly Gly Gly Gly Ser Gln
        115                 120                 125

Val Gln Leu Gln Glu Ser Gly Pro Gly Leu Val Lys Pro Ser Glu Thr
    130                 135                 140

Leu Ser Leu Thr Cys Thr Val Ser Gly Val Ser Leu Pro Asp Tyr Gly
145                 150                 155                 160
```

```
Val Ser Trp Ile Arg Gln Pro Pro Gly Lys Gly Leu Glu Trp Ile Gly
            165                 170                 175

Val Ile Trp Gly Ser Glu Thr Thr Tyr Tyr Asn Ser Ser Leu Lys Ser
            180                 185                 190

Arg Val Thr Ile Ser Lys Asp Asn Ser Lys Asn Gln Val Ser Leu Lys
            195                 200                 205

Leu Ser Ser Val Thr Ala Ala Asp Thr Ala Val Tyr Tyr Cys Ala Lys
    210                 215                 220

His Tyr Tyr Tyr Gly Gly Ser Tyr Ala Met Asp Tyr Trp Gly Gln Gly
225                 230                 235                 240

Thr Leu Val Thr Val Ser Ser
            245
```

<210> SEQ ID NO 152
<211> LENGTH: 247
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 152

```
Gln Val Gln Leu Gln Glu Ser Gly Pro Gly Leu Val Lys Pro Ser Glu
1               5                   10                  15

Thr Leu Ser Leu Thr Cys Thr Val Ser Gly Val Ser Leu Pro Asp Tyr
            20                  25                  30

Gly Val Ser Trp Ile Arg Gln Pro Pro Gly Lys Gly Leu Glu Trp Ile
        35                  40                  45

Gly Val Ile Trp Gly Ser Glu Thr Thr Tyr Tyr Asn Ser Ser Leu Lys
    50                  55                  60

Ser Arg Val Thr Ile Ser Lys Asp Asn Ser Lys Asn Gln Val Ser Leu
65                  70                  75                  80

Lys Leu Ser Ser Val Thr Ala Ala Asp Thr Ala Val Tyr Tyr Cys Ala
                85                  90                  95

Lys His Tyr Tyr Tyr Gly Gly Ser Tyr Ala Met Asp Tyr Trp Gly Gln
            100                 105                 110

Gly Thr Leu Val Thr Val Ser Ser Gly Gly Gly Ser Gly Gly Gly
        115                 120                 125

Gly Ser Gly Gly Gly Ser Gly Gly Gly Ser Glu Ile Val Met
    130                 135                 140

Thr Gln Ser Pro Ala Thr Leu Ser Leu Ser Pro Gly Glu Arg Ala Thr
145                 150                 155                 160

Leu Ser Cys Arg Ala Ser Gln Asp Ile Ser Lys Tyr Leu Asn Trp Tyr
                165                 170                 175

Gln Gln Lys Pro Gly Gln Ala Pro Arg Leu Leu Ile Tyr His Thr Ser
            180                 185                 190

Arg Leu His Ser Gly Ile Pro Ala Arg Phe Ser Gly Ser Gly Ser Gly
        195                 200                 205

Thr Asp Tyr Thr Leu Thr Ile Ser Ser Leu Gln Pro Glu Asp Phe Ala
    210                 215                 220

Val Tyr Phe Cys Gln Gln Gly Asn Thr Leu Pro Tyr Thr Phe Gly Gln
225                 230                 235                 240

Gly Thr Lys Leu Glu Ile Lys
            245
```

```
<210> SEQ ID NO 153
<211> LENGTH: 242
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 153

Glu Ile Val Met Thr Gln Ser Pro Ala Thr Leu Ser Leu Ser Pro Gly
1               5                   10                  15

Glu Arg Ala Thr Leu Ser Cys Arg Ala Ser Gln Asp Ile Ser Lys Tyr
            20                  25                  30

Leu Asn Trp Tyr Gln Gln Lys Pro Gly Gln Ala Pro Arg Leu Leu Ile
        35                  40                  45

Tyr His Thr Ser Arg Leu His Ser Gly Ile Pro Ala Arg Phe Ser Gly
    50                  55                  60

Ser Gly Ser Gly Thr Asp Tyr Thr Leu Thr Ile Ser Ser Leu Gln Pro
65                  70                  75                  80

Glu Asp Phe Ala Val Tyr Phe Cys Gln Gln Gly Asn Thr Leu Pro Tyr
                85                  90                  95

Thr Phe Gly Gln Gly Thr Lys Leu Glu Ile Lys Gly Gly Gly Gly Ser
            100                 105                 110

Gly Gly Gly Gly Ser Gly Gly Gly Ser Gln Val Gln Leu Gln Glu
        115                 120                 125

Ser Gly Pro Gly Leu Val Lys Pro Ser Glu Thr Leu Ser Leu Thr Cys
130                 135                 140

Thr Val Ser Gly Val Ser Leu Pro Asp Tyr Gly Val Ser Trp Ile Arg
145                 150                 155                 160

Gln Pro Pro Gly Lys Gly Leu Glu Trp Ile Gly Val Ile Trp Gly Ser
                165                 170                 175

Glu Thr Thr Tyr Tyr Asn Ser Ser Leu Lys Ser Arg Val Thr Ile Ser
            180                 185                 190

Lys Asp Asn Ser Lys Asn Gln Val Ser Leu Lys Leu Ser Ser Val Thr
        195                 200                 205

Ala Ala Asp Thr Ala Val Tyr Tyr Cys Ala Lys His Tyr Tyr Tyr Gly
    210                 215                 220

Gly Ser Tyr Ala Met Asp Tyr Trp Gly Gln Gly Thr Leu Val Thr Val
225                 230                 235                 240

Ser Ser

<210> SEQ ID NO 154
<211> LENGTH: 242
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 154

Gln Val Gln Leu Gln Glu Ser Gly Pro Gly Leu Val Lys Pro Ser Glu
1               5                   10                  15

Thr Leu Ser Leu Thr Cys Thr Val Ser Gly Val Ser Leu Pro Asp Tyr
            20                  25                  30

Gly Val Ser Trp Ile Arg Gln Pro Pro Gly Lys Gly Leu Glu Trp Ile
        35                  40                  45

Gly Val Ile Trp Gly Ser Glu Thr Thr Tyr Tyr Asn Ser Ser Leu Lys
    50                  55                  60
```

Ser Arg Val Thr Ile Ser Lys Asp Asn Ser Lys Asn Gln Val Ser Leu
65                  70                  75                  80

Lys Leu Ser Ser Val Thr Ala Ala Asp Thr Ala Val Tyr Tyr Cys Ala
                85                  90                  95

Lys His Tyr Tyr Tyr Gly Gly Ser Tyr Ala Met Asp Tyr Trp Gly Gln
            100                 105                 110

Gly Thr Leu Val Thr Val Ser Ser Gly Gly Gly Gly Ser Gly Gly Gly
            115                 120                 125

Gly Ser Gly Gly Gly Gly Ser Glu Ile Val Met Thr Gln Ser Pro Ala
130                 135                 140

Thr Leu Ser Leu Ser Pro Gly Glu Arg Ala Thr Leu Ser Cys Arg Ala
145                 150                 155                 160

Ser Gln Asp Ile Ser Lys Tyr Leu Asn Trp Tyr Gln Gln Lys Pro Gly
            165                 170                 175

Gln Ala Pro Arg Leu Leu Ile Tyr His Thr Ser Arg Leu His Ser Gly
            180                 185                 190

Ile Pro Ala Arg Phe Ser Gly Ser Gly Ser Gly Thr Asp Tyr Thr Leu
            195                 200                 205

Thr Ile Ser Ser Leu Gln Pro Glu Asp Phe Ala Val Tyr Phe Cys Gln
210                 215                 220

Gln Gly Asn Thr Leu Pro Tyr Thr Phe Gly Gln Gly Thr Lys Leu Glu
225                 230                 235                 240

Ile Lys

<210> SEQ ID NO 155
<211> LENGTH: 242
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 155

Asp Ile Gln Met Thr Gln Thr Thr Ser Ser Leu Ser Ala Ser Leu Gly
1               5                   10                  15

Asp Arg Val Thr Ile Ser Cys Arg Ala Ser Gln Asp Ile Ser Lys Tyr
            20                  25                  30

Leu Asn Trp Tyr Gln Gln Lys Pro Asp Gly Thr Val Lys Leu Leu Ile
            35                  40                  45

Tyr His Thr Ser Arg Leu His Ser Gly Val Pro Ser Arg Phe Ser Gly
        50                  55                  60

Ser Gly Ser Gly Thr Asp Tyr Ser Leu Thr Ile Ser Asn Leu Glu Gln
65                  70                  75                  80

Glu Asp Ile Ala Thr Tyr Phe Cys Gln Gln Gly Asn Thr Leu Pro Tyr
            85                  90                  95

Thr Phe Gly Gly Gly Thr Lys Leu Glu Ile Thr Gly Gly Gly Gly Ser
            100                 105                 110

Gly Gly Gly Gly Ser Gly Gly Gly Ser Glu Val Lys Leu Gln Glu
            115                 120                 125

Ser Gly Pro Gly Leu Val Ala Pro Ser Gln Ser Leu Ser Val Thr Cys
130                 135                 140

Thr Val Ser Gly Val Ser Leu Pro Asp Tyr Gly Val Ser Trp Ile Arg
145                 150                 155                 160

Gln Pro Pro Arg Lys Gly Leu Glu Trp Leu Gly Val Ile Trp Gly Ser
            165                 170                 175

```
Glu Thr Thr Tyr Tyr Asn Ser Ala Leu Lys Ser Arg Leu Thr Ile Ile
            180                 185                 190

Lys Asp Asn Ser Lys Ser Gln Val Phe Leu Lys Met Asn Ser Leu Gln
        195                 200                 205

Thr Asp Asp Thr Ala Ile Tyr Tyr Cys Ala Lys His Tyr Tyr Tyr Gly
    210                 215                 220

Gly Ser Tyr Ala Met Asp Tyr Trp Gly Gln Gly Thr Ser Val Thr Val
225                 230                 235                 240

Ser Ser

<210> SEQ ID NO 156
<211> LENGTH: 244
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 156

Asp Ile Val Leu Thr Gln Ser Pro Ala Ser Leu Ala Val Ser Leu Gly
1               5                   10                  15

Gln Arg Ala Thr Ile Ser Cys Arg Ala Ser Glu Ser Val Asp Asn Tyr
            20                  25                  30

Gly Asn Thr Phe Met His Trp Tyr Gln Gln Lys Pro Gly Gln Pro Pro
        35                  40                  45

Lys Leu Leu Ile Tyr Arg Ala Ser Asn Leu Glu Ser Gly Ile Pro Ala
    50                  55                  60

Arg Phe Ser Gly Ser Gly Ser Arg Thr Asp Phe Thr Leu Thr Ile Asn
65                  70                  75                  80

Pro Val Glu Ala Asp Asp Val Ala Thr Tyr Tyr Cys Gln Gln Ser Asn
                85                  90                  95

Glu Asp Pro Pro Thr Phe Gly Ala Gly Thr Lys Leu Glu Leu Lys Gly
            100                 105                 110

Gly Gly Gly Ser Gly Gly Gly Gly Ser Gly Gly Gly Ser Gln Ile
        115                 120                 125

Gln Leu Val Gln Ser Gly Pro Glu Leu Lys Lys Pro Gly Glu Thr Val
    130                 135                 140

Lys Ile Ser Cys Lys Ala Ser Gly Tyr Ile Phe Thr Asn Tyr Gly Met
145                 150                 155                 160

Asn Trp Val Lys Gln Ala Pro Gly Lys Ser Phe Lys Trp Met Gly Trp
                165                 170                 175

Ile Asn Thr Tyr Thr Gly Glu Ser Thr Tyr Ser Ala Asp Phe Lys Gly
            180                 185                 190

Arg Phe Ala Phe Ser Leu Glu Thr Ser Ala Ser Thr Ala Tyr Leu His
        195                 200                 205

Ile Asn Asp Leu Lys Asn Glu Asp Thr Ala Thr Tyr Phe Cys Ala Arg
    210                 215                 220

Ser Gly Gly Tyr Asp Pro Met Asp Tyr Trp Gly Gln Gly Thr Ser Val
225                 230                 235                 240

Thr Val Ser Ser

<210> SEQ ID NO 157
<211> LENGTH: 237
<212> TYPE: PRT
<213> ORGANISM: Artificial Sequence
<220> FEATURE:
```

<223> OTHER INFORMATION: Description of Artificial Sequence: Synthetic
     polypeptide

<400> SEQUENCE: 157

Asp Val Gln Ile Thr Gln Ser Pro Ser Tyr Leu Ala Ala Ser Pro Gly
1               5                   10                  15

Glu Thr Ile Thr Ile Asn Cys Arg Ala Ser Lys Ser Ile Ser Lys Asp
            20                  25                  30

Leu Ala Trp Tyr Gln Glu Lys Pro Gly Lys Thr Asn Lys Leu Leu Ile
        35                  40                  45

Tyr Ser Gly Ser Thr Leu Gln Ser Gly Ile Pro Ser Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Met Tyr Tyr Cys Gln Gln His Asn Lys Tyr Pro Tyr
                85                  90                  95

Thr Phe Gly Gly Gly Thr Lys Leu Glu Ile Lys Gly Gly Gly Gly Ser
            100                 105                 110

Gly Gly Gly Gly Ser Ser Gly Gly Gly Ser Gln Val Gln Leu Gln Gln
        115                 120                 125

Pro Gly Ala Glu Leu Val Arg Pro Gly Ala Ser Val Lys Leu Ser Cys
    130                 135                 140

Lys Ala Ser Gly Tyr Thr Phe Thr Ser Tyr Trp Met Asn Trp Val Lys
145                 150                 155                 160

Gln Arg Pro Asp Gln Gly Leu Glu Trp Ile Gly Arg Ile Asp Pro Tyr
                165                 170                 175

Asp Ser Glu Thr His Tyr Asn Gln Lys Phe Lys Asp Lys Ala Ile Leu
            180                 185                 190

Thr Val Asp Lys Ser Ser Ser Thr Ala Tyr Met Gln Leu Ser Ser Leu
        195                 200                 205

Thr Ser Glu Asp Ser Ala Val Tyr Tyr Cys Ala Arg Gly Asn Trp Asp
    210                 215                 220

Asp Tyr Trp Gly Gln Gly Thr Thr Leu Thr Val Ser Ser
225                 230                 235

<210> SEQ ID NO 158
<211> LENGTH: 249
<212> TYPE: PRT
<213> ORGANISM: Artificial Sequence
<220> FEATURE:
<223> OTHER INFORMATION: Description of Artificial Sequence: Synthetic
     polypeptide

<400> SEQUENCE: 158

Asp Ile Val Leu Thr Gln Ser Pro Asp Ser Leu Ala Val Ser Leu Gly
1               5                   10                  15

Glu Arg Ala Thr Ile Asn Cys Arg Ala Ser Glu Ser Val Asp Asn Tyr
            20                  25                  30

Gly Asn Thr Phe Met His Trp Tyr Gln Gln Lys Pro Gly Gln Pro Pro
        35                  40                  45

Lys Leu Leu Ile Tyr Arg Ala Ser Asn Leu Glu Ser Gly Val Pro Asp
    50                  55                  60

Arg Phe Ser Gly Ser Gly Ser Arg Thr Asp Phe Thr Leu Thr Ile Ser
65                  70                  75                  80

Ser Leu Gln Ala Glu Asp Val Ala Val Tyr Tyr Cys Gln Gln Ser Asn
                85                  90                  95

```
Glu Asp Pro Pro Thr Phe Gly Gln Gly Thr Lys Leu Glu Ile Lys Gly
                100                 105                 110

Gly Gly Gly Ser Gly Gly Gly Ser Gly Gly Gly Ser Gly Gly
            115                 120                 125

Gly Gly Ser Gln Ile Gln Leu Val Gln Ser Gly Ser Glu Leu Lys Lys
        130                 135                 140

Pro Gly Ala Ser Val Lys Val Ser Cys Lys Ala Ser Gly Tyr Ile Phe
145                 150                 155                 160

Thr Asn Tyr Gly Met Asn Trp Val Arg Gln Ala Pro Gly Gln Gly Leu
                165                 170                 175

Glu Trp Met Gly Trp Ile Asn Thr Tyr Thr Gly Glu Ser Thr Tyr Ser
            180                 185                 190

Ala Asp Phe Lys Gly Arg Phe Val Phe Ser Leu Asp Thr Ser Val Ser
        195                 200                 205

Thr Ala Tyr Leu Gln Ile Asn Ala Leu Lys Ala Glu Asp Thr Ala Val
        210                 215                 220

Tyr Tyr Cys Ala Arg Ser Gly Gly Tyr Asp Pro Met Asp Tyr Trp Gly
225                 230                 235                 240

Gln Gly Thr Thr Val Thr Val Ser Ser
                245
```

<210> SEQ ID NO 159
<211> LENGTH: 249
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 159

```
Asp Ile Val Leu Thr Gln Ser Pro Asp Ser Leu Ala Val Ser Leu Gly
1               5                   10                  15

Glu Arg Ala Thr Ile Asn Cys Arg Ala Ser Glu Ser Val Asp Asn Tyr
            20                  25                  30

Gly Asn Thr Phe Met His Trp Tyr Gln Gln Lys Pro Gly Gln Pro Pro
        35                  40                  45

Lys Leu Leu Ile Tyr Arg Ala Ser Asn Leu Glu Ser Gly Val Pro Asp
50                  55                  60

Arg Phe Ser Gly Ser Gly Ser Arg Thr Asp Phe Thr Leu Thr Ile Ser
65                  70                  75                  80

Ser Leu Gln Ala Glu Asp Val Ala Val Tyr Tyr Cys Gln Gln Ser Asn
                85                  90                  95

Glu Asp Pro Pro Thr Phe Gly Gln Gly Thr Lys Leu Glu Ile Lys Gly
                100                 105                 110

Gly Gly Gly Ser Gly Gly Gly Ser Gly Gly Gly Ser Gly Gly
            115                 120                 125

Gly Gly Ser Gln Ile Gln Leu Val Gln Ser Gly Ala Glu Val Lys Lys
        130                 135                 140

Pro Gly Ala Ser Val Lys Val Ser Cys Lys Ala Ser Gly Tyr Ile Phe
145                 150                 155                 160

Thr Asn Tyr Gly Met Asn Trp Val Arg Gln Ala Pro Gly Gln Arg Leu
                165                 170                 175

Glu Trp Met Gly Trp Ile Asn Thr Tyr Thr Gly Glu Ser Thr Tyr Ser
            180                 185                 190

Ala Asp Phe Lys Gly Arg Val Thr Ile Thr Leu Asp Thr Ser Ala Ser
        195                 200                 205
```

```
Thr Ala Tyr Met Glu Leu Ser Ser Leu Arg Ser Glu Asp Thr Ala Val
    210                 215                 220

Tyr Tyr Cys Ala Arg Ser Gly Gly Tyr Asp Pro Met Asp Tyr Trp Gly
225                 230                 235                 240

Gln Gly Thr Thr Val Thr Val Ser Ser
                245

<210> SEQ ID NO 160
<211> LENGTH: 249
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 160

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Glu Ser Val Asp Asn Tyr
            20                  25                  30

Gly Asn Thr Phe Met His Trp Tyr Gln Gln Lys Pro Gly Gln Ala Pro
        35                  40                  45

Arg Leu Leu Ile Tyr Arg Ala Ser Asn Leu Glu Ser Gly Ile Pro Ala
    50                  55                  60

Arg Phe Ser Gly Ser Gly Ser Arg Thr Asp Phe Thr Leu Thr Ile Ser
65                  70                  75                  80

Ser Leu Glu Pro Glu Asp Val Ala Val Tyr Tyr Cys Gln Gln Ser Asn
                85                  90                  95

Glu Asp Pro Pro Thr Phe Gly Gln Gly Thr Lys Leu Glu Ile Lys Gly
            100                 105                 110

Gly Gly Gly Ser Gly Gly Gly Gly Ser Gly Gly Gly Ser Gly Gly
        115                 120                 125

Gly Gly Ser Gln Ile Gln Leu Val Gln Ser Gly Ser Glu Leu Lys Lys
    130                 135                 140

Pro Gly Ala Ser Val Lys Val Ser Cys Lys Ala Ser Gly Tyr Ile Phe
145                 150                 155                 160

Thr Asn Tyr Gly Met Asn Trp Val Arg Gln Ala Pro Gly Gln Gly Leu
                165                 170                 175

Glu Trp Met Gly Trp Ile Asn Thr Tyr Thr Gly Glu Ser Thr Tyr Ser
            180                 185                 190

Ala Asp Phe Lys Gly Arg Phe Val Phe Ser Leu Asp Thr Ser Val Ser
        195                 200                 205

Thr Ala Tyr Leu Gln Ile Asn Ala Leu Lys Ala Glu Asp Thr Ala Val
    210                 215                 220

Tyr Tyr Cys Ala Arg Ser Gly Gly Tyr Asp Pro Met Asp Tyr Trp Gly
225                 230                 235                 240

Gln Gly Thr Thr Val Thr Val Ser Ser
                245

<210> SEQ ID NO 161
<211> LENGTH: 249
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 161
```

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Glu Ser Val Asp Asn Tyr
            20                  25                  30

Gly Asn Thr Phe Met His Trp Tyr Gln Gln Lys Pro Gly Gln Ala Pro
        35                  40                  45

Arg Leu Leu Ile Tyr Arg Ala Ser Asn Leu Glu Ser Gly Ile Pro Ala
50                  55                  60

Arg Phe Ser Gly Ser Gly Ser Arg Thr Asp Phe Thr Leu Thr Ile Ser
65                  70                  75                  80

Ser Leu Glu Pro Glu Asp Val Ala Val Tyr Tyr Cys Gln Gln Ser Asn
                85                  90                  95

Glu Asp Pro Pro Thr Phe Gly Gln Gly Thr Lys Leu Glu Ile Lys Gly
            100                 105                 110

Gly Gly Gly Ser Gly Gly Gly Gly Ser Gly Gly Gly Ser Gly Gly
        115                 120                 125

Gly Gly Ser Gln Ile Gln Leu Val Gln Ser Gly Ala Glu Val Lys Lys
130                 135                 140

Pro Gly Ala Ser Val Lys Val Ser Cys Lys Ala Ser Gly Tyr Ile Phe
145                 150                 155                 160

Thr Asn Tyr Gly Met Asn Trp Val Arg Gln Ala Pro Gly Gln Arg Leu
            165                 170                 175

Glu Trp Met Gly Trp Ile Asn Thr Tyr Thr Gly Glu Ser Thr Tyr Ser
        180                 185                 190

Ala Asp Phe Lys Gly Arg Val Thr Ile Thr Leu Asp Thr Ser Ala Ser
        195                 200                 205

Thr Ala Tyr Met Glu Leu Ser Ser Leu Arg Ser Glu Asp Thr Ala Val
210                 215                 220

Tyr Tyr Cys Ala Arg Ser Gly Gly Tyr Asp Pro Met Asp Tyr Trp Gly
225                 230                 235                 240

Gln Gly Thr Thr Val Thr Val Ser Ser
            245

<210> SEQ ID NO 162
<211> LENGTH: 249
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 162

Gln Ile Gln Leu Val Gln Ser Gly Ser Glu Leu Lys Lys Pro Gly Ala
1               5                   10                  15

Ser Val Lys Val Ser Cys Lys Ala Ser Gly Tyr Ile Phe Thr Asn Tyr
            20                  25                  30

Gly Met Asn Trp Val Arg Gln Ala Pro Gly Gln Gly Leu Glu Trp Met
        35                  40                  45

Gly Trp Ile Asn Thr Tyr Thr Gly Glu Ser Thr Tyr Ser Ala Asp Phe
50                  55                  60

Lys Gly Arg Phe Val Phe Ser Leu Asp Thr Ser Val Ser Thr Ala Tyr
65                  70                  75                  80

Leu Gln Ile Asn Ala Leu Lys Ala Glu Asp Thr Ala Val Tyr Tyr Cys
                85                  90                  95

Ala Arg Ser Gly Gly Tyr Asp Pro Met Asp Tyr Trp Gly Gln Gly Thr

```
            100                 105                 110
Thr Val Thr Val Ser Ser Gly Gly Gly Ser Gly Gly Gly Ser
            115                 120                 125

Gly Gly Gly Gly Ser Gly Gly Gly Ser Asp Ile Val Leu Thr Gln
            130                 135             140

Ser Pro Asp Ser Leu Ala Val Ser Leu Gly Glu Arg Ala Thr Ile Asn
145                 150                 155                 160

Cys Arg Ala Ser Glu Ser Val Asp Asn Tyr Gly Asn Thr Phe Met His
                165                 170                 175

Trp Tyr Gln Gln Lys Pro Gly Gln Pro Pro Lys Leu Leu Ile Tyr Arg
                180                 185                 190

Ala Ser Asn Leu Glu Ser Gly Val Pro Asp Arg Phe Ser Gly Ser Gly
                195                 200                 205

Ser Arg Thr Asp Phe Thr Leu Thr Ile Ser Ser Leu Gln Ala Glu Asp
            210                 215                 220

Val Ala Val Tyr Tyr Cys Gln Gln Ser Asn Glu Asp Pro Pro Thr Phe
225                 230                 235                 240

Gly Gln Gly Thr Lys Leu Glu Ile Lys
                245

<210> SEQ ID NO 163
<211> LENGTH: 249
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 163

Gln Ile Gln Leu Val Gln Ser Gly Ser Glu Leu Lys Lys Pro Gly Ala
1               5                   10                  15

Ser Val Lys Val Ser Cys Lys Ala Ser Gly Tyr Ile Phe Thr Asn Tyr
                20                  25                  30

Gly Met Asn Trp Val Arg Gln Ala Pro Gly Gln Gly Leu Glu Trp Met
            35                  40                  45

Gly Trp Ile Asn Thr Tyr Thr Gly Glu Ser Thr Tyr Ser Ala Asp Phe
        50                  55                  60

Lys Gly Arg Phe Val Phe Ser Leu Asp Thr Ser Val Ser Thr Ala Tyr
65                  70                  75                  80

Leu Gln Ile Asn Ala Leu Lys Ala Glu Asp Thr Ala Val Tyr Tyr Cys
                85                  90                  95

Ala Arg Ser Gly Gly Tyr Asp Pro Met Asp Tyr Trp Gly Gln Gly Thr
                100                 105                 110

Thr Val Thr Val Ser Ser Gly Gly Gly Ser Gly Gly Gly Gly Ser
            115                 120                 125

Gly Gly Gly Gly Ser Gly Gly Gly Ser Glu Ile Val Leu Thr Gln
            130                 135             140

Ser Pro Ala Thr Leu Ser Leu Ser Pro Gly Glu Arg Ala Thr Leu Ser
145                 150                 155                 160

Cys Arg Ala Ser Glu Ser Val Asp Asn Tyr Gly Asn Thr Phe Met His
                165                 170                 175

Trp Tyr Gln Gln Lys Pro Gly Gln Ala Pro Arg Leu Leu Ile Tyr Arg
                180                 185                 190

Ala Ser Asn Leu Glu Ser Gly Ile Pro Ala Arg Phe Ser Gly Ser Gly
                195                 200                 205
```

```
Ser Arg Thr Asp Phe Thr Leu Thr Ile Ser Ser Leu Glu Pro Glu Asp
    210                 215                 220
```

```
Val Ala Val Tyr Tyr Cys Gln Gln Ser Asn Glu Asp Pro Pro Thr Phe
225                 230                 235                 240
```

```
Gly Gln Gly Thr Lys Leu Glu Ile Lys
                245
```

<210> SEQ ID NO 164
<211> LENGTH: 249
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 164

```
Gln Ile Gln Leu Val Gln Ser Gly Ala Glu Val Lys Lys Pro Gly Ala
1               5                   10                  15
```

```
Ser Val Lys Val Ser Cys Lys Ala Ser Gly Tyr Ile Phe Thr Asn Tyr
            20                  25                  30
```

```
Gly Met Asn Trp Val Arg Gln Ala Pro Gly Gln Arg Leu Glu Trp Met
        35                  40                  45
```

```
Gly Trp Ile Asn Thr Tyr Thr Gly Glu Ser Thr Tyr Ser Ala Asp Phe
    50                  55                  60
```

```
Lys Gly Arg Val Thr Ile Thr Leu Asp Thr Ser Ala Ser Thr Ala Tyr
65                  70                  75                  80
```

```
Met Glu Leu Ser Ser Leu Arg Ser Glu Asp Thr Ala Val Tyr Tyr Cys
                85                  90                  95
```

```
Ala Arg Ser Gly Gly Tyr Asp Pro Met Asp Tyr Trp Gly Gln Gly Thr
            100                 105                 110
```

```
Thr Val Thr Val Ser Ser Gly Gly Gly Ser Gly Gly Gly Gly Ser
        115                 120                 125
```

```
Gly Gly Gly Gly Ser Gly Gly Gly Ser Asp Ile Val Leu Thr Gln
    130                 135                 140
```

```
Ser Pro Asp Ser Leu Ala Val Ser Leu Gly Glu Arg Ala Thr Ile Asn
145                 150                 155                 160
```

```
Cys Arg Ala Ser Glu Ser Val Asp Asn Tyr Gly Asn Thr Phe Met His
                165                 170                 175
```

```
Trp Tyr Gln Gln Lys Pro Gly Gln Pro Pro Lys Leu Leu Ile Tyr Arg
            180                 185                 190
```

```
Ala Ser Asn Leu Glu Ser Gly Val Pro Asp Arg Phe Ser Gly Ser Gly
        195                 200                 205
```

```
Ser Arg Thr Asp Phe Thr Leu Thr Ile Ser Ser Leu Gln Ala Glu Asp
    210                 215                 220
```

```
Val Ala Val Tyr Tyr Cys Gln Gln Ser Asn Glu Asp Pro Pro Thr Phe
225                 230                 235                 240
```

```
Gly Gln Gly Thr Lys Leu Glu Ile Lys
                245
```

<210> SEQ ID NO 165
<211> LENGTH: 249
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 165

-continued

```
Gln Ile Gln Leu Val Gln Ser Gly Ala Glu Val Lys Pro Gly Ala
1               5                   10                  15

Ser Val Lys Val Ser Cys Lys Ala Ser Gly Tyr Ile Phe Thr Asn Tyr
            20                  25                  30

Gly Met Asn Trp Val Arg Gln Ala Pro Gly Gln Arg Leu Glu Trp Met
        35                  40                  45

Gly Trp Ile Asn Thr Tyr Thr Gly Glu Ser Thr Tyr Ser Ala Asp Phe
50                  55                  60

Lys Gly Arg Val Thr Ile Thr Leu Asp Thr Ser Ala Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Ser Gly Gly Tyr Asp Pro Met Asp Tyr Trp Gly Gln Gly Thr
            100                 105                 110

Thr Val Thr Val Ser Ser Gly Gly Gly Gly Ser Gly Gly Gly Gly Ser
        115                 120                 125

Gly Gly Gly Gly Ser Gly Gly Gly Ser Glu Ile Val Leu Thr Gln
        130                 135                 140

Ser Pro Ala Thr Leu Ser Leu Ser Pro Gly Glu Arg Ala Thr Leu Ser
145                 150                 155                 160

Cys Arg Ala Ser Glu Ser Val Asp Asn Tyr Gly Asn Thr Phe Met His
            165                 170                 175

Trp Tyr Gln Gln Lys Pro Gly Gln Ala Pro Arg Leu Leu Ile Tyr Arg
        180                 185                 190

Ala Ser Asn Leu Glu Ser Gly Ile Pro Ala Arg Phe Ser Gly Ser Gly
        195                 200                 205

Ser Arg Thr Asp Phe Thr Leu Thr Ile Ser Ser Leu Glu Pro Glu Asp
210                 215                 220

Val Ala Val Tyr Tyr Cys Gln Gln Ser Asn Glu Asp Pro Pro Thr Phe
225                 230                 235                 240

Gly Gln Gly Thr Lys Leu Glu Ile Lys
                245
```

<210> SEQ ID NO 166
<211> LENGTH: 246
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 166

```
Glu Ile Gln Leu Val Gln Ser Gly Ala Glu Val Lys Lys Pro Gly Ala
1               5                   10                  15

Thr Val Lys Ile Ser Cys Lys Gly Ser Gly Phe Asn Ile Glu Asp Tyr
            20                  25                  30

Tyr Ile His Trp Val Gln Gln Ala Pro Gly Lys Gly Leu Glu Trp Met
        35                  40                  45

Gly Arg Ile Asp Pro Glu Asn Asp Glu Thr Lys Tyr Gly Pro Ile Phe
50                  55                  60

Gln Gly Arg Val Thr Ile Thr Ala Asp Thr Ser Thr Asn Thr Val Tyr
65                  70                  75                  80

Met Glu Leu Ser Ser Leu Arg Ser Glu Asp Thr Ala Val Tyr Tyr Cys
                85                  90                  95

Ala Phe Arg Gly Gly Val Tyr Trp Gly Gln Gly Thr Thr Val Thr Val
            100                 105                 110
```

```
Ser Ser Gly Gly Gly Ser Gly Gly Gly Ser Gly Gly Gly
        115                 120                 125

Ser Gly Gly Gly Ser Asp Val Val Met Thr Gln Ser Pro Asp Ser
        130                 135                 140

Leu Ala Val Ser Leu Gly Glu Arg Ala Thr Ile Asn Cys Lys Ser Ser
145                 150                 155                 160

Gln Ser Leu Leu Asp Ser Asp Gly Lys Thr Tyr Leu Asn Trp Leu Gln
                165                 170                 175

Gln Lys Pro Gly Gln Pro Pro Lys Arg Leu Ile Ser Leu Val Ser Lys
                180                 185                 190

Leu Asp Ser Gly Val Pro Asp Arg Phe Ser Gly Ser Gly Ser Gly Thr
                195                 200                 205

Asp Phe Thr Leu Thr Ile Ser Ser Leu Gln Ala Glu Asp Val Ala Val
                210                 215                 220

Tyr Tyr Cys Trp Gln Gly Thr His Phe Pro Gly Thr Phe Gly Gly Gly
225                 230                 235                 240

Thr Lys Val Glu Ile Lys
                245

<210> SEQ ID NO 167
<211> LENGTH: 246
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 167

Asp Val Val Met Thr Gln Ser Pro Asp Ser Leu Ala Val Ser Leu Gly
1               5                   10                  15

Glu Arg Ala Thr Ile Asn Cys Lys Ser Ser Gln Ser Leu Leu Asp Ser
                20                  25                  30

Asp Gly Lys Thr Tyr Leu Asn Trp Leu Gln Gln Lys Pro Gly Gln Pro
            35                  40                  45

Pro Lys Arg Leu Ile Ser Leu Val Ser Lys Leu Asp Ser Gly Val Pro
50                  55                  60

Asp Arg Phe Ser Gly Ser Gly Ser Gly Thr Asp Phe Thr Leu Thr Ile
65                  70                  75                  80

Ser Ser Leu Gln Ala Glu Asp Val Ala Val Tyr Tyr Cys Trp Gln Gly
                85                  90                  95

Thr His Phe Pro Gly Thr Phe Gly Gly Gly Thr Lys Val Glu Ile Lys
            100                 105                 110

Gly Gly Gly Gly Ser Gly Gly Gly Ser Gly Gly Gly Ser Gly
        115                 120                 125

Gly Gly Gly Ser Glu Ile Gln Leu Val Gln Ser Gly Ala Glu Val Lys
        130                 135                 140

Lys Pro Gly Ala Thr Val Lys Ile Ser Cys Lys Gly Ser Gly Phe Asn
145                 150                 155                 160

Ile Glu Asp Tyr Tyr Ile His Trp Val Gln Gln Ala Pro Gly Lys Gly
                165                 170                 175

Leu Glu Trp Met Gly Arg Ile Asp Pro Glu Asn Asp Glu Thr Lys Tyr
                180                 185                 190

Gly Pro Ile Phe Gln Gly Arg Val Thr Ile Thr Ala Asp Thr Ser Thr
                195                 200                 205

Asn Thr Val Tyr Met Glu Leu Ser Ser Leu Arg Ser Glu Asp Thr Ala
```

Val Tyr Tyr Cys Ala Phe Arg Gly Gly Val Tyr Trp Gly Gln Gly Thr
225                 230                 235                 240

Thr Val Thr Val Ser Ser
                245

<210> SEQ ID NO 168
<211> LENGTH: 246
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 168

Glu Ile Gln Leu Val Gln Ser Gly Ala Glu Val Lys Lys Pro Gly Glu
1               5                   10                  15

Ser Leu Arg Ile Ser Cys Lys Gly Ser Gly Phe Asn Ile Glu Asp Tyr
            20                  25                  30

Tyr Ile His Trp Val Arg Gln Met Pro Gly Lys Gly Leu Glu Trp Met
        35                  40                  45

Gly Arg Ile Asp Pro Glu Asn Asp Glu Thr Lys Tyr Gly Pro Ile Phe
50                  55                  60

Gln Gly His Val Thr Ile Ser Ala Asp Thr Ser Ile Asn Thr Val Tyr
65                  70                  75                  80

Leu Gln Trp Ser Ser Leu Lys Ala Ser Asp Thr Ala Met Tyr Tyr Cys
                85                  90                  95

Ala Phe Arg Gly Gly Val Tyr Trp Gly Gln Gly Thr Thr Val Thr Val
            100                 105                 110

Ser Ser Gly Gly Gly Gly Ser Gly Gly Gly Ser Gly Gly Gly Gly
            115                 120                 125

Ser Gly Gly Gly Gly Ser Asp Val Val Met Thr Gln Ser Pro Leu Ser
130                 135                 140

Leu Pro Val Thr Leu Gly Gln Pro Ala Ser Ile Ser Cys Lys Ser Ser
145                 150                 155                 160

Gln Ser Leu Leu Asp Ser Asp Gly Lys Thr Tyr Leu Asn Trp Leu Gln
                165                 170                 175

Gln Arg Pro Gly Gln Ser Pro Arg Arg Leu Ile Ser Leu Val Ser Lys
            180                 185                 190

Leu Asp Ser Gly Val Pro Asp Arg Phe Ser Gly Ser Gly Ser Gly Thr
        195                 200                 205

Asp Phe Thr Leu Lys Ile Ser Arg Val Glu Ala Glu Asp Val Gly Val
    210                 215                 220

Tyr Tyr Cys Trp Gln Gly Thr His Phe Pro Gly Thr Phe Gly Gly Gly
225                 230                 235                 240

Thr Lys Val Glu Ile Lys
                245

<210> SEQ ID NO 169
<211> LENGTH: 246
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 169

Asp Val Val Met Thr Gln Ser Pro Leu Ser Leu Pro Val Thr Leu Gly

```
1               5                   10                  15
Gln Pro Ala Ser Ile Ser Cys Lys Ser Ser Gln Ser Leu Leu Asp Ser
                20                  25                  30

Asp Gly Lys Thr Tyr Leu Asn Trp Leu Gln Gln Arg Pro Gly Gln Ser
                35                  40                  45

Pro Arg Leu Ile Ser Leu Val Ser Lys Leu Asp Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Trp Gln Gly
                85                  90                  95

Thr His Phe Pro Gly Thr Phe Gly Gly Gly Thr Lys Val Glu Ile Lys
                100                 105                 110

Gly Gly Gly Gly Ser Gly Gly Gly Ser Gly Gly Gly Ser
                115                 120                 125

Gly Gly Gly Ser Glu Ile Gln Leu Val Gln Ser Gly Ala Glu Val Lys
130                 135                 140

Lys Pro Gly Glu Ser Leu Arg Ile Ser Cys Lys Gly Ser Gly Phe Asn
145                 150                 155                 160

Ile Glu Asp Tyr Tyr Ile His Trp Val Arg Gln Met Pro Gly Lys Gly
                165                 170                 175

Leu Glu Trp Met Gly Arg Ile Asp Pro Glu Asn Asp Glu Thr Lys Tyr
                180                 185                 190

Gly Pro Ile Phe Gln Gly His Val Thr Ile Ser Ala Asp Thr Ser Ile
                195                 200                 205

Asn Thr Val Tyr Leu Gln Trp Ser Ser Leu Lys Ala Ser Asp Thr Ala
210                 215                 220

Met Tyr Tyr Cys Ala Phe Arg Gly Gly Val Tyr Trp Gly Gln Gly Thr
225                 230                 235                 240

Thr Val Thr Val Ser Ser
                245

<210> SEQ ID NO 170
<211> LENGTH: 246
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 170

Glu Ile Gln Leu Val Gln Ser Gly Ala Glu Val Lys Lys Pro Gly Ala
1               5                   10                  15

Thr Val Lys Ile Ser Cys Lys Gly Ser Gly Phe Asn Ile Glu Asp Tyr
                20                  25                  30

Tyr Ile His Trp Val Gln Gln Ala Pro Gly Lys Gly Leu Glu Trp Met
                35                  40                  45

Gly Arg Ile Asp Pro Glu Asn Asp Glu Thr Lys Tyr Gly Pro Ile Phe
    50                  55                  60

Gln Gly Arg Val Thr Ile Thr Ala Asp Thr Ser Thr Asn Thr Val Tyr
65                  70                  75                  80

Met Glu Leu Ser Ser Leu Arg Ser Glu Asp Thr Ala Val Tyr Tyr Cys
                85                  90                  95

Ala Phe Arg Gly Gly Val Tyr Trp Gly Gln Gly Thr Thr Val Thr Val
                100                 105                 110
```

```
Ser Ser Gly Gly Gly Ser Gly Gly Gly Ser Gly Gly Gly
        115                 120                 125

Ser Gly Gly Gly Ser Asp Val Val Met Thr Gln Ser Pro Leu Ser
    130                 135                 140

Leu Pro Val Thr Leu Gly Gln Pro Ala Ser Ile Ser Cys Lys Ser Ser
145                 150                 155                 160

Gln Ser Leu Leu Asp Ser Asp Gly Lys Thr Tyr Leu Asn Trp Leu Gln
                165                 170                 175

Gln Arg Pro Gly Gln Ser Pro Arg Arg Leu Ile Ser Leu Val Ser Lys
                180                 185                 190

Leu Asp Ser Gly Val Pro Asp Arg Phe Ser Gly Ser Gly Ser Gly Thr
                195                 200                 205

Asp Phe Thr Leu Lys Ile Ser Arg Val Glu Ala Glu Asp Val Gly Val
                210                 215                 220

Tyr Tyr Cys Trp Gln Gly Thr His Phe Pro Gly Thr Phe Gly Gly Gly
225                 230                 235                 240

Thr Lys Val Glu Ile Lys
                245
```

<210> SEQ ID NO 171
<211> LENGTH: 246
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 171

```
Glu Ile Gln Leu Val Gln Ser Gly Ala Glu Val Lys Lys Pro Gly Glu
1               5                   10                  15

Ser Leu Arg Ile Ser Cys Lys Gly Ser Gly Phe Asn Ile Glu Asp Tyr
                20                  25                  30

Tyr Ile His Trp Val Arg Gln Met Pro Gly Lys Gly Leu Glu Trp Met
            35                  40                  45

Gly Arg Ile Asp Pro Glu Asn Asp Glu Thr Lys Tyr Gly Pro Ile Phe
        50                  55                  60

Gln Gly His Val Thr Ile Ser Ala Asp Thr Ser Ile Asn Thr Val Tyr
65                  70                  75                  80

Leu Gln Trp Ser Ser Leu Lys Ala Ser Asp Thr Ala Met Tyr Tyr Cys
                85                  90                  95

Ala Phe Arg Gly Gly Val Tyr Trp Gly Gln Gly Thr Thr Val Thr Val
                100                 105                 110

Ser Ser Gly Gly Gly Gly Ser Gly Gly Gly Gly Ser Gly Gly Gly Gly
            115                 120                 125

Ser Gly Gly Gly Gly Ser Asp Val Val Met Thr Gln Ser Pro Asp Ser
    130                 135                 140

Leu Ala Val Ser Leu Gly Glu Arg Ala Thr Ile Asn Cys Lys Ser Ser
145                 150                 155                 160

Gln Ser Leu Leu Asp Ser Asp Gly Lys Thr Tyr Leu Asn Trp Leu Gln
                165                 170                 175

Gln Lys Pro Gly Gln Pro Pro Lys Arg Leu Ile Ser Leu Val Ser Lys
                180                 185                 190

Leu Asp Ser Gly Val Pro Asp Arg Phe Ser Gly Ser Gly Ser Gly Thr
                195                 200                 205

Asp Phe Thr Leu Thr Ile Ser Ser Leu Gln Ala Glu Asp Val Ala Val
                210                 215                 220
```

Tyr Tyr Cys Trp Gln Gly Thr His Phe Pro Gly Thr Phe Gly Gly Gly
225                 230                 235                 240

Thr Lys Val Glu Ile Lys
                245

<210> SEQ ID NO 172
<211> LENGTH: 246
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 172

Asp Val Val Met Thr Gln Ser Pro Asp Ser Leu Ala Val Ser Leu Gly
1               5                   10                  15

Glu Arg Ala Thr Ile Asn Cys Lys Ser Ser Gln Ser Leu Leu Asp Ser
            20                  25                  30

Asp Gly Lys Thr Tyr Leu Asn Trp Leu Gln Gln Lys Pro Gly Gln Pro
        35                  40                  45

Pro Lys Arg Leu Ile Ser Leu Val Ser Lys Leu Asp Ser Gly Val Pro
    50                  55                  60

Asp Arg Phe Ser Gly Ser Gly Ser Gly Thr Asp Phe Thr Leu Thr Ile
65                  70                  75                  80

Ser Ser Leu Gln Ala Glu Asp Val Ala Val Tyr Tyr Cys Trp Gln Gly
                85                  90                  95

Thr His Phe Pro Gly Thr Phe Gly Gly Gly Thr Lys Val Glu Ile Lys
            100                 105                 110

Gly Gly Gly Gly Ser Gly Gly Gly Gly Ser Gly Gly Gly Gly Ser Gly
        115                 120                 125

Gly Gly Gly Ser Glu Ile Gln Leu Val Gln Ser Gly Ala Glu Val Lys
    130                 135                 140

Lys Pro Gly Glu Ser Leu Arg Ile Ser Cys Lys Gly Ser Gly Phe Asn
145                 150                 155                 160

Ile Glu Asp Tyr Tyr Ile His Trp Val Arg Gln Met Pro Gly Lys Gly
                165                 170                 175

Leu Glu Trp Met Gly Arg Ile Asp Pro Glu Asn Asp Glu Thr Lys Tyr
            180                 185                 190

Gly Pro Ile Phe Gln Gly His Val Thr Ile Ser Ala Asp Thr Ser Ile
        195                 200                 205

Asn Thr Val Tyr Leu Gln Trp Ser Ser Leu Lys Ala Ser Asp Thr Ala
    210                 215                 220

Met Tyr Tyr Cys Ala Phe Arg Gly Gly Val Tyr Trp Gly Gln Gly Thr
225                 230                 235                 240

Thr Val Thr Val Ser Ser
                245

<210> SEQ ID NO 173
<211> LENGTH: 246
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 173

Asp Val Val Met Thr Gln Ser Pro Leu Ser Leu Pro Val Thr Leu Gly
1               5                   10                  15

```
Gln Pro Ala Ser Ile Ser Cys Lys Ser Ser Gln Ser Leu Leu Asp Ser
            20                  25                  30

Asp Gly Lys Thr Tyr Leu Asn Trp Leu Gln Gln Arg Pro Gly Gln Ser
        35                  40                  45

Pro Arg Arg Leu Ile Ser Leu Val Ser Lys Leu Asp Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Trp Gln Gly
                85                  90                  95

Thr His Phe Pro Gly Thr Phe Gly Gly Gly Thr Lys Val Glu Ile Lys
            100                 105                 110

Gly Gly Gly Gly Ser Gly Gly Gly Ser Gly Gly Gly Gly Ser Gly
            115                 120                 125

Gly Gly Gly Ser Glu Ile Gln Leu Val Gln Ser Gly Ala Glu Val Lys
    130                 135                 140

Lys Pro Gly Ala Thr Val Lys Ile Ser Cys Lys Ser Gly Phe Asn
145                 150                 155                 160

Ile Glu Asp Tyr Tyr Ile His Trp Val Gln Gln Ala Pro Gly Lys Gly
                165                 170                 175

Leu Glu Trp Met Gly Arg Ile Asp Pro Glu Asn Asp Glu Thr Lys Tyr
            180                 185                 190

Gly Pro Ile Phe Gln Gly Arg Val Thr Ile Thr Ala Asp Thr Ser Thr
        195                 200                 205

Asn Thr Val Tyr Met Glu Leu Ser Ser Leu Arg Ser Glu Asp Thr Ala
    210                 215                 220

Val Tyr Tyr Cys Ala Phe Arg Gly Gly Val Tyr Trp Gly Gln Gly Thr
225                 230                 235                 240

Thr Val Thr Val Ser Ser
                245

<210> SEQ ID NO 174
<211> LENGTH: 243
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 174

Glu Ile Gln Leu Gln Gln Ser Gly Ala Glu Leu Val Lys Pro Gly Ala
1               5                   10                  15

Ser Val Lys Leu Ser Cys Thr Gly Ser Gly Phe Asn Ile Glu Asp Tyr
            20                  25                  30

Tyr Ile His Trp Val Lys Gln Arg Thr Glu Gln Gly Leu Glu Trp Ile
        35                  40                  45

Gly Arg Ile Asp Pro Glu Asn Asp Glu Thr Lys Tyr Gly Pro Ile Phe
    50                  55                  60

Gln Gly Arg Ala Thr Ile Thr Ala Asp Thr Ser Ser Asn Thr Val Tyr
65                  70                  75                  80

Leu Gln Leu Ser Ser Leu Thr Ser Glu Asp Thr Ala Val Tyr Tyr Cys
                85                  90                  95

Ala Phe Arg Gly Gly Val Tyr Trp Gly Pro Gly Thr Thr Leu Thr Val
            100                 105                 110

Ser Ser Gly Gly Gly Gly Ser Gly Gly Gly Gly Ser Gly Gly Gly Gly
```

```
            115                 120                 125
Ser His Met Asp Val Val Met Thr Gln Ser Pro Leu Thr Leu Ser Val
130                 135                 140

Ala Ile Gly Gln Ser Ala Ser Ile Ser Cys Lys Ser Gln Ser Leu
145                 150                 155                 160

Leu Asp Ser Asp Gly Lys Thr Tyr Leu Asn Trp Leu Leu Gln Arg Pro
        165                 170                 175

Gly Gln Ser Pro Lys Arg Leu Ile Ser Leu Val Ser Lys Leu Asp Ser
            180                 185                 190

Gly Val Pro Asp Arg Phe Thr Gly Ser Gly Ser Gly Thr Asp Phe Thr
            195                 200                 205

Leu Arg Ile Ser Arg Val Glu Ala Glu Asp Leu Gly Ile Tyr Tyr Cys
        210                 215                 220

Trp Gln Gly Thr His Phe Pro Gly Thr Phe Gly Gly Gly Thr Lys Leu
225                 230                 235                 240

Glu Ile Lys

<210> SEQ ID NO 175
<211> LENGTH: 239
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 175

Gln Val Gln Leu Gln Gln Ser Gly Pro Glu Leu Glu Lys Pro Gly Ala
1               5                   10                  15

Ser Val Lys Ile Ser Cys Lys Ala Ser Gly Tyr Ser Phe Thr Gly Tyr
            20                  25                  30

Thr Met Asn Trp Val Lys Gln Ser His Gly Lys Ser Leu Glu Trp Ile
        35                  40                  45

Gly Leu Ile Thr Pro Tyr Asn Gly Ala Ser Ser Tyr Asn Gln Lys Phe
    50                  55                  60

Arg Gly Lys Ala Thr Leu Thr Val Asp Lys Ser Ser Ser Thr Ala Tyr
65                  70                  75                  80

Met Asp Leu Leu Ser Leu Thr Ser Glu Asp Ser Ala Val Tyr Phe Cys
                85                  90                  95

Ala Arg Gly Gly Tyr Asp Gly Arg Gly Phe Asp Tyr Trp Gly Gln Gly
            100                 105                 110

Thr Thr Val Thr Val Ser Ser Gly Gly Gly Ser Gly Gly Gly Gly
            115                 120                 125

Ser Gly Gly Gly Gly Ser Asp Ile Glu Leu Thr Gln Ser Pro Ala Ile
130                 135                 140

Met Ser Ala Ser Pro Gly Glu Lys Val Thr Met Thr Cys Ser Ala Ser
145                 150                 155                 160

Ser Ser Val Ser Tyr Met His Trp Tyr Gln Gln Lys Ser Gly Thr Ser
            165                 170                 175

Pro Lys Arg Trp Ile Tyr Asp Thr Ser Lys Leu Ala Ser Gly Val Pro
        180                 185                 190

Gly Arg Phe Ser Gly Ser Gly Ser Gly Asn Ser Tyr Ser Leu Thr Ile
            195                 200                 205

Ser Ser Val Glu Ala Glu Asp Asp Ala Thr Tyr Tyr Cys Gln Gln Trp
        210                 215                 220

Ser Gly Tyr Pro Leu Thr Phe Gly Ala Gly Thr Lys Leu Glu Ile
```

<210> SEQ ID NO 176
<211> LENGTH: 244
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 176

Gln Val Gln Leu Gln Gln Ser Gly Ala Glu Val Lys Lys Pro Gly Ala
1               5                   10                  15

Ser Val Lys Val Ser Cys Lys Ala Ser Gly Tyr Thr Phe Thr Gly Tyr
            20                  25                  30

Tyr Met His Trp Val Arg Gln Ala Pro Gly Gln Gly Leu Glu Trp Met
        35                  40                  45

Gly Arg Ile Asn Pro Asn Ser Gly Gly Thr Asn Tyr Ala Gln Lys Phe
    50                  55                  60

Gln Gly Arg Val Thr Met Thr Arg Asp Thr Ser Ile Ser Thr Ala Tyr
65                  70                  75                  80

Met Glu Leu Ser Arg Leu Arg Ser Glu Asp Thr Ala Val Tyr Tyr Cys
                85                  90                  95

Ala Arg Gly Arg Tyr Tyr Gly Met Asp Val Trp Gly Gln Gly Thr Met
            100                 105                 110

Val Thr Val Ser Ser Gly Gly Gly Gly Ser Gly Gly Gly Gly Ser Gly
        115                 120                 125

Gly Gly Gly Ser Gly Gly Gly Ser Glu Ile Val Leu Thr Gln Ser
    130                 135                 140

Pro Ala Thr Leu Ser Leu Ser Pro Gly Glu Arg Ala Thr Ile Ser Cys
145                 150                 155                 160

Arg Ala Ser Gln Ser Val Ser Ser Asn Phe Ala Trp Tyr Gln Gln Arg
                165                 170                 175

Pro Gly Gln Ala Pro Arg Leu Leu Ile Tyr Asp Ala Ser Asn Arg Ala
            180                 185                 190

Thr Gly Ile Pro Pro Arg Phe Ser Gly Ser Gly Ser Gly Thr Asp Phe
        195                 200                 205

Thr Leu Thr Ile Ser Ser Leu Glu Pro Glu Asp Phe Ala Ala Tyr Tyr
    210                 215                 220

Cys His Gln Arg Ser Asn Trp Leu Tyr Thr Phe Gly Gln Gly Thr Lys
225                 230                 235                 240

Val Asp Ile Lys

<210> SEQ ID NO 177
<211> LENGTH: 253
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 177

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Gly Tyr
            20                  25                  30

Tyr Met His Trp Val Arg Gln Ala Pro Gly Gln Gly Leu Glu Trp Met
        35                  40                  45

```
Gly Trp Ile Asn Pro Asn Ser Gly Gly Thr Asn Tyr Ala Gln Lys Phe
         50                  55                  60

Gln Gly Arg Val Thr Met Thr Arg Asp Thr Ser Ile Ser Thr Ala Tyr
 65                  70                  75                  80

Met Glu Leu Ser Arg Leu Arg Ser Asp Asp Thr Ala Val Tyr Tyr Cys
                 85                  90                  95

Ala Arg Asp Leu Arg Arg Thr Val Val Thr Pro Arg Ala Tyr Tyr Gly
                100                 105                 110

Met Asp Val Trp Gly Gln Gly Thr Thr Val Thr Val Ser Ser Gly Gly
                115                 120                 125

Gly Gly Ser Gly Gly Gly Ser Gly Gly Gly Ser Gly Gly Gly
            130                 135                 140

Gly Ser Asp Ile Gln Leu Thr Gln Ser Pro Ser Thr Leu Ser Ala Ser
145                 150                 155                 160

Val Gly Asp Arg Val Thr Ile Thr Cys Gln Ala Ser Gln Asp Ile Ser
                165                 170                 175

Asn Ser Leu Asn Trp Tyr Gln Gln Lys Ala Gly Lys Ala Pro Lys Leu
                180                 185                 190

Leu Ile Tyr Asp Ala Ser Thr Leu Glu Thr Gly Val Pro Ser Arg Phe
                195                 200                 205

Ser Gly Ser Gly Ser Gly Thr Asp Phe Ser Phe Thr Ile Ser Ser Leu
                210                 215                 220

Gln Pro Glu Asp Ile Ala Thr Tyr Tyr Cys Gln Gln His Asp Asn Leu
225                 230                 235                 240

Pro Leu Thr Phe Gly Gln Gly Thr Lys Val Glu Ile Lys
                245                 250

<210> SEQ ID NO 178
<211> LENGTH: 246
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 178

Gln Val Gln Leu Val Gln Ser Gly Ala Glu Val Lys Lys Pro Gly Ala
 1                5                  10                  15

Pro Val Lys Val Ser Cys Lys Ala Ser Gly Tyr Thr Phe Thr Gly Tyr
                 20                  25                  30

Tyr Met His Trp Val Arg Gln Ala Pro Gly Gln Gly Leu Glu Trp Met
             35                  40                  45

Gly Trp Ile Asn Pro Asn Ser Gly Gly Thr Asn Tyr Ala Gln Lys Phe
         50                  55                  60

Gln Gly Arg Val Thr Met Thr Arg Asp Thr Ser Ile Ser Thr Ala Tyr
 65                  70                  75                  80

Met Glu Leu Ser Arg Leu Arg Ser Asp Asp Thr Ala Val Tyr Tyr Cys
                 85                  90                  95

Ala Arg Gly Glu Trp Asp Gly Ser Tyr Tyr Asp Tyr Trp Gly Gln
                100                 105                 110

Gly Thr Leu Val Thr Val Ser Ser Gly Gly Gly Gly Ser Gly Gly Gly
            115                 120                 125

Gly Ser Gly Gly Gly Gly Ser Gly Gly Gly Ser Asp Ile Val Leu
            130                 135                 140

Thr Gln Thr Pro Ser Ser Leu Ser Ala Ser Val Gly Asp Arg Val Thr
```

```
              145                 150                 155                 160
Ile Thr Cys Arg Ala Ser Gln Ser Ile Asn Thr Tyr Leu Asn Trp Tyr
                165                 170                 175

Gln His Lys Pro Gly Lys Ala Pro Lys Leu Leu Ile Tyr Ala Ala Ser
            180                 185                 190

Ser Leu Gln Ser Gly Val Pro Ser Arg Phe Ser Gly Ser Gly Ser Gly
            195                 200                 205

Thr Asp Phe Thr Leu Thr Ile Ser Ser Leu Gln Pro Glu Asp Phe Ala
        210                 215                 220

Thr Tyr Tyr Cys Gln Gln Ser Phe Ser Pro Leu Thr Phe Gly Gly Gly
225                 230                 235                 240

Thr Lys Leu Glu Ile Lys
                245

<210> SEQ ID NO 179
<211> LENGTH: 242
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 179

Gln Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Trp Met His Trp Val Arg Gln Pro Gly Lys Gly Leu Val Trp Val
            35                  40                  45

Ser Arg Ile Asn Thr Asp Gly Ser Thr Thr Tyr Ala Asp Ser Val
50                  55                  60

Glu Gly Arg Phe Thr Ile Ser Arg Asp Asn Ala Lys Asn Thr Leu Tyr
65                  70                  75                  80

Leu Gln Met Asn Ser Leu Arg Asp Asp Thr Ala Val Tyr Tyr Cys
                85                  90                  95

Val Gly Gly His Trp Ala Val Trp Gly Gln Gly Thr Thr Val Thr Val
                100                 105                 110

Ser Ser Gly Gly Gly Gly Ser Gly Gly Gly Ser Gly Gly Gly Gly
            115                 120                 125

Ser Gly Gly Gly Gly Ser Asp Ile Gln Met Thr Gln Ser Pro Ser Thr
            130                 135                 140

Leu Ser Ala Ser Val Gly Asp Arg Val Thr Ile Thr Cys Arg Ala Ser
145                 150                 155                 160

Gln Ser Ile Ser Asp Arg Leu Ala Trp Tyr Gln Gln Lys Pro Gly Lys
                165                 170                 175

Ala Pro Lys Leu Leu Ile Tyr Lys Ala Ser Ser Leu Glu Ser Gly Val
            180                 185                 190

Pro Ser Arg Phe Ser Gly Ser Gly Ser Gly Thr Glu Phe Thr Leu Thr
            195                 200                 205

Ile Ser Ser Leu Gln Pro Asp Asp Phe Ala Val Tyr Tyr Cys Gln Gln
        210                 215                 220

Tyr Gly His Leu Pro Met Tyr Thr Phe Gly Gln Gly Thr Lys Val Glu
225                 230                 235                 240

Ile Lys
```

```
<210> SEQ ID NO 180
<211> LENGTH: 241
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 180

Gln Val Gln Leu Val Gln Ser Gly Ala Glu Val Glu Lys Pro Gly Ala
1               5                   10                  15

Ser Val Lys Val Ser Cys Lys Ala Ser Gly Tyr Thr Phe Thr Asp Tyr
                20                  25                  30

Tyr Met His Trp Val Arg Gln Ala Pro Gly Gln Gly Leu Glu Trp Met
            35                  40                  45

Gly Trp Ile Asn Pro Asn Ser Gly Gly Thr Asn Tyr Ala Gln Lys Phe
    50                  55                  60

Gln Gly Arg Val Thr Met Thr Arg Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Ala Ser Gly Trp Asp Phe Asp Tyr Trp Gly Gln Gly Thr Leu Val Thr
            100                 105                 110

Val Ser Ser Gly Gly Gly Gly Ser Gly Gly Gly Gly Ser Gly Gly Gly
        115                 120                 125

Gly Ser Gly Gly Gly Gly Ser Asp Ile Val Met Thr Gln Ser Pro Ser
    130                 135                 140

Ser Leu Ser Ala Ser Val Gly Asp Arg Val Thr Ile Thr Cys Arg Ala
145                 150                 155                 160

Ser Gln Ser Ile Arg Tyr Tyr Leu Ser Trp Tyr Gln Gln Lys Pro Gly
                165                 170                 175

Lys Ala Pro Lys Leu Leu Ile Tyr Thr Ala Ser Ile Leu Gln Asn Gly
            180                 185                 190

Val Pro Ser Arg Phe Ser Gly Ser Gly Ser Gly Thr Asp Phe Thr Leu
        195                 200                 205

Thr Ile Ser Ser Leu Gln Pro Glu Asp Phe Ala Thr Tyr Tyr Cys Leu
    210                 215                 220

Gln Thr Tyr Thr Thr Pro Asp Phe Gly Pro Gly Thr Lys Val Glu Ile
225                 230                 235                 240

Lys

<210> SEQ ID NO 181
<211> LENGTH: 253
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 181

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
                20                  25                  30

Tyr Met His Trp Val Arg Gln Ala Pro Gly Gln Gly Leu Glu Trp Met
            35                  40                  45

Gly Ile Ile Asn Pro Ser Gly Gly Ser Thr Ser Tyr Ala Gln Lys Phe
    50                  55                  60
```

Gln Gly Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Tyr Arg Leu Ile Ala Val Ala Gly Asp Tyr Tyr Tyr Tyr Gly
            100                 105                 110

Met Asp Val Trp Gly Gln Gly Thr Met Val Thr Val Ser Ser Gly Gly
        115                 120                 125

Gly Gly Ser Gly Gly Gly Ser Gly Gly Gly Ser Gly Gly Gly
130                 135                 140

Gly Ser Asp Ile Gln Met Thr Gln Ser Pro Ser Ser Val Ser Ala Ser
145                 150                 155                 160

Val Gly Asp Arg Val Thr Ile Thr Cys Arg Ala Ser Gln Gly Val Gly
            165                 170                 175

Arg Trp Leu Ala Trp Tyr Gln Gln Lys Pro Gly Thr Ala Pro Lys Leu
        180                 185                 190

Leu Ile Tyr Ala Ala Ser Thr Leu Gln Ser Gly Val Pro Ser Arg Phe
    195                 200                 205

Ser Gly Ser Gly Ser Gly Thr Asp Phe Thr Leu Thr Ile Asn Asn Leu
210                 215                 220

Gln Pro Glu Asp Phe Ala Thr Tyr Tyr Cys Gln Gln Ala Asn Ser Phe
225                 230                 235                 240

Pro Leu Thr Phe Gly Gly Gly Thr Arg Leu Glu Ile Lys
                245                 250

<210> SEQ ID NO 182
<211> LENGTH: 250
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 182

Gln Val Gln Leu Val Gln Ser Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Ala Met His Trp Val Arg Gln Ala Pro Gly Lys Gly Leu Glu Trp Val
        35                  40                  45

Ala Val Ile Ser Tyr Asp Gly Ser Asn Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Trp Lys Val Ser Ser Ser Pro Ala Phe Asp Tyr Trp Gly
            100                 105                 110

Gln Gly Thr Leu Val Thr Val Ser Ser Gly Gly Gly Ser Gly Gly
        115                 120                 125

Gly Gly Ser Gly Gly Gly Gly Ser Gly Gly Gly Ser Glu Ile Val
130                 135                 140

Leu Thr Gln Ser Pro Ala Thr Leu Ser Leu Ser Pro Gly Glu Arg Ala
145                 150                 155                 160

Ile Leu Ser Cys Arg Ala Ser Gln Ser Val Tyr Thr Lys Tyr Leu Gly

```
                    165                 170                 175

Trp Tyr Gln Gln Lys Pro Gly Gln Ala Pro Arg Leu Leu Ile Tyr Asp
            180                 185                 190

Ala Ser Thr Arg Ala Thr Gly Ile Pro Asp Arg Phe Ser Gly Ser Gly
        195                 200                 205

Ser Gly Thr Asp Phe Thr Leu Thr Ile Asn Arg Leu Glu Pro Glu Asp
    210                 215                 220

Phe Ala Val Tyr Tyr Cys Gln His Tyr Gly Gly Ser Pro Leu Ile Thr
225                 230                 235                 240

Phe Gly Gln Gly Thr Arg Leu Glu Ile Lys
                245                 250

<210> SEQ ID NO 183
<211> LENGTH: 246
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 183

Gln Val Gln Leu Gln Gln Ser Gly Ala Glu Val Lys Lys Pro Gly Ala
1               5                   10                  15

Ser Val Lys Val Ser Cys Lys Thr Ser Gly Tyr Pro Phe Thr Gly Tyr
            20                  25                  30

Ser Leu His Trp Val Arg Gln Ala Pro Gly Gln Gly Leu Glu Trp Met
        35                  40                  45

Gly Trp Ile Asn Pro Asn Ser Gly Gly Thr Asn Tyr Ala Gln Lys Phe
    50                  55                  60

Gln Gly Arg Val Thr Met Thr Arg Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Ala Arg Asp His Tyr Gly Gly Asn Ser Leu Phe Tyr Trp Gly Gln Gly
            100                 105                 110

Thr Leu Val Thr Val Ser Ser Gly Gly Gly Gly Ser Gly Gly Gly Gly
        115                 120                 125

Ser Gly Gly Gly Gly Ser Gly Gly Gly Gly Ser Asp Ile Gln Leu Thr
    130                 135                 140

Gln Ser Pro Ser Ser Ile Ser Ala Ser Val Gly Asp Thr Val Ser Ile
145                 150                 155                 160

Thr Cys Arg Ala Ser Gln Asp Ser Gly Thr Trp Leu Ala Trp Tyr Gln
                165                 170                 175

Gln Lys Pro Gly Lys Ala Pro Asn Leu Leu Met Tyr Asp Ala Ser Thr
            180                 185                 190

Leu Glu Asp Gly Val Pro Ser Arg Phe Ser Gly Ser Ala Ser Gly Thr
        195                 200                 205

Glu Phe Thr Leu Thr Val Asn Arg Leu Gln Pro Glu Asp Ser Ala Thr
    210                 215                 220

Tyr Tyr Cys Gln Gln Tyr Asn Ser Tyr Pro Leu Thr Phe Gly Gly Gly
225                 230                 235                 240

Thr Lys Val Asp Ile Lys
                245

<210> SEQ ID NO 184
<211> LENGTH: 248
```

<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 184

Gln Val Gln Leu Val Gln Ser Gly Ala Glu Val Lys Lys Pro Gly Ala
1               5                   10                  15

Ser Val Glu Val Ser Cys Lys Ala Ser Gly Tyr Thr Phe Thr Ser Tyr
            20                  25                  30

Tyr Met His Trp Val Arg Gln Ala Pro Gly Gln Gly Leu Glu Trp Met
        35                  40                  45

Gly Ile Ile Asn Pro Ser Gly Gly Ser Thr Gly Tyr Ala Gln Lys Phe
    50                  55                  60

Gln Gly Arg Val Thr Met Thr Arg Asp Thr Ser Thr Ser Thr Val His
65                  70                  75                  80

Met Glu Leu Ser Ser Leu Arg Ser Glu Asp Thr Ala Val Tyr Tyr Cys
                85                  90                  95

Ala Arg Gly Gly Tyr Ser Ser Ser Asp Ala Phe Asp Ile Trp Gly
            100                 105                 110

Gln Gly Thr Met Val Thr Val Ser Gly Gly Gly Ser Gly Gly
            115                 120                 125

Gly Gly Ser Gly Gly Gly Ser Gly Gly Gly Ser Asp Ile Gln
        130                 135                 140

Met Thr Gln Ser Pro Pro Ser Leu Ser Ala Ser Val Gly Asp Arg Val
145                 150                 155                 160

Thr Ile Thr Cys Arg Ala Ser Gln Asp Ile Ser Ser Ala Leu Ala Trp
                165                 170                 175

Tyr Gln Gln Lys Pro Gly Thr Pro Pro Lys Leu Leu Ile Tyr Asp Ala
            180                 185                 190

Ser Ser Leu Glu Ser Gly Val Pro Ser Arg Phe Ser Gly Ser Gly Ser
        195                 200                 205

Gly Thr Asp Phe Thr Leu Thr Ile Ser Ser Leu Gln Pro Glu Asp Phe
    210                 215                 220

Ala Thr Tyr Tyr Cys Gln Gln Phe Ser Ser Tyr Pro Leu Thr Phe Gly
225                 230                 235                 240

Gly Gly Thr Arg Leu Glu Ile Lys
                245

<210> SEQ ID NO 185
<211> LENGTH: 255
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 185

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Gly Ile Ser Trp Val Arg Gln Ala Pro Gly Gln Gly Leu Glu Trp Met
        35                  40                  45

Gly Trp Ile Ser Ala Tyr Asn Gly Asn Thr Asn Tyr Ala Gln Lys Leu
    50                  55                  60

```
Gln Gly Arg Val Thr Met Thr Thr Asp Thr Ser Thr Ser Thr Ala Tyr
 65                  70                  75                  80

Met Glu Leu Arg Ser Leu Arg Ser Asp Asp Thr Ala Val Tyr Tyr Cys
                 85                  90                  95

Ala Arg Val Ala Gly Gly Ile Tyr Tyr Tyr Gly Met Asp Val Trp
            100                 105                 110

Gly Gln Gly Thr Thr Ile Thr Val Ser Ser Gly Gly Gly Ser Gly
            115                 120                 125

Gly Gly Gly Ser Gly Gly Gly Gly Ser Gly Gly Gly Ser Asp Ile
        130                 135                 140

Val Met Thr Gln Thr Pro Asp Ser Leu Ala Val Ser Leu Gly Glu Arg
145                 150                 155                 160

Ala Thr Ile Ser Cys Lys Ser Ser His Ser Val Leu Tyr Asn Arg Asn
                165                 170                 175

Asn Lys Asn Tyr Leu Ala Trp Tyr Gln Gln Lys Pro Gly Gln Pro Pro
            180                 185                 190

Lys Leu Leu Phe Tyr Trp Ala Ser Thr Arg Lys Ser Gly Val Pro Asp
        195                 200                 205

Arg Phe Ser Gly Ser Gly Ser Gly Thr Asp Phe Thr Leu Thr Ile Ser
    210                 215                 220

Ser Leu Gln Pro Glu Asp Phe Ala Thr Tyr Phe Cys Gln Gln Thr Gln
225                 230                 235                 240

Thr Phe Pro Leu Thr Phe Gly Gln Gly Thr Arg Leu Glu Ile Asn
                245                 250                 255

<210> SEQ ID NO 186
<211> LENGTH: 241
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 186

Gln Val Gln Leu Gln Gln Ser Gly Ala Glu Val Lys Lys Pro Gly Ala
 1               5                  10                  15

Ser Val Lys Val Ser Cys Lys Ala Ser Gly Tyr Thr Phe Thr Gly Tyr
             20                  25                  30

Tyr Met His Trp Val Arg Gln Ala Pro Gly Gln Gly Leu Glu Trp Met
         35                  40                  45

Gly Trp Ile Asn Pro Asn Ser Gly Gly Thr Asn Tyr Ala Gln Asn Phe
     50                  55                  60

Gln Gly Arg Val Thr Met Thr Arg Asp Thr Ser Ile Ser Thr Ala Tyr
 65                  70                  75                  80

Met Glu Leu Arg Arg Leu Arg Ser Asp Asp Thr Ala Val Tyr Tyr Cys
                 85                  90                  95

Ala Ser Gly Trp Asp Phe Asp Tyr Trp Gly Gln Gly Thr Leu Val Thr
            100                 105                 110

Val Ser Ser Gly Gly Gly Gly Ser Gly Gly Gly Gly Ser Gly Gly Gly
        115                 120                 125

Gly Ser Gly Gly Gly Gly Ser Asp Ile Arg Met Thr Gln Ser Pro Ser
    130                 135                 140

Ser Leu Ser Ala Ser Val Gly Asp Arg Val Thr Ile Thr Cys Arg Ala
145                 150                 155                 160

Ser Gln Ser Ile Arg Tyr Tyr Leu Ser Trp Tyr Gln Gln Lys Pro Gly
                165                 170                 175
```

```
Lys Ala Pro Lys Leu Leu Ile Tyr Thr Ala Ser Ile Leu Gln Asn Gly
            180                 185                 190

Val Pro Ser Arg Phe Ser Gly Ser Gly Ser Gly Thr Asp Phe Thr Leu
            195                 200                 205

Thr Ile Ser Ser Leu Gln Pro Glu Asp Phe Ala Thr Tyr Tyr Cys Leu
        210                 215                 220

Gln Thr Tyr Thr Thr Pro Asp Phe Gly Pro Gly Thr Lys Val Glu Ile
225                 230                 235                 240

Lys

<210> SEQ ID NO 187
<211> LENGTH: 246
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 187

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Gly Tyr
            20                  25                  30

Tyr Met His Trp Val Arg Gln Ala Pro Gly Gln Gly Leu Glu Trp Met
        35                  40                  45

Gly Arg Ile Asn Pro Asn Ser Gly Gly Thr Asn Tyr Ala Gln Lys Phe
    50                  55                  60

Gln Gly Arg Val Thr Met Thr Thr Asp Thr Ser Thr Ser Thr Ala Tyr
65                  70                  75                  80

Met Glu Leu Arg Ser Leu Arg Ser Asp Asp Thr Ala Val Tyr Tyr Cys
                85                  90                  95

Ala Arg Thr Thr Thr Ser Tyr Ala Phe Asp Ile Trp Gly Gln Gly Thr
            100                 105                 110

Met Val Thr Val Ser Ser Gly Gly Gly Gly Ser Gly Gly Gly Gly Ser
        115                 120                 125

Gly Gly Gly Gly Ser Gly Gly Gly Ser Asp Ile Gln Leu Thr Gln
    130                 135                 140

Ser Pro Ser Thr Leu Ser Ala Ser Val Gly Asp Arg Val Thr Ile Thr
145                 150                 155                 160

Cys Arg Ala Ser Gln Ser Ile Ser Thr Trp Leu Ala Trp Tyr Gln Gln
                165                 170                 175

Lys Pro Gly Lys Ala Pro Asn Leu Leu Ile Tyr Lys Ala Ser Thr Leu
            180                 185                 190

Glu Ser Gly Val Pro Ser Arg Phe Ser Gly Ser Gly Ser Gly Thr Glu
        195                 200                 205

Phe Thr Leu Thr Ile Ser Ser Leu Gln Pro Asp Asp Phe Ala Thr Tyr
    210                 215                 220

Tyr Cys Gln Gln Tyr Asn Thr Tyr Ser Pro Tyr Thr Phe Gly Gln Gly
225                 230                 235                 240

Thr Lys Leu Glu Ile Lys
                245

<210> SEQ ID NO 188
<211> LENGTH: 249
<212> TYPE: PRT
<213> ORGANISM: Artificial Sequence
```

```
<220> FEATURE:
<223> OTHER INFORMATION: Description of Artificial Sequence: Synthetic
      polypeptide

<400> SEQUENCE: 188

Gln Val Gln Leu Val Gln Ser Gly Gly Gly Leu Val Lys Pro Gly Gly
1               5                   10                  15

Ser Leu Arg Leu Ser Cys Glu Ala Ser Gly Phe Ile Phe Ser Asp Tyr
            20                  25                  30

Tyr Met Gly Trp Ile Arg Gln Ala Pro Gly Lys Gly Leu Glu Trp Val
        35                  40                  45

Ser Tyr Ile Gly Arg Ser Gly Ser Ser Met Tyr Tyr Ala Asp Ser Val
50                  55                  60

Lys Gly Arg Phe Thr Phe Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Ala Ser Pro Val Val Ala Ala Thr Glu Asp Phe Gln His Trp Gly
            100                 105                 110

Gln Gly Thr Leu Val Thr Val Ser Ser Gly Gly Gly Ser Gly Gly
        115                 120                 125

Gly Gly Ser Gly Gly Gly Ser Gly Gly Gly Ser Asp Ile Val
        130                 135                 140

Met Thr Gln Thr Pro Ala Thr Leu Ser Leu Ser Pro Gly Glu Arg Ala
145                 150                 155                 160

Thr Leu Ser Cys Arg Ala Ser Gln Ser Val Thr Ser Asn Tyr Leu Ala
                165                 170                 175

Trp Tyr Gln Gln Lys Pro Gly Gln Ala Pro Arg Leu Leu Phe Gly
            180                 185                 190

Ala Ser Thr Arg Ala Thr Gly Ile Pro Asp Arg Phe Ser Gly Ser Gly
            195                 200                 205

Ser Gly Thr Asp Phe Thr Leu Thr Ile Asn Arg Leu Glu Pro Glu Asp
        210                 215                 220

Phe Ala Met Tyr Tyr Cys Gln Gln Tyr Gly Ser Ala Pro Val Thr Phe
225                 230                 235                 240

Gly Gln Gly Thr Lys Leu Glu Ile Lys
                245

<210> SEQ ID NO 189
<211> LENGTH: 249
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 189

Gln Val Gln Leu Val Gln Ser Gly Ala Glu Val Arg Ala Pro Gly Ala
1               5                   10                  15

Ser Val Lys Ile Ser Cys Lys Ala Ser Gly Phe Thr Phe Arg Gly Tyr
            20                  25                  30

Tyr Ile His Trp Val Arg Gln Ala Pro Gly Gln Gly Leu Glu Trp Met
        35                  40                  45

Gly Ile Ile Asn Pro Ser Gly Gly Ser Arg Ala Tyr Ala Gln Lys Phe
50                  55                  60

Gln Gly Arg Val Thr Met Thr Arg Asp Thr Ser Thr Ser Thr Val Tyr
65                  70                  75                  80
```

```
Met Glu Leu Ser Ser Leu Arg Ser Asp Asp Thr Ala Met Tyr Tyr Cys
                 85                  90                  95

Ala Arg Thr Ala Ser Cys Gly Gly Asp Cys Tyr Tyr Leu Asp Tyr Trp
            100                 105                 110

Gly Gln Gly Thr Leu Val Thr Val Ser Ser Gly Gly Gly Gly Ser Gly
            115                 120                 125

Gly Gly Gly Ser Gly Gly Gly Gly Ser Gly Gly Gly Gly Ser Asp Ile
        130                 135                 140

Gln Met Thr Gln Ser Pro Pro Thr Leu Ser Ala Ser Val Gly Asp Arg
145                 150                 155                 160

Val Thr Ile Thr Cys Arg Ala Ser Glu Asn Val Asn Ile Trp Leu Ala
                165                 170                 175

Trp Tyr Gln Gln Lys Pro Gly Lys Ala Pro Lys Leu Leu Ile Tyr Lys
            180                 185                 190

Ser Ser Ser Leu Ala Ser Gly Val Pro Ser Arg Phe Ser Gly Ser Gly
        195                 200                 205

Ser Gly Ala Glu Phe Thr Leu Thr Ile Ser Ser Leu Gln Pro Asp Asp
    210                 215                 220

Phe Ala Thr Tyr Tyr Cys Gln Gln Tyr Gln Ser Tyr Pro Leu Thr Phe
225                 230                 235                 240

Gly Gly Gly Thr Lys Val Asp Ile Lys
                245

<210> SEQ ID NO 190
<211> LENGTH: 244
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 190

Gln Val Gln Leu Val Gln Ser Gly Gly Gly Leu Val Gln Pro Gly Arg
1               5                   10                  15

Ser Leu Arg Leu Ser Cys Ala Ala Ser Gly Phe Thr Phe Asp Asp Tyr
            20                  25                  30

Ala Met His Trp Val Arg Gln Ala Pro Gly Lys Gly Leu Glu Trp Val
        35                  40                  45

Ser Gly Ile Ser Trp Asn Ser Gly Ser Ile Gly Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Lys Asp Gly Ser Ser Ser Trp Ser Trp Gly Tyr Phe Asp Tyr Trp
            100                 105                 110

Gly Gln Gly Thr Leu Val Thr Val Ser Ser Gly Gly Gly Gly Ser Gly
            115                 120                 125

Gly Gly Gly Ser Gly Gly Gly Gly Ser Ser Glu Leu Thr Gln Asp
        130                 135                 140

Pro Ala Val Ser Val Ala Leu Gly Gln Thr Val Arg Thr Thr Cys Gln
145                 150                 155                 160

Gly Asp Ala Leu Arg Ser Tyr Tyr Ala Ser Trp Tyr Gln Gln Lys Pro
                165                 170                 175

Gly Gln Ala Pro Met Leu Val Ile Tyr Gly Lys Asn Asn Arg Pro Ser
```

```
                180                 185                 190
Gly Ile Pro Asp Arg Phe Ser Gly Ser Asp Ser Gly Asp Thr Ala Ser
            195                 200                 205

Leu Thr Ile Thr Gly Ala Gln Ala Glu Asp Glu Ala Asp Tyr Tyr Cys
        210                 215                 220

Asn Ser Arg Asp Ser Ser Gly Tyr Pro Val Phe Gly Thr Gly Thr Lys
225                 230                 235                 240

Val Thr Val Leu

<210> SEQ ID NO 191
<211> LENGTH: 246
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 191

Glu Val Gln Leu Val Glu Ser Gly Gly Gly Leu Val Gln Pro Gly Arg
1               5                   10                  15

Ser Leu Arg Leu Ser Cys Ala Ala Ser Gly Phe Thr Phe Asp Asp Tyr
            20                  25                  30

Ala Met His Trp Val Arg Gln Ala Pro Gly Lys Gly Leu Glu Trp Val
        35                  40                  45

Ser Gly Ile Ser Trp Asn Ser Gly Ser Thr Gly Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Leu Tyr Tyr Cys
                85                  90                  95

Ala Lys Asp Ser Ser Ser Trp Tyr Gly Gly Ser Ala Phe Asp Ile
            100                 105                 110

Trp Gly Gln Gly Thr Met Val Thr Val Ser Ser Gly Gly Gly Ser
        115                 120                 125

Gly Gly Gly Gly Ser Gly Gly Gly Ser Ser Glu Leu Thr Gln
    130                 135                 140

Glu Pro Ala Val Ser Val Ala Leu Gly Gln Thr Val Arg Ile Thr Cys
145                 150                 155                 160

Gln Gly Asp Ser Leu Arg Ser Tyr Tyr Ala Ser Trp Tyr Gln Gln Lys
                165                 170                 175

Pro Gly Gln Ala Pro Val Leu Val Ile Phe Gly Arg Ser Arg Arg Pro
            180                 185                 190

Ser Gly Ile Pro Asp Arg Phe Ser Gly Ser Ser Ser Gly Asn Thr Ala
        195                 200                 205

Ser Leu Ile Ile Thr Gly Ala Gln Ala Glu Asp Glu Ala Asp Tyr Tyr
    210                 215                 220

Cys Asn Ser Arg Asp Asn Thr Ala Asn His Tyr Val Phe Gly Thr Gly
225                 230                 235                 240

Thr Lys Leu Thr Val Leu
                245

<210> SEQ ID NO 192
<211> LENGTH: 246
<212> TYPE: PRT
<213> ORGANISM: Artificial Sequence
<220> FEATURE:
<223> OTHER INFORMATION: Description of Artificial Sequence: Synthetic
``` polypeptide

<400> SEQUENCE: 192

Glu Val Gln Leu Val Glu Ser Gly Gly Gly Leu Val Gln Pro Gly Arg
1               5                   10                  15

Ser Leu Arg Leu Ser Cys Ala Ala Ser Gly Phe Thr Phe Asp Asp Tyr
            20                  25                  30

Ala Met His Trp Val Arg Gln Ala Pro Gly Lys Gly Leu Glu Trp Val
        35                  40                  45

Ser Gly Ile Ser Trp Asn Ser Gly Ser Thr Gly Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Leu Tyr Tyr Cys
                85                  90                  95

Ala Lys Asp Ser Ser Ser Trp Tyr Gly Gly Gly Ser Ala Phe Asp Ile
            100                 105                 110

Trp Gly Gln Gly Thr Met Val Thr Val Ser Ser Gly Gly Gly Gly Ser
        115                 120                 125

Gly Gly Gly Gly Ser Gly Gly Gly Ser Ser Glu Leu Thr Gln
    130                 135                 140

Asp Pro Ala Val Ser Val Ala Leu Gly Gln Thr Val Arg Ile Thr Cys
145                 150                 155                 160

Gln Gly Asp Ser Leu Arg Ser Tyr Tyr Ala Ser Trp Tyr Gln Gln Lys
                165                 170                 175

Pro Gly Gln Ala Pro Val Leu Val Ile Tyr Gly Lys Asn Asn Arg Pro
            180                 185                 190

Ser Gly Ile Pro Asp Arg Phe Ser Gly Ser Ser Ser Gly Asn Thr Ala
        195                 200                 205

Ser Leu Thr Ile Thr Gly Ala Gln Ala Glu Asp Glu Ala Asp Tyr Tyr
    210                 215                 220

Cys Asn Ser Arg Gly Ser Ser Gly Asn His Tyr Val Phe Gly Thr Gly
225                 230                 235                 240

Thr Lys Val Thr Val Leu
                245

<210> SEQ ID NO 193
<211> LENGTH: 251
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 193

Gln Val Gln Leu Val Gln Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Trp Met His Trp Val Arg Gln Ala Pro Gly Lys Gly Leu Val Trp Val
        35                  40                  45

Ser Arg Ile Asn Ser Asp Gly Ser Ser Thr Ser Tyr Ala Asp Ser Val
    50                  55                  60

Lys Gly Arg Phe Thr Ile Ser Arg Asp Asn Ala Lys Asn Thr Leu Tyr
65                  70                  75                  80

Leu Gln Met Asn Ser Leu Arg Ala Glu Asp Thr Ala Val Tyr Tyr Cys

```
                     85                  90                  95
Val Arg Thr Gly Trp Val Gly Ser Tyr Tyr Tyr Met Asp Val Trp
                100                 105                 110

Gly Lys Gly Thr Thr Val Thr Val Ser Ser Gly Gly Gly Ser Gly
            115                 120                 125

Gly Gly Gly Ser Gly Gly Gly Ser Gly Gly Gly Gly Ser Glu Ile
        130                 135                 140

Val Leu Thr Gln Ser Pro Gly Thr Leu Ser Leu Ser Pro Gly Glu Arg
145                 150                 155                 160

Ala Thr Leu Ser Cys Arg Ala Ser Gln Ser Val Ser Ser Asn Tyr Leu
                165                 170                 175

Ala Trp Tyr Gln Gln Lys Pro Gly Gln Pro Pro Arg Leu Leu Ile Tyr
                180                 185                 190

Asp Val Ser Thr Arg Ala Thr Gly Ile Pro Ala Arg Phe Ser Gly Gly
                195                 200                 205

Gly Ser Gly Thr Asp Phe Thr Leu Thr Ile Ser Ser Leu Glu Pro Glu
        210                 215                 220

Asp Phe Ala Val Tyr Tyr Cys Gln Gln Arg Ser Asn Trp Pro Pro Trp
225                 230                 235                 240

Thr Phe Gly Gln Gly Thr Lys Val Glu Ile Lys
                245                 250

<210> SEQ ID NO 194
<211> LENGTH: 250
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 194

Gln Val Gln Leu Val Gln Ser Gly Gly Gly Val Val Gln Pro Gly Arg
1               5                   10                  15

Ser Leu Arg Leu Ser Cys Ala Ala Ser Gly Phe Thr Phe Ser Ser Tyr
                20                  25                  30

Gly Met His Trp Val Arg Gln Ala Pro Gly Lys Gly Leu Glu Trp Val
            35                  40                  45

Ala Val Ile Ser Tyr Asp Gly Ser Asn Lys Tyr Tyr Ala Asp Ser Val
50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Gly Tyr Ser Arg Tyr Tyr Tyr Gly Met Asp Val Trp Gly
                100                 105                 110

Gln Gly Thr Thr Val Thr Val Ser Ser Gly Gly Gly Ser Gly Gly
            115                 120                 125

Gly Gly Ser Gly Gly Gly Ser Gly Gly Gly Ser Glu Ile Val
        130                 135                 140

Met Thr Gln Ser Pro Ala Thr Leu Ser Leu Ser Pro Gly Glu Arg Ala
145                 150                 155                 160

Ile Leu Ser Cys Arg Ala Ser Gln Ser Val Tyr Thr Lys Tyr Leu Gly
                165                 170                 175

Trp Tyr Gln Gln Lys Pro Gly Gln Ala Pro Arg Leu Leu Ile Tyr Asp
                180                 185                 190
```

```
Ala Ser Thr Arg Ala Thr Gly Ile Pro Asp Arg Phe Ser Gly Ser Gly
            195                 200                 205

Ser Gly Thr Asp Phe Thr Leu Thr Ile Asn Arg Leu Glu Pro Glu Asp
        210                 215                 220

Phe Ala Val Tyr Tyr Cys Gln His Tyr Gly Gly Ser Pro Leu Ile Thr
225                 230                 235                 240

Phe Gly Gln Gly Thr Lys Val Asp Ile Lys
                245                 250

<210> SEQ ID NO 195
<211> LENGTH: 249
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 195

Gln Val Gln Leu Val Gln Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Arg Glu Ala Ala Ala Gly His Asp Trp Tyr Phe Asp Leu Trp
            100                 105                 110

Gly Arg Gly Thr Leu Val Thr Val Ser Ser Gly Gly Gly Gly Ser Gly
        115                 120                 125

Gly Gly Gly Ser Gly Gly Gly Gly Ser Gly Gly Gly Ser Asp Ile
    130                 135                 140

Arg Val Thr Gln Ser Pro Ser Ser Leu Ser Ala Ser Val Gly Asp Arg
145                 150                 155                 160

Val Thr Ile Thr Cys Arg Ala Ser Gln Ser Ile Ser Ser Tyr Leu Asn
                165                 170                 175

Trp Tyr Gln Gln Lys Pro Gly Lys Ala Pro Lys Leu Leu Ile Tyr Ala
            180                 185                 190

Ala Ser Ser Leu Gln Ser Gly Val Pro Ser Arg Phe Ser Gly Ser Gly
        195                 200                 205

Ser Gly Thr Asp Phe Thr Leu Thr Ile Ser Ser Leu Gln Pro Glu Asp
    210                 215                 220

Phe Ala Thr Tyr Tyr Cys Gln Gln Ser Tyr Ser Ile Pro Leu Thr Phe
225                 230                 235                 240

Gly Gln Gly Thr Lys Val Glu Ile Lys
                245

<210> SEQ ID NO 196
<211> LENGTH: 247
<212> TYPE: PRT
<213> ORGANISM: Artificial Sequence
<220> FEATURE:
<223> OTHER INFORMATION: Description of Artificial Sequence: Synthetic
      polypeptide
```

<400> SEQUENCE: 196

```
Gln Val Gln Leu Val Gln Ser Trp Ala Glu Val Lys Lys Pro Gly Ala
1               5                   10                  15
Ser Val Lys Val Ser Cys Lys Ala Ser Gly Tyr Thr Phe Thr Ser Tyr
            20                  25                  30
Tyr Met His Trp Val Arg Gln Ala Pro Gly Gln Gly Leu Glu Trp Met
        35                  40                  45
Gly Ile Ile Asn Pro Ser Gly Ser Thr Ser Tyr Ala Gln Lys Phe
    50                  55                  60
Gln Gly Arg Val Thr Met Thr Arg Asp Thr Ser Thr Ser Thr Val Tyr
65                  70                  75                  80
Met Glu Leu Ser Asn Leu Arg Ser Glu Asp Thr Ala Val Tyr Tyr Cys
                85                  90                  95
Ala Arg Ser Pro Arg Val Thr Thr Gly Tyr Phe Asp Tyr Trp Gly Gln
            100                 105                 110
Gly Thr Leu Val Thr Val Ser Gly Gly Gly Gly Ser Gly Gly Gly
        115                 120                 125
Gly Ser Gly Gly Gly Ser Gly Gly Gly Ser Asp Ile Gln Leu
    130                 135                 140
Thr Gln Ser Pro Ser Thr Leu Ser Ala Ser Val Gly Asp Arg Val Thr
145                 150                 155                 160
Ile Thr Cys Arg Ala Ser Gln Ser Ile Ser Ser Trp Leu Ala Trp Tyr
                165                 170                 175
Gln Gln Lys Pro Gly Lys Ala Pro Lys Leu Leu Ile Tyr Lys Ala Ser
            180                 185                 190
Ser Leu Glu Ser Gly Val Pro Ser Arg Phe Ser Gly Ser Gly Ser Gly
        195                 200                 205
Thr Glu Phe Thr Leu Thr Ile Ser Ser Leu Gln Pro Asp Asp Phe Ala
    210                 215                 220
Thr Tyr Tyr Cys Gln Gln Tyr Ser Ser Tyr Pro Leu Thr Phe Gly Gly
225                 230                 235                 240
Gly Thr Arg Leu Glu Ile Lys
                245
```

<210> SEQ ID NO 197
<211> LENGTH: 253
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 197

```
Gln Val Gln Leu Val Gln Ser Gly Ala Glu Val Arg Arg Pro Gly Ala
1               5                   10                  15
Ser Val Lys Ile Ser Cys Arg Ala Ser Gly Asp Thr Ser Thr Arg His
            20                  25                  30
Tyr Ile His Trp Leu Arg Gln Ala Pro Gly Gln Gly Pro Glu Trp Met
        35                  40                  45
Gly Val Ile Asn Pro Thr Thr Gly Pro Ala Thr Gly Ser Pro Ala Tyr
    50                  55                  60
Ala Gln Met Leu Gln Gly Arg Val Thr Met Thr Arg Asp Thr Ser Thr
65                  70                  75                  80
Arg Thr Val Tyr Met Glu Leu Arg Ser Leu Arg Phe Glu Asp Thr Ala
                85                  90                  95
```

```
Val Tyr Tyr Cys Ala Arg Ser Val Val Gly Arg Ser Ala Pro Tyr Tyr
                100                 105                 110

Phe Asp Tyr Trp Gly Gln Gly Thr Leu Val Thr Val Ser Ser Gly Gly
            115                 120                 125

Gly Gly Ser Gly Gly Gly Ser Gly Gly Gly Ser Gly Gly
130                 135                 140

Gly Ser Asp Ile Gln Met Thr Gln Ser Pro Ser Ser Leu Ser Ala Ser
145                 150                 155                 160

Val Gly Asp Arg Val Thr Ile Thr Cys Arg Ala Ser Gln Gly Ile Ser
                165                 170                 175

Asp Tyr Ser Ala Trp Tyr Gln Gln Lys Pro Gly Lys Ala Pro Lys Leu
            180                 185                 190

Leu Ile Tyr Ala Ala Ser Thr Leu Gln Ser Gly Val Pro Ser Arg Phe
            195                 200                 205

Ser Gly Ser Gly Ser Gly Thr Asp Phe Thr Leu Thr Ile Ser Tyr Leu
            210                 215                 220

Gln Ser Glu Asp Phe Ala Thr Tyr Tyr Cys Gln Gln Tyr Tyr Ser Tyr
225                 230                 235                 240

Pro Leu Thr Phe Gly Gly Gly Thr Lys Val Asp Ile Lys
                245                 250

<210> SEQ ID NO 198
<211> LENGTH: 249
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 198

Gln Val Gln Leu Gln Gln Ser Gly Ala Glu Val Lys Lys Pro Gly Ala
1               5                   10                  15

Ser Val Lys Val Ser Cys Lys Ala Ser Gly Tyr Thr Phe Thr Asn Tyr
                20                  25                  30

Tyr Met His Trp Val Arg Gln Ala Pro Gly Gln Gly Leu Glu Trp Met
            35                  40                  45

Gly Ile Ile Asn Pro Ser Gly Gly Tyr Thr Thr Tyr Ala Gln Lys Phe
    50                  55                  60

Gln Gly Arg Leu Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Ile Arg Ser Cys Gly Gly Asp Cys Tyr Tyr Phe Asp Asn Trp
            100                 105                 110

Gly Gln Gly Thr Leu Val Thr Val Ser Ser Gly Gly Gly Gly Ser Gly
            115                 120                 125

Gly Gly Gly Ser Gly Gly Gly Gly Ser Gly Gly Gly Gly Ser Asp Ile
    130                 135                 140

Gln Leu Thr Gln Ser Pro Ser Thr Leu Ser Ala Ser Val Gly Asp Arg
145                 150                 155                 160

Val Thr Ile Thr Cys Arg Ala Ser Glu Asn Val Asn Ile Trp Leu Ala
                165                 170                 175

Trp Tyr Gln Gln Lys Pro Gly Lys Ala Pro Lys Leu Leu Ile Tyr Lys
            180                 185                 190

Ser Ser Ser Leu Ala Ser Gly Val Pro Ser Arg Phe Ser Gly Ser Gly
```

```
                195                 200                 205
Ser Gly Ala Glu Phe Thr Leu Thr Ile Ser Ser Leu Gln Pro Asp Asp
        210                 215                 220

Phe Ala Thr Tyr Tyr Cys Gln Gln Tyr Gln Ser Tyr Pro Leu Thr Phe
225                 230                 235                 240

Gly Gly Gly Thr Lys Val Asp Ile Lys
                245

<210> SEQ ID NO 199
<211> LENGTH: 246
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 199

Gln Ile Thr Leu Lys Glu Ser Gly Pro Ala Leu Val Lys Pro Thr Gln
1               5                   10                  15

Thr Leu Thr Leu Thr Cys Thr Phe Ser Gly Phe Ser Leu Ser Thr Ala
            20                  25                  30

Gly Val His Val Gly Trp Ile Arg Gln Pro Pro Gly Lys Ala Leu Glu
        35                  40                  45

Trp Leu Ala Leu Ile Ser Trp Ala Asp Asp Lys Arg Tyr Arg Pro Ser
50                  55                  60

Leu Arg Ser Arg Leu Asp Ile Thr Arg Val Thr Ser Lys Asp Gln Val
65                  70                  75                  80

Val Leu Ser Met Thr Asn Met Gln Pro Glu Asp Thr Ala Thr Tyr Tyr
                85                  90                  95

Cys Ala Leu Gln Gly Phe Asp Gly Tyr Glu Ala Asn Trp Gly Pro Gly
            100                 105                 110

Thr Leu Val Thr Val Ser Ser Gly Gly Gly Ser Gly Gly Gly Gly
        115                 120                 125

Ser Gly Gly Gly Gly Ser Gly Gly Gly Gly Ser Asp Ile Val Met Thr
130                 135                 140

Gln Ser Pro Ser Ser Leu Ser Ala Ser Ala Gly Asp Arg Val Thr Ile
145                 150                 155                 160

Thr Cys Arg Ala Ser Arg Gly Ile Ser Ser Ala Leu Ala Trp Tyr Gln
            165                 170                 175

Gln Lys Pro Gly Lys Pro Pro Lys Leu Leu Ile Tyr Asp Ala Ser Ser
        180                 185                 190

Leu Glu Ser Gly Val Pro Ser Arg Phe Ser Gly Ser Gly Ser Gly Thr
    195                 200                 205

Asp Phe Thr Leu Thr Ile Asp Ser Leu Glu Pro Glu Asp Phe Ala Thr
        210                 215                 220

Tyr Tyr Cys Gln Gln Ser Tyr Ser Thr Pro Trp Thr Phe Gly Gln Gly
225                 230                 235                 240

Thr Lys Val Asp Ile Lys
                245

<210> SEQ ID NO 200
<211> LENGTH: 247
<212> TYPE: PRT
<213> ORGANISM: Artificial Sequence
<220> FEATURE:
<223> OTHER INFORMATION: Description of Artificial Sequence: Synthetic
      polypeptide
```

<400> SEQUENCE: 200

Glu Val Gln Leu Gln Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
            20                  25                  30

Ala Ile Ser Trp Val Arg Gln Ala Pro Gly Gln Gly Leu Glu Trp Met
        35                  40                  45

Gly Gly Ile Ile Pro Ile Phe Gly Thr Ala Asn Tyr Ala Gln Lys Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Asp Leu Glu Met Ala Thr Ile Met Gly Gly Tyr Trp Gly Gln
            100                 105                 110

Gly Thr Leu Val Thr Val Ser Ser Gly Gly Gly Ser Gly Gly Gly
        115                 120                 125

Gly Ser Gly Gly Gly Ser Gln Ser Ala Leu Thr Gln Pro Ala Ser
    130                 135                 140

Val Ser Gly Ser Pro Gly Gln Ser Ile Thr Ile Ser Cys Thr Gly Thr
145                 150                 155                 160

Ser Ser Asp Val Gly Gly Tyr Asn Tyr Val Ser Trp Tyr Gln Gln His
                165                 170                 175

Pro Gly Lys Ala Pro Lys Leu Met Ile Tyr Asp Val Ser Asn Arg Pro
            180                 185                 190

Ser Gly Val Ser Asn Arg Phe Ser Gly Ser Lys Ser Gly Asn Thr Ala
        195                 200                 205

Ser Leu Thr Ile Ser Gly Leu Gln Ala Glu Asp Glu Ala Asp Tyr Tyr
    210                 215                 220

Cys Ser Ser Tyr Thr Ser Ser Ser Thr Leu Asp Val Val Phe Gly Gly
225                 230                 235                 240

Gly Thr Lys Leu Thr Val Leu
                245

<210> SEQ ID NO 201
<211> LENGTH: 245
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 201

Glu Val Gln Leu Val Glu Ser Gly Gly Gly Val Val Gln Pro Gly Gly
1               5                   10                  15

Ser Leu Arg Leu Ser Cys Ala Ala Ser Gly Phe Thr Phe Asp Asp Tyr
            20                  25                  30

Ala Met His Trp Val Arg Gln Ala Pro Gly Lys Gly Leu Glu Trp Val
        35                  40                  45

Ser Leu Ile Ser Gly Asp Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Val Glu Asp Thr Ala Val Tyr Tyr Cys
                85                  90                  95

Ala Arg Val Phe Asp Ser Tyr Tyr Met Asp Val Trp Gly Lys Gly Thr
            100                 105                 110

Thr Val Thr Val Ser Ser Gly Gly Gly Ser Gly Gly Gly Gly Ser
        115                 120                 125

Gly Ser Gly Gly Ser Glu Ile Val Leu Thr Gln Ser Pro Leu Ser Leu
    130                 135                 140

Pro Val Thr Pro Gly Gln Pro Ala Ser Ile Ser Cys Arg Ser Ser Gln
145                 150                 155                 160

Ser Leu Val Tyr Thr Asp Gly Asn Thr Tyr Leu Asn Trp Phe Gln Gln
                165                 170                 175

Arg Pro Gly Gln Ser Pro Arg Arg Leu Ile Tyr Lys Val Ser Asn Arg
            180                 185                 190

Asp Ser Gly Val Pro Asp Arg Phe Ser Gly Ser Gly Ser Asp Thr Asp
        195                 200                 205

Phe Thr Leu Lys Ile Ser Arg Val Glu Ala Glu Asp Val Gly Ile Tyr
210                 215                 220

Tyr Cys Met Gln Gly Thr His Trp Ser Phe Thr Phe Gly Gln Gly Thr
225                 230                 235                 240

Arg Leu Glu Ile Lys
            245

<210> SEQ ID NO 202
<211> LENGTH: 247
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 202

Gln Val Gln Leu Gln Glu Ser Gly Pro Gly Leu Val Lys Pro Ser Glu
1               5                   10                  15

Thr Leu Ser Leu Thr Cys Thr Val Ser Gly Gly Ser Ile Ser Ser Ser
            20                  25                  30

Ser Tyr Tyr Trp Gly Trp Ile Arg Gln Pro Pro Gly Lys Gly Leu Glu
        35                  40                  45

Trp Ile Gly Ser Ile Tyr Tyr Ser Gly Ser Thr Tyr Tyr Asn Pro Ser
    50                  55                  60

Leu Lys Ser Arg Val Ser Ile Ser Val Asp Thr Ser Lys Asn Gln Phe
65                  70                  75                  80

Ser Leu Lys Leu Lys Tyr Val Thr Ala Ala Asp Thr Ala Val Tyr Tyr
                85                  90                  95

Cys Ala Thr Pro Gly Thr Tyr Tyr Asp Phe Leu Ser Gly Tyr Tyr Pro
            100                 105                 110

Phe Tyr Trp Gly Gln Gly Thr Leu Val Thr Val Ser Ser Gly Gly Gly
        115                 120                 125

Gly Ser Gly Gly Gly Gly Ser Gly Gly Gly Gly Ser Asp Ile Val Met
    130                 135                 140

Thr Gln Ser Pro Ser Ser Leu Ser Ala Ser Val Gly Asp Arg Val Thr
145                 150                 155                 160

Ile Thr Cys Arg Ala Ser Gln Gly Ile Ser Ser Tyr Leu Ala Trp Tyr
                165                 170                 175

Gln Gln Lys Pro Gly Lys Ala Pro Lys Leu Leu Ile Tyr Ala Ala Ser
            180                 185                 190

Thr Leu Gln Ser Gly Val Pro Ser Arg Phe Ser Gly Ser Gly Ser Gly
        195                 200                 205

Thr Asp Phe Thr Leu Thr Ile Ser Ser Leu Gln Pro Glu Asp Phe Ala
        210                 215                 220

Thr Tyr Tyr Cys Gln Gln Leu Asn Ser Tyr Pro Tyr Thr Phe Gly Gln
225                 230                 235                 240

Gly Thr Lys Leu Glu Ile Lys
            245

<210> SEQ ID NO 203
<211> LENGTH: 239
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 203

Gln Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Trp Met Ser Trp Val Arg Gln Ala Pro Gly Lys Gly Leu Glu Trp Val
        35                  40                  45

Ala Asn Ile Asn Glu Asp Gly Ser Ala Lys Phe Tyr Val Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Phe Cys
                85                  90                  95

Ala Arg Asp Leu Arg Ser Gly Arg Tyr Trp Gly Gln Gly Thr Leu Val
            100                 105                 110

Thr Val Ser Ser Gly Gly Gly Ser Gly Gly Gly Ser Gly Gly Gly Gly
        115                 120                 125

Gly Gly Ser Glu Ile Val Leu Thr Gln Ser Pro Gly Thr Leu Ser Leu
    130                 135                 140

Ser Pro Gly Gly Arg Ala Thr Leu Ser Cys Arg Ala Ser Gln Ser Ile
145                 150                 155                 160

Ser Gly Ser Phe Leu Ala Trp Tyr Gln Gln Lys Pro Gly Gln Ala Pro
                165                 170                 175

Arg Leu Leu Ile Tyr Gly Ala Ser Ser Arg Ala Thr Gly Ile Pro Asp
            180                 185                 190

Arg Phe Ser Gly Ser Gly Ser Gly Thr Asp Phe Thr Leu Thr Ile Ser
        195                 200                 205

Arg Leu Glu Pro Glu Asp Phe Ala Val Tyr Tyr Cys Gln Gln Tyr Gly
    210                 215                 220

Ser Ser Pro Pro Thr Phe Gly Leu Gly Thr Lys Leu Glu Ile Lys
225                 230                 235

<210> SEQ ID NO 204
<211> LENGTH: 245
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 204

Glu Val Gln Leu Gln Gln Ser Gly Pro Gly Leu Val Arg Pro Ser Glu
1               5                   10                  15

Thr Leu Ser Leu Thr Cys Thr Val Ser Gly Pro Val Arg Ser Gly
            20                  25                  30

Ser His Tyr Trp Asn Trp Ile Arg Gln Pro Pro Gly Arg Gly Leu Glu
            35                  40                  45

Trp Ile Gly Tyr Ile Tyr Tyr Ser Gly Ser Thr Asn Tyr Asn Pro Ser
50                  55                  60

Leu Glu Asn Arg Val Thr Ile Ser Ile Asp Thr Ser Asn Asn His Phe
65                  70                  75                  80

Ser Leu Lys Leu Ser Ser Val Thr Ala Ala Asp Thr Ala Leu Tyr Phe
                85                  90                  95

Cys Ala Arg Gly Thr Ala Thr Phe Asp Trp Asn Phe Pro Phe Asp Ser
            100                 105                 110

Trp Gly Gln Gly Thr Leu Val Thr Val Ser Ser Gly Gly Gly Gly Ser
            115                 120                 125

Gly Gly Gly Gly Ser Gly Ser Gly Gly Ser Asp Ile Gln Met Thr Gln
130                 135                 140

Ser Pro Ser Ser Leu Ser Ala Ser Ile Gly Asp Arg Val Thr Ile Thr
145                 150                 155                 160

Cys Arg Ala Ser Gln Ser Ile Ser Ser Tyr Leu Asn Trp Tyr Gln Gln
            165                 170                 175

Lys Pro Gly Lys Ala Pro Lys Leu Leu Ile Tyr Ala Ala Ser Ser Leu
            180                 185                 190

Gln Ser Gly Val Pro Ser Arg Phe Ser Gly Ser Gly Ser Gly Thr Asp
            195                 200                 205

Phe Thr Leu Thr Ile Ser Ser Leu Gln Pro Glu Asp Phe Ala Thr Tyr
            210                 215                 220

Tyr Cys Gln Gln Ser Tyr Ser Thr Pro Trp Thr Phe Gly Gln Gly Thr
225                 230                 235                 240

Lys Leu Glu Ile Lys
            245

<210> SEQ ID NO 205
<211> LENGTH: 249
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 205

Gln Val Gln Leu Gln Glu Ser Gly Ala Gly Leu Leu Lys Pro Ser Glu
1               5                   10                  15

Thr Leu Ser Leu Thr Cys Ala Val Tyr Gly Gly Ser Phe Ser Gly Tyr
            20                  25                  30

Tyr Trp Ser Trp Ile Arg Gln Pro Pro Gly Lys Gly Leu Glu Trp Val
            35                  40                  45

Gly Glu Ile Asn His Ser Gly Ser Thr Asn Tyr Asn Pro Ser Leu Lys
            50                  55                  60

Ser Arg Val Thr Ile Ser Val Asp Thr Ser Lys Asn Gln Phe Ser Leu
65                  70                  75                  80

Lys Leu Ser Ser Val Thr Ala Ala Asp Thr Ala Val Tyr Tyr Cys Ala
                85                  90                  95

Arg Gly Ser Gly Leu Val Val Tyr Ala Ile Arg Val Gly Ser Gly Trp
            100                 105                 110

Phe Asp Tyr Trp Gly Gln Gly Thr Leu Val Thr Val Ser Ser Gly Gly

```
                115                 120                 125
Gly Gly Ser Gly Gly Asp Ser Gly Gly Gly Ser Asp Ile Gln
        130                 135                 140

Met Thr Gln Ser Pro Ser Ser Leu Ser Ala Ser Val Gly Asp Arg Val
145                 150                 155                 160

Thr Ile Thr Cys Arg Ala Ser Gln Ser Ile Ser Ser Tyr Leu Asn Trp
                    165                 170                 175

Tyr Gln Gln Lys Pro Gly Lys Ala Pro Lys Leu Leu Met Tyr Ala Ala
                180                 185                 190

Ser Ser Leu Gln Ser Gly Val Pro Ser Arg Phe Ser Gly Ser Gly Ser
            195                 200                 205

Gly Thr Asp Phe Thr Leu Thr Ile Ser Ser Leu Gln Pro Glu Asp Phe
        210                 215                 220

Ala Thr Tyr Tyr Cys Gln Gln Ser Tyr Ser Thr Pro Pro Trp Thr Phe
225                 230                 235                 240

Gly Gln Gly Thr Lys Val Asp Ile Lys
                245
```

<210> SEQ ID NO 206
<211> LENGTH: 255
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 206

```
Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Ser Tyr
            20                  25                  30

Ser Met Asn Trp Val Arg Gln Ala Pro Gly Lys Gly Leu Glu Trp Val
        35                  40                  45

Ser Ser Ile Ser Ser Ser Ser Tyr Ile Tyr Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Asp Pro Ser Ser Gly Ser Tyr Tyr Met Glu Asp Ser Tyr
                100                 105                 110

Tyr Tyr Gly Met Asp Val Trp Gly Gln Gly Thr Thr Val Thr Val Ser
            115                 120                 125

Ser Gly Gly Gly Gly Ser Gly Gly Gly Gly Ser Gly Gly Gly Gly Ser
        130                 135                 140

Asn Phe Met Leu Thr Gln Pro His Ser Val Ser Glu Ser Pro Gly Lys
145                 150                 155                 160

Thr Val Thr Ile Ser Cys Thr Gly Ser Ser Gly Ser Ile Ala Ser Asn
                165                 170                 175

Tyr Val Gln Trp Tyr Gln Gln Arg Pro Gly Ser Ala Pro Thr Thr Val
                180                 185                 190

Ile Tyr Glu Asp Asn Gln Arg Pro Ser Gly Val Pro Asp Arg Phe Ser
            195                 200                 205

Gly Ser Ile Asp Ser Ser Ser Asn Ser Ala Ser Leu Thr Ile Ser Gly
        210                 215                 220
```

Leu Lys Thr Glu Asp Glu Ala Asp Tyr Tyr Cys Gln Ser Tyr Asp Ser
225                 230                 235                 240

Ser Asn Gln Val Val Phe Gly Gly Gly Thr Lys Leu Thr Val Leu
            245                 250                 255

<210> SEQ ID NO 207
<211> LENGTH: 239
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 207

Gln Val Asn Leu Arg Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Glu Met Asn Trp Val Arg Gln Ala Pro Gly Lys Gly Leu Glu Trp Val
        35                  40                  45

Ser Tyr Ile Ser Ser Ser Gly Ser Thr Ile Tyr Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Glu Ala Leu Gly Ser Ser Trp Glu Trp Gly Gln Gly Thr Thr
            100                 105                 110

Val Thr Val Ser Ser Gly Gly Gly Gly Ser Gly Gly Gly Gly Ser Gly
        115                 120                 125

Gly Gly Gly Ser Asp Ile Gln Met Thr Gln Ser Pro Ser Ser Leu Ser
130                 135                 140

Ala Ser Val Gly Asp Arg Val Thr Ile Thr Cys Gln Ala Ser Gln Asp
145                 150                 155                 160

Ile Ser Asn Tyr Leu Asn Trp Tyr Gln Gln Lys Pro Gly Lys Ala Pro
                165                 170                 175

Lys Leu Leu Ile Tyr Asp Ala Ser Asn Leu Glu Thr Gly Val Pro Ser
            180                 185                 190

Arg Phe Ser Gly Ser Gly Ser Gly Thr Asp Phe Thr Phe Thr Ile Ser
        195                 200                 205

Ser Leu Gln Pro Glu Asp Ile Ala Thr Tyr Tyr Cys Gln Gln Tyr Asp
    210                 215                 220

Asn Leu Pro Leu Thr Phe Gly Gly Gly Thr Lys Leu Glu Ile Lys
225                 230                 235

<210> SEQ ID NO 208
<211> LENGTH: 246
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 208

Gln Val Gln Leu Val Gln Ser Gly Ala Glu Val Lys Glu Pro Gly Ala
1               5                   10                  15

Ser Val Lys Val Ser Cys Lys Ala Pro Ala Asn Thr Phe Ser Asp His
            20                  25                  30

Val Met His Trp Val Arg Gln Ala Pro Gly Gln Arg Phe Glu Trp Met
         35                  40                  45

Gly Tyr Ile His Ala Ala Asn Gly Gly Thr His Tyr Ser Gln Lys Phe
     50                  55                  60

Gln Asp Arg Val Thr Ile Thr Arg Asp Thr Ser Ala Asn Thr Val Tyr
 65                  70                  75                  80

Met Asp Leu Ser Ser Leu Arg Ser Glu Asp Thr Ala Val Tyr Tyr Cys
                 85                  90                  95

Ala Arg Gly Gly Tyr Asn Ser Asp Ala Phe Asp Ile Trp Gly Gln Gly
             100                 105                 110

Thr Met Val Thr Val Ser Ser Gly Gly Gly Ser Gly Gly Gly Gly
         115                 120                 125

Ser Gly Gly Gly Gly Ser Gly Gly Gly Ser Asp Ile Val Met Thr
     130                 135                 140

Gln Ser Pro Ser Ser Val Ser Ala Ser Val Gly Asp Arg Val Thr Ile
145                 150                 155                 160

Thr Cys Arg Ala Ser Gln Asp Ile Ser Ser Trp Leu Ala Trp Tyr Gln
                 165                 170                 175

Gln Lys Pro Gly Lys Ala Pro Lys Leu Leu Ile Tyr Ala Ala Ser Ser
             180                 185                 190

Leu Gln Ser Gly Val Pro Ser Arg Phe Asn Gly Ser Gly Ser Gly Thr
         195                 200                 205

Asp Phe Thr Leu Thr Ile Ser Ser Leu Gln Pro Glu Asp Phe Ala Thr
     210                 215                 220

Tyr Tyr Cys Gln Gln Ser Tyr Ser Thr Pro Leu Thr Phe Gly Gly Gly
225                 230                 235                 240

Thr Lys Val Glu Ile Lys
             245

<210> SEQ ID NO 209
<211> LENGTH: 248
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 209

Gln Val Gln Leu Val Gln Ser Gly Gly Gly Leu Val Gln Pro Gly Gly
  1               5                  10                  15

Ser Leu Arg Leu Ser Cys Ala Ala Ser Gly Phe Thr Phe Ser Ser Tyr
                 20                  25                  30

Ser Met Asn Trp Val Arg Gln Ala Pro Gly Lys Gly Leu Glu Trp Val
         35                  40                  45

Ser Tyr Ile Ser Ser Ser Ser Thr Ile Tyr Tyr Ala Asp Ser Val
     50                  55                  60

Lys Gly Arg Phe Thr Ile Ser Arg Asp Asn Ala Lys Asn Ser Leu Tyr
 65                  70                  75                  80

Leu Gln Met Asn Ser Leu Arg Ala Glu Asp Thr Ala Val Tyr Tyr Cys
                 85                  90                  95

Ala Arg Asp Leu Ser Val Arg Ala Ile Asp Ala Phe Asp Ile Trp Gly
             100                 105                 110

Gln Gly Thr Met Val Thr Val Ser Ser Gly Gly Gly Ser Gly Gly
         115                 120                 125

Gly Gly Ser Gly Gly Gly Gly Ser Gly Gly Gly Gly Ser Asp Ile Val
     130                 135                 140

Leu Thr Gln Ser Pro Ser Ser Leu Ser Ala Ser Val Gly Asp Arg Val
145                 150                 155                 160

Thr Ile Thr Cys Gln Ala Ser Gln Asp Ile Ser Asn Tyr Leu Asn Trp
            165                 170                 175

Tyr Gln Gln Lys Pro Gly Lys Ala Pro Lys Leu Leu Ile Tyr Asp Ala
        180                 185                 190

Ser Asn Leu Glu Thr Gly Val Pro Ser Arg Phe Ser Gly Ser Gly Ser
            195                 200                 205

Gly Thr Asp Phe Thr Phe Thr Ile Ser Ser Leu Gln Pro Glu Asp Phe
        210                 215                 220

Ala Thr Tyr Tyr Cys Gln Gln Ala Tyr Ser Thr Pro Thr Phe Gly
225                 230                 235                 240

Pro Gly Thr Lys Val Glu Ile Lys
            245

<210> SEQ ID NO 210
<211> LENGTH: 246
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 210

Glu Val Gln Leu Val Gln Ser Gly Gly Gly Val Val Arg Ser Gly Arg
1               5                   10                  15

Ser Leu Arg Leu Ser Cys Ala Ala Ser Gly Phe Thr Phe Asn Ser Tyr
            20                  25                  30

Gly Leu His Trp Val Arg Gln Ala Pro Gly Lys Gly Leu Glu Trp Val
        35                  40                  45

Ala Leu Ile Glu Tyr Asp Gly Ser Asn Lys Tyr Tyr Gly Asp Ser Val
    50                  55                  60

Lys Gly Arg Phe Thr Ile Ser Arg Asp Lys Ser Lys Ser Thr Leu Tyr
65                  70                  75                  80

Leu Gln Met Asp Asn Leu Arg Ala Glu Asp Thr Ala Val Tyr Tyr Cys
                85                  90                  95

Ala Arg Glu Gly Asn Glu Asp Leu Ala Phe Asp Ile Trp Gly Gln Gly
            100                 105                 110

Thr Leu Val Thr Val Ser Ser Gly Gly Gly Ser Gly Gly Gly Gly
        115                 120                 125

Ser Gly Gly Gly Gly Ser Gly Gly Gly Gly Ser Glu Ile Val Leu Thr
    130                 135                 140

Gln Ser Pro Ser Ser Leu Ser Ala Ser Val Gly Asp Arg Val Thr Ile
145                 150                 155                 160

Thr Cys Gln Ala Ser Gln Phe Ile Lys Lys Asn Leu Asn Trp Tyr Gln
            165                 170                 175

His Lys Pro Gly Lys Ala Pro Lys Leu Leu Ile Tyr Asp Ala Ser Ser
        180                 185                 190

Leu Gln Thr Gly Val Pro Ser Arg Phe Ser Gly Asn Arg Ser Gly Thr
    195                 200                 205

Thr Phe Ser Phe Thr Ile Ser Ser Leu Gln Pro Glu Asp Val Ala Thr
        210                 215                 220

Tyr Tyr Cys Gln Gln His Asp Asn Leu Pro Leu Thr Phe Gly Gly Gly
225                 230                 235                 240

Thr Lys Val Glu Ile Lys

<210> SEQ ID NO 211
<211> LENGTH: 255
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 211

Gln Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Val Ser Ser Asn
            20                  25                  30

Tyr Met Thr Trp Val Arg Gln Ala Pro Gly Lys Gly Leu Glu Trp Val
        35                  40                  45

Ser Val Ile Tyr Ser Gly Gly Ala Thr Tyr Tyr Gly Asp Ser Val Lys
    50                  55                  60

Gly Arg Phe Thr Val Ser Arg Asp Asn Ser Lys Asn Thr Val Tyr Leu
65                  70                  75                  80

Gln Met Asn Arg Leu Thr Ala Glu Asp Thr Ala Val Tyr Tyr Cys Ala
                85                  90                  95

Arg Asp Arg Leu Tyr Cys Gly Asn Asn Cys Tyr Leu Tyr Tyr Tyr Tyr
            100                 105                 110

Gly Met Asp Val Trp Gly Gln Gly Thr Leu Val Thr Val Ser Ser Gly
        115                 120                 125

Gly Gly Gly Ser Gly Gly Gly Ser Gly Gly Gly Ser Gly Gly
    130                 135                 140

Gly Gly Ser Asp Ile Gln Val Thr Gln Ser Pro Ser Ser Leu Ser Ala
145                 150                 155                 160

Ser Val Gly Asp Arg Val Thr Ile Thr Cys Arg Ala Ser Gln Ser Ile
                165                 170                 175

Ser Ser Tyr Leu Asn Trp Tyr Gln Gln Lys Pro Gly Lys Ala Pro Lys
            180                 185                 190

Leu Leu Ile Tyr Ala Ala Ser Ser Leu Gln Ser Gly Val Pro Ser Arg
        195                 200                 205

Phe Ser Gly Ser Gly Ser Gly Thr Asp Phe Thr Leu Thr Ile Ser Ser
    210                 215                 220

Leu Gln Pro Glu Asp Phe Ala Thr Tyr Tyr Cys Gln Gln Ser Tyr Ser
225                 230                 235                 240

Thr Pro Pro Leu Thr Phe Gly Gln Gly Thr Lys Val Glu Ile Lys
                245                 250                 255

<210> SEQ ID NO 212
<211> LENGTH: 247
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 212

Gln Val Gln Leu Val Gln Ser Gly Ala Glu Val Lys Lys Ser Gly Ala
1               5                   10                  15

Ser Val Lys Val Ser Cys Lys Ala Ser Gly Tyr Pro Phe Thr Gly Tyr
            20                  25                  30

Tyr Ile Gln Trp Val Arg Gln Ala Pro Gly Gln Gly Leu Glu Trp Met

```
                35                  40                  45
Gly Trp Ile Asp Pro Asn Ser Gly Asn Thr Gly Tyr Ala Gln Lys Phe
 50                  55                  60

Gln Gly Arg Val Thr Met Thr Arg Asn Thr Ser Ile Ser Thr Ala Tyr
 65                  70                  75                  80

Met Glu Leu Ser Ser Leu Arg Ser Glu Asp Thr Ala Val Tyr Tyr Cys
                 85                  90                  95

Ala Ser Asp Ser Tyr Gly Tyr Tyr Gly Met Asp Val Trp Gly Gln
                100                 105                 110

Gly Thr Leu Val Thr Val Ser Gly Gly Gly Ser Gly Gly
                115                 120                 125

Gly Ser Gly Gly Gly Ser Gly Gly Gly Ser Asp Ile Gln Met
            130                 135                 140

Thr Gln Ser Pro Ser Ser Leu Ser Ala Ser Val Gly Asp Arg Val Thr
145                 150                 155                 160

Phe Thr Cys Arg Ala Ser Gln Gly Ile Ser Ser Ala Leu Ala Trp Tyr
                165                 170                 175

Gln Gln Lys Pro Gly Lys Pro Pro Lys Leu Leu Ile Tyr Asp Ala Ser
                180                 185                 190

Ser Leu Glu Ser Gly Val Pro Ser Arg Phe Ser Gly Ser Gly Ser Gly
                195                 200                 205

Thr Asp Phe Thr Leu Thr Ile Ser Ser Leu Gln Pro Glu Asp Phe Ala
210                 215                 220

Thr Tyr Tyr Cys Gln Gln Phe Asn Asn Tyr Pro Leu Thr Phe Gly Gly
225                 230                 235                 240

Gly Thr Lys Val Glu Ile Lys
                245

<210> SEQ ID NO 213
<211> LENGTH: 245
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 213

Glu Val Gln Leu Val Glu Ser Gly Gly Gly Leu Val Gln Pro Gly Gly
 1               5                  10                  15

Ser Leu Arg Leu Ser Cys Ala Ala Ser Gly Phe Thr Phe Ser Ser Tyr
                 20                  25                  30

Glu Met Asn Trp Val Arg Gln Ala Pro Gly Lys Gly Leu Glu Trp Val
                 35                  40                  45

Ser Tyr Ile Ser Ser Ser Gly Ser Thr Ile Tyr Tyr Ala Asp Ser Val
 50                  55                  60

Lys Gly Arg Phe Thr Ile Ser Arg Asp Asn Ala Lys Asn Ser Leu Tyr
 65                  70                  75                  80

Leu Gln Met Asn Ser Leu Arg Ala Glu Asp Thr Ala Val Tyr Tyr Cys
                 85                  90                  95

Ala Arg Asp Pro Tyr Ser Ser Ser Trp His Asp Ala Phe Asp Ile Trp
                100                 105                 110

Gly Gln Gly Thr Met Val Thr Val Ser Ser Gly Gly Gly Gly Ser Gly
                115                 120                 125

Gly Gly Gly Ser Gly Gly Gly Gly Ser Glu Ile Val Leu Thr Gln Ser
            130                 135                 140
```

```
Pro Gly Thr Leu Ser Leu Ser Pro Gly Glu Arg Ala Thr Leu Ser Cys
145                 150                 155                 160

Arg Ala Ser Gln Ser Val Ser Ser Tyr Leu Ala Trp Tyr Gln Gln
            165                 170                 175

Lys Pro Gly Gln Ala Pro Arg Leu Leu Ile Tyr Gly Ala Ser Arg
            180                 185                 190

Ala Thr Gly Ile Pro Asp Arg Phe Ser Gly Ser Gly Ser Gly Thr Asp
        195                 200                 205

Phe Thr Leu Thr Ile Ser Arg Leu Glu Pro Glu Asp Phe Ala Val Tyr
        210                 215                 220

Tyr Cys Gln Gln Tyr Gly Ser Ser Pro Leu Thr Phe Gly Gly Gly Thr
225                 230                 235                 240

Lys Val Asp Ile Lys
                245

<210> SEQ ID NO 214
<211> LENGTH: 246
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 214

Gln Val Gln Leu Val Glu Ser Gly Gly Gly Leu Val Gln Pro Gly Arg
1               5                   10                  15

Ser Leu Arg Leu Ser Cys Ala Ala Ser Gly Phe Thr Phe Ser Asn Tyr
            20                  25                  30

Ala Met Ser Trp Val Arg Gln Ala Pro Gly Lys Gly Leu Gly Trp Val
        35                  40                  45

Ser Gly Ile Ser Arg Ser Gly Glu Asn Thr Tyr Tyr Ala Asp Ser Val
50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Asp Glu Asp Thr Ala Val Tyr Tyr Cys
            85                  90                  95

Ala Arg Ser Pro Ala His Tyr Tyr Gly Gly Met Asp Val Trp Gly Gln
            100                 105                 110

Gly Thr Thr Val Thr Val Ser Ser Ala Ser Gly Gly Gly Gly Ser Gly
        115                 120                 125

Gly Arg Ala Ser Gly Gly Gly Ser Asp Ile Val Leu Thr Gln Ser
    130                 135                 140

Pro Gly Thr Leu Ser Leu Ser Pro Gly Glu Arg Ala Thr Leu Ser Cys
145                 150                 155                 160

Arg Ala Ser Gln Ser Ile Ser Ser Ser Phe Leu Ala Trp Tyr Gln Gln
            165                 170                 175

Lys Pro Gly Gln Ala Pro Arg Leu Leu Ile Tyr Gly Ala Ser Arg
            180                 185                 190

Ala Thr Gly Ile Pro Asp Arg Phe Ser Gly Ser Gly Ser Gly Thr Asp
        195                 200                 205

Phe Thr Leu Thr Ile Ser Arg Leu Glu Pro Glu Asp Ser Ala Val Tyr
        210                 215                 220

Tyr Cys Gln Gln Tyr His Ser Ser Pro Ser Trp Thr Phe Gly Gln Gly
225                 230                 235                 240

Thr Lys Leu Glu Ile Lys
                245
```

<210> SEQ ID NO 215
<211> LENGTH: 244
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 215

Gln Val Gln Leu Val Glu Ser Gly Gly Gly Leu Val Gln Pro Gly Arg
1               5                   10                  15

Ser Leu Arg Leu Ser Cys Ala Ala Ser Gly Phe Thr Phe Asp Asp Tyr
            20                  25                  30

Ala Met His Trp Val Arg Gln Ala Pro Gly Lys Gly Leu Glu Trp Val
        35                  40                  45

Ser Gly Ile Ser Trp Asn Ser Gly Ser Ile Gly Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Leu Tyr Tyr Cys
                85                  90                  95

Ser Val His Ser Phe Leu Ala Tyr Trp Gly Gln Gly Thr Leu Val Thr
            100                 105                 110

Val Ser Ser Ala Ser Gly Gly Gly Gly Ser Gly Gly Arg Ala Ser Gly
        115                 120                 125

Gly Gly Gly Ser Asp Ile Val Met Thr Gln Thr Pro Leu Ser Leu Pro
    130                 135                 140

Val Thr Pro Gly Glu Pro Ala Ser Ile Ser Cys Arg Ser Ser Gln Ser
145                 150                 155                 160

Leu Leu His Ser Asn Gly Tyr Asn Tyr Leu Asp Trp Tyr Leu Gln Lys
                165                 170                 175

Pro Gly Gln Ser Pro Gln Leu Leu Ile Tyr Leu Gly Ser Asn Arg Ala
            180                 185                 190

Ser Gly Val Pro Asp Arg Phe Ser Gly Ser Gly Ser Gly Thr Asp Phe
        195                 200                 205

Thr Leu Lys Ile Ser Arg Val Glu Ala Glu Asp Val Gly Val Tyr Tyr
    210                 215                 220

Cys Met Gln Ala Leu Gln Thr Pro Tyr Thr Phe Gly Gln Gly Thr Lys
225                 230                 235                 240

Val Glu Ile Lys

<210> SEQ ID NO 216
<211> LENGTH: 243
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 216

Glu Val Gln Leu Leu Glu Ser Gly Gly Gly Leu Val Gln Pro Gly Gly
1               5                   10                  15

Ser Leu Arg Leu Ser Cys Ala Val Ser Gly Phe Ala Leu Ser Asn His
            20                  25                  30

Gly Met Ser Trp Val Arg Arg Ala Pro Gly Lys Gly Leu Glu Trp Val
        35                  40                  45

```
Ser Gly Ile Val Tyr Ser Gly Ser Thr Tyr Tyr Ala Ala Ser Val Lys
    50                  55                  60

Gly Arg Phe Thr Ile Ser Arg Asp Asn Ser Arg Asn Thr Leu Tyr Leu
 65                  70                  75                  80

Gln Met Asn Ser Leu Arg Pro Glu Asp Thr Ala Ile Tyr Tyr Cys Ser
                 85                  90                  95

Ala His Gly Gly Glu Ser Asp Val Trp Gly Gln Gly Thr Thr Val Thr
                100                 105                 110

Val Ser Ser Ala Ser Gly Gly Gly Ser Gly Gly Arg Ala Ser Gly
                115                 120                 125

Gly Gly Ser Asp Ile Val Met Thr Gln Thr Pro Leu Ser Leu Ser
130                 135                 140

Val Thr Pro Gly Gln Pro Ala Ser Ile Ser Cys Lys Ser Ser Gln Ser
145                 150                 155                 160

Leu Leu Arg Asn Asp Gly Lys Thr Pro Leu Tyr Trp Tyr Leu Gln Lys
                165                 170                 175

Ala Gly Gln Pro Pro Gln Leu Leu Ile Tyr Glu Val Ser Asn Arg Phe
                180                 185                 190

Ser Gly Val Pro Asp Arg Phe Ser Gly Ser Gly Ser Gly Thr Asp Phe
                195                 200                 205

Thr Leu Lys Ile Ser Arg Val Glu Ala Glu Asp Val Gly Ala Tyr Tyr
210                 215                 220

Cys Met Gln Asn Ile Gln Phe Pro Ser Phe Gly Gly Gly Thr Lys Leu
225                 230                 235                 240

Glu Ile Lys

<210> SEQ ID NO 217
<211> LENGTH: 249
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 217

Gln Val Gln Leu Val Gln Ser Gly Ala Glu Val Arg Lys Thr Gly Ala
 1               5                  10                  15

Ser Val Lys Val Ser Cys Lys Ala Ser Gly Tyr Ile Phe Asp Asn Phe
                 20                  25                  30

Gly Ile Asn Trp Val Arg Gln Ala Pro Gly Gln Gly Leu Glu Trp Met
             35                  40                  45

Gly Trp Ile Asn Pro Lys Asn Asn Thr Asn Tyr Ala Gln Lys Phe
     50                  55                  60

Gln Gly Arg Val Thr Ile Thr Ala Asp Glu Ser Thr Asn Thr Ala Tyr
 65                  70                  75                  80

Met Glu Val Ser Ser Leu Arg Ser Glu Asp Thr Ala Val Tyr Tyr Cys
                 85                  90                  95

Ala Arg Gly Pro Tyr Tyr Gln Ser Tyr Met Asp Val Trp Gly Gln
                100                 105                 110

Gly Thr Met Val Thr Val Ser Ser Ala Ser Gly Gly Gly Ser Gly
            115                 120                 125

Gly Arg Ala Ser Gly Gly Gly Ser Asp Ile Val Met Thr Gln Thr
        130                 135                 140

Pro Leu Ser Leu Pro Val Thr Pro Gly Glu Pro Ala Ser Ile Ser Cys
145                 150                 155                 160
```

```
Arg Ser Ser Gln Ser Leu Leu His Ser Asn Gly Tyr Asn Tyr Leu Asn
            165                 170                 175

Trp Tyr Leu Gln Lys Pro Gly Gln Ser Pro Gln Leu Leu Ile Tyr Leu
        180                 185                 190

Gly Ser Lys Arg Ala Ser Gly Val Pro Asp Arg Phe Ser Gly Ser Gly
            195                 200                 205

Ser Gly Thr Asp Phe Thr Leu His Ile Thr Arg Val Gly Ala Glu Asp
        210                 215                 220

Val Gly Val Tyr Tyr Cys Met Gln Ala Leu Gln Thr Pro Tyr Thr Phe
225                 230                 235                 240

Gly Gln Gly Thr Lys Leu Glu Ile Lys
            245
```

<210> SEQ ID NO 218
<211> LENGTH: 246
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 218

```
Gln Val Gln Leu Gln Glu Ser Gly Gly Gly Leu Val Gln Pro Gly Gly
1               5                   10                  15

Ser Leu Arg Leu Ser Cys Ala Ala Ser Gly Phe Thr Phe Ser Ser Asp
            20                  25                  30

Ala Met Thr Trp Val Arg Gln Ala Pro Gly Lys Gly Leu Glu Trp Val
        35                  40                  45

Ser Val Ile Ser Gly Ser Gly Gly Thr Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
            85                  90                  95

Ala Lys Leu Asp Ser Ser Gly Tyr Tyr Tyr Ala Arg Gly Pro Arg Tyr
        100                 105                 110

Trp Gly Gln Gly Thr Leu Val Thr Val Ser Ser Ala Ser Gly Gly Gly
    115                 120                 125

Gly Ser Gly Gly Arg Ala Ser Gly Gly Gly Ser Asp Ile Gln Leu
        130                 135                 140

Thr Gln Ser Pro Ser Ser Leu Ser Ala Ser Val Gly Asp Arg Val Thr
145                 150                 155                 160

Ile Thr Cys Arg Ala Ser Gln Ser Ile Ser Ser Tyr Leu Asn Trp Tyr
            165                 170                 175

Gln Gln Lys Pro Gly Lys Ala Pro Lys Leu Leu Ile Tyr Gly Ala Ser
        180                 185                 190

Thr Leu Ala Ser Gly Val Pro Ala Arg Phe Ser Gly Ser Gly Ser Gly
    195                 200                 205

Thr His Phe Thr Leu Thr Ile Asn Ser Leu Gln Ser Glu Asp Ser Ala
        210                 215                 220

Thr Tyr Tyr Cys Gln Gln Ser Tyr Lys Arg Ala Ser Phe Gly Gln Gly
225                 230                 235                 240

Thr Lys Val Glu Ile Lys
            245
```

<210> SEQ ID NO 219

```
<211> LENGTH: 247
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 219

Gln Val Gln Leu Val Gln Ser Gly Ala Glu Val Lys Pro Gly Ala
1               5                   10                  15

Ser Val Lys Val Ser Cys Lys Ala Ser Gly Tyr Thr Phe Ser Asn Tyr
                20                  25                  30

Gly Ile Thr Trp Val Arg Gln Ala Pro Gly Gln Gly Leu Glu Trp Met
            35                  40                  45

Gly Trp Ile Ser Ala Tyr Asn Gly Asn Thr Asn Tyr Ala Gln Lys Phe
    50                  55                  60

Gln Gly Arg Val Thr Met Thr Arg Asn Thr Ser Ile Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Gly Pro Tyr Tyr Tyr Tyr Met Asp Val Trp Gly Lys Gly Thr
                100                 105                 110

Met Val Thr Val Ser Ser Ala Ser Gly Gly Gly Gly Ser Gly Gly Arg
            115                 120                 125

Ala Ser Gly Gly Gly Ser Glu Ile Val Met Thr Gln Ser Pro Leu
    130                 135                 140

Ser Leu Pro Val Thr Pro Gly Glu Pro Ala Ser Ile Ser Cys Arg Ser
145                 150                 155                 160

Ser Gln Ser Leu Leu Tyr Ser Asn Gly Tyr Asn Tyr Val Asp Trp Tyr
                165                 170                 175

Leu Gln Lys Pro Gly Gln Ser Pro Gln Leu Leu Ile Tyr Leu Gly Ser
            180                 185                 190

Asn Arg Ala Ser Gly Val Pro Asp Arg Phe Ser Gly Ser Gly Ser Gly
    195                 200                 205

Thr Asp Phe Lys Leu Gln Ile Ser Arg Val Glu Ala Glu Asp Val Gly
210                 215                 220

Ile Tyr Tyr Cys Met Gln Gly Arg Gln Phe Pro Tyr Ser Phe Gly Gln
225                 230                 235                 240

Gly Thr Lys Val Glu Ile Lys
            245

<210> SEQ ID NO 220
<211> LENGTH: 238
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 220

Glu Val Gln Leu Leu Glu Thr Gly Gly Gly Leu Val Gln Pro Gly Gly
1               5                   10                  15

Ser Leu Arg Leu Ser Cys Ala Val Ser Gly Phe Ala Leu Ser Asn His
                20                  25                  30

Gly Met Ser Trp Val Arg Arg Ala Pro Gly Lys Gly Leu Glu Trp Val
            35                  40                  45

Ser Gly Ile Val Tyr Ser Gly Ser Thr Tyr Tyr Ala Ala Ser Val Lys
    50                  55                  60
```

Gly Arg Phe Thr Ile Ser Arg Asp Asn Ser Arg Asn Thr Leu Tyr Leu
65                  70                  75                  80

Gln Met Asn Ser Leu Arg Pro Glu Asp Thr Ala Ile Tyr Tyr Cys Ser
                85                  90                  95

Ala His Gly Gly Glu Ser Asp Val Trp Gly Gln Gly Thr Thr Val Thr
            100                 105                 110

Val Ser Ser Ala Ser Gly Gly Gly Gly Ser Gly Gly Arg Ala Ser Gly
        115                 120                 125

Gly Gly Gly Ser Glu Ile Val Leu Thr Gln Ser Pro Ala Thr Leu Ser
130                 135                 140

Val Ser Pro Gly Glu Ser Ala Thr Leu Ser Cys Arg Ala Ser Gln Ser
145                 150                 155                 160

Val Ser Ser Asn Leu Ala Trp Tyr Gln Gln Lys Pro Gly Gln Ala Pro
                165                 170                 175

Arg Leu Leu Ile Tyr Gly Ala Ser Thr Arg Ala Ser Gly Ile Pro Asp
            180                 185                 190

Arg Phe Ser Gly Ser Gly Ser Gly Thr Asp Phe Thr Leu Thr Ile Ser
        195                 200                 205

Ser Leu Gln Ala Glu Asp Val Ala Val Tyr Tyr Cys Gln Gln Tyr Gly
    210                 215                 220

Ser Ser Leu Thr Phe Gly Gly Gly Thr Lys Val Glu Ile Lys
225                 230                 235

<210> SEQ ID NO 221
<211> LENGTH: 239
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 221

Glu Val Gln Leu Val Glu Thr Gly Gly Gly Leu Val Gln Pro Gly Gly
1               5                   10                  15

Ser Leu Arg Leu Ser Cys Ala Val Ser Gly Phe Ala Leu Ser Asn His
            20                  25                  30

Gly Met Ser Trp Val Arg Arg Ala Pro Gly Lys Gly Leu Glu Trp Val
        35                  40                  45

Ser Gly Ile Val Tyr Ser Gly Ser Thr Tyr Tyr Ala Ala Ser Val Lys
    50                  55                  60

Gly Arg Phe Thr Ile Ser Arg Asp Asn Ser Arg Asn Thr Leu Tyr Leu
65                  70                  75                  80

Gln Met Asn Ser Leu Arg Pro Glu Asp Thr Ala Ile Tyr Tyr Cys Ser
                85                  90                  95

Ala His Gly Gly Glu Ser Asp Val Trp Gly Gln Gly Thr Thr Val Thr
            100                 105                 110

Val Ser Ser Ala Ser Gly Gly Gly Gly Ser Gly Gly Arg Ala Ser Gly
        115                 120                 125

Gly Gly Gly Ser Glu Ile Val Met Thr Gln Ser Pro Ala Thr Leu Ser
130                 135                 140

Val Ser Pro Gly Glu Arg Ala Thr Leu Ser Cys Arg Ala Ser Gln Ser
145                 150                 155                 160

Val Ser Ser Lys Leu Ala Trp Tyr Gln Gln Lys Pro Gly Gln Ala Pro
                165                 170                 175

Arg Leu Leu Met Tyr Gly Ala Ser Ile Arg Ala Thr Gly Ile Pro Asp

```
            180                 185                 190
Arg Phe Ser Gly Ser Gly Ser Gly Thr Glu Phe Thr Leu Thr Ile Ser
        195                 200                 205

Ser Leu Glu Pro Glu Asp Phe Ala Val Tyr Tyr Cys Gln Gln Tyr Gly
        210                 215                 220

Ser Ser Ser Trp Thr Phe Gly Gln Gly Thr Lys Val Glu Ile Lys
225                 230                 235

<210> SEQ ID NO 222
<211> LENGTH: 241
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 222

Glu Val Gln Leu Val Glu Thr Gly Gly Val Val Gln Pro Gly Gly
1               5                   10                  15

Ser Leu Arg Leu Ser Cys Ala Val Ser Gly Phe Ala Leu Ser Asn His
            20                  25                  30

Gly Met Ser Trp Val Arg Arg Ala Pro Gly Lys Gly Leu Glu Trp Val
        35                  40                  45

Ser Gly Ile Val Tyr Ser Gly Ser Thr Tyr Tyr Ala Ala Ser Val Lys
    50                  55                  60

Gly Arg Phe Thr Ile Ser Arg Asp Asn Ser Arg Asn Thr Leu Tyr Leu
65                  70                  75                  80

Gln Met Asn Ser Leu Arg Pro Glu Asp Thr Ala Ile Tyr Tyr Cys Ser
                85                  90                  95

Ala His Gly Gly Glu Ser Asp Val Trp Gly Gln Gly Thr Thr Val Thr
            100                 105                 110

Val Ser Ser Ala Ser Gly Gly Gly Gly Ser Gly Gly Arg Ala Ser Gly
        115                 120                 125

Gly Gly Gly Ser Glu Ile Val Leu Thr Gln Ser Pro Gly Thr Leu Ser
    130                 135                 140

Leu Ser Pro Gly Glu Arg Ala Thr Leu Ser Cys Arg Ala Ser Gln Ser
145                 150                 155                 160

Val Gly Ser Thr Asn Leu Ala Trp Tyr Gln Gln Lys Pro Gly Gln Ala
                165                 170                 175

Pro Arg Leu Leu Ile Tyr Asp Ala Ser Asn Arg Ala Thr Gly Ile Pro
            180                 185                 190

Asp Arg Phe Ser Gly Gly Gly Ser Gly Thr Asp Phe Thr Leu Thr Ile
        195                 200                 205

Ser Arg Leu Glu Pro Glu Asp Phe Ala Val Tyr Tyr Cys Gln Gln Tyr
    210                 215                 220

Gly Ser Ser Pro Pro Trp Thr Phe Gly Gln Gly Thr Lys Val Glu Ile
225                 230                 235                 240

Lys

<210> SEQ ID NO 223
<211> LENGTH: 239
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 223
```

Gln Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Asp Tyr
            20                  25                  30

Tyr Met Ser Trp Ile Arg Gln Ala Pro Gly Lys Gly Leu Glu Trp Val
        35                  40                  45

Ser Tyr Ile Ser Ser Ser Gly Ser Thr Ile Tyr Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Glu Ser Gly Asp Gly Met Asp Val Trp Gly Gln Gly Thr Thr
            100                 105                 110

Val Thr Val Ser Ser Ala Ser Gly Gly Gly Gly Ser Gly Gly Arg Ala
        115                 120                 125

Ser Gly Gly Gly Gly Ser Asp Ile Gln Met Thr Gln Ser Pro Ser Ser
    130                 135                 140

Leu Ser Ala Ser Val Gly Asp Arg Val Thr Ile Thr Cys Arg Ala Ser
145                 150                 155                 160

Gln Ser Ile Ser Ser Tyr Leu Asn Trp Tyr Gln Gln Lys Pro Gly Lys
                165                 170                 175

Ala Pro Lys Leu Leu Ile Tyr Ala Ala Ser Ser Leu Gln Ser Gly Val
            180                 185                 190

Pro Ser Arg Phe Ser Gly Ser Gly Ser Gly Thr Asp Phe Thr Leu Thr
        195                 200                 205

Ile Ser Ser Leu Gln Pro Glu Asp Phe Ala Thr Tyr Tyr Cys Gln Gln
    210                 215                 220

Ser Tyr Thr Leu Ala Phe Gly Gln Gly Thr Lys Val Asp Ile Lys
225                 230                 235

<210> SEQ ID NO 224
<211> LENGTH: 239
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 224

Glu Val Gln Leu Val Glu Ser Gly Gly Gly Leu Val Gln Pro Gly Gly
1               5                   10                  15

Ser Leu Arg Leu Ser Cys Ala Val Ser Gly Phe Ala Leu Ser Asn His
            20                  25                  30

Gly Met Ser Trp Val Arg Arg Ala Pro Gly Lys Gly Leu Glu Trp Val
        35                  40                  45

Ser Gly Ile Val Tyr Ser Gly Ser Thr Tyr Tyr Ala Ala Ser Val Lys
    50                  55                  60

Gly Arg Phe Thr Ile Ser Arg Asp Asn Ser Arg Asn Thr Leu Tyr Leu
65                  70                  75                  80

Gln Met Asn Ser Leu Arg Pro Glu Asp Thr Ala Ile Tyr Tyr Cys Ser
                85                  90                  95

Ala His Gly Gly Glu Ser Asp Val Trp Gly Gln Gly Thr Thr Val Thr
            100                 105                 110

Val Ser Ser Ala Ser Gly Gly Gly Gly Ser Gly Gly Arg Ala Ser Gly

```
                115                 120                 125
Gly Gly Gly Ser Asp Ile Gln Leu Thr Gln Ser Pro Ser Ser Leu Ser
    130                 135                 140

Ala Ser Val Gly Asp Arg Val Thr Ile Thr Cys Arg Ala Ser Gln Ser
145                 150                 155                 160

Ile Ser Ser Tyr Leu Asn Trp Tyr Gln Gln Lys Pro Gly Lys Ala Pro
                165                 170                 175

Lys Leu Leu Ile Tyr Ala Ala Ser Ser Leu Gln Ser Gly Val Pro Ser
            180                 185                 190

Arg Phe Ser Gly Ser Gly Ser Gly Thr Asp Phe Thr Leu Thr Ile Ser
        195                 200                 205

Ser Leu Gln Pro Glu Asp Phe Ala Thr Tyr Tyr Cys Gln Gln Ser Tyr
    210                 215                 220

Ser Thr Pro Tyr Thr Phe Gly Gln Gly Thr Lys Val Glu Ile Lys
225                 230                 235
```

<210> SEQ ID NO 225
<211> LENGTH: 246
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 225

```
Gln Val Gln Leu Val Gln Ser Gly Gly Gly Leu Val Lys Pro Gly Gly
1               5                   10                  15

Ser Leu Arg Leu Ser Cys Ala Ala Ser Gly Phe Thr Phe Ser Asp Tyr
            20                  25                  30

Tyr Met Ser Trp Ile Arg Gln Ala Pro Gly Lys Gly Leu Glu Trp Val
        35                  40                  45

Ser Tyr Ile Ser Ser Ser Gly Asn Thr Ile Tyr Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Ser Thr Met Val Arg Glu Asp Tyr Trp Gly Gln Gly Thr Leu
            100                 105                 110

Val Thr Val Ser Ser Ala Ser Gly Gly Gly Gly Ser Gly Gly Arg Ala
        115                 120                 125

Ser Gly Gly Gly Gly Ser Asp Ile Val Leu Thr Gln Ser Pro Leu Ser
    130                 135                 140

Leu Pro Val Thr Leu Gly Gln Pro Ala Ser Ile Ser Cys Lys Ser Ser
145                 150                 155                 160

Glu Ser Leu Val His Asn Ser Gly Lys Thr Tyr Leu Asn Trp Phe His
                165                 170                 175

Gln Arg Pro Gly Gln Ser Pro Arg Arg Leu Ile Tyr Glu Val Ser Asn
            180                 185                 190

Arg Asp Ser Gly Val Pro Asp Arg Phe Thr Gly Ser Gly Ser Gly Thr
        195                 200                 205

Asp Phe Thr Leu Lys Ile Ser Arg Val Glu Ala Glu Asp Val Gly Val
    210                 215                 220

Tyr Tyr Cys Met Gln Gly Thr His Trp Pro Gly Thr Phe Gly Gln Gly
225                 230                 235                 240
```

Thr Lys Leu Glu Ile Lys
            245

<210> SEQ ID NO 226
<211> LENGTH: 239
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 226

Gln Val Gln Leu Val Glu Ser Gly Gly Gly Leu Val Gln Pro Gly Gly
1               5                   10                  15

Ser Leu Arg Leu Ser Cys Ala Val Ser Gly Phe Ala Leu Ser Asn His
            20                  25                  30

Gly Met Ser Trp Val Arg Arg Ala Pro Gly Lys Gly Leu Glu Trp Val
        35                  40                  45

Ser Gly Ile Val Tyr Ser Gly Ser Thr Tyr Tyr Ala Ala Ser Val Lys
    50                  55                  60

Gly Arg Phe Thr Ile Ser Arg Asp Asn Ser Arg Asn Thr Leu Tyr Leu
65                  70                  75                  80

Gln Met Asn Ser Leu Arg Pro Glu Asp Thr Ala Ile Tyr Tyr Cys Ser
                85                  90                  95

Ala His Gly Gly Glu Ser Asp Val Trp Gly Gln Gly Thr Thr Val Thr
            100                 105                 110

Val Ser Ser Ala Ser Gly Gly Gly Gly Ser Gly Gly Arg Ala Ser Gly
        115                 120                 125

Gly Gly Gly Ser Asp Ile Arg Leu Thr Gln Ser Pro Ser Pro Leu Ser
    130                 135                 140

Ala Ser Val Gly Asp Arg Val Thr Ile Thr Cys Gln Ala Ser Glu Asp
145                 150                 155                 160

Ile Asn Lys Phe Leu Asn Trp Tyr His Gln Thr Pro Gly Lys Ala Pro
                165                 170                 175

Lys Leu Leu Ile Tyr Asp Ala Ser Thr Leu Gln Thr Gly Val Pro Ser
            180                 185                 190

Arg Phe Ser Gly Ser Gly Ser Gly Thr Asp Phe Thr Leu Thr Ile Asn
        195                 200                 205

Ser Leu Gln Pro Glu Asp Ile Gly Thr Tyr Tyr Cys Gln Gln Tyr Glu
    210                 215                 220

Ser Leu Pro Leu Thr Phe Gly Gly Gly Thr Lys Val Glu Ile Lys
225                 230                 235

<210> SEQ ID NO 227
<211> LENGTH: 240
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 227

Glu Val Gln Leu Val Glu Thr Gly Gly Gly Leu Val Gln Pro Gly Gly
1               5                   10                  15

Ser Leu Arg Leu Ser Cys Ala Val Ser Gly Phe Ala Leu Ser Asn His
            20                  25                  30

Gly Met Ser Trp Val Arg Arg Ala Pro Gly Lys Gly Leu Glu Trp Val
        35                  40                  45

Ser Gly Ile Val Tyr Ser Gly Ser Thr Tyr Tyr Ala Ala Ser Val Lys
    50                  55                  60

Gly Arg Phe Thr Ile Ser Arg Asp Asn Ser Arg Asn Thr Leu Tyr Leu
65                  70                  75                  80

Gln Met Asn Ser Leu Arg Pro Glu Asp Thr Ala Ile Tyr Tyr Cys Ser
                85                  90                  95

Ala His Gly Gly Glu Ser Asp Val Trp Gly Gln Gly Thr Thr Val Thr
            100                 105                 110

Val Ser Ser Ala Ser Gly Gly Gly Ser Gly Gly Arg Ala Ser Gly
        115                 120                 125

Gly Gly Ser Glu Thr Thr Leu Thr Gln Ser Pro Ala Thr Leu Ser
130                 135                 140

Val Ser Pro Gly Glu Arg Ala Thr Leu Ser Cys Arg Ala Ser Gln Ser
145                 150                 155                 160

Val Gly Ser Asn Leu Ala Trp Tyr Gln Gln Lys Pro Gly Gln Gly Pro
                165                 170                 175

Arg Leu Leu Ile Tyr Gly Ala Ser Thr Arg Ala Thr Gly Ile Pro Ala
            180                 185                 190

Arg Phe Ser Gly Ser Gly Ser Gly Thr Glu Phe Thr Leu Thr Ile Ser
            195                 200                 205

Ser Leu Gln Pro Glu Asp Phe Ala Val Tyr Tyr Cys Gln Gln Tyr Asn
210                 215                 220

Asp Trp Leu Pro Val Thr Phe Gly Gln Gly Thr Lys Val Glu Ile Lys
225                 230                 235                 240

<210> SEQ ID NO 228
<211> LENGTH: 241
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 228

Glu Val Gln Leu Val Glu Ser Gly Gly Gly Leu Val Gln Pro Gly Gly
1               5                   10                  15

Ser Leu Arg Leu Ser Cys Ala Val Ser Gly Phe Ala Leu Ser Asn His
            20                  25                  30

Gly Met Ser Trp Val Arg Arg Ala Pro Gly Lys Gly Leu Glu Trp Val
        35                  40                  45

Ser Gly Ile Val Tyr Ser Gly Ser Thr Tyr Tyr Ala Ala Ser Val Lys
    50                  55                  60

Gly Arg Phe Thr Ile Ser Arg Asp Asn Ser Arg Asn Thr Leu Tyr Leu
65                  70                  75                  80

Gln Met Asn Ser Leu Arg Pro Glu Asp Thr Ala Ile Tyr Tyr Cys Ser
                85                  90                  95

Ala His Gly Gly Glu Ser Asp Val Trp Gly Gln Gly Thr Thr Val Thr
            100                 105                 110

Val Ser Ser Ala Ser Gly Gly Gly Ser Gly Gly Arg Ala Ser Gly
        115                 120                 125

Gly Gly Ser Glu Ile Val Leu Thr Gln Ser Pro Gly Thr Leu Ser
130                 135                 140

Leu Ser Pro Gly Glu Arg Ala Thr Leu Ser Cys Arg Ala Ser Gln Ser
145                 150                 155                 160

Ile Gly Ser Ser Ser Leu Ala Trp Tyr Gln Gln Lys Pro Gly Gln Ala
                165                 170                 175

Pro Arg Leu Leu Met Tyr Gly Ala Ser Ser Arg Ala Ser Gly Ile Pro
            180                 185                 190

Asp Arg Phe Ser Gly Ser Gly Ser Gly Thr Asp Phe Thr Leu Thr Ile
            195                 200                 205

Ser Arg Leu Glu Pro Glu Asp Phe Ala Val Tyr Tyr Cys Gln Gln Tyr
210                 215                 220

Ala Gly Ser Pro Pro Phe Thr Phe Gly Gln Gly Thr Lys Val Glu Ile
225                 230                 235                 240

Lys

<210> SEQ ID NO 229
<211> LENGTH: 243
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 229

Gln Val Gln Leu Gln Glu Ser Gly Pro Gly Leu Val Lys Pro Ser Glu
1               5                   10                  15

Thr Leu Ser Leu Thr Cys Thr Val Ser Gly Gly Ser Ile Ser Ser Ser
            20                  25                  30

Tyr Tyr Tyr Trp Gly Trp Ile Arg Gln Pro Pro Gly Lys Gly Leu Glu
        35                  40                  45

Trp Ile Gly Ser Ile Tyr Tyr Ser Gly Ser Ala Tyr Tyr Asn Pro Ser
    50                  55                  60

Leu Lys Ser Arg Val Thr Ile Ser Val Asp Thr Ser Lys Asn Gln Phe
65                  70                  75                  80

Ser Leu Arg Leu Ser Ser Val Thr Ala Ala Asp Thr Ala Val Tyr Tyr
                85                  90                  95

Cys Ala Arg His Trp Gln Glu Trp Pro Asp Ala Phe Asp Ile Trp Gly
            100                 105                 110

Gln Gly Thr Met Val Thr Val Ser Ser Gly Gly Gly Ser Gly Gly
        115                 120                 125

Gly Gly Ser Gly Gly Gly Gly Ser Glu Thr Thr Leu Thr Gln Ser Pro
    130                 135                 140

Ala Phe Met Ser Ala Thr Pro Gly Asp Lys Val Ile Ile Ser Cys Lys
145                 150                 155                 160

Ala Ser Gln Asp Ile Asp Asp Ala Met Asn Trp Tyr Gln Gln Lys Pro
                165                 170                 175

Gly Glu Ala Pro Leu Phe Ile Ile Gln Ser Ala Thr Ser Pro Val Pro
            180                 185                 190

Gly Ile Pro Pro Arg Phe Ser Gly Ser Gly Phe Gly Thr Asp Phe Ser
        195                 200                 205

Leu Thr Ile Asn Asn Ile Glu Ser Glu Asp Ala Ala Tyr Tyr Phe Cys
    210                 215                 220

Leu Gln His Asp Asn Phe Pro Leu Thr Phe Gly Gln Gly Thr Lys Leu
225                 230                 235                 240

Glu Ile Lys

<210> SEQ ID NO 230
<211> LENGTH: 244
<212> TYPE: PRT
<213> ORGANISM: Artificial Sequence
<220> FEATURE:

<223> OTHER INFORMATION: Description of Artificial Sequence: Synthetic
      polypeptide

<400> SEQUENCE: 230

Val Asn Leu Arg Glu Ser Gly Pro Ala Leu Val Lys Pro Thr Gln Thr
1               5                   10                  15

Leu Thr Leu Thr Cys Thr Phe Ser Gly Phe Ser Leu Arg Thr Ser Gly
            20                  25                  30

Met Cys Val Ser Trp Ile Arg Gln Pro Pro Gly Lys Ala Leu Glu Trp
        35                  40                  45

Leu Ala Arg Ile Asp Trp Asp Glu Asp Lys Phe Tyr Ser Thr Ser Leu
    50                  55                  60

Lys Thr Arg Leu Thr Ile Ser Lys Asp Thr Ser Asp Asn Gln Val Val
65                  70                  75                  80

Leu Arg Met Thr Asn Met Asp Pro Ala Asp Thr Ala Thr Tyr Tyr Cys
                85                  90                  95

Ala Arg Ser Gly Ala Gly Gly Thr Ser Ala Thr Ala Phe Asp Ile Trp
            100                 105                 110

Gly Pro Gly Thr Met Val Thr Val Ser Ser Gly Gly Gly Gly Ser Gly
        115                 120                 125

Gly Gly Gly Ser Gly Gly Gly Ser Asp Ile Gln Met Thr Gln Ser
    130                 135                 140

Pro Ser Ser Leu Ser Ala Ser Val Gly Asp Arg Val Thr Ile Thr Cys
145                 150                 155                 160

Arg Ala Ser Gln Asp Ile Tyr Asn Asn Leu Ala Trp Phe Gln Leu Lys
                165                 170                 175

Pro Gly Ser Ala Pro Arg Ser Leu Met Tyr Ala Ala Asn Lys Ser Gln
            180                 185                 190

Ser Gly Val Pro Ser Arg Phe Ser Gly Ser Ala Ser Gly Thr Asp Phe
        195                 200                 205

Thr Leu Thr Ile Ser Ser Leu Gln Pro Glu Asp Phe Ala Thr Tyr Tyr
    210                 215                 220

Cys Gln His Tyr Tyr Arg Phe Pro Tyr Ser Phe Gly Gln Gly Thr Lys
225                 230                 235                 240

Leu Glu Ile Lys

<210> SEQ ID NO 231
<211> LENGTH: 246
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 231

Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Ser Tyr
            20                  25                  30

Ser Met Asn Trp Val Arg Gln Ala Pro Gly Lys Gly Leu Glu Trp Val
        35                  40                  45

Ser Ser Ile Ser Ser Ser Ser Tyr Ile Tyr Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys

```
                      85                  90                  95
Ala Lys Thr Ile Ala Ala Val Tyr Ala Phe Asp Ile Trp Gly Gln Gly
                100                 105                 110

Thr Thr Val Thr Val Ser Ser Gly Gly Gly Ser Gly Gly Gly Gly
            115                 120                 125

Ser Gly Gly Gly Ser Glu Ile Val Leu Thr Gln Ser Pro Leu Ser
    130                 135                 140

Leu Pro Val Thr Pro Glu Glu Pro Ala Ser Ile Ser Cys Arg Ser Ser
145                 150                 155                 160

Gln Ser Leu Leu His Ser Asn Gly Tyr Asn Tyr Leu Asp Trp Tyr Leu
                165                 170                 175

Gln Lys Pro Gly Gln Ser Pro Gln Leu Leu Ile Tyr Leu Gly Ser Asn
                180                 185                 190

Arg Ala Ser Gly Val Pro Asp Arg Phe Ser Gly Ser Gly Ser Gly Thr
                195                 200                 205

Asp Phe Thr Leu Lys Ile Ser Arg Val Glu Ala Glu Asp Val Gly Val
                210                 215                 220

Tyr Tyr Cys Met Gln Ala Leu Gln Thr Pro Tyr Thr Phe Gly Gln Gly
225                 230                 235                 240

Thr Lys Leu Glu Ile Lys
                245

<210> SEQ ID NO 232
<211> LENGTH: 240
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 232

Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Asp Tyr
            20                  25                  30

Tyr Met Ser Trp Ile Arg Gln Ala Pro Gly Lys Gly Leu Glu Trp Val
        35                  40                  45

Ser Tyr Ile Ser Ser Ser Gly Ser Thr Ile Tyr Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Asp Leu Arg Gly Ala Phe Asp Ile Trp Gly Gln Gly Thr Met
                100                 105                 110

Val Thr Val Ser Ser Gly Gly Gly Gly Ser Gly Gly Gly Gly Ser Gly
            115                 120                 125

Gly Gly Gly Ser Ser Tyr Val Leu Thr Gln Ser Pro Ser Val Ser Ala
    130                 135                 140

Ala Pro Gly Tyr Thr Ala Thr Ile Ser Cys Gly Gly Asn Asn Ile Gly
145                 150                 155                 160

Thr Lys Ser Val His Trp Tyr Gln Gln Lys Pro Gly Gln Ala Pro Leu
                165                 170                 175

Leu Val Ile Arg Asp Asp Ser Val Arg Pro Ser Lys Ile Pro Gly Arg
                180                 185                 190
```

Phe Ser Gly Ser Asn Ser Gly Asn Met Ala Thr Leu Thr Ile Ser Gly
            195                 200                 205

Val Gln Ala Gly Asp Glu Ala Asp Phe Tyr Cys Gln Val Trp Asp Ser
        210                 215                 220

Asp Ser Glu His Val Val Phe Gly Gly Gly Thr Lys Leu Thr Val Leu
225                 230                 235                 240

<210> SEQ ID NO 233
<211> LENGTH: 241
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 233

Gln Val Gln Leu Val Gln Ser Gly Ala Glu Val Lys Lys Pro Gly Ala
1               5                   10                  15

Ser Val Lys Val Ser Cys Lys Pro Ser Gly Tyr Thr Val Thr Ser His
            20                  25                  30

Tyr Ile His Trp Val Arg Arg Ala Pro Gly Gln Gly Leu Glu Trp Met
        35                  40                  45

Gly Met Ile Asn Pro Ser Gly Val Thr Ala Tyr Ser Gln Thr Leu
    50                  55                  60

Gln Gly Arg Val Thr Met Thr Ser Asp Thr Ser Ser Ser Thr Val Tyr
65                  70                  75                  80

Met Glu Leu Ser Ser Leu Arg Ser Glu Asp Thr Ala Met Tyr Tyr Cys
                85                  90                  95

Ala Arg Glu Gly Ser Gly Ser Gly Trp Tyr Phe Asp Phe Trp Gly Arg
            100                 105                 110

Gly Thr Leu Val Thr Val Ser Ser Gly Gly Gly Gly Ser Gly Gly Gly
        115                 120                 125

Gly Ser Gly Gly Gly Gly Ser Ser Tyr Val Leu Thr Gln Pro Pro Ser
    130                 135                 140

Val Ser Val Ser Pro Gly Gln Thr Ala Ser Ile Thr Cys Ser Gly Asp
145                 150                 155                 160

Gly Leu Ser Lys Lys Tyr Val Ser Trp Tyr Gln Gln Lys Ala Gly Gln
                165                 170                 175

Ser Pro Val Leu Ile Ser Arg Asp Lys Glu Arg Pro Ser Gly Ile
            180                 185                 190

Pro Asp Arg Phe Ser Gly Ser Asn Ser Ala Asp Thr Ala Thr Leu Thr
        195                 200                 205

Ile Ser Gly Thr Gln Ala Met Asp Glu Ala Asp Tyr Tyr Cys Gln Ala
    210                 215                 220

Trp Asp Asp Thr Thr Val Val Phe Gly Gly Gly Thr Lys Leu Thr Val
225                 230                 235                 240

Leu

<210> SEQ ID NO 234
<211> LENGTH: 245
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 234

Gln Val Gln Leu Gln Glu Ser Gly Pro Gly Leu Val Lys Pro Ser Gln

```
               1               5                  10                 15
            Thr Leu Ser Leu Thr Cys Thr Val Ser Gly Gly Ser Ile Ser Ser Gly
                            20                 25                 30

Gly Tyr Tyr Trp Ser Trp Ile Arg Gln His Pro Gly Lys Gly Leu Glu
                        35                 40                 45

Trp Ile Gly Tyr Ile Tyr Tyr Ser Gly Ser Thr Tyr Tyr Asn Pro Ser
                50                 55                 60

Leu Lys Ser Arg Val Thr Ile Ser Val Asp Thr Ser Lys Asn Gln Phe
            65                 70                 75                 80

Ser Leu Lys Leu Ser Ser Val Thr Ala Ala Asp Thr Ala Val Tyr Tyr
                            85                 90                 95

Cys Ala Arg Ala Gly Ile Ala Ala Arg Leu Arg Gly Ala Phe Asp Ile
                        100                105                110

Trp Gly Gln Gly Thr Met Val Thr Val Ser Ser Gly Gly Gly Gly Ser
                        115                120                125

Gly Gly Gly Gly Ser Gly Gly Gly Ser Asp Ile Val Met Thr Gln
            130                135                140

Ser Pro Ser Ser Val Ser Ala Ser Val Gly Asp Arg Val Ile Ile Thr
            145                150                155                160

Cys Arg Ala Ser Gln Gly Ile Arg Asn Trp Leu Ala Trp Tyr Gln Gln
                        165                170                175

Lys Pro Gly Lys Ala Pro Asn Leu Leu Ile Tyr Ala Ala Ser Asn Leu
                        180                185                190

Gln Ser Gly Val Pro Ser Arg Phe Ser Gly Ser Gly Ser Gly Ala Asp
                        195                200                205

Phe Thr Leu Thr Ile Ser Ser Leu Gln Pro Glu Asp Val Ala Thr Tyr
                    210                215                220

Tyr Cys Gln Lys Tyr Asn Ser Ala Pro Phe Thr Phe Gly Pro Gly Thr
            225                230                235                240

Lys Val Asp Ile Lys
                        245

<210> SEQ ID NO 235
<211> LENGTH: 253
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 235

Gln Val Gln Leu Val Gln Ser Gly Ala Glu Val Lys Lys Pro Gly Ser
1               5                  10                 15

Ser Val Lys Val Ser Cys Lys Ala Ser Gly Gly Thr Phe Ser Ser Tyr
            20                 25                 30

Ala Ile Ser Trp Val Arg Gln Ala Pro Gly Gln Gly Leu Glu Trp Met
        35                 40                 45

Gly Gly Ile Ile Pro Ile Phe Gly Thr Ala Asn Tyr Ala Gln Lys Phe
    50                 55                 60

Gln Gly Arg Val Thr Ile Thr Ala Asp Glu Ser Thr Ser Thr Ala Tyr
65                 70                 75                 80

Met Glu Leu Ser Ser Leu Arg Ser Glu Asp Thr Ala Val Tyr Tyr Cys
                85                 90                 95

Ala Arg Arg Gly Gly Tyr Gln Leu Leu Arg Trp Asp Val Gly Leu Leu
            100                105                110
```

Arg Ser Ala Phe Asp Ile Trp Gly Gln Gly Thr Met Val Thr Val Ser
115                 120                 125

Ser Gly Gly Gly Gly Ser Gly Gly Gly Ser Gly Gly Gly Gly Ser
130                 135                 140

Ser Tyr Val Leu Thr Gln Pro Pro Ser Val Ser Val Ala Pro Gly Gln
145                 150                 155                 160

Thr Ala Arg Ile Thr Cys Gly Gly Asn Asn Ile Gly Ser Lys Ser Val
                165                 170                 175

His Trp Tyr Gln Gln Lys Pro Gly Gln Ala Pro Val Leu Val Leu Tyr
            180                 185                 190

Gly Lys Asn Asn Arg Pro Ser Gly Val Pro Asp Arg Phe Ser Gly Ser
        195                 200                 205

Arg Ser Gly Thr Thr Ala Ser Leu Thr Ile Thr Gly Ala Gln Ala Glu
210                 215                 220

Asp Glu Ala Asp Tyr Tyr Cys Ser Ser Arg Asp Ser Ser Gly Asp His
225                 230                 235                 240

Leu Arg Val Phe Gly Thr Gly Thr Lys Val Thr Val Leu
                245                 250

<210> SEQ ID NO 236
<211> LENGTH: 248
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 236

Glu Val Gln Leu Gln Gln Ser Gly Pro Gly Leu Val Lys Pro Ser Gln
1               5                   10                  15

Thr Leu Ser Leu Thr Cys Ala Ile Ser Gly Asp Ser Val Ser Ser Asn
            20                  25                  30

Ser Ala Ala Trp Asn Trp Ile Arg Gln Ser Pro Ser Arg Gly Leu Glu
        35                  40                  45

Trp Leu Gly Arg Thr Tyr Tyr Arg Ser Lys Trp Tyr Ser Phe Tyr Ala
50                  55                  60

Ile Ser Leu Lys Ser Arg Ile Ile Ile Asn Pro Asp Thr Ser Lys Asn
65                  70                  75                  80

Gln Phe Ser Leu Gln Leu Lys Ser Val Thr Pro Glu Asp Thr Ala Val
                85                  90                  95

Tyr Tyr Cys Ala Arg Ser Ser Pro Glu Gly Leu Phe Leu Tyr Trp Phe
            100                 105                 110

Asp Pro Trp Gly Gln Gly Thr Leu Val Thr Val Ser Ser Gly Gly Asp
        115                 120                 125

Gly Ser Gly Gly Gly Gly Ser Gly Gly Gly Gly Ser Ser Ser Glu Leu
130                 135                 140

Thr Gln Asp Pro Ala Val Ser Val Ala Leu Gly Gln Thr Ile Arg Ile
145                 150                 155                 160

Thr Cys Gln Gly Asp Ser Leu Gly Asn Tyr Tyr Ala Thr Trp Tyr Gln
                165                 170                 175

Gln Lys Pro Gly Gln Ala Pro Val Leu Val Ile Tyr Gly Thr Asn Asn
            180                 185                 190

Arg Pro Ser Gly Ile Pro Asp Arg Phe Ser Ala Ser Ser Ser Gly Asn
        195                 200                 205

Thr Ala Ser Leu Thr Ile Thr Gly Ala Gln Ala Glu Asp Glu Ala Asp
210                 215                 220

Tyr Tyr Cys Asn Ser Arg Asp Ser Ser Gly His His Leu Leu Phe Gly
225                 230                 235                 240

Thr Gly Thr Lys Val Thr Val Leu
                245

<210> SEQ ID NO 237
<211> LENGTH: 246
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 237

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
                20                  25                  30

Ala Met Ser Trp Val Arg Gln Ala Pro Gly Lys Gly Leu Glu Trp Val
            35                  40                  45

Ser Ala Ile Ser Gly Ser Gly Gly Ser Thr Tyr Tyr Ala Asp Ser Val
        50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Val Glu Gly Ser Gly Ser Leu Asp Tyr Trp Gly Gln Gly Thr
            100                 105                 110

Leu Val Thr Val Ser Ser Gly Gly Gly Gly Ser Gly Gly Gly Gly Ser
        115                 120                 125

Gly Gly Gly Gly Ser Glu Ile Val Met Thr Gln Ser Pro Gly Thr Leu
    130                 135                 140

Ser Leu Ser Pro Gly Glu Arg Ala Thr Leu Ser Cys Arg Ala Ser Gln
145                 150                 155                 160

Ser Val Ser Ser Ala Tyr Leu Ala Trp Tyr Gln Gln Lys Pro Gly Gln
                165                 170                 175

Pro Pro Arg Leu Leu Ile Ser Gly Ala Ser Thr Arg Ala Thr Gly Ile
            180                 185                 190

Pro Asp Arg Phe Gly Gly Ser Gly Ser Gly Thr Asp Phe Thr Leu Thr
        195                 200                 205

Ile Ser Arg Leu Glu Pro Glu Asp Phe Ala Val Tyr Tyr Cys Gln His
    210                 215                 220

Tyr Gly Ser Ser Phe Asn Gly Ser Ser Leu Phe Thr Phe Gly Gln Gly
225                 230                 235                 240

Thr Arg Leu Glu Ile Lys
                245

<210> SEQ ID NO 238
<211> LENGTH: 241
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 238

Glu Val Gln Leu Val Glu Thr Gly Gly Gly Leu Val Gln Pro Gly Gly
1               5                   10                  15

Ser Leu Arg Leu Ser Cys Ala Ala Ser Gly Ile Thr Phe Ser Arg Tyr
                20                  25                  30

Pro Met Ser Trp Val Arg Gln Ala Pro Gly Lys Gly Leu Glu Trp Val
            35                  40                  45

Ser Gly Ile Ser Asp Ser Gly Val Ser Thr Tyr Tyr Ala Asp Ser Ala
 50                  55                  60

Lys Gly Arg Phe Thr Ile Ser Arg Asp Asn Ser Lys Asn Thr Leu Phe
 65                  70                  75                  80

Leu Gln Met Ser Ser Leu Arg Asp Glu Asp Thr Ala Val Tyr Tyr Cys
                85                  90                  95

Val Thr Arg Ala Gly Ser Glu Ala Ser Asp Ile Trp Gly Gln Gly Thr
            100                 105                 110

Met Val Thr Val Ser Ser Gly Gly Gly Ser Gly Gly Gly Gly Ser
            115                 120                 125

Gly Gly Gly Gly Ser Glu Ile Val Leu Thr Gln Ser Pro Ala Thr Leu
            130                 135                 140

Ser Leu Ser Pro Gly Glu Arg Ala Thr Leu Ser Cys Arg Ala Ser Gln
145                 150                 155                 160

Ser Val Ser Asn Ser Leu Ala Trp Tyr Gln Gln Lys Pro Gly Gln Ala
                165                 170                 175

Pro Arg Leu Leu Ile Tyr Asp Ala Ser Ser Arg Ala Thr Gly Ile Pro
            180                 185                 190

Asp Arg Phe Ser Gly Ser Gly Ser Gly Thr Asp Phe Thr Leu Thr Ile
            195                 200                 205

Ser Arg Leu Glu Pro Glu Asp Phe Ala Ile Tyr Tyr Cys Gln Gln Phe
210                 215                 220

Gly Thr Ser Ser Gly Leu Thr Phe Gly Gly Gly Thr Lys Leu Glu Ile
225                 230                 235                 240

Lys

<210> SEQ ID NO 239
<211> LENGTH: 248
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 239

Gln Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
                20                  25                  30

Ala Met Ser Trp Val Arg Gln Ala Pro Gly Lys Gly Leu Glu Trp Val
            35                  40                  45

Ser Ala Ile Ser Gly Ser Gly Gly Ser Thr Tyr Tyr Ala Asp Ser Val
 50                  55                  60

Lys Gly Arg Phe Thr Ile Ser Arg Asp Asn Ala Lys Asn Ser Leu Tyr
 65                  70                  75                  80

Leu Gln Met Asn Ser Leu Arg Ala Glu Asp Thr Ala Ile Tyr Tyr Cys
                85                  90                  95

Ala Arg Ala Thr Tyr Lys Arg Glu Leu Arg Tyr Tyr Tyr Gly Met Asp
            100                 105                 110

Val Trp Gly Gln Gly Thr Met Val Thr Val Ser Ser Gly Gly Gly Gly
            115                 120                 125

Ser Gly Gly Gly Gly Ser Gly Gly Gly Ser Glu Ile Val Met Thr
    130                 135                 140

Gln Ser Pro Gly Thr Val Ser Leu Ser Pro Gly Glu Arg Ala Thr Leu
145                 150                 155                 160

Ser Cys Arg Ala Ser Gln Ser Val Ser Ser Phe Leu Ala Trp Tyr
            165                 170                 175

Gln Gln Lys Pro Gly Gln Ala Pro Arg Leu Leu Ile Tyr Gly Ala Ser
            180                 185                 190

Ser Arg Ala Thr Gly Ile Pro Asp Arg Phe Ser Gly Ser Gly Ser Gly
        195                 200                 205

Thr Asp Phe Thr Leu Thr Ile Ser Arg Leu Glu Pro Glu Asp Ser Ala
    210                 215                 220

Val Tyr Tyr Cys Gln Gln Tyr His Ser Ser Pro Ser Trp Thr Phe Gly
225                 230                 235                 240

Gln Gly Thr Arg Leu Glu Ile Lys
            245

<210> SEQ ID NO 240
<211> LENGTH: 248
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 240

Glu Val Gln Leu Val Glu Thr Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Thr Leu Lys Ala Glu Asp Thr Ala Val Tyr Tyr Cys
                85                  90                  95

Ala Arg Ala Thr Tyr Lys Arg Glu Leu Arg Tyr Tyr Gly Met Asp
            100                 105                 110

Val Trp Gly Gln Gly Thr Thr Val Thr Val Ser Ser Gly Gly Gly Gly
        115                 120                 125

Ser Gly Gly Gly Gly Ser Gly Gly Gly Gly Ser Glu Ile Val Leu Thr
    130                 135                 140

Gln Ser Pro Ser Thr Leu Ser Leu Ser Pro Gly Glu Ser Ala Thr Leu
145                 150                 155                 160

Ser Cys Arg Ala Ser Gln Ser Val Ser Thr Thr Phe Leu Ala Trp Tyr
            165                 170                 175

Gln Gln Lys Pro Gly Gln Ala Pro Arg Leu Leu Ile Tyr Gly Ser Ser
            180                 185                 190

Asn Arg Ala Thr Gly Ile Pro Asp Arg Phe Ser Gly Ser Gly Ser Gly
        195                 200                 205

Thr Asp Phe Thr Leu Thr Ile Arg Arg Leu Glu Pro Glu Asp Phe Ala
    210                 215                 220

Val Tyr Tyr Cys Gln Gln Tyr His Ser Ser Pro Ser Trp Thr Phe Gly

```
225                 230                 235                 240
Gln Gly Thr Lys Val Glu Ile Lys
                245

<210> SEQ ID NO 241
<211> LENGTH: 239
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 241

Glu Val Gln Leu Val Glu Thr Gly Gly Gly Leu Val Gln Pro Gly Arg
1               5                   10                  15

Ser Leu Arg Leu Ser Cys Ala Ala Ser Gly Phe Thr Phe Asp Asp Tyr
            20                  25                  30

Ala Met His Trp Val Arg Gln Ala Pro Gly Lys Gly Leu Glu Trp Val
        35                  40                  45

Ser Gly Ile Ser Trp Asn Ser Gly Ser Ile Gly Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Asp Glu Asp Thr Ala Val Tyr Tyr Cys
                85                  90                  95

Ala Arg Val Gly Lys Ala Val Pro Asp Val Trp Gly Gln Gly Thr Thr
            100                 105                 110

Val Thr Val Ser Ser Gly Gly Gly Gly Ser Gly Gly Gly Gly Ser Gly
        115                 120                 125

Gly Gly Gly Ser Asp Ile Val Met Thr Gln Thr Pro Ser Ser Leu Ser
    130                 135                 140

Ala Ser Val Gly Asp Arg Val Thr Ile Thr Cys Arg Ala Ser Gln Ser
145                 150                 155                 160

Ile Ser Ser Tyr Leu Asn Trp Tyr Gln Gln Lys Pro Gly Lys Ala Pro
                165                 170                 175

Lys Leu Leu Ile Tyr Ala Ala Ser Ser Leu Gln Ser Gly Val Pro Ser
            180                 185                 190

Arg Phe Ser Gly Ser Gly Ser Gly Thr Asp Phe Thr Leu Thr Ile Ser
        195                 200                 205

Ser Leu Gln Pro Glu Asp Phe Ala Thr Tyr Tyr Cys Gln Gln Ser Tyr
    210                 215                 220

Ser Thr Pro Tyr Ser Phe Gly Gln Gly Thr Arg Leu Glu Ile Lys
225                 230                 235

<210> SEQ ID NO 242
<211> LENGTH: 246
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 242

Glu Val Gln Leu Val Glu Ser Gly Gly Gly Leu Val Gln Pro Gly Arg
1               5                   10                  15

Ser Leu Arg Leu Ser Cys Thr Ala Ser Gly Phe Thr Phe Asp Asp Tyr
            20                  25                  30

Ala Met His Trp Val Arg Gln Arg Pro Gly Lys Gly Leu Glu Trp Val
```

```
                35                  40                  45
Ala Ser Ile Asn Trp Lys Gly Asn Ser Leu Ala Tyr Gly Asp Ser Val
 50                  55                  60

Lys Gly Arg Phe Ala Ile Ser Arg Asp Asn Ala Lys Asn Thr Val Phe
 65                  70                  75                  80

Leu Gln Met Asn Ser Leu Arg Thr Glu Asp Thr Ala Val Tyr Tyr Cys
                 85                  90                  95

Ala Ser His Gln Gly Val Ala Tyr Tyr Asn Tyr Ala Met Asp Val Trp
                100                 105                 110

Gly Arg Gly Thr Leu Val Thr Val Ser Ser Gly Gly Gly Ser Gly
                115                 120                 125

Gly Gly Gly Ser Gly Gly Gly Ser Glu Ile Val Leu Thr Gln Ser
        130                 135                 140

Pro Gly Thr Leu Ser Leu Ser Pro Gly Glu Arg Ala Thr Leu Ser Cys
145                 150                 155                 160

Arg Ala Thr Gln Ser Ile Gly Ser Ser Phe Leu Ala Trp Tyr Gln Gln
                165                 170                 175

Arg Pro Gly Gln Ala Pro Arg Leu Leu Ile Tyr Gly Ala Ser Gln Arg
                180                 185                 190

Ala Thr Gly Ile Pro Asp Arg Phe Ser Gly Arg Gly Ser Gly Thr Asp
                195                 200                 205

Phe Thr Leu Thr Ile Ser Arg Val Glu Pro Glu Asp Ser Ala Val Tyr
                210                 215                 220

Tyr Cys Gln His Tyr Glu Ser Ser Pro Ser Trp Thr Phe Gly Gln Gly
225                 230                 235                 240

Thr Lys Val Glu Ile Lys
                245

<210> SEQ ID NO 243
<211> LENGTH: 241
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 243

Glu Val Gln Leu Val Glu Ser Gly Gly Gly Leu Val Gln Pro Gly Gly
  1               5                  10                  15

Ser Leu Arg Leu Ser Cys Ala Ala Ser Gly Phe Thr Phe Ser Ser Tyr
             20                  25                  30

Ala Met Ser Trp Val Arg Gln Ala Pro Gly Lys Gly Leu Glu Trp Val
         35                  40                  45

Ser Ala Ile Ser Gly Ser Gly Gly Ser Thr Tyr Tyr Ala Asp Ser Val
 50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Lys Val Val Arg Asp Gly Met Asp Val Trp Gly Gln Gly Thr Thr
                100                 105                 110

Val Thr Val Ser Ser Gly Gly Gly Ser Gly Gly Gly Gly Ser Gly
        115                 120                 125

Gly Gly Gly Ser Glu Ile Val Leu Thr Gln Ser Pro Ala Thr Leu Ser
        130                 135                 140
```

```
Leu Ser Pro Gly Glu Arg Ala Thr Leu Ser Cys Arg Ala Ser Gln Ser
145                 150                 155                 160

Val Ser Ser Ser Tyr Leu Ala Trp Tyr Gln Gln Lys Pro Gly Gln Ala
                165                 170                 175

Pro Arg Leu Leu Ile Tyr Gly Ala Ser Ser Arg Ala Thr Gly Ile Pro
            180                 185                 190

Asp Arg Phe Ser Gly Asn Gly Ser Gly Thr Asp Phe Thr Leu Thr Ile
        195                 200                 205

Ser Arg Leu Glu Pro Glu Asp Phe Ala Val Tyr Tyr Cys Gln Gln Tyr
    210                 215                 220

Gly Ser Pro Pro Arg Phe Thr Phe Gly Pro Gly Thr Lys Val Asp Ile
225                 230                 235                 240

Lys
```

<210> SEQ ID NO 244
<211> LENGTH: 242
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 244

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
                20                  25                  30

Ala Met Ser Trp Val Arg Gln Ala Pro Gly Lys Gly Leu Glu Trp Val
            35                  40                  45

Ser Ala Ile Ser Gly Ser Gly Gly Ser Thr Tyr Tyr Ala Asp Ser Val
50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Ile Pro Gln Thr Gly Thr Phe Asp Tyr Trp Gly Gln Gly Thr
            100                 105                 110

Leu Val Thr Val Ser Ser Gly Gly Gly Gly Ser Gly Gly Gly Gly Ser
        115                 120                 125

Gly Gly Gly Gly Ser Glu Ile Val Leu Thr Gln Ser Pro Gly Thr Leu
130                 135                 140

Ser Leu Ser Pro Gly Glu Arg Ala Thr Leu Ser Cys Arg Ala Ser Gln
145                 150                 155                 160

Ser Val Ser Ser Ser Tyr Leu Ala Trp Tyr Gln Gln Arg Pro Gly Gln
                165                 170                 175

Ala Pro Arg Leu Leu Ile Tyr Gly Ala Ser Ser Arg Ala Thr Gly Ile
            180                 185                 190

Pro Asp Arg Phe Ser Gly Ser Gly Ser Gly Thr Asp Phe Thr Leu Thr
        195                 200                 205

Ile Ser Arg Leu Glu Pro Glu Asp Phe Ala Val Tyr Tyr Cys Gln His
    210                 215                 220

Tyr Gly Ser Ser Pro Ser Trp Thr Phe Gly Gln Gly Thr Arg Leu Glu
225                 230                 235                 240

Ile Lys
```

```
<210> SEQ ID NO 245
<211> LENGTH: 248
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 245

Glu Val Gln Leu Val Glu Thr Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
    50                  55                  60

Lys Gly Arg Phe Thr Met Ser Arg Glu Asn Asp Lys Asn Ser Val Phe
65                  70                  75                  80

Leu Gln Met Asn Ser Leu Arg Val Glu Asp Thr Gly Val Tyr Tyr Cys
                85                  90                  95

Ala Arg Ala Asn Tyr Lys Arg Glu Leu Arg Tyr Tyr Gly Met Asp
            100                 105                 110

Val Trp Gly Gln Gly Thr Met Val Thr Val Ser Ser Gly Gly Gly Gly
        115                 120                 125

Ser Gly Gly Gly Gly Ser Gly Gly Gly Gly Ser Glu Ile Val Met Thr
    130                 135                 140

Gln Ser Pro Gly Thr Leu Ser Leu Ser Pro Gly Glu Ser Ala Thr Leu
145                 150                 155                 160

Ser Cys Arg Ala Ser Gln Arg Val Ala Ser Asn Tyr Leu Ala Trp Tyr
                165                 170                 175

Gln His Lys Pro Gly Gln Ala Pro Ser Leu Leu Ile Ser Gly Ala Ser
            180                 185                 190

Ser Arg Ala Thr Gly Val Pro Asp Arg Phe Ser Gly Ser Gly Ser Gly
        195                 200                 205

Thr Asp Phe Thr Leu Ala Ile Ser Arg Leu Glu Pro Glu Asp Ser Ala
    210                 215                 220

Val Tyr Tyr Cys Gln His Tyr Asp Ser Ser Pro Ser Trp Thr Phe Gly
225                 230                 235                 240

Gln Gly Thr Lys Val Glu Ile Lys
                245

<210> SEQ ID NO 246
<211> LENGTH: 244
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 246

Glu Val Gln Leu Leu Glu Thr Gly Gly Gly Leu Val Gln Pro Gly Gly
1               5                   10                  15

Ser Leu Arg Leu Ser Cys Ala Ala Ser Gly Phe Ser Phe Ser Ser Tyr
            20                  25                  30

Ala Met Ser Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
```

```
                50                  55                  60
Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Lys Ala Leu Val Gly Ala Thr Gly Ala Phe Asp Ile Trp Gly Gln
                100                 105                 110

Gly Thr Leu Val Thr Val Ser Ser Gly Gly Gly Ser Gly Gly Gly
            115                 120                 125

Gly Ser Gly Gly Gly Ser Glu Ile Val Leu Thr Gln Ser Pro Gly
    130                 135                 140

Thr Leu Ser Leu Ser Pro Gly Glu Arg Ala Thr Leu Ser Cys Arg Ala
145                 150                 155                 160

Ser Gln Ser Leu Ser Ser Asn Phe Leu Ala Trp Tyr Gln Gln Lys Pro
                165                 170                 175

Gly Gln Ala Pro Gly Leu Leu Ile Tyr Gly Ala Ser Asn Trp Ala Thr
                180                 185                 190

Gly Thr Pro Asp Arg Phe Ser Gly Ser Gly Ser Gly Thr Asp Phe Thr
                195                 200                 205

Leu Thr Ile Thr Arg Leu Glu Pro Glu Asp Phe Ala Val Tyr Tyr Cys
    210                 215                 220

Gln Tyr Tyr Gly Thr Ser Pro Met Tyr Thr Phe Gly Gln Gly Thr Lys
225                 230                 235                 240

Val Glu Ile Lys

<210> SEQ ID NO 247
<211> LENGTH: 244
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 247

Glu Val Gln Leu Leu Glu Ser Gly Gly Gly Leu Val Gln Pro Gly Gly
 1               5                  10                  15

Ser Leu Arg Leu Ser Cys Ala Ala Ser Gly Phe Thr Phe Ser Ser Tyr
                 20                  25                  30

Ala Met Ser Trp Val Arg Gln Ala Pro Gly Lys Gly Leu Glu Trp Val
             35                  40                  45

Ser Ala Ile Ser Gly Ser Gly Gly Ser Thr Tyr Tyr Ala Asp Ser Val
     50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Val Leu Trp Phe Gly Glu Gly Phe Asp Pro Trp Gly Gln Gly Thr Leu
                100                 105                 110

Val Thr Val Ser Ser Gly Gly Gly Gly Ser Gly Gly Gly Gly Ser Gly
             115                 120                 125

Gly Gly Gly Ser Asp Ile Val Leu Thr Gln Ser Pro Leu Ser Leu Pro
    130                 135                 140

Val Thr Pro Gly Glu Pro Ala Ser Ile Ser Cys Arg Ser Ser Gln Ser
145                 150                 155                 160

Leu Leu His Ser Asn Gly Tyr Asn Tyr Leu Asp Trp Tyr Leu Gln Lys
```

```
                        165                 170                 175

Pro Gly Gln Ser Pro Gln Leu Leu Ile Tyr Leu Gly Ser Asn Arg Ala
                180                 185                 190

Ser Gly Val Pro Asp Arg Phe Ser Gly Ser Gly Ser Gly Thr Asp Phe
            195                 200                 205

Thr Leu Lys Ile Ser Arg Val Glu Ala Glu Asp Val Gly Val Tyr Tyr
        210                 215                 220

Cys Met Gln Ala Leu Gln Thr Pro Leu Thr Phe Gly Gly Gly Thr Lys
225                 230                 235                 240

Val Asp Ile Lys

<210> SEQ ID NO 248
<211> LENGTH: 251
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 248

Gln Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Val Gly Tyr Asp Ser Ser Gly Tyr Tyr Arg Asp Tyr Tyr Gly
            100                 105                 110

Met Asp Val Trp Gly Gln Gly Thr Thr Val Thr Val Ser Ser Gly Gly
        115                 120                 125

Gly Gly Ser Gly Gly Gly Gly Ser Gly Gly Gly Gly Ser Glu Ile Val
    130                 135                 140

Leu Thr Gln Ser Pro Gly Thr Leu Ser Leu Ser Pro Gly Glu Arg Ala
145                 150                 155                 160

Thr Leu Ser Cys Arg Ala Ser Gln Ser Val Ser Ser Ser Tyr Leu Ala
                165                 170                 175

Trp Tyr Gln Gln Lys Pro Gly Gln Ala Pro Arg Leu Leu Ile Tyr Gly
            180                 185                 190

Thr Ser Ser Arg Ala Thr Gly Ile Ser Asp Arg Phe Ser Gly Ser Gly
        195                 200                 205

Ser Gly Thr Asp Phe Thr Leu Thr Ile Ser Arg Leu Glu Pro Glu Asp
    210                 215                 220

Phe Ala Val Tyr Tyr Cys Gln His Tyr Gly Asn Ser Pro Pro Lys Phe
225                 230                 235                 240

Thr Phe Gly Pro Gly Thr Lys Leu Glu Ile Lys
                245                 250

<210> SEQ ID NO 249
<211> LENGTH: 246
<212> TYPE: PRT
```

<213> ORGANISM: Artificial Sequence
<220> FEATURE:
<223> OTHER INFORMATION: Description of Artificial Sequence: Synthetic
      polypeptide

<400> SEQUENCE: 249

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Met Gly Trp Ser Ser Gly Tyr Leu Gly Ala Phe Asp Ile Trp
            100                 105                 110

Gly Gln Gly Thr Thr Val Thr Val Ser Ser Gly Gly Gly Gly Ser Gly
        115                 120                 125

Gly Gly Gly Ser Gly Gly Gly Ser Glu Ile Val Leu Thr Gln Ser
    130                 135                 140

Pro Gly Thr Leu Ser Leu Ser Pro Gly Glu Arg Ala Thr Leu Ser Cys
145                 150                 155                 160

Arg Ala Ser Gln Ser Val Ala Ser Ser Phe Leu Ala Trp Tyr Gln Gln
                165                 170                 175

Lys Pro Gly Gln Ala Pro Arg Leu Leu Ile Tyr Gly Ala Ser Gly Arg
            180                 185                 190

Ala Thr Gly Ile Pro Asp Arg Phe Ser Gly Ser Gly Ser Gly Thr Asp
        195                 200                 205

Phe Thr Leu Thr Ile Ser Arg Leu Glu Pro Glu Asp Phe Ala Val Tyr
    210                 215                 220

Tyr Cys Gln His Tyr Gly Gly Ser Pro Arg Leu Thr Phe Gly Gly Gly
225                 230                 235                 240

Thr Lys Val Asp Ile Lys
            245

<210> SEQ ID NO 250
<211> LENGTH: 249
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 250

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Asn Tyr
            20                  25                  30

Trp Met His Trp Val Arg Gln Ala Pro Gly Gln Gly Leu Glu Trp Met
        35                  40                  45

Gly Ala Thr Tyr Arg Gly His Ser Asp Thr Tyr Tyr Asn Gln Lys Phe
    50                  55                  60

Lys Gly Arg Val Thr Ile Thr Ala Asp Lys Ser Thr Ser Thr Ala Tyr

```
                65                  70                  75                  80
Met Glu Leu Ser Ser Leu Arg Ser Glu Asp Thr Ala Val Tyr Tyr Cys
                    85                  90                  95

Ala Arg Gly Ala Ile Tyr Asn Gly Tyr Asp Val Leu Asp Asn Trp Gly
                100                 105                 110

Gln Gly Thr Leu Val Thr Val Ser Gly Gly Gly Ser Gly Gly
            115                 120                 125

Gly Gly Ser Gly Gly Gly Ser Gly Gly Gly Ser Asp Ile Gln
        130                 135                 140

Met Thr Gln Ser Pro Ser Ser Leu Ser Ala Ser Val Gly Asp Arg Val
145                 150                 155                 160

Thr Ile Thr Cys Ser Ala Ser Gln Asp Ile Ser Asn Tyr Leu Asn Trp
                165                 170                 175

Tyr Gln Gln Lys Pro Gly Lys Ala Pro Lys Leu Leu Ile Tyr Tyr Thr
                180                 185                 190

Ser Asn Leu His Ser Gly Val Pro Ser Arg Phe Ser Gly Ser Gly Ser
            195                 200                 205

Gly Thr Asp Phe Thr Leu Thr Ile Ser Ser Leu Gln Pro Glu Asp Phe
        210                 215                 220

Ala Thr Tyr Tyr Cys Gln Gln Tyr Arg Lys Leu Pro Trp Thr Phe Gly
225                 230                 235                 240

Gln Gly Thr Lys Leu Glu Ile Lys Arg
                245

<210> SEQ ID NO 251
<211> LENGTH: 249
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 251

Asp Ile Gln Met Thr Gln Ser Pro Ser Ser Leu Ser Ala Ser Val Gly
1               5                   10                  15

Asp Arg Val Thr Ile Thr Cys Ser Ala Ser Gln Asp Ile Ser Asn Tyr
            20                  25                  30

Leu Asn Trp Tyr Gln Gln Lys Pro Gly Lys Ala Pro Lys Leu Leu Ile
        35                  40                  45

Tyr Tyr Thr Ser Asn Leu His Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Arg Lys Leu Pro Trp
                85                  90                  95

Thr Phe Gly Gln Gly Thr Lys Leu Glu Ile Lys Arg Gly Gly Gly Gly
                100                 105                 110

Ser Gly Gly Gly Gly Ser Gly Gly Gly Ser Gly Gly Gly Gly Ser
            115                 120                 125

Gln Val Gln Leu Val Gln Ser Gly Ala Glu Val Lys Lys Pro Gly Ser
        130                 135                 140

Ser Val Lys Val Ser Cys Lys Ala Ser Gly Gly Thr Phe Ser Asn Tyr
145                 150                 155                 160

Trp Met His Trp Val Arg Gln Ala Pro Gly Gln Gly Leu Glu Trp Met
                165                 170                 175
```

Gly Ala Thr Tyr Arg Gly His Ser Asp Thr Tyr Tyr Asn Gln Lys Phe
            180                 185                 190

Lys Gly Arg Val Thr Ile Thr Ala Asp Lys Ser Thr Ser Thr Ala Tyr
        195                 200                 205

Met Glu Leu Ser Ser Leu Arg Ser Glu Asp Thr Ala Val Tyr Tyr Cys
    210                 215                 220

Ala Arg Gly Ala Ile Tyr Asn Gly Tyr Asp Val Leu Asp Asn Trp Gly
225                 230                 235                 240

Gln Gly Thr Leu Val Thr Val Ser Ser
                245

<210> SEQ ID NO 252
<211> LENGTH: 250
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 252

Gln Val Gln Leu Val Gln Ser Gly Ala Glu Val Lys Lys Pro Gly Glu
1               5                   10                  15

Ser Leu Lys Ile Ser Cys Lys Gly Ser Gly Tyr Ser Phe Thr Ser Tyr
            20                  25                  30

Trp Ile Gly Trp Val Arg Gln Met Pro Gly Lys Gly Leu Glu Trp Met
        35                  40                  45

Gly Ile Ile Tyr Pro Gly Asp Ser Asp Thr Arg Tyr Ser Pro Ser Phe
    50                  55                  60

Gln Gly Gln Val Thr Ile Ser Ala Asp Lys Ser Ile Ser Thr Ala Tyr
65                  70                  75                  80

Leu Gln Trp Ser Ser Leu Lys Ala Ser Asp Thr Ala Met Tyr Tyr Cys
                85                  90                  95

Ala Arg Leu Gly Gly Ser Leu Pro Asp Tyr Gly Met Asp Val Trp Gly
            100                 105                 110

Gln Gly Thr Met Val Thr Val Ser Ser Ala Ser Gly Gly Gly Gly Ser
        115                 120                 125

Gly Gly Gly Gly Ser Gly Gly Gly Ser Glu Ile Val Leu Thr Gln
    130                 135                 140

Ser Pro Leu Ser Leu Pro Val Thr Pro Gly Glu Pro Ala Ser Ile Ser
145                 150                 155                 160

Cys Arg Ser Ser Gln Ser Leu Leu His Ser Asn Gly Tyr Asn Tyr Leu
                165                 170                 175

Asp Trp Tyr Leu Gln Lys Pro Gly Gln Ser Pro Gln Leu Leu Ile Tyr
            180                 185                 190

Leu Gly Ser Asn Arg Ala Ser Gly Val Pro Asp Arg Phe Ser Gly Ser
        195                 200                 205

Gly Ser Gly Thr Asp Phe Thr Leu Lys Ile Ser Arg Val Glu Ala Glu
    210                 215                 220

Asp Val Gly Val Tyr Tyr Cys Met Gln Ala Leu Gln Thr Leu Ile Thr
225                 230                 235                 240

Phe Gly Gln Gly Thr Lys Val Asp Ile Lys
                245                 250

<210> SEQ ID NO 253
<211> LENGTH: 251
<212> TYPE: PRT
<213> ORGANISM: Artificial Sequence

```
<220> FEATURE:
<223> OTHER INFORMATION: Description of Artificial Sequence: Synthetic
      polypeptide

<400> SEQUENCE: 253

Gln Val Gln Leu Val Gln Ser Gly Ala Glu Val Lys Lys Pro Gly Ala
1               5                   10                  15

Ser Val Arg Val Ser Cys Lys Ala Ser Gly Tyr Ile Phe Thr Asn Tyr
            20                  25                  30

Tyr Val His Trp Val Arg Gln Ala Pro Gly Gln Gly Leu Glu Trp Met
        35                  40                  45

Gly Ile Ile Ser Pro Ser Gly Gly Ser Pro Thr Tyr Ala Gln Arg Leu
    50                  55                  60

Gln Gly Arg Val Thr Met Thr Arg Asp Leu Ser Thr Ser Thr Val Tyr
65                  70                  75                  80

Met Glu Leu Ser Ser Leu Thr Ser Glu Asp Thr Ala Val Tyr Phe Cys
                85                  90                  95

Ala Arg Glu Ser Arg Leu Arg Gly Asn Arg Leu Gly Leu Gln Ser Ser
            100                 105                 110

Ile Phe Asp His Trp Gly Gln Gly Thr Leu Val Thr Val Ser Ser Ala
        115                 120                 125

Ser Gly Gly Gly Gly Ser Gly Gly Gly Gly Ser Gly Gly Gly Gly Ser
    130                 135                 140

Asp Ile Arg Met Thr Gln Ser Pro Pro Ser Leu Ser Ala Ser Val Gly
145                 150                 155                 160

Asp Arg Val Thr Ile Pro Cys Gln Ala Ser Gln Asp Ile Asn Asn His
                165                 170                 175

Leu Asn Trp Tyr Gln Gln Lys Pro Gly Lys Ala Pro Gln Leu Leu Ile
            180                 185                 190

Tyr Asp Thr Ser Asn Leu Glu Ile Gly Val Pro Ser Arg Phe Ser Gly
        195                 200                 205

Ser Gly Ser Gly Thr Asp Phe Thr Leu Thr Ile Ser Ser Leu Gln Pro
    210                 215                 220

Glu Asp Ile Ala Thr Tyr Tyr Cys Gln Gln Tyr Glu Asn Leu Pro Leu
225                 230                 235                 240

Thr Phe Gly Gly Gly Thr Lys Val Glu Ile Lys
                245                 250

<210> SEQ ID NO 254
<211> LENGTH: 249
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 254

Gln Val Gln Leu Val Gln Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80
```

```
Leu Gln Met Asn Ser Leu Arg Ala Glu Asp Thr Ala Val Tyr Tyr Cys
                 85                  90                  95

Ala Lys Glu Asp Thr Ile Arg Gly Pro Asn Tyr Tyr Tyr Gly Met
            100                 105                 110

Asp Val Trp Gly Gln Gly Thr Thr Val Thr Val Ser Ser Ala Ser Gly
        115                 120                 125

Gly Gly Gly Ser Gly Gly Gly Ser Gly Gly Gly Ser Glu Thr
130                 135                 140

Thr Leu Thr Gln Ser Pro Ser Ser Val Ser Ala Ser Val Gly Asp Arg
145                 150                 155                 160

Val Ser Ile Thr Cys Arg Ala Ser Gln Asp Ile Asp Thr Trp Leu Ala
                165                 170                 175

Trp Tyr Gln Leu Lys Pro Gly Lys Ala Pro Lys Leu Leu Met Tyr Ala
            180                 185                 190

Ala Ser Asn Leu Gln Gly Gly Val Pro Ser Arg Phe Ser Gly Ser Gly
            195                 200                 205

Ser Gly Thr Asp Phe Ile Leu Thr Ile Ser Ser Leu Gln Pro Glu Asp
        210                 215                 220

Phe Ala Thr Tyr Tyr Cys Gln Gln Ala Ser Ile Phe Pro Pro Thr Phe
225                 230                 235                 240

Gly Gly Gly Thr Lys Val Asp Ile Lys
                245

<210> SEQ ID NO 255
<211> LENGTH: 250
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 255

Gln Val Gln Leu Val Gln Ser Gly Ala Glu Val Lys Lys Pro Gly Glu
1               5                   10                  15

Ser Leu Lys Ile Ser Cys Lys Gly Ser Gly Tyr Ser Phe Thr Ser Tyr
            20                  25                  30

Trp Ile Gly Trp Val Arg Gln Met Pro Gly Lys Gly Leu Glu Trp Met
        35                  40                  45

Gly Ile Ile Tyr Pro Gly Asp Ser Asp Thr Arg Tyr Ser Pro Ser Phe
    50                  55                  60

Gln Gly Gln Val Thr Ile Ser Ala Asp Lys Ser Ile Thr Thr Ala Tyr
65                  70                  75                  80

Leu Gln Trp Ser Ser Leu Arg Ala Ser Asp Ser Ala Met Tyr Tyr Cys
                85                  90                  95

Ala Arg Gly Gly Tyr Ser Asp Tyr Asp Tyr Tyr Phe Asp Phe Trp Gly
            100                 105                 110

Gln Gly Thr Leu Val Thr Val Ser Ser Ala Ser Gly Gly Gly Gly Ser
        115                 120                 125

Gly Gly Gly Gly Ser Gly Gly Gly Ser Glu Ile Val Met Thr Gln
130                 135                 140

Ser Pro Leu Ser Leu Pro Val Thr Pro Gly Glu Pro Ala Ser Ile Ser
145                 150                 155                 160

Cys Arg Ser Ser Gln Ser Leu Leu His Ser Asn Gly Tyr Asn Tyr Leu
                165                 170                 175

Asp Trp Tyr Leu Gln Lys Pro Gly Gln Ser Pro Gln Leu Leu Ile Tyr
```

```
                        180                 185                 190

Leu Gly Ser Asn Arg Ala Ser Gly Val Pro Asp Arg Phe Ser Gly Ser
                195                 200                 205

Gly Ser Gly Thr Asp Phe Thr Leu Lys Ile Ser Arg Val Glu Ala Glu
        210                 215                 220

Asp Val Gly Val Tyr Tyr Cys Met Gln Ala Leu Gln Thr Pro Phe Thr
225                 230                 235                 240

Phe Gly Gly Gly Thr Lys Val Glu Ile Lys
                245                 250

<210> SEQ ID NO 256
<211> LENGTH: 240
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 256

Gln Val Gln Leu Val Gln Ser Gly Gly Asp Leu Ala Gln Pro Gly Arg
1               5                   10                  15

Ser Leu Arg Leu Ser Cys Ala Ala Ser Gly Phe Thr Phe Asp Asp Tyr
            20                  25                  30

Ala Met His Trp Val Arg Gln Ala Pro Gly Lys Gly Leu Glu Trp Val
        35                  40                  45

Ala Val Ile Trp Pro Asp Gly Gln Lys Tyr Tyr Gly Asp Ser Val
    50                  55                  60

Lys Gly Arg Phe Thr Val Ser Arg Asp Asn Pro Lys Asn Thr Leu Tyr
65                  70                  75                  80

Leu Gln Met Asn Ser Leu Arg Ala Glu Asp Thr Ala Ile Tyr Tyr Cys
                85                  90                  95

Val Arg His Phe Asn Ala Trp Asp Tyr Trp Gly Gln Gly Thr Leu Val
            100                 105                 110

Thr Val Ser Ser Ala Ser Gly Gly Gly Gly Ser Gly Gly Gly Gly Ser
        115                 120                 125

Gly Gly Gly Gly Ser Asp Ile Gln Leu Thr Gln Ser Pro Ser Ser Leu
    130                 135                 140

Ser Ala Tyr Val Gly Gly Arg Val Thr Ile Thr Cys Gln Ala Ser Gln
145                 150                 155                 160

Gly Ile Ser Gln Phe Leu Asn Trp Phe Gln Gln Lys Pro Gly Lys Ala
                165                 170                 175

Pro Lys Leu Leu Ile Ser Asp Ala Ser Asn Leu Glu Pro Gly Val Pro
            180                 185                 190

Ser Arg Phe Ser Gly Ser Gly Ser Gly Thr Asp Phe Thr Phe Thr Ile
        195                 200                 205

Thr Asn Leu Gln Pro Glu Asp Ile Ala Thr Tyr Tyr Cys Gln Gln Tyr
    210                 215                 220

Asp Asp Leu Pro Leu Thr Phe Gly Gly Gly Thr Lys Val Glu Ile Lys
225                 230                 235                 240

<210> SEQ ID NO 257
<211> LENGTH: 248
<212> TYPE: PRT
<213> ORGANISM: Artificial Sequence
<220> FEATURE:
<223> OTHER INFORMATION: Description of Artificial Sequence: Synthetic
      polypeptide
```

```
<400> SEQUENCE: 257

Gln Val Gln Leu Val Gln Ser Gly Gly Gly Val Val Gln Pro Gly Lys
1               5                   10                  15

Ser Leu Arg Leu Ser Cys Ala Ala Ser Gly Phe Thr Phe Ser Ile Phe
            20                  25                  30

Ala Met His Trp Val Arg Gln Ala Pro Gly Lys Gly Leu Glu Trp Val
        35                  40                  45

Ala Thr Ile Ser Tyr Asp Gly Ser Asn Ala Phe Tyr Ala Asp Ser Val
    50                  55                  60

Glu Gly Arg Phe Thr Ile Ser Arg Asp Asn Ser Lys Asp Ser Leu Tyr
65                  70                  75                  80

Leu Gln Met Asp Ser Leu Arg Pro Glu Asp Thr Ala Val Tyr Tyr Cys
                85                  90                  95

Val Lys Ala Gly Asp Gly Gly Tyr Asp Val Phe Asp Ser Trp Gly Gln
            100                 105                 110

Gly Thr Leu Val Thr Val Ser Ser Ala Ser Gly Gly Gly Gly Ser Gly
        115                 120                 125

Gly Gly Gly Ser Gly Gly Gly Ser Glu Ile Val Met Thr Gln Ser
    130                 135                 140

Pro Leu Ser Leu Pro Val Thr Pro Gly Glu Pro Ala Ser Ile Ser Cys
145                 150                 155                 160

Arg Ser Ser Gln Ser Leu Leu His Ser Asn Gly Tyr Asn Tyr Leu Asp
                165                 170                 175

Trp Tyr Leu Gln Lys Pro Gly Gln Ser Pro Gln Leu Leu Ile Tyr Leu
            180                 185                 190

Gly Ser Asn Arg Ala Ser Gly Val Pro Asp Arg Phe Ser Gly Ser Gly
        195                 200                 205

Ser Gly Thr Asp Phe Thr Leu Lys Ile Ser Arg Val Glu Ala Glu Asp
    210                 215                 220

Val Gly Val Tyr Tyr Cys Met Gln Ala Leu Gln Thr Pro Thr Phe Gly
225                 230                 235                 240

Pro Gly Thr Lys Val Asp Ile Lys
                245

<210> SEQ ID NO 258
<211> LENGTH: 245
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 258

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95
```

```
Ala Lys Glu Thr Asp Tyr Tyr Gly Ser Gly Thr Phe Asp Tyr Trp Gly
                100                 105                 110

Gln Gly Thr Leu Val Thr Val Ser Ser Ala Ser Gly Gly Gly Gly Ser
            115                 120                 125

Gly Gly Gly Gly Ser Gly Gly Gly Ser Asp Ile Gln Met Thr Gln
        130                 135                 140

Ser Pro Ser Ser Leu Ser Ala Ser Val Gly Asp Arg Val Thr Ile Ser
145                 150                 155                 160

Cys Arg Ala Ser Gln Gly Ile Gly Ile Tyr Leu Ala Trp Tyr Gln Gln
                165                 170                 175

Arg Ser Gly Lys Pro Pro Gln Leu Leu Ile His Gly Ala Ser Thr Leu
            180                 185                 190

Gln Ser Gly Val Pro Ser Arg Phe Ser Gly Ser Gly Ser Gly Thr Asp
        195                 200                 205

Phe Thr Leu Thr Ile Ser Ser Leu Gln Pro Glu Asp Phe Ala Ser Tyr
210                 215                 220

Trp Cys Gln Gln Ser Asn Asn Phe Pro Pro Thr Phe Gly Gln Gly Thr
225                 230                 235                 240

Lys Val Glu Ile Lys
            245

<210> SEQ ID NO 259
<211> LENGTH: 245
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 259

Gln Val Gln Leu Val Gln Ser Gly Ala Glu Val Lys Lys Pro Gly Ala
1               5                   10                  15

Ser Val Arg Val Ser Cys Lys Ala Ser Gly Tyr Met Phe Thr Asp Phe
            20                  25                  30

Phe Ile His Trp Val Arg Gln Ala Pro Gly Gln Gly Leu Glu Trp Met
        35                  40                  45

Gly Trp Ile Asn Pro Asn Ser Gly Val Thr Lys Tyr Ala Gln Lys Phe
    50                  55                  60

Gln Gly Arg Val Thr Met Thr Arg Asn Thr Ser Ile Ser Thr Ala Tyr
65                  70                  75                  80

Met Glu Leu Ser Ser Leu Arg Ser Glu Asp Thr Ala Val Tyr Tyr Cys
                85                  90                  95

Ala Thr Trp Tyr Ser Ser Gly Trp Tyr Gly Ile Ala Asn Ile Trp Gly
            100                 105                 110

Gln Gly Thr Met Val Thr Val Ser Ser Ala Ser Gly Gly Gly Gly Ser
        115                 120                 125

Gly Gly Gly Gly Ser Gly Gly Gly Ser Asp Ile Gln Leu Thr Gln
        130                 135                 140

Ser Pro Ser Ser Leu Ser Ala Ser Val Gly Asp Arg Val Thr Ile Thr
145                 150                 155                 160

Cys Gln Ala Ser His Asp Ile Ser Asn Tyr Leu His Trp Tyr Gln Gln
                165                 170                 175

Lys Pro Gly Lys Ala Pro Lys Leu Leu Ile Tyr Asp Ala Ser Asn Leu
            180                 185                 190

Glu Thr Gly Val Pro Ser Arg Phe Thr Gly Ser Gly Ser Gly Thr Asp
        195                 200                 205
```

```
Phe Thr Leu Thr Ile Arg Ser Leu Gln Pro Glu Asp Val Ala Ala Tyr
        210                 215                 220

Tyr Cys Gln Gln Ser Asp Asp Leu Pro His Thr Phe Gly Gln Gly Thr
225                 230                 235                 240

Lys Val Asp Ile Lys
            245

<210> SEQ ID NO 260
<211> LENGTH: 244
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 260

Gln Val Gln Leu Val Gln Ser Gly Ala Glu Val Lys Lys Pro Gly Glu
1               5                   10                  15

Ser Leu Lys Ile Ser Cys Lys Gly Ser Gly Tyr Ser Phe Thr Asn Tyr
            20                  25                  30

Trp Ile Gly Trp Val Arg Gln Met Pro Gly Lys Gly Leu Glu Trp Met
        35                  40                  45

Gly Ile Ile Tyr Pro Gly Asp Ser Asp Thr Arg Tyr Ser Pro Ser Phe
    50                  55                  60

Gln Gly Gln Val Thr Ile Ser Ala Asp Lys Ser Ile Ser Thr Ala Tyr
65                  70                  75                  80

Leu Gln Trp Ser Ser Leu Lys Ala Ser Asp Thr Ala Met Tyr Tyr Cys
                85                  90                  95

Ala Arg His Gly Pro Ser Ser Trp Gly Glu Phe Asp Tyr Trp Gly Gln
            100                 105                 110

Gly Thr Leu Val Thr Val Ser Ser Ala Ser Gly Gly Gly Gly Ser Gly
        115                 120                 125

Gly Gly Gly Ser Gly Gly Gly Gly Ser Asp Ile Arg Leu Thr Gln Ser
    130                 135                 140

Pro Ser Ser Leu Ser Ala Ser Val Gly Asp Arg Val Thr Ile Thr Cys
145                 150                 155                 160

Arg Ala Ser Gln Ser Ile Ser Ser Tyr Leu Asn Trp Tyr Gln Gln Lys
                165                 170                 175

Pro Gly Lys Ala Pro Lys Leu Leu Ile Tyr Ala Ala Ser Ser Leu Gln
            180                 185                 190

Ser Gly Val Pro Ser Arg Phe Ser Gly Ser Gly Ser Gly Thr Asp Phe
        195                 200                 205

Thr Leu Thr Ile Ser Ser Leu Gln Pro Glu Asp Phe Ala Thr Tyr Tyr
    210                 215                 220

Cys Gln Gln Ser Tyr Ser Thr Pro Leu Thr Phe Gly Gly Gly Thr Lys
225                 230                 235                 240

Val Asp Ile Lys

<210> SEQ ID NO 261
<211> LENGTH: 246
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 261
```

Asn Ile Met Leu Thr Gln Ser Pro Ser Ser Leu Ala Val Ser Ala Gly
1               5                   10                  15

Glu Lys Val Thr Met Ser Cys Lys Ser Ser Gln Ser Val Phe Phe Ser
            20                  25                  30

Ser Ser Gln Lys Asn Tyr Leu Ala Trp Tyr Gln Gln Ile Pro Gly Gln
        35                  40                  45

Ser Pro Lys Leu Leu Ile Tyr Trp Ala Ser Thr Arg Glu Ser Gly Val
    50                  55                  60

Pro Asp Arg Phe Thr Gly Ser Gly Ser Gly Thr Asp Phe Thr Leu Thr
65                  70                  75                  80

Ile Ser Ser Val Gln Ser Glu Asp Leu Ala Ile Tyr Tyr Cys His Gln
                85                  90                  95

Tyr Leu Ser Ser Arg Thr Phe Gly Gly Gly Thr Lys Leu Glu Ile Lys
            100                 105                 110

Arg Gly Gly Gly Gly Ser Gly Gly Gly Ser Ser Gly Gly Gly Ser
        115                 120                 125

Gln Val Gln Leu Gln Gln Pro Gly Ala Glu Val Val Lys Pro Gly Ala
    130                 135                 140

Ser Val Lys Met Ser Cys Lys Ala Ser Gly Tyr Thr Phe Thr Ser Tyr
145                 150                 155                 160

Tyr Ile His Trp Ile Lys Gln Thr Pro Gly Gln Gly Leu Glu Trp Val
            165                 170                 175

Gly Val Ile Tyr Pro Gly Asn Asp Asp Ile Ser Tyr Asn Gln Lys Phe
            180                 185                 190

Lys Gly Lys Ala Thr Leu Thr Ala Asp Lys Ser Ser Thr Thr Ala Tyr
        195                 200                 205

Met Gln Leu Ser Ser Leu Thr Ser Glu Asp Ser Ala Val Tyr Tyr Cys
    210                 215                 220

Ala Arg Glu Val Arg Leu Arg Tyr Phe Asp Val Trp Gly Ala Gly Thr
225                 230                 235                 240

Thr Val Thr Val Ser Ser
            245

<210> SEQ ID NO 262
<211> LENGTH: 246
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 262

Glu Ile Val Leu Thr Gln Ser Pro Gly Ser Leu Ala Val Ser Pro Gly
1               5                   10                  15

Glu Arg Val Thr Met Ser Cys Lys Ser Ser Gln Ser Val Phe Phe Ser
            20                  25                  30

Ser Ser Gln Lys Asn Tyr Leu Ala Trp Tyr Gln Gln Ile Pro Gly Gln
        35                  40                  45

Ser Pro Arg Leu Leu Ile Tyr Trp Ala Ser Thr Arg Glu Ser Gly Val
    50                  55                  60

Pro Asp Arg Phe Thr Gly Ser Gly Ser Gly Thr Asp Phe Thr Leu Thr
65                  70                  75                  80

Ile Ser Ser Val Gln Pro Glu Asp Leu Ala Ile Tyr Tyr Cys His Gln
                85                  90                  95

Tyr Leu Ser Ser Arg Thr Phe Gly Gln Gly Thr Lys Leu Glu Ile Lys
            100                 105                 110

```
Arg Gly Gly Gly Gly Ser Gly Gly Gly Ser Ser Gly Gly Ser
        115                 120                 125

Gln Val Gln Leu Gln Gln Pro Gly Ala Glu Val Val Lys Pro Gly Ala
        130                 135                 140

Ser Val Lys Met Ser Cys Lys Ala Ser Gly Tyr Thr Phe Thr Ser Tyr
145                 150                 155                 160

Tyr Ile His Trp Ile Lys Gln Thr Pro Gly Gln Gly Leu Glu Trp Val
                165                 170                 175

Gly Val Ile Tyr Pro Gly Asn Asp Asp Ile Ser Tyr Asn Gln Lys Phe
            180                 185                 190

Gln Gly Lys Ala Thr Leu Thr Ala Asp Lys Ser Ser Thr Thr Ala Tyr
        195                 200                 205

Met Gln Leu Ser Ser Leu Thr Ser Glu Asp Ser Ala Val Tyr Tyr Cys
    210                 215                 220

Ala Arg Glu Val Arg Leu Arg Tyr Phe Asp Val Trp Gly Gln Gly Thr
225                 230                 235                 240

Thr Val Thr Val Ser Ser
                245

<210> SEQ ID NO 263
<211> LENGTH: 244
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 263

Glu Val Gln Leu Gln Gln Ser Gly Pro Glu Leu Val Lys Pro Gly Ala
1               5                   10                  15

Ser Met Lys Ile Ser Cys Lys Ala Ser Gly Tyr Ser Phe Thr Gly Tyr
            20                  25                  30

Thr Met Asn Trp Val Lys Gln Ser His Gly Lys Asn Leu Glu Trp Ile
        35                  40                  45

Gly Leu Ile Asn Pro Tyr Asn Gly Gly Thr Ile Tyr Asn Gln Lys Phe
    50                  55                  60

Lys Gly Lys Ala Thr Leu Thr Val Asp Lys Ser Ser Ser Thr Ala Tyr
65                  70                  75                  80

Met Glu Leu Leu Ser Leu Thr Ser Glu Asp Ser Ala Val Tyr Tyr Cys
                85                  90                  95

Ala Arg Asp Tyr Gly Phe Val Leu Asp Tyr Trp Gly Gln Gly Thr Thr
            100                 105                 110

Leu Thr Val Ser Ser Gly Gly Gly Gly Ser Gly Gly Gly Gly Ser Gly
        115                 120                 125

Gly Gly Ser Gly Gly Gly Gly Ser Gln Ile Val Leu Thr Gln Ser
    130                 135                 140

Pro Ser Ile Met Ser Val Ser Pro Gly Glu Lys Val Thr Ile Thr Cys
145                 150                 155                 160

Ser Ala Ser Ser Ser Val Ser Tyr Met His Trp Phe Gln Gln Lys Pro
                165                 170                 175

Gly Thr Ser Pro Lys Leu Cys Ile Tyr Ser Thr Ser Asn Leu Ala Ser
            180                 185                 190

Gly Val Pro Ala Arg Phe Ser Gly Arg Gly Ser Gly Thr Ser Tyr Ser
        195                 200                 205

Leu Thr Ile Ser Arg Val Ala Ala Glu Asp Ala Ala Thr Tyr Tyr Cys
```

210                 215                 220
Gln Gln Arg Ser Asn Tyr Pro Pro Trp Thr Phe Gly Gly Gly Thr Lys
225                 230                 235                 240

Leu Glu Ile Lys

<210> SEQ ID NO 264
<211> LENGTH: 244
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 264

Glu Val Gln Leu Gln Gln Ser Gly Pro Glu Leu Val Lys Pro Gly Ala
1               5                   10                  15

Ser Met Lys Ile Ser Cys Lys Ala Ser Gly Tyr Ser Phe Thr Gly Tyr
                20                  25                  30

Thr Met Asn Trp Val Lys Gln Ser His Gly Lys Asn Leu Glu Trp Ile
            35                  40                  45

Gly Leu Ile Asn Pro Tyr Asn Gly Gly Thr Ile Tyr Asn Gln Lys Phe
    50                  55                  60

Lys Gly Lys Ala Thr Leu Thr Val Asp Lys Ser Ser Thr Ala Tyr
65                  70                  75                  80

Met Glu Leu Leu Ser Leu Thr Ser Glu Asp Ser Ala Val Tyr Tyr Cys
                85                  90                  95

Ala Arg Asp Tyr Gly Phe Val Leu Asp Tyr Trp Gly Gln Gly Thr Thr
            100                 105                 110

Leu Thr Val Ser Ser Gly Gly Gly Gly Ser Gly Gly Gly Gly Ser Gly
        115                 120                 125

Gly Gly Gly Ser Gly Gly Gly Gly Ser Gln Ile Val Leu Thr Gln Ser
    130                 135                 140

Pro Ala Ile Met Ser Ala Ser Pro Gly Glu Lys Val Thr Ile Thr Cys
145                 150                 155                 160

Ser Ala Ser Ser Val Ser Tyr Leu His Trp Phe Gln Gln Lys Pro
                165                 170                 175

Gly Thr Ser Pro Lys Leu Trp Val Tyr Ser Thr Ser Asn Leu Pro Ser
            180                 185                 190

Gly Val Pro Ala Arg Phe Gly Gly Ser Gly Ser Gly Thr Ser Tyr Ser
        195                 200                 205

Leu Thr Ile Ser Arg Met Glu Ala Glu Asp Ala Ala Thr Tyr Tyr Cys
    210                 215                 220

Gln Gln Arg Ser Ile Tyr Pro Pro Trp Thr Phe Gly Gly Gly Thr Lys
225                 230                 235                 240

Leu Glu Ile Lys

<210> SEQ ID NO 265
<211> LENGTH: 244
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 265

Glu Val Gln Leu Gln Gln Ser Gly Pro Glu Leu Val Lys Pro Gly Ala
1               5                   10                  15

Ser Met Lys Ile Ser Cys Lys Ala Ser Gly Tyr Ser Phe Thr Gly Tyr
                 20                  25                  30

Thr Met Asn Trp Val Lys Gln Ser His Gly Lys Asn Leu Glu Trp Ile
             35                  40                  45

Gly Leu Ile Asn Pro Tyr Asn Gly Gly Thr Ile Tyr Asn Gln Lys Phe
50                  55                  60

Lys Gly Lys Ala Thr Leu Thr Val Asp Lys Ser Ser Ser Thr Ala Tyr
65                  70                  75                  80

Met Glu Leu Leu Ser Leu Thr Ser Glu Asp Ser Ala Val Tyr Tyr Cys
                 85                  90                  95

Ala Arg Asp Tyr Gly Phe Val Leu Asp Tyr Trp Gly Gln Gly Thr Thr
            100                 105                 110

Leu Thr Val Ser Ser Gly Gly Gly Ser Gly Gly Gly Gly Ser Gly
            115                 120                 125

Gly Gly Gly Ser Gly Gly Gly Ser Gln Ile Val Leu Thr Gln Ser
            130                 135                 140

Pro Ser Ile Met Ser Val Ser Pro Gly Glu Lys Val Thr Ile Thr Cys
145                 150                 155                 160

Ser Ala Ser Ser Ser Val Ser Tyr Met His Trp Phe Gln Gln Lys Pro
                165                 170                 175

Gly Thr Ser Pro Lys Leu Gly Ile Tyr Ser Thr Ser Asn Leu Ala Ser
            180                 185                 190

Gly Val Pro Ala Arg Phe Ser Arg Gly Ser Gly Thr Ser Tyr Ser
            195                 200                 205

Leu Thr Ile Ser Arg Val Ala Ala Glu Asp Ala Ala Thr Tyr Tyr Cys
210                 215                 220

Gln Gln Arg Ser Asn Tyr Pro Pro Trp Thr Phe Gly Gly Gly Thr Lys
225                 230                 235                 240

Leu Glu Ile Lys

<210> SEQ ID NO 266
<211> LENGTH: 253
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 266

Gln Ala Val Val Thr Gln Pro Pro Ser Ala Ser Gly Thr Pro Gly Gln
1               5                   10                  15

Arg Val Thr Ile Ser Cys Ser Gly Ser Ser Ser Asn Ile Gly Ser Asn
                 20                  25                  30

Thr Val Asn Trp Tyr Gln Gln Val Pro Gly Thr Ala Pro Lys Leu Leu
             35                  40                  45

Ile Tyr Ser Asn Asn Gln Arg Pro Ser Gly Val Pro Asp Arg Phe Ser
50                  55                  60

Gly Ser Lys Ser Gly Thr Ser Ala Ser Leu Ala Ile Ser Gly Leu Gln
65                  70                  75                  80

Ser Glu Asp Glu Ala Asp Tyr Tyr Cys Ala Ala Trp Asp Asp Ser Leu
                 85                  90                  95

Asn Gly Trp Val Phe Gly Gly Gly Thr Lys Leu Thr Val Leu Gly Ser
            100                 105                 110

Arg Gly Gly Gly Gly Ser Gly Gly Gly Ser Gly Gly Gly Gly Ser
            115                 120                 125

```
Leu Glu Met Ala Gln Met Gln Leu Val Gln Ser Gly Ala Glu Val Lys
        130                 135                 140

Glu Pro Gly Glu Ser Leu Arg Ile Ser Cys Lys Gly Ser Gly Tyr Ser
145                 150                 155                 160

Phe Thr Asn Phe Trp Ile Ser Trp Val Arg Gln Met Pro Gly Lys Gly
                165                 170                 175

Leu Glu Trp Met Gly Arg Val Asp Pro Gly Tyr Ser Tyr Ser Thr Tyr
                180                 185                 190

Ser Pro Ser Phe Gln Gly His Val Thr Ile Ser Ala Asp Lys Ser Thr
        195                 200                 205

Ser Thr Ala Tyr Leu Gln Trp Asn Ser Leu Lys Ala Ser Asp Thr Ala
        210                 215                 220

Met Tyr Tyr Cys Ala Arg Val Gln Tyr Ser Gly Tyr Tyr Asp Trp Phe
225                 230                 235                 240

Asp Pro Trp Gly Gln Gly Thr Leu Val Thr Val Ser Ser
                245                 250
```

<210> SEQ ID NO 267
<211> LENGTH: 250
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 267

```
Gln Thr Val Val Thr Gln Pro Pro Ser Ala Ser Gly Thr Pro Gly Gln
1               5                   10                  15

Arg Val Thr Ile Ser Cys Ser Gly Ser Ser Ser Asn Ile Gly Ser Asn
                20                  25                  30

Tyr Val Tyr Trp Tyr Gln Gln Leu Pro Gly Thr Ala Pro Lys Leu Leu
            35                  40                  45

Ile Tyr Arg Ser Asn Gln Arg Pro Ser Gly Val Pro Asp Arg Phe Ser
50                  55                  60

Gly Ser Lys Ser Gly Thr Ser Ala Ser Leu Ala Ile Ser Gly Pro Arg
65                  70                  75                  80

Ser Val Asp Glu Ala Asp Tyr Tyr Cys Ala Ala Trp Asp Asp Ser Leu
                85                  90                  95

Asn Gly Val Val Phe Gly Gly Gly Thr Lys Leu Thr Val Leu Gly Ser
            100                 105                 110

Arg Gly Gly Gly Ser Gly Gly Gly Ser Gly Gly Gly Ser Leu
            115                 120                 125

Glu Met Ala Gln Val Gln Leu Val Gln Ser Gly Ala Glu Val Lys Lys
        130                 135                 140

Pro Gly Ser Ser Val Lys Val Ser Cys Lys Ala Ser Gly Gly Thr Phe
145                 150                 155                 160

Ser Ser Tyr Ala Ile Ser Trp Val Arg Gln Ala Pro Gly Gln Gly Leu
                165                 170                 175

Glu Trp Met Gly Gly Ile Ile Pro Ile Phe Gly Thr Ala Asn Tyr Ala
            180                 185                 190

Gln Lys Phe Gln Gly Arg Val Thr Ile Thr Ala Asp Glu Ser Thr Ser
        195                 200                 205

Thr Ala Tyr Met Glu Leu Ser Ser Leu Arg Ser Glu Asp Thr Ala Val
        210                 215                 220

Tyr Tyr Cys Ala Arg Arg Ile Pro Pro Tyr Tyr Gly Met Asp Val Trp
225                 230                 235                 240
```

Gly Gln Gly Thr Thr Val Thr Val Ser Ser
               245                  250

<210> SEQ ID NO 268
<211> LENGTH: 250
<212> TYPE: PRT
<213> ORGANISM: Artificial Sequence
<220> FEATURE:
<223> OTHER INFORMATION: Description of Artificial Sequence: Synthetic
     polypeptide

<400> SEQUENCE: 268

Asp Ile Gln Met Thr Gln Ser Pro Ser Ser Leu Ser Ala Ser Val Gly
1              5                 10               15

Asp Arg Val Thr Ile Thr Cys Arg Ala Ser Gln Ser Ile Ser Ser Tyr
             20                25               30

Leu Asn Trp Tyr Gln Gln Lys Pro Gly Lys Ala Pro Lys Leu Leu Ile
        35                40               45

Tyr Ala Ala Ser Ser Leu Gln Ser Gly Val Pro Ser Arg Phe Ser Gly
 50                  55                60

Ser Gly Ser Gly Thr Asp Phe Thr Leu Thr Ile Ser Ser Leu Gln Pro
65                   70                  75               80

Glu Asp Phe Ala Thr Tyr Tyr Cys Gln Gln Ser Tyr Ser Thr Pro Leu
             85                90               95

Thr Phe Gly Gly Gly Thr Lys Val Asp Ile Lys Arg Ser Arg Gly Gly
        100               105              110

Gly Gly Ser Gly Gly Gly Gly Ser Gly Gly Gly Ser Leu Glu Met
       115               120              125

Ala Gln Val Gln Leu Gln Gln Ser Gly Pro Gly Leu Val Lys Pro Ser
    130                135               140

Gln Thr Leu Ser Leu Thr Cys Ala Ile Ser Gly Asp Ser Val Ser Ser
145                 150               155              160

Asn Ser Ala Ala Trp Asn Trp Ile Arg Gln Ser Pro Ser Arg Gly Leu
             165               170              175

Glu Trp Leu Gly Arg Thr Tyr Tyr Gly Ser Lys Trp Tyr Asn Asp Tyr
        180               185              190

Ala Val Ser Val Lys Ser Arg Ile Thr Ile Asn Pro Asp Thr Ser Lys
    195                200               205

Asn Gln Phe Ser Leu Gln Leu Asn Ser Val Thr Pro Glu Asp Thr Ala
    210                215               220

Val Tyr Tyr Cys Ala Arg Gly Arg Leu Gly Asp Ala Phe Asp Ile Trp
225                 230               235              240

Gly Gln Gly Thr Met Val Thr Val Ser Ser
               245                  250

<210> SEQ ID NO 269
<211> LENGTH: 246
<212> TYPE: PRT
<213> ORGANISM: Artificial Sequence
<220> FEATURE:
<223> OTHER INFORMATION: Description of Artificial Sequence: Synthetic
     polypeptide

<400> SEQUENCE: 269

Asp Ile Gln Met Thr Gln Ser Pro Ser Thr Leu Ser Ala Ser Val Gly
1              5                 10               15

Asp Arg Val Thr Ile Thr Cys Arg Ala Ser Gln Asn Ile Asn Lys Trp
             20                25               30

Leu Ala Trp Tyr Gln Gln Arg Pro Gly Lys Ala Pro Gln Leu Leu Ile
            35                  40                  45

Tyr Lys Ala Ser Ser Leu Glu Ser Gly Val Pro Ser Arg Phe Ser Gly
    50                  55                  60

Ser Gly Ser Gly Thr Glu Tyr Thr Leu Thr Ile Ser Ser Leu Gln Pro
65                  70                  75                  80

Asp Asp Phe Ala Thr Tyr Tyr Cys Gln Gln Tyr Asn Ser Tyr Ala Thr
                85                  90                  95

Phe Gly Gln Gly Thr Lys Val Glu Ile Lys Arg Ser Arg Gly Gly Gly
            100                 105                 110

Gly Ser Gly Gly Gly Ser Gly Gly Gly Ser Leu Glu Met Ala
            115                 120                 125

Gln Val Gln Leu Val Gln Ser Gly Ala Glu Val Lys Lys Pro Gly Glu
            130                 135                 140

Ser Leu Lys Ile Ser Cys Lys Gly Ser Gly Tyr Asn Phe Ser Asn Lys
145                 150                 155                 160

Trp Ile Gly Trp Val Arg Gln Leu Pro Gly Arg Gly Leu Glu Trp Ile
                165                 170                 175

Ala Ile Ile Tyr Pro Gly Tyr Ser Asp Ile Thr Tyr Ser Pro Ser Phe
            180                 185                 190

Gln Gly Arg Val Thr Ile Ser Ala Asp Thr Ser Ile Asn Thr Ala Tyr
            195                 200                 205

Leu His Trp His Ser Leu Lys Ala Ser Asp Thr Ala Met Tyr Tyr Cys
            210                 215                 220

Val Arg His Thr Ala Leu Ala Gly Phe Asp Tyr Trp Gly Leu Gly Thr
225                 230                 235                 240

Leu Val Thr Val Ser Ser
                245

<210> SEQ ID NO 270
<211> LENGTH: 249
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 270

Gln Ser Val Val Thr Gln Pro Pro Ser Val Ser Val Ala Pro Gly Lys
1               5                   10                  15

Thr Ala Arg Ile Thr Cys Gly Arg Asn Asn Ile Gly Ser Lys Ser Val
            20                  25                  30

His Trp Tyr Gln Gln Lys Pro Gly Gln Ala Pro Val Leu Val Val Tyr
            35                  40                  45

Asp Asp Ser Asp Arg Pro Ser Gly Ile Pro Glu Arg Phe Ser Gly Ser
    50                  55                  60

Asn Ser Gly Asn Thr Ala Thr Leu Thr Ile Ser Arg Val Glu Ala Gly
65                  70                  75                  80

Asp Glu Ala Asp Tyr Tyr Cys Gln Val Trp Asp Ser Ser Ser Asp His
                85                  90                  95

Val Val Phe Gly Gly Gly Thr Lys Leu Thr Val Leu Gly Ser Arg Gly
            100                 105                 110

Gly Gly Gly Ser Gly Gly Gly Ser Gly Gly Ser Leu Glu Met Ala
            115                 120                 125

Glu Val Gln Leu Val Gln Ser Gly Gly Gly Val Val Arg Pro Gly Gly

```
            130                 135                 140
Ser Leu Arg Leu Ser Cys Ala Ala Ser Gly Phe Thr Phe Asp Asp Tyr
145                 150                 155                 160

Gly Met Ser Trp Val Arg Gln Ala Pro Gly Lys Gly Leu Glu Trp Val
                165                 170                 175

Ser Gly Ile Asn Trp Asn Gly Ser Thr Gly Tyr Ala Asp Ser Val
            180                 185                 190

Arg Gly Arg Phe Thr Ile Ser Arg Asp Asn Ala Lys Asn Ser Leu Tyr
                195                 200                 205

Leu Gln Met Asn Ser Leu Arg Ala Glu Asp Thr Ala Leu Tyr Tyr Cys
            210                 215                 220

Ala Arg Glu Arg Gly Tyr Gly Tyr His Asp Pro His Asp Tyr Trp Gly
225                 230                 235                 240

Gln Gly Thr Leu Val Thr Val Ser Ser
                245

<210> SEQ ID NO 271
<211> LENGTH: 251
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 271

Gln Ser Val Leu Thr Gln Pro Pro Ser Val Ser Gly Ala Pro Gly Gln
1               5                   10                  15

Arg Val Thr Ile Ser Cys Thr Gly Ser Ser Asn Ile Gly Ala Gly
                20                  25                  30

Tyr Asp Val His Trp Tyr Gln Gln Leu Pro Gly Thr Ala Pro Lys Leu
                35                  40                  45

Leu Ile Tyr Gly Asn Ser Asn Arg Pro Ser Gly Val Pro Asp Arg Phe
            50                  55                  60

Ser Gly Ser Lys Ser Gly Thr Ser Ala Ser Leu Ala Ile Ser Gly Leu
65              70                  75                  80

Gln Ser Glu Asp Glu Ala Asp Tyr Tyr Cys Ala Ala Trp Asp Asp Ser
                85                  90                  95

Leu Asn Gly Tyr Val Phe Gly Thr Gly Thr Lys Leu Thr Val Leu Gly
                100                 105                 110

Ser Arg Gly Gly Gly Gly Ser Gly Gly Gly Ser Gly Gly Gly Gly
            115                 120                 125

Ser Leu Glu Met Ala Glu Val Gln Leu Val Glu Thr Gly Gly Gly Leu
            130                 135                 140

Leu Gln Pro Gly Gly Ser Leu Arg Leu Ser Cys Ala Ala Ser Gly Phe
145                 150                 155                 160

Ser Val Ser Gly Thr Tyr Met Gly Trp Val Arg Gln Ala Pro Gly Lys
                165                 170                 175

Gly Leu Glu Trp Val Ala Leu Leu Tyr Ser Gly Gly Thr Tyr His
                180                 185                 190

Pro Ala Ser Leu Gln Gly Arg Phe Ile Val Ser Arg Asp Ser Ser Lys
                195                 200                 205

Asn Met Val Tyr Leu Gln Met Asn Ser Leu Lys Ala Glu Asp Thr Ala
            210                 215                 220

Val Tyr Tyr Cys Ala Lys Gly Gly Ala Gly Gly His Phe Asp Ser
225                 230                 235                 240
```

```
Trp Gly Gln Gly Thr Leu Val Thr Val Ser Ser
                245                 250
```

<210> SEQ ID NO 272
<211> LENGTH: 241
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 272

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Gln Ile Asp Pro Trp Gly Gln Glu Thr Leu Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Leu Thr Gly Arg Phe Asp Tyr Trp Gly Gln Gly Thr Leu Val
            100                 105                 110

Thr Val Ser Ser Gly Gly Gly Ser Gly Gly Gly Ser Gly Gly
        115                 120                 125

Gly Gly Ser Thr Asp Ile Gln Met Thr Gln Ser Pro Ser Ser Leu Ser
    130                 135                 140

Ala Ser Val Gly Asp Arg Val Thr Ile Thr Cys Arg Ala Ser Gln Ser
145                 150                 155                 160

Ile Ser Ser Tyr Leu Asn Trp Tyr Gln Gln Lys Pro Gly Lys Ala Pro
                165                 170                 175

Lys Leu Leu Ile Tyr Ser Ala Ser Gln Leu Gln Ser Gly Val Pro Ser
            180                 185                 190

Arg Phe Ser Gly Ser Gly Ser Gly Thr Asp Phe Thr Leu Thr Ile Ser
        195                 200                 205

Ser Leu Gln Pro Glu Asp Phe Ala Thr Tyr Tyr Cys Gln Gln Gly Pro
    210                 215                 220

Gly Thr Pro Asn Thr Phe Gly Gln Gly Thr Lys Val Glu Ile Lys Arg
225                 230                 235                 240

Ala
```

<210> SEQ ID NO 273
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 273

```
Gly Ser Thr Ser Gly Ser Gly Lys Pro Gly Ser Gly Glu Gly Ser Thr
1               5                   10                  15

Lys Gly
```

<210> SEQ ID NO 274

<211> LENGTH: 119
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 274

Gln Val Gln Leu Leu Glu Ser Gly Ala Glu Leu Val Arg Pro Gly Ser
1               5                   10                  15

Ser Val Lys Ile Ser Cys Lys Ala Ser Gly Tyr Ala Phe Ser Ser Tyr
            20                  25                  30

Trp Met Asn Trp Val Lys Gln Arg Pro Gly Gln Gly Leu Glu Trp Ile
        35                  40                  45

Gly Gln Ile Tyr Pro Gly Asp Gly Asp Thr Asn Tyr Asn Gly Lys Phe
    50                  55                  60

Lys Gly Gln Ala Thr Leu Thr Ala Asp Lys Ser Ser Ser Thr Ala Tyr
65                  70                  75                  80

Met Gln Leu Ser Gly Leu Thr Ser Glu Asp Ser Ala Val Tyr Ser Cys
                85                  90                  95

Ala Arg Lys Thr Ile Ser Ser Val Val Asp Phe Tyr Phe Asp Tyr Trp
            100                 105                 110

Gly Gln Gly Thr Thr Val Thr
        115

<210> SEQ ID NO 275
<211> LENGTH: 111
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 275

Glu Leu Val Leu Thr Gln Ser Pro Lys Phe Met Ser Thr Ser Val Gly
1               5                   10                  15

Asp Arg Val Ser Val Thr Cys Lys Ala Ser Gln Asn Val Gly Thr Asn
            20                  25                  30

Val Ala Trp Tyr Gln Gln Lys Pro Gly Gln Ser Pro Lys Pro Leu Ile
        35                  40                  45

Tyr Ser Ala Thr Tyr Arg Asn Ser Gly Val Pro Asp Arg Phe Thr Gly
    50                  55                  60

Ser Gly Ser Gly Thr Asp Phe Thr Leu Thr Ile Thr Asn Val Gln Ser
65                  70                  75                  80

Lys Asp Leu Ala Asp Tyr Phe Tyr Phe Cys Gln Tyr Asn Arg Tyr Pro
                85                  90                  95

Tyr Thr Ser Gly Gly Gly Thr Lys Leu Glu Ile Lys Arg Arg Ser
            100                 105                 110

<210> SEQ ID NO 276
<211> LENGTH: 95
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (11)..(11)
<223> OTHER INFORMATION: Any naturally occurring amino acid

<400> SEQUENCE: 276

```
Ile Leu Trp His Glu Met Trp His Glu Gly Xaa Glu Glu Ala Ser Arg
1               5                   10                  15

Leu Tyr Phe Gly Glu Arg Asn Val Lys Gly Met Phe Glu Val Leu Glu
            20                  25                  30

Pro Leu His Ala Met Met Glu Arg Gly Pro Gln Thr Leu Lys Glu Thr
        35                  40                  45

Ser Phe Asn Gln Ala Tyr Gly Arg Asp Leu Met Glu Ala Gln Glu Trp
50                  55                  60

Cys Arg Lys Tyr Met Lys Ser Gly Asn Val Lys Asp Leu Thr Gln Ala
65                  70                  75                  80

Trp Asp Leu Tyr Tyr His Val Phe Arg Arg Ile Ser Lys Thr Ser
            85                  90                  95

<210> SEQ ID NO 277
<211> LENGTH: 95
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (12)..(12)
<223> OTHER INFORMATION: Any naturally occurring amino acid

<400> SEQUENCE: 277

Ile Leu Trp His Glu Met Trp His Glu Gly Leu Xaa Glu Ala Ser Arg
1               5                   10                  15

Leu Tyr Phe Gly Glu Arg Asn Val Lys Gly Met Phe Glu Val Leu Glu
            20                  25                  30

Pro Leu His Ala Met Met Glu Arg Gly Pro Gln Thr Leu Lys Glu Thr
        35                  40                  45

Ser Phe Asn Gln Ala Tyr Gly Arg Asp Leu Met Glu Ala Gln Glu Trp
50                  55                  60

Cys Arg Lys Tyr Met Lys Ser Gly Asn Val Lys Asp Leu Thr Gln Ala
65                  70                  75                  80

Trp Asp Leu Tyr Tyr His Val Phe Arg Arg Ile Ser Lys Thr Ser
            85                  90                  95

<210> SEQ ID NO 278
<211> LENGTH: 95
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (15)..(15)
<223> OTHER INFORMATION: Any naturally occurring amino acid

<400> SEQUENCE: 278

Ile Leu Trp His Glu Met Trp His Glu Gly Leu Glu Glu Ala Xaa Arg
1               5                   10                  15

Leu Tyr Phe Gly Glu Arg Asn Val Lys Gly Met Phe Glu Val Leu Glu
            20                  25                  30

Pro Leu His Ala Met Met Glu Arg Gly Pro Gln Thr Leu Lys Glu Thr
        35                  40                  45

Ser Phe Asn Gln Ala Tyr Gly Arg Asp Leu Met Glu Ala Gln Glu Trp
50                  55                  60
```

```
Cys Arg Lys Tyr Met Lys Ser Gly Asn Val Lys Asp Leu Thr Gln Ala
 65                  70                  75                  80

Trp Asp Leu Tyr Tyr His Val Phe Arg Arg Ile Ser Lys Thr Ser
                 85                  90                  95

<210> SEQ ID NO 279
<211> LENGTH: 95
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (16)..(16)
<223> OTHER INFORMATION: Any naturally occurring amino acid

<400> SEQUENCE: 279

Ile Leu Trp His Glu Met Trp His Glu Gly Leu Glu Glu Ala Ser Xaa
  1               5                  10                  15

Leu Tyr Phe Gly Glu Arg Asn Val Lys Gly Met Phe Glu Val Leu Glu
                 20                  25                  30

Pro Leu His Ala Met Met Glu Arg Gly Pro Gln Thr Leu Lys Glu Thr
             35                  40                  45

Ser Phe Asn Gln Ala Tyr Gly Arg Asp Leu Met Glu Ala Gln Glu Trp
 50                  55                  60

Cys Arg Lys Tyr Met Lys Ser Gly Asn Val Lys Asp Leu Thr Gln Ala
 65                  70                  75                  80

Trp Asp Leu Tyr Tyr His Val Phe Arg Arg Ile Ser Lys Thr Ser
                 85                  90                  95

<210> SEQ ID NO 280
<211> LENGTH: 95
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (19)..(19)
<223> OTHER INFORMATION: Any naturally occurring amino acid

<400> SEQUENCE: 280

Ile Leu Trp His Glu Met Trp His Glu Gly Leu Glu Glu Ala Ser Arg
  1               5                  10                  15

Leu Tyr Xaa Gly Glu Arg Asn Val Lys Gly Met Phe Glu Val Leu Glu
                 20                  25                  30

Pro Leu His Ala Met Met Glu Arg Gly Pro Gln Thr Leu Lys Glu Thr
             35                  40                  45

Ser Phe Asn Gln Ala Tyr Gly Arg Asp Leu Met Glu Ala Gln Glu Trp
 50                  55                  60

Cys Arg Lys Tyr Met Lys Ser Gly Asn Val Lys Asp Leu Thr Gln Ala
 65                  70                  75                  80

Trp Asp Leu Tyr Tyr His Val Phe Arg Arg Ile Ser Lys Thr Ser
                 85                  90                  95

<210> SEQ ID NO 281
<211> LENGTH: 95
<212> TYPE: PRT
<213> ORGANISM: Artificial Sequence
<220> FEATURE:
<223> OTHER INFORMATION: Description of Artificial Sequence: Synthetic
```

```
        polypeptide
<220> FEATURE:
<221> NAME/KEY: MOD_RES
<222> LOCATION: (20)..(20)
<223> OTHER INFORMATION: Any naturally occurring amino acid

<400> SEQUENCE: 281

Ile Leu Trp His Glu Met Trp His Glu Gly Leu Glu Glu Ala Ser Arg
1               5                   10                  15

Leu Tyr Phe Xaa Glu Arg Asn Val Lys Gly Met Phe Glu Val Leu Glu
            20                  25                  30

Pro Leu His Ala Met Met Glu Arg Gly Pro Gln Thr Leu Lys Glu Thr
        35                  40                  45

Ser Phe Asn Gln Ala Tyr Gly Arg Asp Leu Met Glu Ala Gln Glu Trp
    50                  55                  60

Cys Arg Lys Tyr Met Lys Ser Gly Asn Val Lys Asp Leu Thr Gln Ala
65                  70                  75                  80

Trp Asp Leu Tyr Tyr His Val Phe Arg Arg Ile Ser Lys Thr Ser
                85                  90                  95

<210> SEQ ID NO 282
<211> LENGTH: 95
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (78)..(78)
<223> OTHER INFORMATION: Any naturally occurring amino acid

<400> SEQUENCE: 282

Ile Leu Trp His Glu Met Trp His Glu Gly Leu Glu Glu Ala Ser Arg
1               5                   10                  15

Leu Tyr Phe Gly Glu Arg Asn Val Lys Gly Met Phe Glu Val Leu Glu
            20                  25                  30

Pro Leu His Ala Met Met Glu Arg Gly Pro Gln Thr Leu Lys Glu Thr
        35                  40                  45

Ser Phe Asn Gln Ala Tyr Gly Arg Asp Leu Met Glu Ala Gln Glu Trp
    50                  55                  60

Cys Arg Lys Tyr Met Lys Ser Gly Asn Val Lys Asp Leu Xaa Gln Ala
65                  70                  75                  80

Trp Asp Leu Tyr Tyr His Val Phe Arg Arg Ile Ser Lys Thr Ser
                85                  90                  95

<210> SEQ ID NO 283
<211> LENGTH: 95
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (81)..(81)
<223> OTHER INFORMATION: Any naturally occurring amino acid

<400> SEQUENCE: 283

Ile Leu Trp His Glu Met Trp His Glu Gly Leu Glu Glu Ala Ser Arg
1               5                   10                  15

Leu Tyr Phe Gly Glu Arg Asn Val Lys Gly Met Phe Glu Val Leu Glu
            20                  25                  30
```

Pro Leu His Ala Met Met Glu Arg Gly Pro Gln Thr Leu Lys Glu Thr
            35                  40                  45

Ser Phe Asn Gln Ala Tyr Gly Arg Asp Leu Met Glu Ala Gln Glu Trp
 50                  55                  60

Cys Arg Lys Tyr Met Lys Ser Gly Asn Val Lys Asp Leu Thr Gln Ala
65                  70                  75                  80

Xaa Asp Leu Tyr Tyr His Val Phe Arg Arg Ile Ser Lys Thr Ser
                85                  90                  95

<210> SEQ ID NO 284
<211> LENGTH: 95
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (82)..(82)
<223> OTHER INFORMATION: Any naturally occurring amino acid

<400> SEQUENCE: 284

Ile Leu Trp His Glu Met Trp His Glu Gly Leu Glu Glu Ala Ser Arg
1                   5                  10                  15

Leu Tyr Phe Gly Glu Arg Asn Val Lys Gly Met Phe Glu Val Leu Glu
                20                  25                  30

Pro Leu His Ala Met Met Glu Arg Gly Pro Gln Thr Leu Lys Glu Thr
            35                  40                  45

Ser Phe Asn Gln Ala Tyr Gly Arg Asp Leu Met Glu Ala Gln Glu Trp
 50                  55                  60

Cys Arg Lys Tyr Met Lys Ser Gly Asn Val Lys Asp Leu Thr Gln Ala
65                  70                  75                  80

Trp Xaa Leu Tyr Tyr His Val Phe Arg Arg Ile Ser Lys Thr Ser
                85                  90                  95

<210> SEQ ID NO 285
<211> LENGTH: 95
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (85)..(85)
<223> OTHER INFORMATION: Any naturally occurring amino acid

<400> SEQUENCE: 285

Ile Leu Trp His Glu Met Trp His Glu Gly Leu Glu Glu Ala Ser Arg
1                   5                  10                  15

Leu Tyr Phe Gly Glu Arg Asn Val Lys Gly Met Phe Glu Val Leu Glu
                20                  25                  30

Pro Leu His Ala Met Met Glu Arg Gly Pro Gln Thr Leu Lys Glu Thr
            35                  40                  45

Ser Phe Asn Gln Ala Tyr Gly Arg Asp Leu Met Glu Ala Gln Glu Trp
 50                  55                  60

Cys Arg Lys Tyr Met Lys Ser Gly Asn Val Lys Asp Leu Thr Gln Ala
65                  70                  75                  80

Trp Asp Leu Tyr Xaa His Val Phe Arg Arg Ile Ser Lys Thr Ser
                85                  90                  95

```
<210> SEQ ID NO 286
<211> LENGTH: 95
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (88)..(88)
<223> OTHER INFORMATION: Any naturally occurring amino acid

<400> SEQUENCE: 286

Ile Leu Trp His Glu Met Trp His Glu Gly Leu Glu Glu Ala Ser Arg
1               5                   10                  15

Leu Tyr Phe Gly Glu Arg Asn Val Lys Gly Met Phe Glu Val Leu Glu
                20                  25                  30

Pro Leu His Ala Met Met Glu Arg Gly Pro Gln Thr Leu Lys Glu Thr
            35                  40                  45

Ser Phe Asn Gln Ala Tyr Gly Arg Asp Leu Met Glu Ala Gln Glu Trp
        50                  55                  60

Cys Arg Lys Tyr Met Lys Ser Gly Asn Val Lys Asp Leu Thr Gln Ala
65                  70                  75                  80

Trp Asp Leu Tyr Tyr His Val Xaa Arg Arg Ile Ser Lys Thr Ser
                85                  90                  95

<210> SEQ ID NO 287
<211> LENGTH: 95
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 287

Ile Leu Trp His Glu Met Trp His Glu Gly Leu Ile Glu Ala Ser Arg
1               5                   10                  15

Leu Tyr Phe Gly Glu Arg Asn Val Lys Gly Met Phe Glu Val Leu Glu
                20                  25                  30

Pro Leu His Ala Met Met Glu Arg Gly Pro Gln Thr Leu Lys Glu Thr
            35                  40                  45

Ser Phe Asn Gln Ala Tyr Gly Arg Asp Leu Met Glu Ala Gln Glu Trp
        50                  55                  60

Cys Arg Lys Tyr Met Lys Ser Gly Asn Val Lys Asp Leu Thr Gln Ala
65                  70                  75                  80

Trp Asp Leu Tyr Tyr His Val Phe Arg Arg Ile Ser Lys Thr Ser
                85                  90                  95

<210> SEQ ID NO 288
<211> LENGTH: 95
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 288

Ile Leu Trp His Glu Met Trp His Glu Gly Leu Leu Glu Ala Ser Arg
1               5                   10                  15

Leu Tyr Phe Gly Glu Arg Asn Val Lys Gly Met Phe Glu Val Leu Glu
                20                  25                  30
```

```
Pro Leu His Ala Met Met Glu Arg Gly Pro Gln Thr Leu Lys Glu Thr
            35                  40                  45

Ser Phe Asn Gln Ala Tyr Gly Arg Asp Leu Met Glu Ala Gln Glu Trp
     50                  55                  60

Cys Arg Lys Tyr Met Lys Ser Gly Asn Val Lys Asp Leu Thr Gln Ala
 65                  70                  75                  80

Trp Asp Leu Tyr Tyr His Val Phe Arg Arg Ile Ser Lys Thr Ser
                 85                  90                  95

<210> SEQ ID NO 289
<211> LENGTH: 95
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 289

Ile Leu Trp His Glu Met Trp His Glu Gly Leu Glu Glu Ala Ser Arg
 1               5                  10                  15

Leu Tyr Phe Gly Glu Arg Asn Val Lys Gly Met Phe Glu Val Leu Glu
             20                  25                  30

Pro Leu His Ala Met Met Glu Arg Gly Pro Gln Thr Leu Lys Glu Thr
            35                  40                  45

Ser Phe Asn Gln Ala Tyr Gly Arg Asp Leu Met Glu Ala Gln Glu Trp
     50                  55                  60

Cys Arg Lys Tyr Met Lys Ser Gly Asn Val Lys Asp Leu Leu Gln Ala
 65                  70                  75                  80

Trp Asp Leu Tyr Tyr His Val Phe Arg Arg Ile Ser Lys Thr Ser
                 85                  90                  95

<210> SEQ ID NO 290
<211> LENGTH: 95
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (12)..(12)
<223> OTHER INFORMATION: Any naturally occurring amino acid
<220> FEATURE:
<221> NAME/KEY: MOD_RES
<222> LOCATION: (78)..(78)
<223> OTHER INFORMATION: Any naturally occurring amino acid

<400> SEQUENCE: 290

Ile Leu Trp His Glu Met Trp His Glu Gly Leu Xaa Glu Ala Ser Arg
 1               5                  10                  15

Leu Tyr Phe Gly Glu Arg Asn Val Lys Gly Met Phe Glu Val Leu Glu
             20                  25                  30

Pro Leu His Ala Met Met Glu Arg Gly Pro Gln Thr Leu Lys Glu Thr
            35                  40                  45

Ser Phe Asn Gln Ala Tyr Gly Arg Asp Leu Met Glu Ala Gln Glu Trp
     50                  55                  60

Cys Arg Lys Tyr Met Lys Ser Gly Asn Val Lys Asp Leu Xaa Gln Ala
 65                  70                  75                  80

Trp Asp Leu Tyr Tyr His Val Phe Arg Arg Ile Ser Lys Thr Ser
                 85                  90                  95
```

```
<210> SEQ ID NO 291
<211> LENGTH: 95
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 291

Ile Leu Trp His Glu Met Trp His Glu Gly Leu Ile Glu Ala Ser Arg
1               5                   10                  15

Leu Tyr Phe Gly Glu Arg Asn Val Lys Gly Met Phe Glu Val Leu Glu
            20                  25                  30

Pro Leu His Ala Met Met Glu Arg Gly Pro Gln Thr Leu Lys Glu Thr
        35                  40                  45

Ser Phe Asn Gln Ala Tyr Gly Arg Asp Leu Met Glu Ala Gln Glu Trp
    50                  55                  60

Cys Arg Lys Tyr Met Lys Ser Gly Asn Val Lys Asp Leu Leu Gln Ala
65                  70                  75                  80

Trp Asp Leu Tyr Tyr His Val Phe Arg Arg Ile Ser Lys Thr Ser
                85                  90                  95

<210> SEQ ID NO 292
<211> LENGTH: 95
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 292

Ile Leu Trp His Glu Met Trp His Glu Gly Leu Leu Glu Ala Ser Arg
1               5                   10                  15

Leu Tyr Phe Gly Glu Arg Asn Val Lys Gly Met Phe Glu Val Leu Glu
            20                  25                  30

Pro Leu His Ala Met Met Glu Arg Gly Pro Gln Thr Leu Lys Glu Thr
        35                  40                  45

Ser Phe Asn Gln Ala Tyr Gly Arg Asp Leu Met Glu Ala Gln Glu Trp
    50                  55                  60

Cys Arg Lys Tyr Met Lys Ser Gly Asn Val Lys Asp Leu Leu Gln Ala
65                  70                  75                  80

Trp Asp Leu Tyr Tyr His Val Phe Arg Arg Ile Ser Lys Thr Ser
                85                  90                  95

<210> SEQ ID NO 293
<211> LENGTH: 522
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 293

Met Ala Leu Pro Val Thr Ala Leu Leu Leu Pro Leu Ala Leu Leu Leu
1               5                   10                  15

His Ala Ala Arg Pro Glu Ile Val Met Thr Gln Ser Pro Ala Thr Leu
            20                  25                  30

Ser Leu Ser Pro Gly Glu Arg Ala Thr Leu Ser Cys Arg Ala Ser Gln
        35                  40                  45

Asp Ile Ser Lys Tyr Leu Asn Trp Tyr Gln Gln Lys Pro Gly Gln Ala
    50                  55                  60
```

-continued

```
Pro Arg Leu Leu Ile Tyr His Thr Ser Arg Leu His Ser Gly Ile Pro
65                  70                  75                  80

Ala Arg Phe Ser Gly Ser Gly Ser Gly Thr Asp Tyr Thr Leu Thr Ile
            85                  90                  95

Ser Ser Leu Gln Pro Glu Asp Phe Ala Val Tyr Phe Cys Gln Gln Gly
            100                 105                 110

Asn Thr Leu Pro Tyr Thr Phe Gly Gln Gly Thr Lys Leu Glu Ile Lys
            115                 120                 125

Gly Gly Gly Gly Ser Gly Gly Gly Ser Gly Gly Gly Ser Gln
130                 135                 140

Val Gln Leu Gln Glu Ser Gly Pro Gly Leu Val Lys Pro Ser Glu Thr
145                 150                 155                 160

Leu Ser Leu Thr Cys Thr Val Ser Gly Val Ser Leu Pro Asp Tyr Gly
            165                 170                 175

Val Ser Trp Ile Arg Gln Pro Pro Gly Lys Gly Leu Glu Trp Ile Gly
            180                 185                 190

Val Ile Trp Gly Ser Glu Thr Thr Tyr Tyr Ser Ser Ser Leu Lys Ser
            195                 200                 205

Arg Val Thr Ile Ser Lys Asp Asn Ser Lys Asn Gln Val Ser Leu Lys
210                 215                 220

Leu Ser Ser Val Thr Ala Ala Asp Thr Ala Val Tyr Tyr Cys Ala Lys
225                 230                 235                 240

His Tyr Tyr Tyr Gly Gly Ser Tyr Ala Met Asp Tyr Trp Gly Gln Gly
            245                 250                 255

Thr Leu Val Thr Val Ser Ser Thr Thr Thr Pro Ala Pro Arg Pro Pro
            260                 265                 270

Thr Pro Ala Pro Thr Ile Ala Ser Gln Pro Leu Ser Leu Arg Pro Glu
            275                 280                 285

Ala Cys Arg Pro Ala Ala Gly Gly Ala Val His Thr Arg Gly Leu Asp
            290                 295                 300

Phe Ala Cys Asp Ile Tyr Ile Trp Ala Pro Leu Ala Gly Thr Cys Gly
305                 310                 315                 320

Val Leu Leu Leu Ser Leu Val Ile Thr Leu Tyr Cys Ala Leu Tyr Leu
            325                 330                 335

Leu Arg Arg Asp Gln Arg Leu Pro Pro Asp Ala His Lys Pro Pro Gly
            340                 345                 350

Gly Gly Ser Phe Arg Thr Pro Ile Gln Glu Glu Gln Ala Asp Ala His
            355                 360                 365

Ser Thr Leu Ala Lys Ile Arg Ser Lys Arg Ser Arg Leu Leu His Ser
            370                 375                 380

Asp Tyr Met Asn Met Thr Pro Arg Arg Pro Gly Pro Thr Arg Lys His
385                 390                 395                 400

Tyr Gln Pro Tyr Ala Pro Pro Arg Asp Phe Ala Ala Tyr Arg Ser Gly
            405                 410                 415

Val Gln Val Glu Thr Ile Ser Pro Gly Asp Gly Arg Thr Phe Pro Lys
            420                 425                 430

Arg Gly Gln Thr Cys Val Val His Tyr Thr Gly Met Leu Glu Asp Gly
            435                 440                 445

Lys Lys Phe Asp Ser Ser Arg Asp Arg Asn Lys Pro Phe Lys Phe Met
            450                 455                 460

Leu Gly Lys Gln Glu Val Ile Arg Gly Trp Glu Glu Gly Val Ala Gln
465                 470                 475                 480
```

```
Met Ser Val Gly Gln Arg Ala Lys Leu Thr Ile Ser Pro Asp Tyr Ala
                485                 490                 495

Tyr Gly Ala Thr Gly His Pro Gly Ile Ile Pro Pro His Ala Thr Leu
            500                 505                 510

Val Phe Asp Val Glu Leu Leu Lys Leu Glu
        515                 520

<210> SEQ ID NO 294
<211> LENGTH: 508
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 294

Met Ala Leu Pro Val Thr Ala Leu Leu Leu Pro Leu Ala Leu Leu Leu
1               5                   10                  15

His Ala Ala Arg Pro Glu Ile Val Met Thr Gln Ser Pro Ala Thr Leu
                20                  25                  30

Ser Leu Ser Pro Gly Glu Arg Ala Thr Leu Ser Cys Arg Ala Ser Gln
            35                  40                  45

Asp Ile Ser Lys Tyr Leu Asn Trp Tyr Gln Gln Lys Pro Gly Gln Ala
        50                  55                  60

Pro Arg Leu Leu Ile Tyr His Thr Ser Arg Leu His Ser Gly Ile Pro
65                  70                  75                  80

Ala Arg Phe Ser Gly Ser Gly Ser Gly Thr Asp Tyr Thr Leu Thr Ile
                85                  90                  95

Ser Ser Leu Gln Pro Glu Asp Phe Ala Val Tyr Phe Cys Gln Gln Gly
                100                 105                 110

Asn Thr Leu Pro Tyr Thr Phe Gly Gln Gly Thr Lys Leu Glu Ile Lys
            115                 120                 125

Gly Gly Gly Gly Ser Gly Gly Gly Ser Gly Gly Gly Ser Gln
        130                 135                 140

Val Gln Leu Gln Glu Ser Gly Pro Gly Leu Val Lys Pro Ser Glu Thr
145                 150                 155                 160

Leu Ser Leu Thr Cys Thr Val Ser Gly Val Ser Leu Pro Asp Tyr Gly
                165                 170                 175

Val Ser Trp Ile Arg Gln Pro Pro Gly Lys Gly Leu Glu Trp Ile Gly
            180                 185                 190

Val Ile Trp Gly Ser Glu Thr Thr Tyr Tyr Ser Ser Ser Leu Lys Ser
        195                 200                 205

Arg Val Thr Ile Ser Lys Asp Asn Ser Lys Asn Gln Val Ser Leu Lys
    210                 215                 220

Leu Ser Ser Val Thr Ala Ala Asp Thr Ala Val Tyr Tyr Cys Ala Lys
225                 230                 235                 240

His Tyr Tyr Tyr Gly Gly Ser Tyr Ala Met Asp Tyr Trp Gly Gln Gly
                245                 250                 255

Thr Leu Val Thr Val Ser Ser Thr Thr Thr Pro Ala Pro Arg Pro Pro
            260                 265                 270

Thr Pro Ala Pro Thr Ile Ala Ser Gln Pro Leu Ser Leu Arg Pro Glu
        275                 280                 285

Ala Cys Arg Pro Ala Ala Gly Gly Ala Val His Thr Arg Gly Leu Asp
    290                 295                 300

Phe Ala Cys Asp Ile Tyr Ile Trp Ala Pro Leu Ala Gly Thr Cys Gly
305                 310                 315                 320
```

```
Val Leu Leu Leu Ser Leu Val Ile Thr Leu Tyr Cys Ala Leu Tyr Leu
            325                 330                 335

Leu Arg Arg Asp Gln Arg Leu Pro Pro Asp Ala His Lys Pro Pro Gly
            340                 345                 350

Gly Gly Ser Phe Arg Thr Pro Ile Gln Glu Gln Ala Asp Ala His
            355                 360                 365

Ser Thr Leu Ala Lys Ile Arg Ser Lys Arg Ser Arg Leu Leu His Ser
370                 375                 380

Asp Tyr Met Asn Met Thr Pro Arg Arg Pro Gly Pro Thr Arg Lys His
385                 390                 395                 400

Tyr Gln Pro Tyr Ala Pro Pro Arg Asp Phe Ala Ala Tyr Arg Ser Ile
            405                 410                 415

Leu Trp His Glu Met Trp His Glu Gly Leu Ile Glu Ala Ser Arg Leu
            420                 425                 430

Tyr Phe Gly Glu Arg Asn Val Lys Gly Met Phe Glu Val Leu Glu Pro
            435                 440                 445

Leu His Ala Met Met Glu Arg Gly Pro Gln Thr Leu Lys Glu Thr Ser
    450                 455                 460

Phe Asn Gln Ala Tyr Gly Arg Asp Leu Met Glu Ala Gln Glu Trp Cys
465                 470                 475                 480

Arg Lys Tyr Met Lys Ser Gly Asn Val Lys Asp Leu Leu Gln Ala Trp
            485                 490                 495

Asp Leu Tyr Tyr His Val Phe Arg Arg Ile Ser Lys
            500                 505

<210> SEQ ID NO 295
<211> LENGTH: 528
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 295

Met Ala Leu Pro Val Thr Ala Leu Leu Leu Pro Leu Ala Leu Leu Leu
1               5                   10                  15

His Ala Ala Arg Pro Glu Ile Val Met Thr Gln Ser Pro Ala Thr Leu
            20                  25                  30

Ser Leu Ser Pro Gly Glu Arg Ala Thr Leu Ser Cys Arg Ala Ser Gln
        35                  40                  45

Asp Ile Ser Lys Tyr Leu Asn Trp Tyr Gln Gln Lys Pro Gly Gln Ala
    50                  55                  60

Pro Arg Leu Leu Ile Tyr His Thr Ser Arg Leu His Ser Gly Ile Pro
65                  70                  75                  80

Ala Arg Phe Ser Gly Ser Gly Ser Gly Thr Asp Tyr Thr Leu Thr Ile
            85                  90                  95

Ser Ser Leu Gln Pro Glu Asp Phe Ala Val Tyr Phe Cys Gln Gln Gly
            100                 105                 110

Asn Thr Leu Pro Tyr Thr Phe Gly Gln Gly Thr Lys Leu Glu Ile Lys
        115                 120                 125

Gly Gly Gly Gly Ser Gly Gly Gly Ser Gly Gly Gly Gly Ser Gln
    130                 135                 140

Val Gln Leu Gln Glu Ser Gly Pro Gly Leu Val Lys Pro Ser Glu Thr
145                 150                 155                 160

Leu Ser Leu Thr Cys Thr Val Ser Gly Val Ser Leu Pro Asp Tyr Gly
```

```
            165                 170                 175
Val Ser Trp Ile Arg Gln Pro Pro Gly Lys Gly Leu Glu Trp Ile Gly
            180                 185                 190

Val Ile Trp Gly Ser Glu Thr Thr Tyr Tyr Ser Ser Leu Lys Ser
        195                 200                 205

Arg Val Thr Ile Ser Lys Asp Asn Ser Lys Asn Gln Val Ser Leu Lys
        210                 215                 220

Leu Ser Ser Val Thr Ala Ala Asp Thr Ala Val Tyr Tyr Cys Ala Lys
225                 230                 235                 240

His Tyr Tyr Tyr Gly Gly Ser Tyr Ala Met Asp Tyr Trp Gly Gln Gly
                245                 250                 255

Thr Leu Val Thr Val Ser Ser Thr Thr Thr Pro Ala Pro Arg Pro Pro
            260                 265                 270

Thr Pro Ala Pro Thr Ile Ala Ser Gln Pro Leu Ser Leu Arg Pro Glu
            275                 280                 285

Ala Cys Arg Pro Ala Ala Gly Gly Ala Val His Thr Arg Gly Leu Asp
        290                 295                 300

Phe Ala Cys Asp Ile Tyr Ile Trp Ala Pro Leu Ala Gly Thr Cys Gly
305                 310                 315                 320

Val Leu Leu Leu Ser Leu Val Ile Thr Leu Tyr Cys Gln Arg Arg Lys
                325                 330                 335

Tyr Arg Ser Asn Lys Gly Glu Ser Pro Val Glu Pro Ala Glu Pro Cys
                340                 345                 350

His Tyr Ser Cys Pro Arg Glu Glu Glu Gly Ser Thr Ile Pro Ile Gln
            355                 360                 365

Glu Asp Tyr Arg Lys Pro Glu Pro Ala Cys Ser Pro Arg Ser Lys Arg
        370                 375                 380

Ser Arg Leu Leu His Ser Asp Tyr Met Asn Met Thr Pro Arg Arg Pro
385                 390                 395                 400

Gly Pro Thr Arg Lys His Tyr Gln Pro Tyr Ala Pro Pro Arg Asp Phe
                405                 410                 415

Ala Ala Tyr Arg Ser Gly Val Gln Val Glu Thr Ile Ser Pro Gly Asp
            420                 425                 430

Gly Arg Thr Phe Pro Lys Arg Gly Gln Thr Cys Val Val His Tyr Thr
        435                 440                 445

Gly Met Leu Glu Asp Gly Lys Lys Phe Asp Ser Ser Arg Asp Arg Asn
450                 455                 460

Lys Pro Phe Lys Phe Met Leu Gly Lys Gln Glu Val Ile Arg Gly Trp
465                 470                 475                 480

Glu Glu Gly Val Ala Gln Met Ser Val Gly Gln Arg Ala Lys Leu Thr
            485                 490                 495

Ile Ser Pro Asp Tyr Ala Tyr Gly Ala Thr Gly His Pro Gly Ile Ile
        500                 505                 510

Pro Pro His Ala Thr Leu Val Phe Asp Val Glu Leu Leu Lys Leu Glu
        515                 520                 525
```

<210> SEQ ID NO 296
<211> LENGTH: 514
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 296

-continued

Met Ala Leu Pro Val Thr Ala Leu Leu Leu Pro Leu Ala Leu Leu Leu
1               5                   10                  15

His Ala Ala Arg Pro Glu Ile Val Met Thr Gln Ser Pro Ala Thr Leu
            20                  25                  30

Ser Leu Ser Pro Gly Glu Arg Ala Thr Leu Ser Cys Arg Ala Ser Gln
        35                  40                  45

Asp Ile Ser Lys Tyr Leu Asn Trp Tyr Gln Gln Lys Pro Gly Gln Ala
    50                  55                  60

Pro Arg Leu Leu Ile Tyr His Thr Ser Arg Leu His Ser Gly Ile Pro
65                  70                  75                  80

Ala Arg Phe Ser Gly Ser Gly Ser Gly Thr Asp Tyr Thr Leu Thr Ile
                85                  90                  95

Ser Ser Leu Gln Pro Glu Asp Phe Ala Val Tyr Phe Cys Gln Gln Gly
            100                 105                 110

Asn Thr Leu Pro Tyr Thr Phe Gly Gln Gly Thr Lys Leu Glu Ile Lys
        115                 120                 125

Gly Gly Gly Gly Ser Gly Gly Gly Gly Ser Gly Gly Gly Gly Ser Gln
    130                 135                 140

Val Gln Leu Gln Glu Ser Gly Pro Gly Leu Val Lys Pro Ser Glu Thr
145                 150                 155                 160

Leu Ser Leu Thr Cys Thr Val Ser Gly Val Ser Leu Pro Asp Tyr Gly
                165                 170                 175

Val Ser Trp Ile Arg Gln Pro Pro Gly Lys Gly Leu Glu Trp Ile Gly
            180                 185                 190

Val Ile Trp Gly Ser Glu Thr Thr Tyr Tyr Ser Ser Ser Leu Lys Ser
            195                 200                 205

Arg Val Thr Ile Ser Lys Asp Asn Ser Lys Asn Gln Val Ser Leu Lys
    210                 215                 220

Leu Ser Ser Val Thr Ala Ala Asp Thr Ala Val Tyr Tyr Cys Ala Lys
225                 230                 235                 240

His Tyr Tyr Tyr Gly Gly Ser Tyr Ala Met Asp Tyr Trp Gly Gln Gly
                245                 250                 255

Thr Leu Val Thr Val Ser Ser Thr Thr Thr Pro Ala Pro Arg Pro Pro
            260                 265                 270

Thr Pro Ala Pro Thr Ile Ala Ser Gln Pro Leu Ser Leu Arg Pro Glu
    275                 280                 285

Ala Cys Arg Pro Ala Ala Gly Gly Ala Val His Thr Arg Gly Leu Asp
                290                 295                 300

Phe Ala Cys Asp Ile Tyr Ile Trp Ala Pro Leu Ala Gly Thr Cys Gly
305                 310                 315                 320

Val Leu Leu Leu Ser Leu Val Ile Thr Leu Tyr Cys Gln Arg Arg Lys
                325                 330                 335

Tyr Arg Ser Asn Lys Gly Glu Ser Pro Val Glu Pro Ala Glu Pro Cys
            340                 345                 350

His Tyr Ser Cys Pro Arg Glu Glu Gly Ser Thr Ile Pro Ile Gln
            355                 360                 365

Glu Asp Tyr Arg Lys Pro Glu Pro Ala Cys Ser Pro Arg Ser Lys Arg
    370                 375                 380

Ser Arg Leu Leu His Ser Asp Tyr Met Asn Met Thr Pro Arg Arg Pro
385                 390                 395                 400

Gly Pro Thr Arg Lys His Tyr Gln Pro Tyr Ala Pro Pro Arg Asp Phe
            405                 410                 415

Ala Ala Tyr Arg Ser Ile Leu Trp His Glu Met Trp His Glu Gly Leu

```
            420                 425                 430
Ile Glu Ala Ser Arg Leu Tyr Phe Gly Glu Arg Asn Val Lys Gly Met
            435                 440                 445

Phe Glu Val Leu Glu Pro Leu His Ala Met Met Glu Arg Gly Pro Gln
450                 455                 460

Thr Leu Lys Glu Thr Ser Phe Asn Gln Ala Tyr Gly Arg Asp Leu Met
465                 470                 475                 480

Glu Ala Gln Glu Trp Cys Arg Lys Tyr Met Lys Ser Gly Asn Val Lys
            485                 490                 495

Asp Leu Leu Gln Ala Trp Asp Leu Tyr Tyr His Val Phe Arg Arg Ile
            500                 505                 510

Ser Lys

<210> SEQ ID NO 297
<211> LENGTH: 522
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 297

Met Ala Leu Pro Val Thr Ala Leu Leu Leu Pro Leu Ala Leu Leu Leu
1               5                   10                  15

His Ala Ala Arg Pro Glu Ile Val Met Thr Gln Ser Pro Ala Thr Leu
            20                  25                  30

Ser Leu Ser Pro Gly Glu Arg Ala Thr Leu Ser Cys Arg Ala Ser Gln
        35                  40                  45

Asp Ile Ser Lys Tyr Leu Asn Trp Tyr Gln Gln Lys Pro Gly Gln Ala
    50                  55                  60

Pro Arg Leu Leu Ile Tyr His Thr Ser Arg Leu His Ser Gly Ile Pro
65                  70                  75                  80

Ala Arg Phe Ser Gly Ser Gly Ser Gly Thr Asp Tyr Thr Leu Thr Ile
                85                  90                  95

Ser Ser Leu Gln Pro Glu Asp Phe Ala Val Tyr Phe Cys Gln Gln Gly
            100                 105                 110

Asn Thr Leu Pro Tyr Thr Phe Gly Gln Gly Thr Lys Leu Glu Ile Lys
        115                 120                 125

Gly Gly Gly Gly Ser Gly Gly Gly Gly Ser Gly Gly Gly Gly Ser Gln
    130                 135                 140

Val Gln Leu Gln Glu Ser Gly Pro Gly Leu Val Lys Pro Ser Glu Thr
145                 150                 155                 160

Leu Ser Leu Thr Cys Thr Val Ser Gly Val Ser Leu Pro Asp Tyr Gly
                165                 170                 175

Val Ser Trp Ile Arg Gln Pro Pro Gly Lys Gly Leu Glu Trp Ile Gly
            180                 185                 190

Val Ile Trp Gly Ser Glu Thr Thr Tyr Tyr Ser Ser Ser Leu Lys Ser
        195                 200                 205

Arg Val Thr Ile Ser Lys Asp Asn Ser Lys Asn Gln Val Ser Leu Lys
    210                 215                 220

Leu Ser Ser Val Thr Ala Ala Asp Thr Ala Val Tyr Tyr Cys Ala Lys
225                 230                 235                 240

His Tyr Tyr Tyr Gly Gly Ser Tyr Ala Met Asp Tyr Trp Gly Gln Gly
                245                 250                 255

Thr Leu Val Thr Val Ser Ser Thr Thr Thr Pro Ala Pro Arg Pro Pro
```

```
                    260                 265                 270
Thr Pro Ala Pro Thr Ile Ala Ser Gln Pro Leu Ser Leu Arg Pro Glu
            275                 280                 285

Ala Cys Arg Pro Ala Ala Gly Gly Ala Val His Thr Arg Gly Leu Asp
        290                 295                 300

Phe Ala Cys Asp Ile Tyr Ile Trp Ala Pro Leu Ala Gly Thr Cys Gly
305                 310                 315                 320

Val Leu Leu Leu Ser Leu Val Ile Thr Leu Tyr Cys Lys Arg Gly Arg
                325                 330                 335

Lys Lys Leu Leu Tyr Ile Phe Lys Gln Pro Phe Met Arg Pro Val Gln
            340                 345                 350

Thr Thr Gln Glu Glu Asp Gly Cys Ser Cys Arg Phe Pro Glu Glu Glu
        355                 360                 365

Glu Gly Gly Cys Glu Leu Arg Ser Lys Arg Ser Arg Leu Leu His Ser
    370                 375                 380

Asp Tyr Met Asn Met Thr Pro Arg Arg Pro Gly Pro Thr Arg Lys His
385                 390                 395                 400

Tyr Gln Pro Tyr Ala Pro Pro Arg Asp Phe Ala Ala Tyr Arg Ser Gly
                405                 410                 415

Val Gln Val Glu Thr Ile Ser Pro Gly Asp Gly Arg Thr Phe Pro Lys
            420                 425                 430

Arg Gly Gln Thr Cys Val Val His Tyr Thr Gly Met Leu Glu Asp Gly
        435                 440                 445

Lys Lys Phe Asp Ser Ser Arg Asp Arg Asn Lys Pro Phe Lys Phe Met
    450                 455                 460

Leu Gly Lys Gln Glu Val Ile Arg Gly Trp Glu Glu Gly Val Ala Gln
465                 470                 475                 480

Met Ser Val Gly Gln Arg Ala Lys Leu Thr Ile Ser Pro Asp Tyr Ala
                485                 490                 495

Tyr Gly Ala Thr Gly His Pro Gly Ile Ile Pro Pro His Ala Thr Leu
            500                 505                 510

Val Phe Asp Val Glu Leu Leu Lys Leu Glu
        515                 520

<210> SEQ ID NO 298
<211> LENGTH: 508
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 298

Met Ala Leu Pro Val Thr Ala Leu Leu Leu Pro Leu Ala Leu Leu Leu
1               5                   10                  15

His Ala Ala Arg Pro Glu Ile Val Met Thr Gln Ser Pro Ala Thr Leu
            20                  25                  30

Ser Leu Ser Pro Gly Glu Arg Ala Thr Leu Ser Cys Arg Ala Ser Gln
        35                  40                  45

Asp Ile Ser Lys Tyr Leu Asn Trp Tyr Gln Gln Lys Pro Gly Gln Ala
    50                  55                  60

Pro Arg Leu Leu Ile Tyr His Thr Ser Arg Leu His Ser Gly Ile Pro
65                  70                  75                  80

Ala Arg Phe Ser Gly Ser Gly Ser Gly Thr Asp Tyr Thr Leu Thr Ile
                85                  90                  95
```

```
Ser Ser Leu Gln Pro Glu Asp Phe Ala Val Tyr Phe Cys Gln Gln Gly
                100                 105                 110

Asn Thr Leu Pro Tyr Thr Phe Gly Gln Gly Thr Lys Leu Glu Ile Lys
            115                 120                 125

Gly Gly Gly Gly Ser Gly Gly Gly Gly Ser Gly Gly Gly Gly Ser Gln
        130                 135                 140

Val Gln Leu Gln Glu Ser Gly Pro Gly Leu Val Lys Pro Ser Glu Thr
145                 150                 155                 160

Leu Ser Leu Thr Cys Thr Val Ser Gly Val Ser Leu Pro Asp Tyr Gly
                165                 170                 175

Val Ser Trp Ile Arg Gln Pro Pro Gly Lys Gly Leu Glu Trp Ile Gly
            180                 185                 190

Val Ile Trp Gly Ser Glu Thr Thr Tyr Tyr Ser Ser Leu Lys Ser
            195                 200                 205

Arg Val Thr Ile Ser Lys Asp Asn Ser Lys Asn Gln Val Ser Leu Lys
            210                 215                 220

Leu Ser Ser Val Thr Ala Ala Asp Thr Ala Val Tyr Tyr Cys Ala Lys
225                 230                 235                 240

His Tyr Tyr Tyr Gly Gly Ser Tyr Ala Met Asp Tyr Trp Gly Gln Gly
                245                 250                 255

Thr Leu Val Thr Val Ser Ser Thr Thr Thr Pro Ala Pro Arg Pro Pro
            260                 265                 270

Thr Pro Ala Pro Thr Ile Ala Ser Gln Pro Leu Ser Leu Arg Pro Glu
            275                 280                 285

Ala Cys Arg Pro Ala Ala Gly Gly Ala Val His Thr Arg Gly Leu Asp
            290                 295                 300

Phe Ala Cys Asp Ile Tyr Ile Trp Ala Pro Leu Ala Gly Thr Cys Gly
305                 310                 315                 320

Val Leu Leu Leu Ser Leu Val Ile Thr Leu Tyr Cys Lys Arg Gly Arg
                325                 330                 335

Lys Lys Leu Leu Tyr Ile Phe Lys Gln Pro Phe Met Arg Pro Val Gln
            340                 345                 350

Thr Thr Gln Glu Glu Asp Gly Cys Ser Cys Arg Phe Pro Glu Glu Glu
            355                 360                 365

Glu Gly Gly Cys Glu Leu Arg Ser Lys Arg Ser Arg Leu Leu His Ser
370                 375                 380

Asp Tyr Met Asn Met Thr Pro Arg Arg Pro Gly Pro Thr Arg Lys His
385                 390                 395                 400

Tyr Gln Pro Tyr Ala Pro Pro Arg Asp Phe Ala Ala Tyr Arg Ser Ile
            405                 410                 415

Leu Trp His Glu Met Trp His Glu Gly Leu Ile Glu Ala Ser Arg Leu
            420                 425                 430

Tyr Phe Gly Glu Arg Asn Val Lys Gly Met Phe Glu Val Leu Glu Pro
            435                 440                 445

Leu His Ala Met Met Glu Arg Gly Pro Gln Thr Leu Lys Glu Thr Ser
450                 455                 460

Phe Asn Gln Ala Tyr Gly Arg Asp Leu Met Glu Ala Gln Glu Trp Cys
465                 470                 475                 480

Arg Lys Tyr Met Lys Ser Gly Asn Val Lys Asp Leu Leu Gln Ala Trp
                485                 490                 495

Asp Leu Tyr Tyr His Val Phe Arg Arg Ile Ser Lys
                500                 505
```

-continued

```
<210> SEQ ID NO 299
<211> LENGTH: 206
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 299

Met Ile Leu Trp His Glu Met Trp His Glu Gly Leu Ile Glu Ala Ser
1               5                   10                  15

Arg Leu Tyr Phe Gly Glu Arg Asn Val Lys Gly Met Phe Glu Val Leu
            20                  25                  30

Glu Pro Leu His Ala Met Met Glu Arg Gly Pro Gln Thr Leu Lys Glu
        35                  40                  45

Thr Ser Phe Asn Gln Ala Tyr Gly Arg Asp Leu Met Glu Ala Gln Glu
    50                  55                  60

Trp Cys Arg Lys Tyr Met Lys Ser Gly Asn Val Lys Asp Leu Leu Gln
65                  70                  75                  80

Ala Trp Asp Leu Tyr Tyr His Val Phe Arg Arg Ile Ser Lys Arg Val
                85                  90                  95

Lys Phe Ser Arg Ser Ala Asp Ala Pro Ala Tyr Lys Gln Gly Gln Asn
            100                 105                 110

Gln Leu Tyr Asn Glu Leu Asn Leu Gly Arg Arg Glu Glu Tyr Asp Val
        115                 120                 125

Leu Asp Lys Arg Arg Gly Arg Asp Pro Glu Met Gly Gly Lys Pro Arg
    130                 135                 140

Arg Lys Asn Pro Gln Glu Gly Leu Tyr Asn Glu Leu Gln Lys Asp Lys
145                 150                 155                 160

Met Ala Glu Ala Tyr Ser Glu Ile Gly Met Lys Gly Glu Arg Arg Arg
                165                 170                 175

Gly Lys Gly His Asp Gly Leu Tyr Gln Gly Leu Ser Thr Ala Thr Lys
            180                 185                 190

Asp Thr Tyr Asp Ala Leu His Met Gln Ala Leu Pro Pro Arg
        195                 200                 205

<210> SEQ ID NO 300
<211> LENGTH: 225
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 300

Met Gly Val Gln Val Glu Thr Ile Ser Pro Gly Asp Gly Arg Thr Phe
1               5                   10                  15

Pro Lys Arg Gly Gln Thr Cys Val Val His Tyr Thr Gly Met Leu Glu
            20                  25                  30

Asp Gly Lys Lys Phe Asp Ser Ser Arg Asp Arg Asn Lys Pro Phe Lys
        35                  40                  45

Phe Met Leu Gly Lys Gln Glu Val Ile Arg Gly Trp Glu Glu Gly Val
    50                  55                  60

Ala Gln Met Ser Val Gly Gln Arg Ala Lys Leu Thr Ile Ser Pro Asp
65                  70                  75                  80

Tyr Ala Tyr Gly Ala Thr Gly His Pro Gly Ile Ile Pro Pro His Ala
                85                  90                  95

Thr Leu Val Phe Asp Val Glu Leu Leu Lys Leu Glu Gly Gly Gly Gly
```

```
                100                 105                 110
Ser Arg Val Lys Phe Ser Arg Ser Ala Asp Ala Pro Ala Tyr Lys Gln
            115                 120                 125
Gly Gln Asn Gln Leu Tyr Asn Glu Leu Asn Leu Gly Arg Arg Glu Glu
        130                 135                 140
Tyr Asp Val Leu Asp Lys Arg Gly Arg Asp Pro Glu Met Gly Gly
145                 150                 155                 160
Lys Pro Arg Arg Lys Asn Pro Gln Glu Gly Leu Tyr Asn Glu Leu Gln
                165                 170                 175
Lys Asp Lys Met Ala Glu Ala Tyr Ser Glu Ile Gly Met Lys Gly Glu
            180                 185                 190
Arg Arg Arg Gly Lys Gly His Asp Gly Leu Tyr Gln Gly Leu Ser Thr
        195                 200                 205
Ala Thr Lys Asp Thr Tyr Asp Ala Leu His Met Gln Ala Leu Pro Pro
    210                 215                 220
Arg
225

<210> SEQ ID NO 301
<211> LENGTH: 110
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (26)..(26)
<223> OTHER INFORMATION: Any amino acid

<400> SEQUENCE: 301

Met Gly His His His His His His His Gly Ser Ala Ser Arg Ile
1               5                   10                  15

Leu Trp His Glu Met Trp His Glu Gly Xaa Glu Glu Ala Ser Arg Leu
            20                  25                  30

Tyr Phe Gly Glu Arg Asn Val Lys Gly Met Phe Glu Val Leu Glu Pro
        35                  40                  45

Leu His Ala Met Met Glu Arg Gly Pro Gln Thr Leu Lys Glu Thr Ser
    50                  55                  60

Phe Asn Gln Ala Tyr Gly Arg Asp Leu Met Glu Ala Gln Glu Trp Cys
65                  70                  75                  80

Arg Lys Tyr Met Lys Ser Gly Asn Val Lys Asp Leu Thr Gln Ala Trp
                85                  90                  95

Asp Leu Tyr Tyr His Val Phe Arg Arg Ile Ser Lys Thr Ser
            100                 105                 110

<210> SEQ ID NO 302
<211> LENGTH: 110
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (27)..(27)
<223> OTHER INFORMATION: Any amino acid

<400> SEQUENCE: 302

Met Gly His His His His His His His Gly Ser Ala Ser Arg Ile
1               5                   10                  15
```

```
Leu Trp His Glu Met Trp His Glu Gly Leu Xaa Glu Ala Ser Arg Leu
            20                  25                  30

Tyr Phe Gly Glu Arg Asn Val Lys Gly Met Phe Glu Val Leu Glu Pro
        35                  40                  45

Leu His Ala Met Met Glu Arg Gly Pro Gln Thr Leu Lys Glu Thr Ser
    50                  55                  60

Phe Asn Gln Ala Tyr Gly Arg Asp Leu Met Glu Ala Gln Glu Trp Cys
65                  70                  75                  80

Arg Lys Tyr Met Lys Ser Gly Asn Val Lys Asp Leu Thr Gln Ala Trp
                85                  90                  95

Asp Leu Tyr Tyr His Val Phe Arg Arg Ile Ser Lys Thr Ser
            100                 105                 110

<210> SEQ ID NO 303
<211> LENGTH: 110
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (30)..(30)
<223> OTHER INFORMATION: Any amino acid

<400> SEQUENCE: 303

Met Gly His His His His His His His Gly Ser Ala Ser Arg Ile
1               5                   10                  15

Leu Trp His Glu Met Trp His Gly Leu Glu Glu Ala Xaa Arg Leu
            20                  25                  30

Tyr Phe Gly Glu Arg Asn Val Lys Gly Met Phe Glu Val Leu Glu Pro
        35                  40                  45

Leu His Ala Met Met Glu Arg Gly Pro Gln Thr Leu Lys Glu Thr Ser
    50                  55                  60

Phe Asn Gln Ala Tyr Gly Arg Asp Leu Met Glu Ala Gln Glu Trp Cys
65                  70                  75                  80

Arg Lys Tyr Met Lys Ser Gly Asn Val Lys Asp Leu Thr Gln Ala Trp
                85                  90                  95

Asp Leu Tyr Tyr His Val Phe Arg Arg Ile Ser Lys Thr Ser
            100                 105                 110

<210> SEQ ID NO 304
<211> LENGTH: 110
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (31)..(31)
<223> OTHER INFORMATION: Any amino acid

<400> SEQUENCE: 304

Met Gly His His His His His His His Gly Ser Ala Ser Arg Ile
1               5                   10                  15

Leu Trp His Glu Met Trp His Gly Leu Glu Glu Ala Ser Xaa Leu
            20                  25                  30

Tyr Phe Gly Glu Arg Asn Val Lys Gly Met Phe Glu Val Leu Glu Pro
        35                  40                  45
```

```
Leu His Ala Met Met Glu Arg Gly Pro Gln Thr Leu Lys Glu Thr Ser
 50                  55                  60

Phe Asn Gln Ala Tyr Gly Arg Asp Leu Met Glu Ala Gln Glu Trp Cys
 65                  70                  75                  80

Arg Lys Tyr Met Lys Ser Gly Asn Val Lys Asp Leu Thr Gln Ala Trp
                 85                  90                  95

Asp Leu Tyr Tyr His Val Phe Arg Arg Ile Ser Lys Thr Ser
            100                 105                 110

<210> SEQ ID NO 305
<211> LENGTH: 110
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (34)..(34)
<223> OTHER INFORMATION: Any amino acid

<400> SEQUENCE: 305

Met Gly His His His His His His His Gly Ser Ala Ser Arg Ile
 1               5                  10                  15

Leu Trp His Glu Met Trp His Glu Gly Leu Glu Glu Ala Ser Arg Leu
                 20                  25                  30

Tyr Xaa Gly Glu Arg Asn Val Lys Gly Met Phe Glu Val Leu Glu Pro
             35                  40                  45

Leu His Ala Met Met Glu Arg Gly Pro Gln Thr Leu Lys Glu Thr Ser
 50                  55                  60

Phe Asn Gln Ala Tyr Gly Arg Asp Leu Met Glu Ala Gln Glu Trp Cys
 65                  70                  75                  80

Arg Lys Tyr Met Lys Ser Gly Asn Val Lys Asp Leu Thr Gln Ala Trp
                 85                  90                  95

Asp Leu Tyr Tyr His Val Phe Arg Arg Ile Ser Lys Thr Ser
            100                 105                 110

<210> SEQ ID NO 306
<211> LENGTH: 110
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (35)..(35)
<223> OTHER INFORMATION: Any amino acid

<400> SEQUENCE: 306

Met Gly His His His His His His His Gly Ser Ala Ser Arg Ile
 1               5                  10                  15

Leu Trp His Glu Met Trp His Glu Gly Leu Glu Glu Ala Ser Arg Leu
                 20                  25                  30

Tyr Phe Xaa Glu Arg Asn Val Lys Gly Met Phe Glu Val Leu Glu Pro
             35                  40                  45

Leu His Ala Met Met Glu Arg Gly Pro Gln Thr Leu Lys Glu Thr Ser
 50                  55                  60

Phe Asn Gln Ala Tyr Gly Arg Asp Leu Met Glu Ala Gln Glu Trp Cys
 65                  70                  75                  80

Arg Lys Tyr Met Lys Ser Gly Asn Val Lys Asp Leu Thr Gln Ala Trp
```

```
                    85                  90                  95

Asp Leu Tyr Tyr His Val Phe Arg Arg Ile Ser Lys Thr Ser
            100                 105                 110

<210> SEQ ID NO 307
<211> LENGTH: 110
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (93)..(93)
<223> OTHER INFORMATION: Any amino acid

<400> SEQUENCE: 307

Met Gly His His His His His His His Gly Ser Ala Ser Arg Ile
1               5                   10                  15

Leu Trp His Glu Met Trp His Glu Gly Leu Glu Glu Ala Ser Arg Leu
                20                  25                  30

Tyr Phe Gly Glu Arg Asn Val Lys Gly Met Phe Glu Val Leu Glu Pro
            35                  40                  45

Leu His Ala Met Met Glu Arg Gly Pro Gln Thr Leu Lys Glu Thr Ser
    50                  55                  60

Phe Asn Gln Ala Tyr Gly Arg Asp Leu Met Glu Ala Gln Glu Trp Cys
65                  70                  75                  80

Arg Lys Tyr Met Lys Ser Gly Asn Val Lys Asp Leu Xaa Gln Ala Trp
                85                  90                  95

Asp Leu Tyr Tyr His Val Phe Arg Arg Ile Ser Lys Thr Ser
            100                 105                 110

<210> SEQ ID NO 308
<211> LENGTH: 110
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (96)..(96)
<223> OTHER INFORMATION: Any amino acid

<400> SEQUENCE: 308

Met Gly His His His His His His His Gly Ser Ala Ser Arg Ile
1               5                   10                  15

Leu Trp His Glu Met Trp His Glu Gly Leu Glu Glu Ala Ser Arg Leu
                20                  25                  30

Tyr Phe Gly Glu Arg Asn Val Lys Gly Met Phe Glu Val Leu Glu Pro
            35                  40                  45

Leu His Ala Met Met Glu Arg Gly Pro Gln Thr Leu Lys Glu Thr Ser
    50                  55                  60

Phe Asn Gln Ala Tyr Gly Arg Asp Leu Met Glu Ala Gln Glu Trp Cys
65                  70                  75                  80

Arg Lys Tyr Met Lys Ser Gly Asn Val Lys Asp Leu Thr Gln Ala Xaa
                85                  90                  95

Asp Leu Tyr Tyr His Val Phe Arg Arg Ile Ser Lys Thr Ser
            100                 105                 110

<210> SEQ ID NO 309
```

```
<211> LENGTH: 110
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (97)..(97)
<223> OTHER INFORMATION: Any amino acid

<400> SEQUENCE: 309
```

Met Gly His His His His His His His Gly Ser Ala Ser Arg Ile
1               5                   10                  15

Leu Trp His Glu Met Trp His Glu Gly Leu Glu Glu Ala Ser Arg Leu
            20                  25                  30

Tyr Phe Gly Glu Arg Asn Val Lys Gly Met Phe Glu Val Leu Glu Pro
        35                  40                  45

Leu His Ala Met Met Glu Arg Gly Pro Gln Thr Leu Lys Glu Thr Ser
    50                  55                  60

Phe Asn Gln Ala Tyr Gly Arg Asp Leu Met Glu Ala Gln Glu Trp Cys
65                  70                  75                  80

Arg Lys Tyr Met Lys Ser Gly Asn Val Lys Asp Leu Thr Gln Ala Trp
                85                  90                  95

Xaa Leu Tyr Tyr His Val Phe Arg Arg Ile Ser Lys Thr Ser
            100                 105                 110

```
<210> SEQ ID NO 310
<211> LENGTH: 110
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (100)..(100)
<223> OTHER INFORMATION: Any amino acid

<400> SEQUENCE: 310
```

Met Gly His His His His His His His Gly Ser Ala Ser Arg Ile
1               5                   10                  15

Leu Trp His Glu Met Trp His Glu Gly Leu Glu Glu Ala Ser Arg Leu
            20                  25                  30

Tyr Phe Gly Glu Arg Asn Val Lys Gly Met Phe Glu Val Leu Glu Pro
        35                  40                  45

Leu His Ala Met Met Glu Arg Gly Pro Gln Thr Leu Lys Glu Thr Ser
    50                  55                  60

Phe Asn Gln Ala Tyr Gly Arg Asp Leu Met Glu Ala Gln Glu Trp Cys
65                  70                  75                  80

Arg Lys Tyr Met Lys Ser Gly Asn Val Lys Asp Leu Thr Gln Ala Trp
                85                  90                  95

Asp Leu Tyr Xaa His Val Phe Arg Arg Ile Ser Lys Thr Ser
            100                 105                 110

```
<210> SEQ ID NO 311
<211> LENGTH: 110
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
```

<221> NAME/KEY: MOD_RES
<222> LOCATION: (103)..(103)
<223> OTHER INFORMATION: Any amino acid

<400> SEQUENCE: 311

Met Gly His His His His His His His Gly Ser Ala Ser Arg Ile
1               5                   10                  15

Leu Trp His Glu Met Trp His Glu Gly Leu Glu Ala Ser Arg Leu
            20                  25                  30

Tyr Phe Gly Glu Arg Asn Val Lys Gly Met Phe Glu Val Leu Glu Pro
        35                  40                  45

Leu His Ala Met Met Glu Arg Gly Pro Gln Thr Leu Lys Glu Thr Ser
    50                  55                  60

Phe Asn Gln Ala Tyr Gly Arg Asp Leu Met Glu Ala Gln Glu Trp Cys
65                  70                  75                  80

Arg Lys Tyr Met Lys Ser Gly Asn Val Lys Asp Leu Thr Gln Ala Trp
                85                  90                  95

Asp Leu Tyr Tyr His Val Xaa Arg Arg Ile Ser Lys Thr Ser
            100                 105                 110

<210> SEQ ID NO 312
<211> LENGTH: 110
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 312

Met Gly His His His His His His His Gly Ser Ala Ser Arg Ile
1               5                   10                  15

Leu Trp His Glu Met Trp His Glu Gly Leu Glu Ala Ser Arg Leu
            20                  25                  30

Tyr Phe Gly Glu Arg Asn Val Lys Gly Met Phe Glu Val Leu Glu Pro
        35                  40                  45

Leu His Ala Met Met Glu Arg Gly Pro Gln Thr Leu Lys Glu Thr Ser
    50                  55                  60

Phe Asn Gln Ala Tyr Gly Arg Asp Leu Met Glu Ala Gln Glu Trp Cys
65                  70                  75                  80

Arg Lys Tyr Met Lys Ser Gly Asn Val Lys Asp Leu Thr Gln Ala Trp
                85                  90                  95

Asp Leu Tyr Tyr His Val Phe Arg Arg Ile Ser Lys Thr Ser
            100                 105                 110

<210> SEQ ID NO 313
<211> LENGTH: 110
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 313

Met Gly His His His His His His His Gly Ser Ala Ser Arg Ile
1               5                   10                  15

Leu Trp His Glu Met Trp His Glu Gly Leu Ile Glu Ala Ser Arg Leu
            20                  25                  30

Tyr Phe Gly Glu Arg Asn Val Lys Gly Met Phe Glu Val Leu Glu Pro
        35                  40                  45

Leu His Ala Met Met Glu Arg Gly Pro Gln Thr Leu Lys Glu Thr Ser
 50                  55                  60

Phe Asn Gln Ala Tyr Gly Arg Asp Leu Met Glu Ala Gln Glu Trp Cys
 65                  70                  75                  80

Arg Lys Tyr Met Lys Ser Gly Asn Val Lys Asp Leu Thr Gln Ala Trp
                 85                  90                  95

Asp Leu Tyr Tyr His Val Phe Arg Arg Ile Ser Lys Thr Ser
                100                 105                 110

<210> SEQ ID NO 314
<211> LENGTH: 110
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 314

Met Gly His His His His His His Gly Ser Ala Ser Arg Ile
 1               5                  10                  15

Leu Trp His Glu Met Trp His Glu Gly Leu Glu Ala Ser Arg Leu
                 20                  25                  30

Tyr Phe Gly Glu Arg Asn Val Lys Gly Met Phe Glu Val Leu Glu Pro
                 35                  40                  45

Leu His Ala Met Met Glu Arg Gly Pro Gln Thr Leu Lys Glu Thr Ser
 50                  55                  60

Phe Asn Gln Ala Tyr Gly Arg Asp Leu Met Glu Ala Gln Glu Trp Cys
 65                  70                  75                  80

Arg Lys Tyr Met Lys Ser Gly Asn Val Lys Asp Leu Thr Gln Ala Trp
                 85                  90                  95

Asp Leu Tyr Tyr His Val Phe Arg Arg Ile Ser Lys Thr Ser
                100                 105                 110

<210> SEQ ID NO 315
<211> LENGTH: 110
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 315

Met Gly His His His His His His Gly Ser Ala Ser Arg Ile
 1               5                  10                  15

Leu Trp His Glu Met Trp His Glu Gly Leu Glu Ala Ser Arg Leu
                 20                  25                  30

Tyr Phe Gly Glu Arg Asn Val Lys Gly Met Phe Glu Val Leu Glu Pro
                 35                  40                  45

Leu His Ala Met Met Glu Arg Gly Pro Gln Thr Leu Lys Glu Thr Ser
 50                  55                  60

Phe Asn Gln Ala Tyr Gly Arg Asp Leu Met Glu Ala Gln Glu Trp Cys
 65                  70                  75                  80

Arg Lys Tyr Met Lys Ser Gly Asn Val Lys Asp Leu Leu Gln Ala Trp
                 85                  90                  95

Asp Leu Tyr Tyr His Val Phe Arg Arg Ile Ser Lys Thr Ser
                100                 105                 110

<210> SEQ ID NO 316
<211> LENGTH: 110

```
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 316

Met Gly His His His His His His His Gly Ser Ala Ser Arg Ile
1               5                   10                  15

Leu Trp His Glu Met Trp His Glu Gly Leu Ile Glu Ala Ser Arg Leu
            20                  25                  30

Tyr Phe Gly Glu Arg Asn Val Lys Gly Met Phe Glu Val Leu Glu Pro
        35                  40                  45

Leu His Ala Met Met Glu Arg Gly Pro Gln Thr Leu Lys Glu Thr Ser
    50                  55                  60

Phe Asn Gln Ala Tyr Gly Arg Asp Leu Met Glu Ala Gln Glu Trp Cys
65                  70                  75                  80

Arg Lys Tyr Met Lys Ser Gly Asn Val Lys Asp Leu Leu Gln Ala Trp
                85                  90                  95

Asp Leu Tyr Tyr His Val Phe Arg Arg Ile Ser Lys Thr Ser
            100                 105                 110

<210> SEQ ID NO 317
<211> LENGTH: 110
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 317

Met Gly His His His His His His His Gly Ser Ala Ser Arg Ile
1               5                   10                  15

Leu Trp His Glu Met Trp His Glu Gly Leu Leu Glu Ala Ser Arg Leu
            20                  25                  30

Tyr Phe Gly Glu Arg Asn Val Lys Gly Met Phe Glu Val Leu Glu Pro
        35                  40                  45

Leu His Ala Met Met Glu Arg Gly Pro Gln Thr Leu Lys Glu Thr Ser
    50                  55                  60

Phe Asn Gln Ala Tyr Gly Arg Asp Leu Met Glu Ala Gln Glu Trp Cys
65                  70                  75                  80

Arg Lys Tyr Met Lys Ser Gly Asn Val Lys Asp Leu Leu Gln Ala Trp
                85                  90                  95

Asp Leu Tyr Tyr His Val Phe Arg Arg Ile Ser Lys Thr Ser
            100                 105                 110

<210> SEQ ID NO 318
<211> LENGTH: 120
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 318

Met Gly His His His His His His His Gly Ser Asp Tyr Lys Asp
1               5                   10                  15

Asp Asp Asp Lys Gly Ser Ala Ser Arg Ile Leu Trp His Glu Met Trp
            20                  25                  30

His Glu Gly Leu Glu Glu Ala Ser Arg Leu Tyr Phe Gly Glu Arg Asn
```

```
                35                  40                  45

Val Lys Gly Met Phe Glu Val Leu Glu Pro Leu His Ala Met Met Glu
     50                  55                  60

Arg Gly Pro Gln Thr Leu Lys Glu Thr Ser Phe Asn Gln Ala Tyr Gly
 65                  70                  75                  80

Arg Asp Leu Met Glu Ala Gln Glu Trp Cys Arg Lys Tyr Met Lys Ser
                 85                  90                  95

Gly Asn Val Lys Asp Leu Thr Gln Ala Trp Asp Leu Tyr Tyr His Val
            100                 105                 110

Phe Arg Arg Ile Ser Lys Thr Ser
            115                 120

<210> SEQ ID NO 319
<211> LENGTH: 120
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 319

Met Gly His His His His His His Gly Ser Asp Tyr Lys Asp
  1               5                  10                  15

Asp Asp Asp Lys Gly Ser Ala Ser Arg Ile Leu Trp His Glu Met Trp
             20                  25                  30

His Glu Gly Leu Ile Glu Ala Ser Arg Leu Tyr Phe Gly Glu Arg Asn
         35                  40                  45

Val Lys Gly Met Phe Glu Val Leu Glu Pro Leu His Ala Met Met Glu
     50                  55                  60

Arg Gly Pro Gln Thr Leu Lys Glu Thr Ser Phe Asn Gln Ala Tyr Gly
 65                  70                  75                  80

Arg Asp Leu Met Glu Ala Gln Glu Trp Cys Arg Lys Tyr Met Lys Ser
                 85                  90                  95

Gly Asn Val Lys Asp Leu Thr Gln Ala Trp Asp Leu Tyr Tyr His Val
            100                 105                 110

Phe Arg Arg Ile Ser Lys Thr Ser
            115                 120

<210> SEQ ID NO 320
<211> LENGTH: 120
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 320

Met Gly His His His His His His Gly Ser Asp Tyr Lys Asp
  1               5                  10                  15

Asp Asp Asp Lys Gly Ser Ala Ser Arg Ile Leu Trp His Glu Met Trp
             20                  25                  30

His Glu Gly Leu Leu Glu Ala Ser Arg Leu Tyr Phe Gly Glu Arg Asn
         35                  40                  45

Val Lys Gly Met Phe Glu Val Leu Glu Pro Leu His Ala Met Met Glu
     50                  55                  60

Arg Gly Pro Gln Thr Leu Lys Glu Thr Ser Phe Asn Gln Ala Tyr Gly
 65                  70                  75                  80

Arg Asp Leu Met Glu Ala Gln Glu Trp Cys Arg Lys Tyr Met Lys Ser
```

```
                    85                  90                  95

Gly Asn Val Lys Asp Leu Thr Gln Ala Trp Asp Leu Tyr Tyr His Val
                100                 105                 110

Phe Arg Arg Ile Ser Lys Thr Ser
            115                 120

<210> SEQ ID NO 321
<211> LENGTH: 120
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 321

Met Gly His His His His His His His Gly Ser Asp Tyr Lys Asp
1               5                   10                  15

Asp Asp Asp Lys Gly Ser Ala Ser Arg Ile Leu Trp His Glu Met Trp
                20                  25                  30

His Glu Gly Leu Glu Glu Ala Ser Arg Leu Tyr Phe Gly Glu Arg Asn
            35                  40                  45

Val Lys Gly Met Phe Glu Val Leu Glu Pro Leu His Ala Met Met Glu
        50                  55                  60

Arg Gly Pro Gln Thr Leu Lys Glu Thr Ser Phe Asn Gln Ala Tyr Gly
65                  70                  75                  80

Arg Asp Leu Met Glu Ala Gln Glu Trp Cys Arg Lys Tyr Met Lys Ser
                85                  90                  95

Gly Asn Val Lys Asp Leu Leu Gln Ala Trp Asp Leu Tyr Tyr His Val
                100                 105                 110

Phe Arg Arg Ile Ser Lys Thr Ser
            115                 120

<210> SEQ ID NO 322
<211> LENGTH: 120
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 322

Met Gly His His His His His His His Gly Ser Asp Tyr Lys Asp
1               5                   10                  15

Asp Asp Asp Lys Gly Ser Ala Ser Arg Ile Leu Trp His Glu Met Trp
                20                  25                  30

His Glu Gly Leu Ile Glu Ala Ser Arg Leu Tyr Phe Gly Glu Arg Asn
            35                  40                  45

Val Lys Gly Met Phe Glu Val Leu Glu Pro Leu His Ala Met Met Glu
        50                  55                  60

Arg Gly Pro Gln Thr Leu Lys Glu Thr Ser Phe Asn Gln Ala Tyr Gly
65                  70                  75                  80

Arg Asp Leu Met Glu Ala Gln Glu Trp Cys Arg Lys Tyr Met Lys Ser
                85                  90                  95

Gly Asn Val Lys Asp Leu Leu Gln Ala Trp Asp Leu Tyr Tyr His Val
                100                 105                 110

Phe Arg Arg Ile Ser Lys Thr Ser
            115                 120
```

```
<210> SEQ ID NO 323
<211> LENGTH: 120
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 323

Met Gly His His His His His His Gly Ser Asp Tyr Lys Asp
1               5                   10                  15

Asp Asp Asp Lys Gly Ser Ala Ser Arg Ile Leu Trp His Glu Met Trp
                20                  25                  30

His Glu Gly Leu Glu Ala Ser Arg Leu Tyr Phe Gly Glu Arg Asn
            35                  40                  45

Val Lys Gly Met Phe Glu Val Leu Glu Pro Leu His Ala Met Met Glu
    50                  55                  60

Arg Gly Pro Gln Thr Leu Lys Glu Thr Ser Phe Asn Gln Ala Tyr Gly
65                  70                  75                  80

Arg Asp Leu Met Glu Ala Gln Glu Trp Cys Arg Lys Tyr Met Lys Ser
                85                  90                  95

Gly Asn Val Lys Asp Leu Leu Gln Ala Trp Asp Leu Tyr Tyr His Val
            100                 105                 110

Phe Arg Arg Ile Ser Lys Thr Ser
        115                 120

<210> SEQ ID NO 324
<211> LENGTH: 136
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 324

Met Gly His His His His His His Gly Ser Gly Leu Asn Asp
1               5                   10                  15

Ile Phe Glu Ala Gln Lys Ile Glu Trp His Glu Gly Ser Gly Val Gln
                20                  25                  30

Val Glu Thr Ile Ser Pro Gly Asp Gly Arg Thr Phe Pro Lys Arg Gly
            35                  40                  45

Gln Thr Cys Val Val His Tyr Thr Gly Met Leu Glu Asp Gly Lys Lys
    50                  55                  60

Phe Asp Ser Ser Arg Asp Arg Asn Lys Pro Phe Lys Phe Met Leu Gly
65                  70                  75                  80

Lys Gln Glu Val Ile Arg Gly Trp Glu Glu Gly Val Ala Gln Met Ser
                85                  90                  95

Val Gly Gln Arg Ala Lys Leu Thr Ile Ser Pro Asp Tyr Ala Tyr Gly
            100                 105                 110

Ala Thr Gly His Pro Gly Ile Ile Pro Pro His Ala Thr Leu Val Phe
        115                 120                 125

Asp Val Glu Leu Leu Lys Leu Glu
    130                 135

<210> SEQ ID NO 325
<211> LENGTH: 58
<212> TYPE: DNA
<213> ORGANISM: Artificial Sequence
<220> FEATURE:
<223> OTHER INFORMATION: Description of Artificial Sequence: Synthetic
```

```
      oligonucleotide
<220> FEATURE:
<221> NAME/KEY: modified_base
<222> LOCATION: (2)..(22)
<223> OTHER INFORMATION: a, c, t, g, unknown or other
<220> FEATURE:
<221> NAME/KEY: modified_base
<222> LOCATION: (32)..(52)
<223> OTHER INFORMATION: a, c, t, g, unknown or other

<400> SEQUENCE: 325
gnnnnnnnnn nnnnnnnnnn nnttcaagag annnnnnnnn nnnnnnnnnn nnttttt         58

<210> SEQ ID NO 326
<211> LENGTH: 9
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 326 ttcaagaga                                                              9

<210> SEQ ID NO 327
<211> LENGTH: 40
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MISC_FEATURE
<222> LOCATION: (1)..(40)
<223> OTHER INFORMATION: This sequence may encompass 1-10 'Gly Gly Gly
      Ser' repeating units wherein some positions may be absent
<220> FEATURE:
<223> OTHER INFORMATION: See specification as filed for detailed
      description of substitutions and preferred embodiments

<400> SEQUENCE: 327

Gly Gly Gly Ser Gly Gly Gly Ser Gly Gly Gly Ser Gly Gly Gly Ser
1               5                   10                  15

Gly Gly Gly Ser Gly Gly Gly Ser Gly Gly Gly Ser Gly Gly Gly Ser
            20                  25                  30

Gly Gly Gly Ser Gly Gly Gly Ser
        35                  40

<210> SEQ ID NO 328
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 328

Gly Gly Gly Gly Ser Gly Gly Gly Gly Ser Gly Gly Gly Gly Ser Gly
1               5                   10                  15

Gly Gly Gly Ser
            20

<210> SEQ ID NO 329
<211> LENGTH: 15
<212> TYPE: PRT
<213> ORGANISM: Artificial Sequence
<220> FEATURE:
<223> OTHER INFORMATION: Description of Artificial Sequence: Synthetic
``` peptide

<400> SEQUENCE: 329

Gly Gly Gly Gly Ser Gly Gly Gly Gly Ser Gly Gly Gly Gly Ser
1               5                   10                  15

<210> SEQ ID NO 330
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 330

Gly Gly Gly Ser
1

<210> SEQ ID NO 331
<211> LENGTH: 66
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 331
ggcagcggcg ccaccaactt cagcctgctg aagcaggccg gcgacgtgga ggaaaaccct      60
ggcccc                                                                66

<210> SEQ ID NO 332
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 332

Gly Ser Gly Ala Thr Asn Phe Ser Leu Leu Lys Gln Ala Gly Asp Val
1               5                   10                  15

Glu Glu Asn Pro Gly Pro
            20

<210> SEQ ID NO 333
<211> LENGTH: 66
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 333
gtgaagcaga ccctgaactt cgacctgctg aaactggccg gcgacgtgga gagcaatccc      60
ggccct                                                                66

<210> SEQ ID NO 334
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 334

```
Val Lys Gln Thr Leu Asn Phe Asp Leu Leu Lys Leu Ala Gly Asp Val
1               5                   10                  15

Glu Ser Asn Pro Gly Pro
            20
```

<210> SEQ ID NO 335
<211> LENGTH: 394
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 335

```
Met Ala Leu Pro Val Thr Ala Leu Leu Leu Pro Leu Ala Leu Leu Leu
1               5                   10                  15

His Ala Ala Arg Pro Pro Gly Trp Phe Leu Asp Ser Pro Asp Arg Pro
                20                  25                  30

Trp Asn Pro Pro Thr Phe Ser Pro Ala Leu Leu Val Val Thr Glu Gly
            35                  40                  45

Asp Asn Ala Thr Phe Thr Cys Ser Phe Ser Asn Thr Ser Glu Ser Phe
    50                  55                  60

Val Leu Asn Trp Tyr Arg Met Ser Pro Ser Asn Gln Thr Asp Lys Leu
65                  70                  75                  80

Ala Ala Phe Pro Glu Asp Arg Ser Gln Pro Gly Gln Asp Cys Arg Phe
                85                  90                  95

Arg Val Thr Gln Leu Pro Asn Gly Arg Asp Phe His Met Ser Val Val
                100                 105                 110

Arg Ala Arg Arg Asn Asp Ser Gly Thr Tyr Leu Cys Gly Ala Ile Ser
            115                 120                 125

Leu Ala Pro Lys Ala Gln Ile Lys Glu Ser Leu Arg Ala Glu Leu Arg
    130                 135                 140

Val Thr Glu Arg Arg Ala Glu Val Pro Thr Ala His Pro Ser Pro Ser
145                 150                 155                 160

Pro Arg Pro Ala Gly Gln Phe Gln Thr Leu Val Thr Thr Thr Pro Ala
                165                 170                 175

Pro Arg Pro Pro Thr Pro Ala Pro Thr Ile Ala Ser Gln Pro Leu Ser
            180                 185                 190

Leu Arg Pro Glu Ala Cys Arg Pro Ala Ala Gly Gly Ala Val His Thr
    195                 200                 205

Arg Gly Leu Asp Phe Ala Cys Asp Ile Tyr Ile Trp Ala Pro Leu Ala
210                 215                 220

Gly Thr Cys Gly Val Leu Leu Leu Ser Leu Val Ile Thr Leu Tyr Cys
225                 230                 235                 240

Lys Arg Gly Arg Lys Lys Leu Leu Tyr Ile Phe Lys Gln Pro Phe Met
                245                 250                 255

Arg Pro Val Gln Thr Thr Gln Glu Glu Asp Gly Cys Ser Cys Arg Phe
            260                 265                 270

Pro Glu Glu Glu Glu Gly Gly Cys Glu Leu Arg Val Lys Phe Ser Arg
    275                 280                 285

Ser Ala Asp Ala Pro Ala Tyr Lys Gln Gly Gln Asn Gln Leu Tyr Asn
    290                 295                 300

Glu Leu Asn Leu Gly Arg Arg Glu Glu Tyr Asp Val Leu Asp Lys Arg
305                 310                 315                 320

Arg Gly Arg Asp Pro Glu Met Gly Gly Lys Pro Arg Arg Lys Asn Pro
                325                 330                 335
```

```
Gln Glu Gly Leu Tyr Asn Glu Leu Gln Lys Asp Lys Met Ala Glu Ala
            340                 345                 350

Tyr Ser Glu Ile Gly Met Lys Gly Glu Arg Arg Gly Lys Gly His
            355                 360                 365

Asp Gly Leu Tyr Gln Gly Leu Ser Thr Ala Thr Lys Asp Thr Tyr Asp
370                 375                 380

Ala Leu His Met Gln Ala Leu Pro Pro Arg
385                 390

<210> SEQ ID NO 336
<211> LENGTH: 373
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 336

Pro Gly Trp Phe Leu Asp Ser Pro Asp Arg Pro Trp Asn Pro Pro Thr
1               5                   10                  15

Phe Ser Pro Ala Leu Leu Val Val Thr Glu Gly Asp Asn Ala Thr Phe
            20                  25                  30

Thr Cys Ser Phe Ser Asn Thr Ser Glu Ser Phe Val Leu Asn Trp Tyr
        35                  40                  45

Arg Met Ser Pro Ser Asn Gln Thr Asp Lys Leu Ala Ala Phe Pro Glu
    50                  55                  60

Asp Arg Ser Gln Pro Gly Gln Asp Cys Arg Phe Arg Val Thr Gln Leu
65                  70                  75                  80

Pro Asn Gly Arg Asp Phe His Met Ser Val Val Arg Ala Arg Arg Asn
                85                  90                  95

Asp Ser Gly Thr Tyr Leu Cys Gly Ala Ile Ser Leu Ala Pro Lys Ala
            100                 105                 110

Gln Ile Lys Glu Ser Leu Arg Ala Glu Leu Arg Val Thr Glu Arg Arg
        115                 120                 125

Ala Glu Val Pro Thr Ala His Pro Ser Pro Ser Pro Arg Pro Ala Gly
    130                 135                 140

Gln Phe Gln Thr Leu Val Thr Thr Thr Pro Ala Pro Arg Pro Pro Thr
145                 150                 155                 160

Pro Ala Pro Thr Ile Ala Ser Gln Pro Leu Ser Leu Arg Pro Glu Ala
                165                 170                 175

Cys Arg Pro Ala Ala Gly Gly Ala Val His Thr Arg Gly Leu Asp Phe
            180                 185                 190

Ala Cys Asp Ile Tyr Ile Trp Ala Pro Leu Ala Gly Thr Cys Gly Val
        195                 200                 205

Leu Leu Leu Ser Leu Val Ile Thr Leu Tyr Cys Lys Arg Gly Arg Lys
    210                 215                 220

Lys Leu Leu Tyr Ile Phe Lys Gln Pro Phe Met Arg Pro Val Gln Thr
225                 230                 235                 240

Thr Gln Glu Glu Asp Gly Cys Ser Cys Arg Phe Pro Glu Glu Glu Glu
                245                 250                 255

Gly Gly Cys Glu Leu Arg Val Lys Phe Ser Arg Ser Ala Asp Ala Pro
            260                 265                 270

Ala Tyr Lys Gln Gly Gln Asn Gln Leu Tyr Asn Glu Leu Asn Leu Gly
        275                 280                 285

Arg Arg Glu Glu Tyr Asp Val Leu Asp Lys Arg Arg Gly Arg Asp Pro
```

```
                290             295             300
Glu Met Gly Gly Lys Pro Arg Arg Lys Asn Pro Gln Glu Gly Leu Tyr
305                 310             315                 320

Asn Glu Leu Gln Lys Asp Lys Met Ala Glu Ala Tyr Ser Glu Ile Gly
                325             330             335

Met Lys Gly Glu Arg Arg Arg Gly Lys Gly His Asp Gly Leu Tyr Gln
            340             345             350

Gly Leu Ser Thr Ala Thr Lys Asp Thr Tyr Asp Ala Leu His Met Gln
        355             360             365

Ala Leu Pro Pro Arg
    370

<210> SEQ ID NO 337
<211> LENGTH: 1182
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 337
atggccctcc ctgtcactgc cctgcttctc cccctcgcac tcctgctcca cgccgctaga        60
ccacccggat ggtttctgga ctctccggat cgccgtgga atcccccaac cttctcaccg       120
gcactcttgg ttgtgactga gggcgataat gcgaccttca cgtgctcgtt ctccaacacc       180
tccgaatcat tcgtgctgaa ctggtaccgc atgagcccgt caaaccagac cgacaagctc       240
gccgcgtttc cggaagatcg gtcgcaaccg ggacaggatt gtcggttccg cgtgactcaa       300
ctgccgaatg gcagagactt ccacatgagc gtggtccgcg ctaggcgaaa cgactccggg       360
acctacctgt gcggagccat ctcgctggcg cctaaggccc aaatcaaaga gagcttgagg       420
gccgaactga gagtgaccga gcgcagagct gaggtgccaa ctgcacatcc atccccatcg       480
cctcggcctg cggggcagtt tcagaccctg gtcacgacca ctccggcgcc gcgcccaccg       540
actccggccc caactatcgc gagccagccc ctgtcgctga ggccggaagc atgccgccct       600
gccgccggag gtgctgtgca tacccgggga ttggacttcg catgcgacat ctacatttgg       660
gctcctctcg ccggaacttg tggcgtgctc cttctgtccc tggtcatcac cctgtactgc       720
aagcggggtc ggaaaaagct tctgtacatt ttcaagcagc ccttcatgag gcccgtgcaa       780
accacccagg aggaggacgg ttgctcctgc cggttccccg aagaggaaga aggaggttgc       840
gagctgcgcg tgaagttctc ccggagcgcc gacgcccccg cctataagca gggccagaac       900
cagctgtaca cgaactgaa cctgggacgg cgggaagagt acgatgtgct ggacaagcgg       960
cgcggccggg accccgaaat gggcgggaag cctagaagaa gaaccctca ggaaggcctg      1020 tataacgagc tgcagaagga caagatggcc gaggcctact ccgaaattgg gatgaaggga      1080
gagcggcgga gggaaaggg gcacgacggc ctgtaccaag gactgtccac cgccaccaag      1140
gacacatacg atgccctgca catgcaggcc cttccccctc gc                         1182
```